(12) United States Patent
Cheikh et al.

(10) Patent No.: US 7,655,469 B2
(45) Date of Patent: Feb. 2, 2010

(54) NUCLEIC ACID MOLECULES AND OTHER MOLECULES ASSOCIATED WITH THE CYTOKININ PATHWAY

(75) Inventors: Nordine Cheikh, Davis, CA (US); Jingdong Liu, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 789 days.

(21) Appl. No.: 09/976,054

(22) Filed: Oct. 15, 2001

(65) Prior Publication Data

US 2007/0220622 A1 Sep. 20, 2007

Related U.S. Application Data

(63) Continuation of application No. 09/227,586, filed on Jan. 8, 1999, now abandoned, and a continuation-in-part of application No. 09/210,297, filed on Dec. 8, 1998, now abandoned, and a continuation-in-part of application No. 09/199,129, filed on Nov. 24, 1998, now abandoned.

(60) Provisional application No. 60/067,000, filed on Nov. 24, 1997, provisional application No. 60/069,472, filed on Dec. 9, 1997, provisional application No. 60/071,064, filed on Jan. 9, 1998, provisional application No. 60/074,201, filed on Feb. 10, 1998, provisional application No. 60/074,281, filed on Feb. 10, 1998, provisional application No. 60/074,567, filed on Feb. 12, 1998, provisional application No. 60/074,565, filed on Feb. 12, 1998, provisional application No. 60/075,462, filed on Feb. 19, 1998, provisional application No. 60/075,461, filed on Feb. 19, 1998, provisional application No. 60/075,464, filed on Feb. 19, 1998, provisional application No. 60/075,460, filed on Feb. 19, 1998, provisional application No. 60/075,463, filed on Feb. 19, 1998, provisional application No. 60/077,231, filed on Mar. 9, 1998, provisional application No. 60/077,229, filed on Mar. 9, 1998, provisional application No. 60/077,230, filed on Mar. 9, 1998, provisional application No. 60/078,368, filed on Mar. 18, 1998, provisional application No. 60/080,844, filed on Apr. 7, 1998, provisional application No. 60/083,067, filed on Apr. 27, 1998, provisional application No. 60/083,387, filed on Apr. 29, 1998, provisional application No. 60/083,388, filed on Apr. 29, 1998, provisional application No. 60/085,224, filed on May 13, 1998, provisional application No. 60/085,223, filed on May 13, 1998, provisional application No. 60/085,222, filed on May 13, 1998, provisional application No. 60/086,186, filed on May 21, 1998, provisional application No. 60/086,187, filed on May 21, 1998, provisional application No. 60/086,185, filed on May 21, 1998, provisional application No. 60/086,184, filed on May 21, 1998, provisional application No. 60/086,188, filed on May 21, 1998, provisional application No. 60/089,524, filed on Jun. 16, 1998, provisional application No. 60/089,810, filed on Jun. 18, 1998, provisional application No. 60/089,814, filed on Jun. 18, 1998, provisional application No. 60/090,170, filed on Jun. 22, 1998, provisional application No. 60/092,036, filed on Jul. 8, 1998, provisional application No. 60/099,670, filed on Sep. 9, 1998, provisional application No. 60/099,697, filed on Sep. 9, 1998, provisional application No. 60/100,674, filed on Sep. 16, 1998, provisional application No. 60/101,132, filed on Sep. 21, 1998, provisional application No. 60/101,130, filed on Sep. 21, 1998, provisional application No. 60/101,508, filed on Sep. 22, 1998, provisional application No. 60/101,344, filed on Sep. 22, 1998, provisional application No. 60/101,347, filed on Sep. 22, 1998, provisional application No. 60/101,343, filed on Sep. 22, 1998, provisional application No. 60/104,126, filed on Oct. 13, 1998, provisional application No. 60/104,127, filed on Oct. 13, 1998, provisional application No. 60/104,124, filed on Oct. 13, 1998, provisional application No. 60/104,121, filed on Oct. 13, 1998, provisional application No. 60/111,981, filed on Dec. 11, 1998.

(51) Int. Cl.
*C12N 5/04* (2006.01)
*C12N 15/82* (2006.01)
*C12Q 1/68* (2006.01)
*C07H 21/04* (2006.01)

(52) U.S. Cl. .................. 435/468; 435/6; 435/320.1; 435/325; 435/410; 435/419; 536/23.6

(58) Field of Classification Search ............... 536/23.1, 536/24.4; 435/6
See application file for complete search history.

(56) References Cited

U.S. PATENT DOCUMENTS 5,770,718 A 6/1998 Moffatt .............. 536/23.2

OTHER PUBLICATIONS

Sigma Catalog, Sigma Chemical Company, p. 776, 1990.*

(Continued)

*Primary Examiner*—Marianne P Allen
(74) *Attorney, Agent, or Firm*—Matthew L. Madsen; Ying-Horng Liu; Arnold & Porter LLP

(57) ABSTRACT

The present invention is in the field of plant biochemistry. More specifically the invention relates to nucleic acid sequences from plant cells, in particular, nucleic acid sequences from maize and soybean plants associated with the cytokinin pathway. The invention encompasses nucleic acid molecules that encode proteins and fragments of proteins. In addition, the invention also encompasses proteins and fragments of proteins so encoded and antibodies capable of binding these proteins or fragments. The invention also relates to methods of using the nucleic acid molecules, proteins and fragments of proteins and antibodies, for example for genome mapping, gene identification and analysis, plant breeding, preparation of constructs for use in plant gene expression and transgenic plants.

11 Claims, No Drawings

OTHER PUBLICATIONS

Moffat et al., Plant Molecular Biology, vol. 18, pp. 653-662, 1992.*
Xing et al., Plant Science, 169:37-45, 2005.*
Chen et al., "Metabolism of Cytokinin: Phosphoribosylation of Cytokinin Bases by Adenine Phosphoribosyltransferase from Wheat Germ," *Arch. Biochem. Biophys.* 214:634-641 (1982).
Chen and Kristopeit, "Metabolism of Cytokinin," *Plant Physiol.* 67:494-498 (1981).
Engelbrecht, "Cytokinins in Leaf-Cuttings of *Phaseolus vulgaris* L. during their Development," *Biochem. Physiol. Pflanzen* 163:335-343 (1972).
Esen, "Purification and Partial Characterization of Maize (*Zea mays* L.) β-Glucosidase," *Plant Physiol.* 98:174-182 (1992).
Goldberg, "Plants: Novel Developmental Processes," *Science*, 240:1460-1467 (1988).
Letham, "Zeatin, A Factor Inducing Cell Division Isolated From *Zea Mays*," *Life Sciences* 2:569-573 (1963).
Letham and Palni, "The Biosynthesis and Metabolism of Cytokinins," *Ann. Rev. Plant Physiol*, 34:163-197 (1983).
Moffatt, et al., "The adenine phosporibosyltransferase-encoding gene of *Arabidopsis thaliana*," *Gene* 143:211-216.(1994).
Moffatt, et al., Entrez, Accession #L19637, Aug. 15, 1994.
Moffatt, et al., Entrez, Accession #433050, Aug. 15, 1994.
Moffatt, et al., GeneBank Accession #TAU22442, Nov. 8, 1995.
Reese, "Degradation of Ploymeric Carbohydrates by Microbial Enzymes,"*Recent Adv. Phytochem.* 11:311-367 (1977).
Spychala, et al., "Cloning of human adenosine kinase cDNA: Sequence similarity to microbial ribokinases and fructokinases," *Proc. Natl. Acad. Sci*. 93:1232-1237 (1996).
Spychala, et al., Entrez, Accession #U50196, Apr. 25, 1996.
Spychala, et al., Entrez, Accession #1224125, Apr. 23, 1996.
Su and Howell, "A Single Genetic Locus, *Ckr1*, Defines *Arabidopsis* Mutants in which Root Growth Is Resistant to Low Concentrations of Cytokinin," *Plant Physiol.* 99:1569-1574 (1992).
Vroemen, et al., "Cloining and characterization of the *bgxA* gene from *Ewinia chrysanthemi* D1 which encodes a β-glucosidase/ xylasidase enzyme," *Mol. Gen. Genet* 246:465-477 (1995).
Vroemen, et al., Entrez, Accession #U08606, Oct. 31, 1995.
Vroemen, et al., Entrez, Accession #1045299, Aug. 16, 1995.
Binns,"Cytokinin Accumulation and Action: Biochemical, Genetic, and Molecular Approaches," *Annu. Rev. Plant Physiol. Plant Mol. Biol.* 45:173-196(1994).
Brzobohaty et al., "Release of Active Cytokinin by a β-Glucosidase Localized to the Maize Root Meristem," *Science* 262:1051-1054 (1993).
Cheikh and Jones, "Disruption of Maize Kernel Growth and Development by Heat Stress," *Plant Physiol.* 106:45-51 (1994).

* cited by examiner

```
                              SEQUENCE LISTING

<160> NUMBER OF SEQ ID NOS: 711

<210> SEQ ID NO 1
<211> LENGTH: 254
<212> TYPE: DNA
<213> ORGANISM: Zea mays
<220> FEATURE:
<221> NAME/KEY: unsure
<222> LOCATION: (1)...(254)
<223> OTHER INFORMATION: unsure at all n locations

<400> SEQUENCE: 1
cnacgttgct gcncgatccc aangcgnncc gngacaccat cgacntcttt gtcgagcggt      60
acnangaccn anggatcacc gtggttnctg gtgttgnagc natagggttc attttttggtc    120 ctcctatcgc tttagccatt ggcgcaaaat ttgtgccttg angaagccnn agaanttncc    180
angcgangtg atctccgaag agtattctnt ggaanatngn actnacnaga tagaaatgca    240
tgtcgganct gnac                                                      254

<210> SEQ ID NO 2
<211> LENGTH: 272
<212> TYPE: DNA
<213> ORGANISM: Zea mays
<220> FEATURE:
<221> NAME/KEY: unsure
<222> LOCATION: (1)...(272)
<223> OTHER INFORMATION: unsure at all n locations

<400> SEQUENCE: 2
ggacgccgtc gaacctgttc gtcgagcggt accgcgggat gggcatcgan gncgtagacn      60
gggattgagg ccaagggctt cgtgttcggc cnggcgatcg cgctggctat tggcgctaag    120
ttcatncctc tgcgcaagcc aaggaagctc ccaggtgagg tgatctccga gaagtacgtt    180
ctcgagtacg ggactgattg cctggngatg cgtgtcgggg ccatcgagcg atccggcgng    240
cgggtgntgn tcatcgacga cctggttgcg ca                                  272

<210> SEQ ID NO 3
<211> LENGTH: 318
<212> TYPE: DNA
<213> ORGANISM: Zea mays
<220> FEATURE:
<221> NAME/KEY: unsure
<222> LOCATION: (1)...(318)
<223> OTHER INFORMATION: unsure at all n locations

<400> SEQUENCE: 3
gaggccaggg gcttcgtgtt cggcccggcg atcgcgctgg gctattggcg ctaagttcat      60
acctctgcgc aagccaagga agctcccagg tgagagattc catgaccatg catgttcnnn    120 nnnnnnnnn nnnnnnaacc catctccaca ctctgcactg tacccagctg ttgcttttgt    180
cgatctagtg cccagcctgt ggcgacaccc tgatcaagta tatgtttagc gaggagggtt    240
```

```
cttgcttagc ccataatctc tggacaccgc cagagttgtt tgtctggcct gcatgcagtt    300
gcagtcccgt gaatggga                                                  318

<210> SEQ ID NO 4
<211> LENGTH: 279
<212> TYPE: DNA
<213> ORGANISM: Zea mays

<400> SEQUENCE: 4
gttccaggac atcacgacac tgctgctcga ccccaaggcg ttccgtgaca ccatcgacct    60
cttcgttgag cggtacaagg accaagggat caccgtagtt gctggtgtgg aagctagagg   120
gttcattttt ggtcctccta tcgctcttac gatcggtgct aaatttgtac ctttgaggaa   180
gccgaagaag ttgccaggcg aggtgatctc cgaagaatat tctctggaat acggaactga   240
caagatagag atgcatgttg gagctgtaca ggccaacga                          279

<210> SEQ ID NO 5
<211> LENGTH: 440
<212> TYPE: DNA
<213> ORGANISM: Zea mays
<220> FEATURE:
<221> NAME/KEY: unsure
<222> LOCATION: (1)...(440)
<223> OTHER INFORMATION: unsure at all n locations

<400> SEQUENCE: 5
cgtccgcgcc ggccgacttc gccttttcgt ccccgcgtca gcgtcgcggc tccnntgagc    60
gtgcgcgtca ccggcggcag gcgagggcag gcggtggtgg cgatggcgtn cgctgatgcg   120
cgcttggcgg ngatcgnctc ctncatccng gtnatnccg acttnccaaa gccagggatn    180
atgtttcagg acatcangan gntgntgttc gatcccaagg cgntccgtga caacatatac   240
cattttgtca gcggtacaa ggaccaaggn atcaccntgg aaantaggag ttaaagctag    300
agggntcant ttcggaacaa ctanntctta naannaattg gtcaaaaatn ggtgncnatt   360
gaggaagcnn aatnagntgc cangcnaaat gattttnang aatangaatt ttnggaatnn   420
ggaatnntag ataaaaaant                                                440

<210> SEQ ID NO 6
<211> LENGTH: 470
<212> TYPE: DNA
<213> ORGANISM: Zea mays
<220> FEATURE:
<221> NAME/KEY: unsure
<222> LOCATION: (1)...(470)
<223> OTHER INFORMATION: unsure at all n locations

<400> SEQUENCE: 6
aaggaccaag ggatnaccgt ggttgctggt gttgaagcta gagggttcat ttttggngct    60
gntatgggct ttanccattg gcgcaaaatt tgtgcctttg aggaagccga agaanttgcc   120
aggcgaggtg atctccnaan agtattnttt ggaatatgga actgacaana atagaaatgc   180
atgtcggant tttacaaggc caacaaccgg ccttttttgta ntncaatnat cttnttgnta   240
ccggtggaac attttttcaa nttnnaaaaa ttttttaaac ttttttgaacc aaaagntttt   300 gaaagttcct ttgttanttn naattnncca aaaantnaan gggccaaana aactttgnga   360
cacgggccan attttttttcn tttgggaaaa aaaacacctt aaacngnaan ttttngacnt   420
tttaaaaaan atttttngccc ccccaatnct naaaattttt catttttncca             470
```

```
<210> SEQ ID NO 7
<211> LENGTH: 412
<212> TYPE: DNA
<213> ORGANISM: Zea mays
<220> FEATURE:
<221> NAME/KEY: unsure
<222> LOCATION: (1)...(412)
<223> OTHER INFORMATION: unsure at all n locations

<400> SEQUENCE: 7
atctgattgn caccggtgga acacnctgtt tttctttcaa acttattgaa cgtgttggag      60
naaaggntgt tgagtgtgct tgcntnattg aattggcaga actgaagggc cgagacaaac     120
ttggggacag ggcagttntt gttcttgngg aagcagatgc ttgancggaa cttgggactt    180
ctcttctcag agagttagag ttagcgctgt tgatgctacc tntctggaaa acaacaaagt    240
tncccatgtt ggntanagtn nggctgacac gtaataaaan tttcatncca aattgtgatc    300
ccctgaatga natgacaatg tagacatgat tgctggtcct tgnatactgt gggnttatta    360
ttcacatcaa antaaangga taatcccnga atgggagctn aaaaaaangg ac            412

<210> SEQ ID NO 8
<211> LENGTH: 448
<212> TYPE: DNA
<213> ORGANISM: Zea mays
<220> FEATURE:
<221> NAME/KEY: unsure
<222> LOCATION: (1)...(448)
<223> OTHER INFORMATION: unsure at all n locations

<400> SEQUENCE: 8
ccggcngaag gcnagggcag gcggtgntcg cgatggcgtt cntcgacgcg cgcttngggg      60
agattncctc ntgcatccgc gtnatncnng acttcntnaa ancagggatc atntannang     120
acataangac antgatgctc gacccnaaag cgttccgtga caccatcgac gtcttcnttg     180
agcggtacaa ggaccaaagg gatcaccgta attgctggtg tggaagctag agggttcatt    240
tttggncttc tatcgctcta ccatnaatgc gaaatttgta ccttttagga agcctaaaaa    300
atttccaagc caggttaatc tncgaaagaa tattctcttg aatnccnaaa ctnanaaana    360
taaatatnca ttttggganct ttacaancca aacnaattgg gcttttngta tttcnatnat    420
nttattntca cnagtnnaac aattttttt                                       448

<210> SEQ ID NO 9
<211> LENGTH: 437
<212> TYPE: DNA
<213> ORGANISM: Zea mays
<220> FEATURE:
<221> NAME/KEY: unsure
<222> LOCATION: (1)...(437)
<223> OTHER INFORMATION: unsure at all n locations

<400> SEQUENCE: 9
agacgcgtgg gcggggtcga agaggagctt ggagcttgga ccgacccgag ccccaccgag      60
cgagagagag gaaataatgg gtgaagaggc cagctgcaac gccgtcagcg cgatggaggc     120
cgccaccaac gccaggccgg ccaaggagaa cggacgcgcg ccggctgtgg cggaggtagt    180
ggcccaggag gcggccactg accccggct gcagggcatc tccgacgcca tccgcgtcgt     240
gccgcacttc cccaagcacg gcatcatgtt caacgacatc accacgctgc tgctgcgccc    300
cagggtgttc aaggacgccg tcgacctgtt cgtcgagcgc taccgcggga tgcgcatcga    360
cgccgtcgcc gggatcgagg ccaggggctt catatttggc ccggcagtcc attggctatt    420
```

```
gggcgccnaa ttcaaaa                                              437

<210> SEQ ID NO 10
<211> LENGTH: 461
<212> TYPE: DNA
<213> ORGANISM: Zea mays
<220> FEATURE:
<221> NAME/KEY: unsure
<222> LOCATION: (1)...(461)
<223> OTHER INFORMATION: unsure at all n locations

<400> SEQUENCE: 10
gactgattgc ctggagatgc gtgtcggggc catcgagcga tccggcgagc gggtgctggt    60
catcgacgac ctggttgcga ccggagggac actctgtgct gcgatcaggc ttctagaacg   120
tgctggagcc gatgtggtcg agtgcgcgtg tgtcatcggg ctcccgaaat tcaaggattt   180
gtacaagttg aatggaaaac ctgtatacgt gctggttgag tctcgtgaat aatcggagaa   240
atgacaactt atgctcaggt gtcagagtga tcagggatat tggctgttta ctccttgcta   300
ctgcgattga acagtggagg gacgacatgg acaaggacaa gtatattcng tgcatcacta   360
aatcttggtg aggggagaga ttgtagtggt ttaagctgag tanttgaana acctgtaatt   420
tctgcacnga acatgatngn tattagtttn attccaccac t                      461

<210> SEQ ID NO 11
<211> LENGTH: 262
<212> TYPE: DNA
<213> ORGANISM: Zea mays

<400> SEQUENCE: 11
ggaaggtgag gtgatctccg agaagtacgt tctcgagtac gggactgatt gcctggagat    60
gcgtgtcggg gccatcgagc gatccggcga gcgggtgctg gtcatcgacg acctggttgc   120
gaccggagga cactctgtgc tgcgatcagg cttctagaac gtgctggagc cgatgtggtc   180
gagtgcgcgt gtgtcattgg gctcccgaaa ttcaaggatt tgtacaagtt gaatggaaaa   240
cctgtatacg tgctggttga gt                                           262

<210> SEQ ID NO 12
<211> LENGTH: 253
<212> TYPE: DNA
<213> ORGANISM: Zea mays
<220> FEATURE:
<221> NAME/KEY: unsure
<222> LOCATION: (1)...(253)
<223> OTHER INFORMATION: unsure at all n locations

<400> SEQUENCE: 12
ggaaggtgag gtgatctccg agaagtacgt tctncgagta cgggactgat tgcctggaga    60
tgcgtgtcgg ggccatcgag cgatccggcg agcgggtgct ggtccatcga cgacctggtt   120
gcgaccggag ggacactact gtgctgcgat caggcttcta gaacgtgctg gagccgatgt   180
ggtcgagtgc gctgtgtcat tgggctcccg aaattcaagg attgtacaat tgatggaaaa   240
cctgtatacg tgc                                                      253

<210> SEQ ID NO 13
<211> LENGTH: 463
<212> TYPE: DNA
<213> ORGANISM: Zea mays
<220> FEATURE:
<221> NAME/KEY: unsure
<222> LOCATION: (1)...(463)
```

<223> OTHER INFORMATION: unsure at all n locations

<400> SEQUENCE: 13

```
tagagggttc attttcggtc ctcctatcgc tttagccatc ggcgcaaaat ttgtgccttt      60
gaggaagccg aagaagttgc caggcgaggt gatctccgaa gagtattctt tggaatatgg     120
aactgacaag atagaaatgc atgttggagc tgtacaggcc aacgaccggg ctcttgtagt     180
cgatgatctt attgctaccg gtggaacact ctgtgcagct gtcaaactta ttgaacgtgt     240
tggagcaaag gttgttgagt gtgcttgtgt cattgaattg ccagaactga agggtcgaga     300
caagcttggg gacaggccag tttttgtcct tgtggaagca gacgcctgag cggaatttgg     360
gaattctcag agagtttggt gcccgtcgat gcttcctctn tggagacaac acaagtttnc     420
catggtacca tgttggctat tttctggctt gacccgtaat aaa                       463
```

<210> SEQ ID NO 14
<211> LENGTH: 300
<212> TYPE: DNA
<213> ORGANISM: Zea mays

<400> SEQUENCE: 14

```
agcggtacaa ggaccaaggg atcaccgtgg ttgctggtgt tgaagctaga gggttcattt      60
tcggtcctcc tatcgcttta gccatcggcg caaaatttgt gcctttgagg aagccgaaga     120
agttgccagg cgaggtgatc tccgaagagt attctttgga atatggaact gacaagatag     180
aaatgcatgt tggagctgta caggccaacg accgggctct tgtagtcgat gatcttattg     240
ctaccggtgg aacactctgt gcagctgtca aacttattga acgtgttgga gcaaaggttg     300
```

<210> SEQ ID NO 15
<211> LENGTH: 288
<212> TYPE: DNA
<213> ORGANISM: Zea mays

<400> SEQUENCE: 15

```
gagggttcat ttttggtcct cctatcgctt tagccattgg cgcaaaattt gtgcctttga      60
ggaagccgaa gaagttgcca ggcgaggtga tctccgaaga gtattctttg gaatatggaa     120
ctgacaagat agaaatgcat gtcggagctg tacaggccaa cgaccgggct cttgtagtcg     180
atgatcttat tgctaccggt ggaacactat gtgcagctgt caaacttatt gaacgtgttg     240
gagcaaaggt tgttgagtgt gcttgtgtca ttgaattgcc agaactga                  288
```

<210> SEQ ID NO 16
<211> LENGTH: 297
<212> TYPE: DNA
<213> ORGANISM: Zea mays
<220> FEATURE:
<221> NAME/KEY: unsure
<222> LOCATION: (1)...(297)
<223> OTHER INFORMATION: unsure at all n locations

<400> SEQUENCE: 16

```
gctttagcca ttggcgcaaa atttgtgcct ttgaggaagc cgaagaagtt gccaggcgag      60
gtgatctccg aagagtattc tttggaatat ggaactgaca agatagaaat gcatgtcgga     120
gctgtacagg ccaacgaccg ggctcttgta gtcgatgatc ttattgctac cggtggaaca     180
ctatgtgcag ctgtcncact tattgaacgt gttggagcaa aggttgttga gtgtgcttgt     240
gtcattgaat gccagaactg aagggccgag acaagcttgg ggacaggcca gttttg        297
```

```
<210> SEQ ID NO 17
<211> LENGTH: 289
<212> TYPE: DNA
<213> ORGANISM: Zea mays
<220> FEATURE:
<221> NAME/KEY: unsure
<222> LOCATION: (1)...(289)
<223> OTHER INFORMATION: unsure at all n locations

<400> SEQUENCE: 17
gcaaaatttg tgcctttgag gaagccgaag aagttgccag gcgaggtgat ctccgaagag      60
tattctttgg aatatggaac tgacaagata gaaatgcatg tcggagctgt acaggccaac     120
gaccgggctc ttgtagtcga tgatcttatt gctaccggtg gaacactatg tgcagctgtc     180
aaacttattg aacgtgttgg agcaaaggtt gttgagtgtg cttgtgtcat tgaattgcca     240
gaactgaagg gccgagacaa cttggggana ggccattttg gcctggngg               289

<210> SEQ ID NO 18
<211> LENGTH: 276
<212> TYPE: DNA
<213> ORGANISM: Zea mays

<400> SEQUENCE: 18
ttttggtcct cctatcgctt tagccattgg cgcaaaattt gtgcctttga ggaagccgaa      60
gaagttgcca ggcgaggtga tctccgaaga gtattctttg gaatatggaa ctgacaagat     120
agaaatgcat gtcggagctg tacaggccaa cgaccgggct cttgtagtcg atgatcttat     180
tgctaccggt ggaacactat gtgcagctgt caaacttatt gaacgtgttg gagcaaaggt     240
tgttgagtgt gcttgtgtca tgaattgcca gaactg                              276

<210> SEQ ID NO 19
<211> LENGTH: 267
<212> TYPE: DNA
<213> ORGANISM: Zea mays

<400> SEQUENCE: 19
accaagggat caccgtggtt gctggtgttg aagctagagg gttcattttt ggtcctccta      60
tcgctttagc cattggcgca aaatttgtgc ctttgaggaa gccgaagaag ttgccaggcg     120
aggtgatctc cgaagagtat tctttggaat atggaactga caagatagaa atgcatgtcg     180
gagctgtaca ggccaacgac cgggctcttg tagtcgatga tcttattgct accggtggaa     240
cactatgtgc agctgtcaaa cttattg                                        267

<210> SEQ ID NO 20
<211> LENGTH: 244
<212> TYPE: DNA
<213> ORGANISM: Zea mays

<400> SEQUENCE: 20
caagatagag atgcatgttg gagctgtaca ggccaacgat cgggctcttg tagtcgatga      60
tcttattgcc accggtggaa cactctgtgc agctgtcaaa cttattgaac gtgttggagc     120
aaaggttgtt gagtgtgctt gcgtcattga attggcagaa ctgaagggcc gagacaaact     180
tggggacagg ccagttttg ttcttgtcga agcagatgct tgagcggaac ttgggacttc     240
tctt                                                                244

<210> SEQ ID NO 21
<211> LENGTH: 266
<212> TYPE: DNA
<213> ORGANISM: Zea mays

<400> SEQUENCE: 21
```

```
ccgggctctt gtagtcgatg atcttattgc taccggtgga acactatgtg cagctgtcaa    60
acttattgaa cgtgttggag caaaggttgt tgagtgtgct tgtgtcattg aattgccaga   120
actgaagggc cgagacaagc ttggggacag gccagttttt gtccttgtgg aagcagacgc   180
ctgagcggaa cttgggactt ctcagagagt tggcgccgt cgatgctccc tctctggaga   240
caacacagtt tcccatgtta ccatgt                                       266
```

<210> SEQ ID NO 22
<211> LENGTH: 231
<212> TYPE: DNA
<213> ORGANISM: Zea mays

<400> SEQUENCE: 22

```
gatcttattg ctaccggtgg aacactatgt gcagctgtca aacttattga acgtgttgga    60
gcaaaggttg ttgagtgtgc ttgtgtcatt gaattgccag actgaaggg ccgagacaag   120 cttggggaca ggccagtttt tgtccttgtg gaagcagacg cctgagcgga acttgggact   180
tctcagagag tttggcgccg tcgatgctcc ctctctggag acaacacagt t           231
```

<210> SEQ ID NO 23
<211> LENGTH: 174
<212> TYPE: DNA
<213> ORGANISM: Zea mays

<400> SEQUENCE: 23

```
ctttggaata tggaactgac aagatagaaa tgcatgttgg agctgtacag gccaacgacc    60
gggctcttgt agtcgatgat cttattgcta ccggtggaac actctgtgca gctgtcaaac   120
ttattgaacg tgttggagca aaggttgttg agtgtgcttg tgtcattgaa ttgc         174
```

<210> SEQ ID NO 24
<211> LENGTH: 275
<212> TYPE: DNA
<213> ORGANISM: Zea mays
<220> FEATURE:
<221> NAME/KEY: unsure
<222> LOCATION: (1)...(275)
<223> OTHER INFORMATION: unsure at all n locations

<400> SEQUENCE: 24

```
atcagtgcga aatttgtact tcttaggctt cctcaaaggt gatctccgaa gaatattctc    60
tggaatacgg aactgacaag atagagatgc atgttggagc tgtacaggcc aacgatcggc   120
tcttgtagtc gatgatctat tgccaccggt ncaacactct gtgcagctgt caaactattg   180
aacgtgttgg agcaaaggtt gttgagtgtg ctgcgtcatg aatggcagaa ctgaagggcc   240
gagacaaact tggggacagg ccatttgtn cttga                              275
```

<210> SEQ ID NO 25
<211> LENGTH: 229
<212> TYPE: DNA
<213> ORGANISM: Zea mays

<400> SEQUENCE: 25

```
gttgagtgtg cttgtgtcat tgaattgcca gaactgaagg gccgagacaa gcttggggac    60
aggccagttt ttgtccttgt ggaagcagac gcctgagcgg aacttgggac ttctcagaga   120
gtttggcgcc gtcgatgctc cctctctgga gacaacacag tttcccatgt taccatgttg   180 gctatttct ggctgacgcg taataaagtt ttattccaaa ttgtgatcc                229
```

```
<210> SEQ ID NO 26
<211> LENGTH: 119
<212> TYPE: DNA
<213> ORGANISM: Zea mays
<220> FEATURE:
<221> NAME/KEY: unsure
<222> LOCATION: (1)...(119)
<223> OTHER INFORMATION: unsure at all n locations

<400> SEQUENCE: 26
ggaatatgga actgacaaga taganatgca tgtcggagct gtacaggcca acgaccgggc     60
ttcttgtagt cgatgattct tattgctacc ggtggaacac tatgtgcagc tgtcaacaa    119

<210> SEQ ID NO 27
<211> LENGTH: 431
<212> TYPE: DNA
<213> ORGANISM: Zea mays
<220> FEATURE:
<221> NAME/KEY: unsure
<222> LOCATION: (1)...(431)
<223> OTHER INFORMATION: unsure at all n locations

<400> SEQUENCE: 27
cttgcatccc gtccccgtcc gcgccggccg acgccgcctt ttcgtcccccg cgtcagcgtc    60 gcggctccac tgagcgtgcg tgtcaccggc gggaggcaag ggcaggcggt ggtggcgatg   120
gcgtccgctg acgcgcgctt ggcggggatc gcctcctcca tccgcgtcat ccccgacttc   180
cccaagccag ggatcatgtt ccaggacatc acgacgttgc tgctcgatcc caaggcgttc   240
cgtgacacca tcgacctctt tgtcgagcgg tacaaggacc aagggatcac cgtggttgct   300
ggtgttgaag ctagagggtt catttttggt cctcctatcg ctttagccat ggcgcaaaa    360 tttgtgcctt tgaggaaacc gaagaagttn ccaagccaag gttatttccc naanaattat   420
cctttggaaa a                                                        431

<210> SEQ ID NO 28
<211> LENGTH: 460
<212> TYPE: DNA
<213> ORGANISM: Zea mays
<220> FEATURE:
<221> NAME/KEY: unsure
<222> LOCATION: (1)...(460)
<223> OTHER INFORMATION: unsure at all n locations

<400> SEQUENCE: 28
gccacgccgt cccggcagtc nttggcattc ccgtcccgtc ggcgcccggc cgaccccgct    60
ttttcgtccc cgcgtcaagc gtcgcgggct tccactgaag cgtgcgttgt caccggcggg   120
gaggcaaggg caggcggtgg tggcgatggc gtcccgctga cgcgcgcttg gcggggatcg   180
cctcctccat ccgcgtcatc tccgacttcc ccaagccagg gatcatgttc caggacatca   240
cgacgttgct gctcgatccc aaggcgttcc gtgacaccat cgacctcttt gtcgagcggt   300
acaaggacca agggatcacc gtggttgctg gtgttgaagc tagagggttc attttggtc    360 ctcctatcgc tttagccatt ggcgcaaaat ttgtgccttt gaggaaaccc gaagaagttg   420
ccaggccaag gtgatctccg aagaggtatt cttttggaat                         460

<210> SEQ ID NO 29
<211> LENGTH: 431
<212> TYPE: DNA
<213> ORGANISM: Zea mays
<220> FEATURE:
<221> NAME/KEY: unsure
```

```
<222> LOCATION: (1)...(431)
<223> OTHER INFORMATION: unsure at all n locations

<400> SEQUENCE: 29
cgcgtctcgt ccccgtccgc atccgcgtcc gcgccgcctt ttcgtcccg cgtcggcgtc    60 gcggctccac tgggcgtacg cgtcaccggc ggaaggcgag ggcaggcggt ggtcgcgatg   120
gcgtccgccg acgcgcgctt ggcggggatt gcctcctcca tccgcgtcat ccccgacttc   180
cccaagccag ggatcatgtt ccaggacatc acgacactgc tgctcgaccc caaggcgttc   240
cgtgacacca tcgacgtctt cgttgagcgg tacaaggacc aagggatcac cgtagttgct   300
ggtgtggaag ctanagggtt cattttggt cctcctatcg ctctaaccat cantgcgaaa    360
ttttgtacct ttganggaac ctaaagaaat tnncaaggcn aaggtgatnt ccgaaanaat    420
aatccnctgg g                                                        431

<210> SEQ ID NO 30
<211> LENGTH: 472
<212> TYPE: DNA
<213> ORGANISM: Zea mays
<220> FEATURE:
<221> NAME/KEY: unsure
<222> LOCATION: (1)...(472)
<223> OTHER INFORMATION: unsure at all n locations

<400> SEQUENCE: 30
gccagtcttg catcccgtcc ccgtccgcgc cggccgacgc cgccttntcg tcccgcgtc    60 agcgtcgcgg ctccactgag cgtgcgtgtc accggcggga ggcaagggca ggcggtggtg   120
gcgatggcgt ncgctgacgc gcgcttggcg gggatcgcct cctccatccg cgtcatcccc   180
gactttccca agccagggat catgttccag gacatcacga cgtttgctnc tnnatnccaa   240
ggcgttccgt gacaccatcg acctcnttgt cgagcggtac aaggaccaag ggatcaccgt   300
ggttgctggt gttgaancta gagggttcat ttttggtcct tctatngctt tagccattgg   360
cgcaaaaatt gngcccttta agaaanccga ataaatntca ncnaggngat ttnngaagaa    420 nttttttga aanttggact tttccananat naantggttt tnngnngttt nc            472

<210> SEQ ID NO 31
<211> LENGTH: 271
<212> TYPE: DNA
<213> ORGANISM: Zea mays
<220> FEATURE:
<221> NAME/KEY: unsure
<222> LOCATION: (1)...(271)
<223> OTHER INFORMATION: unsure at all n locations

<400> SEQUENCE: 31
gcgagggcag gcggtggtcg cgatggcgtc cgccgacgcg cgcttggngg ggattgcctc    60
ctccatccgc gtcatccccg acttcccaa gccaggatc atgttccagg acancacgac     120
actgctgctc gaccccaagg cgttccgtga caccatcgan ctcttcgttg agcngtacaa   180
ggaccaaggg atcaccgtag ttgctggtgt ggaagctaga gggttcatt ttggtccctc    240 ctatcgctct agccatcggt gctaaatttg t                                  271

<210> SEQ ID NO 32
<211> LENGTH: 294
<212> TYPE: DNA
<213> ORGANISM: Zea mays
<220> FEATURE:
<221> NAME/KEY: unsure
<222> LOCATION: (1)...(294)
```

<223> OTHER INFORMATION: unsure at all n locations

<400> SEQUENCE: 32

```
gtctcgcatc ccgtccccgt ccgcnccggc cgacgccgcc ttttcgtccc cgcgtcaggt      60
ncgcgggctc cactgagcgt gcgcgtcacc ggcggcagga gagggcaggc ggtggtggcg     120
atggcgtccg ctgatgcgcg cttggcgggg atcgcctcct ccatccgcgt catccccgac     180
ttccccaagc cagggatcat gtttcaggac atcacgacgt tgctgctcga tcccaaggcg     240
ttccgtgaca ccatcgacct ctttgtcgag cggtacaagg aacaagggat cacg           294
```

<210> SEQ ID NO 33
<211> LENGTH: 285
<212> TYPE: DNA
<213> ORGANISM: Zea mays
<220> FEATURE:
<221> NAME/KEY: unsure
<222> LOCATION: (1)...(285)
<223> OTHER INFORMATION: unsure at all n locations

<400> SEQUENCE: 33

```
gtccccgtcc gcgccggccg acgccgcctt ttcgtccccg cgtcaggttc gcgggctcca      60
ctgagcgtgc gtgtcaccng ngggaggcaa gggcaggcgg tggtggcgat ggcgtccgct     120
gacgcgcgct tggcggggat cgcctcctcc atccgcgtca tccccgactt ccccaagcca     180
gggatcatgt tccaggacat cacgacgttg ctgctcgatc ccaaggcgtt ccgtgacacc     240
atcgacctct ttgtcgagcg gtacaaggac caaggatcac cgtgg                     285
```

<210> SEQ ID NO 34
<211> LENGTH: 269
<212> TYPE: DNA
<213> ORGANISM: Zea mays
<220> FEATURE:
<221> NAME/KEY: unsure
<222> LOCATION: (1)...(269)
<223> OTHER INFORMATION: unsure at all n locations

<400> SEQUENCE: 34

```
cngacgctgg gcgccggccg acgccgcctt ttcgtccccg cgtcaggtcc gcgggctcca      60
ctgagcgtac gtgtcaccgg cgggaggcaa gggcaggcgg tggtggcgat ggcgtccgct     120
gacgcgcgct tggcggggat cgcctcctcc atccgcgtca tccccgactt ccccaagcca     180
gggatcatgt tccaggacat cacgacgttg ctgctcgatc ccaaggcgtt ccgtgacacc     240
atcgacctct ttgtcgagcg gtacaagga                                       269
```

<210> SEQ ID NO 35
<211> LENGTH: 285
<212> TYPE: DNA
<213> ORGANISM: Zea mays
<220> FEATURE:
<221> NAME/KEY: unsure
<222> LOCATION: (1)...(285)
<223> OTHER INFORMATION: unsure at all n locations

<400> SEQUENCE: 35

```
cgcatcccgt ccccgtccgc nccggcngac gccgcctttt cgtccccgcn tcaggtccgc      60
ggctccactg agcgtgcgcg tcaccggcgg caggcgaggn caggcggtgg tggcgatggc     120
gtccgctgat gcgcgcttgg cggggatcgc ctcctccatc cgcgtcatcc ccgacttccc     180
caagccaggg atnatgtttc aggacatcac gacgttgctg ctcgatccca agggcgttcc     240
gtgacaccat cgacctcttt gtcgagcggt acaaggacca agggg                     285
```

<210> SEQ ID NO 36
<211> LENGTH: 287
<212> TYPE: DNA
<213> ORGANISM: Zea mays
<220> FEATURE:
<221> NAME/KEY: unsure
<222> LOCATION: (1)...(287)
<223> OTHER INFORMATION: unsure at all n locations

<400> SEQUENCE: 36

```
cnagtntcgc atcccgtccc cgtccgcacn ggcngangcc gcctttncgt ccccgcgtca      60
ntncgaggac tccactganc gtgcgcgtna ccggcggcag gcgaggncag gcggtggtgg     120
cgatggcgtc cgcngatgcg cgcttggcgg ggatngcctc ctccatccnc gtcatcccg      180
acttccccaa nccagggatc atgtttcagg acatcacgac gttgctgctc gatcncaagg     240
cgttccgtga caccatcgac ntctttgtcg ancngtacaa ggaccaa                   287
```

<210> SEQ ID NO 37
<211> LENGTH: 458
<212> TYPE: DNA
<213> ORGANISM: Zea mays
<220> FEATURE:
<221> NAME/KEY: unsure
<222> LOCATION: (1)...(458)
<223> OTHER INFORMATION: unsure at all n locations

<400> SEQUENCE: 37

```
ttcacncgtn cggtttncgc ttttcggcat nccgtccccg tccgcgcggg gncgattncg      60
ncttttcgtn ngcgcgtcag ngtcgcggct ccactgagcg tgcgtgtcac cggcgggagg     120
caagggcagg cggtggtggc natggcgtcc gctgacgcgc ncttggcggg gatcgcctnc     180
tncatncgcn tcatccccga cttccccaag ccagggatca tgttccagga catcacgacg     240
ttgctgctcg atcccaaggc gttncgttga caccatcgac ctnttttgtc gaancggtac     300
aaggaccaan ggatcaccgt ggnttgctgg tgttgaagct agagggttna ttttttggtc     360
cttctatcgc tttanccatt ggcgcaaaat ttgtgccttt gaagaanccc aaaaaagttg     420
ccacgcnaan gtgaacttcc gaaaaaggtt cttttgga                              458
```

<210> SEQ ID NO 38
<211> LENGTH: 272
<212> TYPE: DNA
<213> ORGANISM: Zea mays
<220> FEATURE:
<221> NAME/KEY: unsure
<222> LOCATION: (1)...(272)
<223> OTHER INFORMATION: unsure at all n locations

<400> SEQUENCE: 38

```
cngacgctgg ggcgccgtcc ccgtccgcgc cggccgncgc cgccttttcg tnccgcgtc       60
agntgcgcgg ctacactgag cgtgcgtgtc accggcgana ggcaagggca ggcggtggtg     120
gcgntggcgt ccgntgncgc gcgcttggcg gggntcgcct cctccatccg cgtcatcccc     180
gncttcccca agccagggnt cntgttccag gacntcacgn cgttgctgct ngntccaag      240
gcgttncgng ncaccntngn cntctttgtc ga                                   272
```

<210> SEQ ID NO 39
<211> LENGTH: 216
<212> TYPE: DNA
<213> ORGANISM: Zea mays

<400> SEQUENCE: 39

```
caagggcagg cggtggtggc gatggcgtcc gctgacgcgc gcttggcggg gatcgcctcc      60
tccatccgcg tcatcccgga cttccccaag ccagggatca tgttccagga catcacgacg     120
ttgtgctcga tcccaaggcg ttccgtgaca ccatgacttt tgtcgacggt acaggacaag     180
gatcacgtgg ttctgtgttg agctagaggt catttt                               216
```

<210> SEQ ID NO 40
<211> LENGTH: 312
<212> TYPE: DNA
<213> ORGANISM: Zea mays
<220> FEATURE:
<221> NAME/KEY: unsure
<222> LOCATION: (1)...(312)
<223> OTHER INFORMATION: unsure at all n locations

<400> SEQUENCE: 40

```
ancctcgcgt cccgtccgcn tccgcgccgc ctttttcgtc cccgcgtccg cgtcgcggct      60
tccactgggc gtgcgcgtca ccggcgggag gcgagggcag gcggtggtcg cgatggcgtc     120
cgccgacgcg cgcttggcgg ggattgcctc ntccatccgc gtcaatcccc gacttcccca     180
agccaaggat catgttccag gacatcaacg acaatgctgc tcgaccccaa agcgttccgt     240
gacaccatcg aactcttcgt tgancggtaa naagaacaan ggattaaccg taantgctgg     300
tgtngaaact aa                                                         312
```

<210> SEQ ID NO 41
<211> LENGTH: 237
<212> TYPE: DNA
<213> ORGANISM: Zea mays

<400> SEQUENCE: 41

```
tgtgcggggc tacttcgctt ggtctctggt ggacaacttt gaatggaccg cgggctacac      60
cgaacgttac ggcatagtct acgttgaccg taatgacggc tacaaacgct acatgaagaa     120
gtcagccaag tggttgaaag agttcaacac tgagaaggct ggcagcgcct aatgatgtgc     180
catgcataaa agaccgggtc tgtgtgattt gaattctata ttttatttg cacctcc         237
```

<210> SEQ ID NO 42
<211> LENGTH: 280
<212> TYPE: DNA
<213> ORGANISM: Zea mays
<220> FEATURE:
<221> NAME/KEY: unsure
<222> LOCATION: (1)...(280)
<223> OTHER INFORMATION: unsure at all n locations

<400> SEQUENCE: 42

```
gncgggcatc ccantggtcc ttggatgggg anttcgtgga tctacntann tcctgaaggc      60
tannggatnt agcttatnat cangaagaac aaatacggaa anccacccat ctacatcact     120
gagaacggga tgngtgacgt tgancatggc gatctaccca tggaagttgc cttggatgac     180
cacannagng tanattanct ncagcgcgac atcganantc ttanggcgtc aaganacttg     240
ggagcnaatg tgcagggcta cttcgcntgg nctctattgg                           280
```

<210> SEQ ID NO 43
<211> LENGTH: 282
<212> TYPE: DNA
<213> ORGANISM: Zea mays
<220> FEATURE:
<221> NAME/KEY: unsure

```
<222> LOCATION: (1)...(282)
<223> OTHER INFORMATION: unsure at all n locations

<400> SEQUENCE: 43
cggnacntgg tatgcttctg tgactatgga attttgtaaa cagcttttaa tgcatgttgg      60
agtatttatt aatttttgtat acttctttga aaatgagctt ggtgttgtat ttgcaaatca    120
tcagatggtg actatatggg aatgtatttg gttacccaat gtggaatggt ttattttcat    180
gattttgtgt taacagaagt tttaaccttt aagggtctgt ttggttgggc tgtggctgtg    240
aaaaaagttg ctgtgggctg tgagctgtga aaaaagctgc tg                       282

<210> SEQ ID NO 44
<211> LENGTH: 294
<212> TYPE: DNA
<213> ORGANISM: Zea mays

<400> SEQUENCE: 44
accatcgcta cgtgggagat ctggagatcc tgcagtcgct gggagtcaac gcctacagat    60
tctccatctc atgggcgagg gttctaccaa gaggccgggt tggtggcgtc aatgcaggcg   120
gggtagcttt ctacaaccgc ctgatcgatg cgctcctgca gaaaggaata cagccattcg   180
tcactctgaa ccatttcgac atgccgcgcg agctggaggt ccggtacgtg gctggctgga   240
cgctgggatc cggaggagt acgagcacta cgcggacgtc tgcttcgggg cgtt          294

<210> SEQ ID NO 45
<211> LENGTH: 279
<212> TYPE: DNA
<213> ORGANISM: Zea mays
<220> FEATURE:
<221> NAME/KEY: unsure
<222> LOCATION: (1)...(279)
<223> OTHER INFORMATION: unsure at all n locations

<400> SEQUENCE: 45
gaaaaagctt cttcctggat ccagccattt ggttggtttt tggcttttag gggggcaaaa    60
gccaaagcca aaattcaaac caaacacacc cagtcatttt ggcttttcta tatacaatgc   120
tttaactatg tatttagata tagtgtatat ttaagtgcac tataaaagat gcccctcca    180 tcccnnaata aaatgtgttt tacctttta gttgatacat gcaataatga atatattttgt   240 cttacatatg tgtctagatt catcatcatc catttgaac                          279

<210> SEQ ID NO 46
<211> LENGTH: 140
<212> TYPE: DNA
<213> ORGANISM: Zea mays

<400> SEQUENCE: 46
gtcatattct ccagcaccgt ggctaataat gtattgttgc agtacaaaaa aaaaaatata    60
atccacaagg taaatttctt aatctataac cactatttga aattggtagt ctacaatcta   120
tttgatgctt taagtgaact                                               140

<210> SEQ ID NO 47
<211> LENGTH: 291
<212> TYPE: DNA
<213> ORGANISM: Zea mays

<400> SEQUENCE: 47
aggaaaacaa attatacaac tttcatgagt atttaagagc aagcacacgg gctcagttga    60
```

```
tgaattccct gaatcacatt tcccatatgg ctcggaacaa cggttgggtg gaaatgcccc      120
aatggagtat gcaagcttta caataagatt tggctcattg aatgtgaccc agtgctttac      180
tcggtcacca aacatcttga agcaaagctc aacgaagtag gtgaagtcct ccctgaatag      240
aaataaagaa acaaccacat atgaacttac ggcatcttcg tagataaagc t              291
```

<210> SEQ ID NO 48
<211> LENGTH: 315
<212> TYPE: DNA
<213> ORGANISM: Zea mays

<400> SEQUENCE: 48

```
cccaggacaa aaatgcgcta acccaaccgg gaactcgctc accgagccat acattgttgc       60
ccacaacctc ctccgagctc acgctgagac tgtccatgag tacaacaagc attacagagg      120
taacaaggac gcacagatag ggattgcatt cgacgtgatg ggccgtgtgc catatgacaa      180
tatgtttctc gacggccagg cccaagaaag gtccattgat tataacctag gatggttcat      240
ggagccggta gttcgcggcg actaccctt ctccatgaga tcattgatca aggatcggct       300
accctacttc accga                                                        315
```

<210> SEQ ID NO 49
<211> LENGTH: 290
<212> TYPE: DNA
<213> ORGANISM: Zea mays
<220> FEATURE:
<221> NAME/KEY: unsure
<222> LOCATION: (1)...(290)
<223> OTHER INFORMATION: unsure at all n locations

<400> SEQUENCE: 49

```
ctgccagcgt atgggcctga cgggaaaccc attggtcctc ctgtacgtat atctttccaa       60
cactatatga atttgttcac attattctan atttatgttt aaagtgattg gtgtaaaaaa      120
ttcatccaaa aatataagca cagaagaatg tttgctcatg gatgaaatta tacgtgttga      180
gtagcaaatg ttttgtgttg gcagtaaagc agaacaaatc tttactttt tgtggaaata       240 tgcatgttgt taactagtga ataatattcg ctacaatttg cagatgggaa                  290
```

<210> SEQ ID NO 50
<211> LENGTH: 299
<212> TYPE: DNA
<213> ORGANISM: Zea mays
<220> FEATURE:
<221> NAME/KEY: unsure
<222> LOCATION: (1)...(299)
<223> OTHER INFORMATION: unsure at all n locations

<400> SEQUENCE: 50

```
ctaatatgga cggaaaaaaa atgccacaaa caactatatt ttagcggaat gattaataat       60
ctaatggtat acatgacgta tgggcttcta agcaagccat gtgcagaaat gcagaatcng      120
cccatagccg gcatcgacgg acctgggcat gttgggctgg agtcctaaga tgaccttttt      180
gcgagatatt tgactcaaac aatctaacca actcaactaa actagatact tttggctctt      240
ttatttcttt tcacgaaact ttttgtcaac gtaggttttt agtttggtat acttattaa       299
```

<210> SEQ ID NO 51
<211> LENGTH: 250
<212> TYPE: DNA
<213> ORGANISM: Zea mays

<400> SEQUENCE: 51

```
ggccggtcta gtccgaggct ccatcgacta cgtcggagtc aaccagtaca ctgcctacta    60
cgtgcgtgat cgacggccaa acgctacggc ggcgccgccc agctactcgt ccgactggca   120
cgctgagttc gtctatgaac gcgacggtgt gccgattgga ccaagggcga actcagactg   180
gctctacatc gtgccttggg gactgtacaa agccgtcacc tacgtcaagg agaagtacgg   240
caaccccacg                                                          250
```

```
<210> SEQ ID NO 52
<211> LENGTH: 237
<212> TYPE: DNA
<213> ORGANISM: Zea mays

<400> SEQUENCE: 52
gggaccgact acccttcttc actgacgagg agcgagagaa gctagtgggc tcatatgaca    60
tgctggggtt aaactactac acctcaaggt tctccaaaca catcgatatc acgcaacaca   120
acacactaag gctcaacact gacgatgcat atgccagtca ggaaacgaaa gggcctgacg   180
gcgagcccat tggtcctccg atggggaatt ggatctacct gtatcctcaa ggcctaa      237
```

```
<210> SEQ ID NO 53
<211> LENGTH: 315
<212> TYPE: DNA
<213> ORGANISM: Zea mays
<220> FEATURE:
<221> NAME/KEY: unsure
<222> LOCATION: (1)...(315)
<223> OTHER INFORMATION: unsure at all n locations

<400> SEQUENCE: 53
anacaatctt cagaatactc tgggggctg gatttctgac aagattgtgg agtactttgc     60
attgtatgca gaagcttgct ttgcaaattt tggagacagg gtaaagcatt ggataacaat   120
caatgaacct ctccaaactg caatcaatgg ttatgggatt ggaattttg cacctggagg    180 atgccaaggt gaaactgcta gatgttactt ggctgcccat caccaaatct tggctcatgc   240
tgctgctgtt gatgttatag aagaaaatcg aggctgcaca agtgtgaagt agggtgggtg   300
tgattgtgaa tgggc                                                    315
```

```
<210> SEQ ID NO 54
<211> LENGTH: 339
<212> TYPE: DNA
<213> ORGANISM: Zea mays
<220> FEATURE:
<221> NAME/KEY: unsure
<222> LOCATION: (1)...(339)
<223> OTHER INFORMATION: unsure at all n locations

<400> SEQUENCE: 54
gggcgctgga tccgcgggcg gcggtgaatc gcgtgcgggc tgacgtgagc gctgagcggg     60
attcgcggcg ggggcagtct acgctccact cttaatagtt gtagagatac ttttataaaa   120
gtacttttta tgcaaaattg acgcatataa atatcaggtt ccaaaaacta aataacaaaa   180
tagttatttg tagtcaaaat tttataagtt tgactcgaac cttatccaaa acgcaacta    240 ataggaaacc ggagggagta cgtgaccaaa caccaccatt taagaccgac ggagaaccac   300
atggacatgg ggcgtgnttg ggaaggtgcc cagtanccc                          339
```

```
<210> SEQ ID NO 55
<211> LENGTH: 187
<212> TYPE: DNA
```

<213> ORGANISM: Zea mays

<400> SEQUENCE: 55

```
gatttataac ctaggatggt tcatggagcc ggtcgttcgc ggcgactacc ctttctccat      60
gagatcattg atcaaggatc ggctacccta ctttaccgac gacgagaaag agaagctagt     120
gggttcgtat gacataatgg ggataaacta ctacacctcg aggttttcca agcacatcga     180
catctcg                                                              187
```

<210> SEQ ID NO 56
<211> LENGTH: 271
<212> TYPE: DNA
<213> ORGANISM: Zea mays

<400> SEQUENCE: 56

```
cctttttacaa actcaactga agatcaaaaa gcagcgcaaa gggccaggga cttccatatt     60
ggttggtttc ttgatccatt aataaatggg caatatccaa cgataatgca agacattgtg    120
aaagaccggc taccaagttt cacacctgaa caggccaagc tagtcaaggg ctcatcagat    180
tatttcggga tcaatcaata tactacatac tacattgcag atcaacaaac tcctccgcag    240
gaccaccgag ctactcgtcc gactggggcg t                                   271
```

<210> SEQ ID NO 57
<211> LENGTH: 275
<212> TYPE: DNA
<213> ORGANISM: Zea mays

<400> SEQUENCE: 57

```
cgaaagaaca cctctgtttt ctctgtttga aagatgagct taatcctata aacgcacaca     60
agaagctaac ttaagaagcg ttcccatgca tacgcattag cttggctaga tgagtcacta    120
tgacaatgac cgggtccagt gatgtgtctg gtctaatcgg gatcgtccgg caagaaaaga    180
aatgaaatca ggtgcattga acctgagctt gtcatatacc caccacatct caaaatataa    240
acatatattc atcaatcatc tacgaatgca atttg                               275
```

<210> SEQ ID NO 58
<211> LENGTH: 315
<212> TYPE: DNA
<213> ORGANISM: Zea mays

<400> SEQUENCE: 58

```
cgcagagggg cagggtcggg atcctgctgg atttcgtgtg gtacgagccc ctcacgggcg     60
gactcagccg ccgaccgggc cgccgctcaa aggtccagag acttccacgt cggatggttc    120
ctgcacccca tcgtctacgg cgagtacccc aagtcggtcc ggaagagcgt caagggcagg    180
ctccccaagt tcacggctga ggaggccggt ctagtccgag gctccatcga ctacgtcgga    240
gtcaaccagt acactgccta ctacgtgcgt gatcgacgga caaacgctag gcggcgcgcc    300
cagtacttcg tccga                                                     315
```

<210> SEQ ID NO 59
<211> LENGTH: 287
<212> TYPE: DNA
<213> ORGANISM: Zea mays

<400> SEQUENCE: 59

```
atcgccccga cggggatgta cgggtgcgtg aactacctca aggagaagta tgggaatcca     60
acgatctaca taacggagaa cggtactcaa cggaattccg tgtttcgcat gaacacgcca    120
```

```
cgccgcatac caagggaatc gtatttacat cgatctttt tttatttctt ttctgtgtta      180
ccaggaatgg accagcctgg aaacttgacc cgagaccagt acctgcgcga cgccacgagg      240
gtgcggttct acaggagcta catcggccag ctgaagaagg ccataga                    287

<210> SEQ ID NO 60
<211> LENGTH: 297
<212> TYPE: DNA
<213> ORGANISM: Zea mays
<220> FEATURE:
<221> NAME/KEY: unsure
<222> LOCATION: (1)...(297)
<223> OTHER INFORMATION: unsure at all n locations

<400> SEQUENCE: 60
agaatggacc aacctggtga tgtcagtatt actcagggtg tgcatgacac agtaagaatc      60
cgttattaca gagactacat aactgagctc aagaaggcaa tagatgatgg tgccagantc      120
attgggtact ttgcgtggtc gctgcttgac aacttcgagt ggaggcttgg gtacacttcg      180
cggtttggct tggtgtacgt ggactacaag actctgaaga ggtaccccaa ggactcagct      240
ttctggttca agcatatgct gtccaagaaa aggagtagag aattgcagac aagagga        297

<210> SEQ ID NO 61
<211> LENGTH: 284
<212> TYPE: DNA
<213> ORGANISM: Zea mays
<220> FEATURE:
<221> NAME/KEY: unsure
<222> LOCATION: (1)...(284)
<223> OTHER INFORMATION: unsure at all n locations

<400> SEQUENCE: 61
acggaacctt atatcgttgc tcataatttt ctcttgtcac atgctgctgc tgtgtcaaga      60
taccgtaaca gtatcaggc tgctcagaaa ggaaaggttg aatagttct ggacttcaat      120 tggtatgaag ctctcacaaa ctcaaccgaa gaccaagcag cggctcaaag agcaagggtt      180
tccangttgg ttggtttgct gatcccatta taaatggnnt tatccccagn tatgccagnt      240
ntngnaaaag agnggctgcc cattttactc nggagnaagc taat                      284

<210> SEQ ID NO 62
<211> LENGTH: 278
<212> TYPE: DNA
<213> ORGANISM: Zea mays
<220> FEATURE:
<221> NAME/KEY: unsure
<222> LOCATION: (1)...(278)
<223> OTHER INFORMATION: unsure at all n locations

<400> SEQUENCE: 62
ggccaaccaa agggctggat ctaggaagca gcttttcta aaagctgact ttctcacagt       60
gcaaatctga aagcacccct aaacctgctt ttagtgactt ttcggatgga actgtgaaaa      120
catatatcga ngaactttta acgacttta gtgattccca ccaaacggtt tttagctttt      180
taacgactca cagctacagc agcttttcc acagctcaca gcccacagca atttttcac       240 agcccacagt tcaaccaaac agacctatat anccatgg                             278

<210> SEQ ID NO 63
<211> LENGTH: 269
<212> TYPE: DNA
<213> ORGANISM: Zea mays
<220> FEATURE:
```

```
<221> NAME/KEY: unsure
<222> LOCATION: (1)...(269)
<223> OTHER INFORMATION: unsure at all n locations

<400> SEQUENCE: 63
gtgtggtacg agccgctgac caagtccgtg gaggacgagt acgcggcgca ccgggctcgg      60
atgttcaccc ttggctggtt cctgcacccc atcacctacg ccactaccc ggagacgatg     120 cagaagatcg tcatggggag gctgcccaac ttcaccttcg agcagtctgc catggtcaaa    180
ggctcagcgg actacgtcgc catcaaccac tacaccacgt actacgccag caacttcgtc    240
aacgccacag agaccactta ccgcaangt                                      269

<210> SEQ ID NO 64
<211> LENGTH: 207
<212> TYPE: DNA
<213> ORGANISM: Zea mays

<400> SEQUENCE: 64
gccccaggat cctgggtgat ttcacagctt tcgccgactt ctgcttcaag acgtacggcg     60
accgggtgaa gaactggttc accatcaacg agccgaggat gatggcccag catggctacg    120
gcgacggctt cttccccccc gccagatgca ccggctgcca gttcggcggc aactccgcca    180
ccgagccgta catcgccggc caccacc                                        207

<210> SEQ ID NO 65
<211> LENGTH: 290
<212> TYPE: DNA
<213> ORGANISM: Zea mays
<220> FEATURE:
<221> NAME/KEY: unsure
<222> LOCATION: (1)...(290)
<223> OTHER INFORMATION: unsure at all n locations

<400> SEQUENCE: 65
ccaacttcac cttcgagcag tctgccatgg tcaaaggctc agcggactac gtcncccata     60
caaccactac accacgtact acgccagcaa cttcgtcaac gccacagaga ccaactaccg    120
caacgattgg aatgcaaaga tttcgtatga gcgagatgng tgtgcccatt ggcaaaaggg    180
cgtactcgga ctggctttac gtcgntccat gggggctcta caaggctctg atttggacca    240
aggngaattc aacagccctg tgatgctcat cggagagaac ggattgaccc                290

<210> SEQ ID NO 66
<211> LENGTH: 288
<212> TYPE: DNA
<213> ORGANISM: Zea mays
<220> FEATURE:
<221> NAME/KEY: unsure
<222> LOCATION: (1)...(288)
<223> OTHER INFORMATION: unsure at all n locations

<400> SEQUENCE: 66
acagcttctc ttttcattct acacaattta tttatncnga tactccctcc gtctcaaaat     60
ataattcatt ttagactaaa catatattca ttagttaacc tatgaatata gtttgtatgt    120
atatctacat tcattatcaa ttattcgaat gtggacggag aactatattt tgggacggag    180
ggagtactac ttggctttat ctgataccat tntttatttt gctttctaca caatttacgn    240
cagggcanct catacaatta ttcagatntt naactggagt tcagtcat                 288

<210> SEQ ID NO 67
<211> LENGTH: 294
```

```
<212> TYPE: DNA
<213> ORGANISM: Zea mays
<220> FEATURE:
<221> NAME/KEY: unsure
<222> LOCATION: (1)...(294)
<223> OTHER INFORMATION: unsure at all n locations

<400> SEQUENCE: 67
cgccgagcng cacactccag cgtcgagcnc tacgtcgtca cccacaactg catcctggcg        60
cacgctgccg tncgccgncn tctacancng cagctaancg tgccgaacag cagggcgtng       120
tcggnatcaa natctacacc ttctggaact accccttctc cntgcgtncc gcngaagtcc       180
aggccacgca gngttcgntn nattcatgat cggntggatg gtnaaccgt tngngnangg        240 tgatanccte aagtgatgaa gagganagtc gggtcngttt cccaggttna ctaa            294

<210> SEQ ID NO 68
<211> LENGTH: 289
<212> TYPE: DNA
<213> ORGANISM: Zea mays
<220> FEATURE:
<221> NAME/KEY: unsure
<222> LOCATION: (1)...(289)
<223> OTHER INFORMATION: unsure at all n locations

<400> SEQUENCE: 68
gatggccaag cacggcgggc ggggccccag catctgggac gccttcatag aggttcccgg        60
gaccatccct aacaatgcca ccgctgacgt gacggtcgac gagtatcatc ggtacaagga      120
agatgtgaac ataatgaaga acatgggctt tgtgcgtacc gattttcgat ctcttggtcg      180
aggattttcc nagatggganc tggcaaggta aaccagnang gagtggatta ctacaacagg     240
ctcanagntt annncncaaa aaannnanng ncngnaaaaa attctctnt                  289

<210> SEQ ID NO 69
<211> LENGTH: 289
<212> TYPE: DNA
<213> ORGANISM: Zea mays
<220> FEATURE:
<221> NAME/KEY: unsure
<222> LOCATION: (1)...(289)
<223> OTHER INFORMATION: unsure at all n locations

<400> SEQUENCE: 69
catcggtaca angnccatgt ncttcattnt gttcacatct tccttgtacc gatgatactc       60
gtcgaccgtc acgtcagcgg tggcattgtt acaaggaaga tgtgaacata atgaagaaca     120
tgggctttga tgcgtaccga ttttcgatct cttggtcgag gattttccca gatggaactg     180
gcaaggtaaa ccaggaagga gncgattact acaacaggct tcatagatta catgctccag     240
caaggtatcg cgccgtatgc aaatctctac cattatgacc tcccattgg                289

<210> SEQ ID NO 70
<211> LENGTH: 278
<212> TYPE: DNA
<213> ORGANISM: Zea mays
<220> FEATURE:
<221> NAME/KEY: unsure
<222> LOCATION: (1)...(278)
<223> OTHER INFORMATION: unsure at all n locations

<400> SEQUENCE: 70
ttcagcttag ctagcaangg ggnggatcat ggcnacgctt gtcgctnctg ccatgaagca        60
acgctgnann ccatnctgtg cnttaggagg cncctagtag ganccaacaa taagagtttc      120
```

```
tcanggcacc acctnnncgt cttcttctnn atagancagc aagcgcaggt gtaagcttag    180
gtttactana cgatctggna gagtaggcag ctcaanatgg agtccaaatg ttngnnaccc    240
tcggaaatnn cacaaaggga ntggttcccc tctgattc                            278
```

<210> SEQ ID NO 71
<211> LENGTH: 296
<212> TYPE: DNA
<213> ORGANISM: Zea mays
<220> FEATURE:
<221> NAME/KEY: unsure
<222> LOCATION: (1)...(296)
<223> OTHER INFORMATION: unsure at all n locations

<400> SEQUENCE: 71

```
gtggaggctt gggtacactt cgcggtttgg cttggtgtac gtggactaca agactctgaa     60
gncgtacccc aaggattcag ctttctggtt caagcatatg ctgtccaaga aaaggagcta    120
gagaattgca gacaagagga ccactggctt cacgtgtcat acaaaagttc actctgcaaa    180
tcctcttagt atgtcagatt tagcttaagg aaccgtgcag acaattgagt ctcaaggctc    240
gacatctcta gcttcgttaa ntgttgcaag gcaataaatt ggtatcttcg aaaaaa       296
```

<210> SEQ ID NO 72
<211> LENGTH: 301
<212> TYPE: DNA
<213> ORGANISM: Zea mays
<220> FEATURE:
<221> NAME/KEY: unsure
<222> LOCATION: (1)...(301)
<223> OTHER INFORMATION: unsure at all n locations

<400> SEQUENCE: 72

```
gcaccatctc atcctttctn angnngctgn ngtnaggacg ataccgcnac aagtatcann     60
ttgaccagaa ggggaagatt ggaattctnc tggatttcgt gtggnacgaa cctttnagcg    120
acagcaatnn ggnncaggct ggagnacanc gagccngacg acnttcacct aggctggttt    180
ccttganncc attgtacatg gncggtancg tactcgatgc aagagatgag aaagacagct    240
accgttgttc agcgatgaag aagccaggat gntgaaaggc tctatagact atgttggcat    300
c                                                                     301
```

<210> SEQ ID NO 73
<211> LENGTH: 277
<212> TYPE: DNA
<213> ORGANISM: Zea mays

<400> SEQUENCE: 73

```
ccctaacaat gccaccgctg acgtgacggt cgacgagtat catcggtaca aggaagatgt     60
gaacataatg aagaacatgg gctttgatgc gtaccgattt tcgatctctt ggtcgaggat    120
tttcccagat ggaactggca aggtaaacca ggaaggagtg gattactaca acaggctcat    180
agattacatg ctccagcaag gtatcgcgcc gtatgcaaat ctctaccata tgactcccat    240
ggcactccat gaacagtact gggctggctt agcccaa                              277
```

<210> SEQ ID NO 74
<211> LENGTH: 277
<212> TYPE: DNA
<213> ORGANISM: Zea mays
<220> FEATURE:
<221> NAME/KEY: unsure
<222> LOCATION: (1)...(277)
<223> OTHER INFORMATION: unsure at all n locations

<400> SEQUENCE: 74

```
acaatgctag agtccatnta tctaggtttt atgctggtga aaaacttttg aagtaaaaga      60
nagtctgtta gacttgtact tggtccnttt gtcatgcaac attttcagga agatgtcgac     120
ctcatgaaaa gtttgaattt tgatgcctac cggtttctna tctcatggtc caggatcttc     180
ccagatggcg agggaagagt caatccagaa ggtgttgcct attacaacaa tctgataaac     240
tacctgcttc ggaaaggcat tacaccgtac gccaatc                              277
```

<210> SEQ ID NO 75
<211> LENGTH: 311
<212> TYPE: DNA
<213> ORGANISM: Zea mays

<400> SEQUENCE: 75

```
attagcttgg ctagatgagt cactatgaca atgaccgggt ccagtgatgt gctggtctaa      60
tcgggatcgt ccggcaagaa aagaaatgaa atcaggtgca ttgaacctga gcttgtcata     120
tacccaccac atctcaaaat ataaacatat attcatcatc catctacgat gcaattgtat     180
gaacgttata ttagtgggtg ttgttggata tattaccatt agagtagtcc aagtgtggtt     240
atatatcggg tagttatatc ccaacaacac cccttatatc atcatctata ggcggaaaaa     300
gcacaacatt t                                                          311
```

<210> SEQ ID NO 76
<211> LENGTH: 337
<212> TYPE: DNA
<213> ORGANISM: Zea mays
<220> FEATURE:
<221> NAME/KEY: unsure
<222> LOCATION: (1)...(337)
<223> OTHER INFORMATION: unsure at all n locations

<400> SEQUENCE: 76

```
gactggttcg ccgtgcntca nngnacgtgt atggcattgt cnacgtcgac cgcaanaata      60
antgcacgcg ctaacatgaa ggaatctgcn caagtngttg aaacngttca ncgccgcgac     120
agaagnccag cangangntn cttncgccan cttagaaatc ggggnccnca tgatgtggnn     180
gcagcccata aacaactggt gtgtngttcg aancgaaaat tntctannnt tnnccgccag     240
agaagttnag aggnatactc tccagcacgt ggctaataag cattgtgcca attcatctgg     300
ccttgtcagc ntgcataata ngtgctggtt tcctgtt                              337
```

<210> SEQ ID NO 77
<211> LENGTH: 341
<212> TYPE: DNA
<213> ORGANISM: Zea mays
<220> FEATURE:
<221> NAME/KEY: unsure
<222> LOCATION: (1)...(341)
<223> OTHER INFORMATION: unsure at all n locations

<400> SEQUENCE: 77

```
cggggcgnga gccggaggtg ancngcgccg acttccccga cggcttcgtc ttcggcgtng      60
ctacctantg cgtaccagnt tgaaggagcg agaaggncag ggaggcaaag gagacagcat     120
atgggatgta tttacagatg acaaagaaca tgtnttagac agaagcaatg gagaaattgc     180
anctgatcac taccatcgat acaaggaaga cattgagctc aggcaagtct aggttttagc     240
gcatacagat tttctatatc ttgggcgcgt atatttcctg atggctgggn cnnaatgtca     300
```
tgatcaagga gtcgccttct ataatgacct catcattann g          341

<210> SEQ ID NO 78
<211> LENGTH: 328
<212> TYPE: DNA
<213> ORGANISM: Zea mays
<220> FEATURE:
<221> NAME/KEY: unsure
<222> LOCATION: (1)...(328)
<223> OTHER INFORMATION: unsure at all n locations

<400> SEQUENCE: 78
gacttggcag actccttcat gtagcgcgtg cagttattgt tgcggtcgac gtagacaatg     60
ccataacgtt cggtgaagcc ggcgaactgt tgcttgaggc cattccgcga ancacaactc   120
ttacaatatg catgcgccgg ccgacgacga cgcgcgctgc ctctcgtgag cttctgttca   180
agtgatgcat gtttcaaggc atccatggat gctttacgta tatgcgtatt aattagccgt   240
gtcagggaac cggacagaag ggggtgttgt tttatattta cgtcttctgg tgatcaaata   300
aaggggaata tatgttggat gtgtnaat                                       328

<210> SEQ ID NO 79
<211> LENGTH: 327
<212> TYPE: DNA
<213> ORGANISM: Zea mays
<220> FEATURE:
<221> NAME/KEY: unsure
<222> LOCATION: (1)...(327)
<223> OTHER INFORMATION: unsure at all n locations

<400> SEQUENCE: 79
gccaagcacg gcgggcgggg ccccagcatc tgggacgcct tcatagaggt tcccgggacc     60
atccctaaca atgccaccgc tgacgtgacg gtcgacgagt atcatcggta caaggaagat   120
gtgaacataa tgaagaacat gggctttgat gcgtaccggt ttcgatcntt ggnnaggatt   180
tcccagatgg actggcaagg tgaacccagg aaggagtgga tataccaacc aggtcataga   240
tacatgctcc cagcaagtat ccgcgcgtat gncaaannct acattatgac tccattgcnn   300
catgacatac tgggtgntta ccaagat                                       327

<210> SEQ ID NO 80
<211> LENGTH: 295
<212> TYPE: DNA
<213> ORGANISM: Zea mays
<220> FEATURE:
<221> NAME/KEY: unsure
<222> LOCATION: (1)...(295)
<223> OTHER INFORMATION: unsure at all n locations

<400> SEQUENCE: 80
aaatatatat cgaagaactt ttaacgactt ttagtagntt ccaccaaacg atntttagct     60
ttgnaacggc tcacagccta cagcagctng tnttcatagc tcataacaac tttnttcaca   120
gaccaaacag acccatagat ttgtncgtca catcacgttc gtgtatggct ggccctggcg   180
tttcatgacc gctcgtttcc tccgccagcg cagtagcgcc gctannnnnn nnnnnnnnnn   240
nnncgtgctg gctcgccact gccagtttcg caccatgttg ttgtacttnt atccg          295

<210> SEQ ID NO 81
<211> LENGTH: 274
<212> TYPE: DNA
<213> ORGANISM: Zea mays
<220> FEATURE:
<221> NAME/KEY: unsure

```
<222> LOCATION: (1)...(274)
<223> OTHER INFORMATION: unsure at all n locations

<400> SEQUENCE: 81
cgcntattgc cacgtcaaga nacgaatggn cctgacggga atcccattgg tccttggntg      60
ggcaatccga ggnnctacct atatcctgaa ggcctaaagg atctgcttat gatcntgaag     120
aacaaatncg gaaacccacc catctacatc actgagaacg ggatgggtga cgntgaccat     180
ggngatctac ccatggaagn tgcttggatg accacanaag agtacattac cttcagcgca     240
catcgcaact cttaaggagc aagagacttg ngag                                 274

<210> SEQ ID NO 82
<211> LENGTH: 249
<212> TYPE: DNA
<213> ORGANISM: Zea mays

<400> SEQUENCE: 82
cgcgggtggt ggccgcccta gggtacgacg acggcaggtt cgcgccgggg aggtgcacgg      60
ggtgcgaggc cggggggggac tcgggcaccg agccctacgt cgtggcgcac cacctcatcc    120
tctcccacgc cgccgccgtc cagaggtacc gccgcaggca ccagccgacg cagaggggca    180
gggtcgggat cctgctggat tcgtgtggt acgagcccct cacggcggac tcagccgccg     240
accgggccg                                                             249

<210> SEQ ID NO 83
<211> LENGTH: 287
<212> TYPE: DNA
<213> ORGANISM: Zea mays
<220> FEATURE:
<221> NAME/KEY: unsure
<222> LOCATION: (1)...(287)
<223> OTHER INFORMATION: unsure at all n locations

<400> SEQUENCE: 83
ctttcggaga aagggtaaa aaactggttn accttcaaca agccgaggtg cgtccctngc      60
tctgggctac aacaatggct tgcacgcacc ggnaaggtgt cccgggtgcc cgccggang    120 caactcnacn acggagcctt accttgtcgc acaacatcct caacccttc tcatgcaacc    180 tgctgtcaag gcnataccgc cnacaagtta tcancttcac caagaaaggg gaaaaattgg   240
aaattcncct ggaatttcgt ngtgggtaca aaacctttca anccaaa                  287

<210> SEQ ID NO 84
<211> LENGTH: 394
<212> TYPE: DNA
<213> ORGANISM: Zea mays

<400> SEQUENCE: 84
ggaaaaaagg aacgggaaga gagggtctgt ttggttgaga ggtagatgtg aaaaaagttg     60
tttgtgaatt gtaaactgtg gaaaaagttg ttgtgggctg tgagctgtta aaaaactaca   120
aaatgtttgg tggaaactac taaaagtcgt taaaagttct tcgatatatg ttttcacagt   180
tccatctaaa agcaggtaca taggtgcttt gaggtcaaag tgggttgagt cggggggcgac 240 gccgttctct caattttttg ggatcacgcc tccaccaaaa actactccgg gttttacctc   300
gtccctacgt gaatctcatc caaacactat tggaattgtg gccgccctat tccatcccct   360
ccaatataca tccaaccaaa acattaatgt tgtc                                394

<210> SEQ ID NO 85
```

<211> LENGTH: 436
<212> TYPE: DNA
<213> ORGANISM: Zea mays

<400> SEQUENCE: 85

| | | | | | |
|---|---|---|---|---|---|
| agaaactaaa | gcttcagaag | ggtaggcgtt | catatcacat | agagaatata | tgcaatcctt | 60 |
| gacgtagaat | gtttggtagt | gatttacccc | gatgaagtca | atttggttct | tcaatagttt | 120 |
| cttctctcct | tctgtaaatt | ttggcaaatt | tggacctaag | atttggcgca | tctggtgagg | 180 |
| atagtcacca | aagaaaaagg | gatccaagat | cctgttttag | catatatcat | caagtgagca | 240 |
| ttcaatcgtg | aagaccaaaa | gttagttcca | atcgtaaaag | ttagcatata | tgatggaagg | 300 |
| ttactgaatc | aattgatacc | atggagcatc | gaaagacaga | gctcggctta | ctgccaagtg | 360 |
| gtcctccgtg | ataatcctga | atgggtcaaa | acaacctaag | ttgtaatgaa | attcctacaa | 420 |
| aagccacctt | gcttgg | | | | | 436 |

<210> SEQ ID NO 86
<211> LENGTH: 414
<212> TYPE: DNA
<213> ORGANISM: Zea mays
<220> FEATURE:
<221> NAME/KEY: unsure
<222> LOCATION: (1)...(414)
<223> OTHER INFORMATION: unsure at all n locations

<400> SEQUENCE: 86

| | | | | | |
|---|---|---|---|---|---|
| tgntgcacag | cggaggcttg | actttcaact | tggatggnac | ctatatccan | tanatnttgg | 60 |
| tgattaccca | gaaagcatgc | gtcaacgact | gggcattgat | nttccaacct | tctcaganaa | 120 |
| ngataaagag | ttcatgagga | ncacaattga | ttttgttgga | gtanatcatt | atacttcaag | 180 |
| antcattgct | catctccana | atccanncga | tgtntatttc | taccangtgc | aacaaatgga | 240 |
| gcgaatataa | taatgganta | ttggtnaaaa | aattggtgaa | agggcngcat | ctgaatggct | 300 |
| tttcananttt | ccttggggcc | ttcataagtc | acttanttan | atancgaata | agtacantan | 360 |
| tccagcaatt | tatgttactg | aanantggca | tggatgaaga | agacatcaat | ccgc | 414 |

<210> SEQ ID NO 87
<211> LENGTH: 367
<212> TYPE: DNA
<213> ORGANISM: Zea mays
<220> FEATURE:
<221> NAME/KEY: unsure
<222> LOCATION: (1)...(367)
<223> OTHER INFORMATION: unsure at all n locations

<400> SEQUENCE: 87

| | | | | | |
|---|---|---|---|---|---|
| ctcantgntc | aaaacnagtt | gagnagcaat | atttgttana | tgtggagagg | caattngana | 60 |
| gggggngga | tgnttaaaan | ggtgggaagg | cnaacggtct | tgttaacat | gcaataaatg | 120 |
| tanaaggagc | tgtacaccta | naggtncgan | tacatatttc | caatanncaa | ctgtagaatt | 180 |
| tatattatna | angtcttana | attactncac | ataanatnnt | attatnncan | ncttatgntg | 240 |
| atgatntttta | caacaancat | tacaattnt | acnacacttg | tatagggctt | gcgtttnact | 300 |
| ttatnnatca | tgtgccatac | ngaacatttt | ttatgnataa | anntgncnat | taaaantact | 360 |
| gntacat | | | | | | 367 |

<210> SEQ ID NO 88
<211> LENGTH: 335
<212> TYPE: DNA
<213> ORGANISM: Zea mays

```
<220> FEATURE:
<221> NAME/KEY: unsure
<222> LOCATION: (1)...(335)
<223> OTHER INFORMATION: unsure at all n locations

<400> SEQUENCE: 88
cataaggata atgacggant ctncnnngac ttnanctggn actatgatct tacncacnna      60
nggngnggnc caatncatgn acgnnggaga gccnntnact ttcacattna ctgngnagtt     120
natccattga taaacggaca ctatccacag atnatgcaag atctcaatga acgacaatnt     180
gcccacattc actcctganc atnctaaact ggtanaacgt ctccctagac tacatatgct     240
atcaacgant acacatccac ctacatcaat nntcaaaatc tgtgatcacc tgactcccan     300
taactactcn nncnattgac acnatcacta tactg                                335

<210> SEQ ID NO 89
<211> LENGTH: 375
<212> TYPE: DNA
<213> ORGANISM: Zea mays
<220> FEATURE:
<221> NAME/KEY: unsure
<222> LOCATION: (1)...(375)
<223> OTHER INFORMATION: unsure at all n locations

<400> SEQUENCE: 89
tagcacgtcg acttctcaga agactactca cctaagctca acgccgacga cgcctatgcc      60
actgcagaaa tctttggacc tgacgggaat tctattggtc ctcctatggg gaaatccatg     120
gatctacatg taccctaaag gcctaaagga tctccntatg atcnnggaag accaaatccn     180
gaaacccnct anctatatcc ngagaccgga anccgggacc tttgcccca aagganaatc     240 cncgatccat gcaananncc ntngnannga ctnccnagna ggcttggatt accctccncn     300 ccccatntn aannnntnna annatncagt tnancctggg ggccngaccn nncccngcn      360 cttnacangg ncctt                                                       375

<210> SEQ ID NO 90
<211> LENGTH: 406
<212> TYPE: DNA
<213> ORGANISM: Zea mays
<220> FEATURE:
<221> NAME/KEY: unsure
<222> LOCATION: (1)...(406)
<223> OTHER INFORMATION: unsure at all n locations

<400> SEQUENCE: 90
ctgagtaacg ccgatgtcgc ggtcgatcag taccaccggt tcgaggagga tatacaggtc      60
atggcggaca tggggatgga cgcgtaccgc ttttcgattg cctggtcgag gattctgccc     120
aatggtaccg gccaagtcaa ccaggccggc gtcgaccant acaacaggtt natcgatgca     180
ctgntatcga aagggattga gccatacntg accntgtacc antggnacnt ccccnaggcc     240
ntgaaanaca ggtncaacgg atggntggac aggcaaatag ngtacaantt ccnagtacnc     300
cnagacatgc ttttaggnct tttgaganac gcgtgagang ctntgtnaca ccttnaaaag     360
agccacacan ggtccctgca cagggataaa accccgntct annaaa                    406

<210> SEQ ID NO 91
<211> LENGTH: 418
<212> TYPE: DNA
<213> ORGANISM: Zea mays
<220> FEATURE:
<221> NAME/KEY: unsure
<222> LOCATION: (1)...(418)
```

<223> OTHER INFORMATION: unsure at all n locations

<400> SEQUENCE: 91

```
actggctctg aacaataagc cctgaatcat ggtctcattc ctacaacagg tcccgcatcg      60
atgcaacatg tcctgattct taaaaggaac atgttgtcat ccacacaact acaaatccgt     120
actatgaaaa tacatttcta attagaccga ggaaaccatg aagatggatg gaagcagaac     180
acccaaggag accaaaaggg agaccagcaa ggcaggtccg ttcgaggtgg ctgaagccga     240
accagccggc cggccgcctg aaccagtctg cggggtagca gccttggagc ccgtccccga     300
aagcatgtct ctgaaccagt acgccgagtc cttggggtac cgcttcagcg tcgcgaagtc     360
gacgtagacg atgccgaact tggacgtgta gcccgacagc cactngaagt tgttcagg      418
```

<210> SEQ ID NO 92
<211> LENGTH: 426
<212> TYPE: DNA
<213> ORGANISM: Zea mays
<220> FEATURE:
<221> NAME/KEY: unsure
<222> LOCATION: (1)...(426)
<223> OTHER INFORMATION: unsure at all n locations

<400> SEQUENCE: 92

```
cggacnnttg ggtttctctt ggcacatgct actgcngttg caagataccg tacgaaatat      60
cagggtctat atatgcttgg aagttggaac aatggctgct cagaagggta aggtcgnaat     120
agtcctggac ttcaactggt acgaggctct tacaaactca cctgatgacn aagcatcatc     180
ccaaagagcc agggacttcn acattngntg gnntgntgat ccattgataa acggacncta     240
ttnacagata atgcannatc tcgtgnagga gatgctgnct aggttcactn atnaacntgc     300
taaactgntg aatnctcggn gactacatct tntcaacgag gacncatcta tntacantaa     360
ngggcagaat cttgtcaact ggnncccaat anctctttcn nattgnnnag ttcaatatgt     420
tttgga                                                                426
```

<210> SEQ ID NO 93
<211> LENGTH: 500
<212> TYPE: DNA
<213> ORGANISM: Zea mays
<220> FEATURE:
<221> NAME/KEY: unsure
<222> LOCATION: (1)...(500)
<223> OTHER INFORMATION: unsure at all n locations

<400> SEQUENCE: 93

```
cgaaggnaca gtcccttggt tggaactttg ggctgattat gtgcttgtgg ntgtgcgggt      60
gggttcgatg ggaagtttac cggcttcttc acgggaaact tacggacnca tacgcatttc     120
gagggtccga aggactcttc cacgactacg aagaataaac atggaaattt attcactcat     180
actatggaga atggaactgg ggacgccgac attaaggaga tattctcatt tacggaggac     240
gttccaaacg atcataaaag gtcagaccat acttagtgtt atactgtcat ctccaaggaa     300
ctaacagatc cggactaaa cgcgtaaggt catcctgtcc ggctctcgtc ggataatccc      360
gaacggcctg ttggtcctat tgaatgccac ggtaccgctc atgctgattg taataacaat     420
cgtatgtgtc atacgaagga gctcgttaag cggccgaaat agcctaatgt tgtgaagaat     480
ttaataagaa gacctccatt                                                  500
```

<210> SEQ ID NO 94
<211> LENGTH: 501

```
<212> TYPE: DNA
<213> ORGANISM: Zea mays
<220> FEATURE:
<221> NAME/KEY: unsure
<222> LOCATION: (1)...(501)
<223> OTHER INFORMATION: unsure at all n locations

<400> SEQUENCE: 94 aaggggggggg aggaaagccc ntggtnggac ctttgggctg nttatgtgct tgttatgtgc    60
ttgttatgtg cttgnatttg cacagggtcc gtgcccgatg caacgggctg cgcgttacat   120
ggaatactgc cctcggacaa ataggttgaa gaaaggcttc gggatactaa ttcaggacgg   180
cctccagagt tagcggcctg cggcgatcat tttcctctta cgagactacc ggtcagggaa   240
tgatcatttc ctcctaagga tgagtagaag gagaagtctg ttggccttca caatacgccg   300
gggccaaatc atcatattct atggcctctt aaaaatactg acactcnatt aaatcntcta   360
ttcgcgtcta atatcgatga tgttcatgtt agctaagaag ccaatgggtt cgatgggaaa   420
tttaccggct tcctcacggg aaacntacgg actctacgct ttcgaaggtc ccgaaggatc   480
ttcacgatac gaaagaataa a                                             501

<210> SEQ ID NO 95
<211> LENGTH: 464
<212> TYPE: DNA
<213> ORGANISM: Zea mays
<220> FEATURE:
<221> NAME/KEY: unsure
<222> LOCATION: (1)...(464)
<223> OTHER INFORMATION: unsure at all n locations

<400> SEQUENCE: 95
cgtaatctgg tncgaacnaa tgacaaacat tttcgattga cattgaaagc taccaanaag    60
ggngcacgag ttcagctagg atgggntcgc ggacccgttc ttcttcggag actacccngc   120
gacgatncgg gctngggttg gagagaggct gnccaagntc accgnagacn angctgccct   180
tgtcaagggg gccctggact tcatgggcat aaaccactac accactttct acacgaggca   240
taactgacac caacatcatc ggacggctgc tgaacnacac tttggcggac accgaaacca   300
tcancctgcc cttcgacaaa aacggngaag cccattggag atcgggctaa ttcgatatgg   360
ctgtacatcg tacccagcgg gatcaggaag ctgatgaact atgtcaagga gcggggccaa   420
tacccaacgg tttacatnac tgaaaatggg atgggccact gcnc                    464

<210> SEQ ID NO 96
<211> LENGTH: 447
<212> TYPE: DNA
<213> ORGANISM: Zea mays
<220> FEATURE:
<221> NAME/KEY: unsure
<222> LOCATION: (1)...(447)
<223> OTHER INFORMATION: unsure at all n locations

<400> SEQUENCE: 96
ctcaagcact agaanagaag tacttnttta ttcttanata agactcataa caagngnggn    60
aattattaca aaaactngng gtaacgtgtn cttcgacaac tttggtgaca aggtgaagaa   120
ttggttgacc tttaatgagc ccnatacatt tacttcattt tcctatggaa ccntnntctc   180
tgccccanga cgatgctcac cnntactaga ctgagccatc ccaactggat aattcactcn   240
tctnaacctt acattnctgn ccacaacatt cttctagccc annctnaggc tgttnatctt   300
tacaacaagt attacaaggn cnaagaacgg ccncataggt cttgcatttg atgtantnan   360
```

```
tcntttnnna tantcaacat tatttctaga ttaactttt naantangnt tcatnnacat      420
tacttaatta tanttnttt atcctt                                          447

<210> SEQ ID NO 97
<211> LENGTH: 289
<212> TYPE: DNA
<213> ORGANISM: Zea mays
<220> FEATURE:
<221> NAME/KEY: unsure
<222> LOCATION: (1)...(289)
<223> OTHER INFORMATION: unsure at all n locations

<400> SEQUENCE: 97
cgatccgtca tggcgactgc tgcgccattg ttnntntccc acgtctcct cctccnccct      60 ctccctggcg ctcggcgccc atggcgtgaa cgtgaagccc gggagcacc acatcctcaa     120 caggcagagc ttcccccgg ggttcgtctt cggcacggcg tcgtcggcgt accaggtgga    180
ggggaacacn cacaggtacg ggcgcgggcc ctgcatctgg dcaccttcc tcaagtatcc     240 aggcactact cctgataacg cgaccgcgga cgtgacagtc gacgagtac              289

<210> SEQ ID NO 98
<211> LENGTH: 211
<212> TYPE: DNA
<213> ORGANISM: Zea mays
<220> FEATURE:
<221> NAME/KEY: unsure
<222> LOCATION: (1)...(211)
<223> OTHER INFORMATION: unsure at all n locations

<400> SEQUENCE: 98
ggcgctcggn gcccatggcg tgaacgtgaa gcccggggan caccacatcc tcaacaggca     60
gagcttcccc ccggggttcg tctttggnac ggcgtcgtcg gcgtaccagg tggaggggaa   120
cacgcacagg tacgggcgcg ggccctgcat ctgggacacc ttcctcaagt atccaggcac   180
tactcctgat aacgcgaccg cggacgtgac a                                  211

<210> SEQ ID NO 99
<211> LENGTH: 435
<212> TYPE: DNA
<213> ORGANISM: Zea mays
<220> FEATURE:
<221> NAME/KEY: unsure
<222> LOCATION: (1)...(435)
<223> OTHER INFORMATION: unsure at all n locations

<400> SEQUENCE: 99
ccgagctact cgtccgactg gggcgtccaa tattactttc aaaggaatgg cgtgcaaatg     60
ggncngatgg cgcactcaat ntggctttac atcgtcccat cgggcatgta tggagtcgtg   120
aactacctaa aggaaaagta ccataatcca atcatcatca tatcggaaaa cggaatggat   180
cagcctggaa acctcacgcg cgaggagtac gtgcacgacg ccgtgaggat cgacttctac   240
aagaactacc tgacggagct aaagagaggg atcgacggcg cgcgaacgt gatcggctac   300 ttcgcgtggt ctntcctgga caacttcnag tggctgtcgg ctacacgtcc aagttcggca   360
tcgtctacgt cgacttcgcg acgctgaanc ggtaccccaa ggactcggng tactggttca   420
aaacatgctt tcggg                                                    435

<210> SEQ ID NO 100
<211> LENGTH: 314
<212> TYPE: DNA
<213> ORGANISM: Zea mays
```

```
<220> FEATURE:
<221> NAME/KEY: unsure
<222> LOCATION: (1)...(314)
<223> OTHER INFORMATION: unsure at all n locations

<400> SEQUENCE: 100
gttcgtgaaa ctacctaaag gaaaagtacc ataatccaat catcatcata tcgganaacg      60
gaatggatca gcctggaaac ctcacgcgcg aggagtacgt gcacgacgcc gtgaggatcg     120
atttctacaa gaactacctg acggagctaa agacagggat cgacggcggc gcgaacgtga     180
tcggctactt cgcgtggtct ctcctggaca acttcgagtg gctgtcgggc tacacgtcca     240
agttcggcat cgtctacgtc gattcgcgac gctcaacggt accccaagga tcggcgtact     300
ggttcagaga catg                                                       314

<210> SEQ ID NO 101
<211> LENGTH: 277
<212> TYPE: DNA
<213> ORGANISM: Zea mays

<400> SEQUENCE: 101
ggatcagcct ggaaacctca cgcgcgagga gtacgtgcac gacgccgtga ggatcgactt      60
ctacaagaac tacctgacgg agctaaagag agggatcgac ggcggcgcga acgtgatcgg     120
ctacttcgcg tggtctctcc tggacaactt cgagtggctg tcgggctaca cgtccaagtt     180
cggcatcgtc tacgtcgact cgcgacgct gaagcggtac cccaaggact cggcgtactg     240
gttcagagac atgctttcgg ggacgggctc caaggct                              277

<210> SEQ ID NO 102
<211> LENGTH: 255
<212> TYPE: DNA
<213> ORGANISM: Zea mays

<400> SEQUENCE: 102
gtaccataat ccaatcatca tcatatcgga aaacggaatg gatcagcctg gaaacctcac      60
gcgcgaggag tacgtgcacg acgccgtgag gatcgatttc tacaagaact acctgacgga     120
gctaaagaga gggatcgacg gcggcgcgaa cgtgatcggc tacttcgcgt ggtctctcct     180
ggacaacttc gagtggctgt cgggctacac gtccaagttc ggcatcgtct acgtcgactt     240
cgcgacgctc aagcg                                                      255

<210> SEQ ID NO 103
<211> LENGTH: 274
<212> TYPE: DNA
<213> ORGANISM: Zea mays
<220> FEATURE:
<221> NAME/KEY: unsure
<222> LOCATION: (1)...(274)
<223> OTHER INFORMATION: unsure at all n locations

<400> SEQUENCE: 103
gcgcactcaa tttggcttta catcgtccca tcgggcatgt atggagtcgt gaacnaccta      60
aaggaaaagt accataatcc aatcatcatc atatcggaaa acggaatgga tcagcctgga    120
aacctcacgc gcgaggagta cgtgcacgac gccgtganga tcgatttcta caagaactac    180
ctgacggagc taaagagagg gatcgacggc ggcgcgaacg tgatcggcta ttcgcgtggt    240
ctctctggac aattcgagtg gtgtcgggta cacg                                 274

<210> SEQ ID NO 104
```

```
<211> LENGTH: 216
<212> TYPE: DNA
<213> ORGANISM: Zea mays

<400> SEQUENCE: 104
tgcaaattgg acagatggcg cactcaattt ggctttacat cgtcccatcg ggcatgtatg      60
gagtcgtgaa ctacctaaag gaaaagtacc ataatccaat catcatcata tcggaaaacg     120
gaatggatca gcctggaaac ctcacgcgcg aggagtacgt gcacgacgcc gtgaggatcg     180
atttctacaa gaactacctg acggagctaa agagag                               216

<210> SEQ ID NO 105
<211> LENGTH: 274
<212> TYPE: DNA
<213> ORGANISM: Zea mays
<220> FEATURE:
<221> NAME/KEY: unsure
<222> LOCATION: (1)...(274)
<223> OTHER INFORMATION: unsure at all n locations

<400> SEQUENCE: 105
gatcaatcaa tatactacat actacattgc agatcaacaa actcctccgc nggggnacc       60 gagctactcg tccgactggg gcgtccaata ttactttcaa aggaatggcg tgcnaattgg     120
acagatggcg cactcaattt ggctttacat cgtcccatcg ggcatgtatg gagtcgtgaa     180
ctacctaaag gaaaagtacc ataatccaat catcatcatn tcggaanacg gaatggatca     240
gcctggaaac ctcacgcgcg aggagtacgt gcac                                 274

<210> SEQ ID NO 106
<211> LENGTH: 254
<212> TYPE: DNA
<213> ORGANISM: Zea mays
<220> FEATURE:
<221> NAME/KEY: unsure
<222> LOCATION: (1)...(254)
<223> OTHER INFORMATION: unsure at all n locations

<400> SEQUENCE: 106
gatcaatcaa tatactacat actacattgc agatcaacaa actcctccgc agggaccacc      60
gagctactcg tccgactggg gcgtccaata ttactttcaa aggaatggcg tgcaaatngg     120
acatatggng cacncaattt ggctttacat cgtcccatcg ggcatgtatg gagtcgtgaa     180
ctacctaaag gaaaagtacc ataatccaat catcatcana ncnggaaagg gtatggntcn     240
ccncntggaa acct                                                       254

<210> SEQ ID NO 107
<211> LENGTH: 189
<212> TYPE: DNA
<213> ORGANISM: Zea mays
<220> FEATURE:
<221> NAME/KEY: unsure
<222> LOCATION: (1)...(189)
<223> OTHER INFORMATION: unsure at all n locations

<400> SEQUENCE: 107
gggaccaccg agctacnacg tccgacncng gcgtccaat attactttca aaggaatggc       60
gtgcaaattg gacagatggc gcacttcaat ttggctttac atcgtcccat cgggcatgta    120
tggagtcgtg aacncaccta aggnaaagt accataatcc aatcatcatc atatcggaaa     180
acggaatgg                                                             189
```

```
<210> SEQ ID NO 108
<211> LENGTH: 353
<212> TYPE: DNA
<213> ORGANISM: Zea mays
<220> FEATURE:
<221> NAME/KEY: unsure
<222> LOCATION: (1)...(353)
<223> OTHER INFORMATION: unsure at all n locations

<400> SEQUENCE: 108
cggaaaccca cccatctaca tcactgagaa cgggatgggt gacgttgacc atggcgatct      60
acccatggaa gttgccttgg atgaccacaa aagagtacat tacctccagc gccacatcgc     120
aactcttaag gagtcaagag acttgggagc gaatgtgcag ggctacttcg cttggtctct     180
attgacaact tcgaatggtt ctccggctac acggaacgtt acggcatcgt ctatgttgac     240
cgcaacgatg gctgcaaacg ctacatgaag cggtcagcca agtggttcaa agagttcaat     300
gctgcgaaga aagcggctgc caagaagatt cttacgccag cttagaatcg ntg            353

<210> SEQ ID NO 109
<211> LENGTH: 326
<212> TYPE: DNA
<213> ORGANISM: Zea mays
<220> FEATURE:
<221> NAME/KEY: unsure
<222> LOCATION: (1)...(326)
<223> OTHER INFORMATION: unsure at all n locations

<400> SEQUENCE: 109
aacccaccca tctacatcac tgagaacggg atgggtgacg ttgaccatgg cgatctaccc      60
atggaagttg ccttggatga ccacaaaaga gtacattacc tccagcgnca catcgcaact    120
cttaaggagt caagagactt gggagcgaat gtgcagggct acttcgcttg gnctctattg    180
gacaacttcg aatggttctc cggctacacg gaacgttacg catcgtcta tgttgaccgc     240 aacgatggct gcaaacgcta catgaagcgg tcagccaagt ggttcaaaga gttcangctg    300
cgaagaaagc ggctgccaga agntct                                          326

<210> SEQ ID NO 110
<211> LENGTH: 256
<212> TYPE: DNA
<213> ORGANISM: Zea mays
<220> FEATURE:
<221> NAME/KEY: unsure
<222> LOCATION: (1)...(256)
<223> OTHER INFORMATION: unsure at all n locations

<400> SEQUENCE: 110
catgnatnct acctatatcc tgaaggccta aagganctgc ttatnancat gaagaacaaa      60
tacggaaacc cacccatcta catcactgag aacgggatgg gtgacgttga ccatggcgat    120
ctacccatgg aagttgcctt ggatgaccac aaaagagtac attacctcca gcgccacatc    180
gcaactctta aggagtcaag agacttggga gcgaatgtgc agggctactt cgcttggtct    240
ctattggaca acttcg                                                     256

<210> SEQ ID NO 111
<211> LENGTH: 278
<212> TYPE: DNA
<213> ORGANISM: Zea mays

<400> SEQUENCE: 111
atatggctcc actcgtcgct actgccacga tgaaccacgc tgtggcccat ctgctaggac      60
```

```
ccaatcatga gagtttctca cggcaccatc tttcttcctc gctgcagcaa aacagtaagc    120
gaaggtgtaa tcttagcttc aggccacgag ctgctgagag tcagaatgga agccaaacgc    180
tgagcccctc ggaagtccct aaaagagact ggttcccctc tgacttcatc tttggtgccg    240
ccacttcagc gtaccaaatt gaaggtggat ggaacgag                            278

<210> SEQ ID NO 112
<211> LENGTH: 274
<212> TYPE: DNA
<213> ORGANISM: Zea mays

<400> SEQUENCE: 112
atatggctcc actcgtcgct actgccacga tgaaccacgc tgtggcccat ctgctaggac    60
ccaatcatga gagtttctca cggcaccatc tttcttcctc gctgcagcaa aacagtaagc    120
gaaggtgtaa tcttagcttc aggccacgag ctgctgagag tcagaatgga agccaaacgc    180
tgagcccctc ggaagtccct aaaagagact ggttcccctc tgacttcatc tttggtgccg    240
ccacttcagc gtaccaaatt gaaggtggat ggaa                                274

<210> SEQ ID NO 113
<211> LENGTH: 232
<212> TYPE: DNA
<213> ORGANISM: Zea mays

<400> SEQUENCE: 113
atatggctcc actcgtcgct actgccacga tgaaccacgc tgtggcccat ctgctaggac    60
ccaatcatga gagtttctca cggcaccatc tttcttcctc gctgcagcaa aacagtaagc    120
gaaggtgtaa tcttagcttc aggccacgag ctgctgagag tcagaatgga agccaaacgc    180
tgagcccctc ggaagtccct aaaagagact ggttcccctc tgacttcatc tt            232

<210> SEQ ID NO 114
<211> LENGTH: 233
<212> TYPE: DNA
<213> ORGANISM: Zea mays

<400> SEQUENCE: 114
atatggctcc actcgtcgct actgccacga tgaaccacgc tgtggcccat ctgctaggac    60
ccaatcatga gagtttctca cggcaccatc tttcttcctc gctgcagcaa aacagtaagc    120
gaaggtgtaa tcttagcttc aggccacgag ctgctgagag tcagaatgga agccaaacgc    180 tgagggcct cggaagtccc taaaagagac tggttcccct ctgacttcat ctt             233

<210> SEQ ID NO 115
<211> LENGTH: 162
<212> TYPE: DNA
<213> ORGANISM: Zea mays
<220> FEATURE:
<221> NAME/KEY: unsure
<222> LOCATION: (1)...(162)
<223> OTHER INFORMATION: unsure at all n locations

<400> SEQUENCE: 115
gagagagaaa aaatatggct ccactcgtcg ctactgccac gatgaaccac gctgtggccc    60
atctgctagg acccaatcat gagagtttct cacggcacca tctttcttcc tcgctgcagc    120
aaaacagtaa gcgaaggtgt aatcttagct tcaggccang ng                       162

<210> SEQ ID NO 116
<211> LENGTH: 233
```

```
<212> TYPE: DNA
<213> ORGANISM: Zea mays
<220> FEATURE:
<221> NAME/KEY: unsure
<222> LOCATION: (1)...(233)
<223> OTHER INFORMATION: unsure at all n locations

<400> SEQUENCE: 116
taccaaggct ggttaggccc aaaaattgtg gacatatttg ctgactatgc tgatttttgt      60
ttcaagactt ttggcaatcg agtcaagaac tggttcacat taaatgagcc aaggatagta     120
gcattccttg gttatgataa agggcttaac ccccctaacc ggtgcacaca atgcactgcc     180
ggtgggaact catcgacaga accttacatt gttgttcata acattcncct atc             233

<210> SEQ ID NO 117
<211> LENGTH: 349
<212> TYPE: DNA
<213> ORGANISM: Zea mays
<220> FEATURE:
<221> NAME/KEY: unsure
<222> LOCATION: (1)...(349)
<223> OTHER INFORMATION: unsure at all n locations

<400> SEQUENCE: 117
ggaagatgtt gatctcatga gaagcctaaa tttngatgca taccggtttt caatctcctg      60
gtccaggatc ttcnccagat ggcgaaggga naattaatna cgaaggagta caatatnaca     120
acaatcttat agactacatg gttaagcaag gccttactcc ttacgccaac cttaaccact     180
atgatcttcc gcttgcgctt cagaagaagt accaaggctg gttaggccca aaaattgtgg     240
acatatttgc tgactatgct gattttgtt tcaagactt tggcatcgag tcaaganctg      300
gttcacatna attgagccaa ggatagtagc attccttggt tatgataac                  349

<210> SEQ ID NO 118
<211> LENGTH: 203
<212> TYPE: DNA
<213> ORGANISM: Zea mays

<400> SEQUENCE: 118
taaccactat gatcttccgc ttgcgcttca gaagaagtac caaggctggt taggcccaaa      60
aattgtggac atatttgctg actatgctga ttttgtttc aagactttg gcaatcgagt      120 caagaactgg ttcacattaa atgagccaag gatagtagca ttccttggtt atgataaagg     180 gcttaaccccc cctaaccggt gca                                              203

<210> SEQ ID NO 119
<211> LENGTH: 303
<212> TYPE: DNA
<213> ORGANISM: Zea mays
<220> FEATURE:
<221> NAME/KEY: unsure
<222> LOCATION: (1)...(303)
<223> OTHER INFORMATION: unsure at all n locations

<400> SEQUENCE: 119
gattactaca acaggctcat agattacatg ctccagcaag gtatcgcgcc gtatgcaaat      60
ctctaccatt atgacctccc attggcactc catgaacagt acctgggctg gcttagccca     120
aagattgtgg aggcgtttgc agactacgcc gagttctgcn tccacgcgtt cggagacagg     180
gtgaagaact ggtttacctt caacgagccg aggtgcgtcg ctgntctggg ctacgaacat     240
ggcttgcacg caccggggaag gtgttccggt gccccgccgg agcaactcca ccacggnanc    300
```

```
gta                                                                  303

<210> SEQ ID NO 120
<211> LENGTH: 220
<212> TYPE: DNA
<213> ORGANISM: Zea mays
<220> FEATURE:
<221> NAME/KEY: unsure
<222> LOCATION: (1)...(220)
<223> OTHER INFORMATION: unsure at all n locations

<400> SEQUENCE: 120
ggattactac aacaggctca tagattacat gctccagcaa ggtatcgcgc cgtatgcaaa      60
tctctaccat tatgacctcc cattggcact ccatgaacag tacctgggct ggcttagccc     120
aaagattgtg gaggcgtttg cagactacgc cgagttctgc ttcnacggtt cggagacagg     180
gtgaagaact ggtttacctt caacgagccg aggtgcgtcg                           220

<210> SEQ ID NO 121
<211> LENGTH: 355
<212> TYPE: DNA
<213> ORGANISM: Zea mays

<400> SEQUENCE: 121
gacggatcgg actcaccttg cttggttggt ggtacgagcc tgggacgcag actcccgacg      60
atgtcgcggc agccgcacgg atgaacgact ccacatcgg atggttcatg catcctatgg     120
tgttcgggga ctaccctccg gtgatgagga ggaacgtcgg gtccaggctg ccgaccttca     180
cggacgagga ggcggcgcga gtgaggggt ctttcgactt cgtcggattc aaccactaca     240
tcgtcgtcta cgtcaaggct gatcttggcc gcctagacga ccaagtgcga gactacatgg     300
gcgatgcagc cgtgaatatg accatgccgt tctcaatcag caacagttcc gttcg          355

<210> SEQ ID NO 122
<211> LENGTH: 282
<212> TYPE: DNA
<213> ORGANISM: Zea mays

<400> SEQUENCE: 122
caagttcggc atcgtctacg tggacttcaa cacgctcgaa cgccacccga aggcgtcggc      60
ctactggttc agggacatgc ttcagaagca ttgagatctc cagagccgag cctgagcacg     120
gaaggtacca ttttgttcag cttcgcctag tgtttgggat ggcccaatgg ttcaaatccg     180
gctcagtgcc tggctaccaa aatgggaaca aaggacagct accccgatca attgtgatgt     240
tgtgtgtttg tgggtatgtt ctctctggag tttgagctgt gg                        282

<210> SEQ ID NO 123
<211> LENGTH: 234
<212> TYPE: DNA
<213> ORGANISM: Zea mays
<220> FEATURE:
<221> NAME/KEY: unsure
<222> LOCATION: (1)...(234)
<223> OTHER INFORMATION: unsure at all n locations

<400> SEQUENCE: 123
ggacttcaac acgctcgaac gccacccgaa ggcgtcggcc tactggttca gggacatgct      60
tcagaagcat tgagatctcc aganccgagc ctgagcacgg aaggtaccat tttgttcagc     120
ttcgcctagt gtttgggatg gcccaatggt tcaaatccgg ctcagtgcct ggctaccaaa     180
atgggaacaa aggacagcta ccccgatcaa ttgtgatgtt gtgtgtttgt gggt           234
```

<210> SEQ ID NO 124
<211> LENGTH: 314
<212> TYPE: DNA
<213> ORGANISM: Zea mays

<400> SEQUENCE: 124

```
cactgggaca cgcctcaagc actggtagac aagtacggtg cttttttaga tcggaggatt    60
gtaaaagatt acacagattt cgctatggtg tgcttcgaga acttcggtga caaagtgaaa   120
aattggttga catttaacga gccccaaacg ttttcttctt tttcctatgg aatcgggttg   180
tgtgccccag ggcggtgctc cccaggacaa aaatgtgcta acccaattgg aaactcactt   240
atcgagccat acattgttgg tcacaacctt ctcctagccc atgctgaggc tgttgatctt   300
tacaacaagc atta                                                     314
```

<210> SEQ ID NO 125
<211> LENGTH: 261
<212> TYPE: DNA
<213> ORGANISM: Zea mays

<400> SEQUENCE: 125

```
attgtaaaag attacacaga cttcgctaag gtgtgctttg agaacttcgg tgataaagta    60
aacaattggt tgacctttaa tgagccccaa acgttttctt cttttcata cggaaccggg    120
ctatgcgccc cagggcggtg caccccagga caaaaatgtg ctaacccaat tggaaactcg   180
ctcactgagc catacactgt tggccataac ccttctccgag cccacgctga ggctgttgat   240
ctttacaaca gtattacaa g                                              261
```

<210> SEQ ID NO 126
<211> LENGTH: 222
<212> TYPE: DNA
<213> ORGANISM: Zea mays
<220> FEATURE:
<221> NAME/KEY: unsure
<222> LOCATION: (1)...(222)
<223> OTHER INFORMATION: unsure at all n locations

<400> SEQUENCE: 126

```
attggttgan ctttaatgag ccccaaacgt tttcttcttt ttcatacgga ancgggctat    60
gcgncccagg gcggtgcacc ccaggacaaa aatgtgctaa ccnaattgga aactngctca   120
ctgagccata cactgttggc cataaccttc nccgagccca cgctgaggct gttgatcttt   180
acaaaagtat tacangggtg agaatggann tanggctnnn tt                      222
```

<210> SEQ ID NO 127
<211> LENGTH: 382
<212> TYPE: DNA
<213> ORGANISM: Zea mays

<400> SEQUENCE: 127

```
gaggagagga gaggagagac tagacccgct agctgaggcc gggcggcgcg ctggacacga    60
acatgatggg gagaaaggcg ctcggctgtg ctcctcttct cctcctcttg gccgccgccg   120
tcgctccggc cgagctcagc gtcggggcgg cggctgcctc gggcgcggtc acccgggccg   180
acttccccgc ggggttcgtc ttcggcgtcg gctcctccgc gtaccaggtc gaaggtgcag   240
ttgcagagga cggaaggaag cctagcatct gggacacatt cacacatgaa ggctattccc   300
ttgacaacgc cacaggcgat gtaactgcgg atcaagtatc ataagtacaa ggacgacgta   360
```

```
aaagcttctg catgaagaaa tt                                             382
```

<210> SEQ ID NO 128
<211> LENGTH: 412
<212> TYPE: DNA
<213> ORGANISM: Zea mays
<220> FEATURE:
<221> NAME/KEY: unsure
<222> LOCATION: (1)...(412)
<223> OTHER INFORMATION: unsure at all n locations

<400> SEQUENCE: 128

```
ggagagacta gacccgctag ctgaggccgg gcggcgcgct ggacacgaac atgatgggga     60
gaaaggcgct cggctgtgct cctcttctcc tcctcttggc cgccgccgtc gctccggccg    120
agctcagcgt cggggcggcg gctgcctcgg gcgcggtcac ccgggccgac ttccccgcgg    180
ggttcgtctt cggcgtcggc tcctccgcgt accaggtcga aggtgcagtt gcagaggacg    240
gaaggaagcc tagcatctgg gacacattca cacatgaagg ctattccctt gacaacgcca    300
caggcgatgt aaactgcgga tcagtatcat aagtacaagg accaacgtaa aagctttctt    360
gcatgaagaa tgggtggtcg aatgccctac ccggatgtcg aattggnccc cc            412
```

<210> SEQ ID NO 129
<211> LENGTH: 306
<212> TYPE: DNA
<213> ORGANISM: Zea mays
<220> FEATURE:
<221> NAME/KEY: unsure
<222> LOCATION: (1)...(306)
<223> OTHER INFORMATION: unsure at all n locations

<400> SEQUENCE: 129

```
gagactagac ccgctagctg angccgggcg gcgcgctgga cacgaacatg atggggagaa     60
aggcgctcgg ctgtgctcct cttctcctcc tcttgnccgc cgccgtcgct ccggccgagc    120
tcagcgtcgg gggcggcggc tgcctcgggc gcggtcaccc gggccgactt ccccgcgggg    180
ttcgtcttcg gcgtcgggtc ctccgggtac cagtcgaagg tgcngttgca gaggacggaa    240
ggaagcctag catctgggac acnttcacac atgaaggcta ttcccttgac aacgccacag    300 gcgntg                                                               306
```

<210> SEQ ID NO 130
<211> LENGTH: 318
<212> TYPE: DNA
<213> ORGANISM: Zea mays
<220> FEATURE:
<221> NAME/KEY: unsure
<222> LOCATION: (1)...(318)
<223> OTHER INFORMATION: unsure at all n locations

<400> SEQUENCE: 130

```
gnanatgaga ngaganacta gacccgctag ctgangccgg gcggcgcgct ggacacgaac     60
atgatgggga gaanngcgct cggctgtgct cctcttctcc tcctcttggc cgccnccgtc    120
gctccggccg anctcagcgt cgggncggcg gctgcctcgg gcgcggtcac ccgggccgac    180
ttccccncng gttcgtctt cngcgtcggc tcctccgcgt accaggtcga aggtgcagtt     240
gcagaggacg gaaggaagcc tagcatcttg nacacattca cacatgaang ctattcncca    300
gacaacgcta natggatg                                                  318
```

<210> SEQ ID NO 131
<211> LENGTH: 409

```
<212> TYPE: DNA
<213> ORGANISM: Zea mays
<220> FEATURE:
<221> NAME/KEY: unsure
<222> LOCATION: (1)...(409)
<223> OTHER INFORMATION: unsure at all n locations

<400> SEQUENCE: 131
ggaccctggg acatggaacc tgacgccagt cagctaccag gatgattggc atgttggttt      60
tgtctacgaa cgaaatggag ttcctattgg cgctcacnca aactcctact ggctgtacat     120
tgtgccgtgg ggcatcaaca aggctgtcag ctatgtcaag gaaacttaca aaatcctac      180 aatgatcctt gctgaaaacg gaatggacca acctggtgat gtcagtatta ctcagggtgt     240
gcatgacaca gtaagaatcc gttattacag agactacatn actgagctca agaaagcaat     300
agatgatggt gccagagtca ttgggtactt tgcgtggtcg ctgcttgaca acttcgantg     360
gaagcttggg tacacctcnc cggtttggcc ttgngtacct tgaacaaaa               409

<210> SEQ ID NO 132
<211> LENGTH: 283
<212> TYPE: DNA
<213> ORGANISM: Zea mays

<400> SEQUENCE: 132
gccagggatg gtgaaaggct ctatagacta tgttggcatc aaccactaca cttctttcta      60
catgaaggac cctgggacat ggaacctgac gccagtcagc taccaggatg attggcatgt     120
tggttttgtc tacgaacgaa atggagttcc attggcgctc acgcaaactc ctactggctg     180
tacattgtgc cgtggggcat caacaaggct gtcagctatg tcaaggaaat tacaaaaatc     240
ctacaatgat cctgctgaaa cggaatggac caacctggtg atg                      283

<210> SEQ ID NO 133
<211> LENGTH: 189
<212> TYPE: DNA
<213> ORGANISM: Zea mays

<400> SEQUENCE: 133
ggcatcaacc actacacttc tttctacatg aaggaccctg ggacatggat cctgacacca      60
gtcagctacc aggatgattg gcatgttggt tttgtctacg aacgaaatgg agttcctatt     120
ggcgctcacg caaactccta ctggctgtac attgtgccgt ggggcatcaa caaggctgtc     180
agctatgtc                                                            189

<210> SEQ ID NO 134
<211> LENGTH: 158
<212> TYPE: DNA
<213> ORGANISM: Zea mays

<400> SEQUENCE: 134
ggcatgttgg ttttgtctac gaacgaaatg gagttcctat tggcgctcac gcaaactcct      60
actggctgta cattgtgccg tggggcatca acaaggctgt cagctatgtc aaggaaactt     120
acaaaaatcc tacaatgatc cttgctgaaa acggaatg                           158

<210> SEQ ID NO 135
<211> LENGTH: 262
<212> TYPE: DNA
<213> ORGANISM: Zea mays
<220> FEATURE:
<221> NAME/KEY: unsure
<222> LOCATION: (1)...(262)
```

<223> OTHER INFORMATION: unsure at all n locations

<400> SEQUENCE: 135

```
gtcagctacc aggatgattg gcatgttggt ttggccacgg aacggaaaat ggagttccta      60
attggcgctc acggcaacnc cctatggctg taacattgtg ccgtggggca tcaacaaagg     120
ctgtcagcta atgtcnagga aactttacca aaaatcctac aatgatcctt gctgaaaacg     180
gaatggacca actggtgatg tcagtattac tcagggtgtg catgacacag taagaatcgg     240
tattacagag actacataac tg                                              262
```

<210> SEQ ID NO 136
<211> LENGTH: 476
<212> TYPE: DNA
<213> ORGANISM: Zea mays
<220> FEATURE:
<221> NAME/KEY: unsure
<222> LOCATION: (1)...(476)
<223> OTHER INFORMATION: unsure at all n locations

<400> SEQUENCE: 136

```
acgcgtacag attctccatc tcttggtcca gaatactgcc gaagggaacg ctcgaaggag      60
ggattaatca ggccggcatc aagtactaca aaaagctcat caacttattg atagagaacg     120
gaatagagcc atttgtaaca atttttcatt gggacgtccc tcaagcactg aagacaagt     180
acggtggctt tttaggcgac aggattgtaa aggattacac agacttcgct aaggtgtgct     240
ttgagaactt cggtgacaag gtgaagaatt ggttgacctt taacgagcca cagacattta     300
caacctttc gtacggaacg ggagttttg cccctggacg gtgctcacca ggagaaaaat      360
gtgctcagcc tattgctaac tcactcaccg aaccatacat tggtggccac aacatncttn     420
gagcccacgc tatgactggt gacctntaca acaagaatta caagggttca gacggc         476
```

<210> SEQ ID NO 137
<211> LENGTH: 486
<212> TYPE: DNA
<213> ORGANISM: Zea mays
<220> FEATURE:
<221> NAME/KEY: unsure
<222> LOCATION: (1)...(486)
<223> OTHER INFORMATION: unsure at all n locations

<400> SEQUENCE: 137

```
cgctcgaagg aggtattaat caggccggca tcaagtacta caaaaagctc atcaacntat      60
tgatagagaa cggaatagag ccatttgtaa caattttca ttgggaccgt ccctcaagca     120
ctggaagaca agtacggtgg cttttaggc gacaggattg taaggatta cacagacttc      180
gctaaggtgt gctttgagaa cttcggtgac aaggtgaaga attggttgac ctttaacgag     240
ccacagacat ttacaacctt ttcgtacgga acgggagttt tgcccctgg acggtgctca     300
ccaggagaaa aatgtgctca gcctattgct aactcactca ccgaaccata cattgctggc     360
cacaacatcc ttcgagccca cgctatgact gttgacctct acaacaagaa ttacaagggt     420
cagacgggcc gcattgggct tgcgtttgac gtaatgggtc gcggtgccat atggaaatca     480
tttctt                                                                486
```

<210> SEQ ID NO 138
<211> LENGTH: 442
<212> TYPE: DNA
<213> ORGANISM: Zea mays
<220> FEATURE:
<221> NAME/KEY: unsure

```
<222> LOCATION: (1)...(442)
<223> OTHER INFORMATION: unsure at all n locations

<400> SEQUENCE: 138
acgcgtacag attctccatc tcttggtcca gaatactgcc gaagggaacg ctcgaaggag    60
gtattaatca ggccggcatc aagtactaca aaaagctcat caacttattg atagagaacg   120
gaatagagcc atttgtaaca attttcatt gggacgtccc tcaagcactg aagacaagt    180 acggtggctt tttaggcgac aggattgtaa aggattacac agacttcgct aaggtgtgct   240
ttgagaactt cggtgacaag gtgaagaatt ggttgacctt taacgagcca cagacattta   300 caacctttc gtacggaacg ggagttttg ccctggacg gtgctcacca ggagaaaaat    360
gtgctcagcc tattgctaac tcactcaccg aaccatacat tgctggccac aacattcttn   420
gagcccacct tttgactggt ga                                            442

<210> SEQ ID NO 139
<211> LENGTH: 410
<212> TYPE: DNA
<213> ORGANISM: Zea mays
<220> FEATURE:
<221> NAME/KEY: unsure
<222> LOCATION: (1)...(410)
<223> OTHER INFORMATION: unsure at all n locations

<400> SEQUENCE: 139
tgcggatgtc agattgctaa aggaaatagg catgggcgng tacagattct ccntcnnttg    60
gtccagaata ctgccgaagg gaacgctcga aggaggtatt aatcaggccg gcatcaagta   120
ctacaaaaag ctcatcaact tattgataga gaacggaata gagccatttg taacaatttt   180
tcattgggac gtccctcaag cactggaaga caagtacggt ggcttttttag gcgacaggat   240 tgtaaaggat tacacagact tcgctaaggt gtgctttgag aacttcggtg acaaggtgaa   300
gaattggttg acctttaacg agccacagac atttacaacc ttttcgtacc ggaacgggag   360
tttttgcccc tggacagtgc tnaccaggag aaaaaatgtg ctcagnctat                410

<210> SEQ ID NO 140
<211> LENGTH: 439
<212> TYPE: DNA
<213> ORGANISM: Zea mays
<220> FEATURE:
<221> NAME/KEY: unsure
<222> LOCATION: (1)...(439)
<223> OTHER INFORMATION: unsure at all n locations

<400> SEQUENCE: 140
ctcaagcact ggaagacaag tacggtggct ttttaggcga caggattgta aaggattaca    60
cagacttcgc taaggtgtgc tttgagaact tcggtgacaa ggtgaagaat tggttgacct   120 taacgagcc acagacattt acaacctttt cgtacggaac gggagttttt gccctggac    180 ggtgctcacc aggagaaaaa tgtgctcagc ctattgctaa ctcactcacc gaaccataca   240
ttgctggcca acatccctt cgagcccacg ctatgactgt tgacctctac aacaagaatt   300
acangggtac agacggnccg cattgggctt gcgtttgacg taatgggtcg cgtgccatat   360
ggaaatacat ttctcgatga acaggcccag gaaaggtcct tngatcaaaa cctangatgg   420
ttctttggan cctgtggtc                                                439

<210> SEQ ID NO 141
<211> LENGTH: 326
<212> TYPE: DNA
```

<213> ORGANISM: Zea mays

<400> SEQUENCE: 141

| gattactgaa ggaaataggg atggactcct ataggttctc catctcttgg tccagaatac | 60 |
| tgccgaatgg cacactcgaa ggaggtatta atccatatgg catcaagtac tacaaaaatc | 120 |
| tcatcaactt gttggtagag aacggcatag agccatttgt gacaattttc cactgggaca | 180 |
| cgcctcaagc actggtagac aagtatggtg cttttttaga tgagaggatt gtaaaagatt | 240 |
| acacagactt cgctaaggtg tgctttgaga acttcggtga taaagtaaac aattggttga | 300 |
| cctttaatga gccccaaacg ttttct | 326 |

<210> SEQ ID NO 142
<211> LENGTH: 414
<212> TYPE: DNA
<213> ORGANISM: Zea mays
<220> FEATURE:
<221> NAME/KEY: unsure
<222> LOCATION: (1)...(414)
<223> OTHER INFORMATION: unsure at all n locations

<400> SEQUENCE: 142

| gtaaaggatt acacagactt cgctaaggtg tgctttgaga acttcggtga caaggtgggng | 60 |
| aattggttga cctttaacga gccacagaca tttacaaacct tttcgtacgg aacgggagtt | 120 |
| tttgcccctg gacggtgctc accaggagaa aaatgtgctc agcctattgc taactcactn | 180 |
| accgaaccat acattgctgg ccacaacatt cttcgagccc acgctatgac tgttgaccct | 240 |
| tacaacaaga attacaaggg tacanaacgn cccattgggc ttgcgtttga cctaatgggt | 300 |
| ccgggccata ntggaaatac atttntngat taanaaggcc angaaagggg ccttgantca | 360 |
| aaaacctaga ttgttcnttg aacctntggt cctggngant taccctttt tatt | 414 |

<210> SEQ ID NO 143
<211> LENGTH: 420
<212> TYPE: DNA
<213> ORGANISM: Zea mays
<220> FEATURE:
<221> NAME/KEY: unsure
<222> LOCATION: (1)...(420)
<223> OTHER INFORMATION: unsure at all n locations

<400> SEQUENCE: 143

| aggacccagg gctctnatng atagagancn gaatntaagc catttgtaac aattcancag | 60 |
| ggggngggtc catcaancac tggaagacaa gtacggnggc tttttaagcg acaggatacg | 120 |
| taaaggatta cacagacttc gctaaggtgt gctttgagaa ctncggtgac aaggngaaga | 180 |
| attggttgac ctttaacgag ccacagacat ttacaacctt tncgtacgga acgggagttt | 240 |
| ttgcccctgg acggtgctca ccaggagaaa aatgtgctca ncctattgct aactcactca | 300 |
| ccgaaccata cattgctggc cacaacatcc ttcgagccca cnctatgact gttgacctnt | 360 |
| acaacaagaa ttacaagggt tcanacggcc gcattgggct tgcgtttgac ntaatgggtc | 420 |

<210> SEQ ID NO 144
<211> LENGTH: 419
<212> TYPE: DNA
<213> ORGANISM: Zea mays
<220> FEATURE:
<221> NAME/KEY: unsure
<222> LOCATION: (1)...(419)
<223> OTHER INFORMATION: unsure at all n locations

<400> SEQUENCE: 144

```
aggacgcgtg ggcttatnga tagagaacgg aatagagcca tttgtaacaa tttttcatgg      60
ggancgtccn tcaagcactg aagacaagt  acggtggctt tttangcgac aggattgtaa     120
aggattacac agacttcgct aangtgtgct ttgagaactt cggtgacaag gtgaagaatt     180
ggttgacctt taacgagcca cagacattta caacctttc  gtacggaacg ggagttttg      240 cccctggacg gtgctcacca ggagaaaaat gtgctcancc tattgctaac tcactcaccg     300
aaccatacat tgctggccac aacatccttc gagcccacgc tatgactggt gaccttntac    360
aacaagaatt acaaggggta cagacgggcg gattgggctt gcgtttggac gtaatgggt     419
```

<210> SEQ ID NO 145
<211> LENGTH: 262
<212> TYPE: DNA
<213> ORGANISM: Zea mays

<400> SEQUENCE: 145

```
gtccagaata ctgccgaagg gaacgctcga aggaggtatt aatcaggccg gcatcaagta      60
ctacaaaaag ctcatcaact tattgataga gaacggaata gagccatttg taacaatttt    120
tcattgggac gtccctcaag cactggaaga caagtacggt ggcttttag  gcgacaggat    180 tgtaaaggat tacacagact tcgctaaggt gtgctttgag aacttcggtg acaaggtgaa    240
gaattggttg accttttaacg ag                                             262
```

<210> SEQ ID NO 146
<211> LENGTH: 188
<212> TYPE: DNA
<213> ORGANISM: Zea mays

<400> SEQUENCE: 146

```
cagacttcgc taaggtgtgc tttgagaact tcggtgacaa ggtgaagaat tggttgacct      60 taacgagcc  acagacattt acaaccttt  cgtacggaac gggagtttt  gcccctggac    120 ggtgctcacc aggagaaaaa tgtgctcagc ctattgctaa ctcactcacc gaaccataca    180
ttgctggc                                                              188
```

<210> SEQ ID NO 147
<211> LENGTH: 442
<212> TYPE: DNA
<213> ORGANISM: Zea mays
<220> FEATURE:
<221> NAME/KEY: unsure
<222> LOCATION: (1)...(442)
<223> OTHER INFORMATION: unsure at all n locations

<400> SEQUENCE: 147

```
gggaaatcca tggatctaca tgtaccctaa aggcctaaag gatctcctta tgatcatgaa      60
gaacaaatac ggaaacccgc ctatctatat caccgagaac ggaatcgggg acgttgacac    120
aaaggataat cctctatcca tgcaagatgc gttggacgac tacaagaggc tagattacct    180
ccagcgccac atctcagtta tcaaagaatc aatagacttg ggggcggacg tgcgcggcca    240
cttcacatgg tctctgttgg acaacttcga gtggtctagt ggctacaccg agcgttacgg    300
catcatctac gtcgaccgtg acgacggcta caggcgctac ctgaagcgct cagctaagtg    360
gctgcgagag ttcaacggag ctgccaaaaa ggctgaaaag aangntctta cgccagctta    420
gaatgtaggt gggggtgnna gt                                              442
```

<210> SEQ ID NO 148

```
<211> LENGTH: 450
<212> TYPE: DNA
<213> ORGANISM: Zea mays
<220> FEATURE:
<221> NAME/KEY: unsure
<222> LOCATION: (1)...(450)
<223> OTHER INFORMATION: unsure at all n locations

<400> SEQUENCE: 148
agcacgtcga cttctcagaa gactactcac ntaagctcan nnccgacgac gcctatgcca      60
ctgggggaaa ttngnggacc tgacgggaat tctattggtc ctcctatggg aaatccatgg     120
atctacatgt accctaaagg cctaaaggat ctccttatga tcatgaagaa caaatacgga     180
aacccgccta tctatatnac cgagaacgga atcggggacg ttgacacaaa ggataatcct     240
ctatccatgc aagatgcgtt ggacgactac aagaggctng attacctnca tcgccacatn     300
tcaattatca aagaatcaat agacttgggg gcggacgttc gcggcacttt acatggtctn     360
tgttggacaa ctttnagtgg tctantggct acaccgagcc gttacggnat tatntacgtn     420
gacngggacn accggntaca ngcctanctt                                       450

<210> SEQ ID NO 149
<211> LENGTH: 444
<212> TYPE: DNA
<213> ORGANISM: Zea mays
<220> FEATURE:
<221> NAME/KEY: unsure
<222> LOCATION: (1)...(444)
<223> OTHER INFORMATION: unsure at all n locations

<400> SEQUENCE: 149
ggataaatta ctatacctca aggttctcta agcacgtcga cttctcagaa gactactgac      60
ctaagctcaa cgccgacgac gcctatgcca ctgcagaaat ctttggacct gacgggaatt     120
ctattggtcc tcctatggga aatccatgga tctacatgta ccctaaaggc ctaaaggatc     180
tccttatgat catgaagaac aaatacggaa acccgcctat ctatatcacc gagaacggaa     240
tcggggacgt tgacacaaag gataatcctc tatccatgca agatgcgttg gacgactaca     300
agaggctaga ttacctcagc gccacatctc aagttatcaa agaatcaata gacttggggg     360
ccggacgtgc gccgncactt nacatggnct tgttggaca acttcgagtg gctaatggn      420
tacccgagcg gttccggntt attt                                             444

<210> SEQ ID NO 150
<211> LENGTH: 435
<212> TYPE: DNA
<213> ORGANISM: Zea mays
<220> FEATURE:
<221> NAME/KEY: unsure
<222> LOCATION: (1)...(435)
<223> OTHER INFORMATION: unsure at all n locations

<400> SEQUENCE: 150
gcgggttcct atgacatatt ggggataaat tactatacct caaggntctc taagcacggn      60
ggncttctna naagactact cacctaaagc tcaacgccga cgacgcctat gccactgcag     120
aaatctttgg acctgacggg aattctattg gtcctccta tgggaaatcc atgggatcta     180
catgtaccct aaaggcctaa aggatctcct tatgatcatg aagaacaaat acggaaaccc     240
gcctatctat atcaccgaga acggaatcgg ggacgttgac acaaggata atcctctatc      300
catgcaagat gccttggacc aactncaaga ggctagatta ccttcagcgc cacatctnaa     360
ttatcaaaga atcaatagac ttgggggccg gacgttcgcc gncacttnac atggnctctg     420
```

```
ntggacaact tcnag                                                          435

<210> SEQ ID NO 151
<211> LENGTH: 230
<212> TYPE: DNA
<213> ORGANISM: Zea mays
<220> FEATURE:
<221> NAME/KEY: unsure
<222> LOCATION: (1)...(230)
<223> OTHER INFORMATION: unsure at all n locations

<400> SEQUENCE: 151
caacgccgac gacgcctatn ccactgcaga aatctttgga cctgacggga attctattgg         60
tcctcctatg ggaaatccat ggatctacat gtaccctaaa ggcctaaagg atcttcttat        120
gatcatgaag aacaaatacg gaaacccgcc tatctatatc accgagaacg gaatcgggga        180
cgttgacaca aaggacaatc ctctatccat gcaagatgcg ttggaggact                   230

<210> SEQ ID NO 152
<211> LENGTH: 246
<212> TYPE: DNA
<213> ORGANISM: Zea mays

<400> SEQUENCE: 152
cgcctatcta tatcaccgag aacggaatcg gggacgttga cacaaaggac aatcctctat         60
ccatgcaaga tgcgttggag gactacaaga ggctagatta cctccagcgc cacatctcag        120
ttattaaaga atcaatagac ttgggggcgg acgtgcgcgg ccacttcaca tggtctctgt        180
tggacaactt cgagtggtct agtggctaca ccgagcgtta cggcatcatc tacgtcgacc        240
gtgacg                                                                    246

<210> SEQ ID NO 153
<211> LENGTH: 320
<212> TYPE: DNA
<213> ORGANISM: Zea mays
<220> FEATURE:
<221> NAME/KEY: unsure
<222> LOCATION: (1)...(320)
<223> OTHER INFORMATION: unsure at all n locations

<400> SEQUENCE: 153
cccggnccga cntccccgcg gggttcgtct tcngcgtcgg cnccncccgc gtaccagnnc         60
cgaaggtgca gttgcagagg acggaaggaa gcctagcatc tggacacat tcacacatga        120 aggctatncc cttgacaacn ccacaggcga tgtaacnncg gatcagtatc ataagtacaa        180
ggacgacgta aagcttctgc atgagatngg tgtcgatnnc ctaccggatg tcgattncct        240
ggcctcgact tatcccagat ggtcggggag ccgtgaatcc gaagngctgg agtatnacaa        300
caatctcata gatgagtcct                                                    320

<210> SEQ ID NO 154
<211> LENGTH: 301
<212> TYPE: DNA
<213> ORGANISM: Zea mays
<220> FEATURE:
<221> NAME/KEY: unsure
<222> LOCATION: (1)...(301)
<223> OTHER INFORMATION: unsure at all n locations

<400> SEQUENCE: 154
acgacaaaag caaagcaaag cagcncaaaa aagtttagcc agctagcaag acatggctcc         60
```

```
acttgttgct gctgccacga atgcacactg cccatagaag ccacatagta ggacccaaca    120
atgagaattt tccaaggcac caaccttgtt catcacaaaa cagaaacaag agactcaggc    180
ttaggtcacg agcacaaagg ataagcagtc agctgcttgc aagccgaaag cttatggccc    240
tgggcaaatn ccctaanagg ggatggtttt cctcctagct tcatcttggt ggcggccacg    300
c                                                                    301
```

```
<210> SEQ ID NO 155
<211> LENGTH: 266
<212> TYPE: DNA
<213> ORGANISM: Zea mays
<220> FEATURE:
<221> NAME/KEY: unsure
<222> LOCATION: (1)...(266)
<223> OTHER INFORMATION: unsure at all n locations

<400> SEQUENCE: 155
angcanagcg ttcaggatan acatngctgc cacctttgcc ttcatcnctc tccngctacn    60
ggtctgcgtc cagagcgcgg cncntgttcn tcggcttcac aaggagcgag tnccctgaag   120
ntttcgtcnt cggatccgcn acnncggctt atcagtatga nggtgctgtn ggtgaggatg   180
gtaggagccc aagcatctgg gacaccttca ctcacgcagg ganaatnccg gacaaaagca   240
atggtgatgt agccgccgac nggtac                                        266
```

```
<210> SEQ ID NO 156
<211> LENGTH: 238
<212> TYPE: DNA
<213> ORGANISM: Zea mays
<220> FEATURE:
<221> NAME/KEY: unsure
<222> LOCATION: (1)...(238)
<223> OTHER INFORMATION: unsure at all n locations

<400> SEQUENCE: 156
gaacgctggg tcgacccanc ggcgtccgct tctgcttgtc aatcggggtt tcagcttagt    60
ttggagggtg tangagttga ttcagctcgg tttggatgnc actaagattg aaggagcgag   120
aagggaggga ggcaaaggag acagcatatg ggatgtattt acagatgaca agaacatgt    180 cttagacaga agcaatggag aaattgcagt tgatcactac catcgataca aggaagac    238
```

```
<210> SEQ ID NO 157
<211> LENGTH: 233
<212> TYPE: DNA
<213> ORGANISM: Zea mays
<220> FEATURE:
<221> NAME/KEY: unsure
<222> LOCATION: (1)...(233)
<223> OTHER INFORMATION: unsure at all n locations

<400> SEQUENCE: 157
cagacgcgtg ggtcgaccan cgcgtccgct tctgcttgtc aatcggggtt tcagcttagt    60
ttggagggtg tggagttgat tcagctcggt ttggatggac taagattgaa ggagcgagaa   120
gggagggagg caaaggagac agcatatggg atgtatttac agatgacaaa gaacatgtct   180
tagacagaag caatggataa attgcagttg atcactacca tcgatacaag gaa          233
```

```
<210> SEQ ID NO 158
<211> LENGTH: 462
<212> TYPE: DNA
<213> ORGANISM: Zea mays
<220> FEATURE:
<221> NAME/KEY: unsure
```

<222> LOCATION: (1)...(462)
<223> OTHER INFORMATION: unsure at all n locations

<400> SEQUENCE: 158

```
caaggagaca cctctaccca tggaggatgc cttaaatgac tacaaaaggc tagattacat      60
cnagcgccac atcgctactc ttaaggaatc aatagacttg ggatcaaatg tgcaaggcta     120
cttcgcttgg tctctgctgg acaactttga atggttcgcc ggcttcaccg aacgttatgg     180
cattgtctac gtcgaccgca acaataactg cacgcgctac atgaaggagt ctgccaagtg     240
gttgaaacag ttcaacgccg cgaagaagcc cagcaagaag attcttacgc cagcttagaa     300
atcgggggcc tcatgatgtg ggtgcagccc ataaaaaact ggtgtgtggt ttcgaaccga     360
aaattttctg ttttttttccg ccacgagagg ttctggaggc atactctcca gcaccgtggc   420
taataacgca ttgttccaat tcagtctggc cttgtcatgc at                        462
```

<210> SEQ ID NO 159
<211> LENGTH: 463
<212> TYPE: DNA
<213> ORGANISM: Zea mays
<220> FEATURE:
<221> NAME/KEY: unsure
<222> LOCATION: (1)...(463)
<223> OTHER INFORMATION: unsure at all n locations

<400> SEQUENCE: 159

```
gtgctttgat aacttcggcg acaaggtgaa gaattggttg acctttaatg agccccagac      60
attnncttcc ttttcctacg gaactggggt ctttgcccca ggtcggtgct cacctggact     120
agactgtgcc tacccaactg ggaattcact cgtcgagcct tacactgctg gccataacat     180
tctcctagcc cacgctgagg ctgttgatct ttacaacaag cattcaagc gcgacgacac     240
ccgcataggg cttgcgtttg acgtaatggg tcgtgtgcca tacggaacat cgtttctgga   300
taaacaggcc gaagaaaggt cctgggacat caacctagga tggttcttag agccagtggt   360
tcgtggtgac tacccccttct ccatgagatc attggctagg gaacgactac ccttcttcaa   420
ggacgagcag aaggagaagc tcgccggntc ctataacatg ttg                      463
```

<210> SEQ ID NO 160
<211> LENGTH: 466
<212> TYPE: DNA
<213> ORGANISM: Zea mays
<220> FEATURE:
<221> NAME/KEY: unsure
<222> LOCATION: (1)...(466)
<223> OTHER INFORMATION: unsure at all n locations

<400> SEQUENCE: 160

```
gcgagaacgg ccgcataggt cttgcatttg atgtaatggg tcgtgtgcca tacggaacat      60
catttctaga tgaacaggcc aaagaaaggt ccatggacat taacctagga tggttcttgg    120
agcctgtggt tcgtggtgac tacccccttct caatgagatc gttagcgagg gaacgactac   180
ccttcttcag tgacaaacag caagagaagc ttgtgggatc ctataacatg ttgggaataa   240
actactacac ctcaatattc tccaaacata tcgacatctc accaaaatac tcgcctgttc   300
tcaacactga cgacgcctac gctagtcaag aaacgtatgg gcctgacggg aaacccattg   360
gtcctnctat gggaaatccg tggatctact tatacccaga aggcctaaag gatatcctta   420
tgatcatgaa gaacaaatat gggaaacccc acctatctac atnact                   466
```

<210> SEQ ID NO 161

<211> LENGTH: 441
<212> TYPE: DNA
<213> ORGANISM: Zea mays
<220> FEATURE:
<221> NAME/KEY: unsure
<222> LOCATION: (1)...(441)
<223> OTHER INFORMATION: unsure at all n locations

<400> SEQUENCE: 161

```
agattacaca tactttgcta aggtgtgctt tgataacttc ggcgacaagg tgaagaanng      60
gtggaccttt aatgagcccc agacatttac ttccttttcc tacggaactg gggtctttgc     120
cccaggtcgg tgctcacctg gactagactg tgcctaccca actgggaatt cactcgtcga     180
gccttacact gctggccata acattctcct agcccacgct gaggctgttg atctttacaa     240
caagcattac aagcgcgacg acacccgcat agggcttgcg tttgacgtaa tgggtcgtgt     300
gccatacgga acatcgtttc tggataaaca ggccgaagaa aggtcctggg acatcaacct     360
aggatggttc ttagagccag tggttcgtgg tgactacccc ttctccatga gatcattggc     420
tagggaacga ctacccttct t                                              441
```

<210> SEQ ID NO 162
<211> LENGTH: 444
<212> TYPE: DNA
<213> ORGANISM: Zea mays
<220> FEATURE:
<221> NAME/KEY: unsure
<222> LOCATION: (1)...(444)
<223> OTHER INFORMATION: unsure at all n locations

<400> SEQUENCE: 162

```
caccaaacta ctcacctgtg ctcaacactg acgacgccta cgccagtcaa gaagttaacg      60
gggctgacgg gaagcccatn ggtcctccta tgggaaatcc atggatctac atgtaccctg     120
agggcttgaa ggatctcctt atgatcatga agaacaaata cggaaaccca cctatctaca     180
tcacggagaa cggaatcggg gatgttgata ccaaggagac acctctaccc atggaggatg     240
ccttaaatga ctacaaaagg ctagattaca tccagcgcca catcgctact cttaaggaat     300
caatagactt gggatcaaat gtgcaaggct acttcgcttg gtctctgctg acaactttg      360
aatggttcgc cggcttcacc gaacgttatg gcattgtcta cgtcgaccgn aacaataact     420
gnacgcgcta catgaangag tctg                                           444
```

<210> SEQ ID NO 163
<211> LENGTH: 470
<212> TYPE: DNA
<213> ORGANISM: Zea mays
<220> FEATURE:
<221> NAME/KEY: unsure
<222> LOCATION: (1)...(470)
<223> OTHER INFORMATION: unsure at all n locations

<400> SEQUENCE: 163

```
ctcacctgtg ctcaacactg acgacgcctt tnccagtcna gaagttaacg ggcctgacgg      60
gaagcccatt ggtcctccta tgggaaatcc atggatctac atgtaccctg agggcttgaa     120
ggatctcctt atgatcatga agaacaaata cggaaaccca cctatctaca tcacggagaa     180
cggaatcggg gatgttgata ccaaggagac acctctaccc atggaggatg ccttaaatga     240
ctacaaaagg ctagattaca tccagcgcca catcgctact cttaaggaat caatagactt     300
gggatcaaat gtgcaaggct acttcgcttg gtctctgctg acaactttg aatggtcgc      360
cggcttaccc gaacgttatg gcattgtcta cntcgacccg aacaatnact gnacgcgcta     420
```

```
catgaangag tctgccaagt gggtgaaaca gttcaacgnc nccnaaaaaa         470
```

```
<210> SEQ ID NO 164
<211> LENGTH: 435
<212> TYPE: DNA
<213> ORGANISM: Zea mays
<220> FEATURE:
<221> NAME/KEY: unsure
<222> LOCATION: (1)...(435)
<223> OTHER INFORMATION: unsure at all n locations

<400> SEQUENCE: 164
tanacaatgc cataacgttc ggtgaagccg gcgaaccatt caaagttgtc cagcagagac    60
caagcgaagt agccttgcac atttgatccc aagtctattg attccttaag agtagcgatg   120
tggcgctgga tgtaatctag cctttttgtag tcatttaagg catcctccat gggtagaggt   180
gtctccttgg tatcaacatc cccgattccg ttctccgtga gtagataggt gggtttccg    240
tatttgttct tcatgatcat aaggagatcc ttcaagccct cagggtacat gtagatccat   300
ggatttccca taggaggacc aatgggcttc ccgtcaggcc cgttaacttc ttgactggcg   360
taggcgtcgt cagtgttgag cacaggtgag tagtttggtg agatatcgat gttttggag    420
aaccgtgagg tgtat                                                     435
```

```
<210> SEQ ID NO 165
<211> LENGTH: 459
<212> TYPE: DNA
<213> ORGANISM: Zea mays
<220> FEATURE:
<221> NAME/KEY: unsure
<222> LOCATION: (1)...(459)
<223> OTHER INFORMATION: unsure at all n locations

<400> SEQUENCE: 165
cagaaggaga agctcgccgg ttcctataac nttgtnggtn gttaaactac tacacctcac    60
ggggntccga aaacatcgat atctcaccaa actactcacc tgtgctcaac actgacgacg   120
cctacgccag tcaagaagtt aacgggcctg acgggaagcc cattggtcct cctatgggaa   180
atccatggat ctacatgtac cctgagggct tgaaggatct ccttatgatc atgaagaaca   240
aatacggaaa cccaccctatc tacatcacgg agaacgaaat cggggatgtt gataccaagg   300
agacacctct acccatggag gatgccttaa atgactacaa aaggctagat tacatccagc   360
gccacatcgc tactcttaag gaatcaatag acttgggatc aaatgtgcaa ggntacttcg   420
cttggnctct gctggacaac tttgaatggg ttcgccggc                         459
```

```
<210> SEQ ID NO 166
<211> LENGTH: 466
<212> TYPE: DNA
<213> ORGANISM: Zea mays
<220> FEATURE:
<221> NAME/KEY: unsure
<222> LOCATION: (1)...(466)
<223> OTHER INFORMATION: unsure at all n locations

<400> SEQUENCE: 166
aagggaattt tnattgaatg ctctaccggt ccggaattcc cggggtagaa gattacacat    60
actttgctaa ggtgtgcttt gataacttcg gcgacaaggt gaagaattgg ttgacnttta   120
nggagcccca gacattnact tccttttcct acgaactgg ggtctttgcc ccaggtcggt    180
gctcacctgg actagactgt gcctacccaa ctgggaattc actcgtcgag ccttacactg   240
```

```
ctggccataa cattctccta gcccacgctg aggctgttga tctttacaac aagcattaca      300
agcgcnacga cacccgcata gggcttgcgt ttgacgtaat gggtcgtgtg ccatacggaa      360
catcgtttct ggataaacag gccgaanaaa ggtcctggga catcaaccta ggatggttct      420
tagagccagt ggttcgtggt gactacccct tctccatgag atcatt                    466
```

<210> SEQ ID NO 167
<211> LENGTH: 478
<212> TYPE: DNA
<213> ORGANISM: Zea mays
<220> FEATURE:
<221> NAME/KEY: unsure
<222> LOCATION: (1)...(478)
<223> OTHER INFORMATION: unsure at all n locations

<400> SEQUENCE: 167

```
gatgttgata ccaaggagac acctctaccc atggaggatg ccttaaatga ctacaaaagg       60
ntagattnca tccagcgcca catcgctact cttaaggaat caatagactt gggatcaaat      120
gtgcaaggct acttcgcttg gtctctgctg acaactttg aatggttcgc cggcttcacc      180
gaacgttatg gcattgtcta cgtcgaccgc aacaataact gcacgcgcta catgaaggag      240
tctgccaagt ggttgaaaca gttcaacgcc gcgaagaacc cagcaagaag attcttacgc      300
cagcttagaa atcgggggcc tcatgatgtg ggtgcagccc ataaaaaact ggtgtgtggg      360
ttggaaccga aaattttctg gttttttccg nccgagaggg tctggangca tactnttcaa      420
cacccgnggc taataacgca ttggtncaat tcaatctggc cttgtcatgc ctgcaata       478
```

<210> SEQ ID NO 168
<211> LENGTH: 447
<212> TYPE: DNA
<213> ORGANISM: Zea mays
<220> FEATURE:
<221> NAME/KEY: unsure
<222> LOCATION: (1)...(447)
<223> OTHER INFORMATION: unsure at all n locations

<400> SEQUENCE: 168

```
ctcaagcact agaagagaag tacggcggat tcttagataa gactcataag aggnttggaa       60
atgattacaa aaacttcgct aaggtgtgct tcgacaactt tggtgacaag gtgaagaatt      120
ggttgacctt taatgagccc cagacattta cttcattttc ctatggaacc ggggtctttg      180
ccccaggacg atgctcaccg ggactagact gtgccatccc aactgggaat tcactcgtcg      240
aaccttacat tgctggccac aacattcttc tagcccacgc tgaggctgtt gatctttaca      300
acaagtatta caagggcgag aacggnccgc ataggtcttg catttgatgt aatgggtcgt      360
gtgccatacn gaacatcatt tctagatnaa caggcccaan naagggccct ngacattaac      420
ctangatggn tcntngganc ctgtgnt                                          447
```

<210> SEQ ID NO 169
<211> LENGTH: 454
<212> TYPE: DNA
<213> ORGANISM: Zea mays
<220> FEATURE:
<221> NAME/KEY: unsure
<222> LOCATION: (1)...(454)
<223> OTHER INFORMATION: unsure at all n locations

<400> SEQUENCE: 169

```
cgtacgcgcg agctnggnct ntggcgtttg cccatttcg gtnctcacct ggactagact        60
gtgcctnccc angtgggaat tcactcgtcg agccttacac tgctggccat aacattctcc      120
```

| | |
|---|---|
| tagcccacgc tgaggctgtt gatctttaca acaagcatta caagcgcgac gacacccgca | 180 |
| tagggcttgc gtttgacgta atgggtcgtg tgccatacgg aacatcgttt ctggataaac | 240 |
| aggccgaaga aggtcctgg gacatcaacc taggatggtt cttagagcca gtggttcgtg | 300 |
| gtgactaccc cttctccatg agatcattgg ctagggaacg actacccttc ttcaaggacg | 360 |
| agcagaagga gaagctcgcg gtcctataac atgttggggt taaactacta cacctcacgg | 420 |
| ttctcaaaaa catcgatatc tcaccaaact actc | 454 |

<210> SEQ ID NO 170
<211> LENGTH: 439
<212> TYPE: DNA
<213> ORGANISM: Zea mays

<400> SEQUENCE: 170

| | |
|---|---|
| cgctgaggct gttgatcttt acaacaagca ttacaagcgc gacgacaccc gcatgggggt | 60 |
| tgcgtttgac gtaatgggtc gtgtgccata cggaacatcg tttctggata acaggccga | 120 |
| agaaaggtcc tgggacatca acctaggatg gttcttagag ccagtggttc gtggtgacta | 180 |
| ccccttctcc atgagatcat tggctaggga acgactaccc ttcttcaagg acgagcagaa | 240 |
| ggagaagctc gccggttcct ataacatgtt ggggttaaac tactacacct cacggttctc | 300 |
| caaaaacatc gatatctcac caaactactc acctgtgctc aacacttgac gacgcctacg | 360 |
| ccagtcaaga aagttaacgg gcctgacggg aagcccattg gtccttctat gggaaatcca | 420 |
| tggatctaca tgtaccctg | 439 |

<210> SEQ ID NO 171
<211> LENGTH: 434
<212> TYPE: DNA
<213> ORGANISM: Zea mays
<220> FEATURE:
<221> NAME/KEY: unsure
<222> LOCATION: (1)...(434)
<223> OTHER INFORMATION: unsure at all n locations

<400> SEQUENCE: 171

| | |
|---|---|
| gcattgtaga agattacaca tactttgcta aggtgtgctt tgataacttc ggcgacnngg | 60 |
| tgaagaattg gttgaccttt aatgagcccc agacatttac ttccttttcc tacgaaactg | 120 |
| gggtctttgc cccaggtcgg tgctcacctg gactagactg tgcctaccca actgggaatt | 180 |
| cactcgtcga gccttacact gctggccata acattctcct agcccacgct gaggctgttg | 240 |
| atctttacaa caagcattac aagcgcgacg acacccgcat agggcttgcg tttgacgtaa | 300 |
| tgggtcgtgt gccatacnga acatcgtttc tggataaaca ggccgaanaa aggtctgggg | 360 |
| acatcaacct aagatggttc ttaaaaaccan tgggtngtng ngactacccc ttcttcatgg | 420 |
| aattttnggg ttgg | 434 |

<210> SEQ ID NO 172
<211> LENGTH: 464
<212> TYPE: DNA
<213> ORGANISM: Zea mays
<220> FEATURE:
<221> NAME/KEY: unsure
<222> LOCATION: (1)...(464)
<223> OTHER INFORMATION: unsure at all n locations

<400> SEQUENCE: 172

| | |
|---|---|
| gtacatncag cgccacatng ctactcttaa ggtttcaata gacttgggat caaatgtgca | 60 |

```
agggtncttc gcttggtctc tgctggacaa cttttgaatgg ntcgccggct tcaccgaacg      120
ttatggcatt gtctacgtcg accgcaacaa taactgcacg cgctacatga aggagtctgc      180
caagtggttg aaacagttca acgccgcnaa gaanccagc aagaagattc ttacgccagc       240
ttagaaatcg ggggcctcat gatgtgggtg cagnccataa aaaactggtg tgtggtttgg     300
aaccgaaaat tttctggntt tttccnccac gagaggttct ggaggcatac tctccaacac     360
cgtggctaat aacgcattgg tccaattcaa gctggccttg catgcatgca ataaataaag     420
tgatgggttt ncctggttca aaaaacntan naaaaaaagg gggg                      464

<210> SEQ ID NO 173
<211> LENGTH: 426
<212> TYPE: DNA
<213> ORGANISM: Zea mays

<400> SEQUENCE: 173
agcagctcaa aactctagct agctaccagg ggggaaaatg gctccacttc tcgccgcagc      60
catgaaccac gctacccatc cagtccttag aagccatcta ggacccaaca atgagagttt     120
ctcacgacac cacctatctt cttcaccaca agcagtaag cgaaggttta accttagctt      180
tacgccacga tctgcaaggg taggcaatga aaatggagtc caattgttga gccccctcgga   240 aatccctcga agggactggt tccctctga cttcatcttt ggtgccgcca cttcagcgta     300
ccaaattgaa ggtgcatgga acgaagatgg aaaggggga agcaattggg atcacttctg     360
ccacaatttt ccggaaagga taatggacgg gagcaatgca gacattggga gcgaattcgt      420
accaaa                                                                426

<210> SEQ ID NO 174
<211> LENGTH: 396
<212> TYPE: DNA
<213> ORGANISM: Zea mays
<220> FEATURE:
<221> NAME/KEY: unsure
<222> LOCATION: (1)...(396)
<223> OTHER INFORMATION: unsure at all n locations

<400> SEQUENCE: 174
caaatgtgca aggctacttc gcttggtctc tgctggacaa cttttgaatgg ttcgccggct    60 tcaccgaacg ttatggcatt gtctacgtcg accgcaacaa taactgcacg cgctacatga    120
aggagtctgc caagtggttg aaacagttca acgccgcgaa gaagcccagc aagaagattc    180
ttacgccagc ttagaaatcg ggggcctcat gatgtgggtg cagcccataa aaaactggtg    240
tgtggtttgg aaccgaaaat tttctgnttt tttccgccac gagaggttct ggaggcatac    300
tctncagcac cgtggctaat aacgcattgt tccaattcaa tctggccttg tcatgcatgc    360
aataaataaa gtgatgggtt tccctggttc aatatc                              396

<210> SEQ ID NO 175
<211> LENGTH: 435
<212> TYPE: DNA
<213> ORGANISM: Zea mays
<220> FEATURE:
<221> NAME/KEY: unsure
<222> LOCATION: (1)...(435)
<223> OTHER INFORMATION: unsure at all n locations

<400> SEQUENCE: 175
aggagaagct cgccggttcc tataacatgt tgggggttaaa ctactacacc tcacggttct    60
ccaaaaacat cgatatctca ccaaaactact cacctgtgct caacactgac gacgcctacg   120
```

```
ccagtcaaga agttaacggg cctgacggga agcccattgg tcctcctatg ggaaatccat      180
ggatctacat gtaccctgag ggcttgaagg atctccttat gatcatgaag aacaaatacg      240
gaaacccacc tatctacatc acggagaacg gaatcgggga tgttgatacc aaggagacac      300
ctctacccat ggaggatgcc ttaaatgact acaaaaggct agattacatn caagcgccac      360
atcgctactc ttaaggaatc aatagacttg ggatcaaaat gtgcaanggg tactttgctt      420
gggctctgnt ggaca                                                       435

<210> SEQ ID NO 176
<211> LENGTH: 453
<212> TYPE: DNA
<213> ORGANISM: Zea mays
<220> FEATURE:
<221> NAME/KEY: unsure
<222> LOCATION: (1)...(453)
<223> OTHER INFORMATION: unsure at all n locations

<400> SEQUENCE: 176
gacgtaatgg gtcgtgtgcc atacggaana tcgtttctgg ataaacaggc cgaagaaagg      60
ncctgggaca tcaacctagg atggttctta gagccagtgg ttcgtggtga ctacccctc      120 tccatgagat cattggctag gaacgactac cccttcttca aggacgagca aaggagaag      180 ctcgccggtt cctataacat gttggggtta aactactaca cctcacggtt ctccaaaaac      240
atcgatatct caccaaacta ctcacctgtg ctcaacactg acgacgccta cgccagtcaa      300
gaagttaacg ggcctgacgg gaagcccatt ggtcctccta tgggaaatcc atggatctca      360
tgtaccctga gggcttgaag gatctccttt atgaatcatg aagnaccaat tccggaaacc      420
cacctatcta cattaccgga gaacgggatt cgg                                   453

<210> SEQ ID NO 177
<211> LENGTH: 409
<212> TYPE: DNA
<213> ORGANISM: Zea mays
<220> FEATURE:
<221> NAME/KEY: unsure
<222> LOCATION: (1)...(409)
<223> OTHER INFORMATION: unsure at all n locations

<400> SEQUENCE: 177
tccctataat gagtcgtatt agtanggcat cangtactac agaancctca tcaacttgtt      60
gctagaaanc ggcatnnngc catatgtaac aattttccac tgggatgtac ctcaagcact      120
agaggagaag tncggcggct tcctagatnn gagtcataag ngcattgtcg aagattacac      180
atactttgct aaggtgtgct ttgataactt cggcgacaag gtgaagaatt ggttgacctt      240
taatgagccc cagacattta cttccttttc ctacggaact ggggtctttg ccccaggtcg      300
gtgctcacct ggactagact gtgcctaccc anctgggaat tcactcgtcg agccttacac      360
tgctggccat aacattctcc tancccacgc tgaggctgtt gatctttac                  409

<210> SEQ ID NO 178
<211> LENGTH: 371
<212> TYPE: DNA
<213> ORGANISM: Zea mays
<220> FEATURE:
<221> NAME/KEY: unsure
<222> LOCATION: (1)...(371)
<223> OTHER INFORMATION: unsure at all n locations

<400> SEQUENCE: 178
```

```
ttaaactact acacctcacg gttctccaaa aacatcgata tctcaccaaa ctactcacct    60
gtgctcaaca ctgacgacgc ctacgccagt ccaagaagtt aacgggcctg acgggaagcc   120
cattggtcct cctatgggaa atccatggat ctacatgtac cctgagggct tgaaggatct   180
ccttatgatc atgaagaaca aatacggaaa cccanctatc tacatcacgg agaacggaat   240
cggggatgtt gataccaagg agacacctct acccatggag gatgccttaa atgactacaa   300
aaggctagat tacatccagc gccacatcgc tactcttaag gaatcaatag acttgggatc   360
aatgtgcaag g                                                        371

<210> SEQ ID NO 179
<211> LENGTH: 342
<212> TYPE: DNA
<213> ORGANISM: Zea mays
<220> FEATURE:
<221> NAME/KEY: unsure
<222> LOCATION: (1)...(342)
<223> OTHER INFORMATION: unsure at all n locations

<400> SEQUENCE: 179
gttctagcta gctagcaaag ggggggaaaa tggctccgct tctcgctgct gccatgaacc    60
acgctgcagc ccatcctggc cttaggagcc acctagtagg acccaacaat gagagtttcn   120
cacggcacca cctgccgtct tcttctccac agagcagcaa gcgaaggtgt aaccttagct   180
ttactacacg atctgcaaga gtaggcagcc aaaatggagt ccaaatgttg agcccctcgg   240
aaatcccaca aagggactgg ttcccctctg acttcacctt cggtgccgcc acttcagcgt   300
accaaattga aggtgcttgg aatgaagatg gaaaggggga aa                     342

<210> SEQ ID NO 180
<211> LENGTH: 464
<212> TYPE: DNA
<213> ORGANISM: Zea mays
<220> FEATURE:
<221> NAME/KEY: unsure
<222> LOCATION: (1)...(464)
<223> OTHER INFORMATION: unsure at all n locations

<400> SEQUENCE: 180
gttctagcta gctagcaaag ggggggaaaa tggctccgct tctcgctgct gccatgaacc    60
acgctgcagc ccatcctggc cttaggagcc acctagtagg acccaacaat gagagtttct   120
cacggcacca cctgccgtct tcttctccac agagcagcaa gcgaaggtgt aaccttagct   180
ttactacacg atctgcaaga gtaggcagcc aaaatggagt ccaaatgttg agcccctcgg   240
aaatcccaca aagggactg gtcccctct gacttcacct tcngtgccga cacttcagng   300
gtnccaaatt gaaggtgctt ggaatgaaga tggaaagggg gaaagcaact gggatcactt   360
ntggcacaat cattcggaaa ggatactggg acgggagcna attcanaaca ttggagcgaa   420
tttcgtacca ntatgtacaa aaacgggacg ttnagatttg ctna                   464

<210> SEQ ID NO 181
<211> LENGTH: 463
<212> TYPE: DNA
<213> ORGANISM: Zea mays
<220> FEATURE:
<221> NAME/KEY: unsure
<222> LOCATION: (1)...(463)
<223> OTHER INFORMATION: unsure at all n locations

<400> SEQUENCE: 181
ggtcaagtaa cgngggtcga nccangcctc taaatagact cnnattacta aggtgtgctt    60
```

```
tgataacttc ggcgacaang tgaagaattg gttgaccttt aatgagcccc agacatttac    120
ttccttttcc tacggaactg gggtctttgc cccaggtcgg tgctcacctg gactaagact    180
gtgcctaccc aactgggaat tcactcgtcg agccttacac tgctggccat aacattctcc    240
tagcccacgc tgaggctgtt gatctttaca acaagcatta caagcgcgac gacacccgca    300
tagggcttgc gtttgacgta atgggtcgtg tgccatacgg aacatcgttt ctgggataaa    360
canggccgaa gaaaagtcct gggaaatcaa cctanggatg ggtcctaaag ccaattgntc    420
ntggtgaacn accccntcnc aananattat tggctaggga aca                     463

<210> SEQ ID NO 182
<211> LENGTH: 337
<212> TYPE: DNA
<213> ORGANISM: Zea mays

<400> SEQUENCE: 182
gggaaatcca tggatctaca tgtaccctga gggcttgaag gatctcctta tgatcatgaa     60
gaacaaatac ggaaacccac ctatctacat cacggagaac ggaatcgggg atgttgatac    120
caaggagaca cctctacccca tggaggatgc cttaaatgac tacaaaaggc tagattacat    180
ccagcgccac atcgctactc ttaaggaatc aatagacttg ggatcaaatg tgcaaggcta    240
cttcgcttgg tctctgctgg acaactttga atggttcgcc ggcttcaccg aacgttatgg    300
cattgtctac gtcgaccgca acaattactg cacgcgt                            337

<210> SEQ ID NO 183
<211> LENGTH: 343
<212> TYPE: DNA
<213> ORGANISM: Zea mays
<220> FEATURE:
<221> NAME/KEY: unsure
<222> LOCATION: (1)...(343)
<223> OTHER INFORMATION: unsure at all n locations

<400> SEQUENCE: 183
acggaacatc gtttctggat aaacaggccg aagaaaggtc ctgggacatc aacctaggat     60
gnttcttaga gccagtggtt cgtggtgact accccttctc catgagatca ttggctaggg    120
aacgactacc cttcttcaag gacgagcaga aggagaagct cgccggttcc tataacatgt    180
tggggttaaa ctactacacc tcacggttct ccaaaaacat cgatatctca ccaaactact    240
cacctgtgct caacactgac gacgcctacg ccagtcaaga agttaacggg cctgacggga    300
agcccatggt cctcctatgg gaaatccatg gatctacatg tac                     343

<210> SEQ ID NO 184
<211> LENGTH: 415
<212> TYPE: DNA
<213> ORGANISM: Zea mays
<220> FEATURE:
<221> NAME/KEY: unsure
<222> LOCATION: (1)...(415)
<223> OTHER INFORMATION: unsure at all n locations

<400> SEQUENCE: 184
ccactgagga tgtacctcaa gcactagaag agaagtacgg cggcttccta gataagagtc     60
ataagagcat tgtagaagat tacacatact ttgctaaggt gtgctttgat aacttcggcg    120
acaaggtgaa gaattggttg accttttaatg agccccagac atttacttcc ttttcctacg    180
gaactggggt ctttgcccca ggtcggtgct cacctggact agactgtgcc tacccaactg    240
```

```
ggaattcact cgtcgagcct tacactgctg gccataacat tctcctagcc cacgctgagg    300
ctgttgatct ttacaacaag cattacaaag cgcgacgaca acccgcataa gggcttgccg    360
ttggacgtta atgggtccnt gttgccatac ggaaacatcg tttctggata aacag         415
```

```
<210> SEQ ID NO 185
<211> LENGTH: 443
<212> TYPE: DNA
<213> ORGANISM: Zea mays
<220> FEATURE:
<221> NAME/KEY: unsure
<222> LOCATION: (1)...(443)
<223> OTHER INFORMATION: unsure at all n locations

<400> SEQUENCE: 185
ggcattgtct acgtcgaccg caaaaataac tacacgcgct acatgaagga gtcagccang     60
tggttaaaag agttcaatac tgcgaagaag cctagcaaga agattattac gccagcttaa    120
aaacatggga cctcgtgatg tgggtacggt gccacccatg aaataaaaac ctagtgtgtg    180
gtttgaaacc taaattttc ttttcttt ttgcaccatg agagaggtag tggagtcata       240
ttctccagca ccgtggctaa taatgtattg ttgcagtaca atctagcatt gtcgtcatgc    300
aataaataaa gtgactggtt tccctatttc aaannnnnnn nnnnnnnnnn nccgcccttt    360
tttttatct cattccgtat tttatttcct ttttcaaact ccactctgca aacagtgtca    420
aacagtgttg tcatctacag ttt                                            443
```

```
<210> SEQ ID NO 186
<211> LENGTH: 329
<212> TYPE: DNA
<213> ORGANISM: Zea mays

<400> SEQUENCE: 186
attggtcctc ctatgggaaa tccatggatc tacatgtacc ctgagggctt gaaggatctc     60
cttatgataa tgaagaacaa atacggaaac ccacctatct acatcaccga aacggaatc    120
ggggatgttg ataccaaaga gacacctcta cccatggagg ctgccttaaa tgactacaaa    180
aggctagatt acatccagcg ccacatcgct actcttaagg aatcaataga cttgggatca    240
aatgtgcaag gctacttcgc ttggtctctg ctggacaact ttgaatggtt tgccggcttc    300
accgaacgtt atggcattgt ctacgtcga                                      329
```

```
<210> SEQ ID NO 187
<211> LENGTH: 332
<212> TYPE: DNA
<213> ORGANISM: Zea mays
<220> FEATURE:
<221> NAME/KEY: unsure
<222> LOCATION: (1)...(332)
<223> OTHER INFORMATION: unsure at all n locations

<400> SEQUENCE: 187
caaagctcta gttctagcta gctagcaaan gggggaaaa tggctccgct tctcgctgct      60
gccatgaacc acgctgcagc ccatcctggc cttaggagcc acctagtagg acccaacaat    120
gagagtttct cacggcacca cctgccgtct tcttctccac agagcagcaa gcgaaggtgt    180
aaccttagct ttactacacg atctgcaaga gtaggcagcc aaaatggagt ccaaatgttg    240
agccctcgg aaatcccaca aagggactgg ttcccctctg acttcacctt cggtgccgcc     300
acttcagcgt accaaattga aggtgcttgg aa                                  332
```

<210> SEQ ID NO 188
<211> LENGTH: 487
<212> TYPE: DNA
<213> ORGANISM: Zea mays
<220> FEATURE:
<221> NAME/KEY: unsure
<222> LOCATION: (1)...(487)
<223> OTHER INFORMATION: unsure at all n locations

<400> SEQUENCE: 188
gcgcggacgc cctgggacat caacctanga tngtnnttag agccactggn gcattggtga      60 ctaccccctgg nccgnganat catnggctng ggaacgacta cccttntnca angccganca    120
naangagaan ctnccggntc ctataacatg ttncggttaa actactacac ctcacggttc     180
tccanaaaca tcgatatctc accaaactac tcacctgtgc tcaacactga cgaccccta c    240 nccngtcaag annttaacgn gcctcacngg aancccattg gtcctcctat cggaaatcca    300
tgnatctaca tgnaccctga gggcttgaag gatcttctta tgatcatgan naacnantac    360
tggaaaccca cctatctaca tcacggataa ccgaatccng gatgntgatc caatgaagac    420
acctttancc atggnacgat ccttananta ctnccaaaan cttgattaca ntcancggca    480 attngtt                                                              487

<210> SEQ ID NO 189
<211> LENGTH: 343
<212> TYPE: DNA
<213> ORGANISM: Zea mays

<400> SEQUENCE: 189
caaagctcta gttctagcta gctagcaaag gggggaaaa tggctccgct tctcgctgct      60
gccatgaacc acgctgcagc ccatcctggc cttaggagcc acctagtagg acccaacaat    120
gagagtttct cacggcacca cctgccgtct tcttctccac agagcagcaa gcgaaggtgt    180
aaccttagct ttactacacg atctgcaaga gtaggcagcc aaaatggagt ccaaatgttg    240
agcccctcga atcccacaa agggactggt tcccctctga cttcaccttc ggtgccgcca    300
ttcagcgtac caaattgaag gtgcttggaa tgaagatgga aag                      343

<210> SEQ ID NO 190
<211> LENGTH: 331
<212> TYPE: DNA
<213> ORGANISM: Zea mays

<400> SEQUENCE: 190
agcagctcaa agctctagtt ctagctagct agcaaagggg gggaaaatgg ctccgcttct     60
cgctgctgcc atgaaccacg ctgcagccca tcctggcctt aggagccacc tagtaggacc    120
caacaatgag agtttctcac ggcaccacct gccgtcttct tctccacaga gcagcaagcg    180
aaggtgtaac cttagcttta ctacacgatc tgcaagagta ggcagccaaa atggagtcca    240
aatgttgagc ccctcggaaa tcccacaaag ggactggttc ccctctgact tcaccttcgg    300
tgccgccact tcagcgtacc aaattgaagg t                                   331

<210> SEQ ID NO 191
<211> LENGTH: 324
<212> TYPE: DNA
<213> ORGANISM: Zea mays

<400> SEQUENCE: 191
caaagctcta gttctagcta gctagcaaag gggggaaaa tggctccgct tctcgctgct      60

| | |
|---|---|
| gccatgaacc acgctgcagc ccatcctggc cttaggagcc acctagtagg acccaacaat | 120 |
| gagagtttct cacggcacca cctgccgtct tcttctccac agagcagcaa gcgaaggtgt | 180 |
| aaccttagct ttactacacg atctgcaaga gtaggcagcc aaaatggagt ccaaatgttg | 240 |
| agcccctcgg aaatcccaca aagggactgg ttcccctctg acttcacctt cggtgccgcc | 300 |
| acttcagcgt accaaattga aggt | 324 |

<210> SEQ ID NO 192
<211> LENGTH: 322
<212> TYPE: DNA
<213> ORGANISM: Zea mays

<400> SEQUENCE: 192

| | |
|---|---|
| gaaaatggct ccgcttctcg ctgctgccat gaaccacgct gcagcccatc ctggccttag | 60 |
| agccaccta gtaggaccca acaatgagag tttctcacgg caccacctgc cgtcttcttc | 120 |
| tccacagagc agcaagcgaa ggtgtaacct tagctttact acacgatctg caagagtagg | 180 |
| cagccaaaat ggagtccaaa tgttgagccc ctcggaaatc ccacaaaggg actggttccc | 240 |
| ctctgacttc accttcggtg ccgccacttc agcgtaccaa attgaaggtg cttggaatga | 300 |
| agatggaaag ggggaaagca ac | 322 |

<210> SEQ ID NO 193
<211> LENGTH: 324
<212> TYPE: DNA
<213> ORGANISM: Zea mays

<400> SEQUENCE: 193

| | |
|---|---|
| cgacgacacc cgcatagggc ttgcgtttga cgtaatgggt cgtgtgccat acggaacatc | 60 |
| gtttctggat aaacaggccg aagaaggtc ctgggacatc aacctaggat ggttcttaga | 120 |
| gccagtggtt cgtggtgact accccttctc catgagatca ttggctaggg aacgactacc | 180 |
| cttcttcaag gacgagcaga aggagaagct cgccggttcc tataacatgt tggggttaaa | 240 |
| ctactacacc tcacggttct ccaaaaacat cgatatctca ccaaactact cacctgtgct | 300 |
| caacactgac gacgcctacg ccat | 324 |

<210> SEQ ID NO 194
<211> LENGTH: 331
<212> TYPE: DNA
<213> ORGANISM: Zea mays

<400> SEQUENCE: 194

| | |
|---|---|
| cttgttgcta gaaaacggca tagagccata tgtaacaatt ttccactggg atgtacctca | 60 |
| agcactagaa gagaagtacg gcggcttcct agataagagt cataagagca ttgtagaaga | 120 |
| ttacacatac tttgctaagg tgtgctttga taacttcggc gacaaggtga agaaggttga | 180 |
| cctttaatga gccccagaca tttacttcct tttcctacgg aactgggtc tttgccccag | 240 |
| gtcggtgctc acctggacta gactgtgcct acccaactgg gaattcactc gtcgagcctt | 300 |
| acactgctgg ccataacatt ctcctagccc a | 331 |

<210> SEQ ID NO 195
<211> LENGTH: 320
<212> TYPE: DNA
<213> ORGANISM: Zea mays

<400> SEQUENCE: 195

| | |
|---|---|
| gaggctgttg atctttacaa caagcattac aagcgcgacg acacccgcat agggcttgcg | 60 |

```
tttgacgtaa tgggtcgtgt gccatacgga acatcgtttc tggataaaca ggccgaagaa      120
aggtcctggg acatcaacct aggatggttc ttagagccag tggttcgtgg tgactacccc      180
ttctccatga gatcattggc tagggaacga ctacccttct tcaaggacga gcagaaggag      240
aagctcgccg gttcctataa catgttgggg ttaaactact acacctcacg gttctccaaa      300
aacatcgata tctcaccaaa                                                  320
```

```
<210> SEQ ID NO 196
<211> LENGTH: 322
<212> TYPE: DNA
<213> ORGANISM: Zea mays
<220> FEATURE:
<221> NAME/KEY: unsure
<222> LOCATION: (1)...(322)
<223> OTHER INFORMATION: unsure at all n locations

<400> SEQUENCE: 196
gggaacgact acccttcttc aaggacgagc agaaggagaa gctcgccggt tcctataaca       60
tgttggggtt aaactactac acctcacggt tctccaaaaa catcgatatc tcaccaaact      120
actcacctgt gctcaacact gacgacgcct acgccagtca agaagttaac gggcctgacg      180
ggaagcccat tggtcctcct atgggaaatc catggatcta catgtaccct gagggcttga      240
aggatctcct tatgatcatg aagaacaaat acggaaaccc acctatctnc atcacggaga      300
acggaatcgg ggatgttgat ac                                               322
```

```
<210> SEQ ID NO 197
<211> LENGTH: 330
<212> TYPE: DNA
<213> ORGANISM: Zea mays
<220> FEATURE:
<221> NAME/KEY: unsure
<222> LOCATION: (1)...(330)
<223> OTHER INFORMATION: unsure at all n locations

<400> SEQUENCE: 197
cnggcctgac gggaagccca ttggtcctcc tatgggaaat ccatggatct acatgtaccc       60
tgagggcttg aaggatctcc ttatgatcat gaagaacaaa tacggaaacc cacctatcta      120
catcacggag aacggaatcg gggatgttga taccaaggag acacctctac ccatggagga      180
tgccttaaat gactacaaaa ggctagatta catccagcgc cacatcgcta ctcttaagga      240
atcaatagac ttgggatcaa atgtgcaagg ctacttcgct ggtctctgct ggacaacttt      300
gaatggttcg ccggcttcac cgaacgntat                                       330
```

```
<210> SEQ ID NO 198
<211> LENGTH: 318
<212> TYPE: DNA
<213> ORGANISM: Zea mays

<400> SEQUENCE: 198
caaagctcta gttctagcta gctagcaaag gggggaaaa tggctccgct tctcgctgct        60
gccatgaacc acgctgcagc ccatcctggc cttaggagcc acctagtagg acccaacaat      120
gagagtttct cacggcacca cctgccgtct tcttctccac agagcagcaa gcgaaggtgt      180
aaccttagct ttactacacg atctgcaaga gtaggcagca aaaatggagt ccaaatgttg      240 agccctcgg aaatcccaca aagggactgg ttcccctctg acttcacctt cggtgccgcc       300
acttcagcgt accaaatt                                                    318
```

<210> SEQ ID NO 199
<211> LENGTH: 318
<212> TYPE: DNA
<213> ORGANISM: Zea mays

<400> SEQUENCE: 199

```
agcaattcag acattggagc gaattcgtac catatgtaca aaacggacgt cagattgctc      60
aaggaaatgg gcatggacgc atataggttc tctatctctt ggcccagaat actgccgaag     120
ggaaccaaag aaggaggtat taacccggat ggcatcaagt actacagaaa cctcatcaac     180
ttgttgctag aaaacggcat agagccatat gtaacaattt tccactggga tgtacctcaa     240
gcactagaag agaagtacgg cggcttccta gataagagtc ataagagcat tgtagaagat     300
tacacatact ttgctaag                                                   318
```

<210> SEQ ID NO 200
<211> LENGTH: 341
<212> TYPE: DNA
<213> ORGANISM: Zea mays
<220> FEATURE:
<221> NAME/KEY: unsure
<222> LOCATION: (1)...(341)
<223> OTHER INFORMATION: unsure at all n locations

<400> SEQUENCE: 200

```
cggacntggg cntagctagc aggggggaa atggctccac ttctcgccgc agccatganc      60
cacgctgccc atccagtcct tagaagccat ctaggaccca acaatgagag tttctcacga     120
caccacctat cttcttcanc gcaaagcagt aaagcgaagg tttaaccttt gctttacgcc     180
acgatctgca agagtaggca atcaaaatgg agtccaattg ttgagcccctt cggaaatccc    240 tcgaagggac tggttccccct ccgacttcat ctttggtgcc gccacttcag cgtaccaaat    300
tgaaggtgct tggaacgaag atggaaaggg ggaaagcaat t                         341
```

<210> SEQ ID NO 201
<211> LENGTH: 323
<212> TYPE: DNA
<213> ORGANISM: Zea mays
<220> FEATURE:
<221> NAME/KEY: unsure
<222> LOCATION: (1)...(323)
<223> OTHER INFORMATION: unsure at all n locations

<400> SEQUENCE: 201

```
cctagtagga cccaacaatg agagtttctc acggcaccac ctgccgtctt cttctccaca      60
gagcagcaag cgaaggtgta accttagctt actacacgat ctgcaagagt aggcagccaa     120
aatggagtcc aaatgttgag cccctcggaa atcccacaaa gggactggtt cccctctgac     180
ttcaccttcg gtgccgccac ttcagcgtac caaattgaag gtgcttggaa tgaagatgga     240
aagggggaaa gcaactggga tcacttctgc cacaatcatc cggaaangat actggacngg     300
agcaattcag acattggagc gaa                                             323
```

<210> SEQ ID NO 202
<211> LENGTH: 318
<212> TYPE: DNA
<213> ORGANISM: Zea mays

<400> SEQUENCE: 202

```
aaaatggagt ccaaatgttg agcccctcgg aaatcccaca aagggactgg ttcccctctg      60
acttcacctt cggtgccgcc acttcagcgt accaaattga aggtgcttgg aatgaagatg     120
```

```
gaaaggggga aagcaactgg gatcacttct gccacaatca tccggaaagg atactggacg      180
ggagcaattc agacattgga gcgaattcgt accatatgta caaaacggac gtcagattgc      240
tcaaggaaat gggcatggac gcatataggt tctctatctc ttggcccaga atactgccga      300
aggaaccaaa gaaggagg                                                    318

<210> SEQ ID NO 203
<211> LENGTH: 312
<212> TYPE: DNA
<213> ORGANISM: Zea mays

<400> SEQUENCE: 203
gccatatgta acaatttcc actgggatgt acctcaagca ctagaagaga agtacggcgg       60
cttcctagat aagagtcata agagcattgt agaagattac acatactttg ctaaggtgtg     120
ctttgataac ttcggcgaca aggtgaagaa ttggttgacc tttaatgagc ccagacatt      180 tacttccttt tcctacggaa ctggggtctt tgccccaggt cggtgctcac ctggactaga     240
ctgtgcctac ccaactggga attcactcgt cgagccttac actgctggcc ataacattct     300
cctagcccac gc                                                          312

<210> SEQ ID NO 204
<211> LENGTH: 315
<212> TYPE: DNA
<213> ORGANISM: Zea mays
<220> FEATURE:
<221> NAME/KEY: unsure
<222> LOCATION: (1)...(315)
<223> OTHER INFORMATION: unsure at all n locations

<400> SEQUENCE: 204
gttctagcta gctagcaaan gggggggaaaa tggctccgct tctcgctgct gccatgaacc     60
acgctgcagc ccatcctggc cttaggagcc acctagtagg acccaacaat gagngtttct     120
cacggaacca cctgccgtct tcttctccac agagcagcaa gcgaaggtgt aaccttagct     180
ttactacacg atctgcaaga gtaggcagcc aaaatgttgag tccaaatgttg agcccctcgg    240 aaatcccaca aagggactgg ttcccctctg acttcacctt cggtgccgcc acttcagcgt     300
accaaattga aggtg                                                       315

<210> SEQ ID NO 205
<211> LENGTH: 321
<212> TYPE: DNA
<213> ORGANISM: Zea mays

<400> SEQUENCE: 205
gtacggcggg attcttagat aagactcata agaggattgt aaatgattac aaaaacttcg     60
ctaaggtgtg cttcgacaac tttggtgaca aggtgaagaa ttggttgacc tttaatgagc     120
cccagacatt tacttcattt tcctatggaa ccggggtctt tgccccagga cgatgctcac     180
cgggactaga ctgtgccatc ccaactggga attcactcgt cgaaccttac attgctggcc     240
acaacattct tctagcccac gctgaggctg ttgatcttta caacaagtat tacaagggcg     300
agaacggccg cataggtctt g                                                321

<210> SEQ ID NO 206
<211> LENGTH: 335
<212> TYPE: DNA
<213> ORGANISM: Zea mays
<220> FEATURE:
```

```
<221> NAME/KEY: unsure
<222> LOCATION: (1)...(335)
<223> OTHER INFORMATION: unsure at all n locations

<400> SEQUENCE: 206
tctacatgta cccctgagggc ttgaaggatc tccttatgat antgaagaac aaatacggaa      60
acccacctat ctacatcacc gagaacggaa tccggggatg ttgataccaa agagacacct     120
ctacccatgg aggctgcctt aaatgactac aaaaggctag attacatcca gcgccacata     180
cgctactctt aaggaatcaa tagacttggg atcaaatgtg caaggctact tcgcttggtc     240
tctgctggac aactttgant ggtttgccgg cttcaccgaa cgttatggcn tgtctacgtc     300
gaccgcaaca ataactgcac gcgctacatg aagga                                335

<210> SEQ ID NO 207
<211> LENGTH: 346
<212> TYPE: DNA
<213> ORGANISM: Zea mays
<220> FEATURE:
<221> NAME/KEY: unsure
<222> LOCATION: (1)...(346)
<223> OTHER INFORMATION: unsure at all n locations

<400> SEQUENCE: 207
gaagaacaaa tacggaaacc cacctatcta catcacngag aacggaatcg gggatgttga      60
taccaaggag acacctctac ccatggagga tgccttaaat gactacaaaa ggctagatta     120
catccagcgc cacatcgcta ctcttnaggn atcnatagac ttgggatcaa atgtgcaagg     180
ctacttcgct tggtctctgc tggacaactt tgaatggttc gccggcttca ccgaacgtta     240
tggcattgtc tacgtcgacc gcaacnataa ctgcacgngt acatgaagga gtctgccaag     300
tggttgaaac ngttcnacgc nncgaagaag ccccngcaag aagatt                    346

<210> SEQ ID NO 208
<211> LENGTH: 360
<212> TYPE: DNA
<213> ORGANISM: Zea mays
<220> FEATURE:
<221> NAME/KEY: unsure
<222> LOCATION: (1)...(360)
<223> OTHER INFORMATION: unsure at all n locations

<400> SEQUENCE: 208
taacattctc ctagcccacg ctgaggctgt tgatctttac aacaagcatt acaagcgcga      60 cgacaccgc atagggattg cgtttgacgt aatgggtcgt gtgccatacg aacatcgtt      120 tctggataaa caggccgaag aaaggtcctg ggacatcaac ctaggatggt tcttagagcc     180
agtggttcgt ggtgactacc ccttctccat gagatcattg gctagggaac gactacccctt    240 cttcaaggac gagcagaagg agaagctcgc cggttcctat aacattgttg gggttaacta     300
tacacctcag gttctccaaa aacatcgata tctcaccaac tatcactgtg ctcaacntga     360

<210> SEQ ID NO 209
<211> LENGTH: 307
<212> TYPE: DNA
<213> ORGANISM: Zea mays

<400> SEQUENCE: 209
gctagctagc aaagggggg aaaatggctc cgcttctcgc tgctgccatg aaccacgctg      60
cagcccatcc tggccttagg agccaccttag taggacccaa caatgagagt ttctcacggc    120
accacctgcc gtcttcttct ccacagagca gcaagcgaag gtgtaacctt agctttacta    180
```

```
cacgatctgc aagagtaggc agccaaaatg gagtccaaat gttgagcccc tcggaaatcc      240
cacaaaggga ctggttcccc tctgacttca ccttcggtgc cgccacttca gcgtaccaaa      300
ttgaagg                                                                307

<210> SEQ ID NO 210
<211> LENGTH: 321
<212> TYPE: DNA
<213> ORGANISM: Zea mays
<220> FEATURE:
<221> NAME/KEY: unsure
<222> LOCATION: (1)...(321)
<223> OTHER INFORMATION: unsure at all n locations

<400> SEQUENCE: 210 gggggaaaa tggctccact tctcgccgca gccatgaacc acgctaccca tccagtcctt      60
agaagccatc taggacccaa caatgngagt ttctcacgac accacctatc ttcttcacca    120
caaagcagta agcgaaggtt taaccttagc tttacgccac gatctgcaag ggtaggcaat    180
gaaaatggag tccaattgtt gagcccctcg gaaatccctc gaagggactg gttcccctct    240
gacttcatct ttggtgccgc cacttcagcg taccaaattg aaggtgcatg gaacgaagat    300
ggaaaggggg aaagcaattg g                                              321

<210> SEQ ID NO 211
<211> LENGTH: 308
<212> TYPE: DNA
<213> ORGANISM: Zea mays

<400> SEQUENCE: 211
caaagctcta gttctagcta gctagcaaag gggggaaaa tggctccgct tctcgctgct      60
gccatgaacc acgctgcagc ccatcctggc cttaggagcc acctagtagg acccaacaat    120
gagagtttct cacggcacca cctgccgtct tcttctccac agagcagcaa gcgaaggtgt    180
aaccttagct ttactacacg atctgcaaga gtaggcagcc aaaatggagt ccaaatgttg    240
agcccctcgg aaatcccaca aagggactgg ttcccctctg acttcacctt cggtgccgcc    300
acttcagc                                                             308

<210> SEQ ID NO 212
<211> LENGTH: 320
<212> TYPE: DNA
<213> ORGANISM: Zea mays

<400> SEQUENCE: 212
actgacgacg cctacgccag tcaagaagtt aacgggcctg acgggaagcc cattggtcct      60
cctatgggaa atccatggat ctacatgtac cctgagggct tgaaggatct ccttatgatc    120
atgaagaaca aatacggaaa cccacctatc tacatcacgg agaacggaat cggggatgtt    180
gataccaagg agacacctct acccatggag gatgccttaa atgactacaa aggctagat     240 tacatccagc gccacatcgc tactcttaag gaatcaatag acttgggatc aaatgtgcaa    300
ggctattcgc tggtctctgc                                                320

<210> SEQ ID NO 213
<211> LENGTH: 331
<212> TYPE: DNA
<213> ORGANISM: Zea mays
<220> FEATURE:
<221> NAME/KEY: unsure
<222> LOCATION: (1)...(331)
```

<223> OTHER INFORMATION: unsure at all n locations

<400> SEQUENCE: 213

```
caaaactcta gctagctacc angggggaaa atggctccac ttctcgccgc agccatgaac    60
cacgctaccc atccagtcct tagaagccat ctaggaccca acaatgagag tttctcacga   120
caccaactat cttcttcacc acaaagcagt aagcgaaggt ttaaccttag ctttacgcca   180
cgatctgcaa gggtaggcaa tgaaaatgga gtccaattgt tgagcccctc ggaaatccct   240
cgaagggact ggttcccctc tgacttcaac tttggtggcg gcacttcagc gtanccaatt   300
gaaagtgcat ggaacgaaga tggaaagggg g                                  331
```

<210> SEQ ID NO 214
<211> LENGTH: 304
<212> TYPE: DNA
<213> ORGANISM: Zea mays

<400> SEQUENCE: 214

```
cattctccta gcccacgctg aggctgttga tctttacaac aagcattaca agcgcgacga    60
cacccgcata gggcttgcgt ttgacgtaat gggtcgtgtg ccatacggaa catcgtttct   120
ggataaacag gccgaagaaa ggtcctggga catcaaccta ggatggttct tagagccagt   180
ggttcgtggt gactacccct ctccatgag atcattggct agggaacgac tacccttctt    240
caaggacgag cagaaggaga agctcgccgg ttcctataac atgttggggt taaactacta   300
cacc                                                                304
```

<210> SEQ ID NO 215
<211> LENGTH: 307
<212> TYPE: DNA
<213> ORGANISM: Zea mays

<400> SEQUENCE: 215

```
caaaactcta gctagctagc agggggggaa atggctccac ttctcgccgc agccatgaac    60
cacgctgccc atccagtcct tagaagccat ctaggaccca acaatgagag tttctcacga   120
caccacctat cttcttcacc gcaaagcagt aagcgaaggt ttaaccttag ctttacgcca   180
cgatctgcaa gagtaggcaa tcaaaatgga gtccaattgt tgagcccttc ggaaatccct   240
cgaagggact ggttcccctc cgacttcatc tttggtgccg ccacttcagc gtaccaaatt   300
gaaggtg                                                             307
```

<210> SEQ ID NO 216
<211> LENGTH: 323
<212> TYPE: DNA
<213> ORGANISM: Zea mays

<400> SEQUENCE: 216

```
ctctagttct agctagctag caagggggg gaaaatggct ccgcttctcg ctgctgccat    60
gaaccacgct gcagcccatc ctggccttag gagccaccta gtaggaccca acaaatgaga   120
gtttctcacg gcaacaacct gccgtcttct tctccacaga gcagcaagcg aaaggtgtaa   180
ccttagcttt actacacgat ctgcaagagt aggcagccaa aatggagtcc aaatgttgag   240
cccctcggaa atcccacaaa gggactggtt ccctctgac ttcaccttcg gtgccgccac    300
ttcagcgtac caaattgaag gtg                                           323
```

<210> SEQ ID NO 217
<211> LENGTH: 303

```
<212> TYPE: DNA
<213> ORGANISM: Zea mays
<220> FEATURE:
<221> NAME/KEY: unsure
<222> LOCATION: (1)...(303)
<223> OTHER INFORMATION: unsure at all n locations

<400> SEQUENCE: 217
anaaaacggc atagagccat atgtaacaat tttccactgg gatgtacctc aagcactaga    60
agagaagtac ggcggcttcc tagataagag tcataagagc attgtagaag attacacata   120
ctttgctaag gtgtgctttg taacttcgg cgacaaggtg aagaattggt tgacctttaa   180
tgagccccag acatttactt cctttcctca cggaactggg gtctttgccc caggtcggtg   240
ctcacctgga ctagactgtg cctacccaac tgggaattca ctcgtcgagc cttacactgc   300
tgg                                                                  303

<210> SEQ ID NO 218
<211> LENGTH: 303
<212> TYPE: DNA
<213> ORGANISM: Zea mays
<220> FEATURE:
<221> NAME/KEY: unsure
<222> LOCATION: (1)...(303)
<223> OTHER INFORMATION: unsure at all n locations

<400> SEQUENCE: 218
gctagattac atccagcgcc acatcgctac tcttaaggaa tcaatagact tgggatcaaa    60
tgtgcaaggc tacttcgctt ggtctctgct ggacaacttt gaatggttcg ccggcttcac   120
cgaacgttat ggcattgtct acgtcgaccg caacaataan tgcacgcgct acatgaagga   180
gtctgccaag tggttgaaac agttcaacgc cgcgaagaag cccagcaaga agattcttac   240
gccagcttag aaatcggggg cctcatgatg tgggtgcagc cataaaaaaa ctggtgtgtg   300
gtt                                                                  303

<210> SEQ ID NO 219
<211> LENGTH: 309
<212> TYPE: DNA
<213> ORGANISM: Zea mays
<220> FEATURE:
<221> NAME/KEY: unsure
<222> LOCATION: (1)...(309)
<223> OTHER INFORMATION: unsure at all n locations

<400> SEQUENCE: 219
caaagctcta gttctagcta gctagcaaag gggggaaaa tggctccgct tctcgctgct    60
gccatgaacc acgctgcagc ccatcctggc cttaggagcc acctagtang acccaacaat   120
gagagtttct cacggcacca cctgccgtct tcttctccac agagcagcaa gcgaaggtgt   180
aaccttagct ttactacacg atctgcaaga gtaggcagcc aaaatggagt ccaaatgttg   240
agcccctcgg aaatcccaca aagggactgg ttcccctctg acttcacttc ggtgccgcca   300
cttcagcgt                                                            309

<210> SEQ ID NO 220
<211> LENGTH: 299
<212> TYPE: DNA
<213> ORGANISM: Zea mays

<400> SEQUENCE: 220
caaagctcta gttctagcta gctagcaaag gggggaaaa tggctccgct tctcgctgct    60
```

```
gccatgaacc acgctgcagc ccatcctggc cttaggagcc acctagtagg acccaacaat    120
gagagtttct cacggcacca cctgccgtct tcttctccac agagcagcaa gcgaaggtgt    180
aaccttagct ttactacacg atctgcaaga gtaggcagcc aaaatggagt ccaaatgttg    240
agcccctcgg aaatcccaca aagggactgg tttccctctg acttcacctt cggtgccgc     299
```

<210> SEQ ID NO 221
<211> LENGTH: 312
<212> TYPE: DNA
<213> ORGANISM: Zea mays
<220> FEATURE:
<221> NAME/KEY: unsure
<222> LOCATION: (1)...(312)
<223> OTHER INFORMATION: unsure at all n locations

<400> SEQUENCE: 221

```
cnancagctc aaagctctag ttctagctag ctagcaaagg gggggaaaat ggctccnctt    60
ctcgctgctg ccatgaacca cgctgcagcn catcctggcc ttaggagcca cctagtagga    120
cccaacaatg agagtttctc acggcaccac ctgcngtctt cttctccaca gagcagcaag    180
cgaaggtgta accttagctt tactacacga tctgcaagag taggcagcca aaatggagtc    240
caaatgttga gcccctcgga aatcncacaa agggactggt tccctctga cttcaccttc     300 ggtgccgcca ct                                                        312
```

<210> SEQ ID NO 222
<211> LENGTH: 309
<212> TYPE: DNA
<213> ORGANISM: Zea mays

<400> SEQUENCE: 222

```
caattttcca ctgggatgta cctcaagcac tagaagagaa gtacggcggc ttcctagata    60
agagtcataa gagcattgta gaagattaca catactttgc taaggtgtgc tttgataact    120
tcggcgacaa ggtgaagaat tggttgacct ttaatgagcc ccagacattt acttcctttt    180
cctacggaac tggggtcttt gccccaggtc ggtgctcacc tggactagac tgtgcctacc    240
caactgggaa ttcactcgtc gagccttaca ctgctggcca taacattctc ctagcccagc    300
tgaggctgt                                                            309
```

<210> SEQ ID NO 223
<211> LENGTH: 305
<212> TYPE: DNA
<213> ORGANISM: Zea mays

<400> SEQUENCE: 223

```
gcaccacctg ccgtcttctt ctccacagag cagcaagcga aggtgtaact tagctttact    60
acacgatctg caagagtagg cagccaaaat ggagtccaaa tgttgagccc ctcggaaatc    120
ccacaaaggg actggttccc ctctgacttc accttcggtg ccgccacttc agcgtaccaa    180
attgaaggtg cttggaatga agatggaaag ggggaaagca actgggatca cttctgccac    240
aatcatccgg aaaggatact ggacgggagc aattcagaca ttggagcgaa ttcgtaccat    300
atgta                                                                305
```

<210> SEQ ID NO 224
<211> LENGTH: 319
<212> TYPE: DNA
<213> ORGANISM: Zea mays
<220> FEATURE:
<221> NAME/KEY: unsure

```
<222> LOCATION: (1)...(319)
<223> OTHER INFORMATION: unsure at all n locations

<400> SEQUENCE: 224
aacccaccta tctacatcaa ngagaacgga atcgnggatg ttgataccaa ggagacacct      60
ctacccatgg aggatgcctt aaatgactac aaaaggctag attacatcca gcgccacatc    120
gctactctta aggaatcaat agacttggga tcaaatgtgc aaggctactt cgcttggtct    180
ctgctggaca actttgaatg gttcgccggc ttcaccgaac gttatggcat tgtctacgtc    240
gaccgcaaca ataactgcac gcgctacatg aaggagtctg ccagtggttg aaacagttca    300
ngccgcgaag aagcccagc                                                  319

<210> SEQ ID NO 225
<211> LENGTH: 297
<212> TYPE: DNA
<213> ORGANISM: Zea mays

<400> SEQUENCE: 225
tttacttcct tttcctacgg aactggggtc tttgccccag gtcggtgctc acctggacta     60
gactgtgcct acccaactgg gaattcactc gtcgagcctt acactgctgg ccataacatt    120
ctcctagccc acgctgaggc tgttgatctt tacaacaagc attacaagcg cgacgacacc    180
cgcatagggc ttgcgtttga cgtaatgggt cgtgtgccat acggaacatc gtttctggat    240
aaacaggccg aagaaaggtc ctgggacatc aacctaggat ggttcttaga gccagtg       297

<210> SEQ ID NO 226
<211> LENGTH: 337
<212> TYPE: DNA
<213> ORGANISM: Zea mays
<220> FEATURE:
<221> NAME/KEY: unsure
<222> LOCATION: (1)...(337)
<223> OTHER INFORMATION: unsure at all n locations

<400> SEQUENCE: 226
ctctgctggg acaactttga atggttcgcc ggcttcaccg aacgttatgg gcattgtcta     60
cgtcgaccgc aacaataact gcaacgcgct aacatgaagg agtctgccaa gtggttgaaa    120
cagttcaacg ccgcgaagaa gcccagcaag aagattctta cgccagctta gaaatcgggg    180
gcctcatgat gtggntgcag cccataaaaa actggtgtgt ggtttcgaac cgaaaatttt    240
ctgttttttt tccgccacga gaggttctgg aggcatactc tccagcaccg tggctaataa    300
cgcattgttc cattcagtct ggccttgtca tgcatgc                              337

<210> SEQ ID NO 227
<211> LENGTH: 317
<212> TYPE: DNA
<213> ORGANISM: Zea mays
<220> FEATURE:
<221> NAME/KEY: unsure
<222> LOCATION: (1)...(317)
<223> OTHER INFORMATION: unsure at all n locations

<400> SEQUENCE: 227
cacggcacca cctgccgtct tcttctccac agagcagcaa gcgaaggtgt aaccntagct     60
ttacnacacg atctgcaaga gtaggcagcc aaaatggagt ccaaatgttg agcccctcgg    120
aaatcccaca aagggactgg ttcccctctg acttcaactt cggtgccgcc acttcagcgt    180
accaaattga agntgcttgg aatgaagatg gaaaggggga aagcaactgg gatcacttct    240
```

```
ggcacaatca tcggaaagga tactggacgg gagcnantca gacattggag cgaantcgta    300
ccatatgtac aaacggg                                                  317
```

<210> SEQ ID NO 228
<211> LENGTH: 320
<212> TYPE: DNA
<213> ORGANISM: Zea mays
<220> FEATURE:
<221> NAME/KEY: unsure
<222> LOCATION: (1)...(320)
<223> OTHER INFORMATION: unsure at all n locations

<400> SEQUENCE: 228

```
tgccgnnttc ttctncacag agcagcangc gtaggtgtaa ccttagcttt actacacgnt    60
ctgcaagagt aggcngccaa aatggantcc aaatgttgag cccctcggaa atcccacaaa    120
gggactggtt cccctctgac ttcaccttcg gtgccgccac ttcagcgtac caaattgaag    180
gtgcttggaa tgaagatgga aaggggggaaa gcaactggga tcacttctgc cacaatcatc    240
cggaaaggat actggacngg agcaattcag acattggagc gaattcgtcc atatgttcaa    300
aacggacgtc agattgctna                                                320
```

<210> SEQ ID NO 229
<211> LENGTH: 343
<212> TYPE: DNA
<213> ORGANISM: Zea mays
<220> FEATURE:
<221> NAME/KEY: unsure
<222> LOCATION: (1)...(343)
<223> OTHER INFORMATION: unsure at all n locations

<400> SEQUENCE: 229

```
gcgacgacac ccgcataggg cttgcgtttg acgtaatggg tcgtgtgcca tacngaacat    60
cgtttctgga taaacaggcc gaagaaaggt catgggacat caacctagga tggttcttag    120
agccagtggt tcgtggtgac taccccttct ccatgagatc attggctagg gaacgactac    180
ccttcttcaa ggacgagcag aaggagaagc tcgccggttc ctataacatg ttggggttaa    240
actactacac ctcacggttc tccaaaaaca tcgacatctc accaaactat cactgtgctc    300
aacatgacga ccgcctacgc catcaagaag tangggctga cgg                     343
```

<210> SEQ ID NO 230
<211> LENGTH: 300
<212> TYPE: DNA
<213> ORGANISM: Zea mays

<400> SEQUENCE: 230

```
agcagctcaa agctctagtt ctagctagct agcaaagggg gggaaaatgg ctccgcttct    60
cgctgctgcc atgaaccacg ctgcagccca tcctggcctt aggagccacc tagtaggacc    120
caacaatgag agtttctcac ggcaccacct gccgtcttct tctccacaga gcagcaagcg    180
aaggtgtaac cttagcttta ctacacgatc tgcaagagta ggcagccaaa atggagtcca    240
aatgttgagc ccctcggaaa tcccacaaag ggactggttc ccctctgact tcaccttcgg    300
```

<210> SEQ ID NO 231
<211> LENGTH: 295
<212> TYPE: DNA
<213> ORGANISM: Zea mays

<400> SEQUENCE: 231

```
ctcaaagctc tagttctagc tagctagcaa aggggggaa aatggctccg cttctcgctg    60
```

```
ctgccatgaa ccacgctgca gcccatcctg gccttaggag ccacctagta ggacccaaca      120
atgagagttt ctcacggcac cacctgccgt cttcttctcc acagagcagc aagcgaaggt      180
gtaaccttag ctttactaca cgatctgcaa gagtaggcag ccaaaatgga gtccaaatgt      240
tgagcccctc ggaaatccca caaagggact ggttcccctc tgacttcacc ttcgg          295
```

```
<210> SEQ ID NO 232
<211> LENGTH: 461
<212> TYPE: DNA
<213> ORGANISM: Zea mays
<220> FEATURE:
<221> NAME/KEY: unsure
<222> LOCATION: (1)...(461)
<223> OTHER INFORMATION: unsure at all n locations

<400> SEQUENCE: 232
agccacaatt ttccgnaaag gataatggga cggggagcat tgcaagacat tgggccgatt      60
ncgtaccata tngtacaaaa cggatngtca gattgctnga aggaaatggg catggacgca     120
tataggttct ctatctcttg gcctagaata ctggcctaaa ggggaacggt ccaaaggagg     180
tattaaccag gatggcatcg attactacaa aaaggctcat caacttgttg ctagagaatg     240
gcatagagcc atatgtaaca attttccact gggatgtccc tcaagcacta aagagaagt     300 acggcggatt cttagataag actcataaga ggattgtaaa tgattacaaa aacttcgcta     360
aggtgtgctt cgacaacttt ggtgacaang tgaagaantg gttgancntt aatgaagccc     420
caaacattta cctcaatttc ccaanngaaa ccggggtcct t                         461
```

```
<210> SEQ ID NO 233
<211> LENGTH: 290
<212> TYPE: DNA
<213> ORGANISM: Zea mays

<400> SEQUENCE: 233
ctcgtcgagc cttacactgc tggccataac attctcctag cccacgctga ggctgttgat      60
ctttacaaca agcattacaa gcgcgacgac acccgcatag gcttgcgtt tgacgtaatg      120 ggtcgtgtgc catacggaac atcgtttctg ataaacagg ccgaagaaag gtcctgggac     180
atcaacctag gatggttctt agagccagtg gttcgtggtg actacccctt ctccatgaga     240
tcattggcta gggaacgact acccttcttc aaggacgagc agaaggagaa                 290
```

```
<210> SEQ ID NO 234
<211> LENGTH: 290
<212> TYPE: DNA
<213> ORGANISM: Zea mays

<400> SEQUENCE: 234
gaaggatctc cttatgatca tgaagaacaa atacggaaac ccacctatct acatcacgga      60
gaacggaatc ggggatgttg ataccaagga gacacctcta cccatggagg atgccttaaa     120
tgactacaaa aggctagatt acatccagcg ccacatcgct actcttaagg aatcaataga     180
cttgggatca aatgtgcaag gctacttcgc ttggtctctg ctggacaact ttgaatggtt     240
cgccggcttc accgaacgtt atggcattgt ctacgtcgac cgcaacaata                 290
```

```
<210> SEQ ID NO 235
<211> LENGTH: 291
<212> TYPE: DNA
<213> ORGANISM: Zea mays
```

<400> SEQUENCE: 235

```
cgctgaggct gttgatcttt acaacaagca ttacaagcgc gacgacaccc gcatagggct      60
tgcgtttgac gtaatgggtc gtgtgccata cggaacatcg tttctggata aacaggccga     120
agaaaggtca tgggacatca acctaggatg gttcttagag ccagtggttc gtggtgacta     180
cccctttctcc atgagatcat tggctaggga acgactaccc ttcttcaagg acgagcagaa    240
ggagaagctc gccggttcct ataacatgtt ggggttaaac tactacacct c              291
```

<210> SEQ ID NO 236
<211> LENGTH: 288
<212> TYPE: DNA
<213> ORGANISM: Zea mays

<400> SEQUENCE: 236

```
gtcataagag cattgtagaa gattacacat actttgctaa ggtgtgcttt gataacttcg      60
gcgacaaggt gaagaattgg ttgacccttta atgagcccca gacatttact tccttttcct   120
acggaactgg ggtctttgcc ccaggtcggt gctcacctgg actagactgt gcctacccaa    180
ctgggaattc actcgtcgag ccttacactg ctggccataa cattctccta gcccacgctg    240
aggctgttga tctttacaac aagcattaca agcgcgacga cacccgca                 288
```

<210> SEQ ID NO 237
<211> LENGTH: 288
<212> TYPE: DNA
<213> ORGANISM: Zea mays

<400> SEQUENCE: 237

```
gggacatcaa cctaggatgg ttcttagagc cagtggttcg tggtgactac cccttctcca      60
tgagatcatt ggctagggaa cgactaccct tcttcaagga cgagcagaag gagaagctcg    120
ccggttccta taacatgttg ggggttaaact actacacctc acggttctcc aaaaacatcg    180
atatctcacc aaactactca cctgtgctca acactgacga cgcctacgcc agtcaagaag   240
ttaacgggcc tgacgggaag cccattggtc ctcctatggg aaatccat                 288
```

<210> SEQ ID NO 238
<211> LENGTH: 290
<212> TYPE: DNA
<213> ORGANISM: Zea mays
<220> FEATURE:
<221> NAME/KEY: unsure
<222> LOCATION: (1)...(290)
<223> OTHER INFORMATION: unsure at all n locations

<400> SEQUENCE: 238

```
caagcgcgac gacacccgca tagggcttgc gtttgacgta atgggtcgtg tgccatacgg      60
aacatcgttt ctggataaac aggccgaaga aaggtcctgg gacatcaacc taggatggtt   120
cttagagcca gnggttcgtg gtgactaccc cttctccatg agatcattgg ctaggaacg    180
actaccccttc ttcaaggacg agcagaagga gaagctcgcc ggttcctata acatgttggg   240
gttaaactac tacacctcac ggttctccaa aaacatcgat atctcaccaa                290
```

<210> SEQ ID NO 239
<211> LENGTH: 292
<212> TYPE: DNA
<213> ORGANISM: Zea mays
<220> FEATURE:
<221> NAME/KEY: unsure
<222> LOCATION: (1)...(292)
<223> OTHER INFORMATION: unsure at all n locations

<400> SEQUENCE: 239

```
tgcatggcta cttcgcttgg tctctgctgg ataactttga atggtacgcc ggctacaccg      60
aacgttatgg cattgtctac gtcgaccgca aaaataacta cacgcgctac atgaaggagt     120
cagccaagtg gttaaaagag ttcaatactg cgaagaagcc tagcaagaag attattacgc    180
cagcttaaaa acatgggacc tcgtgatgtg ggtacggtgc cacccatgaa ataaaaacct    240
agtgtgtggt ttgaaaccta aatttttcnt tttcnttttt gcaccatgag ag            292
```

<210> SEQ ID NO 240
<211> LENGTH: 291
<212> TYPE: DNA
<213> ORGANISM: Zea mays
<220> FEATURE:
<221> NAME/KEY: unsure
<222> LOCATION: (1)...(291)
<223> OTHER INFORMATION: unsure at all n locations

<400> SEQUENCE: 240

```
ggaaaatggc tccgcttctc gctgctgcca tgaaccacgc tgcagcccat cctggcctta      60
ggagccacct agnaggaccc aacaatgaga gtttctcacg gcaccacctg ccgtcttctt    120
ctccacagag cagcaagcga aggtgtaacc ttagctttac tacacgatct gcaagagtag    180
gcagccaaaa tggagtccaa atgttgagcc cctcggaaat cccacaaagg gactggttcc    240
cctctgactt caccttcggt gccgccactt cagcgtacca aattgaaggt g             291
```

<210> SEQ ID NO 241
<211> LENGTH: 319
<212> TYPE: DNA
<213> ORGANISM: Zea mays
<220> FEATURE:
<221> NAME/KEY: unsure
<222> LOCATION: (1)...(319)
<223> OTHER INFORMATION: unsure at all n locations

<400> SEQUENCE: 241

```
ggatcaaatg tgcaaggcta cttcgcttgg tctctgcngg acaactttga atngttcgcc      60
ggcttcaccg aacgttatgg cattgtctac gtcgaccgca acaataactg cacgcgctac    120
atgaaggagt ctgccaagtg gttgaaacag ttcaacgccg cgaagaagcc cagcaagaag    180
attcttacgc cagcttagaa atcggggggcc tcatgatgtg ggtgcagcnc ataaaaaact    240
ggtgtgtggt ttcgaaccgn natttctgtt tttccgccac gagagttctg gaggcatact    300
ctccagcacc gtgctaata                                                  319
```

<210> SEQ ID NO 242
<211> LENGTH: 286
<212> TYPE: DNA
<213> ORGANISM: Zea mays

<400> SEQUENCE: 242

```
cgcctacgcc agtcaagaag ttaacgggcc tgacgggaag cccattggtc ctcctatggg      60
aaatccatgg atctacatgt accctgaggg cttgaaggat ctccttatga tcatgaagaa    120
caaatacgga aacccaccta tctacatcac ggagaacgga atcggggatg ttgataccaa    180
ggagacacct ctacccatgg aggatgcctt aaatgactac aaaaggctag attacatcca    240
gcgccacatc gctactctta aggaatcaat agacttggga tcaaat                    286
```

<210> SEQ ID NO 243

```
<211> LENGTH: 298
<212> TYPE: DNA
<213> ORGANISM: Zea mays

<400> SEQUENCE: 243
gtacggcggc ttcctagaaa acggcataga gccatatgta acaatttttcc actgggatgt      60 acctcaagca ctagaagaga agtacggcgg cttcctagat aagagtcata agagcattgt     120
agaagattac acatactttg ctaaggtgtg ctttgataac ttcggcgaca aggtgaagaa     180
ttggttgacc tttaatgagc cccagacatt tacttccttt tcctacggaa ctggggtctt     240
tgccccaggt cggtgctcac ctggactaga ctgtgcctac ccaactggga attcactc       298

<210> SEQ ID NO 244
<211> LENGTH: 326
<212> TYPE: DNA
<213> ORGANISM: Zea mays
<220> FEATURE:
<221> NAME/KEY: unsure
<222> LOCATION: (1)...(326)
<223> OTHER INFORMATION: unsure at all n locations

<400> SEQUENCE: 244
aattgaaggt gcttggaatg aanatggaaa ngnggaaagc aactgggatc acttctgcca      60
caatcatccg gaaangatac tggacgggag caattcagac attggagcga nttcgtacca     120
tatgtacaaa acggacgtca gattgctcaa ggaaatgggc atggacgcat ataggttctc     180
tatctcttgg gcccagaata ctgccgaagg aaccaaagaa ggaggtatta acccggatgg     240
catcaagtac tacagaaacc tcntcaactt gttgctggaa aacggcntan agccatntgt     300 aacantttttc cactgggatg taccto                                          326

<210> SEQ ID NO 245
<211> LENGTH: 284
<212> TYPE: DNA
<213> ORGANISM: Zea mays

<400> SEQUENCE: 245
cccagacatt tacttcattt tcctatggaa ccggggtctt tgccccagga cgatgctcac      60
cgggactaga ctgtgccatc ccaactggga attcactcgt cgaaccttac attgctggcc     120
acaacattct tctagcccac gctgaggctg ttgatcttta caacaagtat tacaagggcg     180
agaacggccg cataggtctt gcatttgatg taatgggtcg tgtgccatac ggaacatcat     240
ttctagatga acaggccaaa gaaaggtcca tggacattaa ccta                      284

<210> SEQ ID NO 246
<211> LENGTH: 295
<212> TYPE: DNA
<213> ORGANISM: Zea mays

<400> SEQUENCE: 246
gaaaggggga aagcaactgg gatcacttct gccacaatca tccggaaagg atactggacg      60
ggagcaattc agacattgga gcgaattcgt accatatgta caaaacggac gtcagattgc     120
tcaaggaaat gggcatggac gcatataggt tctctatctc ttggcccaga atactgccga     180
agggaaccaa agaaggaggt attaacccgg atggcatcaa gtactacaga aacctcatca     240
acttgttgct ggaaaacggc atagagccat atgtaacaat tttccatggg atgta         295

<210> SEQ ID NO 247
<211> LENGTH: 294
```

```
<212> TYPE: DNA
<213> ORGANISM: Zea mays
<220> FEATURE:
<221> NAME/KEY: unsure
<222> LOCATION: (1)...(294)
<223> OTHER INFORMATION: unsure at all n locations

<400> SEQUENCE: 247
caacttgttg ctagaaaacg gcatagagcc atatgtaaca attttccact gggatgtacc      60
tcaagcacta gaagagaagt acggcggctt cctagataan agtcataaga gcattgtaga     120
agattacaca tactttgcta aggtgtgcnt tgataacttc ggcgacaagg tgaagaattg     180
gttgaccttt aatgagcccc agacatttac ttccttttcc tacggaactg ggtctttgc     240 cccaggtcgg tgctcactgg actagactgt gcctacccaa ctgggaattc actc           294

<210> SEQ ID NO 248
<211> LENGTH: 284
<212> TYPE: DNA
<213> ORGANISM: Zea mays
<220> FEATURE:
<221> NAME/KEY: unsure
<222> LOCATION: (1)...(284)
<223> OTHER INFORMATION: unsure at all n locations

<400> SEQUENCE: 248
gaattggttg acctttaatg agccccagac atttacttcc ttttcctacg gaactggggt     60
ctttgcccca ggtcggtgct cacctggact agactgtgcc tacccaactg gaattcact    120 cgtcgagcct acactgctg gccataacat tctcctagcc cacgctgagg ctgttgatct     180
ttacaacaag cattacaagc gcgacgacac ncgcataggg cttgcgtttg acgtaatggg    240
tcgtgtgcca tacggaacat cgtttctgga taaacangcc gaag                      284

<210> SEQ ID NO 249
<211> LENGTH: 284
<212> TYPE: DNA
<213> ORGANISM: Zea mays
<220> FEATURE:
<221> NAME/KEY: unsure
<222> LOCATION: (1)...(284)
<223> OTHER INFORMATION: unsure at all n locations

<400> SEQUENCE: 249
ctttacaaca agcattacaa gcgcgacgac acccgcatag gcttncgtt tgacgtaatg      60 ggtcgtgtgc catacggaac atcgtttctg gataaacagg ccgaagaaag gtcctgggac    120
atcaacctag gatggttctt agagccagtg gttcgtggtg actacccctt ctccatgaga    180
tcattggcta gggaacgact acccttcttc aaggacgagc agaaggagaa gctcgccggt    240
tcctataaca tgttggggtt aaactactac acctcacggt tctc                      284

<210> SEQ ID NO 250
<211> LENGTH: 304
<212> TYPE: DNA
<213> ORGANISM: Zea mays
<220> FEATURE:
<221> NAME/KEY: unsure
<222> LOCATION: (1)...(304)
<223> OTHER INFORMATION: unsure at all n locations

<400> SEQUENCE: 250
agaagattac acatactttg ctaaggtgtg ctttgataac ttcggcgaca aggtgaagaa      60
ttggttgacc tttaatgagc cccagacatt tacttccttt tcctacggaa ctggggtctt    120
```

```
tgccccaggt cggtgctcac ctggactaga ctgtgcctac ccaactggga attcactcgt      180
cgagccttac actgctggcc ataacattct cctagcccan gctgaggctg ttgatcttta      240
caaccnngca ttacangcgc gacgacaccc gcatagggct tgcgntttga cgtaatgggt      300 ngtg                                                                   304

<210> SEQ ID NO 251
<211> LENGTH: 287
<212> TYPE: DNA
<213> ORGANISM: Zea mays

<400> SEQUENCE: 251
caaagctcta gttctagcta gctagcaaag gggggaaaa tggctccgct tctcgctgct        60
gccatgaacc acgctgcagc ccatcctggc cttaggagcc acctagtagg acccaacaat      120
gagagtttct cacggcacca cctgccgtct tcttctccac agagcagcaa gcgaaggtgt      180
aaccttagct ttactacacg atctgcaaga gtaggcagcc aaaatggagt ccaaatgttg      240
agcccctcgg aaatcccaca aagggatggt tcccctctga cttcact                    287

<210> SEQ ID NO 252
<211> LENGTH: 291
<212> TYPE: DNA
<213> ORGANISM: Zea mays

<400> SEQUENCE: 252
aatggctcca cttctcgccg cagccatgaa ccacgctacc catccagtcc ttagaagcca       60
tctaggaccc aacaatgaga gtttctcacg acaccaccta tcttcttcac cacaaagcag      120
taagcgaagg tttaacctta gctttacgcc acgatctgca agggtaggca atgaaaatgg      180
agtccaattg ttgagcccct cggaaatccc tcgaagggac tggttcccct ctgacttcat      240
ctttggtgcc gccacttcag cgtaccaaat tgaaggtgca tggaacgaag a               291

<210> SEQ ID NO 253
<211> LENGTH: 285
<212> TYPE: DNA
<213> ORGANISM: Zea mays
<220> FEATURE:
<221> NAME/KEY: unsure
<222> LOCATION: (1)...(285)
<223> OTHER INFORMATION: unsure at all n locations

<400> SEQUENCE: 253
gngctacatg aaggagtctg ccaagtggtt ganacagttc aacgccgcga agaagcccag       60
caagaagatt cttacgccag cttagaaatc ggggcctca tgatgtgggt gcagcccata      120
aaaaactggt gtgtggtttc gaaccgaaaa ttttctgttt ttttccgcca cgagangttc      180
tggaggcata ctctccagca ccgtggctaa taacgcattg ttccaattca gtctggcctt      240
gtcatgcatg caatanttaa agtgatgggt ttccctgttt caaaa                      285

<210> SEQ ID NO 254
<211> LENGTH: 278
<212> TYPE: DNA
<213> ORGANISM: Zea mays

<400> SEQUENCE: 254
gccatatgta acaattttcc actgggatgt acctcaagca ctagaagaga agtacggcgg       60
cttcctagat aagagtcata agagcattgt agaagattac acctacttcg ctaaggtgtg      120
ctttgataac ttcggcgaca aggtgaagaa ttggttgacc tttaatgagc cccagacatt      180
```

```
tacttccttt tcctacggaa ctggggtctt tgccccaggg cggtgctcac ctggactaga      240
ctgtgcctac ccaactggga attcactcgt cgagcctt                              278

<210> SEQ ID NO 255
<211> LENGTH: 282
<212> TYPE: DNA
<213> ORGANISM: Zea mays
<220> FEATURE:
<221> NAME/KEY: unsure
<222> LOCATION: (1)...(282)
<223> OTHER INFORMATION: unsure at all n locations

<400> SEQUENCE: 255
cggcgacaag gtgaagaatt ggttgacctt taatgagccc cagacattta cttccttttc      60
ctacggaact ggggtctttg ccccaggtcg gtgctnacct ggactagact gtggctaccc     120
aactgggaat tcactcgtcg agccttacac tgctggccat aacattctcc tagcccacgc     180
tgaggctgtt gatctttaca acaagcatta caagcgcgac gacacccgca tagggcttgc     240
gtttgacgta atgggtcgtg tgccatacng aacatcgttt ct                        282

<210> SEQ ID NO 256
<211> LENGTH: 288
<212> TYPE: DNA
<213> ORGANISM: Zea mays

<400> SEQUENCE: 256
caaaactcta gctagctagc agggggggaa atggctccac ttctcgccgc agccatgaac      60
cacgctgccc atccagtcct tagaagccat ctaggaccca acaatgagag tttctcacga     120
caccacctat cttcttcacc gcaaagcagt aagcgaaggt ttaaccttag ctttacgcca     180
cgatctgcaa gagtaggcaa tcaaaatgga gtccaattgt tgagcccttc ggaaatccct     240
cgaagggact ggttcccctc cgattcatct ttggtgccgc cacttcag                  288

<210> SEQ ID NO 257
<211> LENGTH: 277
<212> TYPE: DNA
<213> ORGANISM: Zea mays
<220> FEATURE:
<221> NAME/KEY: unsure
<222> LOCATION: (1)...(277)
<223> OTHER INFORMATION: unsure at all n locations

<400> SEQUENCE: 257
gaagaattgg ttgacccttta atgagcccca gacatttact tccttttcct acggaactgg      60
ggtctttgcc ccaggtcggt gctcacctgg actagactgt gcctacccaa ctgggaattc     120
actcgtcgag ccttacactg ctggccataa cattctccta gcccacgctg aggctgttga     180
tctttacaac aagcattaca agcgcgacga cacccgcata gggcttgcgt ttgacgtaat     240
gggtcgtgtg ccatacggaa catcgtttct ggncaaa                              277

<210> SEQ ID NO 258
<211> LENGTH: 274
<212> TYPE: DNA
<213> ORGANISM: Zea mays

<400> SEQUENCE: 258
gttctagcta gctagcaaag ggggggaaaa tggctccgct tctcgctgct gccatgaacc      60
acgctgcagc ccatcctggc cttaggagcc acctagtagg acccaacaat gagagtttct    120
```

```
cacggcacca cctgccgtct tcttctccac agagcagcaa gcgaaggtgt aaccttagct    180
ttactacacg atctgcaaga gtaggcagcc aaaatggagt ccaaatgttg agcccctcgg    240
aaatcccaca aagggactgg ttcccctctg actt                                274
```

<210> SEQ ID NO 259
<211> LENGTH: 274
<212> TYPE: DNA
<213> ORGANISM: Zea mays

<400> SEQUENCE: 259

```
cttatacccca gaaggcctaa aggatatcct tatgatcatg aagaacaaat atggaaaccc    60
acctatctac atcactgaga acggaatcgg ggatgttgat acaaaggaga aacctctacc   120
catggaggct gccttaaatg actacaaaag gctagattac atccagcgcc acatctcaac   180
tctcaaggag tcaatagact tgggagcaaa tgtgcatggc tacttcgctt ggtctctgct   240
ggataacttt gaatggtacg ccggctacac cgaa                              274
```

<210> SEQ ID NO 260
<211> LENGTH: 293
<212> TYPE: DNA
<213> ORGANISM: Zea mays
<220> FEATURE:
<221> NAME/KEY: unsure
<222> LOCATION: (1)...(293)
<223> OTHER INFORMATION: unsure at all n locations

<400> SEQUENCE: 260

```
cgggacgtgg ncnanaagct ctagttctag ctagctagca aaggggggga aaatggctcc    60
gcttctcgct gcagcnatga accacgctgc agcccatcct ggccttagga gccacctagt   120
aggacccaac aatgagagtt tctcacggca ccacctgccg tcttcttctc cacagagcag   180
caagcgaagg tgtaaccctta gctttactac acgatctgca agagtaggca gccaaaatgg   240
agtccaaatg ttgagcccct cggaaatccc acaaagggac tggttcccct ctg         293
```

<210> SEQ ID NO 261
<211> LENGTH: 279
<212> TYPE: DNA
<213> ORGANISM: Zea mays

<400> SEQUENCE: 261

```
cttcgctaag gtgtgctttg ataacttcgg cgacaaggtg aagaattggt tgacctttaa    60
tgagccccag acatttactt cctttcccta cggaactggg gtctttgccc cagggcggtg   120
ctcacctgga ctagactgtg cctacccaac tgggaattca ctcgtcgagc cttacactgc   180
tggccataac attctcctag cccacgctga ggctgttgat cttacaaca agcattacaa    240 gcgcgacgac acccgcatag ggcttgcgtt tgacgtaat                         279
```

<210> SEQ ID NO 262
<211> LENGTH: 274
<212> TYPE: DNA
<213> ORGANISM: Zea mays
<220> FEATURE:
<221> NAME/KEY: unsure
<222> LOCATION: (1)...(274)
<223> OTHER INFORMATION: unsure at all n locations

<400> SEQUENCE: 262

```
acggaactgg ggtctttgcc ccaggtcggt gctcacctgg actagactgt gcctacccaa    60
ctgggaattc actcgtcgag ccttacantg ctggccataa cattctccta gcccacgctg   120
```

```
aggctgttga tctttacaac aagcattaca agcgcgacga cacccgcata gggcttgcgt    180
ttgangtaat gggtcgtgtg ccatacggaa catcgtttct ggataaacag gccgaagaaa    240
ggtcctggga catcaaccta ggatggttct taga                                274

<210> SEQ ID NO 263
<211> LENGTH: 276
<212> TYPE: DNA
<213> ORGANISM: Zea mays
<220> FEATURE:
<221> NAME/KEY: unsure
<222> LOCATION: (1)...(276)
<223> OTHER INFORMATION: unsure at all n locations

<400> SEQUENCE: 263
ggcatggacg catataggtt ctctatctct tggcctagaa tactgcctan nggaacggtc     60
gaaggaggta ttaaccagga tggcatcgat tactacaaaa ggctcatcaa cttgttgcta    120
gagaatggca tagagccata tgtaacaatt ttccactggg atgtccctca agcactagaa    180
gagaagtacg gcggattctt agataagact cataagagga ttgtaaatga ttacaaaaac    240
ttcgctaagg tgtgcttcga caactttggt gacaag                              276

<210> SEQ ID NO 264
<211> LENGTH: 276
<212> TYPE: DNA
<213> ORGANISM: Zea mays
<220> FEATURE:
<221> NAME/KEY: unsure
<222> LOCATION: (1)...(276)
<223> OTHER INFORMATION: unsure at all n locations

<400> SEQUENCE: 264
atgagcccca gacatttact tccttttcct acggaactgg ggtctttgcc ccaggtcggt     60
gctcacctgg actagactgt gcctacccaa ctnngaattc actcgtcgag ccttacactg    120
ctggccataa cattctccta gcccacgctg aggctgttga tctttacaac aagcattaca    180
agcgcgacga cacccgcata nggcttgcgt ttgacgtaat gggtcgtgtg ccatacggaa    240
catcgtttct ggataaacag gccgaagaaa ggtcct                              276

<210> SEQ ID NO 265
<211> LENGTH: 274
<212> TYPE: DNA
<213> ORGANISM: Zea mays
<220> FEATURE:
<221> NAME/KEY: unsure
<222> LOCATION: (1)...(274)
<223> OTHER INFORMATION: unsure at all n locations

<400> SEQUENCE: 265
ggttctccaa aaacatcgat atctcaccaa actactcacc tgtgctcaac antgacgacg     60
cctacgccag tcaagaagtt aacgggcctg acgggaagcc cattggtcct cctatgggaa    120
atccatggat ctacatgtac cctgagggct tgaaggatct ccttatgatc atgaagaaca    180
aatacggaaa cccacctatc tacatcacgg agaacggaat cggggatgtt gataccaagg    240
agacacctct acccatggag gatgccttaa atga                                274

<210> SEQ ID NO 266
<211> LENGTH: 280
<212> TYPE: DNA
<213> ORGANISM: Zea mays
```

-continued

```
<400> SEQUENCE: 266
gaactggggt ctttgcccca ggtcggtgct cacctggact agactgtgcc tacccaactg      60
ggaattcact tcgtcgagcc ttacactgct ggccataaca ttctcctagc ccacgctgag     120
gctgttgatc tttacaacaa gcattacaag cgcgacgaca cccgcatagg gcttgcgttt     180
gacgtaatgg gtcgtgtgcc atacggaaca tcgtttctgg ataaacaggc cgaagaaagg     240
tcctgggaca tcaacctagg atggttctta gagccagtgg                           280

<210> SEQ ID NO 267
<211> LENGTH: 279
<212> TYPE: DNA
<213> ORGANISM: Zea mays

<400> SEQUENCE: 267
cattgtagaa gattacacat actttgctaa ggtgtgcttt gataacttcg gcgacaaggt      60
gaagaattgg ttgaccttta atgagcccca gacatttact tccttttcct acggaactgg     120
ggtctttgcc ccaggtcggt gctcacctgg actagactgt gcctacccaa ctgggaattc     180
actcgtcgag ccttacactg ctggccataa catctcctag cccacgctga ggctgttgat     240
ctttacaaca agcattacaa gcgcgacgac acccgcata                            279

<210> SEQ ID NO 268
<211> LENGTH: 271
<212> TYPE: DNA
<213> ORGANISM: Zea mays
<220> FEATURE:
<221> NAME/KEY: unsure
<222> LOCATION: (1)...(271)
<223> OTHER INFORMATION: unsure at all n locations

<400> SEQUENCE: 268
gntaacgggc ctgacgggaa gcccattggt cctcctatgg gaaatccatg gatctacatg      60
taccctgagg gcttgaagga tctccttatg atcatgaaga acaaatacgg aaacccacct     120
atctacatca cggagaacgg aatcggggat gttgatacca aggagacacc tctacccatg     180
gaggatgcct taaatgacta caaaaggcta gattacatcc agcgccacat cgctactctt     240
aaggaatcaa tagacttggg atcaaatgtg c                                    271

<210> SEQ ID NO 269
<211> LENGTH: 291
<212> TYPE: DNA
<213> ORGANISM: Zea mays

<400> SEQUENCE: 269
ttcggtttca cacttttttca gagaagatta cacatacttt gctaaggtgt gctttgataa      60
cttcggcgac aaggtgaaga attggttgac ctttaatgag ccccagacat ttacttcctt     120
ttcctacgga actggggtct ttgccccagg tcggtgctca cctggactag actgtgccta     180
cccaactggg aattcactcg tcgagcctta cactgctggc cataacattc tcctagccca     240
cgctgaggct gttgatcttt acaacaagca ttacaagcgc gacgacaccc g              291

<210> SEQ ID NO 270
<211> LENGTH: 278
<212> TYPE: DNA
<213> ORGANISM: Zea mays
<220> FEATURE:
<221> NAME/KEY: unsure
<222> LOCATION: (1)...(278)
<223> OTHER INFORMATION: unsure at all n locations
```

```
<400> SEQUENCE: 270
gcagctcaaa gctctagttc tagctagcta gcaaangggg ggaaaatggc tccgcttctc    60
gctgctgcca tgaaccacgc tgcagcccat cctggcctta ggagccacct agtaggaccc   120
aacaatgaga gtttctcacg gcaccacctg ccgtcttctt ctccacagag cagcaagcga   180
aggtgtaacc ttagctttac tacacgatct gcaagagtag gcagccaaaa tggagtccaa   240
atgttgagcc cctcggaaat cccacaaagg gactggtt                            278

<210> SEQ ID NO 271
<211> LENGTH: 312
<212> TYPE: DNA
<213> ORGANISM: Zea mays
<220> FEATURE:
<221> NAME/KEY: unsure
<222> LOCATION: (1)...(312)
<223> OTHER INFORMATION: unsure at all n locations

<400> SEQUENCE: 271
attcgtacca tatgtacaaa acggacgtca gattgctcaa ggaaatgggc atggacgcat    60
aggttctcta tctcttggcc cagaatactg ccgaaggaac caagaaagga ggtattaacc   120
cgnatggcat caagtactac agaaacctca tcaacttgtt gctagaaaac ggcatagagc   180
catatgtaac aattttccac tgggatgtac ctcaagcact agaagagaag tacggcggct   240
tcctagataa gagtcataag agcattgtag aagattacac atactttgct aaggtgtgct   300
ttgataactt cg                                                       312

<210> SEQ ID NO 272
<211> LENGTH: 276
<212> TYPE: DNA
<213> ORGANISM: Zea mays
<220> FEATURE:
<221> NAME/KEY: unsure
<222> LOCATION: (1)...(276)
<223> OTHER INFORMATION: unsure at all n locations

<400> SEQUENCE: 272
gagccccaga catttacttc cttttcctac ggaactgggg tctttgcccc aggtcggtgc    60
tcacctggac tagactgtgc ctacccaact gggaattcac tcgtcgagcc ttacactgct   120
ggccataaca ttctcctagc ccacgctgag gctgttgatc tttacaacaa gcattacaag   180
cgcgacgaca cccgcatagg gcttgcgttt gacgtaatgg gtcgtgtgcc atacggaaca   240
tcgttctgga taaacaggcc gaagaaangt cctggg                             276

<210> SEQ ID NO 273
<211> LENGTH: 267
<212> TYPE: DNA
<213> ORGANISM: Zea mays

<400> SEQUENCE: 273
ggccataaca ttctcctagc ccacgctgag gctgttgatc tttacaacaa gcattacaag    60
cgcgacgaca cccgcatagg gcttgcgttt gacgtaatgg gtcgtgtgcc atacggaaca   120
tcgtttctgg ataaacaggc cgaagaaagg tcctgggaca tcaacctagg atggttctta   180
gagccagtgg ttcgtggtga ctacccttc tccatgagat cattggctag ggaacgacta   240
cccttcttca aggacgagca gaaggag                                       267

<210> SEQ ID NO 274
```

```
<211> LENGTH: 276
<212> TYPE: DNA
<213> ORGANISM: Zea mays

<400> SEQUENCE: 274
gccatctagg acccaacaat gagagtttct cacgacacca cctatcttct tcaccacaaa      60
gcagtaagcg aaggtttaac cttagcttta cgccacgatc tgcaagggta ggcaatgaaa     120
atggagtcca attgttgagc ccctcggaaa tccctcgaag ggactggttc ccctctgact     180
tcatctttgg tgccgccact tcagcgtacc aaattgaagg tgcatggaac gaagatggaa     240 aggggggaaag caattgggat cacttctgcc acaatt                              276

<210> SEQ ID NO 275
<211> LENGTH: 267
<212> TYPE: DNA
<213> ORGANISM: Zea mays

<400> SEQUENCE: 275
caaaaacatc gacatctcac caaactactc acctgtgctc aacactgacg acgcctacgc      60
cagtcaagaa gttaacgggc ctgacgggaa gcccattggt cctcctatgg gaaatccatg     120
gatctacatg taccctgagg gcttgaagga tctccttatg ataatgaaga acaaatacgg     180
aaacccacct atctcatca ccgagaacgg aatcggggat gttgatacca agagacacc      240 tctacccatg gaggctgcct taaatga                                         267

<210> SEQ ID NO 276
<211> LENGTH: 271
<212> TYPE: DNA
<213> ORGANISM: Zea mays
<220> FEATURE:
<221> NAME/KEY: unsure
<222> LOCATION: (1)...(271)
<223> OTHER INFORMATION: unsure at all n locations

<400> SEQUENCE: 276
tgctacatga aggagtctgc caagtggttg anacagttca acgccgcgaa gaagcccagc      60
aagaagattc ttacgccagc ttagaaatcg ggggcctcat gatgtgggtg cagcccataa     120
aaaactggtg tgtggtttcg aaccgaaaat tttctgtttt tttccgccac gagangttct     180
ggaggcatac tctccagcac cgtggctaat aacgcattgt tccaattcag tctggccttg     240
tcatgcatgc aataaataaa gtgatgggtt t                                    271

<210> SEQ ID NO 277
<211> LENGTH: 285
<212> TYPE: DNA
<213> ORGANISM: Zea mays
<220> FEATURE:
<221> NAME/KEY: unsure
<222> LOCATION: (1)...(285)
<223> OTHER INFORMATION: unsure at all n locations

<400> SEQUENCE: 277
cggnacntgg ngnaaggnag tctgccaagt ggttgaaaca gttcaacgcc gcgaagaagc      60
ccagcaagaa gattcttacg ccagcttaga aatcgggggc tcatgatgt gggtgcagcc     120 cataaaaaac tggtgtgtgg tttcgaaccg aaaatttttct gttttttttcc gccacgagag    180 gttctggagg catactctcc agcaccgtgg ctaataacgc attgttccaa ttcagtctgg     240
ccttgtcatg catgcaataa ataaagtgat gggtttccct gtttc                     285
```

```
<210> SEQ ID NO 278
<211> LENGTH: 268
<212> TYPE: DNA
<213> ORGANISM: Zea mays

<400> SEQUENCE: 278
cggaaaccca cctatctaca tcacggagaa cggaatcggg gatgttgata ccaaggagac      60
acctctaccc atggaggatg ccttaaatga ctacaaaagg ctagattaca tccagcgcca     120
catcgctact cttaaggaat caatagactt gggatcaaat gtgcaaggct acttcgcttg     180
gtctctgctg gacaactttg aatggttcgc cggcttcacc gaacgttatg gcattgtcta     240
cgtcgaccgc aacaataact gcacgcgc                                        268

<210> SEQ ID NO 279
<211> LENGTH: 318
<212> TYPE: DNA
<213> ORGANISM: Zea mays

<400> SEQUENCE: 279
gcagctcaaa gctctagttc tagctagcta gcaaaggggg ggaaaatggc tccgcttctc      60
gctgctgcca tgaaccacgc tgcagcccat cctggcctta ggagccacct agtaggaccc     120
aacaatgaga gtttctcacg gcaccacctg ccgtcttctt ctccacagag cagcaagcga     180
aggtgtaact tagctttact acacgatctg caagagtagg cagccaaaat ggagtccaaa     240
tgttgagccc ctcggaaatc ccacaaaggg actggttccc tctgacttca cttcggtgcc     300
ggcaacttca gcgtacca                                                   318

<210> SEQ ID NO 280
<211> LENGTH: 264
<212> TYPE: DNA
<213> ORGANISM: Zea mays

<400> SEQUENCE: 280
ctctgctgga taactttgaa tggtacgccg gctacaccga acgttatggc attgtctacg      60
tcgaccgcaa aaataactac acgcgctaca tgaaggagtc agccaagtgg ttaaaagagt     120
tcaatactgc gaagaagcct agcaagaaga ttattacgcc agcttaaaaa catgggacct     180
cgtgatgtgg gtacggtgcc acccatgaaa taaaaaccta gtgtgtggtt tgaaacctaa     240
atttttcttt ttcttttttg cacc                                            264

<210> SEQ ID NO 281
<211> LENGTH: 264
<212> TYPE: DNA
<213> ORGANISM: Zea mays

<400> SEQUENCE: 281
caaagctcta gttctagcta gctagcaaag gggggaaaa tggctccgct tctcgctgct      60
gccatgaacc acgctgcagc ccatcctggc cttaggagcc acctagtagg acccaacaat     120
gagagtttct cacggcacca cctgccgtct tcttctccac agagcagcaa gcgaaggtgt     180
aaccttagct ttactacacg atctgcaaga gtaggcagcc aaaatggagt ccaaatgttg     240
agcccctcgg aaatcccaca aagg                                            264

<210> SEQ ID NO 282
<211> LENGTH: 265
<212> TYPE: DNA
<213> ORGANISM: Zea mays
```

<400> SEQUENCE: 282
gggatgttga taccaaggag acacctctac ccatggagga tgccttaaat gactacaaaa    60
ggctagatta catccagcgc cacatcgcta ctcttaagga atcaatagac ttgggatcaa   120
atgtgcaagg ctacttcgct tggtctctgc tggacaactt tgaatggttc gccggcttca   180
ccgaacgtta tggcattgtc tacgtcgacc gcaacaataa ctgcacgcgc tacatgaagg   240
agtctgccaa gtggttgaaa cagtt                                         265

<210> SEQ ID NO 283
<211> LENGTH: 284
<212> TYPE: DNA
<213> ORGANISM: Zea mays
<220> FEATURE:
<221> NAME/KEY: unsure
<222> LOCATION: (1)...(284)
<223> OTHER INFORMATION: unsure at all n locations

<400> SEQUENCE: 283
tttgccccan gtcggtgctc acctggacta gactgtgnct acccaactgg gaattcactc    60
gtccgagcct tacactgctg gccataacat tctcctagcc cacgctgagg ctgttgatct   120
ttacaacaag cattacaagc gcgacgacac ccgcatagggg cttgcgtttg acgtaatggg   180
tcgtgtgcca tacggaacat cgtttctgga taaacaggcc gaagaaangt ctgggacatc   240
aacctaggat ggttcttaga gccagtggtt cgtggtgact ancc                    284

<210> SEQ ID NO 284
<211> LENGTH: 270
<212> TYPE: DNA
<213> ORGANISM: Zea mays

<400> SEQUENCE: 284
ataaactact acacctcaat attctccaaa catatcgaca tctcaccaaa atactcgcct    60
gttctcaaca ctgacgacgc ctacgctagt caagaaacgt atgggcctga cgggaaaccc   120
attggtcctc ctatgggaaa tccgtggatc tacttatacc cagaaggcct aaaggatatc   180
cttatgatca tgaagaacaa atatggaaac ccacctatct acatcactga aacggatcg    240 gggatgttga tacaaaggag aaacctctac                                    270

<210> SEQ ID NO 285
<211> LENGTH: 269
<212> TYPE: DNA
<213> ORGANISM: Zea mays

<400> SEQUENCE: 285
agcagctcaa agctctagtt ctagctagct agcaaagggg gggaaaatgg ctccgcttct    60
cgctgctgcc atgaaccacg ctgcagccca tcctggcctt aggagccacc tagtaggacc   120
caacaatgag agtttctcac ggcaccacct gccgtcttct tctccacaga gcagcaagcg   180
aaggtgtaac cttagcttta ctacacgatc tgcaagagta ggcagccaaa atggagtcca   240
aatgttgagc ccctcggaaa tcccacaaa                                     269

<210> SEQ ID NO 286
<211> LENGTH: 264
<212> TYPE: DNA
<213> ORGANISM: Zea mays

<400> SEQUENCE: 286
tgagccccag acatttactt cctttcccta cggaactggg gtctttgccc caggtcggta    60

```
ctcacctgga ctagactgtg cctacccaac tgggaattca ctcgtcgagc cttacactgc    120
tggccataac attctcctag cccacgctga ggctgttgat ctttacaaca agcattacaa    180
gcgcgacgac acccgcatag ggcttgcgtt tgacgtaatg ggtcgtgtgc catacggaac    240
atcgtttctg gataaacagg ccga                                          264

<210> SEQ ID NO 287
<211> LENGTH: 263
<212> TYPE: DNA
<213> ORGANISM: Zea mays

<400> SEQUENCE: 287
gttggggtta aactactaca cctcacggtt ctccaaaaac atcgatatct caccaaacta     60
ctcacctgtg ctcaacactg acgacgccta cgccagtcaa gaagttaacg ggcctgacgg    120
gaagcccatt ggtcctccta tgggaaatcc atggatctac atgtaccctg agggcttgaa    180
ggatctcctt atgatcatga agaacaaata cggaaaccca cctatctaca tcacggagaa    240
cggaatcggg gatgttgata cca                                          263

<210> SEQ ID NO 288
<211> LENGTH: 274
<212> TYPE: DNA
<213> ORGANISM: Zea mays

<400> SEQUENCE: 288
atttgtgcag gaatcgggga tgttgatacc aaggagacac ctctacccat ggaggatgcc     60
ttaaatgact ataaaaggct agattacatc cagcgccaca tcgctactct taaggaatca    120
atagacttgg gatcaaatgt gcaaggctac ttcgcttggt tctgctggaa caactttgaa    180
tggttcgccg gcttcaccga acgttatggc attgtctacg tcgaccgcaa caataactgc    240
acgcgctaca tgaaggagtc tgccaagtgg ttga                              274

<210> SEQ ID NO 289
<211> LENGTH: 299
<212> TYPE: DNA
<213> ORGANISM: Zea mays
<220> FEATURE:
<221> NAME/KEY: unsure
<222> LOCATION: (1)...(299)
<223> OTHER INFORMATION: unsure at all n locations

<400> SEQUENCE: 289
aaagctctag ttctagctag cnagcaaagg gggggaaaat ggctccgctt ctcgcngctg     60
ccatgaacca cgctgcagcc canccctggcc ttaggagcca cctagtagga ccccaacaan    120
gagagtttct cacggcacca cctgccgtct tcttctccac agagcagcaa gcgaaggtgn    180
aaccnnagcn ttactacacg atcngcaaga gtaggcagcc aaaatggagt tcaaatgttg    240
agcccctcgg aaattccaca aagggactgg ttcccctctg acttnacctt cggtggngg     299

<210> SEQ ID NO 290
<211> LENGTH: 262
<212> TYPE: DNA
<213> ORGANISM: Zea mays

<400> SEQUENCE: 290
ctctagctag ctagcagggg gggaaatggc tccacttctc gccgcagcca tgaaccacgc     60
tgcccatcca gtccttagaa gccatctagg acccaacaat gagagtttct cacgacacca    120
```

```
cctatcttct tcaccgcaaa gcagtaagcg aaggtttaac cttagcttta cgccacgatc      180
tgcaagagta ggcaatcaaa atggagtcca attgttgagc ccttcggaaa tccctcgaag      240
ggactggttc ccctccgact tc                                               262

<210> SEQ ID NO 291
<211> LENGTH: 261
<212> TYPE: DNA
<213> ORGANISM: Zea mays

<400> SEQUENCE: 291
ggaaaatggc tccgcttctc gctgctgcca tgaaccacgc tgcagcccat cctggcctta       60
ggagccacct agtaggaccc aacaatgaga gtttctcacg gcaccacctg ccgtcttctt      120
ctccacagag cagcaagcga aggtgtaacc ttagctttac tacacgatct gcaagagtag      180
gcagccaaaa tggagtccaa atgttgagcc cctcggaaat cccacaaagg gactggttcc      240
cctctgactt caccttcggt g                                                261

<210> SEQ ID NO 292
<211> LENGTH: 424
<212> TYPE: DNA
<213> ORGANISM: Zea mays
<220> FEATURE:
<221> NAME/KEY: unsure
<222> LOCATION: (1)...(424)
<223> OTHER INFORMATION: unsure at all n locations

<400> SEQUENCE: 292
acagctctag ttctanctan ctancaaggg gngggaaaat ggctccgctt ctcgctgctg       60
ccatgaacca cnctgcancc catcctggcc ttaggagcca cctagtacga cccaacattg      120
agagtttctc acggcaccac ctgccgtctt cttctccaca gagcagcatc gcnaaggtgt      180
aaccttagcn ttactacacg atctgcaaga gtaggcagcc aaantggant cnaantgttg      240
agccccncng aaatcncaca aagggacngg tncccctctg acttcacctt cggtgcncgc      300
cncntcagcg tancanggnt caatgtgctt ggaanganga tggaancggg gaaancgnct      360
gggatnantt cngcganagt catccggaaa ngatatggac tggancactt cagacattgg      420
atca                                                                   424

<210> SEQ ID NO 293
<211> LENGTH: 306
<212> TYPE: DNA
<213> ORGANISM: Zea mays
<220> FEATURE:
<221> NAME/KEY: unsure
<222> LOCATION: (1)...(306)
<223> OTHER INFORMATION: unsure at all n locations

<400> SEQUENCE: 293
gctagcnagc naaggggggg anaatngctc cgcttctcgc tgctgccatg anccacgctg       60
cagcccatcc tggccttagg agccacctag taggacccaa caatgagagt tctcacggc      120 accacctgcc gtcttcttct ccacagagca gcaagcnaag gtgtaacctt agctttacta      180
cacgatctgc aagantaggc agccaaaatg gagtccaaat gttgagcncc tcggaaatcc      240
cacaaaggga ctggttcncn tctgacttca anttggtgnn ggcaattnag gtaacaaatt      300
gaaggt                                                                 306

<210> SEQ ID NO 294
<211> LENGTH: 277
```

```
<212> TYPE: DNA
<213> ORGANISM: Zea mays

<400> SEQUENCE: 294
gcagctcaaa actctagcta gctaccaggg gggaaaatgg ctccacttct cgccgcagcc      60
atgaaccacg ctacccatcc agtccttaga agccatctag acccaacaa tgagagtttc     120
tcacgacacc acctatcttc ttcaccacaa agcagtaagc gaaggtttaa ccttagcttt    180
acgccacgat ctgcaagggt aggcaatgaa aatggagtcc aattgttgag cccctcggaa    240
atccctcgaa gggactggtt cccctctgac ttcatct                             277

<210> SEQ ID NO 295
<211> LENGTH: 260
<212> TYPE: DNA
<213> ORGANISM: Zea mays

<400> SEQUENCE: 295
cgtcaataga cttgggagca aatgtgcatg gctacttcgc ttggtctctg ctggataact      60
ttgaatggta cgccggctac accgaacgtt atggcattgt ctacgtcgac cgcaaaaata    120
actacacgcg ctacatgaag gagtcagcca agtggttaaa agagttcaat actgcgaaga    180
agcctagcaa gaagattatt acgccagctt aaaaacatgg gacctcgtga tgtgggtacg    240
gtgccaccca tgaaataaat                                                260

<210> SEQ ID NO 296
<211> LENGTH: 258
<212> TYPE: DNA
<213> ORGANISM: Zea mays

<400> SEQUENCE: 296
gccaagtggt tgaaacagtt caacgccgcg aagaagccca gcaagaagat tcttacgcca      60
gcttagaaat cgggggcctc atgatgtggg tgcagcccat aaaaaactgg tgtgtggttt    120
cgaaccgaaa attttctgtt tttttccgcc acgagaggtt ctggaggcat actctccagc    180
accgtggcta ataacgcatt gttccaattc agtctggcct tgtcatgcat gcaataaata    240
aagtgatggg tttccctg                                                  258

<210> SEQ ID NO 297
<211> LENGTH: 266
<212> TYPE: DNA
<213> ORGANISM: Zea mays

<400> SEQUENCE: 297
agcaattcag acattggagc gaattcgtac catatgtaca aaacggacgt cagattgctc      60
aaggaaatgg gcatggacgc atataggttc tctatctctt ggcccagaat actgccgaag    120
gaaccaaaga aggaggtatt aacccggatg gcatcaagta ctacagaaac ctcatcaact    180
tgttgctaga aaacggcata gagccatatg taacaatttc cactgggatg tacctcaagc    240
actagaagag aagtacggcg gcttcc                                         266

<210> SEQ ID NO 298
<211> LENGTH: 270
<212> TYPE: DNA
<213> ORGANISM: Zea mays

<400> SEQUENCE: 298
tacaagcgcg acgacacccg catagggctt gcgtttgacg taatgggtcg tgtgccatac      60
```

```
ggaacatccg tttctggata aacaggccga agaaaggtca tgggacatca acctaggatg    120
gttcttagag ccagtggttc gtggtgacta ccccttctcc atgagatcat tggctaggga    180
acgactaccc ttcttcaagg acgagcagaa ggagaagctc gccggttcct ataacatgtt    240
ggggttaaac tactcacct cacggttctc                                      270

<210> SEQ ID NO 299
<211> LENGTH: 287
<212> TYPE: DNA
<213> ORGANISM: Zea mays
<220> FEATURE:
<221> NAME/KEY: unsure
<222> LOCATION: (1)...(287)
<223> OTHER INFORMATION: unsure at all n locations

<400> SEQUENCE: 299
attacaccta cttcgctaag gtgtgctttg ataacttcgg cgacaaggtg aagaattggt    60
tgacctttaa tgagcccag acatttactt cctttcccta cggaactggg gtctttgccc    120
cagggcggtg ctcacctgga ctagactgtg cctacccaac tgggaattca ctcgtcgagc    180
cttacactgc tggccataac attctcctag cccacgctga ggctgttgat ctttacaaca    240
agcatacaag gcgacgacac ccgcatangg ctgcgttgac gtatggg                  287

<210> SEQ ID NO 300
<211> LENGTH: 252
<212> TYPE: DNA
<213> ORGANISM: Zea mays

<400> SEQUENCE: 300
cttatgatca tgaagaacaa atacggaaac ccacctatct acatcacgga gaacggaatc    60
ggggatgttg ataccaagga gacacctcta cccatggagg atgccttaaa tgactacaaa    120
aggctagatt acatccagcg ccacatcgct actcttaagg aatcaataga cttgggatca    180
aatgtgcaag gctacttcgc ttggtctctg ctggacaact ttgaatggtt cgccggcttc    240
accgaacgtt at                                                        252

<210> SEQ ID NO 301
<211> LENGTH: 256
<212> TYPE: DNA
<213> ORGANISM: Zea mays

<400> SEQUENCE: 301
cttctccatg agatcattgg ctagggaacg actacccttc ttcaaggacg agcagaagga    60
gaagctcgcc ggttcctata acatgttggg gttaaactac tacacctcac ggttctccaa    120
aaacatcgac atctcaccaa actactcacc tgtgctcaac actgacgacg cctacgccag    180
tcaagaagtt aacgggcctg acaggaagcc cattggtcct cctatgggaa atccatggat    240
ctacatgtac cctgag                                                    256

<210> SEQ ID NO 302
<211> LENGTH: 255
<212> TYPE: DNA
<213> ORGANISM: Zea mays
<220> FEATURE:
<221> NAME/KEY: unsure
<222> LOCATION: (1)...(255)
<223> OTHER INFORMATION: unsure at all n locations

<400> SEQUENCE: 302
tcaacttgtt gctagaaaac ggcatagagc catatgtaac aatttnccac tgggatgtac    60
```

```
ctcaagcact agaagagaag tacggcggct tcctagataa gagtcataag agcattgtag    120
aagattacac atactttgct aaggtgtgct ttgataactt cggcgacaag gtgaagaatt    180
ggttgacctt taatgagccc cagacattta cttcctttc ctacggaact ggggtctttg    240
ccccaggtcg gtgct                                                    255

<210> SEQ ID NO 303
<211> LENGTH: 264
<212> TYPE: DNA
<213> ORGANISM: Zea mays
<220> FEATURE:
<221> NAME/KEY: unsure
<222> LOCATION: (1)...(264)
<223> OTHER INFORMATION: unsure at all n locations

<400> SEQUENCE: 303
cggacgctgg tgnactacaa aaggctagat tacatccagc gccacatcgc tactcttaag    60
gaancaatag acttgggatc aaatgtgcaa ggctacttcg cttggtctct gctggacaac   120
tttgaatggt tcgccggctt caccgaacgt tatggcattg tctacgtcga ccgcaacaat   180
aactgcacgc gctacatgaa ggagtctgcc aagtggttga acagttcaa cgccgcgaag   240 aagcccagca agaagattct tacg                                         264

<210> SEQ ID NO 304
<211> LENGTH: 252
<212> TYPE: DNA
<213> ORGANISM: Zea mays

<400> SEQUENCE: 304
attacacata ctttgctaag gtgtgctttg ataacttcgg cgacaaggtg aagaattggt    60
tgacctttaa tgagcccag acatttactt ccttttccta cggaactggg gtctttgccc   120
caggtcggtg ctcacctgga ctagactgtg cctacccaac tgggaattca ctcgtcgagc   180
cttacactgc tggccataac attctcctag cccacgctga ggctgttgat ctttacaaca   240
agcattacaa gg                                                      252

<210> SEQ ID NO 305
<211> LENGTH: 279
<212> TYPE: DNA
<213> ORGANISM: Zea mays
<220> FEATURE:
<221> NAME/KEY: unsure
<222> LOCATION: (1)...(279)
<223> OTHER INFORMATION: unsure at all n locations

<400> SEQUENCE: 305
ctcnncgagc cttacacngc tggccataan attctcctag cccangnnga ngnngttgat    60
ctttacaaca agcatnanaa ncgcgacgac acncgnatag gcttgcgtt tgacgtaatg    120 ggtcgtgtgc catanggaac atcgtttctg gataaacagg cngaagaaag gtcntgggac   180
atcaacctag gatggttctt agagncagtg gttcgtggtg actanccctt ctccatgaga   240
tcattggcta gggaacgact acccttcttc aaggacgag                         279

<210> SEQ ID NO 306
<211> LENGTH: 251
<212> TYPE: DNA
<213> ORGANISM: Zea mays

<400> SEQUENCE: 306
```

-continued

```
caaagaagga ggtattaacc cggatggcat caagtactac agaaacctca tcaacttgtt      60
gctagaaaac ggcatagagc catatgtaac aattttccac tgggatgtac ctcaagcact     120
agaagagaag tacggcggct tcctagataa gagtcataag agcattgtag aagattacac     180
atactttgct aaggtgtgct ttgataactt cggcgacaag gtgaagaatt ggttgacctt     240
taatgagccc c                                                          251

<210> SEQ ID NO 307
<211> LENGTH: 254
<212> TYPE: DNA
<213> ORGANISM: Zea mays

<400> SEQUENCE: 307
agcagctcaa agctctagtt ctagctagct agcaaagggg gggaaaatgg ctccgcttct      60
cgctgctgcc atgaaccacg ctgcagccca tcctggcctt aggagccacc tagtaggacc     120
caacaatgag agtttctcac ggcaccacct gccgtcttct tctccacaga gcagcaagcg     180
aaggtgtaac cttagcttta ctacacgatc tgcaagagta ggcagccaaa atggagtcca     240
aatgttgagc ccct                                                       254

<210> SEQ ID NO 308
<211> LENGTH: 275
<212> TYPE: DNA
<213> ORGANISM: Zea mays
<220> FEATURE:
<221> NAME/KEY: unsure
<222> LOCATION: (1)...(275)
<223> OTHER INFORMATION: unsure at all n locations

<400> SEQUENCE: 308
gcgctacatg aaggagtctg ccaagtggtt gaancagttc aacgccgcga agangcccag      60
caagaagatt cttacgccag cttagaaatc gggggcctca tgatgtgggt gcagcccatn     120
aaaaactggt gtgtggtttc gaaccgaaaa ttttctgttt ttttccgcca cgagaggttc     180
tggaggcata ctctccagca ccgtggctaa taacgcattg ttccaattca gtctggcctt     240
gtcatgcatg cataantnga tgatgggttc cctgt                                275

<210> SEQ ID NO 309
<211> LENGTH: 248
<212> TYPE: DNA
<213> ORGANISM: Zea mays

<400> SEQUENCE: 309
ctctagttct agctagctag caaaggggg gaaaatggct ccgcttctcg ctgctgccat       60
gaaccacgct gcagcccatc ctggccttag gagccaccta gtagga ccca acaatgagag    120 tttctcacgg caccacctgc cgtcttcttc tccacagagc agcaagcgaa ggtgtaacct    180
tagctttact acacgatctg caagagtagg cagccaaaat ggagtccaaa tgttgagccc    240
ctcggaaa                                                              248

<210> SEQ ID NO 310
<211> LENGTH: 261
<212> TYPE: DNA
<213> ORGANISM: Zea mays
<220> FEATURE:
<221> NAME/KEY: unsure
<222> LOCATION: (1)...(261)
<223> OTHER INFORMATION: unsure at all n locations

<400> SEQUENCE: 310
```

```
cggacgctgg ccggcgacaa ggtgaagaat tggttgacct ttaatgagcc ccagacattt      60
acntcctttt cctacggaac tggggtcttt gccccaggtc ggtgctcacc tggactagac     120
tgtgcctacc caactgggaa ttcactcgtc gagccttaca ctgctggcca taacattctc     180
ctagcccacg ctgaggctgt tgatctttac aacaagcatt acaagcgcga cgacacccgc     240
atagggcttg cgtttgacgt a                                               261

<210> SEQ ID NO 311
<211> LENGTH: 300
<212> TYPE: DNA
<213> ORGANISM: Zea mays
<220> FEATURE:
<221> NAME/KEY: unsure
<222> LOCATION: (1)...(300)
<223> OTHER INFORMATION: unsure at all n locations

<400> SEQUENCE: 311
aacaagcatt acaagcgcga cgacacccgg catagggctt gcgtttgacc gtaatgggtc      60
gtgtgccata cggaacatcg tttctggata acaggccga agaaaggtcc tgggacatca     120
acctaggatg gttcttagag ccagtggttc gtggtgacta cccctctcca tgagatcatt     180
ggctagggaa cgactaccct cttcaaggac gagcanaagg agaagctcgc cggttcctat     240
aacagttggg gttaactata cacctcaggt tctccaaaaa catcgatatc tcaccaacta     300

<210> SEQ ID NO 312
<211> LENGTH: 332
<212> TYPE: DNA
<213> ORGANISM: Zea mays
<220> FEATURE:
<221> NAME/KEY: unsure
<222> LOCATION: (1)...(332)
<223> OTHER INFORMATION: unsure at all n locations

<400> SEQUENCE: 312
cttgcatttg acgtaatggg tcgtgtccca tacganaagt cggcgtttac ggatcaacag      60
gccgaacaaa ggtcctggga cattaaccta ggatggttct tggagccggt tgttcgtggt     120
gactaatccn ttctccatga gatcattggc aagggaacga ctaccttct tcactgacaa     180 agagcaagag aagctagtgg gttcctatga catgttgggg ttaaactatt atacctcaag     240
gttctctaaa aacatcgata tctcaccaaa ctactcgcca gtgctcaaca ctgacgacgc     300
atatgccagt caagaaacga atgggcctga cg                                   332

<210> SEQ ID NO 313
<211> LENGTH: 258
<212> TYPE: DNA
<213> ORGANISM: Zea mays

<400> SEQUENCE: 313
gttgcgctgt gtgttatttt ttatgaaata aaaatctaga tggttgtgtt tatgatagat      60
gttactatac ggtcgcactt gccgtcaatt caattttat ttgtgcagga atcggggatg     120
ttgataccaa ggagacacct ctacccatgg aggatgcctt aaatgactac aaaaggctag     180
attacatcca gcgccacatc gctactctta aggaatcaat agacttggga tcaaatgtgc     240
aaggctactt cgcttggt                                                   258

<210> SEQ ID NO 314
<211> LENGTH: 244
<212> TYPE: DNA
```

<213> ORGANISM: Zea mays

<400> SEQUENCE: 314

```
caacttgttg ctagaaaacg gcatagagcc atatgtaaca attttccact gggatgtacc      60
tcaagcacta gaagagaagt acggcggctt cctagataag agtcataaga gcattgtaga     120
agattacaca tactttgcta aggtgtgctt tgataacttc ggcgacaagg tgaagaattg     180
gttgaccttt aatgagcccc agacatttac ttcctttttcc tacggaactg ggtctttgc    240
ccca                                                                  244
```

<210> SEQ ID NO 315
<211> LENGTH: 259
<212> TYPE: DNA
<213> ORGANISM: Zea mays

<400> SEQUENCE: 315

```
tcgagcttta cactgctggc cataacattc tcctagccca cgctgaggct gttgatcttt      60
acaacaagca ttaacaagcg gcgacgacac ccgcataggg cttgcgtttg acgtaatggg    120
tcgtgtgcca tacggaacat cgtttctgga taaacaggcc gaagaaaggt catgggacat    180
caacctagga tggttcttag agccagtggt tcgtggtgac taccccttct ccatgagatc    240
attggctagg gaacgacta                                                  259
```

<210> SEQ ID NO 316
<211> LENGTH: 239
<212> TYPE: DNA
<213> ORGANISM: Zea mays

<400> SEQUENCE: 316

```
gtgtaacctt agctttacta cacgatctgc aagagtaggc agccaaaatg gagtccaaat      60
gttgagcccc tcggaaatcc cacaaaggga ctggttcccc tctgacttca ccttcggtgc    120
cgccacttca gcgtaccaaa ttgaaggtgc ttggaatgaa gatggaaagg gggaaagcaa    180
ctgggatcac ttctgccaca atcatccgga aaggatactg gacgggagca attcagaca     239
```

<210> SEQ ID NO 317
<211> LENGTH: 253
<212> TYPE: DNA
<213> ORGANISM: Zea mays
<220> FEATURE:
<221> NAME/KEY: unsure
<222> LOCATION: (1)...(253)
<223> OTHER INFORMATION: unsure at all n locations

<400> SEQUENCE: 317

```
ggttaaacta cnacacctca cggttctcca nnancatcga tntctcacca aacnactcac      60
ctgtgctcaa cactgacgac gcctacgcca gtcaagaagt taacgggcct gacgggaagc    120
ccnttggtcc tcctatggga aatccatgga tctacatgta ccctgagggc ttgaaggatc    180
tccttatgat catgaagaac aaatacggaa acccacctat ctacatcacg gngancggaa    240
tcggggntgt tga                                                        253
```

<210> SEQ ID NO 318
<211> LENGTH: 241
<212> TYPE: DNA
<213> ORGANISM: Zea mays

<400> SEQUENCE: 318

```
caaattgaag gtgcttggaa tgaagatgga aaggggaaa gcaactggga tcacttctgc       60
```

```
cacaatcatc cggaaaggat actggacggg agcaattcag acattggagc gaattcgtac    120
catatgtaca aaacggacgt cagattgctc aaggaaatgg gcatggacgc ataggttc      180 tctatctctt ggcccagaat actgccgaag gaaccaaaga aggaggtatt aacccggatg    240
g                                                                    241

<210> SEQ ID NO 319
<211> LENGTH: 242
<212> TYPE: DNA
<213> ORGANISM: Zea mays

<400> SEQUENCE: 319
agcagctcaa agctctagtt ctagctagct agcaaagggg gggaaaatgg ctccgcttct     60
cgctgctgcc atgaaccacg ctgcagccca tcctggcctt aggagccacc tagtaggacc    120
caacaatgag gtttctcac ggcaccacct gccgtcttct tctccacaga gcagcaagcg    180
aaggtgtaac cttagcttta ctacacgatc tgcaagagta ggcagccaaa atggagtcca    240
aa                                                                   242

<210> SEQ ID NO 320
<211> LENGTH: 236
<212> TYPE: DNA
<213> ORGANISM: Zea mays

<400> SEQUENCE: 320
caaagctcta gttctagcta gctagcaaag ggggggaaaa tggctccgct tctcgctgct     60
gccatgaacc acgctgcagc ccatcctggc cttaggagcc acctagtagg acccaacaat    120
gagagtttct cacggcacca cctgccgtct tcttctccac agagcagcaa gcgaaggtgt    180
aaccttagct ttactacacg atctgcaaga gtaggcagcc aaaatggagt ccaaat        236

<210> SEQ ID NO 321
<211> LENGTH: 241
<212> TYPE: DNA
<213> ORGANISM: Zea mays
<220> FEATURE:
<221> NAME/KEY: unsure
<222> LOCATION: (1)...(241)
<223> OTHER INFORMATION: unsure at all n locations

<400> SEQUENCE: 321
cttnaatgac tacaaaaggc tagattacat ccagcgccac atcgctactc ttaaggaatc     60
aatagacttg ggatcaaatg tgcaaggcta cttcgcttgg actctgctgg acaactttga    120
atggattgcc ggcttcaccg aacgttatgg cattgtctac gtcgaccgca acaataactg    180
cacgcgctac atgaaggagt ctgccaagtg gttgaaagag ttcaacaccg cgaaaaagcc    240
c                                                                    241

<210> SEQ ID NO 322
<211> LENGTH: 341
<212> TYPE: DNA
<213> ORGANISM: Zea mays
<220> FEATURE:
<221> NAME/KEY: unsure
<222> LOCATION: (1)...(341)
<223> OTHER INFORMATION: unsure at all n locations

<400> SEQUENCE: 322
gccgcnggga accaccagaa ggaggtatta acccggatgg catcaagtac tacagaaacc     60
```

```
tcatcaactt gttgctagaa aacggcatag agccatatgt aacaattttc cactgggatg      120
tacctcaagc actagaagag aagtacggcg gcttcctaga taagagtcat aagagcattg      180
tagaaattac acatactttg ctaaggtgtg ctttgataac ttcggcgaca aggtgaagat      240
tggttgacct ttaatgagcc ccagacttta cttccttttc ctacggaatg gggtctttgc      300
cccagtcggt gctcactgga tagatgtgcc tacccactgg g                          341
```

<210> SEQ ID NO 323
<211> LENGTH: 269
<212> TYPE: DNA
<213> ORGANISM: Zea mays
<220> FEATURE:
<221> NAME/KEY: unsure
<222> LOCATION: (1)...(269)
<223> OTHER INFORMATION: unsure at all n locations

<400> SEQUENCE: 323

```
caaagctcta gttctagcta gctagcaaag gggggaaaa tggctcngnt tctncgctgc        60
tgccatgaac cacgctgcag cccatcctgg ccttaggagc nacctagtag gncccaacaa      120
tgagagtttc tcacggcacc acctgcngtc ttcttctcca cagagcagca agcnaaggtg      180
taaccttcgc tttactacac natctgcaag agtaggcagc caaaatggag tcnaaatntt      240 ganccctcg gaaatcccac aaagggant                                         269
```

<210> SEQ ID NO 324
<211> LENGTH: 316
<212> TYPE: DNA
<213> ORGANISM: Zea mays
<220> FEATURE:
<221> NAME/KEY: unsure
<222> LOCATION: (1)...(316)
<223> OTHER INFORMATION: unsure at all n locations

<400> SEQUENCE: 324

```
gacatttacn tccttttcct acggnctggg gtctttgccc caggtcggtg ctcacctgga       60
ctagactgtg cctacccaac tgngaattna ctcgtcgagc cttanactgc tggccataac      120
atnctcctag cccacgctga ggctgttgat ctttacaaca agcattacaa gcgcgacgac      180
acncgcntag ggcttgcgtt tnacgtnatg ggtcgtgtgc catacggnac atcgtttctg      240
ganaacaggc cgnagaaagt cctgggacat caancnatna tggntctaga ccagtngtcg      300
ggtgactacc cctctc                                                      316
```

<210> SEQ ID NO 325
<211> LENGTH: 277
<212> TYPE: DNA
<213> ORGANISM: Zea mays
<220> FEATURE:
<221> NAME/KEY: unsure
<222> LOCATION: (1)...(277)
<223> OTHER INFORMATION: unsure at all n locations

<400> SEQUENCE: 325

```
caaagctcta gttctagcta nctagcaaan nggggganaa tggctccgct tttcgctgcn       60
gccatgaacc acgctgcagc ccatcctggc cttaggagcc ncctagtagg acccaacgat      120
gagagntntc acggcaccan ctgccgtctt cttctccaca gagcagcaan cgaaggtgta      180
acnttagctt tactacacga tntgcaagag taggcagcca aaatggagtc cnnatgttga      240 gccctcgga aatcccgcaa agggantggt tcccctc                                277
```

```
<210> SEQ ID NO 326
<211> LENGTH: 247
<212> TYPE: DNA
<213> ORGANISM: Zea mays
<220> FEATURE:
<221> NAME/KEY: unsure
<222> LOCATION: (1)...(247)
<223> OTHER INFORMATION: unsure at all n locations

<400> SEQUENCE: 326
ancagctcaa agctctagtt ctagctagct agcaaagggg gggaaaatgg ctccgcttct      60
cgctgctgcc atgaaccacg ctgcagccca tcctggcctt aggagccacc tagtaggacc    120
caacaatgag agtttctcac ggcaccacct gccgtcttct tctccacaga gcagcaagcg    180
aaggtgtaac ttagctttac tacacgatct gcaagagtag gcagccaaaa tggagtccaa    240
atgttga                                                              247

<210> SEQ ID NO 327
<211> LENGTH: 252
<212> TYPE: DNA
<213> ORGANISM: Zea mays
<220> FEATURE:
<221> NAME/KEY: unsure
<222> LOCATION: (1)...(252)
<223> OTHER INFORMATION: unsure at all n locations

<400> SEQUENCE: 327
agacattgga gcgaattcgt accatatgta caaaacggat gtcagattgc tgaaggaaat     60
gggcatggac gcatataggt tctctatctc ttggcctaga atactgccta nnggaacggt    120
cgaaaggggt attaaccagg atggcatcna ttactacana aggctcatcn acttgntgct    180
agaggatggc ntagangcat atgnaacnat tttccactgg gatgtccctc aagcactaga    240
agagaagtac gg                                                         252

<210> SEQ ID NO 328
<211> LENGTH: 231
<212> TYPE: DNA
<213> ORGANISM: Zea mays

<400> SEQUENCE: 328
ctgggaattc actcgtcgag ccttacactg ctggccataa cattctccta gcccacgctg     60
aggctgttga tctttacaac aagcattaca agcgcgacga caccgcata gggcttgcgt    120 ttgacgtaat gggtcgtgtg ccatacggaa catcgtttct ggataaacag ccgaagaaa    180 ggtcatggga catcaaccta ggatggttct tagagccagt ggttcgtggt g             231

<210> SEQ ID NO 329
<211> LENGTH: 237
<212> TYPE: DNA
<213> ORGANISM: Zea mays
<220> FEATURE:
<221> NAME/KEY: unsure
<222> LOCATION: (1)...(237)
<223> OTHER INFORMATION: unsure at all n locations

<400> SEQUENCE: 329
caaagctcta gttctagcta gctagcnaan gggggaaaa tggctccgct tctcgctgct      60
gccatgaacc acgctgcagc ccatcctggc cttaggagcc acctagtagg acccaacaat    120
gagagtttct cacggcacca cctgccgtct tcttctccac agagcagcaa gcgaaggtgt    180
aaccttagct ttactacacg atctgcanga gtaggcagcc aaaatggagt ccaantg       237
```

```
<210> SEQ ID NO 330
<211> LENGTH: 264
<212> TYPE: DNA
<213> ORGANISM: Zea mays
<220> FEATURE:
<221> NAME/KEY: unsure
<222> LOCATION: (1)...(264)
<223> OTHER INFORMATION: unsure at all n locations

<400> SEQUENCE: 330
acnccttntc natgagatna ttggctaggg aacgactacc cttcttcaag gacgagcaga      60
aggagaagct tcgccggttc ctataanatg ttggggttaa actactacac ctcacggttc     120
tccaaaaaca tcgatatctc acnaaactan tcacctgtgc tcaacactga ccaccgccnn     180
cgccagtcaa gaagttaacg ggcctgangg gaagcccant ggtcctccta tgggaaatcc     240
atggatctac atgtaccctg aggg                                            264

<210> SEQ ID NO 331
<211> LENGTH: 228
<212> TYPE: DNA
<213> ORGANISM: Zea mays

<400> SEQUENCE: 331
cacatacttt gctaaggtgt gctttgataa cttcggcgac aaggtgaaga attggttgac      60
ctttaatgag ccccagacat ttacttcctt ttcctacgga actgggtct ttgccccagg     120 tcggtgctca cctggactag actgtgccta cccaactggg aattcactcg tcgagcctta    180
cactgctggc cataacattc tcctagccca cgctgaggct gttgatct                  228

<210> SEQ ID NO 332
<211> LENGTH: 233
<212> TYPE: DNA
<213> ORGANISM: Zea mays
<220> FEATURE:
<221> NAME/KEY: unsure
<222> LOCATION: (1)...(233)
<223> OTHER INFORMATION: unsure at all n locations

<400> SEQUENCE: 332
aganaggtcc tgggacatca acctaggatg gttcttagag ccagtggtnc gtggtgacta      60
acccttctcc atgagatcat tggctaggga acgactaccc ttcttcaagg acgagcagaa    120
ggagaagctc gccggttcct ataacatgtt ggggttaaac tactacacct cacggttctc    180
caaaaacatc gatatctcac caaactactc acctgtgctc aacactgacg acg            233

<210> SEQ ID NO 333
<211> LENGTH: 235
<212> TYPE: DNA
<213> ORGANISM: Zea mays
<220> FEATURE:
<221> NAME/KEY: unsure
<222> LOCATION: (1)...(235)
<223> OTHER INFORMATION: unsure at all n locations

<400> SEQUENCE: 333
ctctacccat ggaggatgcc ttaaatgact acaaaaggct agattacatc cagcgccaca      60
tcgctactct taaggaatca atagacttgg gatcaaatgt gcaaggctac ttcgcttggt    120
ctctgctgga caactttgaa tggttcgccg gcttcaccga acgttatggc attgtctacg    180
tcgaccgcaa caataactgc acgcgctaca tgaaggagtc tncnaagngg ttnaa          235
```

<210> SEQ ID NO 334
<211> LENGTH: 268
<212> TYPE: DNA
<213> ORGANISM: Zea mays
<220> FEATURE:
<221> NAME/KEY: unsure
<222> LOCATION: (1)...(268)
<223> OTHER INFORMATION: unsure at all n locations

<400> SEQUENCE: 334

```
aaaataactg ttgatacgga cgtcagattg ctcaaggaaa tgggcatgga cgcntatagg      60
ttctctatct cttggcccag aatactgccg aaggaaccaa agaaggaggt attaacccgg     120
atggcatcaa gtactacaga aacctcatca acttgttgct agaaaacggc atagagccat    180
atgtaacaat tttccactgg gatgtacctc angcactnga agagaagtac ggcggcttcc    240
tagatangag tcatggagca tgttnaag                                        268
```

<210> SEQ ID NO 335
<211> LENGTH: 241
<212> TYPE: DNA
<213> ORGANISM: Zea mays
<220> FEATURE:
<221> NAME/KEY: unsure
<222> LOCATION: (1)...(241)
<223> OTHER INFORMATION: unsure at all n locations

<400> SEQUENCE: 335

```
ttcggtngcc gccacttcag cgtaccaaat tgaaggtgct tggaatgang atngaaaggg      60
ggaaagcaac tgggatcact tctgccacaa tcatccggaa aggatactgg acgggagcaa    120
ttcagacatt ggagcgaatt cgtaccatat gtacaaaacg gacgtcagat tgctcaagga    180
aatgggcatg gacgcatata ggttctctan ctcttggccc agaatactgc cgaaggaacc    240
a                                                                     241
```

<210> SEQ ID NO 336
<211> LENGTH: 240
<212> TYPE: DNA
<213> ORGANISM: Zea mays
<220> FEATURE:
<221> NAME/KEY: unsure
<222> LOCATION: (1)...(240)
<223> OTHER INFORMATION: unsure at all n locations

<400> SEQUENCE: 336

```
ggacaacttt gaatggttcg ccggcttcac cgaacgttat ggcnttgtct acgtcgaccg      60
caacaataac tgcacgcgct acatgaagga gtctgccaag tggttgaaac agttcaacgc    120
cgcgaagaag cccagcaaga ngattcttnn gccagcttng aaatcggggg cctcatgatg    180
tgggtgcagc ccataaaaaa ctggtgtgtg gtttcgaann gaaaatttgc tgttttttncg   240
```

<210> SEQ ID NO 337
<211> LENGTH: 226
<212> TYPE: DNA
<213> ORGANISM: Zea mays

<400> SEQUENCE: 337

```
cgctactctt aaggaatcaa tagacttggg atcaaatgtg caaggctact tcgcttggtc      60
tctgctggac aactttgaat ggttcgccgg cttcaccgaa cgttatggca ttgtctacgt    120
cgaccgcaac aataactgca cgcgctacat gaaggagtct gccaagtggt tgaaacagtt    180
caacgccgcg aagaagccca gcaagaagat tcttacgcca gcttag                   226
```

<210> SEQ ID NO 338
<211> LENGTH: 227
<212> TYPE: DNA
<213> ORGANISM: Zea mays

<400> SEQUENCE: 338

| cacccgcata | gggcttgcgt | ttgacgtaat | gggtcgtgtg | ccatacggaa | catcgtttct | 60 |
| ggataaacag | gccgaagaaa | ggtcctggga | catcaaccta | ggatggttct | tagagccagt | 120 |
| ggttcgtggt | gactacccct | tctccatgag | atcattggct | agggaacgac | tacccttctt | 180 |
| caaggacgag | cagaaggaga | agctcgccgg | ttcctataac | atgttgg | | 227 |

<210> SEQ ID NO 339
<211> LENGTH: 229
<212> TYPE: DNA
<213> ORGANISM: Zea mays

<400> SEQUENCE: 339

| gtaccatatg | tacaaaacgg | acgtcagatt | gctcaaggaa | atgggcatgg | acgcatatag | 60 |
| gttctctatc | tcttggccca | gaatactgcc | gaaggaacca | agaaggagg | tattaacccg | 120 |
| gatggcatca | agtactacag | aaacctcatc | aacttgttgc | tagaaaacgg | catagagcca | 180 |
| tatgtaacaa | ttttccactg | ggatgtacct | caagcactag | aagagaagt | | 229 |

<210> SEQ ID NO 340
<211> LENGTH: 266
<212> TYPE: DNA
<213> ORGANISM: Zea mays
<220> FEATURE:
<221> NAME/KEY: unsure
<222> LOCATION: (1)...(266)
<223> OTHER INFORMATION: unsure at all n locations

<400> SEQUENCE: 340

| ggaaaatggc | tccgcttctc | gctgctgcca | tgaaccacnc | tgcagcccat | cctggcctta | 60 |
| ggagccacct | agtaggaccc | aacaatgaga | gtttctcacg | gcaccacctg | ccgtcttctt | 120 |
| ctccacagag | cagacaagcg | aaggtgtaac | ttagctttac | tacacgatct | gcaagagtag | 180 |
| gcagccaaaa | tggagtccaa | atgttgagcc | cctcggaaat | cccacaaagg | gatggttcta | 240 |
| tctgacttca | ccttcggtgc | cgccac | | | | 266 |

<210> SEQ ID NO 341
<211> LENGTH: 223
<212> TYPE: DNA
<213> ORGANISM: Zea mays

<400> SEQUENCE: 341

| ccagacattt | acttcctttt | cctacggaac | tggggtcttt | gccccaggtc | ggtgctcacc | 60 |
| tggactagac | tgtgcctacc | caactgggaa | ttcactcgtc | gagccttaca | ctgctggcca | 120 |
| taacattctc | ctagcccacg | ctgaggctgt | tgatctttac | aacaagcatt | acaagcgcga | 180 |
| cgacacccgc | atagggcttg | cgtttgacgt | aatgggtcgt | gtg | | 223 |

<210> SEQ ID NO 342
<211> LENGTH: 262
<212> TYPE: DNA
<213> ORGANISM: Zea mays
<220> FEATURE:
<221> NAME/KEY: unsure
<222> LOCATION: (1)...(262)
<223> OTHER INFORMATION: unsure at all n locations

<400> SEQUENCE: 342

```
gcccagcaag aagattctta cgccagctta gaaatcngcg gcctcatgat gtgggtgcag      60
cccataaaaa actggtgtgt ggtttcgaac cgaaaatttt ctgttttttt ccgccacgag     120
aggttctgga ggcatantct ccagcaccgt ggctaataac gcattgttcc aattcngtct     180
ggccttgtca tgcatgcaat aaataaagtg atgggtttcc ctgtttcaaa nannannnna     240
aagnnganga ggaggncggn gg                                              262
```

<210> SEQ ID NO 343
<211> LENGTH: 224
<212> TYPE: DNA
<213> ORGANISM: Zea mays

<400> SEQUENCE: 343

```
acttcggcga caaggtgaag aattggttga cctttaatga gccccagaca tttacttcct      60
tttcctacgg aactggggtc tttgccccag gtcggtgctc acctggacta gactgtgcct     120
acccaactgg gaattcactc gtcgagcctt acactgctgg ccataacatt ctcctagccc     180
acgctgaggc tgttgatctt tacaacaagc attacaagcg cgac                      224
```

<210> SEQ ID NO 344
<211> LENGTH: 324
<212> TYPE: DNA
<213> ORGANISM: Zea mays
<220> FEATURE:
<221> NAME/KEY: unsure
<222> LOCATION: (1)...(324)
<223> OTHER INFORMATION: unsure at all n locations

<400> SEQUENCE: 344

```
gtcctcctgt atgtatatct ttgattttt ttattgtaat atgcatattg gtaactagtg       60
aataatattt actacactaa tttgcagatg ggaaatccat ggatctacat gtaccctgag     120
ggcttgaagg atctccttat gatcatgaag aacaaatacg gaaacccacc tatctacatc     180
acggagaacg gaatcgggga tgttgatacc aaggagacac ctctacccat ggaggatgcc     240
ttaaatgact acaaaaggct agattacatc cagcgccaca tcgctactct taaggnatcc     300
atagacttgg gtcaaatgtg caag                                             324
```

<210> SEQ ID NO 345
<211> LENGTH: 308
<212> TYPE: DNA
<213> ORGANISM: Zea mays
<220> FEATURE:
<221> NAME/KEY: unsure
<222> LOCATION: (1)...(308)
<223> OTHER INFORMATION: unsure at all n locations

<400> SEQUENCE: 345

```
ggtcgtgtcc catacgaaaa gtcggcgttt acggatcaac aggccgaaca aaggtcctgg      60
gacattaacc taggatggtt cttggganccg gttgttcgtg gtgactatcc cttctccatg    120
agatcattgg caagggaacg actacccttc ttcactgaca aagagcaaga gaagctagtg     180
ggttcctatg acatgttggg gttaaactat tatacctcaa ggttctctaa aaacatcgat     240
atctcaccaa actactcgcc agtgctcaac actgacgacg catatgccag tcaagaaacg     300
aatgggct                                                               308
```

<210> SEQ ID NO 346

```
<211> LENGTH: 290
<212> TYPE: DNA
<213> ORGANISM: Zea mays

<400> SEQUENCE: 346
atcccttctc catgagatca ttggcaaggg aacgactacc cttcttcact gacaaagagc      60
aagagaagct agtgggttcc tatgacatgt tggggttaaa ctattatacc tcaaggttct     120
ctaaaaacat cgatatctca ccaaactact cgccagtgct caacactgac gacgcatatg     180
ccagtcaaga aacgaatggg cctgacggga atcccattgg tccttggatg gggaattcgt     240
ggatctacct atatcctgaa ggcctaaagg atctgcttat gatcatgaag                290

<210> SEQ ID NO 347
<211> LENGTH: 341
<212> TYPE: DNA
<213> ORGANISM: Zea mays
<220> FEATURE:
<221> NAME/KEY: unsure
<222> LOCATION: (1)...(341)
<223> OTHER INFORMATION: unsure at all n locations

<400> SEQUENCE: 347
cgaaggtgta accttagctt tactacacga tctgcaagag taggcagcca aaatggagtc      60
caaatgttga gccctcgga atcccacaaa gggactggtt cccctctgac ttcaccttcg     120
gtgccgccat tcagcgtacc aaattgaagg tgcttggaat gaagatggaa aggggggaag     180
caactgggat cattctgcca caatcatccg gaaaggatat ggacnggnnn nantcagaca     240
ttggagcgaa ttcgtaccat atgtacanaa cggacgtnag attgctcagg aaatgggcat     300
ggacgcatat angttctctn tntctgggcc cagatnctgc c                         341

<210> SEQ ID NO 348
<211> LENGTH: 286
<212> TYPE: DNA
<213> ORGANISM: Zea mays

<400> SEQUENCE: 348
gacgcatagg gcttgcattt gacgtaatgg gtcgtgtccc atacgaaaag tcggcgttta      60
cggatcaaca ggccgaacaa aggtcctggg acattaacct aggatggttc ttggagccgg     120
ttgttcgtgg tgactatccc ttctccatga gatcattggc aagggaacga ctacccttct     180
tcactgacaa agagcaagag aagctagtgg gttcctatga catgttgggg ttaaactatt     240
atacctcaag gttctctaaa aacatcgata tctcaccaaa ctactc                    286

<210> SEQ ID NO 349
<211> LENGTH: 220
<212> TYPE: DNA
<213> ORGANISM: Zea mays

<400> SEQUENCE: 349
gctagattac atccagcgcc acatcgctac tcttaaggaa tcaatagact tgggatcaaa      60
tgtgcaaggc tacttcgctt ggtctctgct ggacaacttt gaatggtttg ccggcttcac     120
cgaacgttat ggcattgtct acgtcgaccg caacaataac tgcacgcgct acatgaagga     180
gtctgccaag tggttgaaag agttcaacac cgcgaaaaag                           220

<210> SEQ ID NO 350
<211> LENGTH: 480
<212> TYPE: DNA
<213> ORGANISM: Zea mays
```

```
<220> FEATURE:
<221> NAME/KEY: unsure
<222> LOCATION: (1)...(480)
<223> OTHER INFORMATION: unsure at all n locations

<400> SEQUENCE: 350
anaaaacggn atanagccat atgtaacaat ctttcactgg gatgtncctc aagcacngag      60
aagngaagta cngcggcttc ctagntaaga gtcatangag cattgtanaa gattacacat    120
actntgctaa ggtgtgcttt gataacttnn gcgacaaggt gaagaaattg gttgaccttt    180
aatgagcccc anacatttac ttcttttcc tacngaactg gggtcctttg cnccaagttn     240
ggtgctnacc tggactagac tgtgncttnc caantgggaa ttcnctnatt gangctttac    300
aaatggttgg cccattaaca tttttctaaa ccactcttaa gctngttgat ctttaccanc    360
aancnnttnn ntcncnanca caccngnatt nggctttgct tttnactnaa angggtcttg    420
ntccntacng taacaatcnn ttnnttgana aanangtccn nataaaangg cnntnggaca    480

<210> SEQ ID NO 351
<211> LENGTH: 260
<212> TYPE: DNA
<213> ORGANISM: Zea mays
<220> FEATURE:
<221> NAME/KEY: unsure
<222> LOCATION: (1)...(260)
<223> OTHER INFORMATION: unsure at all n locations

<400> SEQUENCE: 351
cggatgtcag attgctgaag gaaatgggca tggacgcata taggttctct atctcttggc     60
ctagaatact gcctaaggga acggtcgaag gaggtattaa ccggatggca tcgattacta   120
caaaaggctc atcaacttgt tgctagagaa tggcatagag ccatatgtaa caattttccc    180
actgggatgt ccctcaagca ctagaagaga gttacggcgg tttntnggat aagtcccnta    240
gggggttnnn aantgnttnc                                                260

<210> SEQ ID NO 352
<211> LENGTH: 228
<212> TYPE: DNA
<213> ORGANISM: Zea mays
<220> FEATURE:
<221> NAME/KEY: unsure
<222> LOCATION: (1)...(228)
<223> OTHER INFORMATION: unsure at all n locations

<400> SEQUENCE: 352
gggaaaatgg ctccgcttct cgctgctgcc atgaaccacg ctgcagcccg tcctggcctt     60
aggagccacc tagtaggacc caacaatgag agtttctcan ggcaccacct gccgtcttct    120
tctccacaga gcagcaagcg aaggtgtaac cttagcttta ctacacgatc ngcnagagta    180
ggcagccaag atggagtccn natgttgagc ccctcggaaa tcccacaa                 228

<210> SEQ ID NO 353
<211> LENGTH: 222
<212> TYPE: DNA
<213> ORGANISM: Zea mays
<220> FEATURE:
<221> NAME/KEY: unsure
<222> LOCATION: (1)...(222)
<223> OTHER INFORMATION: unsure at all n locations

<400> SEQUENCE: 353
ggaatcaata gacttgggat caaatgtgca aggctacttc gcttggtctc tgctggacaa     60
```

```
ctttgaatgg tttgccggct tcaccgaacg ttatggcatt gtctacgtcg accgcaacaa    120
taactgcacg cgctacatga aggagtctgc caagtggttg aaaganttca acaccgcgaa    180
aaagcccagc aagaagattc ttacgccagc ttaaaaanng gg                      222
```

```
<210> SEQ ID NO 354
<211> LENGTH: 223
<212> TYPE: DNA
<213> ORGANISM: Zea mays

<400> SEQUENCE: 354
gaatcaatag acttggggat caaatgtgca aggctacttc gcttggtctc tgctggacaa    60
ctttgaatgg ttcgccggct tcaccgaacg ttatggcatt gtctacgtcg accgcaacaa    120
taactgcacg cgctacatga aggagtctgc caagtggttg aaacagttca acgccgcgaa    180
gaagcccagc aagaagattc ttacgccagc ttagaaatcg ggg                     223
```

```
<210> SEQ ID NO 355
<211> LENGTH: 217
<212> TYPE: DNA
<213> ORGANISM: Zea mays

<400> SEQUENCE: 355
gcagctcaaa gctctagttc tagctagcta gcaaaggggg ggaaaatggc tccgcttctc    60
gctgctgcca tgaaccacgc tgcagcccat cctggcctta ggagccacct agtaggaccc    120
aacaatgaga gtttctcacg gcaccacctg ccgtcttctt ctccacagag cagcaagcga    180
aggtgtaacc ttagctttac tacacgatct gcaagag                            217
```

```
<210> SEQ ID NO 356
<211> LENGTH: 214
<212> TYPE: DNA
<213> ORGANISM: Zea mays
<220> FEATURE:
<221> NAME/KEY: unsure
<222> LOCATION: (1)...(214)
<223> OTHER INFORMATION: unsure at all n locations

<400> SEQUENCE: 356
acctgagggc ttgaaggatc tccttatgat catgaagaac aaatacggaa acccaccctat   60 ctacatcacg gagaacggaa tcggggatgt tgataccaag gagacacctc tacccatgga   120
ggatgcctta aatgactaca aaaggctaga ttacatccag cgccacatcg ctactcttaa   180
ggnatcaata gacttgggat caaatgtgca aggc                               214
```

```
<210> SEQ ID NO 357
<211> LENGTH: 223
<212> TYPE: DNA
<213> ORGANISM: Zea mays
<220> FEATURE:
<221> NAME/KEY: unsure
<222> LOCATION: (1)...(223)
<223> OTHER INFORMATION: unsure at all n locations

<400> SEQUENCE: 357
caaagctcta gttctagcta gctagcaaag gggggaaaa tggctccgct tctcgctgct    60
gccatgaacc acgctgcagc ccatcctggc cttaggagcc acctagtagg acccaacaat   120
gagagtttct cacggcacca cctgccgtct tcttctncac agaggaacaa gcgaaagtgt   180
accttagctt tactacacga tctgcaagag taggcagcca aaa                     223
```

```
<210> SEQ ID NO 358
<211> LENGTH: 251
<212> TYPE: DNA
<213> ORGANISM: Zea mays
<220> FEATURE:
<221> NAME/KEY: unsure
<222> LOCATION: (1)...(251)
<223> OTHER INFORMATION: unsure at all n locations

<400> SEQUENCE: 358
cttaaatgac tacaaaaggc tagattacat ccagcgccac atcgctactc ttaaggaatc    60
aatagacttg ggatcaaatg tgcaaggcta cttcgcttgg actctgctgg acaactttga   120
atggattgcc ggcttcaccg aacgttatgg cattgtctac gtcgaccgca acaataactg   180
cacgcgctca tgaaggagtc tgccaagtgg ttgnaagagt caacaccggn gaaaagccc    240 acaagaagat t                                                        251

<210> SEQ ID NO 359
<211> LENGTH: 268
<212> TYPE: DNA
<213> ORGANISM: Zea mays
<220> FEATURE:
<221> NAME/KEY: unsure
<222> LOCATION: (1)...(268)
<223> OTHER INFORMATION: unsure at all n locations

<400> SEQUENCE: 359
cttacgccag cttagaaatc gggggcctca tgatgtgggt gcagcccata aaaaactggn    60
gtgtggtttc gaaccgaaaa ttttctgttt ttttccgcca cgagangttc tggaggcata   120
ctctccagca ccgtggctaa taacgcattg ttccaattca gtctggcctt gtcatgcatg   180
caataaataa agtgatgggt ttccctgtta nanaaacnnn ngnnagtcaa gnccntgacg   240
aaantggcat cgatancanc tcggngcg                                      268

<210> SEQ ID NO 360
<211> LENGTH: 286
<212> TYPE: DNA
<213> ORGANISM: Zea mays
<220> FEATURE:
<221> NAME/KEY: unsure
<222> LOCATION: (1)...(286)
<223> OTHER INFORMATION: unsure at all n locations

<400> SEQUENCE: 360
gaaaggtcat gggacatcaa cctaggatgg ttcttagagc cagtggttcg tggtgactac    60
cccttctcca tgagatgcat tggctaggga acgactaccc ttcttcaagg acgagcagaa   120
ggagaagctc gccggttcct ataacatgtt ggggttaaac tactacacct gcacggttct   180
ccaaaaacat cgacatctgc accaaaactan tgcacctgtg ctcaacatga cgacgcctac   240
gccatcaaga agttaacggg ctgacgggaa gcccattggt ctctat                  286

<210> SEQ ID NO 361
<211> LENGTH: 337
<212> TYPE: DNA
<213> ORGANISM: Zea mays
<220> FEATURE:
<221> NAME/KEY: unsure
<222> LOCATION: (1)...(337)
<223> OTHER INFORMATION: unsure at all n locations

<400> SEQUENCE: 361
gggaacgact acgcttnttc aaggacgagc aganggagaa gctcgcnggt tcctataana    60
```

```
tgttggggtt aaactactac acctnacggt tntccanaaa catcgactcn cnaccaaact    120
actcacacnt gctcaacact gacgacgcta cgcnagtnaa gaagttaacg ggcctgacgg    180
gagccnttgg tcctcctatg ggntctccat ggatctacat gtaccctgag ggcttgttng    240
gatctcttat gatcatgaag aacaaatacg gaaacccacn tatctanatn aggagangga    300
atcggggatg ttgataccan gagacactct acccatg                            337
```

<210> SEQ ID NO 362
<211> LENGTH: 312
<212> TYPE: DNA
<213> ORGANISM: Zea mays
<220> FEATURE:
<221> NAME/KEY: unsure
<222> LOCATION: (1)...(312)
<223> OTHER INFORMATION: unsure at all n locations

<400> SEQUENCE: 362

```
cnaaagctct agttctagct agctagcaaa gggggggaaa atggctcngc ttctcgctgc    60
tgccatgaac cangctgcag cccatcctgg ccttaggagc nacctagtag gacccaacaa   120
atggagngtt tctcacggca ccacctgccg tcttcttctc canagagcag caagcgaagg   180
tgtaacctta gctttactac acggtctgca aggnntaggc agccaaaatg gnggtcccaa   240
atnttncagc ccctcntnga atccntgnaa ggnnctggcc ccctncnnt ttaaaatncg   300 gngcagcnaa tt                                                       312
```

<210> SEQ ID NO 363
<211> LENGTH: 217
<212> TYPE: DNA
<213> ORGANISM: Zea mays
<220> FEATURE:
<221> NAME/KEY: unsure
<222> LOCATION: (1)...(217)
<223> OTHER INFORMATION: unsure at all n locations

<400> SEQUENCE: 363

```
gaagattctt acgccagctt agaaatcggg ggcctcatga tgtgggtgca gcccataaaa    60
aactggtgtg tggtttcgaa ccgaaaattt tctgtttttt tccgccacga gaggttctgg   120
aggcatactc tccagcaccg ttggnaataa cgcattgttc caattcagtc tggcttgtca   180
tgcatgcant aaataaagtg atgggtttcc ctgnttc                            217
```

<210> SEQ ID NO 364
<211> LENGTH: 199
<212> TYPE: DNA
<213> ORGANISM: Zea mays

<400> SEQUENCE: 364

```
gttgggaata aactactaca cctcaatatt ctccaaacat atcgacatct caccaaaata    60
ctcgcctgtt ctcaacactg acgacgccta cgctagtcaa gaaacgtatg ggcctgacgg   120
gaaacccatt ggtcctccta tgggaaatcc gtggatctac ttatacccag aaggcctaaa   180
ggatatcctt atgatcatg                                                199
```

<210> SEQ ID NO 365
<211> LENGTH: 200
<212> TYPE: DNA
<213> ORGANISM: Zea mays

<400> SEQUENCE: 365

```
ggaacgacta cccttcttca aggacgagca gaaggagaag ctcgccggtt cctataacat    60
```

```
gttggggtta aactactaca cctcacggtt ctccaaaaac atcgatatct caccaaacta    120
ctcacctgtg ctcaacactg acgacgccta cgccagtcaa gaagttaacg ggcctgacgg    180
gaagcccatt ggtcctccta                                                200

<210> SEQ ID NO 366
<211> LENGTH: 265
<212> TYPE: DNA
<213> ORGANISM: Zea mays

<400> SEQUENCE: 366
ggtgactatc ccttctccat gagatcattg gcaagggaac gactacccct cttcactgac    60
aaagagcaag agaagctagt gggttcctat gacatgttgg ggttaaacta ttatacctca    120
aggttctcta aaaacatcga tatctcacca aactactcgc cagtgctcaa cactgacgac    180
gcatatgcca gtcaagaaac gaatgggcct gacgggaatc ccattggtcc ttggatgggg    240
aattcgtgga tctacctata tcctg                                          265

<210> SEQ ID NO 367
<211> LENGTH: 211
<212> TYPE: DNA
<213> ORGANISM: Zea mays

<400> SEQUENCE: 367
caagcagctc aaagctctag ttctagctag ctagcaaagg ggggaaaat ggcaccgctt     60 ctcgctgctg ccatgaacca cgctgcagcc catcctggcc ttaggagcca cctagtagga    120
cccaacaatg agagtttctc acggcaccac ctgccgtctt cttctccaca gagcagcaag    180
cgaaggtgta accttagctt tactacacga t                                   211

<210> SEQ ID NO 368
<211> LENGTH: 239
<212> TYPE: DNA
<213> ORGANISM: Zea mays
<220> FEATURE:
<221> NAME/KEY: unsure
<222> LOCATION: (1)...(239)
<223> OTHER INFORMATION: unsure at all n locations

<400> SEQUENCE: 368
cttatatgnc tacnaaaggg ttgatnacat cnagngccnc atcnctantg ttantnaatc    60
tatngacttg ggatcaantg gncgatgctn cttcgnttgg antctgctgg acaactttga    120
angnattgcc ggcttcaccg aacgttatgg cattgtctac gtcgaccgca acaataactg    180
cacgcgctac atgaaggagt ctgccaagtg gttgaaagag ttcaacaccg cgaaaaagc     239

<210> SEQ ID NO 369
<211> LENGTH: 195
<212> TYPE: DNA
<213> ORGANISM: Zea mays

<400> SEQUENCE: 369
cgacgacacc cgcatagggc ttgcgtttga cgtaatgggt cgtgtgccat acggaacatc    60
gtttctggat aaacaggccg aagaaaggtc ctgggacatc aacctaggat ggttcttaga    120
gccagtggtt cgtggtgact accccttctc catgagatca ttggctaggg aacgactacc    180
cttcttcaag gacga                                                    195

<210> SEQ ID NO 370
```

```
<211> LENGTH: 193
<212> TYPE: DNA
<213> ORGANISM: Zea mays

<400> SEQUENCE: 370
caaagctcta gttctagcta gctagcaaag gggggaaaa tggctccgct tctcgctgct      60
gccatgaacc acgctgcagc ccatcctggc cttaggagcc acctagtagg acccaacaat    120
gagagtttct cacggcacca cctgccgtct tcttctccac agagcagcaa gcgaaggtgt    180
aaccttagct tta                                                        193

<210> SEQ ID NO 371
<211> LENGTH: 198
<212> TYPE: DNA
<213> ORGANISM: Zea mays

<400> SEQUENCE: 371
caaagctcta gttctagcta gctagcaaag gggggaaaa tggctccgct tctgcgctgc      60
tgccatgaac cacgctgcag cccatcctgg ccttaggagc cacctagtag gacccaacaa    120
tgagagtttc tcacggcacc acctgccgtc ttcttctcca cagagcagca agcgaaggtg    180
taaccttagc tttactac                                                  198

<210> SEQ ID NO 372
<211> LENGTH: 328
<212> TYPE: DNA
<213> ORGANISM: Zea mays
<220> FEATURE:
<221> NAME/KEY: unsure
<222> LOCATION: (1)...(328)
<223> OTHER INFORMATION: unsure at all n locations

<400> SEQUENCE: 372
attggaaact cgctcactga gccatacact gttggccata accttctccg agcccacgct      60
gaggctgttg atctttacaa caagtattac aagggtgaga atggacgcat agggcttgca    120
tttgacgtaa tgggtcgtgt cccatacgaa aagtcggcgt ttacggatca acaggccgaa    180
caaaggtcct gggacattaa cctaggatgg ttcttggagc cggttgttcg tggtgactat    240
ccctctccat gagatcatgg caaggaacga ctacccttct tcatgacaaa gagcaagaga    300
agctatgggt tctatgacng ttgggtta                                        328

<210> SEQ ID NO 373
<211> LENGTH: 239
<212> TYPE: DNA
<213> ORGANISM: Zea mays
<220> FEATURE:
<221> NAME/KEY: unsure
<222> LOCATION: (1)...(239)
<223> OTHER INFORMATION: unsure at all n locations

<400> SEQUENCE: 373
gaaaggtcct gggacatcaa ccanggatgg ttcttangag ccagtggtan cgtggtgact      60
aacccttctc catgagatca ttggctaggg aacgactacc cttcttcaag gacgagcaga    120
aggagaagct cgccggttcc tataacatgt tggggttaaa ctactacacc tcacggttct    180
ccaaaaacat cgatatctca ccaaaactact cacctgtgtc acatgangac gcctagcca    239

<210> SEQ ID NO 374
<211> LENGTH: 212
<212> TYPE: DNA
<213> ORGANISM: Zea mays
```

```
<220> FEATURE:
<221> NAME/KEY: unsure
<222> LOCATION: (1)...(212)
<223> OTHER INFORMATION: unsure at all n locations

<400> SEQUENCE: 374
agcagctcaa agctctagtt ctagctagct agcaaagggg gggaaaatgg ctccgcttct      60
cgctgctgcc atgaaccacg ctgcagccca tcctggcctt aggagccacc tagtangacc     120
caacaatgag agtttctcac ggcaccacct gcngtcttct tctncacaga gcggcaagcg     180
aaggngtaac ctgagcttta ctanangttt gc                                   212

<210> SEQ ID NO 375
<211> LENGTH: 221
<212> TYPE: DNA
<213> ORGANISM: Zea mays
<220> FEATURE:
<221> NAME/KEY: unsure
<222> LOCATION: (1)...(221)
<223> OTHER INFORMATION: unsure at all n locations

<400> SEQUENCE: 375
caagantagg cagccaaaat ggagtccaaa tgttgagccc ctcggaaatc ccacaaaggg      60
actggttccc ctctgacttc accttcggtg ccgccacttc agcgtaccaa attgaaggtg     120
cttggaatga agatggaaag ggggaaagca actgggatca cttctgcnac aatcatccgg     180
aaaggatctg gnngggagca ttccagacat gggncgattt c                         221

<210> SEQ ID NO 376
<211> LENGTH: 212
<212> TYPE: DNA
<213> ORGANISM: Zea mays
<220> FEATURE:
<221> NAME/KEY: unsure
<222> LOCATION: (1)...(212)
<223> OTHER INFORMATION: unsure at all n locations

<400> SEQUENCE: 376
ctagctagct agcaggggg gaaatggctc cacttctcgc cgcagccatg aaccacgctg       60
ctcatccagt ccttagaagc catctaggan ccaacaatga gagtttctca cgacaccacc     120
tatnttcttc accgcaaagc agtaagcgaa ggtttaacct tagctttacg ccagatctgc     180
aaagnaggca atcaaaatgg agtccattgt tg                                   212

<210> SEQ ID NO 377
<211> LENGTH: 180
<212> TYPE: DNA
<213> ORGANISM: Zea mays

<400> SEQUENCE: 377
caaagctcta gttctagcta gctagcaaag ggggggaaaa tggctccgct tctcgctgct      60
gccatgaacc acgctgcagc ccatcctggc cttaggagcc acctagtagg acccaacaat     120
gagagtttct cacggcacca cctgccgtct tcttctccac agagcagcaa gcgaaggtgt     180

<210> SEQ ID NO 378
<211> LENGTH: 266
<212> TYPE: DNA
<213> ORGANISM: Zea mays
<220> FEATURE:
<221> NAME/KEY: unsure
<222> LOCATION: (1)...(266)
<223> OTHER INFORMATION: unsure at all n locations
```

```
<400> SEQUENCE: 378
aatcaataga cttgggatca aatgtgcaag gtacttcgct tgggctctgc tggacaactt      60
tgaatgggtc gccgcttcac cgaacgttat ggcattgcta cgcgaccgca acantaactg     120
cacgcgctca tgaaggagct gcaagtggtt gaaacagttc aacgccgcga agaacccaca     180
agaagattct tacgccagct tagaaatcgg gggcctcatg atgtgggtgc agnccataaa     240
aactggnggt ggttcgaacc gaaatt                                          266

<210> SEQ ID NO 379
<211> LENGTH: 274
<212> TYPE: DNA
<213> ORGANISM: Zea mays
<220> FEATURE:
<221> NAME/KEY: unsure
<222> LOCATION: (1)...(274)
<223> OTHER INFORMATION: unsure at all n locations

<400> SEQUENCE: 379
catcgtttct ggataaacag gccgaagaaa ggtcctggga catcaaccta ggatggttct      60
tagagccagt ggttcgtggt gactaccct tctccangag ntnagtggct aggggangg      120 ggannenctg cncttgggtg ttatgnnggg gnaagncngn gggggnectn aaaaaattng    180 gggtnaactt gacaccctca cggntctcca aaaacatcga tatctcacca aactactcac     240
ctgtgctcaa cactgacgac gcctacgcca gtca                                 274

<210> SEQ ID NO 380
<211> LENGTH: 209
<212> TYPE: DNA
<213> ORGANISM: Zea mays
<220> FEATURE:
<221> NAME/KEY: unsure
<222> LOCATION: (1)...(209)
<223> OTHER INFORMATION: unsure at all n locations

<400> SEQUENCE: 380
cgtccaattc nattttatt tgtgcaggaa tcggggatgt tganaccaag gagacacctc      60
tacccatgga ggatgcctta nntgactaca anaggctaga ttacatccag cgccacatcg    120
ctactcttaa ggaatcaata gacttgggat caaatgtggc aatgctactt cgcttggtct    180
ctgctggaca actttgaatg gttcgccgg                                       209

<210> SEQ ID NO 381
<211> LENGTH: 183
<212> TYPE: DNA
<213> ORGANISM: Zea mays

<400> SEQUENCE: 381
ggtgcttgga atgaagatgg aaaggggaa agcaactggg atcacttctg ccacaatcat       60
ccggaaagga tactggacgg gagcaattca gacattgag cgaattcgta ccatatgtac    120
aaaacggacg tcagattgct caaggaaatg ggcatggacg catatagttc tctatctctt    180
ggc                                                                  183

<210> SEQ ID NO 382
<211> LENGTH: 238
<212> TYPE: DNA
<213> ORGANISM: Zea mays

<400> SEQUENCE: 382
gggtgagaat ggacgcatag ggcttgcatt tgacgtaatg ggtcgtgtcc catacgaaaa      60
```

```
gtcggcgttt acggatcaac aggccgaaca aagtcctgg gacattaacc taggatggtt      120
cttggagccg gttgttcgtg gtgactatcc cttctccatg agatcattgg caagggaacg    180
actacccttc ttcactgaca aagagcaaga gaagctagtg ggttcctatg acatgttg      238
```

<210> SEQ ID NO 383
<211> LENGTH: 167
<212> TYPE: DNA
<213> ORGANISM: Zea mays
<220> FEATURE:
<221> NAME/KEY: unsure
<222> LOCATION: (1)...(167)
<223> OTHER INFORMATION: unsure at all n locations

<400> SEQUENCE: 383

```
caatttccca ctgggatgta cctcaagcac tagaagagaa gtacggcggc ttcctagata    60
agagtcataa gagcattgta gaagattaca catactttgc taaggtgtgc tttgataact    120
tcggcgacaa ggtgaagaat tggttgacct ttaatgagcc cnagact                  167
```

<210> SEQ ID NO 384
<211> LENGTH: 210
<212> TYPE: DNA
<213> ORGANISM: Zea mays
<220> FEATURE:
<221> NAME/KEY: unsure
<222> LOCATION: (1)...(210)
<223> OTHER INFORMATION: unsure at all n locations

<400> SEQUENCE: 384

```
canaactact cacctgtgct caacactgac gacgcctacg ccagtcaaga aantaacggg    60
cctgacggga agcccattgg tcctcctatg ggaaatccat ggatctacat gtaccctgag   120
ggcttgaagg atctccttat gatcatgaag aacanatang ganncccant tatntggtna   180
cggaaancgg nngttggata gngnnccccc                                     210
```

<210> SEQ ID NO 385
<211> LENGTH: 360
<212> TYPE: DNA
<213> ORGANISM: Zea mays
<220> FEATURE:
<221> NAME/KEY: unsure
<222> LOCATION: (1)...(360)
<223> OTHER INFORMATION: unsure at all n locations

<400> SEQUENCE: 385

```
cagaaacctc atcaacntgn tgctaganaa cgggcataga gccatatgta acaattttcc    60
actgggatgt acctcncagc actagaagag aagtacggcg gcttccctag ataagagtca   120
tangagnagt gtagangatt anacatactt gtgctnaggt gtgttggnat aactcncgnc   180
gnacataggt gaaagaattg agtaganctg antgagcncc cagacantta anttcgnntn   240
tccnaacngg aactgtnggn cttgtgcncc caggtcggtg ctcanctggg actagactgt   300 gcctaccccca actgggnntt cactcgtcga gcctnncact gctggcnata acattctcct   360
```

<210> SEQ ID NO 386
<211> LENGTH: 150
<212> TYPE: DNA
<213> ORGANISM: Zea mays

<400> SEQUENCE: 386

```
gccccaggtc ggtgctcacc tggactagac tgtgcctacc caactgggaa ttcactcgtc    60
```

```
gagccttaca ctgctggcca taacattctc ctagcccacg ctgaggctgt tgatctttac      120
aacaagcatt acaagcgcga cgacacccgc                                       150
```

<210> SEQ ID NO 387
<211> LENGTH: 164
<212> TYPE: DNA
<213> ORGANISM: Zea mays

<400> SEQUENCE: 387

```
ggttctccaa aaacatcgat atctcaccaa actactcacc tgtgctcaac actgacgacg       60
ctacgccagt caagaagtta acgggcctga cgggaagccc attggtcctc ctatgggaaa      120
tccatggatc tacatgtacc ctgaagggtt gaaagatctc ctat                       164
```

<210> SEQ ID NO 388
<211> LENGTH: 148
<212> TYPE: DNA
<213> ORGANISM: Zea mays
<220> FEATURE:
<221> NAME/KEY: unsure
<222> LOCATION: (1)...(148)
<223> OTHER INFORMATION: unsure at all n locations

<400> SEQUENCE: 388

```
ctctagttct agctagctag caaaggggn gaaaatggct ccgcttctcg ctgctgcnat        60
gaaccacgct gcagcccatc ctggccttag gagccaccta gtaggaccca acaatgagag      120
tttctcacgg caccacctgc cgtcttct                                         148
```

<210> SEQ ID NO 389
<211> LENGTH: 219
<212> TYPE: DNA
<213> ORGANISM: Zea mays

<400> SEQUENCE: 389

```
aaatgtgcta acccaattgg aaactcgctc actgagccat acactgttgg ccataacctt       60
ctccgagccc acgctgaggc tgttgatctt tacaacaagt attacaaggg tgagaatgga      120
cgcatagggc ttgcatttga cgtaatgggt cgtgtcccat acgaaaagtc ggcgtttacg      180
gatcaacagg ccgaacaaag gtcctgggac attaaccta                             219
```

<210> SEQ ID NO 390
<211> LENGTH: 160
<212> TYPE: DNA
<213> ORGANISM: Zea mays
<220> FEATURE:
<221> NAME/KEY: unsure
<222> LOCATION: (1)...(160)
<223> OTHER INFORMATION: unsure at all n locations

<400> SEQUENCE: 390

```
gattacacat actttgctaa ggtgtgcttt gataacttcg gcgacaaggt gaagaattgg       60 ttgacccttta atgagcccca gacattactt ccttttccta cggaactggg gtctttnccc     120
cangtcggng ctcantggac tagactgtgc ctacccannt                            160
```

<210> SEQ ID NO 391
<211> LENGTH: 139
<212> TYPE: DNA
<213> ORGANISM: Zea mays

<400> SEQUENCE: 391

```
caacactgac gacgcctacg ccagtcaaga agttaacggg cctgacggga agcccattgg       60
```

```
tcctcctatg ggaaatccat ggatctacat gtaccctgag ggcttgaagg atctccttat    120
gatcatgaag aacaaatag                                                 139

<210> SEQ ID NO 392
<211> LENGTH: 150
<212> TYPE: DNA
<213> ORGANISM: Zea mays
<220> FEATURE:
<221> NAME/KEY: unsure
<222> LOCATION: (1)...(150)
<223> OTHER INFORMATION: unsure at all n locations

<400> SEQUENCE: 392
gctcctagcc cacgctgagg ctgttgatct ttacaacaag cattacaagc gcgacgacac    60
nncgcatagg gcttgcgttt gacgtaatgg gtcgtgtgcc atacgaaaca tcgtttctgg    120
ataaacaggc cgaagaaagg tcctgggatt                                     150

<210> SEQ ID NO 393
<211> LENGTH: 175
<212> TYPE: DNA
<213> ORGANISM: Zea mays

<400> SEQUENCE: 393
tggacagtga gggcttgcat ttgacgtaat gggtcgtgtc ccatacgaaa agtcggcgtt    60
tacggatcaa caggccgaac aaaggtcctg gacattaac ctaggatggt tcttggagcc     120
ggttgttcgt ggtgactatc ccttctccat gagatcattg gcaagggaac gacta         175

<210> SEQ ID NO 394
<211> LENGTH: 133
<212> TYPE: DNA
<213> ORGANISM: Zea mays
<220> FEATURE:
<221> NAME/KEY: unsure
<222> LOCATION: (1)...(133)
<223> OTHER INFORMATION: unsure at all n locations

<400> SEQUENCE: 394
cggatgtcag attgctgaag gaaatgggca tggacgcata taggttctct atctcttggc    60
cnanaatact gcctaaggna acggtcgaag gaggtattaa ccaggatggc atcgattact    120
acaaaaggct cat                                                       133

<210> SEQ ID NO 395
<211> LENGTH: 129
<212> TYPE: DNA
<213> ORGANISM: Zea mays

<400> SEQUENCE: 395
cagaaacctc atcaacttgt tgctagaaaa cggcatagag ccatatgtaa caattttcca    60
ctgggatgta cctcaagcac tagaagagaa gtacggcggc ttcctagata agagtcataa    120
gagcattgt                                                            129

<210> SEQ ID NO 396
<211> LENGTH: 127
<212> TYPE: DNA
<213> ORGANISM: Zea mays
<220> FEATURE:
<221> NAME/KEY: unsure
<222> LOCATION: (1)...(127)
<223> OTHER INFORMATION: unsure at all n locations
```

```
<400> SEQUENCE: 396
gggataaaca ggccgaagaa aggtcctggg acatcaacct aggatggttc ntagagccag      60
tggttcgtgg tgactacccc ttctccatga gatcattggc tagggaacga ctacccttct     120
tcaagga                                                               127

<210> SEQ ID NO 397
<211> LENGTH: 126
<212> TYPE: DNA
<213> ORGANISM: Zea mays

<400> SEQUENCE: 397
ctctagttct agctagctag caaagggggg gaaaatggct ccgcttctcg ctgctgccat      60
gaaccacgct gcagcccatc ctggccttag gagccaccta gtaggaccca acaatgagag     120
tttctc                                                                126

<210> SEQ ID NO 398
<211> LENGTH: 238
<212> TYPE: DNA
<213> ORGANISM: Zea mays
<220> FEATURE:
<221> NAME/KEY: unsure
<222> LOCATION: (1)...(238)
<223> OTHER INFORMATION: unsure at all n locations

<400> SEQUENCE: 398
cngnncgntg ggtcgaccca ccgcgtccgc nccaacgcgt ccgcggacgc gtgggcaaag      60
cagctcaaag ctctagtact agctagctag caaagggggg gaanntggct ccgcttactc     120
gctgctgcca tgaaccacgc tgcagcccat cctggcctta ggagccacct agtaggaccc     180
aacaatgaga gtttctcacg gcaccacctg ccgtcttctt ctccacagag cagcaagg      238

<210> SEQ ID NO 399
<211> LENGTH: 131
<212> TYPE: DNA
<213> ORGANISM: Zea mays

<400> SEQUENCE: 399
agaatactgc cgaagggaac caaagaagga ggtattaacc cggatggcat caagtactac      60
agaacacctc atcaacttgt tgctagaaaa cggcatagag ccatatgtaa caattttcca     120
ctgggatgta c                                                          131

<210> SEQ ID NO 400
<211> LENGTH: 132
<212> TYPE: DNA
<213> ORGANISM: Zea mays
<220> FEATURE:
<221> NAME/KEY: unsure
<222> LOCATION: (1)...(132)
<223> OTHER INFORMATION: unsure at all n locations

<400> SEQUENCE: 400
agcagctcaa agctctagtt cnagcnagcn agcaaagggg gggaaaatgg ctccgcttct      60
cgcngcngcc atgnacncac gctgcagccc anccnggcct taggagccac cnagtaggnc     120
ccaacaatga ga                                                         132

<210> SEQ ID NO 401
<211> LENGTH: 116
<212> TYPE: DNA
<213> ORGANISM: Zea mays
```

```
<220> FEATURE:
<221> NAME/KEY: unsure
<222> LOCATION: (1)...(116)
<223> OTHER INFORMATION: unsure at all n locations

<400> SEQUENCE: 401
ancagctcaa agctctagtt ctagctagct agcaaanggg gggaaaatgg ctccgcttct      60
cgctgctgcc atgaaccacg ctgcagccca tcctggcctt aggagccact agtagg        116

<210> SEQ ID NO 402
<211> LENGTH: 123
<212> TYPE: DNA
<213> ORGANISM: Zea mays

<400> SEQUENCE: 402
cgctgagccc ctcggaagtc cctaaaagag actggttccc ctctgacttc atctttggtg     60
ccgccacttc agcgtaccaa attgaaggtg gatggaacga ggatggaaag aagccaagca    120
cat                                                                  123

<210> SEQ ID NO 403
<211> LENGTH: 132
<212> TYPE: DNA
<213> ORGANISM: Zea mays

<400> SEQUENCE: 403
ggacgcatag ggcttgcatt tgacgtaatg ggtcgtgtcc catacgaaaa gtcggcgttt     60
acggatcaac aggccgaaca aaggtcctgg gacattaacc taggatggtt cttggagccg    120
gttgttcgtg gt                                                        132

<210> SEQ ID NO 404
<211> LENGTH: 105
<212> TYPE: DNA
<213> ORGANISM: Zea mays
<220> FEATURE:
<221> NAME/KEY: unsure
<222> LOCATION: (1)...(105)
<223> OTHER INFORMATION: unsure at all n locations

<400> SEQUENCE: 404
gaggctgttg atctttacaa caagcattac aagcgcgacg acacccgcat agggcttgcg     60
nttgacgnaa tgggtcgngt gccatacgga anntccgttc nnggg                    105

<210> SEQ ID NO 405
<211> LENGTH: 92
<212> TYPE: DNA
<213> ORGANISM: Zea mays
<220> FEATURE:
<221> NAME/KEY: unsure
<222> LOCATION: (1)...(92)
<223> OTHER INFORMATION: unsure at all n locations

<400> SEQUENCE: 405
ggagacatcg tttctggata aacaggccga agaaaggtcc tgggacatca acctaggatg     60
gttcttagag ccagtngttc gtggtgacta cc                                   92

<210> SEQ ID NO 406
<211> LENGTH: 443
<212> TYPE: DNA
<213> ORGANISM: Zea mays
<220> FEATURE:
<221> NAME/KEY: unsure
<222> LOCATION: (1)...(443)
```

<223> OTHER INFORMATION: unsure at all n locations

<400> SEQUENCE: 406

```
gacagggtga agaactgttt tancttcaac gagccgaggt gcgtcggngg tcngggctac      60
gacaatggct tgcacgcacc gggaaggtgt tccgggtgcc ccgccggagg caactccacc     120
acggagccgt accttgtcgc acaccatctc atcctttctc atgcagctgc ngtcaggcga     180
taccgcgaca agtatcagct tcaccagaag gggaagattg gaattctcct ggatttcgtg     240
tggtacgaac ctttcagcga cagcaatgcn gaccaggctg cagcacagcg agccagggac     300
ttccacctaa gctggttcct tgaccccatt gtcatggacc gtcccgtact ngatgcaaga     360
aaatgnccaa nacaagnttn ccgntggtta accattgaaa aaaccncgat ggtgnaaagg     420
tttatngacn atttttggnt tca                                             443
```

<210> SEQ ID NO 407
<211> LENGTH: 291
<212> TYPE: DNA
<213> ORGANISM: Zea mays
<220> FEATURE:
<221> NAME/KEY: unsure
<222> LOCATION: (1)...(291)
<223> OTHER INFORMATION: unsure at all n locations

<400> SEQUENCE: 407

```
aactggttta cctttcaacg agccgaggtg cgtcgctgct ctgggctacg acaatggctt      60
gcacgcaccg ggaaggtgtt ccgggtgccc cgccggagga actccaccac ggagccgtac     120
cttgtcgcac accatctcat cctttctcat gcagctgcgg tcaggcgata ccgcgacaag     180
tatcagcttc accagaaggg gaagattgga atctcctgga tttcgtgtgg tacgaaccttt    240 tcagcgacan aatgcggacc aggctgcagc acagcgagcc aggattccac t              291
```

<210> SEQ ID NO 408
<211> LENGTH: 256
<212> TYPE: DNA
<213> ORGANISM: Zea mays
<220> FEATURE:
<221> NAME/KEY: unsure
<222> LOCATION: (1)...(256)
<223> OTHER INFORMATION: unsure at all n locations

<400> SEQUENCE: 408

```
tgcgtcgctg ctctgggcta cgacaatggc ttgcacgcac cgggaaggtg ttccgggtgc      60
cccgccggag gaactccacc acggagccgt accttgtcgc acaccatctc atcctttctc     120
atgcagctgc tgtnaggnga taccgcnaca agtatnanct tcaccagaag gggaagattg     180
gaantattat agattttntg tngtangaac ctttatctac ancaatgcng acnangctgc     240
agcacagcna gccang                                                     256
```

<210> SEQ ID NO 409
<211> LENGTH: 306
<212> TYPE: DNA
<213> ORGANISM: Zea mays
<220> FEATURE:
<221> NAME/KEY: unsure
<222> LOCATION: (1)...(306)
<223> OTHER INFORMATION: unsure at all n locations

<400> SEQUENCE: 409

```
acaccatctc atcctntctc atgcagctgc ngtcaggcga tnccgcgaca agtatcagct      60
tcaccagaag gggaagattg gaattctcct ggatttcgtg tggtacgaac ctttcagcga     120
```

```
cagcaatgcg gaccaggctg cagcacagcg anccagggnc tttcacctag gctggttcct    180 tganccatt gtacatggac ggtacccgta ctcgatgnaa gagatgccna agacaggnta    240
ccgttgttca gcgatgnaga agccaggatg gtgaaangct ctatngatta tgttggcatc    300
aaccac                                                             306

<210> SEQ ID NO 410
<211> LENGTH: 285
<212> TYPE: DNA
<213> ORGANISM: Zea mays
<220> FEATURE:
<221> NAME/KEY: unsure
<222> LOCATION: (1)...(285)
<223> OTHER INFORMATION: unsure at all n locations

<400> SEQUENCE: 410
cgcacaccat ctcatccttt ctcatgcagc tgcggtcagg cgataccgcg acaagtatca     60
gcttcaccag aaggggaaga ttggnattct cctggatttt gtgtggtacg aacctttcag    120
cgacagcaat gcggaccagg ctgcagcaca gcgagccagg gacttccacc taggctggtt    180
ccttgacccc attgtacatg gacggtaccc gtactcgatg caagagattg ccaaagacag    240
gctaccgttg ttcagcgatn aagaagccag gatggtgaaa ggctc                   285

<210> SEQ ID NO 411
<211> LENGTH: 202
<212> TYPE: DNA
<213> ORGANISM: Zea mays
<220> FEATURE:
<221> NAME/KEY: unsure
<222> LOCATION: (1)...(202)
<223> OTHER INFORMATION: unsure at all n locations

<400> SEQUENCE: 411
ttggaattct cctggatttc gtgtggtacg aacctttcag cgacagcaat gcggaccagg     60
ctggcagcac agcgagccag ggacttccac ctaggctggt tccttgaccc cattgtacat    120
ggacggtacc cgtactcgat gcaagagatt gccaaagana ggctaccgtt gttcagcgtg    180 aaganccong gatggtgaaa gt                                            202

<210> SEQ ID NO 412
<211> LENGTH: 427
<212> TYPE: DNA
<213> ORGANISM: Zea mays
<220> FEATURE:
<221> NAME/KEY: unsure
<222> LOCATION: (1)...(427)
<223> OTHER INFORMATION: unsure at all n locations

<400> SEQUENCE: 412
gtctgccatg ggtcaaangg ctcangcggg anttacgtcg ggcattcaaa ccactacacc     60
cacgtactta cgcccagcaa ctttcgtcaa acgcccacag aagaccaaac ttaccgcaan    120
cgattgggaa tgcaaagatt tcgtatgagc gagatggtgt gcccattggc aaaagggcgt    180
actcggactg gctttacgtc gttccatggg ggctctacaa ggctctgatt tggaccaagg    240
agaagttcaa cagccctgtg atgctcatcg gagagaacgg aattgaccag cctggaaatg    300
agaccttgcc gttcgctctg tacgacaagt tcaggataga ctacttcgag aagtacctgt    360
acgagctcca gtcgccata cgcgacggtg caaacgtctt cggctacttc gcgtggtcgc    420
tgctgga                                                            427
```

<210> SEQ ID NO 413
<211> LENGTH: 292
<212> TYPE: DNA
<213> ORGANISM: Zea mays

<400> SEQUENCE: 413

| | |
|---|---|
| agaccaacta ccgcaacgat tggaatgcaa agatttcgta tgagcgagat ggtgtgccca | 60 |
| ttggcaaaag ggcgtactcg gactggcttt acgtcgttcc atggggctc tacaaggctc | 120 |
| tgatttggac caaggagaag ttcaacagcc ctgtgatgct catcggagag aacggaattg | 180 |
| accagcctgg aaatgagacc ttgccgttcg ctctgtacga caattcagga tagactattc | 240 |
| gagaagtacc tgtacgagct ccagtggcgc atacgcgac ggtgcaaacg tc | 292 |

<210> SEQ ID NO 414
<211> LENGTH: 467
<212> TYPE: DNA
<213> ORGANISM: Zea mays
<220> FEATURE:
<221> NAME/KEY: unsure
<222> LOCATION: (1)...(467)
<223> OTHER INFORMATION: unsure at all n locations

<400> SEQUENCE: 414

| | |
|---|---|
| ggcctgcagc gccagcgcag cgcctctctg ctactgtgct ggctgacgcc ggtggggngt | 60 |
| gagcgaactg cgagctgctg ccaccctgc tgccgcggtc gaccgccggc cccggaccga | 120 |
| gatggacgct cggtgggcgg tgctgctcgc gctgctggtc gccagcggcg cgtccgtgt | 180 |
| ctgcgccgcc gctggggcca agggcgccaa ctggctgggc gggctgagcc gcgcgtcgtt | 240 |
| ccccaagggg ttcgtgttcg ggacggcgac gtnggcgtac caggtcgagg gcgccgngtn | 300 |
| caccaacggn cggggcccct tcatctggga ttcattcgcg cacgttccaa gaaatattgc | 360 |
| anggaatcaa aatggaaacg tttcaatgga tcaataccat cgntncaagg aaanacgtcg | 420 |
| attctcatga aaaggttgaa cttttgatgc ctaccggntc tnaatnt | 467 |

<210> SEQ ID NO 415
<211> LENGTH: 441
<212> TYPE: DNA
<213> ORGANISM: Zea mays
<220> FEATURE:
<221> NAME/KEY: unsure
<222> LOCATION: (1)...(441)
<223> OTHER INFORMATION: unsure at all n locations

<400> SEQUENCE: 415

| | |
|---|---|
| ggcnagcgag tgtggctgcc gcttnctctg cgagtnaggc gccatttaat aattcaattg | 60 |
| gaccnccaag cccacgcttc cgaattcacc gactcctcct ncacgccgcg tcagatcgc | 120 |
| tcaggccttc gcttccagca actccaccac tcagnccacc cgccggagca atggggagca | 180 |
| cngggcgcga gccggaggtt acccgcgccg acttncccga tggcttcgnc ttcggcgttg | 240 |
| ccacctgcgt gtaccagatt ganggagcga gaagggaggg aggcaaagga gacagcatat | 300 |
| gggatgtatt tacagatgac aaagaacatg tcttanacag aagcaatgga gaaattgcaa | 360 |
| gttgatcact accatcgatc aaggaaagac attgagctna tggcaaagtc taggntttag | 420 |
| cgcatacaga tttctatatc t | 441 |

<210> SEQ ID NO 416
<211> LENGTH: 407
<212> TYPE: DNA
<213> ORGANISM: Zea mays

```
<220> FEATURE:
<221> NAME/KEY: unsure
<222> LOCATION: (1)...(407)
<223> OTHER INFORMATION: unsure at all n locations

<400> SEQUENCE: 416
gggcgaagtt ccgtgctcgc gctgcttctc ctgctttccg ccggaggagc ccgagcgtcc      60
tacgacggcg agggcgaggc aggggcaggg gcagaggaga aggagaaggc tgcggcgtgg     120
acgggcgggc tgagccggcg gagctttccc aaggggttcg tgttcgggac ggcggcgtcg     180
gcctaccagg tggagggcat ggcgcacaag gacggccgcg ggccgagcat ttgggacgcc     240
ttcatcaaga tccccgtagt acacttgtat ggattgcata tgaaaatgca tcgatcgtgg     300
attgaattgg cttgacatgg ttggatnatg gcatggcaaa tggcggcgtc ctgcttttca     360
ggcgaaattc gcaaacaacg ccaaccgcgg acgttaactg ttgacga                   407

<210> SEQ ID NO 417
<211> LENGTH: 307
<212> TYPE: DNA
<213> ORGANISM: Zea mays
<220> FEATURE:
<221> NAME/KEY: unsure
<222> LOCATION: (1)...(307)
<223> OTHER INFORMATION: unsure at all n locations

<400> SEQUENCE: 417
ctcgctcact tcttcccagc ggagtgcgca gtcgtcatgg ctaangctag ccgtggtcgt      60
gtcggcggcg gcgggcgaag ttccgtgctc gcgctgcttc tcctgctttc cgccggagga     120
gcccgagcgt cctacgacgg cgagggcgag gcaggggcag gggcagagga gaaggagaag     180
gctgcgncgt ggacgggcgg gctgagccgg cggacttttcc caaggggttc gtgttcggga    240
cggcgncgtc ggcctaccag gtggagggca tgncgcacaa ggacggccgc tggcctagca     300
tttggta                                                              307

<210> SEQ ID NO 418
<211> LENGTH: 272
<212> TYPE: DNA
<213> ORGANISM: Zea mays

<400> SEQUENCE: 418
ctagagtcca ggtctcactc gcgaccgaga gccacagaga aatgggggcc cctgctcgtc      60
cctggcgccg gcacgtcttc ctcgtcgtgt cgctgcagct gctccttgtg gcgccatggc     120
aggacgagac ggccgctcga gctctcaatt tcaccaggca ggatttcccc agggccttcg     180
tctttggtgc cggcacgtca gcttatcagt acgaagggca accgatgaag acggaaggag     240
ccccaagcat atgggacaat ttactcatgc ag                                   272

<210> SEQ ID NO 419
<211> LENGTH: 452
<212> TYPE: DNA
<213> ORGANISM: Zea mays
<220> FEATURE:
<221> NAME/KEY: unsure
<222> LOCATION: (1)...(452)
<223> OTHER INFORMATION: unsure at all n locations

<400> SEQUENCE: 419
tcggaatagt cctggacttc aactggtacg aggctcttac aaactcacct gatgaccaag      60
cagcagccca aagagccagg gacttccaca ttggctggtt tgttgatcca ttgataaacg     120
```

```
gacactatcc acagataatg caagatctcg tgaaggagag gctgcccagg ttcactcctg    180
agcaggctaa actggtgaag ggctcggcag actacatcgg tatcaacgag tacacatcca    240
gctacatgaa ggggcagaag ctggtccagc tggcgcccag tagctactct gccgattggc    300
aggttcaata tgttttgca cgcaatggca aaccgattgg accacaggcg aattctaagt    360
ggctctacat cgccccgacg gggatgtacn ggtgcgtgaa ctaccttaag gagaagtatg    420
ggaatncaac gatctacata acggagaacg ga                                  452
```

<210> SEQ ID NO 420
<211> LENGTH: 450
<212> TYPE: DNA
<213> ORGANISM: Zea mays
<220> FEATURE:
<221> NAME/KEY: unsure
<222> LOCATION: (1)...(450)
<223> OTHER INFORMATION: unsure at all n locations

<400> SEQUENCE: 420

```
atcttcccgg atggcgaagg gaaagtcaat ccagaaggtg tagcgtatta caatanttng    60
ataaactatc tgcttcagca aggcatgact ccttacatca acctttacca ctatgatctt   120
cctcttgcgc ttgagaagaa atatggaggg tggttaagcg cgaagatggc ggacttgttt   180
acagactatg ctgacttctg ttttaagacc tacggcgatc gcgtaaagca ctggtttaca   240
ttcaatgagc caaggatagt agcgctactt ggctatgaca cagggtcaaa tcctcctcaa   300
aggtgcacca gatcgctgc tggtgggaat tcagcaaccg aaccttacat agttgctcat   360
aattttctct tggcacatgc tactgcagtt gcaagatacc gtacgaaata tcangctgct   420
caaaanggta aggtccgaat agtcctggac                                    450
```

<210> SEQ ID NO 421
<211> LENGTH: 464
<212> TYPE: DNA
<213> ORGANISM: Zea mays
<220> FEATURE:
<221> NAME/KEY: unsure
<222> LOCATION: (1)...(464)
<223> OTHER INFORMATION: unsure at all n locations

<400> SEQUENCE: 421

```
tgcagttgca agataccgta cgaaatatca ggctgctcag aagggtaagg tcggaatagt    60
cctggacttc aactggtacg aggctcttac aaactcacct gatgaccaag cagcagccca   120
aagagccagg gacttccaca ttggctggtt tgttgatcca ttgataaacg gacactatcc   180
acagataatg caagatctcg tgaaggagag gctgcccagg ttcactcctg agcaggctaa   240
actggtgaag ggctcggcag actacatcgg tatcaacgag tacacattca gctacatgaa   300
ggggcagaag ctggtccagc tggcgcccag tagctactct gccgattggc aggttcaata   360 tgttttgca cgcaatggca aaccgattgg accacaagcg aattctaaag tggctctaca   420
tngncccgac ngggatgtcc nggtgcgtga actancttaa gggg                    464
```

<210> SEQ ID NO 422
<211> LENGTH: 471
<212> TYPE: DNA
<213> ORGANISM: Zea mays
<220> FEATURE:
<221> NAME/KEY: unsure
<222> LOCATION: (1)...(471)
<223> OTHER INFORMATION: unsure at all n locations

<400> SEQUENCE: 422

```
ccaagttcac tcctgagcag gctaaactgg gtgaagggct cggcagacta catcggtatc    60
aacgagtaca catccagcta catgaagggg cagaagctgg tccagctggc gcccagtagc   120
tactctgccg attggcaggt tcaatatgtt tttgcacgca atggcaaacc gattggacca   180
caggcgaatt ctaagtggct ctacatcgcc ccgacgggga tgtacgggtg cgtgaactac   240
ctcaaggaga agtatgggaa tccaacgatc tacataacgg aagaacggaa tggaccagcc   300
tggaaacttg acccgagacc agtacctgcg cgacgccacg agggtgcggt tctacaggag   360
ctacatcggc caactgaaga aaggccatag accaagggag cgaacgtggc tgggctactt   420
cgccctgggt ctctcctccn acaacttcga ntggctggca agggttactc c            471

<210> SEQ ID NO 423
<211> LENGTH: 465
<212> TYPE: DNA
<213> ORGANISM: Zea mays
<220> FEATURE:
<221> NAME/KEY: unsure
<222> LOCATION: (1)...(465)
<223> OTHER INFORMATION: unsure at all n locations

<400> SEQUENCE: 423
cagaagggta aggtcggaat agtcctggac ttcaactggt acgaggctct tacaaactca    60
cctgatgacc aagcagcagc ccaaagagcc agggactttnc acattggctg ggtttgttga  120
tccattgata aacggacact atccacagat aatgcaagat ctcgtgaagg agaggctgcc   180
caggttcact cctgagcagg ctaaactggg tgaaggggct cggcagacta catcggtatc   240
aacgaagtac acattcagct acatgaaggg gcagaagctg gtccagctgg cncccaatag   300
ctactctgcc gattggcagg ttcaatatgt ttttgcacgc aatggcaaac cgattggacc   360
acaggcgaat tctaaagtgg ctctacattg ccccgacggg gatgtacngg tgcgtgaact   420
acctcaagga gaagtatggg aatncaacga tctacataac ggaga                   465

<210> SEQ ID NO 424
<211> LENGTH: 463
<212> TYPE: DNA
<213> ORGANISM: Zea mays
<220> FEATURE:
<221> NAME/KEY: unsure
<222> LOCATION: (1)...(463)
<223> OTHER INFORMATION: unsure at all n locations

<400> SEQUENCE: 424
ctttaccact atgatcttcc tcttgcgctt gagaagaaat atggagggtg gttaagcgcg    60
aagatggcgg acttgtttac agactatgct gacttctgtt ttaagaccta cggcgatcgc   120
ggtaaagcac tggtttacat tcaatgagcc aaggatagta gcgctacttg gctatgacac   180
agggtcaaat cctcctcaaa ggtgcaccag atgcgctgct ggtgggaatt cagcaaccga   240
accttacata gttgctcata atttctctt ggcacatgct actgcagttg caagataccg   300
taccgaaata tcaggctgct canaagggta aggtcggaa tagtcctgga cttcaactgg   360
gaccaaggct nttacaaact tnaccttgat gacccaagca nnangcccna aaaagccagg   420
ggccttncac atggctnggt ttggtngatc cattgataaa ccg                     463

<210> SEQ ID NO 425
<211> LENGTH: 319
<212> TYPE: DNA
<213> ORGANISM: Zea mays
```

```
<400> SEQUENCE: 425
tgctactgca gttgcaagat accgtacgaa atatcaggct gctcagaagg gtaaggtcgg      60
aatagtcctg gacttcaact ggtacgaggc tcttacaaac tcacctgatg accaagcagc     120
agcccaaaga gccagggact tccacattgg ctggtttgtt gatccattga taaacggaca     180
ctatccacag ataatgcaag atctcgtgaa ggagaggctg cccaggttca ctcctgagca     240
ggctaaactg gtgaagggct cggcagacta catcggtatc aacgagtaca catccagcta     300
catgaagggc agaactggt                                                  319

<210> SEQ ID NO 426
<211> LENGTH: 453
<212> TYPE: DNA
<213> ORGANISM: Zea mays
<220> FEATURE:
<221> NAME/KEY: unsure
<222> LOCATION: (1)...(453)
<223> OTHER INFORMATION: unsure at all n locations

<400> SEQUENCE: 426
atcttcccgg atggcgaagg gaaagtcant ccagaaggtg tagccgtatt acaatagttn      60
gataaactat ctgcttcagc aaggcatgac tccttacatc aacctttacc actatgatct     120
tnctcttgcg cttgagaaga aatatggagg gtggttaagc gcgaagatgg cggacttgtt     180
tacagactat gctgacttct gttttaagac ctacngcgat cgcgtaaagc actggtttac     240
attcaatgag ccaaggatag tagcgctact tggctatgac acagggtcaa attctcctca     300
aaggtgcacc aaatgcnctg ctggtnggaa ttcagcaacc gancnttaca tatttgctca     360
taattatctn ttggcacatn ctantncagt tgcnnagatn ccggacgaan ttnnngctgc     420
tcanaaanng ttagngtnag gaattantcc tgg                                  453

<210> SEQ ID NO 427
<211> LENGTH: 377
<212> TYPE: DNA
<213> ORGANISM: Zea mays
<220> FEATURE:
<221> NAME/KEY: unsure
<222> LOCATION: (1)...(377)
<223> OTHER INFORMATION: unsure at all n locations

<400> SEQUENCE: 427
ctacctcaag gagaagtatg ggaatccaac gatctacata acggagaacg gaatggacca      60
gcctggaaac ttgacccgag accagtacct gcgcgacgcc acgagggtgc ggttctacag     120
gagctacatc ggccagctga agaaggccat agaccaggga gcgaacgtgg ctggctactt     180
ctcctggtct ctcctcgaca attcgagtgg ctggcagggt actcgtccaa gttcggcatc     240
gtctacgtgg acttcaacac gctcgaacgc cacccgaagg cgtcggccta ctngttcang     300
gacatgcttc agaagcattg agatctccag agccgagcct gagcacggaa ngtaccattt     360
tgttcagctt cgcctag                                                    377

<210> SEQ ID NO 428
<211> LENGTH: 302
<212> TYPE: DNA
<213> ORGANISM: Zea mays

<400> SEQUENCE: 428
cggacttgtt tacagactat gctgacttct gttttaagac ctacggcgat cgcgtaaagc      60
actggtttac attcaatgag ccaaggatag tagcgctact tggctatgac acagggtcaa     120
```

```
atcctcctca aaggtgcacc agatgcgctg ctggtgggaa ttcagcaacc gaaccttaca      180
tagttgctca taattttctc ttggcacatg ctactgcagt tgcaagatac cgtacgaaat      240
atcaggctgc tcagaagggt aaggtcggaa tagtcctgga cttcaactgg tacgaggctc      300
tt                                                                    302

<210> SEQ ID NO 429
<211> LENGTH: 455
<212> TYPE: DNA
<213> ORGANISM: Zea mays
<220> FEATURE:
<221> NAME/KEY: unsure
<222> LOCATION: (1)...(455)
<223> OTHER INFORMATION: unsure at all n locations

<400> SEQUENCE: 429
ccangccttc ggaaaccgnt tggnccanag gncaattcta angggnttta nattnggccc      60
gaccgggatn taccgggtnc ctnnacctan cttaagggan aaagatnggg aatccaacga     120
tctacataac ggagaacgga atggaccaac ctggaaactt gacccgagac cagtacctgc     180
gcgacgccac gagggtgcgg ttctacagga gctacatcgg ccagctgaag aaggccatag     240 accaggagc gaacgtggct ggctacttcg cctggtctct cctcgacaac ttcgagtggc      300
tggcagggta ctcgtccaag ttcggcatcg tctacgtgga cttcaacacg ctcgaacgcc     360 accccgaaggc gtcggcctac tggttcaagg gacatgcttc agaagcattg agatctncag   420
agcccgagcc tgagcacgga aggtaccatt tttgt                                455

<210> SEQ ID NO 430
<211> LENGTH: 312
<212> TYPE: DNA
<213> ORGANISM: Zea mays

<400> SEQUENCE: 430
cagaagggta aggtcggaat agtcctggac ttcaactggt acgaggctct tacaaactca      60
cctgatgacc aagcagcagc ccaaagagcc agggacttcc acattggctg gtttgttgat     120
ccattgataa acggacacta tccacagata atgcaagatc tcgtgaagga gaggctgccc     180
aggttcactc ctgagcaggc taaactggtg aagggctcgg cagactacat cggtatcaac     240
gagtacacat ccagctacat gaaggggcag aagctggtcc agctggcgcc cagtagctac     300
tctgccgatt gg                                                         312

<210> SEQ ID NO 431
<211> LENGTH: 305
<212> TYPE: DNA
<213> ORGANISM: Zea mays

<400> SEQUENCE: 431
cgaaatatca ggctgctcag aagggtaagg tcggaatagt cctggacttc aactggtacg      60
aggctcttac aaactcacct gatgaccaag cagcagccca agagccagg gacttccaca     120 ttggctggtt tgttgatcca ttgataaacg gacactatcc acagataatg caagatctcg    180
tgaaggagag gctgcccagg ttcactcctg agcaggctaa actggtgaag gctcggcag     240 actacatcgg tatcaacgag tacacatcca gctacatgaa ggggcagaag ctggtccagc    300
tggcg                                                                305

<210> SEQ ID NO 432
```

```
<211> LENGTH: 299
<212> TYPE: DNA
<213> ORGANISM: Zea mays
<220> FEATURE:
<221> NAME/KEY: unsure
<222> LOCATION: (1)...(299)
<223> OTHER INFORMATION: unsure at all n locations

<400> SEQUENCE: 432
tgctactgca gttgcaagat accgtacgaa atatcaggct gctcagaagg gtaaggtcgg      60
aatagtcctg gacttcaact ggtacgaggc tcttacaaac tcacctgatg accaagcagc    120
agcccaaaga gccagggact tccacattgg ctggtttgtt gatccattga taaacggaca    180
ctatccacag ataatgcaag atctcgtgaa ggagaggctg cccaggttca ctcctgagca    240
ggctaaactg gtgaanggct cggcagacta catcggtatc aacgagtaca catccagct    299

<210> SEQ ID NO 433
<211> LENGTH: 323
<212> TYPE: DNA
<213> ORGANISM: Zea mays

<400> SEQUENCE: 433
gctggtccag ctggcgccca gtagctactc tgccgattgg caggttcaat atgttttgc     60 acgcaatggc aaaccgattg gaccacaggc gaattctaag tggctctaca tcgccccgac    120
ggggatgtac gggtgcgtga actacctcaa ggagaagtat gggaatccaa cgatctacat    180
aacggagaac ggaatggacc agcctggaaa cttgacccga ccagtacc tgcgcgacgc     240 cacgagggtg cggttctaca ggagctacat cggccagctg aagaaggcca tagaccaggg    300
agcgaacgtg gctggctact tcg                                           323

<210> SEQ ID NO 434
<211> LENGTH: 295
<212> TYPE: DNA
<213> ORGANISM: Zea mays

<400> SEQUENCE: 434
ggcgaattct aagtggctct acatcgcccc gacggggatg tacgggtgcg tgaactacct     60
caaggagaag tatgggaatc caacgatcta cataacggag aacggaatgg accagcctgg    120
aaacttgacc cgagaccagt acctgcgcga cgccacgagg gtgcggttct acaggagcta    180
catcggccag ctgaagaagg ccatagacca gggagcgaac gtggctggct acttcgcctg    240
gtctctcctc gacaacttcg agtggctggc agggtactcg tccaagttcg gcatc         295

<210> SEQ ID NO 435
<211> LENGTH: 287
<212> TYPE: DNA
<213> ORGANISM: Zea mays

<400> SEQUENCE: 435
tcttcctctt gcgcttgaga agaaatatgg agggtggtta agcgcgaaga tggcggactt     60
gtttacagac tatgctgact tctgttttaa gacctacggc gatcgcgtaa agcactggtt    120
tacattcaat gagccaagga tagtagcgct acttggctat gacacagggt caaatcctcc    180 tcaaggtgc accagatgcg ctgctggtgg gaattcagca accgaacctt acatagttgc     240
tcataatttt ctcttggcac atgctactgc agttgcaaga taccgta                 287

<210> SEQ ID NO 436
<211> LENGTH: 472
```

```
<212> TYPE: DNA
<213> ORGANISM: Zea mays
<220> FEATURE:
<221> NAME/KEY: unsure
<222> LOCATION: (1)...(472)
<223> OTHER INFORMATION: unsure at all n locations

<400> SEQUENCE: 436
gggacnncga gattnantgg tttgtcagat ccattgataa acnggacact anncacacat      60
gggtnnggga tntnatnaag gagagcctgc ccancttcac tcctgagcag nctagactgg     120
ngaagggctc ganagactac atcggtatca acgagtacac atccagctac atgaaggggc    180
anaagctggt ccanntgcgc ccagtancta ctctgccgat tggcaggttc aatatgngtt    240
tgcacgcaat gncanaccga ttggaccaca gnnaagttct aagtggctct acatcgcccn    300
nacggggatg tacgggtgcg tgaactacct caangagaag tatgngaatc caacggatct    360
acataacgga gaacggaatg gaccaacctg gaaacttgac ccgagaccag tacctgcgcg    420
annccacgaa ngtgcggntc tacaggaact acatnggcca tntnaataaa gg            472

<210> SEQ ID NO 437
<211> LENGTH: 301
<212> TYPE: DNA
<213> ORGANISM: Zea mays
<220> FEATURE:
<221> NAME/KEY: unsure
<222> LOCATION: (1)...(301)
<223> OTHER INFORMATION: unsure at all n locations

<400> SEQUENCE: 437
agataccgta cgaaanatca ggctgctcag aagggtaagg tcggaatagt cctggacttc     60
aactggtacg aggctcttac aaactcacct gatgaccaag cagcagccca aagagccagg    120
gacttccaca ttggctggtt tgttgattcc attgataaac ggacactatc cacagataat    180
gcaagatctc gtgaaggaga ggctgcccag gttcactcct gagcaggcta aactggtgaa    240
aggctcggca gactacatcg gtatcaacga gtacacatcc agctacatga aggggcagaa    300
g                                                                     301

<210> SEQ ID NO 438
<211> LENGTH: 297
<212> TYPE: DNA
<213> ORGANISM: Zea mays

<400> SEQUENCE: 438
caagcagcag cccaaagagc cagggacttc cacattggct ggtttgttga tccattgata     60
aacggacact atccacagat aatgcaagat ctcgtgaagg agaggctgcc caggttcact    120
cctgagcagg ctaaactggt gaagggctcg gcagactaca tcggtatcaa cgagtacaca    180
tccagctaca tgaaggggca gaagctggtc cagctggcgc ccagtagcta ctctgccgat    240
tggcaggttc aatatgtttt tgcacgcaat ggcaaaccga ttggaccaca ggcgaat        297

<210> SEQ ID NO 439
<211> LENGTH: 281
<212> TYPE: DNA
<213> ORGANISM: Zea mays
<220> FEATURE:
<221> NAME/KEY: unsure
<222> LOCATION: (1)...(281)
<223> OTHER INFORMATION: unsure at all n locations

<400> SEQUENCE: 439
```

```
gttttaagac ctacggcgat cgcgtaaagc actggtttac attcaatgag ccaaggatag      60
tagcgctact tggctatgac acagggtcaa atcctcctca aaggtgcacc agatgcgctg     120
ctggtgggaa ttcagcaacc gaaccttaca tagttgcnca taattttctc ttggcacatg     180
ctactgcagt tgcaagatac cgtacgaaat atcaggctgc tcagaagggt aaggtcggaa     240
tagtcctgga cttcaactgg tacgaggctc ttacaaactc a                         281
```

<210> SEQ ID NO 440
<211> LENGTH: 306
<212> TYPE: DNA
<213> ORGANISM: Zea mays
<220> FEATURE:
<221> NAME/KEY: unsure
<222> LOCATION: (1)...(306)
<223> OTHER INFORMATION: unsure at all n locations

<400> SEQUENCE: 440

```
cggaatggac cagcctggaa acttgacccg agaccagtac ctgcgcgacg ccacgagggt      60
gcggttctac aggagctaca tcggccagct gaagaaggcc atagaccagg gagcgaacgt     120
ggctggctac ttcncctggt ctctcctcga caacttcgag tggctggcag ggtactcgtc     180
caagttcggc atcgtctacg tggacttcna cacgctcgaa cgccacccga aggcgtcggc     240
ctactngttc agggacatgc ttcagaagcn tgagatctcc aganccgagc ctgagcacgg     300
aagtac                                                                306
```

<210> SEQ ID NO 441
<211> LENGTH: 294
<212> TYPE: DNA
<213> ORGANISM: Zea mays
<220> FEATURE:
<221> NAME/KEY: unsure
<222> LOCATION: (1)...(294)
<223> OTHER INFORMATION: unsure at all n locations

<400> SEQUENCE: 441

```
gggacttcca cattggctgg tttgttgatc cantgataaa cggacactat ccacagataa      60
tgcaagatct cgtgaaggag aggctgccca ggttcactcc tgagcaggct aaactggtga     120
agggctcggc agactacatc ggtatcaacg agtacacatc cagctacatg aaggggcaga     180
agctggtcca gctggcgccc agtagctact ctgccgattg gcaggttcaa tatgtttttg     240
cacgcaatgg caaaccgatt ggaccacagg cgaattctaa gtggctctac atcg           294
```

<210> SEQ ID NO 442
<211> LENGTH: 471
<212> TYPE: DNA
<213> ORGANISM: Zea mays
<220> FEATURE:
<221> NAME/KEY: unsure
<222> LOCATION: (1)...(471)
<223> OTHER INFORMATION: unsure at all n locations

<400> SEQUENCE: 442

```
gcgtccacca acggccgggg cccctccatc tggattcat tcgcgcacgt cccaggaaat       60
attgcnggga atcaaaatgg agacgttgca gtggatcaat accatcgcta caaggaagac     120
gtcgatctca tgaaaagttt gaactttgat gcctaccggt tctcaatctc atggtccagg     180
atcttcccgg atgcgaagg gaaagtcaat ccagaaggtg tagcgtatta caataatttg      240
ataaactatc tgcttcagca aggcatgact ccttacatca accttttacca ctatgatctt    300 cctcttgcgc ttgagaagaa atatgggagg gtggttaagc cgcgaaagat ggcgggactt     360
```

```
ggttacagac tatgctgact tctggtttaa gacctacggn gaatcgcgtn aaagcactgg      420
gttacanttc atgngnccaa ggttagtacc gctacttggg ttttnaacaa g              471

<210> SEQ ID NO 443
<211> LENGTH: 452
<212> TYPE: DNA
<213> ORGANISM: Zea mays
<220> FEATURE:
<221> NAME/KEY: unsure
<222> LOCATION: (1)...(452)
<223> OTHER INFORMATION: unsure at all n locations

<400> SEQUENCE: 443
gttcttgatc agattgttga cttttatttg nnnggncaga aagntanngn cnggaanagt      60
cctggacttc aacnggtacg aggctcttac aaactcacct gatgaccaag caancancnn      120
aaanagccag gnacttgcac atnggcnggn nngtagatcc attgataaac ggacactatc      180
cacagataan gcaagatctc gcgaaggaga ggctgcccag gttcactccn gagcaggcta      240
aactggtgaa gggctcgnca gactacatcn gtatcaacga gtacatcc aactacatga       300 anggggcana anctggganca gctggccccc agganctact ctgccgaatg gcaggttcaa    360
tatgtnnttg cacgcaatgg caaacccatt ggaccacaag ccaatctaag nggctctana    420
tngccccgac cgggattgta cnggtncctg aa                                   452

<210> SEQ ID NO 444
<211> LENGTH: 264
<212> TYPE: DNA
<213> ORGANISM: Zea mays

<400> SEQUENCE: 444
cagaagggta aggtcggaat agtcctggac ttcaactggt acgaggctct tacaaactca      60
cctgatgacc aagcagcagc ccaaagagcc agggacttcc acattggctg gtttgttgat     120
ccattgataa acggacacta tccacagata atgcaagatc tcgtgaagga gaggctgccc     180
aggttcactc ctgagcaggc taaactggtg aagggctcgg cagactacat cggtatcaac     240
gagtacacat ccagctacat gaag                                            264

<210> SEQ ID NO 445
<211> LENGTH: 263
<212> TYPE: DNA
<213> ORGANISM: Zea mays

<400> SEQUENCE: 445
ggctatgaca cagggtcaaa tcctcctcaa aggtgcacca gatgcgctgc tggtgggaat      60
tcagcaaccg aaccttacat agttgctcat aattttctct ggcacatgc tactgcagtt     120 gcaagatacc gtacgaaata tcaggctgct cagaagggta aggtcggaat agtcctggac     180
ttcaactggt acgaggctct tacaaactca cctgatgacc aagcagcagc ccaaagagcc     240
agggacttcc acattggtgg ttt                                             263

<210> SEQ ID NO 446
<211> LENGTH: 297
<212> TYPE: DNA
<213> ORGANISM: Zea mays

<400> SEQUENCE: 446
gatgaccaag cagcagccca agagccagg gacttccaca ttgggctggt tgttgatcc       60
```

```
attgataaac ggacactatc cacagataat gcaagatctc gtgaaggaga ggctgcccag      120
gttcactcct gagcaggcta aactggtgaa gggctcggca gactacatcg gtatcaacga      180
gtacacatcc agctcatga aggggcagaa gctggtccag ctggcgccca gtagctactc       240
tgccgattgg cagttcaata tgttttttgca cgcaatggca aaccgattgg accacag        297
```

<210> SEQ ID NO 447
<211> LENGTH: 298
<212> TYPE: DNA
<213> ORGANISM: Zea mays
<220> FEATURE:
<221> NAME/KEY: unsure
<222> LOCATION: (1)...(298)
<223> OTHER INFORMATION: unsure at all n locations

<400> SEQUENCE: 447

```
cggacacnat ccacagataa tgcaagatct cgtgaaggag aggctgccca ggttcactcc      60
tgagcaggct aaactggtga agggctcggc agactacatc ggtatcaacg agtacacatc     120
cagctacatg aaggggcaga agctggtcca gctggcgccc agtagctact ctgccgattg     180
gcaggttcaa tatgttttg cacgcaatgg caaaccgatt ggaccacagg cgaattctaa      240
gtggctctac atcgccccga cggggatgta cgggtgcgtg aatcacctcn aggagaag       298
```

<210> SEQ ID NO 448
<211> LENGTH: 301
<212> TYPE: DNA
<213> ORGANISM: Zea mays

<400> SEQUENCE: 448

```
cactcctgag caggctaaac tggtgaaggg ctcggcagac tacatcggta tcaacgagta     60
cacatccagc tacatgaagg ggcagaagct ggtccagctg gcgcccagta gctactctgc     120
cgattggcag gttcaatatg ttttttgcacg caatggcaaa ccgattggac acaggcgaa    180 ttctaagtgg ctctacatcg ccccgacggg gatgtacggg tgcgtgaact acctcaagga    240
gaagtatggg aatccaacga tctacataac ggagaacgga atggaccagc ctggaaactt    300
g                                                                       301
```

<210> SEQ ID NO 449
<211> LENGTH: 322
<212> TYPE: DNA
<213> ORGANISM: Zea mays
<220> FEATURE:
<221> NAME/KEY: unsure
<222> LOCATION: (1)...(322)
<223> OTHER INFORMATION: unsure at all n locations

<400> SEQUENCE: 449

```
tcggtatcaa cgagtacaca tccagctaca tgaaggggca gaagctggtc cagctggcgc     60
ccagtagcta ctctgccgat tggcaggttc aatatgtttt tgcacgcant ggcaaaccga    120
ttggaccaca ggcgaattct aagtggctct acatcgcccc gacggggatg tacgggtgcg    180
tgaactacct caaggagaag tatgggaatc caacgatcta catnacggag aacggaatgg    240
accagcctgg aaattgaccc gagaccagta cctgcgcgac gccacgaggg tgcggttcta    300
caggagtaca tcggccanct ga                                               322
```

<210> SEQ ID NO 450
<211> LENGTH: 459
<212> TYPE: DNA
<213> ORGANISM: Zea mays

```
<220> FEATURE:
<221> NAME/KEY: unsure
<222> LOCATION: (1)...(459)
<223> OTHER INFORMATION: unsure at all n locations

<400> SEQUENCE: 450
cangnnnntc agaanggtna ggncggaatt tccngtact nnaactggta cgaggctctg      60
nggaacngnc ctnatgacca agcannannc canagagccn gngacttcca cattggctgg    120
nttgntgatc catngataaa cggacactat ccacagatna tgcaagatct cgngaaggaa    180
aggctgncca ngttcactcc tgagcaggct aaactggtga agggctcggc agactacatc    240
ggtatcaacg agtacacatc cagctncatg aaggggcaga agctggtcca gctggcgccc    300
antaactact ctgccnattg gcaagttcaa tatntnttng cacccantng caaaaccnat    360
tnntccaaca gcgaattcta agtggggtct acatcacccc cgacaggngn tgtaccgggt    420
gccntgaact accctnaaag ganaaagnat ngggaattc                           459

<210> SEQ ID NO 451
<211> LENGTH: 272
<212> TYPE: DNA
<213> ORGANISM: Zea mays
<220> FEATURE:
<221> NAME/KEY: unsure
<222> LOCATION: (1)...(272)
<223> OTHER INFORMATION: unsure at all n locations

<400> SEQUENCE: 451
gtcggaatag tcctgggact tcaactggta cgaggctctt acaaactcac ctgatgacca     60
agcagcagcc caaagagcca gggacttcca cattggctgg tttgttgatc cattgataaa   120
cggacactat ccacagataa tgcaagatct cgtgaaggag aggctgccca ggttcactcc   180
tgnncaggct aaactggtga agggctcggc agactacatc ggtatcaacg agtacacatc   240
cagctacatg aaggggcaga agctggtcca gc                                  272

<210> SEQ ID NO 452
<211> LENGTH: 447
<212> TYPE: DNA
<213> ORGANISM: Zea mays
<220> FEATURE:
<221> NAME/KEY: unsure
<222> LOCATION: (1)...(447)
<223> OTHER INFORMATION: unsure at all n locations

<400> SEQUENCE: 452
gcgacgtcgg cgtaccaggt cgagggcgcc gcgtccacca acggccgagg cccctccacc     60
tgggacgcgt tcgtgcacac cccaggaaac attgtataca atcagacggc agatgtcgca   120
gtggatcaat atcatcgcta cagggaagat gtcgacctca tgaaaagttt gaattttgat   180
gcctaccggt tttcaatctc atggtccagg atcttcccag atggcgaggg aagagtcaat   240
ccagaaggtg ttgcctatta caacaatctg ataaactacc tgcttcggaa aggcattaca   300
ccgtacgcca atccttacca ttcccgattc tcccctcttg cgcttcaaga caagtatgg    360 gagggtgggt taaatngcca agatggcgaa nactgttcac aagnctangc cgaacttccg   420
gttttaaaga ctttggggga accgtng                                        447

<210> SEQ ID NO 453
<211> LENGTH: 244
<212> TYPE: DNA
<213> ORGANISM: Zea mays
```

```
<400> SEQUENCE: 453
cgtacgaaat atcaggctgc tcagaagggt aaggtcggaa tagtcctgga cttcaactgg      60
tacgaggctc ttacaaactc acctgatgac caagcagcag cccaaagagc agggacttc     120 cacattggcg gtttgttgat ccattgataa acggacacta tccacagata atgcaagatc    180
tcgtgaagga gaggctgccc aggttcactc ctgagcaggc taaactggtg aagggctcgg    240
caga                                                                  244

<210> SEQ ID NO 454
<211> LENGTH: 258
<212> TYPE: DNA
<213> ORGANISM: Zea mays

<400> SEQUENCE: 454
gcaagatctc gtgaaggaga ggctgcccag gttcactcct gagcaggcta aactggtgaa      60
gggctcggca gactacatcg gtatcaacga gtacacatcc agctcatga aggggcagaa     120 gctggtccag ctggcgccca gtagctactc tgccgattgg caggttcaat atgttttgc     180 acgcaatggc aaaccgattg gaccacaggc gaattctaag tggctctaca tcgccccgac    240
ggggatgtac gggtgcgt                                                   258

<210> SEQ ID NO 455
<211> LENGTH: 263
<212> TYPE: DNA
<213> ORGANISM: Zea mays
<220> FEATURE:
<221> NAME/KEY: unsure
<222> LOCATION: (1)...(263)
<223> OTHER INFORMATION: unsure at all n locations

<400> SEQUENCE: 455
acggacacta tccacagata atgcaagatc tcgtgaagga gaggctgccc aggttcactc      60
ctgagcaggc taaactggtg aagggctcgg cagactacat cggtatcaac gagtacacat    120
ccagctacat gaaggggcag aagctggtcc agctggcgcc cagtagctac tctgccgatt    180
ggcaggttca atatgttttt gcacgcaatg gcaaaccgat tggaccacag gcgaattcta    240
agtggctcta catcgccccg ang                                             263

<210> SEQ ID NO 456
<211> LENGTH: 266
<212> TYPE: DNA
<213> ORGANISM: Zea mays

<400> SEQUENCE: 456
gcaaccgaac cttacatagt tgctcataat tttctcttgg cacatgctac tgcagttgca      60
agataccgta cgaaatatca ggctgctcag aagggtaagg tcggaatagt cctggacttc    120
aactggtacg agggctctta caaactcacc tgatgaccaa gcagcagccc aaagagccag    180
ggacttccac attggctggt tgttgatcc attgataaac ggacactatc cacagatatg    240
cagatctcgt gaaggagagg ctgccc                                          266

<210> SEQ ID NO 457
<211> LENGTH: 231
<212> TYPE: DNA
<213> ORGANISM: Zea mays

<400> SEQUENCE: 457
agcgcgaaga tggcggactt gtttacagac tatgctgact tctgttttaa gacctacggc      60
```

-continued

```
gatcgcgtaa agcactggtt tacattcaat gagccaagga tagtagcgct acttggctat        120
gacacagggt caaatcctcc tcaaaggtgc accagatgcg ctgctggtgg gaattcagca        180
accgaacctt acatagttgc tcataatttt ctcttggcac atgctactgc a                 231
```

<210> SEQ ID NO 458
<211> LENGTH: 248
<212> TYPE: DNA
<213> ORGANISM: Zea mays
<220> FEATURE:
<221> NAME/KEY: unsure
<222> LOCATION: (1)...(248)
<223> OTHER INFORMATION: unsure at all n locations

<400> SEQUENCE: 458

```
anctggtcca gctggcgccc agtagctact ctgccgattg gcaggttcaa tatgtttttg        60
cacgcaatgg caaaccgatt ggaccacagg cganttctaa gtggctctac atcgccccga       120
cggggatgta cgggtgcgtg aactacctca aggagaagta tgggaatcca acgatctaca       180
taacggagaa cggaatggac cagcctggaa acttgacccg agaccagtac ctgcgcgacg       240
ccacgagg                                                               248
```

<210> SEQ ID NO 459
<211> LENGTH: 482
<212> TYPE: DNA
<213> ORGANISM: Zea mays
<220> FEATURE:
<221> NAME/KEY: unsure
<222> LOCATION: (1)...(482)
<223> OTHER INFORMATION: unsure at all n locations

<400> SEQUENCE: 459

```
gtggctctac atcgcccnga cggggatgta cgggtgcgtg aactacctca aggagaagta        60
tgggaatcca acgatctaca taacggagaa cggaatggac cagcctggaa acttgacccg       120
agaccagtac ctgcgctacg ccacgagggt gcngttctac angagctaca tcggccagct       180
naagaaggcc atagacnagg gancgaannt ggnttgntac ttcgntntgg tctcttctcg       240
acaacttnga gtggctggca nnngtncttn gtttaangtt tggcattagt taccgtggac       300
ttnaanacgc tcgaacttca ccctaaaggc gtcngnctac tggttcaagg ganatgcttt       360
nataagcant tgagatcttt ngtangccna nctgaacacc ggnaaggtcc attttttnttt      420 aactttngcc taaatggttn ggaatgggcc aatggtttaa anttcgggtt aatggcttgg       480
tt                                                                     482
```

<210> SEQ ID NO 460
<211> LENGTH: 223
<212> TYPE: DNA
<213> ORGANISM: Zea mays

<400> SEQUENCE: 460

```
ggtccagctg gcgcccagta gctactctgc cgattggcag gttcaatatg tttttgcacg        60
caatggcaaa ccgattggac cacaggcgaa ttctaagtgg ctctacatcg ccccgaacgg       120
ggatgtacgg gtgcgtgaac tacctcaagg agaagtatgg gaatccaacg atctacataa       180
cggagaacgg aatggaccag cctggaaact tgacccgaga cca                         223
```

<210> SEQ ID NO 461
<211> LENGTH: 274
<212> TYPE: DNA

```
<213> ORGANISM: Zea mays

<400> SEQUENCE: 461
aaaatggaga cgttgcagtg gatcaatacc atcgctacaa ggaagacgtc gatctcatga     60
aaagtttgaa ctttgatgcc taccggttct caatctcatg gtccaggatc ttcccggatg    120
gcgaagggaa agtcaatcca gaaggtgtag cgtattacaa taatttgata aactatctgc    180
ttcagcaagg catgactcct tacatcaacc tttaccacta tgatcttcct cttgcgcttg    240
agaagaaata tggagggtgg ttaagcgcga agat                                274

<210> SEQ ID NO 462
<211> LENGTH: 196
<212> TYPE: DNA
<213> ORGANISM: Zea mays

<400> SEQUENCE: 462
cccaggttca ctcctgagca ggctaaactg gtgaagggct cggcagacta catcggtatc     60
aacgagtaca catccagcta catgaagggg cagaagctgg tccagctggc gcccagtagc    120
tactctgccg attggcaggt tcaatatgtt tttgcacgca atggcaaacc gattggacca    180
caggcgaatt ctaagt                                                     196

<210> SEQ ID NO 463
<211> LENGTH: 184
<212> TYPE: DNA
<213> ORGANISM: Zea mays
<220> FEATURE:
<221> NAME/KEY: unsure
<222> LOCATION: (1)...(184)
<223> OTHER INFORMATION: unsure at all n locations

<400> SEQUENCE: 463
aganatatgg agggtggtta agcgcgaaga tggcggactt gtttacagac tatgctgact     60
tctgttttaa gacctacggc gatcgcgtaa agcactggtt tacattcaat gagccaagga    120
tagtagcgct acttggctat gacacagggt caaatcctcc tcaaaggtgc accagatgcg    180
ctgg                                                                  184

<210> SEQ ID NO 464
<211> LENGTH: 192
<212> TYPE: DNA
<213> ORGANISM: Zea mays
<220> FEATURE:
<221> NAME/KEY: unsure
<222> LOCATION: (1)...(192)
<223> OTHER INFORMATION: unsure at all n locations

<400> SEQUENCE: 464
gaaggagagg ctgcccaggt tcactcctga gcaggctaaa ctggtgaagg gctcggcaga     60
ctacatcggt atcaacgagt acacatccag ctacatgaag gggcagaagc tggtccagct    120
ggcgcccagt agctactctg ccgattggca ggttcaatat gttttttgcac ncnatggcaa   180 accgattgga cc                                                         192

<210> SEQ ID NO 465
<211> LENGTH: 354
<212> TYPE: DNA
<213> ORGANISM: Zea mays
<220> FEATURE:
<221> NAME/KEY: unsure
<222> LOCATION: (1)...(354)
<223> OTHER INFORMATION: unsure at all n locations
```

<400> SEQUENCE: 465

```
aaaaacatag gctgctcaga agggtaaggt cggaatagtc ctgganttca actggtacga      60
ggctcttaca aactcacctg atgaccaagc agcaacncaa agagccaggg acttccacat     120
tggctggttt gtngatncat tgataaacgg acatatccnc agataatgca agatctcgtg     180
aaggagaggt gcccaggtnc acnctgagna ggctaaactg gtgaagggnn tnggnagact     240
acatcgtntc acggagtaca cntcnagtac angaaggggc aaaactggtc cagtgnngcc     300
cantagtact ntccngnttg gcaggntcat atgttgngat taatncttgt nttt           354
```

<210> SEQ ID NO 466
<211> LENGTH: 266
<212> TYPE: DNA
<213> ORGANISM: Zea mays
<220> FEATURE:
<221> NAME/KEY: unsure
<222> LOCATION: (1)...(266)
<223> OTHER INFORMATION: unsure at all n locations

<400> SEQUENCE: 466

```
ccgcgcgtcg ttccccaagg ggttcgtgtt cgggacggcg acgtcggcgt accaggtcga      60
gggcgccgcg tccaccaacg gccgcngccc ctccatctgg gattcantcg cgcacgtccc     120
aggaaatatt gcagggaatc aaaatggaga cgttgcagtg gatcaatacc atcgctacaa     180
ggaagacgtc gatctcatga aaagtttgaa cttttgatgcc taccggttct caatctcatg     240
gtccaggatc ttcccggatg gcgaag                                          266
```

<210> SEQ ID NO 467
<211> LENGTH: 286
<212> TYPE: DNA
<213> ORGANISM: Zea mays
<220> FEATURE:
<221> NAME/KEY: unsure
<222> LOCATION: (1)...(286)
<223> OTHER INFORMATION: unsure at all n locations

<400> SEQUENCE: 467

```
gnnaccgana cttacatagt tgcncataat tnnnctcntg gcacangcta ctgcngttgc      60
nagataccgt acganatatc aggctgctca gaagggtaag gtcggantag tcctggactt     120
naantggtan gaggctctta caaactcacc tgatgngcca agcagcagcc caaagagcca     180
gggacttcca cattggctgg tttgttgatc cattgataaa cggacactat ccacagataa     240
tgcaagatct cgtgaaggag aggctgccca ggttcactcc tgagca                    286
```

<210> SEQ ID NO 468
<211> LENGTH: 351
<212> TYPE: DNA
<213> ORGANISM: Zea mays
<220> FEATURE:
<221> NAME/KEY: unsure
<222> LOCATION: (1)...(351)
<223> OTHER INFORMATION: unsure at all n locations

<400> SEQUENCE: 468

```
ggcggacttg tttacagact atgctgactn ctgttttaag acctacggcg atcgcgtana      60
gcactggtnt acnttncaat gagccaaggn nagaggcgct acttggctat gacacagggt     120
caaatcctcc tcaaaggtgc accagatgcg cngctggtgg gattcngcna ccgaaccnta     180
catngttgct cataatttnc ncttggcaca tgctactgtn ttgcaaganc cggacganaa     240
```

```
tcaggctgct cagaagggna ggtnggaata cccnggnttc cantgnctag gncgtncnaa        300
tcactgatga cnagcgagna gcccnaaagn cagggcttnn acattgcggn t                 351

<210> SEQ ID NO 469
<211> LENGTH: 197
<212> TYPE: DNA
<213> ORGANISM: Zea mays
<220> FEATURE:
<221> NAME/KEY: unsure
<222> LOCATION: (1)...(197)
<223> OTHER INFORMATION: unsure at all n locations

<400> SEQUENCE: 469
ctttgatnac ctaccggttc tcaatctcat ggtccaggat cttcccngat ggcgaaggga        60
aagtcaatcc agaaggtgta gcgtattaca ataatttgat aaactatctg cttcagcaag       120
gcatgacncc cttacatcaa cctttaccac tatgatcntc ctcttgcgct tgagaagaaa       180
tatggagggt ggttaag                                                      197

<210> SEQ ID NO 470
<211> LENGTH: 245
<212> TYPE: DNA
<213> ORGANISM: Zea mays

<400> SEQUENCE: 470
cgctacaagg aagacgtcga tctcatgaaa agtttgaact tgatgccta ccggttctca        60 atctcatggt ccaggatctt cccggatggc gaagggaaag tcaatccaga aggtgtagcg       120
tattacaata atttgataaa ctatctgctt cagcaaggca tgactcctta catcaacctt       180
taccactatg atcttcctct tgcgcttgag aagaaatatg gagggtggtt aagcgcgaag       240
atggc                                                                   245

<210> SEQ ID NO 471
<211> LENGTH: 166
<212> TYPE: DNA
<213> ORGANISM: Zea mays
<220> FEATURE:
<221> NAME/KEY: unsure
<222> LOCATION: (1)...(166)
<223> OTHER INFORMATION: unsure at all n locations

<400> SEQUENCE: 471
gnnncgttgc agtggatcaa taccatcgct acaaggaaga cgtcgatctc atgaaaagtt        60
tgaactttga tgcctaccgg ttctcaatct catggtccag atctncccg gatggcgnag       120 ggaaagtcaa tccagaaggt gtagcgtatt acaataattt gataaa                      166

<210> SEQ ID NO 472
<211> LENGTH: 99
<212> TYPE: DNA
<213> ORGANISM: Zea mays

<400> SEQUENCE: 472
gcgtattaca ataatttgat aaactatctg cttcagcaag gcatgactcc ttacatcaac        60
ctttaccact atgatcttcc tcttgcgctt gagaagaaa                               99

<210> SEQ ID NO 473
<211> LENGTH: 455
<212> TYPE: DNA
<213> ORGANISM: Zea mays
<220> FEATURE:
<221> NAME/KEY: unsure
```

```
<222> LOCATION: (1)...(455)
<223> OTHER INFORMATION: unsure at all n locations

<400> SEQUENCE: 473
gaaaagtttg aactttgatg cctaccggtt ctcaatctca tggnccanga tctttccggn       60
tggngaaagg aaangcaatc caaaaagggt aaccgnatta caataatttg gtaaactatn      120
tggtttaaca agggntgnaa ttcttanatt aaaccttacc cctattgaac tttccttttg      180
cgccttgnaa agaaaatatn ggagggtggg nttaanccc aaaaatggcg ggactttgtt       240
tacaggacta tgctgacttc tgggtttaag acctacggcg atcgcgtaaa gcactgggtt      300
tacattcaat gagccaagga tagtaaccgc tacttggcta tgacacangg tcaaatcctt     360
ctcaaangtg caccagatgc gctgctggtg ggaattcaag caacccgaac cttacataag     420
ttgctcataa ttttctcttt tnggggcac atgct                                 455

<210> SEQ ID NO 474
<211> LENGTH: 315
<212> TYPE: DNA
<213> ORGANISM: Zea mays

<400> SEQUENCE: 474
ggccaagcta gtcaagggct catcaggtgt gaaattggta gccggtcttt cacaatgtct      60
tgcattatct ttggatattg cccatttatt aatggatcaa gaaaccaacc aatatggaag    120
tccctggccc tttgcgctgc ttttgatct tcagttgagt ttgtaaaagg ttcataccag      180
ttgaagtcaa gaactatccc gaccttgcct ttctgagttg cctggtattt attgcggtat    240
cttgcaactg cagtagcatg atataggaga atgttatgaa caacaatgta aggttctgtc    300
gatgagttcc caccg                                                      315

<210> SEQ ID NO 475
<211> LENGTH: 285
<212> TYPE: DNA
<213> ORGANISM: Zea mays
<220> FEATURE:
<221> NAME/KEY: unsure
<222> LOCATION: (1)...(285)
<223> OTHER INFORMATION: unsure at all n locations

<400> SEQUENCE: 475
ctcatgctac tgtcagttgc aagataccgc aataaatacc aggcaactca nnaaggcaan      60
gtcgggatnc ttcttgantt caactggtat gaacctttta caaactcaac tgaagatcaa    120
ancgcnccgc aaagggccag ggacttccat attggttggt ttcttgatcc attaataant    180
gggcaatatc caaagataat gcaagacatt gtgaaagacc ggctaccaag tttnacacct    240
gaacaggcca agctagtcaa gggctcatca gactatttcg ggatc                     285

<210> SEQ ID NO 476
<211> LENGTH: 327
<212> TYPE: DNA
<213> ORGANISM: Zea mays
<220> FEATURE:
<221> NAME/KEY: unsure
<222> LOCATION: (1)...(327)
<223> OTHER INFORMATION: unsure at all n locations

<400> SEQUENCE: 476
gctccgtaaa gctcgcggtg cttgctcttc tgctagcngc agcagctcac cacggtctgc      60
tgccgtgccg acggcgcgat gctactgggc tcaacccgga gatctacgac gccggcgcgc    120
```

```
tgagcngccg cgcgttcccg gatggcttcg tctactggac ggctgcgtcg gcgtaccagg    180
tcgaggggat ggccaagcac ggcgggcggg gccccagcat ctgggacgcc ttcatagagg    240
ttcccgggac catccctaac aatgccaccg tgacgtgacg gtcgacgagt atcatcggta    300
caaggaagat gtgaacataa tgaagaa                                         327
```

```
<210> SEQ ID NO 477
<211> LENGTH: 180
<212> TYPE: DNA
<213> ORGANISM: Zea mays
<220> FEATURE:
<221> NAME/KEY: unsure
<222> LOCATION: (1)...(180)
<223> OTHER INFORMATION: unsure at all n locations

<400> SEQUENCE: 477
```

```
cgcggtgctt gctcttctgc tagcggcagn agctcaccac ggtctgctgc cgctgccgac    60
ggcgcgatgc tactggctca acccggagat ctacgacgcc ggcgcgctga gccgccgcgc   120
gttcccggat ggattcgtct tcgggacggc tgcgtcggcg taccaggtcg aggggatggc   180
```

```
<210> SEQ ID NO 478
<211> LENGTH: 434
<212> TYPE: DNA
<213> ORGANISM: Zea mays
<220> FEATURE:
<221> NAME/KEY: unsure
<222> LOCATION: (1)...(434)
<223> OTHER INFORMATION: unsure at all n locations

<400> SEQUENCE: 478
```

```
ccctatagtn agtcgtatta aaagcgcggc ctgtgtctcc ggcctttgcc gcttccacag    60
ggagtccggg gccatgcatg agctccgtaa agctcgcggt gcttgctcta ctgctagcgg   120
nagcagctca ccacggtctg ctgccgctgc cgacggcgcg atgctactgg ctcaaccccgg   180 agatctacga cgccggcggg ctgagccgcc gcgcgttccc ggacagnttc gtcttcggga   240
cggccggcgt cggcgtacca gggtcgannng gatggccan gcacaggcgg ngcgggngcn   300
ccangcatct gggangcctt catnggaggn tcctgggac agcccnaana ntgncaccnc    360
ggncgnnacg gtcnacgaat tatcagcggt ttcaanggna cgatgntnga gnnnnggaaa    420
gagcatgngg cttt                                                       434
```

```
<210> SEQ ID NO 479
<211> LENGTH: 233
<212> TYPE: DNA
<213> ORGANISM: Zea mays
<220> FEATURE:
<221> NAME/KEY: unsure
<222> LOCATION: (1)...(233)
<223> OTHER INFORMATION: unsure at all n locations

<400> SEQUENCE: 479
```

```
cagacgctng gcgagnaatc atcgaagact tcaccgcgta cncagacgtg tncttccgga    60
gcttcggcga aagggtgaag cactggatca cggtgaacga gcccaacatc gagcccatcg   120
gcggctacga ccaaggctac ctcccgccgc gccgctgctc ctaccgtttt ggactgggcg   180
tcaatgcacc cacggcaact ccacgacgga nccgtagccg tcncccanca cct           233
```

```
<210> SEQ ID NO 480
<211> LENGTH: 268
<212> TYPE: DNA
<213> ORGANISM: Glycine max
```

<400> SEQUENCE: 480

```
ctttattgca gaacgtgttg gggtgcatgt tgtggagtgt gcttgtgtga ttgaattgcc      60
agagttaaag gggcgggaaa ggttgggaga caagtcgcta tttgtcttga ttaatggggg    120
agcctgatct ttttccaag tgattgtgtt tttattagct ggctcttgtt aggagcttta    180
ttgatgactg cttagatttc cttaagatac attttgatgc tgcggaaacg gaaagcgtgc    240
tttgtttgag cgcgctcagt tctgctca                                       268
```

<210> SEQ ID NO 481
<211> LENGTH: 227
<212> TYPE: DNA
<213> ORGANISM: Glycine max
<220> FEATURE:
<221> NAME/KEY: unsure
<222> LOCATION: (1)...(227)
<223> OTHER INFORMATION: unsure at all n locations

<400> SEQUENCE: 481

```
aatgtttcaa gacataacga cattgttgtt ggatcacaag gcgtttaaag acactgtcga     60
cnttttttgtc gatcgttaca gagacatggc acatttccgt tgttgccgga attgaggcta   120
gggggttcat gtttggtccc tcaattgcgt tgggcattgg tgcaaagttt gttccnttac   180
gcaaacacgg aagctgccan gtgaagtaat ttcagnaaaa tatgctc                  227
```

<210> SEQ ID NO 482
<211> LENGTH: 259
<212> TYPE: DNA
<213> ORGANISM: Glycine max
<220> FEATURE:
<221> NAME/KEY: unsure
<222> LOCATION: (1)...(259)
<223> OTHER INFORMATION: unsure at all n locations

<400> SEQUENCE: 482

```
cgactntcnt aagccaggaa tnttgnntna ggacataacc acgctgcttc nggatnccaa     60
aggcttttcaa agacaccatt gacntgtttg nngagaggta cagagatcaa aacatcaatg   120
tngtcgcagg agttgaagct agaggcttta tatttggtcc acccagtgca ntaggcantg   180
gagcaaaaant tgtccccang agganaccca anaaattgcc ggggngggtt atcncagagg   240
ggtatcnttg gnggaggga                                                 259
```

<210> SEQ ID NO 483
<211> LENGTH: 142
<212> TYPE: DNA
<213> ORGANISM: Glycine max

<400> SEQUENCE: 483

```
aatggagatg catgtagggg ctgtacaacc tggagaacga gccttaatca tagatgatct     60
tattgccact gggggaacgt taggtgcagc aattaagctt ctagaacgtg ttggggtgca   120
tgttgtggag tgtgctgtgt ga                                             142
```

<210> SEQ ID NO 484
<211> LENGTH: 270
<212> TYPE: DNA
<213> ORGANISM: Glycine max
<220> FEATURE:
<221> NAME/KEY: unsure
<222> LOCATION: (1)...(270)
<223> OTHER INFORMATION: unsure at all n locations

```
<400> SEQUENCE: 484
tttttctctc tgtactcaga ctcacttccc cacttattta tacantgtcg gcttacaaag      60
accaggatac ccgtcttcat ngcatcanan ctaaggtncg tgtcgtcccc aatttcccca     120
gatccggaat tgaagctcga ggttttattt ttggtcctcc cattgcgctg gctataggag     180
caaagtttgt accattgagg aaaccaaagg agttgcctgg aaaagttatt tctcangaat     240
atattctgga atatggaagg gactgtcttg                                      270

<210> SEQ ID NO 485
<211> LENGTH: 247
<212> TYPE: DNA
<213> ORGANISM: Glycine max
<220> FEATURE:
<221> NAME/KEY: unsure
<222> LOCATION: (1)...(247)
<223> OTHER INFORMATION: unsure at all n locations

<400> SEQUENCE: 485
gactnttcna acataatacn nttnnttcgn ttgtgnttgg ttgcgcacgc aagnacgtta      60
caataatggc ttcgaagnat tctcaacaag acacgcgctt agcgannatc gcctctgcaa     120
tccgngtcat ccccgacttt cctaagccag ggnttttgtg ncaggacata accncgntgc     180
ttcttgntac naaggctttc naagacacca ttganttgtn tgtngagagg tacagaganc     240
aaaacat                                                               247

<210> SEQ ID NO 486
<211> LENGTH: 268
<212> TYPE: DNA
<213> ORGANISM: Glycine max

<400> SEQUENCE: 486
ttgatacaaa ggctttcaaa gacaccgttg acttgtttgt tgagaggtac agagatcaaa      60
acatcaatgt tgtcgcagga gttgaagcaa ggggctttat atttggtcca cccattgcat     120
tagctattgg agcaaaattt gtccccatga ggaaacccaa taattgcct ggggaggtta      180 tctcagaaga gtattctttg gagtatggaa cagacaaaat ggagatgcat gtagggcctg     240
tacaacctgg agaacgagcc ttaatcat                                        268

<210> SEQ ID NO 487
<211> LENGTH: 261
<212> TYPE: DNA
<213> ORGANISM: Glycine max
<220> FEATURE:
<221> NAME/KEY: unsure
<222> LOCATION: (1)...(261)
<223> OTHER INFORMATION: unsure at all n locations

<400> SEQUENCE: 487
ggtgctgaag tggtggaatg tgcctgtgtc attggtgtgc ctgatgtcaa ggggcagtgc      60
aggcgtattg gaaagccact ttatgttctt gttgagccgc gtaaagcaga taaatgttac     120
ccagattgac atactaaagg acgctgggtg tgagnnacac aggccataat gtgatcctta     180
agttttaggc tgatggagtc gtgttcatgg caattgtcaa atatcatcct gggaaatgtt     240
catcctgttt catatcttat c                                               261

<210> SEQ ID NO 488
<211> LENGTH: 283
<212> TYPE: DNA
<213> ORGANISM: Glycine max
```

<400> SEQUENCE: 488

```
gttcctttac gcaaaccacg gaagctgcca ggtgaagtaa tttcagaaaa atatgctcta      60
gaatatggaa ctgattgctt ggagttgcat gttggtgctg cccagcccgg tgaacgggcc     120
ataataattg atgacttggt ggccacaggt ggaactctgt cagcaggagt aaaacttcta     180
gaacgtgttg gggctgaagt ggtggaatgt gctgtgtcat tggtgtgccg atgtcaaggg     240
gcatgcagga gtattggaaa gccactttat gttctgttga gcc                      283
```

<210> SEQ ID NO 489
<211> LENGTH: 447
<212> TYPE: DNA
<213> ORGANISM: Glycine max
<220> FEATURE:
<221> NAME/KEY: unsure
<222> LOCATION: (1)...(447)
<223> OTHER INFORMATION: unsure at all n locations

<400> SEQUENCE: 489

```
aaaggaacca accactctt tctttcaccg atcatacata caatgtcgac ttacagagac      60
gaggatcccc gtcttcatga catcaaaact aagattcgtg ttgtccctaa tttccccaaa    120
cctggaattg aagctcgggg tttcattttt ggttctccca ttgctctggc aataggagca    180
aagtttgtac cattgaggaa accaaaaaaa attgcctggc aaagttattt ctcaagagta    240
tattctggaa tatggnanag actgtcttga gatgcatgtt ggggccgttg aacctggtga    300
gcgtgcttta gtggttgatg atttgattgc cactggtgga actctctgtg cagccatggg    360
cttactnana gcnaattggg aancanaggt nnttggnntt ncggntgtgt aattnaattg    420
ccannanttt aaagggcgtn aannggg                                         447
```

<210> SEQ ID NO 490
<211> LENGTH: 264
<212> TYPE: DNA
<213> ORGANISM: Glycine max

<400> SEQUENCE: 490

```
gttcgccgaa gagaatggcc tcaagggaga ccccagactc caagccattt cccaagccat      60
cagagtcgtc cctcacttcc ccaaacatgg aataatgttc caagacataa cgacattgct    120
gttggatcac aaggcgttta aagacaccgt cgacattttt gtcgatcgtt acagagacat    180
gcacatttcc gtagttgctg gaattgaggc aaggggggttc atgtttggtc cctcaattgc    240
gttgggcatt ggtgcaaagt ttgt                                            264
```

<210> SEQ ID NO 491
<211> LENGTH: 261
<212> TYPE: DNA
<213> ORGANISM: Glycine max
<220> FEATURE:
<221> NAME/KEY: unsure
<222> LOCATION: (1)...(261)
<223> OTHER INFORMATION: unsure at all n locations

<400> SEQUENCE: 491

```
ggagacccca gactccaanc catttcccaa gccatcagag tcgtccctca cttccccaaa      60
catggaataa tgttccaaga cataacgaca ttggctgttg gatcacaagg cgtttaaaga    120
caccgtcgac attnttgncg atcgntacag agacatgcac atttccgtag ttgctggaat    180
tgaggcaagg gggtncatgt ttggtccctc aattgcnttg gcattggtg caaagtttgt     240
```
tcctttacgc aaaccacgga a    261

<210> SEQ ID NO 492
<211> LENGTH: 292
<212> TYPE: DNA
<213> ORGANISM: Glycine max
<220> FEATURE:
<221> NAME/KEY: unsure
<222> LOCATION: (1)...(292)
<223> OTHER INFORMATION: unsure at all n locations

<400> SEQUENCE: 492
aacgctcaaa ccatcctttt ctttcgctct tcttccattc cacactaaaa agtaacngtt    60
tcggagggaa acacaataca acacaaaaag ccccccccac aaagcaaatc acctttttttt    120 tcctttcaaa atgttcgccg aagagaatgg cctcaaggga accccagac tccaagccat    180 ttcccaagcc atcagagtcg tccctcactt ccccaaacat ggaataatgt tccaagacat    240
aacgacattg ctgttggatc acaaggcgtt aaagacacc gtcgacattt tt    292

<210> SEQ ID NO 493
<211> LENGTH: 262
<212> TYPE: DNA
<213> ORGANISM: Glycine max
<220> FEATURE:
<221> NAME/KEY: unsure
<222> LOCATION: (1)...(262)
<223> OTHER INFORMATION: unsure at all n locations

<400> SEQUENCE: 493
aaccatcctt ttctttcgct cttcttccat tccacactac anagtanatn anttcggagg    60
gaaacacaat acaacacaaa aagccccccc cacaangcaa atcaccttttt ttttcctttc    120 aaaatgttcg ccgaagagaa tggcctcaag ggagacccca gactccaagc catttcccaa    180
gccatcagag tcgtccctca cttccccaaa catggaataa tgttccaaga cataacgaca    240
ttgctgttgg atcacaaggc gt    262

<210> SEQ ID NO 494
<211> LENGTH: 306
<212> TYPE: DNA
<213> ORGANISM: Glycine max
<220> FEATURE:
<221> NAME/KEY: unsure
<222> LOCATION: (1)...(306)
<223> OTHER INFORMATION: unsure at all n locations

<400> SEQUENCE: 494
ctttcttttg ctcttcatcc attccacacc aaaaagtaac agtttcngtt tcggagggaa    60
aacacaanac aaaaagcccc ctcccccaa agcaaatcac ctttttttct ttcagttatt    120
caaaaaatgt tcgccgaaga gaatggactc aagggagacc ctagactcca agccatttcc    180
caagccatca gagtcgtccc tcacttccc atacatggaa taatgtttcc agacataacg    240
acattgttgt tggatcacaa ggcgtttaaa gacactgtcg acattttttgt ngatcgttac    300 agagac    306

<210> SEQ ID NO 495
<211> LENGTH: 281
<212> TYPE: DNA
<213> ORGANISM: Glycine max

<400> SEQUENCE: 495
atccattcca caccaaaaag taactccttt cagtttcgga gggaaacaca acacaaaaag    60

```
cccccctcccc ccaaagcaaa tacacctttt tttctttcag ttattcaaaa aatgttcgcc      120
gaagagaatg gactcaaggg agaccctaga ctccaagcca tttcccaagc catcagagtc      180
gtccctcact tccccataca tggaataatg tttcaagaca taacgacatt gttgttggat      240
cacaaggcgt ttaaagacat gtcgactttt tgtcgatcgt t                          281

<210> SEQ ID NO 496
<211> LENGTH: 287
<212> TYPE: DNA
<213> ORGANISM: Glycine max

<400> SEQUENCE: 496
aaagctcaga cccaaacctt tcttttgctc ttcatccatt ccacaccaaa aagtaacagt      60
ttcagtttcg gagggaaaca caacacaaaa agcccctcc ccccaaagca aatcaccttt       120
ttttctttca gttattcaaa aaatgttcgc cgaaggaatg gactcaaggg agaccctaga     180
ctccaagcca tttcccaagc catcagagtc gtccctcact tccccataca tggaataatg     240
tttcaagaca taacgacatt gttgttggat cacaaggcgt ttaaaga                   287

<210> SEQ ID NO 497
<211> LENGTH: 269
<212> TYPE: DNA
<213> ORGANISM: Glycine max

<400> SEQUENCE: 497
caaagctcag acccaaacct tcttttgct cttcatccat tccacaccaa aaagtaacac      60
cttcagtttc ggagggaaac acaacacaaa aagcccctc ccccaaagc aaatcacctt      120 tttttctttc agttattcaa aaaatgttcg ccgaagagaa tggactcaag ggagaccta      180 gactccaagc catttcccaa gccatcagag tcgtccctca cttccccata catggaataa     240
tgtttcaaga cataacgaca ttgttgttg                                        269

<210> SEQ ID NO 498
<211> LENGTH: 262
<212> TYPE: DNA
<213> ORGANISM: Glycine max
<220> FEATURE:
<221> NAME/KEY: unsure
<222> LOCATION: (1)...(262)
<223> OTHER INFORMATION: unsure at all n locations

<400> SEQUENCE: 498
caacaagaca cgcgcttagc gagaatcgcc tctgcaatcc gagtcatccc cgactttcct      60
aagccaggaa ttttgtttca ggacataacc acgctgcttc tnaacacaaa ggctttcaaa     120
gacaccattg acttgtttgt ngagaggtac agagatcaaa acatcaatgt tgtcgcagga    180
gttgaagcta gaggctttat atttggtcca cccattgcat tagctattgg agcaaaattt    240
gtccccatga ggaaacccaa ta                                               262

<210> SEQ ID NO 499
<211> LENGTH: 268
<212> TYPE: DNA
<213> ORGANISM: Glycine max

<400> SEQUENCE: 499
gctttctaaa ttctccaccc ctccgttcca ctgcttcgtc gcaacacgtt acaataatgg      60
cttcgaagaa ttctcaacaa gacacgcgct tagcgagaat cgcctctgca atccgagtca    120
```

```
tccccgactt tcctaagcca ggaattttgt ttcaggacat aaccacgctg cttcttgata     180
caaaggcttt caaagacacc attgacttgt ttgttgagag gtacagagat caaaacatca     240
atgttgtcgc aggagttgaa gctagagg                                        268

<210> SEQ ID NO 500
<211> LENGTH: 363
<212> TYPE: DNA
<213> ORGANISM: Glycine max

<400> SEQUENCE: 500
gaagtgaaga gaatgcgggt tgtttgttgt tccaattcag gcgtgagtgc tttccctagt      60
tgtcttagat tccctccact gatcgcaatt tcaacaacac cctcttcgat ccgctttcta    120
aattctccac ccctccgttc cactgcttcg tcgcaacacg ttacaataat ggcttcgaag    180
aattctcaac aagacacgcg cttagcgaga atcgcctctg caatccgagt catccccgac    240
tttcctaagc caggaatttt gtttcaggac ataaccacgc tgcttcttga tacaaaggct    300
ttcaaagaca ccattgactt gtttgttgag aggtacagag atcaaaacat caatgttgtc    360
gca                                                                  363

<210> SEQ ID NO 501
<211> LENGTH: 286
<212> TYPE: DNA
<213> ORGANISM: Glycine max

<400> SEQUENCE: 501
cccagattcc ctccactcat tgcaatttct tcgatccgct ttctaaattc cacacccctc     60
cgttccactg cttcgccgcg acaagttaca agaatggctt cgaagaatgc tcaacaagac    120
acgcgcttag ccagaatcgc ctctgcgatc cgagtcatcc ccgactttcc taagccagga    180
attttgtttc aggacataac cacgctgctt cttgatacaa aggctttcaa agacaccgtt    240
gacttgtttg ttgagaggta cagagatcaa acatcaatg ttgtcg                    286

<210> SEQ ID NO 502
<211> LENGTH: 222
<212> TYPE: DNA
<213> ORGANISM: Glycine max
<220> FEATURE:
<221> NAME/KEY: unsure
<222> LOCATION: (1)...(222)
<223> OTHER INFORMATION: unsure at all n locations

<400> SEQUENCE: 502
ttctaaattc tccaccccctc cgttccactg cttcgtcgca anacgttaca ataatggctt    60
cgaagaattc tcaacaagac acgcgcttag cgagaatcgc ctctgcaatc cgagtcatcc    120
ccgactttcc taagccagga attttgtttc aggacataac cacgctgctt cttgatacaa    180
aggctttcaa agacaccatt gacttgtttg ttgagaggta ca                       222

<210> SEQ ID NO 503
<211> LENGTH: 285
<212> TYPE: DNA
<213> ORGANISM: Glycine max
<220> FEATURE:
<221> NAME/KEY: unsure
<222> LOCATION: (1)...(285)
<223> OTHER INFORMATION: unsure at all n locations

<400> SEQUENCE: 503
tgccactctt ccatctttcc cttgtcccag attcnctcca ctcattgcaa tttcttcgat     60
```

```
ccgctttcta aattccacac ccctccgttc cactgcttcg ccgcgacaag ttacaagaat      120
ggcttcgaag aatgctcaac aagacacgcg cttagccaga atcgcctctg cgatccgagt      180
catccccgac tttcctaagc caggaatttt gtttcaggac ataaccacgc tgcttcttga      240
tacaaaggct ttcaaagaca ccgttgactt gtttgttgan cttcc                      285
```

```
<210> SEQ ID NO 504
<211> LENGTH: 264
<212> TYPE: DNA
<213> ORGANISM: Glycine max
<220> FEATURE:
<221> NAME/KEY: unsure
<222> LOCATION: (1)...(264)
<223> OTHER INFORMATION: unsure at all n locations

<400> SEQUENCE: 504
tgccactctt ccatctttcc cttgtcccag attccctcca cttcattgca atttcttcga       60
tccgctttct aaatnccaca cccntccgtt ccnctgcttc gncgcgacaa gtttacnaga      120
atggcttcga agaatgctca acaagacacg cgcttancca gantcgcctc tgcgatccga      180
gtcatccccg actttcctaa gccaggaatt ttgtttcagg ataaccac gctgcttctn       240 gatacaaagg ctttcaaaga cacg                                             264
```

```
<210> SEQ ID NO 505
<211> LENGTH: 263
<212> TYPE: DNA
<213> ORGANISM: Glycine max
<220> FEATURE:
<221> NAME/KEY: unsure
<222> LOCATION: (1)...(263)
<223> OTHER INFORMATION: unsure at all n locations

<400> SEQUENCE: 505
caggcgtgag tgccactctt ccatctttcc cttgtcccag attcccncca ctcatngcna       60
ttncttcgat ccgntttcta aatnccacac ccctccgttc cactgcttcg ccgcgacaag      120
ttacaagaat ggcttcgaag aatgctcaac aagacacgcg cttagccaga atcgcctctg      180
cgatccgagn catccccgac tttcctaagc caggaatttt gtttcaggac ataaccncgc      240
tgcttcttga tacaaaggct ttc                                              263
```

```
<210> SEQ ID NO 506
<211> LENGTH: 437
<212> TYPE: DNA
<213> ORGANISM: Glycine max
<220> FEATURE:
<221> NAME/KEY: unsure
<222> LOCATION: (1)...(437)
<223> OTHER INFORMATION: unsure at all n locations

<400> SEQUENCE: 506
aagacgacag aagggggaaa tgaaaaaagt gacangaant gangagaatg cgggttgttt       60
gttgttccaa ttcangcgtn agtgctttcc ctagttgtct tanattccct ccactgatcg      120
caatttcaac aacaccctct tcgatccgcn ttctaaattc tccanccctc cgttccactg      180
cttcgtcgca acacgttaca ataatggctt cnangaattc tcaacaagga cacgcgctta      240
acgagaatcg cctctgcaat ccgagtcatc cccgactttc ctaagccagg aattttgttt      300
cangacataa ccacgctgct tcttgataca aangctttca aangacacca ttgacttgtt      360
tgnttaanag gtacaagaga tnagtaacat caatgttgtc cccangagtt tgaanctaga      420
```

```
ggcnttaaaa tttgggg                                                    437

<210> SEQ ID NO 507
<211> LENGTH: 271
<212> TYPE: DNA
<213> ORGANISM: Glycine max

<400> SEQUENCE: 507
gcgggttgtt tgttgttcca attcaggcgt gagtgctttc cctagttgtc ttagattccc       60
tccactgatc gcaatttcaa caacaccctc ttcgatccgc tttctaaatt ctccaccact      120
ccgttccact gcttcgtcgc aacagttaca ataatggctt cgaagaattc tcaacaagac     180
acgcgcttag cgagaatcgc ctctgcaatc cgagtcatcc ccgactttcc taagccagga     240
attttgtttc aggacataac cacgctgctt c                                    271

<210> SEQ ID NO 508
<211> LENGTH: 228
<212> TYPE: DNA
<213> ORGANISM: Glycine max

<400> SEQUENCE: 508
gccactcttc catctttccc ttgtcccaga ttccctccac tcattgcaat ttcttcgatc       60 cgcttttctaa attccacacc cctccgttcc actgcttcgc cgcgacaagt tacaagaatg     120
gcttcgagaa tgctcaacaa gacacgcgct tagccagaat cgcctctgcg atccgagtca     180
tccccgactt tcctaagcca ggaattttgt ttcaggacat aaccacgt                   228

<210> SEQ ID NO 509
<211> LENGTH: 335
<212> TYPE: DNA
<213> ORGANISM: Glycine max
<220> FEATURE:
<221> NAME/KEY: unsure
<222> LOCATION: (1)...(335)
<223> OTHER INFORMATION: unsure at all n locations

<400> SEQUENCE: 509
ttctctctgt actcaaactc acttccccac ttatttatac aatgtcggct tacaaagacc       60
aggatacccg tcttcatggc atcaaaacta agattcgtgt cgtccccaat ttccccaaat     120
ccggtattat gttccaagac attactactc tattgcttga tcccaaagca tttaaggaca     180
caatagattt gttcgttgag cggtacaagg gcaaaaacat ttctgttgtt gcaggnattg     240
aagctcgagg tttatttttt ggtcctccca ttgcgctggc tataggagca aagtttgtac     300
catgaggana ccaaagaagt tgctggaaag ttatt                                335

<210> SEQ ID NO 510
<211> LENGTH: 462
<212> TYPE: DNA
<213> ORGANISM: Glycine max
<220> FEATURE:
<221> NAME/KEY: unsure
<222> LOCATION: (1)...(462)
<223> OTHER INFORMATION: unsure at all n locations

<400> SEQUENCE: 510
aactcccagc gcacangtaa cggtatcnga attcccggct cgacccacgc gtnaagtacg       60
gctgcnaaga cgacagaagg gganctctct tattgttgtt ctcttcttct tttcttgttt     120
ccttttccat tcttctttt ctctctgtac tcaaactcac ntccccactt anttatacaa      180
tgtcggctta naaanaccan gatacccgtc ttcatggcat caanactaat attcgtgtcg     240
```

```
tccccaattt ccccaaatcc ggtattatgt tccaagacat tactactcna ttgcttgatc      300
ccaaagcatt taaggacaca atagatttgt tcgttgancg gtanaagggc aaaaacattt      360
ctgttgttgc aggaattgaa gctcgaggtt ttattttttgg tcnncccatt gcgctgggct     420
ataggganca gagttttgta cnattgagga aaccaangaa gt                        462
```

<210> SEQ ID NO 511
<211> LENGTH: 251
<212> TYPE: DNA
<213> ORGANISM: Glycine max
<220> FEATURE:
<221> NAME/KEY: unsure
<222> LOCATION: (1)...(251)
<223> OTHER INFORMATION: unsure at all n locations

<400> SEQUENCE: 511

```
cttttccatt cttcttttnc tctctgtact caaactcact tccccactta tttatacaat      60
gtcggcttac aaagaccagg atacccgtct tcatggcatc aaaactaaga ttcgtgtcgt     120
ccccaatttc cccaaatccg gtattatgtt ccaagacatt actactctat tgcttgatcc     180
caaagcattt aaggacacaa tagatttgtt cgttgagcgg tacaagggca aaacatttc     240 tgttgttgca g                                                          251
```

<210> SEQ ID NO 512
<211> LENGTH: 281
<212> TYPE: DNA
<213> ORGANISM: Glycine max
<220> FEATURE:
<221> NAME/KEY: unsure
<222> LOCATION: (1)...(281)
<223> OTHER INFORMATION: unsure at all n locations

<400> SEQUENCE: 512

```
ctcttcttct tttcttgtnt cctttccat tcttcttttt ctctctgtac tcaaactcac      60
ttccccactt atttatacaa tgtcggctta caaagaccag gatacccgtc ttcatggcat    120
caaaactaag attcgtgtcg tcccaatttc cccaaatccg gtattatgtt ccaagacatt    180
actactctat tgcttgatcc caaagcattt aaggacacaa tagatttgtt cgttgagcgg    240
tacaagggca aaacatttc tgttgttgca ggaattgaag c                         281
```

<210> SEQ ID NO 513
<211> LENGTH: 254
<212> TYPE: DNA
<213> ORGANISM: Glycine max

<400> SEQUENCE: 513

```
cttttattgc ttcctttccc attcttcatc ttcttctctc tgaaccgtac tcaaactcca      60 ctttccact tatttataca atgtcggctt acaaagacca ggatccccgt cttcatggca     120
tcaaaactaa gattcgtgtc gtccccaatt tccccaaatc cggtcttatg ttcctagaca    180
ttactactct attgcttgat cccaaagcat ttaaggactc aatagatttg ttcgtggagc    240
ggtacaaggg caaa                                                      254
```

<210> SEQ ID NO 514
<211> LENGTH: 222
<212> TYPE: DNA
<213> ORGANISM: Glycine max
<220> FEATURE:
<221> NAME/KEY: unsure
<222> LOCATION: (1)...(222)

-continued

<223> OTHER INFORMATION: unsure at all n locations

<400> SEQUENCE: 514
ctcgancnnc ttcgaagcng cttcttcttt tcttntttcc ttttncattc ttctttttct      60
ctctgtacan aaactcactt ccacacttat taatanataa tnngcttaca aagaccanga     120
tacccgtctt natggcatca aaactaatat tcgtgtcgtc cccaatttcc ccaaatccgg     180
tattatgttc caagacatta ctactctatt gcttgatccc aa                        222

<210> SEQ ID NO 515
<211> LENGTH: 259
<212> TYPE: DNA
<213> ORGANISM: Glycine max
<220> FEATURE:
<221> NAME/KEY: unsure
<222> LOCATION: (1)...(259)
<223> OTHER INFORMATION: unsure at all n locations

<400> SEQUENCE: 515
gttgttcttc tctttctttt ntngcttcct ttcccantct tcatcttctt ctcnctgaac      60
cgtactcaaa ctcactttcc cacttattta tacaatgtcg gcttacaaag ancaggatcc     120
ccgtcttcnt ggcntcaaaa ctaagattcg tgtcgtcccc aatttcccca aatccggtct    180
tatgttccta gacattacta ctctattgct tgatcccaaa gcattnaaag gatncnatag    240
atttggtcgt gggagcggt                                                   259

<210> SEQ ID NO 516
<211> LENGTH: 269
<212> TYPE: DNA
<213> ORGANISM: Glycine max

<400> SEQUENCE: 516
tgcatgtatc tatgaatgat ggaaccacca caaacgaggt tgatgatcaa cgttttcata      60
gtgagtttct tagcactact tgtgaacttg gtggtgggag tgctcggcgc tgataactat     120
agcagagatg attttcctct tgactttgtt ttcggttcag gaacctctgc ttatcaggtg    180
gaaggagctg ctaacaaaga tggaagaact cctagcatct gggacacctt tgcctacgct    240
ggatatgccc atggagaaaa tggagatgt                                       269

<210> SEQ ID NO 517
<211> LENGTH: 287
<212> TYPE: DNA
<213> ORGANISM: Glycine max
<220> FEATURE:
<221> NAME/KEY: unsure
<222> LOCATION: (1)...(287)
<223> OTHER INFORMATION: unsure at all n locations

<400> SEQUENCE: 517
caaatctgat canaaggcta cagnaagagc aattgacttc atgtatggat ggtttatgga      60
tccattaaca tctggagant atcccaacag catgcgatca cttgtgagga caagnttanc     120
naagtngnct ncngngcaat ccanactact tatngngttc attnnattnt cttggcctaa    180
anctattact cnacancata tgcctctgac gnncctgntn naagcgaacc cgtcctagct    240
actnaacagn ttctctggtc actccngcat atggaacgtg ntgggga                  287

<210> SEQ ID NO 518
<211> LENGTH: 261
<212> TYPE: DNA
<213> ORGANISM: Glycine max

```
<220> FEATURE:
<221> NAME/KEY: unsure
<222> LOCATION: (1)...(261)
<223> OTHER INFORMATION: unsure at all n locations

<400> SEQUENCE: 518
canntctgnt cannaggcta caganagagc aattgacttc atgtatggnt ggttnatgga      60
tccattaana tctggagact atnccnncag catgcganca cttgtgngga caagattacc     120
anagtttnnt gcagagcnat ccnaactacn tattggttca ttngntntca ttagcctaaa     180
ctattactct acaacatatg cctctgacgc acctgatcta agcgaagccg tcctagctac     240
ttaacngatt ctcttgtcan t                                               261

<210> SEQ ID NO 519
<211> LENGTH: 250
<212> TYPE: DNA
<213> ORGANISM: Glycine max

<400> SEQUENCE: 519
tgttcttatg tggttatgaa tgtgcttctt ttaggaaaag caaaagggaa ggattgggat      60
cctcttggat tttgtttggt atgagcctct tacaagatca aaggctgaca attttgcagc    120
tcaaagagcc agagactttc atattggatg gtaaaaatct tagcatttgt taactgagga    180
tcctatattg caagtacaag tctttagtta tgaatgtgaa ttttcccctg caaagacttt    240
cacacgcttg                                                            250

<210> SEQ ID NO 520
<211> LENGTH: 239
<212> TYPE: DNA
<213> ORGANISM: Glycine max
<220> FEATURE:
<221> NAME/KEY: unsure
<222> LOCATION: (1)...(239)
<223> OTHER INFORMATION: unsure at all n locations

<400> SEQUENCE: 520
aaacatggag cttccactcc tagcacatca ngcactcttt gcactaagct tttgcatctc      60
aattttcttg gcatcgtgtg atgatgattt tctatccgtg aaaaagaatt caagttcatc    120
tccatttcct agcaactttc ttttnggaac tgcatcttct tcatatcagt ttgaaggagc    180
ttacttgact gatggtaagg gactaaataa ctgggatgtt ttcactcata agccaggca     239

<210> SEQ ID NO 521
<211> LENGTH: 251
<212> TYPE: DNA
<213> ORGANISM: Glycine max
<220> FEATURE:
<221> NAME/KEY: unsure
<222> LOCATION: (1)...(251)
<223> OTHER INFORMATION: unsure at all n locations

<400> SEQUENCE: 521
cttagagatg aagaatgtga tagacaagcc gtgaaaaggg cctnggcttt tgttgtagcc      60
tggtccttag atcccttggt ttttggtgag taccctccng agatgcactc tattctcggg    120
agtcagttgc caagattctc tcctgaggag aagagtctca taaaaggcag catagacttc    180
attggcatca ataactatgg aactctctat gccaaggact gctccctcac tgcttgtcct    240
cttggaacag a                                                          251

<210> SEQ ID NO 522
```

```
<211> LENGTH: 246
<212> TYPE: DNA
<213> ORGANISM: Glycine max
<220> FEATURE:
<221> NAME/KEY: unsure
<222> LOCATION: (1)...(246)
<223> OTHER INFORMATION: unsure at all n locations

<400> SEQUENCE: 522
aaaagattat gagcattatg ccantacntg cttcaaagct tttggagaca gagttaagca    60
ctggattacc ttcaatgagc ctcataactt tgcactccat ggttatgntt taggcattca   120
agcacaggaa gatgttccct tttgggtcat cttctntgta agaaaggana atcatccact   180
gagccataca ttgttgctcn taacattctc ttgtcacatg ctgctgccta tagaagctac   240
caacta                                                              246

<210> SEQ ID NO 523
<211> LENGTH: 255
<212> TYPE: DNA
<213> ORGANISM: Glycine max
<220> FEATURE:
<221> NAME/KEY: unsure
<222> LOCATION: (1)...(255)
<223> OTHER INFORMATION: unsure at all n locations

<400> SEQUENCE: 523
anatagtgta aataaatact caattatata tgattcacta tagtattttt aaataatgaa    60
aaagaaaata tagtaaatgt ttatggcaaa ataaaaatag ggaggacttc cgtaactatg   120 ctgactttg cttcaagaca tttggtgatc gggtgaagca ctgggtaacc ctaaatgaac    180
catatggcta cagcgtgaat gggctacagt ggtggaagtt tgcacccagg tagatgttct   240
aactacgttg gaaaa                                                    255

<210> SEQ ID NO 524
<211> LENGTH: 272
<212> TYPE: DNA
<213> ORGANISM: Glycine max
<220> FEATURE:
<221> NAME/KEY: unsure
<222> LOCATION: (1)...(272)
<223> OTHER INFORMATION: unsure at all n locations

<400> SEQUENCE: 524
gcaattcaac ngctgacaaa ttggctagcg aaagagcnag agcattcanc ttcaattggt    60
tcttggaccc aatcatattc ggnaagtacc ctacagagat ggagaacgtt cttgaagcc   120 tcttgcccaa attttccagc tacgaaaaag agaaactcaa gagaggattg gatttcattg   180
gcgtcaatta ctacacggct ttctatgtcc aagattgcat gtactccgct tgtaaaccag   240
gacccgggat ctccagaaca gagggttcat ac                                 272

<210> SEQ ID NO 525
<211> LENGTH: 286
<212> TYPE: DNA
<213> ORGANISM: Glycine max
<220> FEATURE:
<221> NAME/KEY: unsure
<222> LOCATION: (1)...(286)
<223> OTHER INFORMATION: unsure at all n locations

<400> SEQUENCE: 525
gcaaaaaatg aaaacccaaa gtgcttctct cctctgtctt tttctctctc ttgctatcct    60
tttggntaat ngnaatggtn naantnnaat ncaannancn gaanngncaan gccacaatgt   120
```

```
ttcacnattc acnagaagcc ttttcccttc nanttttctc tttggaattg gtncttctgn    180
ttacaaggna gaaggagnag naantgtagn tgggagagga ccaagnatat gggacacaan    240
cactagncag cntantgaaa agatttgggn tcatagcacc gngaac                  286
```

<210> SEQ ID NO 526
<211> LENGTH: 278
<212> TYPE: DNA
<213> ORGANISM: Glycine max
<220> FEATURE:
<221> NAME/KEY: unsure
<222> LOCATION: (1)...(278)
<223> OTHER INFORMATION: unsure at all n locations

<400> SEQUENCE: 526

```
ccttgatata ggaatggctc aaatgtaaag ggatattatg tatggtcttt gttcgacaat    60
tttgaatggt cttccggttt tacatcaaga tttggaatga tttatgtaga ttacaaaaat   120
gatttgaaga gatacaagan attctctgca tatggtttga gaattttctg aagaaagaaa   180
ccaaactata tggttctagc aaatagtatt atgaaatttg tttacaaaat agttatatat   240
atttgtaaat aattatttga tttgtatttg gtcattct                           278
```

<210> SEQ ID NO 527
<211> LENGTH: 269
<212> TYPE: DNA
<213> ORGANISM: Glycine max
<220> FEATURE:
<221> NAME/KEY: unsure
<222> LOCATION: (1)...(269)
<223> OTHER INFORMATION: unsure at all n locations

<400> SEQUENCE: 527

```
ctcgagncag ctcanagagc tcannatccc tnagtctggg gctggtttac tctgatcctt    60
tgatgtttgg ggattatcca agctcaatga ggactagagt aggaagcagg ctaccgaaat   120
tttcgcaatc agaagctgct cttgttaagg gttcattaga ttttgttgga atcaatcatt   180
acaccacatt ttatgcaaaa gacaattcta ctaatttaat tggaaccctg gctccatgat   240
tccattgcag actctggngc cgttacccc                                     269
```

<210> SEQ ID NO 528
<211> LENGTH: 280
<212> TYPE: DNA
<213> ORGANISM: Glycine max

<400> SEQUENCE: 528

```
caagtctcaa accatggcgt ttagaggagg cactatgttg atattaacaa tgatggcatt    60
acttgagatt cagatatgct catcggagat aaaccgtgga aactttccaa atggcttcgt   120
atttggcact gcctcttcag cttttcagta tgaaggggca gtgaaagaag acggaagggg   180
accctctgtg tgggacactt tttcacatac ttttggcaaa ataattgatt tcagcaatgc   240
tgatgttgcg gtggatcagt accaccgata cgaagaagat                         280
```

<210> SEQ ID NO 529
<211> LENGTH: 259
<212> TYPE: DNA
<213> ORGANISM: Glycine max
<220> FEATURE:
<221> NAME/KEY: unsure
<222> LOCATION: (1)...(259)
<223> OTHER INFORMATION: unsure at all n locations

<400> SEQUENCE: 529

```
cttaaaacca tttgtcacgc tgttacattg ggacctccca caagctcttg aagatgaata      60 tangggatt tctcaaacct gaaatagtgt aaataaatac tcaattatat atgattcact     120
atagtatttt taaataatga aaagaaaat atagtaaatg tttatggaaa aataaaaata     180
gggaggactt ccgtaactat gctgactttt gcttcaagac atttggtgat cgggtgaagc    240
actgggtaac cctaaatga                                                  259
```

<210> SEQ ID NO 530
<211> LENGTH: 259
<212> TYPE: DNA
<213> ORGANISM: Glycine max
<220> FEATURE:
<221> NAME/KEY: unsure
<222> LOCATION: (1)...(259)
<223> OTHER INFORMATION: unsure at all n locations

<400> SEQUENCE: 530

```
gggtttgcat ganaccacaa ggataaacta ttacaaaggc tatttgactc aactaaagaa      60
agcagttgat gatggagcaa atgtggttgg ggaatttgca tggtcantgc ngggataaac    120
ttgaatggaa ggttggggtt acacatcaaa ggtttggcat gtctatgttg atttcaaaac    180
cctcaaggag ataccccaa gatgtcggca tactggttca agcaaactcc attaccaaaa    240
aggagtatta atagcnggg                                                  259
```

<210> SEQ ID NO 531
<211> LENGTH: 256
<212> TYPE: DNA
<213> ORGANISM: Glycine max
<220> FEATURE:
<221> NAME/KEY: unsure
<222> LOCATION: (1)...(256)
<223> OTHER INFORMATION: unsure at all n locations

<400> SEQUENCE: 531

```
caaccacatg tcacactaca caactgtgat cttccgcagg cacttgagga tgaatatgga      60
ggatgggtta gtcgtgatat cataaganac ttcacaaact atgcagatgt gtgttttaga    120
gagtttggtg atagantcca gtactggact actgtnaatg ancccaatgc ctttgccttg    180
ggtggctatg atcaaggaac ctcccctcct cagcgatgtt ctccccccatt ttgcactaca    240 aacagcacta ggggca                                                     256
```

<210> SEQ ID NO 532
<211> LENGTH: 272
<212> TYPE: DNA
<213> ORGANISM: Glycine max
<220> FEATURE:
<221> NAME/KEY: unsure
<222> LOCATION: (1)...(272)
<223> OTHER INFORMATION: unsure at all n locations

<400> SEQUENCE: 532

```
ggcattaagc agaatcataa tctttcatca catgcatcat atggcgcttc tacttgtcgc      60
tctcttggct cttgttacta cattaccatc ggttactgtt ggagaagtgc tttcacccat    120
tctcgacgtt gcttcactga accgaaccag ttttcccaag ggctttangc ngggcagga    180 tccgcatcgt atcagtacga aggtggggca aacgaagtgg caaaggacca agtatatggg    240
atacctacca caaatatcca gataaaattg tg                                   272
```

<210> SEQ ID NO 533
<211> LENGTH: 240
<212> TYPE: DNA
<213> ORGANISM: Glycine max
<220> FEATURE:
<221> NAME/KEY: unsure
<222> LOCATION: (1)...(240)
<223> OTHER INFORMATION: unsure at all n locations

<400> SEQUENCE: 533

```
tnaataccag actgagcagg gggggggaaat cggcattgtc ctacactgtg actcatttga      60
gccgttgagc aattccacag cagataaaatt ggctactgaa agagcacaat cattcagcat    120
taattggatc ttggatccaa tcttatttgg taagtaccca aaagagatgg agatgattct    180
aggaaccacc ttacctaaat tttccagtaa tgacaaagca aaactgaggg caaggacgga    240
```

<210> SEQ ID NO 534
<211> LENGTH: 249
<212> TYPE: DNA
<213> ORGANISM: Glycine max

<400> SEQUENCE: 534

```
ggtgaatggg attcctacat gtgctgaccc agaccttctc aaagggataa tcagaggcca     60
gtggggtcta gacggatata ttgtttcaga ttgtgattca gtggaagtct attacaatgc    120
aattcattac actgcaactc ctgaagatgc agtggctctt gcactgaaag caggtttaaa    180
catgaactgt ggcgattttc ttaaaaaata cactgcaaat gctgtaaact tgaaaaaagt    240
agatgtagc                                                             249
```

<210> SEQ ID NO 535
<211> LENGTH: 437
<212> TYPE: DNA
<213> ORGANISM: Glycine max
<220> FEATURE:
<221> NAME/KEY: unsure
<222> LOCATION: (1)...(437)
<223> OTHER INFORMATION: unsure at all n locations

<400> SEQUENCE: 535

```
tacggctgcg anaagacgac agaagggctt cccaaaaagt ccacaaaaat actggtagca     60
ggaagtcatg ctaacaattt gggttatcaa tgtggaggat ggacaattac ctggcagggg    120
cttggtggca atgatctcac ttcaggtaca accatccttg atgctgtgaa acaaaccgtt    180
gatcctgcca ctgaagttgt cttcaatgaa atcctgata agaactttgt caagtcatac    240
aaatttgact atgccattgt tgttgtggga gaacacactt atgccgaaac atttggtgac    300
agtttgaatc tgactatggc tgatcctggt ccaagtacca tcaccaatgt gtgtggggct    360
attcnatgcc tagttgttcc tgtcactggc cgccantttg tgattaagcc atatctaacc    420
aaaatcgatg cacttgg                                                   437
```

<210> SEQ ID NO 536
<211> LENGTH: 376
<212> TYPE: DNA
<213> ORGANISM: Glycine max
<220> FEATURE:
<221> NAME/KEY: unsure
<222> LOCATION: (1)...(376)
<223> OTHER INFORMATION: unsure at all n locations

<400> SEQUENCE: 536

```
agacgacaga anggagagat ggattgatga aaattcacat gccangctac ttcagctcga     60
```

```
tcagcaaggg tgtggcaacc attatggcct cttactccan ttggaatgga gtaaaaatnc    120
atgctcanca tgatcttatt actggcttcc tcaataatac tctccatttc aagggctttg    180
tcanttcaga ttttgagggt cttgatagga tcacctctcc acctcgtgca aatatcactt    240
attcaattta agcaggagtt tctgctggca ttgacatgtt catggttnca aagcattnca    300
canaattcat agatnttcta accatgttgg tgaaaaataa acacattccc atgagtcnaa    360
ttgatgatnc antggg                                                    376
```

<210> SEQ ID NO 537
<211> LENGTH: 459
<212> TYPE: DNA
<213> ORGANISM: Glycine max
<220> FEATURE:
<221> NAME/KEY: unsure
<222> LOCATION: (1)...(459)
<223> OTHER INFORMATION: unsure at all n locations

<400> SEQUENCE: 537

```
cttnaggaga ggggcccngg ttattgagcc ccgncanttg tgaaaatant ttnccatnat     60
ncccaaattt gnttcaagac ntttggagat tgannttana attggatnac ctttaatnga    120
cccngtgtng gnggnnngtn ntggcnnnta ntannggttc tttngcccct gaaaaatnct    180
caaaggattn tgggantngt ccagttggca actnaggcnc tgagcctacn ttgttgccca    240
cantttgata ttgtcacatg cagctgctgt tcaaagatac cgagagaagt atcaagaaaa    300
gcaaaaggga aggattgggg atcctcttgg attttggttg gtatgagcct cttacaagat    360
caaangcccg ncaatttanc acttaaanaa ncccanacct ttatgttnga ngggtcaatc    420
attccccctg gttatgngag ggttccacca ncccnttta                           459
```

<210> SEQ ID NO 538
<211> LENGTH: 472
<212> TYPE: DNA
<213> ORGANISM: Glycine max
<220> FEATURE:
<221> NAME/KEY: unsure
<222> LOCATION: (1)...(472)
<223> OTHER INFORMATION: unsure at all n locations

<400> SEQUENCE: 538

```
cgacggccga cgcgtacgcc cacgcgtccg agaagtttct gttgatcnnt accatcgcta     60
caaagaagat atngnncngg nggccagctn gaanggggat gcctaccggt tctcaatctc    120
gtggtccaga attttccaa atggaactgg ccaantaaan tggaaaggtg tagcatacta    180
caataggntg atcaattact tgctagaaaa aggtattact ccatatgcaa atctctacca    240
ttatgatctt ctttancact tgaagagagg tacaacggaa tattgnaccg gcaagntgtg    300
aatgatttng caanattatg cagaatttng nttnaagan ttntngaaga tagaattaaa    360
aantngantg acgttnaaaa gaancctnaa gnaggnagnt tgncatggcn aagaaaaang    420
ggattntatn nncccggaa aaannnttaa aaagaatntn ggnaatagnc aa             472
```

<210> SEQ ID NO 539
<211> LENGTH: 443
<212> TYPE: DNA
<213> ORGANISM: Glycine max
<220> FEATURE:
<221> NAME/KEY: unsure
<222> LOCATION: (1)...(443)
<223> OTHER INFORMATION: unsure at all n locations

<400> SEQUENCE: 539

```
ggctttacaa cgtaccatgg ggcatgtaca aatcattgat gtacataaag gaacgttatg    60
gaaacccaac tgtgntcnta tccgaaaatg gtaacattat atatcaattt cttgcttttt   120 ccttttttg gcttggtgat tctgttgttt caatgtcatg tgacatattt tatgacatgt    180
aggcatggat gatccgggta acgtgactct tcccaagggt ttgcatgaca ccacaaggat   240
aaactattac aaaggctatt tgactcaact aaagaaggca gttgatgatg gagctaatgt   300
ggttggatac tttgcatggt cattgctgga taactttgaa tggaggttgg gttacacatc   360
aaggnttggc attgnctatg ttgatttcaa acccctcaag agatacccta agatgtcagc   420
atactggttc aagcaactca ttg                                           443
```

<210> SEQ ID NO 540
<211> LENGTH: 253
<212> TYPE: DNA
<213> ORGANISM: Glycine max

<400> SEQUENCE: 540

```
gctaatgtgg ttggatactt tgcatggtca ttgctggata actttgaatg gaggttgggt    60
tacacatcaa ggtttggcat tgtctatgtt gatttcaaaa ccctcaagag atacccctaag  120 atgtcagcat actggttcaa gcaactcatt gccaaaaaga agtactaata gctgggctga   180
acatctactt tctaagcttc tagttgcttc agataatcat gttttagtgg ttttggttga   240
gttaaaagta gtt                                                      253
```

<210> SEQ ID NO 541
<211> LENGTH: 249
<212> TYPE: DNA
<213> ORGANISM: Glycine max
<220> FEATURE:
<221> NAME/KEY: unsure
<222> LOCATION: (1)...(249)
<223> OTHER INFORMATION: unsure at all n locations

<400> SEQUENCE: 541

```
ctaatgnggt tggatacttt gcntggttca ttgctggata actttgaatg gaggttgggt    60
nacacatcan ggtttggcat tgtctatgtn gattncaaaa ccctcangan atanccctaag  120 atgncagcat actggntcan gcaactcatt gccannnagn agtactaata gctgggctga   180
acatctactt tctaagcttc tagttgcatc agataatcat gttttagtgg ttttggttga   240
gttaaaagc                                                           249
```

<210> SEQ ID NO 542
<211> LENGTH: 248
<212> TYPE: DNA
<213> ORGANISM: Glycine max

<400> SEQUENCE: 542

```
ttttttttgc cataaaagat cattttattc taagacttgc attaatcaag tcacatgatt    60
acagttacag aactactttt aactcaacca aaaccactaa acatgattta tctgaagcaa   120
ctagaagctt agaaagtaga tgttcagccc agctattagt acttcttttt ggcaatgagt   180
tgcttgaacc agtatgctga catcttaggg tatctcttga gggttttgaa atcaacatag   240
acaatgcc                                                            248
```

<210> SEQ ID NO 543
<211> LENGTH: 249
<212> TYPE: DNA

```
<213> ORGANISM: Glycine max
<220> FEATURE:
<221> NAME/KEY: unsure
<222> LOCATION: (1)...(249)
<223> OTHER INFORMATION: unsure at all n locations

<400> SEQUENCE: 543
ggagttcttg agagaaaacg gcgacaacga nagccgttcc gtctcgcgga gtgacttccc      60
tcccaacttc atcttcggag ttgccacttc tgcatatcag atagaaggtg cttgtaagga     120
gggtggtaga ggtcctagca tatgggatgc ctttacacac acggnaggaa aaattcttga    180
caaaagcaat ggtgatgttg cagttaatca ttatcatcgg tacatggnag atattgatct    240
natagccna                                                             249

<210> SEQ ID NO 544
<211> LENGTH: 252
<212> TYPE: DNA
<213> ORGANISM: Glycine max
<220> FEATURE:
<221> NAME/KEY: unsure
<222> LOCATION: (1)...(252)
<223> OTHER INFORMATION: unsure at all n locations

<400> SEQUENCE: 544
ggagttcttg agagaaaacg gcgacaacga aaaccgttcc gtctcgcgga gtgacttccc      60
tcccaacttc atcttcggag ttgccacttc tgcatatcag atagaaggtg cttgtaagga     120
gggtggtaga ggtcctagca tatgggatgc ctttacacac acggaaggaa aaattcttga    180
caaaagcaat ggtgatgttg cagttaatca ttatcatcgg tacatggnag atattgatct    240
atagccaagt tg                                                         252

<210> SEQ ID NO 545
<211> LENGTH: 276
<212> TYPE: DNA
<213> ORGANISM: Glycine max

<400> SEQUENCE: 545
cggcgattga gagggagagt ttgagaatgg tgaagaagga ggagttcttg agagaaaacg      60
gcgacaacga aaaccgttcc gtctcgcgga gtgacttccc tcccaacttc atcttcggag    120
ttgccacttc tgcatatcag atagaaggtg cttgtaagga gggtggtaga ggtcctagca    180
tatgggatgc ctttacacac acggaaggaa aaattcttga caaaagcaat ggtgatgttg    240
cagttaatca tatcatcggt acatggaaga tattga                              276

<210> SEQ ID NO 546
<211> LENGTH: 240
<212> TYPE: DNA
<213> ORGANISM: Glycine max
<220> FEATURE:
<221> NAME/KEY: unsure
<222> LOCATION: (1)...(240)
<223> OTHER INFORMATION: unsure at all n locations

<400> SEQUENCE: 546
agcngtgnaa aangctgcag aggcagcaca cgagctgtat tgatactacn ttgctgtacn      60
tcaatttcat gtccaaagtt gtgatgaaat tgaagatgta atcagcagat ctcaatttcc    120
agaagggttc cttttcggaa caggcacttc ctcttaccag attgaaggag cgtattttga    180
agatggaaag ggtttaagca attgggatgc ttttagtcat acaccaggan agataaaaaa    240
```

<210> SEQ ID NO 547
<211> LENGTH: 263
<212> TYPE: DNA
<213> ORGANISM: Glycine max
<220> FEATURE:
<221> NAME/KEY: unsure
<222> LOCATION: (1)...(263)
<223> OTHER INFORMATION: unsure at all n locations

<400> SEQUENCE: 547

```
tttttttggtt gcatcatgtc tgccatcact aatcattgga acaaaatgaa aatgctgcag      60
aggcagctaa ganctgtatt gatactgttt tgctgtnttc aatttcatgt ccaaagttgt     120
gatgaaattg aagatgtaat cagcagatct caatttccag aagggttcct tttcggaaca     180
ggcacttcct cttaccagat tgaaggagcg tattttgaag atggaaaggg tttaagcnat     240
tgggagcttt tagtcataca cca                                             263
```

<210> SEQ ID NO 548
<211> LENGTH: 477
<212> TYPE: DNA
<213> ORGANISM: Glycine max
<220> FEATURE:
<221> NAME/KEY: unsure
<222> LOCATION: (1)...(477)
<223> OTHER INFORMATION: unsure at all n locations

<400> SEQUENCE: 548

```
ggaaggattg ggatcctctt ggattttgtt tggtatgagc ctcttacaag atcaaaggcc      60
gacaatttag cagctcaaag agccagagac tttcatgttg gatggttcat tcatcccctt     120
gtttatggag agtntccaac aaccattcaa aatattgttg ggaatagact ccccaaattc     180
actagtgaag aagttaaaat cgtgaaaggg ttcaatagat tttgttggaa tnanccantt     240
tcntacgnct cnngtttgac cntttaaggc aaaacttaaa ncccangttt ttaangggct     300
tggaatcccg aattggtntt ccaanaacgg ggtgnccatt tgnnccaagg ntttttttta     360
ttgggtttta acgnnccctg gggggtgttt caaaaaattg gtgggcntaa aagggaccct     420
tttgggaaac cccccgngng gttnttccca aaaggggnng ggtnanaccc ggnaanc       477
```

<210> SEQ ID NO 549
<211> LENGTH: 402
<212> TYPE: DNA
<213> ORGANISM: Glycine max
<220> FEATURE:
<221> NAME/KEY: unsure
<222> LOCATION: (1)...(402)
<223> OTHER INFORMATION: unsure at all n locations

<400> SEQUENCE: 549

```
ggatgacgtt taacgaacct cgtgtggtgg ctgctcttgg ctatgataat ggtttctttg      60
cccctggaag atgctcaaaa gaatatggga attgtactgc tggcaactca ggcactgagc     120
cttacattgt tgcccacaat ttgatattgt cgcatgcagc anctgttcaa agataccgag     180
cgaagtacca agaaaagcaa aagggaagga ttgggatcct cttggatttt gtttggtatg     240
agcctcttac aagatcaaag gctgacaatt ttgcagctca aagagccaga gactttcata     300
ttggatggtt cattcatccc cttgtttatg gagagtatcc aaaaaccatt caaaatattg     360
ttgggaatan actccccaaa ntcactantt aagaanttta aa                       402
```

<210> SEQ ID NO 550
<211> LENGTH: 473
<212> TYPE: DNA

<213> ORGANISM: Glycine max
<220> FEATURE:
<221> NAME/KEY: unsure
<222> LOCATION: (1)...(473)
<223> OTHER INFORMATION: unsure at all n locations

<400> SEQUENCE: 550

```
gtttaatgaa cctcgtgtgg tggctgctct tggctatgat aatggtttct ttgccccngg      60
aagatgctca aagaatatg ggaattgtac agctggcaac tcaggcactg agccttacat     120
tgttgcccac aatttgatat tgtcacatgc agctgctgtt caaagatacc gagagaagta     180
tcaagaaaag caaagggaa ggattgggat cctcttggat tttgtttggt atgagcctct     240
tacaagatca aaggccgaca atttagcagc tcaaagagcc agagactttc atgttggatg     300
gttcattcat cccccttgttt atggagagta tccaacaacc attcaaaata ttggtgggaa     360
tagactcccc aaattcacta gtgaagaaa gttaaaatcc gtgaaagggg tcaatagaat     420
tttggtngga atcaanccat nttcttcgtc tacatgnatt aaacctatta aac            473
```

<210> SEQ ID NO 551
<211> LENGTH: 276
<212> TYPE: DNA
<213> ORGANISM: Glycine max
<220> FEATURE:
<221> NAME/KEY: unsure
<222> LOCATION: (1)...(276)
<223> OTHER INFORMATION: unsure at all n locations

<400> SEQUENCE: 551

```
ctcaggcact gagccttaca ttgttgccca caatttgata ttntcgcatg cagcagctgt      60
tcaaagatac cgagcgaagt accaagaaaa gcaaaaggga aggattggga tcctcttgga     120
ttttgtttgg tatgagcctc ttacaagatc aaaggctgac aattttgcag ctcaaagagc     180
cagagacttt catattggat ggttcattca tcccccttgtt tatggagagt atccaaaaac     240
cattcaaaat attgttggga atagactccc caaatt                              276
```

<210> SEQ ID NO 552
<211> LENGTH: 251
<212> TYPE: DNA
<213> ORGANISM: Glycine max
<220> FEATURE:
<221> NAME/KEY: unsure
<222> LOCATION: (1)...(251)
<223> OTHER INFORMATION: unsure at all n locations

<400> SEQUENCE: 552

```
gtttaacgaa cctcgtgtgg tggctgctct tggctatgat aatggtttct ttgcccctgg      60
aagatgctca aagantatg ggaattgtac tgctggcaac tcaggcactg agccttacat     120
tgttgcccac aatttgatat tgtcgcatgc agcagctgtt caaagatacc gagcgaagta     180
ccaaganaag caaagggaa ggattgggat cctctgtaaa tttgtttggt atgagcctct     240
tacaagatca a                                                         251
```

<210> SEQ ID NO 553
<211> LENGTH: 261
<212> TYPE: DNA
<213> ORGANISM: Glycine max
<220> FEATURE:
<221> NAME/KEY: unsure
<222> LOCATION: (1)...(261)
<223> OTHER INFORMATION: unsure at all n locations

<400> SEQUENCE: 553

```
acggattatt gngtcgccaa gttgtgaaag attttgcaga ttatgcagaa ttttgtttca      60
agacttttgg agatagagtt aagaattgga tgacgtttaa cgaacctcgt gtggtggctg    120
ctcttggcta tgataatggt ttctttgccc ctggaagatg ctcaaaagaa tatgggaatt    180
gtactgctgg caactcaggc actgagcctt acattgttgc ccacaattga tattgtcgca    240
tgcagcagct gttcaaagat a                                              261
```

```
<210> SEQ ID NO 554
<211> LENGTH: 259
<212> TYPE: DNA
<213> ORGANISM: Glycine max
<220> FEATURE:
<221> NAME/KEY: unsure
<222> LOCATION: (1)...(259)
<223> OTHER INFORMATION: unsure at all n locations

<400> SEQUENCE: 554
```

```
cgaaaagcaa aagggaagga ttggnatcct cttggatttt ntttggtatg agcctcttac     60
aagatcaaag gctgacaatt tgcagctcc aaagagccca gagactttca tattggatgg    120
ttcattcatc cccttgttta tggagagtat ccaaaaacca ttcaaaatat tgttgggaat    180
agactcccca aattcactag tgaagaagtt aaaatcgtga agggttcgat tgattttgtt    240
ggaatcaacc agtatacta                                                 259
```

```
<210> SEQ ID NO 555
<211> LENGTH: 232
<212> TYPE: DNA
<213> ORGANISM: Glycine max

<400> SEQUENCE: 555
```

```
gagagaagta tcaagaaaag caaaagggaa ggattgggat cctcttggat tttgtttggt     60
atgagcctct tacaagatca aaggccgaca atttagcagc tcaaagagcc agagactttc    120
atgttggatg gttcattcat ccccttgttt atggagagta ccaacaacc attcaaaata    180 ttgttgggaa tagactcccc aaattcacta gtgaagaagt taaaatcgtg ag            232
```

```
<210> SEQ ID NO 556
<211> LENGTH: 265
<212> TYPE: DNA
<213> ORGANISM: Glycine max
<220> FEATURE:
<221> NAME/KEY: unsure
<222> LOCATION: (1)...(265)
<223> OTHER INFORMATION: unsure at all n locations

<400> SEQUENCE: 556
```

```
tttaacgaac ctcgtgtggt ggctgctctt ggctatgata atggtttctt tgcccctgga     60
agatgctcaa angaatatgg gaattgtact gctggcaact caggcactga gccttacatt    120
gttgcccaca atttgatatt gtccatgcag cagctgttca aagataccga gcgaagtacc    180
aagaaaagca aagggaagg attgggatcc tcttggattt gtttggtatg agcctcttac    240
aagatcaaag gctgacaatt tgcag                                          265
```

```
<210> SEQ ID NO 557
<211> LENGTH: 256
<212> TYPE: DNA
<213> ORGANISM: Glycine max

<400> SEQUENCE: 557
```

```
tagagttaag aattggatga cgtttaacga acctcgtgtg gtggctgctc ttggctatga    60
taatggtttc tttgcccctg aagatgctc aaaagaatat gggaattgta ctgctggcaa   120
ctcaggcact gagccttaca ttgttgccca caatttgata ttgtcgcatg cagcagctgt   180
tcaaagatac cgagcgaagt accaagaaaa gcaaagggaa ggattggga tcctcttgga    240 ttttgtttgg tatgag                                                  256
```

<210> SEQ ID NO 558
<211> LENGTH: 443
<212> TYPE: DNA
<213> ORGANISM: Glycine max
<220> FEATURE:
<221> NAME/KEY: unsure
<222> LOCATION: (1)...(443)
<223> OTHER INFORMATION: unsure at all n locations

<400> SEQUENCE: 558

```
aagacgacag aagggggact ggaatgcagg atttgcttat gcaaagaatg gagtgcctat    60
tggtcctaga gctaattctt attggcttta caatgtacca tggggcatgt acaaatcatt   120
gatatacata aaggaacgtt atggaaaccc aactgttatc ttatctgaaa atggcatgga   180
tgatccgggt aatgtgactc ttcccaaggg tttgcatgac accacaagga taaactatta   240
caaaggctat ttgactcaac taaagaaagc agttgatgat ggagcanatg tggttgggta   300
ctttgcatgg tcattgctgg ataactttga atggaggttg ggttacacat caaggtttgg   360
cattgtctat gttgatttca aaccccctca aganataccc naaagatntn tgggaannng   420
gggtncancc aatgncntta cca                                           443
```

<210> SEQ ID NO 559
<211> LENGTH: 397
<212> TYPE: DNA
<213> ORGANISM: Glycine max

<400> SEQUENCE: 559

```
aagacgacag aagggtatga tcctcatcaa tcaaaaccta agtcccagg ctatcaaatg     60 gactggaatg caggatttgc ttatgcaaag aatggagtgc ctattggtcc tagagctaat   120
tcttattggc tttacaatgt accatggggc atgtacaaat cattgatata cataaaggaa   180
cgttatggaa acccaactgt tatcttatct gaaaatggca tggatgatcc gggtaatgtg   240
actcttccca agggtttgca tgacaccaca aggataaact attacaaagg ctatttgact   300
caactaaaga aagcagttga tgatggagca atgtggttg ggtactttgc atggtcattg    360
ctggataact ttgaatggaa gtttgggtta cacatca                            397
```

<210> SEQ ID NO 560
<211> LENGTH: 505
<212> TYPE: DNA
<213> ORGANISM: Glycine max
<220> FEATURE:
<221> NAME/KEY: unsure
<222> LOCATION: (1)...(505)
<223> OTHER INFORMATION: unsure at all n locations

<400> SEQUENCE: 560

```
ccgaatttcc ggcncgaccc acgcgtccgc ccacgcgtgc gcgctttctt taaccattan    60
gcgtttaaaa tantttctat acngtnnggt aacggggntc tttnggntcg gnttatntga   120
acattgaana tncaaagaac ggagtgccta ttggtccaan ggcttattct tattggntnt   180
acaacgtacc atggggcatg tncaaancat tgatgtacat aaaggaacgt tatggaaacc   240
```

```
caactgagat cttatccgaa aatggcatgg atgatccggg taacgngact cttaccaagg      300
gttttgcaat gacaccacaa ggatnaacta ttacaaaagc tattntgact caactaacga      360
aggcaattna nnattgagct aatgttngtt ggatactttg catcggtcan tgcttggata      420
aacttttgaa tngaannntg ggttaccnnt naanggtttg gcattaggct atgtttgatt      480
tcaaaacctt natnanaacc cctaa                                            505
```

<210> SEQ ID NO 561
<211> LENGTH: 247
<212> TYPE: DNA
<213> ORGANISM: Glycine max

<400> SEQUENCE: 561

```
ggctatcaaa tggactggaa tgcaggattt gcttatgcaa agaatggagt gcctattggt       60
cctagagcta attcttattg gctttacaat gtaccatggg gcatgtacaa atcattgata      120
tacataaagg aacgttatgg aaacccaact gttattttat ctgaaaatgg catggatgat      180
ccgggtaatg tgactcttcc caagggtttg catgacacca caaggataaa ctattacaaa      240
ggctatt                                                                247
```

<210> SEQ ID NO 562
<211> LENGTH: 250
<212> TYPE: DNA
<213> ORGANISM: Glycine max

<400> SEQUENCE: 562

```
aggctatcaa atggactgga atgcaggatt tgcttatgca agaatggag tgcctattgg        60 tcctagagct aattcttatt ggctttacaa tgtaccatgg gcatgtaca aatcattgat       120 atacataaag gaacgttatg gaaacccaac tgttatttta tctgaaaatg catggatga      180 tccgggtaat gtgactcttc ccaagggttt gcatgacacc acaaggataa actattacaa      240
aggctatttg                                                             250
```

<210> SEQ ID NO 563
<211> LENGTH: 451
<212> TYPE: DNA
<213> ORGANISM: Glycine max
<220> FEATURE:
<221> NAME/KEY: unsure
<222> LOCATION: (1)...(451)
<223> OTHER INFORMATION: unsure at all n locations

<400> SEQUENCE: 563

```
cgctttcttt aaccattatt gattaaaata ttttctatac atttccataa ctntctcttt       60
tggtttggtt tatatgaaca ttgaagatgc aaagaacgga gtgcctattg gtccaagggc      120
ttattcttat tggctttaca acgtaccatg gggcatgtac aaatcattga tgtacataaa      180
ggaacgttat ggaaacccaa ctgtgttctt atccgaaaat ggcatggatg atccgggtaa      240
cgtgactctt nccaagggtt tgcatgacac acaaggata aactattaca aaggctattt      300
gactcaacta aagaaggcag ttgatgatgg agctaatgtg gttggatact ttgcatggca      360
ttgntggata actttgaatg ganggtgggt tacacatnaa aggnttggca ttggctatgg      420
tgattcnaaa accctaagag aatnccttag a                                    451
```

<210> SEQ ID NO 564
<211> LENGTH: 394
<212> TYPE: DNA

```
<213> ORGANISM: Glycine max
<220> FEATURE:
<221> NAME/KEY: unsure
<222> LOCATION: (1)...(394)
<223> OTHER INFORMATION: unsure at all n locations

<400> SEQUENCE: 564
ttatatgaac nttgaagatg caaacaacgg aaagcctatt ggtccaaang cttattctta      60
ttngcnttac aacgtaccat ngggcatgtc aaatcattga tgcacataaa ngaacnntat    120
ggaaacccaa ctgcgttctt atcccaaaat ggcatggatn atcccgntaa ccntnactnt    180
tcccaanggt ttgcatnaca ccacaaggat naactattan naaagctatt tgactcaact    240
aaanaaagca nttgatgatn gancntaatg nngttngaaa cctttncatg gncanttgnc    300
tgganaactt taaanngagn ttgggttccc catcaagntt tggcaattnn ccatttntta    360
atttnaaaan cccttnanaa naaanccctt aaaa                                394

<210> SEQ ID NO 565
<211> LENGTH: 232
<212> TYPE: DNA
<213> ORGANISM: Glycine max

<400> SEQUENCE: 565
aatcaaccaa tatactacgt actacatgta tgatcctcat caagcaaaac ctaaagtccc     60
aggctatcaa atggactgga atgcaggatt tgcttatgca agaacggag tgcctattgg    120
tccaagggct tattcttatt ggctttacaa cgtaccatgg gcatgtaca aatcattgat    180
gtacataaag gaacgttatg gaaacccaac tgtgttctta tccgaaaatg gc           232

<210> SEQ ID NO 566
<211> LENGTH: 267
<212> TYPE: DNA
<213> ORGANISM: Glycine max
<220> FEATURE:
<221> NAME/KEY: unsure
<222> LOCATION: (1)...(267)
<223> OTHER INFORMATION: unsure at all n locations

<400> SEQUENCE: 566
aaccattcaa aatattgttg ggantagact ccccaaattc actagtgaag nagttaaaat     60
cgtgaagggt tcgattgatt tgttggaat caaccagtat actacgttct tcatttatga    120
tcctcatcaa tcaaaaccta agtcccagg ctatcaaatg gactggaatg caggatttgc    180
ttatgcanag aatggagtgc ctattggtcc tagagctaat tcttattggc tttacaatgt    240
accatggggc atgtacaaat cattgat                                        267

<210> SEQ ID NO 567
<211> LENGTH: 257
<212> TYPE: DNA
<213> ORGANISM: Glycine max
<220> FEATURE:
<221> NAME/KEY: unsure
<222> LOCATION: (1)...(257)
<223> OTHER INFORMATION: unsure at all n locations

<400> SEQUENCE: 567
gggaatagac tccccaaatt cactagtgaa gaagttaaaa tcgtgaaggg ttcgattgat     60
tttgttggaa tcaaccagta tactacgttc tntcatttat gatcctcatc aatcaaaacc    120
taaagtccca ggctatcaaa tggactggaa tgcaggattt gcttatgcaa gaatggagt    180
gcctantggt cctagagcta attcttattg gctttacaat gtaccatggg gcatgtacaa    240
```

```
atcattgnta tncataa                                              257

<210> SEQ ID NO 568
<211> LENGTH: 281
<212> TYPE: DNA
<213> ORGANISM: Glycine max

<400> SEQUENCE: 568
gaagaagtta aaatcgtgaa gggttcaata gattttgttg gaatcaacca atatactacg    60
tactacatgt atgatcctca tcaagcaaaa cctaaagtcc caggctatca aatggactgg   120
aatgcaggat ttgcttatgc aaagaacgga gtgcctattg gtccaagggc ttattcttat   180
tggctttaca acgtaccatg gggcatgtac aaatcattga tgtacataaa ggaacgttat   240
ggaaacccaa ctgtgttctt atccgaaaat ggcatggatg a                      281

<210> SEQ ID NO 569
<211> LENGTH: 145
<212> TYPE: DNA
<213> ORGANISM: Glycine max

<400> SEQUENCE: 569
caaagaacgg agtgcctatt ggtccaaggg cttattctta ttggctttac aacgtaccat    60
ggggcatgta caaatcattg atgtacataa aggaacgtta tggaaaccca actgtgttct   120
tatccgaaaa tggcatggat gatcc                                        145

<210> SEQ ID NO 570
<211> LENGTH: 402
<212> TYPE: DNA
<213> ORGANISM: Glycine max
<220> FEATURE:
<221> NAME/KEY: unsure
<222> LOCATION: (1)...(402)
<223> OTHER INFORMATION: unsure at all n locations

<400> SEQUENCE: 570
aagacgacag aagggcagtg tacattaccg aaaatggcgt tgcggaatca agaatgact     60 cacttgcaat caatgaagcc cgaaaggatg gtattcgaat tagataccat gatggccatc   120
tcaaatccct gcttcatgcg atcaaagata gagttaatgt gaaggctac tatatatggt   180 cattttcang atagctttga atgggatgct ggttacacag ctcgatttgg catcatatat   240
gtggannaca agaacaattt gagtagatac cctaagtcct ctgcgttttg gctgaaaaca   300
atgctgttac tgcgtttgcc aaatcaacat gatctcntat agggtaaann antnngtncn   360
ncannggncn nngnaannag cggggggctc tanaaggatt ca                     402

<210> SEQ ID NO 571
<211> LENGTH: 268
<212> TYPE: DNA
<213> ORGANISM: Glycine max
<220> FEATURE:
<221> NAME/KEY: unsure
<222> LOCATION: (1)...(268)
<223> OTHER INFORMATION: unsure at all n locations

<400> SEQUENCE: 571
gtcaccatag tgactttctt ctttgaacca aaatctaata gtgatgctga tcncaaggca    60
gcaaggcgag ctctggactt tatgtttggc tggtttgcta atcccattac atttggtgac   120
tatcctgaga gtatgagatc tttagttggt tctagactcc ccacattcac caaagctcaa   180
```

```
tctgaaagtc tcaaaggttc atatgatttt cttggtataa attcattaca cctcaaattt    240
cgtggaatat gctccaccaa ccaccatt                                       268

<210> SEQ ID NO 572
<211> LENGTH: 258
<212> TYPE: DNA
<213> ORGANISM: Glycine max

<400> SEQUENCE: 572
gttggtataa attattacac ctcaaatttc gtggaatatg ctccaccaac caccactaac    60
aagacctatt ttcatggata tgctagccaa actttcttcg accaggaatg gtgtacccat    120
tggcacaccg actcctctga gctggctctt tatctatccg agggaattt ataagctcat     180 gacatacata agggacaact acaataatcc accagtgtac attaccgaaa atggcgttgc    240
ggaatcaaag aatgactc                                                  258

<210> SEQ ID NO 573
<211> LENGTH: 185
<212> TYPE: DNA
<213> ORGANISM: Glycine max

<400> SEQUENCE: 573
caccagtgta cattaccgaa aatggcgttg cggaatcaaa gaatgactca cttgcaatca    60
atgaagcccg aaaggatggt attcgaatta gataccatga tgggccatct caaatccctg    120
cttcatgcga tcaaagatag agttaatgtg aagggctact atatatggtc attttcagat    180
agctt                                                                185

<210> SEQ ID NO 574
<211> LENGTH: 163
<212> TYPE: DNA
<213> ORGANISM: Glycine max
<220> FEATURE:
<221> NAME/KEY: unsure
<222> LOCATION: (1)...(163)
<223> OTHER INFORMATION: unsure at all n locations

<400> SEQUENCE: 574
ctaagggaca actacaataa tccaccagtg tacattaccg aaaatggcgt tgcggaatca    60
aagaatgact cacttgcaat caatgaagcc cgaaaggatg gtattcgaat tagataccat    120
gatggccatc tcaaatccct gcttcatgga tcanagatag agt                      163

<210> SEQ ID NO 575
<211> LENGTH: 329
<212> TYPE: DNA
<213> ORGANISM: Glycine max
<220> FEATURE:
<221> NAME/KEY: unsure
<222> LOCATION: (1)...(329)
<223> OTHER INFORMATION: unsure at all n locations

<400> SEQUENCE: 575
agcaatgaaa gcaataagtc cctccttcct ctgccttata attcttgtga ccctttttngc    60 tggtagcatt gaaagtgcac cagcaaacgt gaagccaagc cattatgctg cacccttcaa    120
taggagtgtt tttcttctgg ttttctattt ggaataggct ctgcagctta ccagatagaa    180
ggagcagcag ctatagatgg cagaggacca agtatatggg acacctatac taaacagcaa    240
ccagggaaga tttgggatca tagtgatgga agtctagcaa ttgattttta tcaccggtac    300
aagagcgaca taaagatggt gaaagaagt                                      329
```

<210> SEQ ID NO 576
<211> LENGTH: 290
<212> TYPE: DNA
<213> ORGANISM: Glycine max
<220> FEATURE:
<221> NAME/KEY: unsure
<222> LOCATION: (1)...(290)
<223> OTHER INFORMATION: unsure at all n locations

<400> SEQUENCE: 576

| | | | | | |
|---|---|---|---|---|---|
| gncaataagt | ccctccttcc | nctgccttat | aattnttgtg | acccttttgg | ctggtagcat | 60 |
| tgaaagtgca | ccagcaaacg | tgaagccaag | ccattatgct | gcacccttca | ataggagtgt | 120 |
| ttttccttct | ggttttctat | ttggaatagg | ctctgcagct | taccagatag | aaggagcagc | 180 |
| agctatagat | ggcagaggac | caagtatatg | ggacacctat | actaaacagc | aaccagggaa | 240 |
| gatttgggat | catagtgatg | gaagtctagc | aattgatttt | tatcaccggt | | 290 |

<210> SEQ ID NO 577
<211> LENGTH: 283
<212> TYPE: DNA
<213> ORGANISM: Glycine max
<220> FEATURE:
<221> NAME/KEY: unsure
<222> LOCATION: (1)...(283)
<223> OTHER INFORMATION: unsure at all n locations

<400> SEQUENCE: 577

| | | | | | |
|---|---|---|---|---|---|
| gtccctcctt | cctctgcctt | ataattcttg | tgacccttttt | ngctggtagc | attgaaagtg | 60 |
| caccagcaaa | cgtgaagcca | agccattatg | ctgcacccttt | caataggagt | gttttttcctt | 120 |
| ctggttttct | atttggaata | ggctctgcag | cttaccagat | agaaggagca | gcagctatag | 180 |
| atggcagang | accaagtata | tgggacacct | atactaaaca | gcaaccaggg | aagatttggg | 240 |
| atcatagtga | tggaagtcta | gcaattgatt | nttatcaccg | gta | | 283 |

<210> SEQ ID NO 578
<211> LENGTH: 284
<212> TYPE: DNA
<213> ORGANISM: Glycine max
<220> FEATURE:
<221> NAME/KEY: unsure
<222> LOCATION: (1)...(284)
<223> OTHER INFORMATION: unsure at all n locations

<400> SEQUENCE: 578

| | | | | | |
|---|---|---|---|---|---|
| gcaatgaaag | caataagtcc | ctccttcctc | tgccttataa | ttcttgtgac | cctttttngct | 60 |
| ggtagcattg | aaagtgcacc | agcaaacgtg | aagccaagcc | attatgctgc | acccttcaat | 120 |
| aggagtgttt | ttccttctgg | ttttctattt | ggataggct | ctgcagctta | ccagatagaa | 180 |
| ggagcagcag | ctatagatgg | cagaggacca | agtatatggg | acacctatac | taaacagcaa | 240 |
| ccagggaaga | ttgggatcat | agtgatggaa | gtctagcatt | gttt | | 284 |

<210> SEQ ID NO 579
<211> LENGTH: 264
<212> TYPE: DNA
<213> ORGANISM: Glycine max
<220> FEATURE:
<221> NAME/KEY: unsure
<222> LOCATION: (1)...(264)
<223> OTHER INFORMATION: unsure at all n locations

<400> SEQUENCE: 579

```
gtccctcctt cctctgcctt ataattcttg tgacccttt  ggctggtagc attgaaagtg      60
caccagcaaa cgtgaagcca agccattatg ctgcacccct caataggagt gttttcctt      120 ctggttttct atttggaata ggctctgcag cttaccagat agaaggagca gcagctatag     180
atggcagagg accaagtata tgggacacct atactnnnnc agcaaccagg gaagntttgg     240
gatcatagat ggaagtctag caat                                             264

<210> SEQ ID NO 580
<211> LENGTH: 226
<212> TYPE: DNA
<213> ORGANISM: Glycine max
<220> FEATURE:
<221> NAME/KEY: unsure
<222> LOCATION: (1)...(226)
<223> OTHER INFORMATION: unsure at all n locations

<400> SEQUENCE: 580
gtccctcctt cctctgcctt ataattcttg tgaccctttt ngctggtagc attgaaagtg      60
caccagcaaa cgtgaagcca agccattatg ctgcacccct caataggagt gttttcctt     120 ctggttttct atttggaata ggctctgcag cttaccagat agaaggagca gcagctatag    180
atggcagagg accaagtata tgggacacct atactaaaca gcaacc                   226

<210> SEQ ID NO 581
<211> LENGTH: 258
<212> TYPE: DNA
<213> ORGANISM: Glycine max
<220> FEATURE:
<221> NAME/KEY: unsure
<222> LOCATION: (1)...(258)
<223> OTHER INFORMATION: unsure at all n locations

<400> SEQUENCE: 581
gcaatgaaag caataagtcc ctccttcctc tgccttataa ttcttgtgac ccttttngct      60
ggtagcattg aaagtgcacc agcaaacgtg aagccaagcc attatgctgc acccttcaat    120
aggagtgttt ttccttctgg ttttctattt ggaataggct ctgcagctta ccagatagaa    180
ggagcagcag ctatagatgg cagaggacca ngtntatggg acacctatac taaaacagca    240
accagggaag atttggga                                                   258

<210> SEQ ID NO 582
<211> LENGTH: 255
<212> TYPE: DNA
<213> ORGANISM: Glycine max
<220> FEATURE:
<221> NAME/KEY: unsure
<222> LOCATION: (1)...(255)
<223> OTHER INFORMATION: unsure at all n locations

<400> SEQUENCE: 582
ataagtccct ccttcctctg ccttataatt cttgtgaccc ttttngctgg tagcattgaa      60
agtgcaccag caaacgtgaa gccaagccat tatgctgcac ccttcaatag gagtgttttt    120
ccttctggtt ttctatttgg aataggctct gcagcttacc agatagaagg agcagcagct    180
atagatggca gaggaccaag tatatgggac actatactaa acagcaacca gggaagattt    240
gggatcatag tgatg                                                      255

<210> SEQ ID NO 583
<211> LENGTH: 266
<212> TYPE: DNA
<213> ORGANISM: Glycine max
```

```
<220> FEATURE:
<221> NAME/KEY: unsure
<222> LOCATION: (1)...(266)
<223> OTHER INFORMATION: unsure at all n locations

<400> SEQUENCE: 583
atgaaagcna taagtccctc cttcctctgc cttataattc ttgtgaccct tttngctggt        60
agcattgaaa gtgcaccagc aaacgtgaag ccaagccatt atgctgcacc cttcaatagg       120 agtgttttc cttctgtttt ctatttggaa taggctctgc agcttaccag atagaaggag        180
cngcagctat agatggcaga ggaccaagta tatgggacac ctatactaaa cagcaaccag       240
ggaagatttg ggatcatagt gatgga                                           266

<210> SEQ ID NO 584
<211> LENGTH: 275
<212> TYPE: DNA
<213> ORGANISM: Glycine max
<220> FEATURE:
<221> NAME/KEY: unsure
<222> LOCATION: (1)...(275)
<223> OTHER INFORMATION: unsure at all n locations

<400> SEQUENCE: 584
taagtctntc cttcctctgc cttatanttc ttgtgancct tttngtaggt agcattgaaa        60
gtgcaccagc aaacgtgaag ccaagccatt atgctgcacc cttcaatagg agtgttttc       120 cttctggttt tctatntggn ntaggctctg cagcttacca gatagaaggn gcagcagcta       180
tagatggcag angaccaagt atntgggaca ccgatactna acagnaacag ggncnattgg       240
gatcatngtg atggagncna gncaattgat tntnt                                 275

<210> SEQ ID NO 585
<211> LENGTH: 223
<212> TYPE: DNA
<213> ORGANISM: Glycine max
<220> FEATURE:
<221> NAME/KEY: unsure
<222> LOCATION: (1)...(223)
<223> OTHER INFORMATION: unsure at all n locations

<400> SEQUENCE: 585
gtccctcctt cctctgcctt ataattcttg tannccstant ngctggtagc attgaaagtg       60
caccangcaa acgtgaagcc aagccattat gctgcaccct tcaataggag tgttttcct       120 tctggttttc tatttggaat aggctctgca gcttaccaga tagaaggagc agcagctata       180
gatggcagag gnccaagtat atgggacacc ttatactaaa cag                         223

<210> SEQ ID NO 586
<211> LENGTH: 239
<212> TYPE: DNA
<213> ORGANISM: Glycine max
<220> FEATURE:
<221> NAME/KEY: unsure
<222> LOCATION: (1)...(239)
<223> OTHER INFORMATION: unsure at all n locations

<400> SEQUENCE: 586
gcaatgaaag caataagtcc ctccttcctc tgccttataa ttcttgtgac ccttttttngct      60 ggtagcattg aaagtgcacc agcaaacgtg aagccaagcc attatgctgc acccttcaat      120
aggagtgttt ttcctctggt tttctatttg gaataggctc tgcagcttac cagatagaag      180
gagcagcagc tatagatggc agagggacca agtatatggg acacctatac taaacagca       239
```

```
<210> SEQ ID NO 587
<211> LENGTH: 279
<212> TYPE: DNA
<213> ORGANISM: Glycine max
<220> FEATURE:
<221> NAME/KEY: unsure
<222> LOCATION: (1)...(279)
<223> OTHER INFORMATION: unsure at all n locations

<400> SEQUENCE: 587
atcctaaaaa catgcgagcn ctggtgggaa gtagattgcc taagttcacc aaatggcaag      60
ccaagctagt gaatgcatca tttgatttta ttggcttaaa ctattactcc tctggttata    120
ttaatggtgt ccctccaagc aacgacaaac ccaatttcct aacagattct cgcaccaaca    180
cttcatttga acgcaatgga agaccccctag gtctaagggc cgcttcagtt tggatatact    240
tttatccaag gggacttcta gatcttctgt tatatacca                            279

<210> SEQ ID NO 588
<211> LENGTH: 258
<212> TYPE: DNA
<213> ORGANISM: Glycine max

<400> SEQUENCE: 588
ctaaaaacat gcgagccctg gtgggaagta gattgcctaa gttcaccaaa tggcaagcca      60
agctagtgaa tggatcattt gattttattg gcttaaacta ttactcctct ggttatatta    120
atggtgtccc tccaagcaac gacaaaccca atttctaac agattctcgc accaacactt    180
catttgaacg caatggaaga cccctaggtc taagggccgc ttcagtttgg atatacttttt   240 atccaagggg acttctag                                                  258

<210> SEQ ID NO 589
<211> LENGTH: 278
<212> TYPE: DNA
<213> ORGANISM: Glycine max
<220> FEATURE:
<221> NAME/KEY: unsure
<222> LOCATION: (1)...(278)
<223> OTHER INFORMATION: unsure at all n locations

<400> SEQUENCE: 589
gnntgggaac cattaacaaa aggagagtat cctaaaaaca tgcgagccct ggtgggaagt      60
agattgccta agttcaccaa atgggcaagc cnagctagtg aatggatcat ttgattttat    120
tggcttaaac tattactcct ctggttatat taatggtgtc cctccaagca acgacaaacc    180
caatttccta acagattctc gcaccaacac ttcatttgaa cgcnatggaa gaccccctagg   240 tctaagggcc gcttcagttt ggatatactt ttatccaa                             278

<210> SEQ ID NO 590
<211> LENGTH: 266
<212> TYPE: DNA
<213> ORGANISM: Glycine max
<220> FEATURE:
<221> NAME/KEY: unsure
<222> LOCATION: (1)...(266)
<223> OTHER INFORMATION: unsure at all n locations

<400> SEQUENCE: 590
ataatatggc atttaaaggc tatttcgttt tggggcctca tagctcttgt tgtcgttggc      60
acttccaaag ttcatgcgca aatagaagca gataaagttt cacctattat tgactttcc    120 ctcaatcgga acagtttccc tgaaggcttc atctttgggg cggcatcatn cctcctacca    180
```

-continued

```
gttcgaaggt gcagcanagg aaggtggtag aggaccaagt gtatgggata cttcacccat    240
aaatntccag ataagatcaa ggatgg                                        266
```

<210> SEQ ID NO 591
<211> LENGTH: 281
<212> TYPE: DNA
<213> ORGANISM: Glycine max

<400> SEQUENCE: 591

```
gatccttgaa tagatcacat aacatgggca tcattgggca tgcaacacgt ttattgttag    60
cagcacgtta agatcagttg ttactcgtgc ggaaccacct aaacctggtc ctcttttcga   120
tcttagttca ttcaatcgcc acagctttcc ggcaggcttc actttcgggg catcatcttc   180
cgcgtaccag tttgaaggtg cggcaaaaga atatggtaga ggaccaagta tatgggatac   240
tttcatcaat caacatccag taagatagca gatggaacga a                      281
```

<210> SEQ ID NO 592
<211> LENGTH: 429
<212> TYPE: DNA
<213> ORGANISM: Glycine max
<220> FEATURE:
<221> NAME/KEY: unsure
<222> LOCATION: (1)...(429)
<223> OTHER INFORMATION: unsure at all n locations

<400> SEQUENCE: 592

```
ccangattan tgccattttg tgggttggtt atcccgggca agctggggga actgccattg    60
ctgatgtant cnttggtaca actaacccag gangaaggtt acccatgaca tggtacccac   120
aaggttactt ggccaaagtg cccatgacaa acatggacat gcgtccaaac ccaacaacan   180
ggtacccaag aagaacctat agattctaca aangtcctgt antgttccca ttcggacatg   240
gcctaagtta ctcaanattc anccacagct tancacttgc ccccaaacag gtctcagtgc   300
ccataatgag cctccaagcc ttgacaaact caaccctctc aagcaaagca nttaangtga   360
gccatgccaa ttctgatgac tcattggaga tgganttcca cgttgatgtn aaaaaccaan   420
gctcaatgg                                                          429
```

<210> SEQ ID NO 593
<211> LENGTH: 281
<212> TYPE: DNA
<213> ORGANISM: Glycine max
<220> FEATURE:
<221> NAME/KEY: unsure
<222> LOCATION: (1)...(281)
<223> OTHER INFORMATION: unsure at all n locations

<400> SEQUENCE: 593

```
caaaatacat cataagatat ggcattcgac gcttatttcc ttttgggcct catagctctt    60
gttcttgtta gcacttccaa agttacatgc gncntagaag cagatacagt ttcacctgtt   120
attgacattt cactcaaccg gaacagnttc cagaagggtt catctttggg gcgggatctt   180
cctcgtacca gttcgaaggt gcagcaaatg atggtggtag aggaccaagc gtatgggata   240
ccttcaccca taattatcct ggtaagatca ttgatagaac a                      281
```

<210> SEQ ID NO 594
<211> LENGTH: 271
<212> TYPE: DNA
<213> ORGANISM: Glycine max
<220> FEATURE:

<221> NAME/KEY: unsure
<222> LOCATION: (1)...(271)
<223> OTHER INFORMATION: unsure at all n locations

<400> SEQUENCE: 594

```
taagatatgg cattcgacgc ttatttcctt ttgggcctca tagctcttgt tcttgttagc      60
acttccaaag ttanatgcgn antagaagca gatacagttt cacctgttat tgacatttca     120
ctcaaccgga acagnttcca gaagggttca tctttggggc gggatcttcc tcgtaccagt    180
tcgaaggtgc agcaaatgat ggtggtagag gaccaagcgt atgggatacc ttcacccata    240
attatcctgg taagatcatt gatagaagca a                                    271
```

<210> SEQ ID NO 595
<211> LENGTH: 253
<212> TYPE: DNA
<213> ORGANISM: Glycine max
<220> FEATURE:
<221> NAME/KEY: unsure
<222> LOCATION: (1)...(253)
<223> OTHER INFORMATION: unsure at all n locations

<400> SEQUENCE: 595

```
aaaaacatat cacacaatat ggcattcaag ggctatttcc ttctcggcct cgttactctt      60
gttcttgtta atcttccaa agttacatgc gaancnagaa tcggttaata cagtttcacc      120
cattattgac atttcactca atcggaagag nttcccagaa gggttcatat ttggggcggg     180
atcttcctcg taccagttcg aaggggcagc aaaggaaggt ggtagaggac caagtgtatg     240
ggataccttc acc                                                        253
```

<210> SEQ ID NO 596
<211> LENGTH: 284
<212> TYPE: DNA
<213> ORGANISM: Glycine max
<220> FEATURE:
<221> NAME/KEY: unsure
<222> LOCATION: (1)...(284)
<223> OTHER INFORMATION: unsure at all n locations

<400> SEQUENCE: 596

```
gaaaaacata tcacacaata tggnattcaa gggntatttc cttctgcggc ntcgttactc      60
ttgttcttng ntaaatcttc caaagttaca tgccgaancc gaatcagtta atacagtttc    120
acccattatt gacatttgca ctcaatcgga agagnnttcc cagaagggtt catatttggg    180
gcgggatctt ccgcgtacca gttcgaaggg gcagcaaagg aaggtggtag aggaccaagt    240
gtatgggata ccttgcaccc ataattatcc aggaaagatc atgg                     284
```

<210> SEQ ID NO 597
<211> LENGTH: 378
<212> TYPE: DNA
<213> ORGANISM: Glycine max

<400> SEQUENCE: 597

```
gtaagaaagg aaaatcatcc actgagccat acattgttgc tcataacatt ctcttgtcac      60
atgctgctgc ctatagaagc taccaactac atttcaagga acaacaagga ggtcaaatag    120
gaatagcact agatgtcatt tggtatgaac ctataacaga acttgatgaa gacaaagacg    180
cagcagcaag agctatggac ttttcacttg gatggttcct tgacccactt ttctttggaa    240
aatatcctct ctcaatggag aaacttgtag ctaagagatt gccggagatt tctgatacag    300
cctcaaaatt tcttgtggga tctttggatt ttattggcat aaatcactac acctcagtct    360
```

```
atactcgtaa cgacagga                                                 378

<210> SEQ ID NO 598
<211> LENGTH: 251
<212> TYPE: DNA
<213> ORGANISM: Glycine max

<400> SEQUENCE: 598
accaactaca tttcaaggaa caacaaggag gtcaaatagg aatagcacta gatgtcattt    60
ggtatgaacc tataacagaa cttgatgaag acaaagacgc agcagcaaga gctatggact   120
tttcacttgg atggttcctt gacccacttt tctttggaaa atatcctctc tcaatggaga   180
aacttgtagc taagagattg ccggagattt ctgatacagc ctcaaaattt cttgtgggat   240
ctttggattt t                                                        251

<210> SEQ ID NO 599
<211> LENGTH: 252
<212> TYPE: DNA
<213> ORGANISM: Glycine max

<400> SEQUENCE: 599
tatcatcggt acatggaaga tattgatctt atagccaagt tgggatttga tgcttataga    60
ttttcaattt cttggtctcg gattttcccc gatggcttag gaacgaaaat caatgacgaa   120
gggataactt tttataacaa cattattaat ggtcttcttg aaagaggtat acaaccttat   180
gtaactttgt accattggga tcttccgctg catcttcacg agtcgatggg aggatggtta   240
aataaacaaa tc                                                       252

<210> SEQ ID NO 600
<211> LENGTH: 418
<212> TYPE: DNA
<213> ORGANISM: Glycine max
<220> FEATURE:
<221> NAME/KEY: unsure
<222> LOCATION: (1)...(418)
<223> OTHER INFORMATION: unsure at all n locations

<400> SEQUENCE: 600
agaacactcc attgttgaca ttgagaagag aagagaagcn ggagaatgca atgggggctt    60
tgtacatgtc agttatggag atactcttgt tcctcttcat attcatatgc tctctcacac   120
caatctcaca gtcacaggga ttacatcaat ctccccettt tctctttggc acttcttctt   180
cttcgtacca gtatgaagga gcttatttga gtgatggcaa agggataagc aactgggatg   240
tcttcactca caaaccaggt agtatatctg acgaaagcaa cggtgatgtt gctgttgatc   300
aataccaccg gtatctggag gatattgatc taatggaagc tataaaaggt caatagctac   360
cggttttcaa tatcatgggc aagaattcta ccaaaaggaa gatttggaga agtaaact    418

<210> SEQ ID NO 601
<211> LENGTH: 278
<212> TYPE: DNA
<213> ORGANISM: Glycine max

<400> SEQUENCE: 601
ttcatatgct ctctcacacc aatctcacag tcacagggat tacatcaatc tccccctttt    60
ctctttggca cttcttcttc ttcgtaccag tatgaaggag cttatttgag tgatggcaaa   120
gggataagca actgggatgt cttcactcac aaaccaggta gtatatctga cgaaagcaac   180
```

```
ggtgatgttg ctgttgatca ataccaccgg tatctggagg atattgatct aatggaagct    240
ataaaagtca atagctaccg gttttcaata tcatgggc                            278

<210> SEQ ID NO 602
<211> LENGTH: 426
<212> TYPE: DNA
<213> ORGANISM: Glycine max
<220> FEATURE:
<221> NAME/KEY: unsure
<222> LOCATION: (1)...(426)
<223> OTHER INFORMATION: unsure at all n locations

<400> SEQUENCE: 602
aaacgacaga aggggatcga agcaaaaaat gaaaacccaa agtgcttctc tcctctgtct     60 tttctctct cttgctatcc ttttggctag tggcactgct gcaagtgcaa ctccaagaag    120
cgcagtgcca agccaccatg tttcaacatt caacagaagc ctttttcctt ccacttttct    180
ctttggaatt ggttcttctg cttaccaggc agaaggagca gcaagtgtag atgggagagg    240
accaagcata tggacacct acactagaca gcatactgaa aagatttggg atcatagcac    300
cggtgacatg ggaactgant tttatcatcc atacaagggg tgacataaaa attagcgaaa    360
gaaanttggg ctggactcct tcanattccc caactcaang gtcaagaata ttcccaaaag    420
ggcaag                                                              426

<210> SEQ ID NO 603
<211> LENGTH: 425
<212> TYPE: DNA
<213> ORGANISM: Glycine max
<220> FEATURE:
<221> NAME/KEY: unsure
<222> LOCATION: (1)...(425)
<223> OTHER INFORMATION: unsure at all n locations

<400> SEQUENCE: 603
aagacgacag aagggatcg aagcaaaaaa tgaaaaccca agtgcttct ctcctctgtc      60 ttttctctc tcttgctatc cttttggcta gtggcactgc tgcaagtgca actccaagaa    120
gcgcagtgcc aagccaccat gtttcaacat tcaacagaag ccttttcct tccactttc     180 tctttggaat tggttcttct gcttaccagg cagaaggagc agcaagtgta ggtgggagag    240
gaccaagcat atgggacacc ggacacnagg acagcatact gaaaagattt gggatcatag    300
caccggtgac atgggaagtg aatttttaagc anccgagnca anggttacat nanaattgcg    360
aaaggnantt gggccgggac cctttnanat tccnnaagnt caggggggcaa gaatatgccg    420 aaagg                                                               425

<210> SEQ ID NO 604
<211> LENGTH: 270
<212> TYPE: DNA
<213> ORGANISM: Glycine max
<220> FEATURE:
<221> NAME/KEY: unsure
<222> LOCATION: (1)...(270)
<223> OTHER INFORMATION: unsure at all n locations

<400> SEQUENCE: 604
gcggattttc gtggctacgc aaacttctgc ttcaagacct ttggagacag agtcaaatat     60
tgggtcactt tgaatgaacc cttatcattt agtctcaatg ctacaatgg tggcaccttt    120 ggcaccaggt agatgttcaa atacgttgcc aattgtagtg ctggcgattc atccactgaa    180
ccctatatcg ttggacacta cttattactt gcncatgaat ctgctgccac attatacaag    240
```

```
acaaatatca ggctcgtcaa aaaggacaat                                    270
```

<210> SEQ ID NO 605
<211> LENGTH: 338
<212> TYPE: DNA
<213> ORGANISM: Glycine max
<220> FEATURE:
<221> NAME/KEY: unsure
<222> LOCATION: (1)...(338)
<223> OTHER INFORMATION: unsure at all n locations

<400> SEQUENCE: 605

```
tgaaaaccca aagtgcttct ctcctctgtc tttttctctc tcttgctatc cttttggcta    60
gtncgcactg ctgcaagtgc aactccaaga agcgcagtgc caagccacca tgtttcaaca   120
ttcaacagaa gccttttttcc ttccactttt tctctttggaa ttggttcttc tgcttaccag  180
gcagaaggag cagcaagtgt agatgggaga ggaccaagca tatgggacac ctacactaga   240
cagcatactg aaaagatttg ggatcatagc accggtgaca tgggagctga tttttatcat   300
cgatacaagg gtgacataaa aatagcgaaa gaaattgg                            338
```

<210> SEQ ID NO 606
<211> LENGTH: 324
<212> TYPE: DNA
<213> ORGANISM: Glycine max
<220> FEATURE:
<221> NAME/KEY: unsure
<222> LOCATION: (1)...(324)
<223> OTHER INFORMATION: unsure at all n locations

<400> SEQUENCE: 606

```
aaaaatgana acccaaagtg cttctctcct ctgtcttttt ctctctcttg ctatcctttt    60
ggctagtnng cactgctgca agtgcaatcc aagaagcgca gtgccaagcc accatgtttc   120
aacattcaac agaagccttt ttccttccac tttttctcttt ggaattggtt cttctgctta  180
ccaggcagaa ggagcagcaa gtgtagatgg gagaggacca agcatatggg acacctacac   240
tagacagcat actgaaaaga tttgggatca tagcaccggt gacatgggag ctgattttat  300
catcgataca agggtgacat aaaa                                          324
```

<210> SEQ ID NO 607
<211> LENGTH: 243
<212> TYPE: DNA
<213> ORGANISM: Glycine max
<220> FEATURE:
<221> NAME/KEY: unsure
<222> LOCATION: (1)...(243)
<223> OTHER INFORMATION: unsure at all n locations

<400> SEQUENCE: 607

```
caccggtgac atgggagctg attttatca tcgatacaag ggtgacataa aaatagcgaa    60
agaaattngg gctgtactct ttcagattct nctatctcat ggtcaagaat attcccaaag   120
ggcaagggag cagttaaccc ccttgggggtt aaattctaca acaatgtcat cgatgagatc  180
ctagcaaatg gtttaaaacc ttttgtcact cttttttcatt gggactttcc acaagctctt  240
gaa                                                                 243
```

<210> SEQ ID NO 608
<211> LENGTH: 300
<212> TYPE: DNA
<213> ORGANISM: Glycine max
<220> FEATURE:

```
<221> NAME/KEY: unsure
<222> LOCATION: (1)...(300)
<223> OTHER INFORMATION: unsure at all n locations

<400> SEQUENCE: 608
gatagcaaga gagaganaaa gacagaggag agangcactg ctgcaagtgc aactccaaga      60
agcgcagtgc caagccacca tgtttcaaca ttcaacagaa gccttttcc ttccactttt      120 ctctttggan ttggttcttc tgcttaccag gcagaaggag cagcaagtgt agatgggaga    180
ggaccaagca tatgggacac ctacactaga cagcatactg aaaagatttg ggatcatagc    240
accggtgaca tggagctga tttttatcat cgatacaagg gtgataaaaa tagcgaaaga    300

<210> SEQ ID NO 609
<211> LENGTH: 253
<212> TYPE: DNA
<213> ORGANISM: Glycine max
<220> FEATURE:
<221> NAME/KEY: unsure
<222> LOCATION: (1)...(253)
<223> OTHER INFORMATION: unsure at all n locations

<400> SEQUENCE: 609
gnggcactgc tgcaagtgca actccaagaa gcgcagtgcc aagccaccat gtttcaacat     60
tcaacagaag ccttttcct tccacttttc tctttggaat tggttcttct gcttaccagg    120
cagaaggagc agcaagtgta gatgggagag gaccaagcat atgggacacc tacactagac   180
agcatactga aaagatttgg gatcatagca ccggtgacat gggagctgat ttttatcatc    240
gatacaaggg tga                                                         253

<210> SEQ ID NO 610
<211> LENGTH: 291
<212> TYPE: DNA
<213> ORGANISM: Glycine max

<400> SEQUENCE: 610
caaaatgaaa acccaaagtg cttctctcct ctgtcttttt ctctctcttg ctatcctttt     60
ggctagtcgc actgctgcaa gtgcaactcc aagaagcgca gtgccaagcc accatgtttc   120
aacattcaac agaagccttt ttccttccac ttttctcttt ggacttggtt cttctgctta    180
ccaggcagaa ggagcagcaa gtgtagatgg gagaggacca agcatatggg acacctacac   240
tagacagcat actgaaaaga tttgggatca tagcaccggt gacatgggag c              291

<210> SEQ ID NO 611
<211> LENGTH: 286
<212> TYPE: DNA
<213> ORGANISM: Glycine max
<220> FEATURE:
<221> NAME/KEY: unsure
<222> LOCATION: (1)...(286)
<223> OTHER INFORMATION: unsure at all n locations

<400> SEQUENCE: 611
ccaaagtgct tctctcctct gtctttttct ctctcttgct atccttttgg ctagtngcag     60
tgctgcaagt gcaactccaa gaagcgcagt gccaagccac catgtttcaa cattcaacag    120
aagccttttt ccttccactt ttctctttgg anttggttct tctgcttacc aggcagaagg    180
agcagcaagt gtagatggga gaggaccaag catatgggac acctacacta gacagcatac   240
tgaaaagatt tgggatcata gcaccggtga catgggagct gatttt                      286
```

```
<210> SEQ ID NO 612
<211> LENGTH: 246
<212> TYPE: DNA
<213> ORGANISM: Glycine max

<400> SEQUENCE: 612
agatgttcta aatacgttgc caattgtagt gctggcgatt catccactga accctatatc      60
gttggacact acttattact tgctcatgaa tctgctgcca cattatacaa gacaaaatat     120
caggctcgtc aaaaaggaca aattgggatc actaatccaa cacactactt tttgccaaaa    180
tctcaaagtg ctgcagatta caaggcagca agtagagctc tgggctcttc tttggttggt    240
attctg                                                                246

<210> SEQ ID NO 613
<211> LENGTH: 285
<212> TYPE: DNA
<213> ORGANISM: Glycine max
<220> FEATURE:
<221> NAME/KEY: unsure
<222> LOCATION: (1)...(285)
<223> OTHER INFORMATION: unsure at all n locations

<400> SEQUENCE: 613
ccaaagtgct tctctcctct gtcttttct ctctcttgct atcctttgg ctagtncgca        60 ctgctgcaag tgcaactcca agaagcgcag tgccaagcca ccatgtttca acattcaaca    120
gaagcctttt tccttccact tttctctttg ganttggttc ttctgcttac caggcagaag    180
gagcagcaag tgtagatggg ngaggaccaa gcatatggga cacctacact agacagcata    240
ctgaaaagat ttgggatcat agcaccggtg acatgggagc tgatt                    285

<210> SEQ ID NO 614
<211> LENGTH: 286
<212> TYPE: DNA
<213> ORGANISM: Glycine max
<220> FEATURE:
<221> NAME/KEY: unsure
<222> LOCATION: (1)...(286)
<223> OTHER INFORMATION: unsure at all n locations

<400> SEQUENCE: 614
caaaaaatga aacccaaag tgcttctctc ctctgtcttt ttctctctct tgctatcctt       60
ttggctagtn cgcactgctg caagtgcaac tccaagaagc gcagtgccaa gccaccatgt    120
ttcaacattc aacagaagcc ttttttcctt cactttctc tttggaattg gttcttctgc     180
ttaccaggca gaaggagcag caagtgtaga tgggagagga ccaagcatat gggacaccta    240
cactagacag catactgaaa agatttggga tcatagcacc ggtgac                   286

<210> SEQ ID NO 615
<211> LENGTH: 186
<212> TYPE: DNA
<213> ORGANISM: Glycine max
<220> FEATURE:
<221> NAME/KEY: unsure
<222> LOCATION: (1)...(186)
<223> OTHER INFORMATION: unsure at all n locations

<400> SEQUENCE: 615
caaacttctg cttcaagacc tttggagaca gagtcaaata ttgggtcact ttgaatgaac      60
cctatcattt agtcctcaat ggctacaatg gtggcacctt gcaccaggt agatgttcta     120 aataacgttg ccaattgtag tgctggcgat tcatccactg anccctannt nnttggacac    180
```

-continued

```
tactta                                                              186

<210> SEQ ID NO 616
<211> LENGTH: 278
<212> TYPE: DNA
<213> ORGANISM: Glycine max
<220> FEATURE:
<221> NAME/KEY: unsure
<222> LOCATION: (1)...(278)
<223> OTHER INFORMATION: unsure at all n locations

<400> SEQUENCE: 616
gaaaacccaa agtgcttctc tcctctgtct ttttctgctc tgcttgctat ccttttggct    60
agtngcactg ctgcaagtgc aactccaaga agcgcagtgc caagccacca tgtttcaaca   120
ttcaacagaa gccttttttcc ttccactttt ctctttggaa ttggttcttc tgcttaccag   180
gcagaaggag cagcaagtgt agatgggaga ggaccaagca tatgggacac ctacactaga   240
cagcatactg aaaagatttg ggatcatagc accggtga                            278

<210> SEQ ID NO 617
<211> LENGTH: 277
<212> TYPE: DNA
<213> ORGANISM: Glycine max
<220> FEATURE:
<221> NAME/KEY: unsure
<222> LOCATION: (1)...(277)
<223> OTHER INFORMATION: unsure at all n locations

<400> SEQUENCE: 617
cccaaagtgc ttctctcctc tgtcttttc tctctcttgc tatccttttg gctagtngca    60
ctgctgcaag tgcaactcca agaagcgcag tgccaagcca ccatgtttca acattcaaca   120
gaagcntttt tccttccact tttctctttg gtgttggttc ttctgcttac caggcagaag   180
gagcagcaag tgtagatgng agaggaccaa gcatatggga cacctacact agacagcata   240
ctgaaaagga tttgggatca tagcaccggt gacatgg                             277

<210> SEQ ID NO 618
<211> LENGTH: 277
<212> TYPE: DNA
<213> ORGANISM: Glycine max
<220> FEATURE:
<221> NAME/KEY: unsure
<222> LOCATION: (1)...(277)
<223> OTHER INFORMATION: unsure at all n locations

<400> SEQUENCE: 618
gaaaacccaa agtgcttctc tcctctgtct ttttctctct cttgctatcc ttttggctag    60
tngcactgct gcaagtgcaa ctccaagaag cgcagtgcca agccaccatg tttcaacatt   120
caacagaagc cttttttcctn ccactttttct ctttggaatt ggttcttctg cttaccaggc   180
agaaggagca gcaagtgtag atgggagagg accaagcata tgggacacct acactagaca   240
gcatactgaa aagattggga tcatagcacc ggtgaca                             277

<210> SEQ ID NO 619
<211> LENGTH: 271
<212> TYPE: DNA
<213> ORGANISM: Glycine max
<220> FEATURE:
<221> NAME/KEY: unsure
<222> LOCATION: (1)...(271)
<223> OTHER INFORMATION: unsure at all n locations

<400> SEQUENCE: 619
```

-continued

```
aaatgaaaac ccaaagtgct tctctcctct gtcttttct ctctcttgct atccttttgg    60
ctagtngcac tgctgcaagt gcaactccaa gaagcgcagt gccaagccac catgttcaac   120
attcaacaga agccttttc cttccactt tctctttgga cttggttctt ctgcttacca    180
ggcagaagga gcagcaagtg tagatgggag aggaccaagc atatgggaca cctacactag   240
acagcatant gaaaagattg gggntcatan c                                  271
```

<210> SEQ ID NO 620
<211> LENGTH: 255
<212> TYPE: DNA
<213> ORGANISM: Glycine max
<220> FEATURE:
<221> NAME/KEY: unsure
<222> LOCATION: (1)...(255)
<223> OTHER INFORMATION: unsure at all n locations

<400> SEQUENCE: 620

```
cccaaagtgc ttctctcctc tgtcttttc tctctcttgc tatccttttg gctagtngca    60
ctgctgcaag tgcaactcca agaagcgcag tgccaagcca ccatgtttca acattcaaca   120
gaagcctttt tccttccact tttctctttg gaattggttc ttctgcttac caggcagaag   180
gagcagcaag tgtagatggg agaggaccaa gcatatggga cacctacact agacagcata   240
ctgaaaagat ttggg                                                    255
```

<210> SEQ ID NO 621
<211> LENGTH: 260
<212> TYPE: DNA
<213> ORGANISM: Glycine max
<220> FEATURE:
<221> NAME/KEY: unsure
<222> LOCATION: (1)...(260)
<223> OTHER INFORMATION: unsure at all n locations

<400> SEQUENCE: 621

```
aaacccaaa gtgcttctct cctctgtctt tttctctctc ttgctatcct tttggctagt    60
ngcactgctg caagtgcaac tccaagaagc gcagtgccaa gccaccatgt ttcaacattc   120
aacagaagcc ttttccttc cacttttctc tttggaattg gttcttctgc ttaccaggca   180
gaaggagcag caagtgtaga tgggagagga ccaagcatat gggacaccta cactagacag   240
catactgaaa agatttggga                                               260
```

<210> SEQ ID NO 622
<211> LENGTH: 261
<212> TYPE: DNA
<213> ORGANISM: Glycine max
<220> FEATURE:
<221> NAME/KEY: unsure
<222> LOCATION: (1)...(261)
<223> OTHER INFORMATION: unsure at all n locations

<400> SEQUENCE: 622

```
aaatgaaaac ccaaagtgct tctctcctct gtcttttct ctctcttgct atccttttgg    60
ctagtngcac tgctgcaagt gcaactncca agaagcgcag tgccaagcca ccatgtttca   120
acattcaaca gaagccttt tccttccact tttctctttg ganttggttc ttctgcttac   180
caggcagaag gagcagcaag tgtagatggg agaggaccaa gcatatggga cacctacact   240
agacagcata ctgaaaagat t                                             261
```

<210> SEQ ID NO 623

```
<211> LENGTH: 279
<212> TYPE: DNA
<213> ORGANISM: Glycine max
<220> FEATURE:
<221> NAME/KEY: unsure
<222> LOCATION: (1)...(279)
<223> OTHER INFORMATION: unsure at all n locations

<400> SEQUENCE: 623
tgaatgaacc cttatcnttt agtctcaatg ggctacnatg gtggcacctt tgcaccaggt      60
agatgttcna aatancgttg caattggtag tgnntgggna ttaatcnatt gaacccaata    120
ncgttggcca ctacttatta cttgctcatn aatctgctgc cacattatnc aagacaaaat    180
atcaggcncg tcaaaaagga caaattggga tcactaatcc aacacactac tttttgccaa    240
aatctcaaag tgctgcagat tacaaggcag caagtagag                            279

<210> SEQ ID NO 624
<211> LENGTH: 255
<212> TYPE: DNA
<213> ORGANISM: Glycine max
<220> FEATURE:
<221> NAME/KEY: unsure
<222> LOCATION: (1)...(255)
<223> OTHER INFORMATION: unsure at all n locations

<400> SEQUENCE: 624
tgaaacccca aagtgcttct ctcctctgtc tttttctctc tcttgctatc ctttnggcta     60
gtngcactgc tgcaagtgca actccaagaa gcgcagtgcc aagccaccat gtttcaacat   120
tcaacagaag ccttttttcct tccacttttc tctttggaat tggttcttct gcttaccagg   180
cagaaggagc agcaagtgta gatgggagag gaccaagcat atgggacacc tacactagac   240
agcatactga aaaga                                                      255

<210> SEQ ID NO 625
<211> LENGTH: 254
<212> TYPE: DNA
<213> ORGANISM: Glycine max
<220> FEATURE:
<221> NAME/KEY: unsure
<222> LOCATION: (1)...(254)
<223> OTHER INFORMATION: unsure at all n locations

<400> SEQUENCE: 625
agtgcttctc tcctctgtct ttttctctct cttgctatcc ttttggctag tngcactgct     60
gcaagtgcaa ctccaagaag cgcagtgcca agccaccatg tttcaacatt caacagaagc    120
cttttccctt ccacttttct ctttggantt ggttcttctg cttaccaggc agaaggagca    180
gcaagtgtag atgggagagg accaagcata tgggacacct acactagaca gcatactgaa    240
aagatttggg atca                                                       254

<210> SEQ ID NO 626
<211> LENGTH: 264
<212> TYPE: DNA
<213> ORGANISM: Glycine max
<220> FEATURE:
<221> NAME/KEY: unsure
<222> LOCATION: (1)...(264)
<223> OTHER INFORMATION: unsure at all n locations

<400> SEQUENCE: 626
gttctaggct cccaaaattc acaaaagctg aatctgaagg tctaaaaaat tccatagatt      60
ttccttggtg tgaattacta caccacttat tatgcggaac atgctgaacc tgtcagtgcc    120
```

```
aaccgaacct tctacacaga catacnacnn ngtctcagta cggaaaggaa tggtctacat      180
gttggaaccc cgactgattt gaattggctc tttatctttc caaagggaat tcatcttcta      240
ggggcacaca taaaggataa atac                                             264
```

```
<210> SEQ ID NO 627
<211> LENGTH: 146
<212> TYPE: DNA
<213> ORGANISM: Glycine max
<220> FEATURE:
<221> NAME/KEY: unsure
<222> LOCATION: (1)...(146)
<223> OTHER INFORMATION: unsure at all n locations

<400> SEQUENCE: 627
tggtggcacc tttncaccag gtagatgttc taaatacgtt gccaattgta gtgctggcga      60
ttcanccact gtaccctata tcgttggaca ctacttatta cttgctcatg aatctgntgc     120
cacattatac aagacaaaat atcagg                                           146
```

```
<210> SEQ ID NO 628
<211> LENGTH: 258
<212> TYPE: DNA
<213> ORGANISM: Glycine max

<400> SEQUENCE: 628
cccaaagtgc ttctctcctc tgtcttttc tctctcttgc tatcctttg gctagttgca       60 ctgctgcaag tgcaactcca agaagcgcag tgccaagcca ccatgtttca acattcaaca    120
gaagcctttt tccttccact tttctctttg gaattggttc ttctgcttac caggcagaag    180
gagcagcaag tgtagatggg agaggaccaa gcatatggga cacctacact agacagcata    240
tgaaaagatt tgggatca                                                   258
```

```
<210> SEQ ID NO 629
<211> LENGTH: 260
<212> TYPE: DNA
<213> ORGANISM: Glycine max
<220> FEATURE:
<221> NAME/KEY: unsure
<222> LOCATION: (1)...(260)
<223> OTHER INFORMATION: unsure at all n locations

<400> SEQUENCE: 629
aaacccaaag tgnttctctc ctctgtnttt ttctctctct tgctatcctt ttggctagtn     60
gcactgctgc aantgcaact ccaagaagcg cagtgccaag ccaccatgtt tcaacattca    120
acagaagcct ttttccttcc acttttctct ntggtantgg ttcttctgct taccaggcag    180
aaggagcagc aagtgtagat gggagangac caagcatatg ggacacctac actagacagc    240
atactgaaaa gattgggatc                                                 260
```

```
<210> SEQ ID NO 630
<211> LENGTH: 261
<212> TYPE: DNA
<213> ORGANISM: Glycine max
<220> FEATURE:
<221> NAME/KEY: unsure
<222> LOCATION: (1)...(261)
<223> OTHER INFORMATION: unsure at all n locations

<400> SEQUENCE: 630
ganaacccaa agtgcttctc tcctctgtct ttttctctct cttgctatcc ttttggctag     60
```

```
tngcactgct gcaagtgcaa cttccaagaa gcgcagtgcc aagccaccat gtttcaacat    120
tcaacagaag ccttttcct tccactttc tctttggact tggttcttct gcttaccagg     180
cagaaggagc agcaagtgta gatgggagag gaccaagcnt atgggacacc tacactagac    240
agcatactgn naagatttgg g                                               261

<210> SEQ ID NO 631
<211> LENGTH: 271
<212> TYPE: DNA
<213> ORGANISM: Glycine max
<220> FEATURE:
<221> NAME/KEY: unsure
<222> LOCATION: (1)...(271)
<223> OTHER INFORMATION: unsure at all n locations

<400> SEQUENCE: 631
ganaacccaa agtgcttctc tcctctgtct ttttctctct cttgctatcc ttttggctag     60
tngcactgct gcaagtgcaa ctccaagaag cgcagtgcca agccaccatg tttcaacatt    120
caacagaagc ctttttcctt ccactttct ctttggaatt ggttcttctg cttaccaggc     180
agaaggagca gcaagtgtag atgggagagg accaagcata tgggacacct acactagaca    240
gcatactgaa aagattggga tcatagcacc g                                   271

<210> SEQ ID NO 632
<211> LENGTH: 259
<212> TYPE: DNA
<213> ORGANISM: Glycine max
<220> FEATURE:
<221> NAME/KEY: unsure
<222> LOCATION: (1)...(259)
<223> OTHER INFORMATION: unsure at all n locations

<400> SEQUENCE: 632
aatgaaaacc caaagtgctt ctctcctctg tcttttctc tctcttgcta tccttttggc     60
tagtngcact gctgcaagtg caactccaag aagcgcagtg ccaagcacca tgtttcaaca    120
ttcaacagaa ccttttcc ttccactttt ctctttggaa ttggttcttc tgcttaccag     180
gcagaaggag cagcaagtgt agatgggaga ggaccaagca tatgggacac ctacactaga    240
cagcatactg aaaagattg                                                 259

<210> SEQ ID NO 633
<211> LENGTH: 253
<212> TYPE: DNA
<213> ORGANISM: Glycine max

<400> SEQUENCE: 633
gtgcttctct cctctgtctt tttctctctc ttgctatcct ttggctagt ggcactgctg     60 caagtgcaac tccaagagc gcagtgccaa gccaccatgt tcaacattc aacagaagcc     120 ttttcctc cacttttctc tttggaattg gttcttctgc ttaccaggca gaaggagcag    180
caagtgtaga tgggagagga ccaagcatat ggacacctac actagacagc atactgaaaa    240
gatttgggat cat                                                       253

<210> SEQ ID NO 634
<211> LENGTH: 261
<212> TYPE: DNA
<213> ORGANISM: Glycine max
<220> FEATURE:
<221> NAME/KEY: unsure
<222> LOCATION: (1)...(261)
<223> OTHER INFORMATION: unsure at all n locations
```

```
<400> SEQUENCE: 634
gcttctctcc tctgtctttt tctctctctt gctatccttt tggctagtgg cactgctgca      60
agtgcaactc caagaagcgc agtgccaagc caccatgttt caacattcaa cagaagcctt     120
tttccttcca cttttctctt tgganttggt tcttctgctt accaggcaga nggagcagca     180
agtgtagatg ggagaggact aagcatatgg gacacctaca ctagacagca tactgaaaag     240
atttgggatc atagcaccgg t                                                261

<210> SEQ ID NO 635
<211> LENGTH: 272
<212> TYPE: DNA
<213> ORGANISM: Glycine max
<220> FEATURE:
<221> NAME/KEY: unsure
<222> LOCATION: (1)...(272)
<223> OTHER INFORMATION: unsure at all n locations

<400> SEQUENCE: 635
aatgaaaacc caaagtgctt ctctcctctg tcttttctc tctcttgcta tccttttggc       60
tagtngcact gctgcaagtg caacttccaa gaagcgcagt gccaagccac catgnttcaa     120
cattcaacag aagcctttt ccttccagtt ntctntttgg aattggttct tcngcttacc     180
aggcagaagg agcngcaagt gtananggga gaggaccaag canatgggag anatacacna    240
gngaggatan tgaaaagntt tggggtcata gc                                   272

<210> SEQ ID NO 636
<211> LENGTH: 248
<212> TYPE: DNA
<213> ORGANISM: Glycine max
<220> FEATURE:
<221> NAME/KEY: unsure
<222> LOCATION: (1)...(248)
<223> OTHER INFORMATION: unsure at all n locations

<400> SEQUENCE: 636
aaaaatgaaa ncccaaagtg cttctctcct ctgtcttttt ctctctcttg ctatcctttt      60
ggctagtggc actgctgcaa gtgcaactcc aagaagcgca gtgccaagcc accatgtttc     120
aacattcaac agaagccttt tccttccac ttttctcttt ggacttggtt cttctgctta     180
ccaggcagaa ggagcagcaa gtgtagatgg gagaggacca agcatatggg acacctacac    240
tagacagc                                                              248

<210> SEQ ID NO 637
<211> LENGTH: 246
<212> TYPE: DNA
<213> ORGANISM: Glycine max
<220> FEATURE:
<221> NAME/KEY: unsure
<222> LOCATION: (1)...(246)
<223> OTHER INFORMATION: unsure at all n locations

<400> SEQUENCE: 637
aaaatgaaaa cccaaagtgc ttctctcctc tgtctttttc tctctcttgc tatccttttg      60
gctagtngca ctgntgcaag tgcaactcca agaagcgcag tgccaagcca ccatgtttca    120
acattcaaca gaagcctttt tccttccact tttctctttg ganttggttc ttctgcttac     180
caggcagaag gagcagcaag tgtagatggg agaggaccaa gcatatggga cacctacact    240
agacag                                                                246
```

<210> SEQ ID NO 638
<211> LENGTH: 243
<212> TYPE: DNA
<213> ORGANISM: Glycine max
<220> FEATURE:
<221> NAME/KEY: unsure
<222> LOCATION: (1)...(243)
<223> OTHER INFORMATION: unsure at all n locations

<400> SEQUENCE: 638
cccaaagtgc ttctctcctc tgtcttttc tctctcttgc tatccttttg gctagtngca      60
ctgctgcaag tgcaactcca agaagcgcag tgccaagcca ccatgtttca acattcaaca    120
gaagcctttt tccttccact tttctctttg gaattggttc ttctgcttac caggcagaag    180
gagcagcaag tgtagatggg agaggaccaa gcatatggga cacctacact agacagcata    240
ctg                                                                  243

<210> SEQ ID NO 639
<211> LENGTH: 246
<212> TYPE: DNA
<213> ORGANISM: Glycine max
<220> FEATURE:
<221> NAME/KEY: unsure
<222> LOCATION: (1)...(246)
<223> OTHER INFORMATION: unsure at all n locations

<400> SEQUENCE: 639
tgaaaaccca aagtgcttct ctcctctgtc tttttctctc tcttgctatc cttttggcta     60
gtngcactgc tgcaagtgca actccaagaa gcgcagtgcc aagccaccat gtttcaacat   120
tcaacagaag cctttttcct tccacttttc tctttgggct tggttcttct gcttaccagg   180
cagaaggagc agcaagtgta gatgggagag gaccaagcat atgggacacc tacactagac   240
agcata                                                              246

<210> SEQ ID NO 640
<211> LENGTH: 247
<212> TYPE: DNA
<213> ORGANISM: Glycine max
<220> FEATURE:
<221> NAME/KEY: unsure
<222> LOCATION: (1)...(247)
<223> OTHER INFORMATION: unsure at all n locations

<400> SEQUENCE: 640 gaaacccaa agtgcttctc tcctctgtct ttttctctct cttgctatcc ttttggctag      60
tngcactgct gcaagtgcaa cttccaagaa gcgcagtgcc aagccaccat gtttcaanca   120
ttcaacagag cccttttcc ttccactttt ctctttggan ttggttcttc tgcttaccag    180
gcagaaggag cagcaagtgt agatgggaga ggaccaagca tatgggacac ctacactaga   240
cagcata                                                              247

<210> SEQ ID NO 641
<211> LENGTH: 270
<212> TYPE: DNA
<213> ORGANISM: Glycine max
<220> FEATURE:
<221> NAME/KEY: unsure
<222> LOCATION: (1)...(270)
<223> OTHER INFORMATION: unsure at all n locations

<400> SEQUENCE: 641
gatcgaagca naanatgaaa acccaaagtg cttctctcc tctgccnttt tctctctctt      60

```
ggctaatcct tttgggctag tngcactggc tgcaagtgca actccaagaa gcgcagtgcc    120
aagccaccat gtttcagcat tcaacagaag ccttttttcct tccactttc tctttggaat    180 tggttcttct gcttaccagg cagaaggagc agcaagtgta gatgggagag gnccaagcat    240
atgggacacc tacactagac agcatactga                                     270

<210> SEQ ID NO 642
<211> LENGTH: 255
<212> TYPE: DNA
<213> ORGANISM: Glycine max
<220> FEATURE:
<221> NAME/KEY: unsure
<222> LOCATION: (1)...(255)
<223> OTHER INFORMATION: unsure at all n locations

<400> SEQUENCE: 642
taaatgnaaa cccaaagtgc ttctctcctc tgtcttttc tctctctngc tatccttttg    60
gctantngca ctgctgcaag tgcaactcca ngaagcgcag tgccaagcca ccatgtttca   120
acattcaaca gaagcctttt tccttcnact tttctctttg gaattggttc ttctgcttac   180
caggcagaag gagcagcaag tgtagatggg agaggaccna ncatatggga cacctacact   240
agacagcata ctgnc                                                     255

<210> SEQ ID NO 643
<211> LENGTH: 252
<212> TYPE: DNA
<213> ORGANISM: Glycine max
<220> FEATURE:
<221> NAME/KEY: unsure
<222> LOCATION: (1)...(252)
<223> OTHER INFORMATION: unsure at all n locations

<400> SEQUENCE: 643
gatcgaagca aaaatgaaa acccaaagtg cttctctcct ctgtctttt ctctctcttg     60 ctatccttt ggctagtggc actgctgcan ccgcaactcc aagaagcgca gtgccaagcc   120
accatgtttc aacattcaac agaagccttt tccttccac ttttctcttt ggaattggtt   180
cttctgctta ccaggcagaa ggagcancaa gtgtagatgg gagaggacca agcatatggg   240
acacctacac ta                                                        252

<210> SEQ ID NO 644
<211> LENGTH: 239
<212> TYPE: DNA
<213> ORGANISM: Glycine max
<220> FEATURE:
<221> NAME/KEY: unsure
<222> LOCATION: (1)...(239)
<223> OTHER INFORMATION: unsure at all n locations

<400> SEQUENCE: 644 tgaaaccca agtgcttct ctcctctgtc tttttctctc tcttgctatc cttttggcta    60
gtggcactgc tgcaagtgna antccaagaa gcgcagtgcc aagccaccat gtttcaacat   120
tcaacagaag ccttttttcct tccactttc tctttggant tggttcttct gcttaccagg   180
cagaaggagc agcaagtgta gatgggagag gaccaagcat atgggacacc tacactaga    239

<210> SEQ ID NO 645
<211> LENGTH: 254
<212> TYPE: DNA
<213> ORGANISM: Glycine max
```

```
<400> SEQUENCE: 645
gatcgaagca aaaaatgaaa acccaaagtg cttctctcct ctgtcttttt cactctcttg      60 ctatccttttt ggctagtggc actgctgcaa gtgcaactcc aagaagcgca gtgccaagcc    120
accatgtttc aacattcaac agaagccttt tccttccac ttttctcttt ggaattggtt     180
cttctgctca ccaggcagaa ggagcagcaa gtgtagatgg gagaggacca agcatatggg     240
acacctacac taga                                                        254

<210> SEQ ID NO 646
<211> LENGTH: 119
<212> TYPE: DNA
<213> ORGANISM: Glycine max

<400> SEQUENCE: 646
ccgggagagt atgaaatctt cagtaggttc taggctccca aaattcacaa aagctgaatc      60
tgaaggtcta aaaaattcca tagattttct tggtgtgaat tactacacca cttattatg     119

<210> SEQ ID NO 647
<211> LENGTH: 249
<212> TYPE: DNA
<213> ORGANISM: Glycine max
<220> FEATURE:
<221> NAME/KEY: unsure
<222> LOCATION: (1)...(249)
<223> OTHER INFORMATION: unsure at all n locations

<400> SEQUENCE: 647
cttgctgcct tgtnctctgc agcaagtaga nctctggact tcttctntgg ttggtnttct      60
gatccggttt tctatggtga ctatccggcg agtatgnant cttcagtagc ntctaggntc    120
ccanaattca cnaaagctga ntctgaaggt ctanaaantt ccatagnttt tcttggtgtg    180
nnttantnca ncacttnttn tgcggaacat gctgaacctg tcagtgccaa ccgaacntct    240
acacagaca                                                              249

<210> SEQ ID NO 648
<211> LENGTH: 250
<212> TYPE: DNA
<213> ORGANISM: Glycine max
<220> FEATURE:
<221> NAME/KEY: unsure
<222> LOCATION: (1)...(250)
<223> OTHER INFORMATION: unsure at all n locations

<400> SEQUENCE: 648
ggaagcaaaa natgaaaacc caaagtgctt ctctcctcan tcttttctc tctcttgcta      60 tccttttggc tagtggcact gctgcaagtg caactccaag aagcgcagtg ccaagccacc    120
atgtttcaac attcaacaga agcctttttc cttccacttt tctctttgga attggttctt    180
ctgcttacca ggcagaagga gcagcaagtg tagatgggag aggaccaagc atatgggaca    240
cctacactag                                                            250

<210> SEQ ID NO 649
<211> LENGTH: 237
<212> TYPE: DNA
<213> ORGANISM: Glycine max
<220> FEATURE:
<221> NAME/KEY: unsure
<222> LOCATION: (1)...(237)
<223> OTHER INFORMATION: unsure at all n locations

<400> SEQUENCE: 649
```

```
caaaaaatga aaacccaaag tgcttctctc ctctgtcttt ttctctctnt tgctatcctt      60
ttggctagtg gcactgctgc aagtgcaact ccaagaagcg cagtgccaag ccaccatgtt     120
tcaacattca acagaagcct ttttccttcc acttttctct ttggaattgg ttcttctgct     180
taccaggcag aaggagcagc aagtgtagat gggagaggac caagcatatg ggacacc       237

<210> SEQ ID NO 650
<211> LENGTH: 252
<212> TYPE: DNA
<213> ORGANISM: Glycine max
<220> FEATURE:
<221> NAME/KEY: unsure
<222> LOCATION: (1)...(252)
<223> OTHER INFORMATION: unsure at all n locations

<400> SEQUENCE: 650
gatcgaagca aaaatgaaa acccaaagtg cttctgctcc tctgtctttt tctctctctt      60
gctatccttt tggctagtng cactgctgca agtgcaactc caagaagcgc agtgccaagc    120
caccatgntt caacattcaa cagaagcctt tttccttcca cttttctctt tggaattggt    180
tcttctgctt accaggcaga aggagcagca agtgtagatg ggagaggacc aagcatatgg    240
gacacctaca tt                                                         252

<210> SEQ ID NO 651
<211> LENGTH: 251
<212> TYPE: DNA
<213> ORGANISM: Glycine max

<400> SEQUENCE: 651
gatcgaagca aaaatgaaa acccaaagtg cttctctcct ctgtcttttt ctctctcttg      60
ctatcctttt ggctagtggc actgctgcaa gtgcaactcc aagaagcgca gtgccaagcc    120
accatgtttc aacattcaac agaagccttt tccttccact tttctcttt ggaattggtt     180 cttctgctta ccaggcagaa ggagcagcaa gtgtagatgg gagaggacca agcatatggg    240
acacctacac t                                                          251

<210> SEQ ID NO 652
<211> LENGTH: 251
<212> TYPE: DNA
<213> ORGANISM: Glycine max

<400> SEQUENCE: 652
gatcgaagca aaaatgaaa acccaaagtg cttctctcct ctgtcttttt ctctctcttg      60 ctacccttt ggctagtggc actgctgcaa gtgcaactcc aagaagcgca gtgccaagcc     120
accatgtttc aacattcaac agaagccttt tccttccact tttctcttt ggaattggtt     180 cttctgctta ccaggcagaa ggagcagcaa gtgtagatgg gagaggacca agcatatggg    240
acacctacac t                                                          251

<210> SEQ ID NO 653
<211> LENGTH: 257
<212> TYPE: DNA
<213> ORGANISM: Glycine max
<220> FEATURE:
<221> NAME/KEY: unsure
<222> LOCATION: (1)...(257)
<223> OTHER INFORMATION: unsure at all n locations

<400> SEQUENCE: 653
```

```
gggacatcga agcaaaaaat gaaaacccaa antgctttct ctcctctgtc tttttctctc      60
tcttgctatc cttttggcta ntngcactgc tgcaagtgca actccaagaa gcgcagtgcc     120
aagccaccat ntttcaacat tcaacagaag cctctttcct tccactttc tctttggaat     180 tggttcttct gcttaccagg cagaaggagc agcaagtgna gatgggagag gaccaagcnt     240
atgggacacc tacacta                                                    257
```

<210> SEQ ID NO 654
<211> LENGTH: 270
<212> TYPE: DNA
<213> ORGANISM: Glycine max
<220> FEATURE:
<221> NAME/KEY: unsure
<222> LOCATION: (1)...(270)
<223> OTHER INFORMATION: unsure at all n locations

<400> SEQUENCE: 654

```
gatcgaagca aaaatgaaa acccaaagtg cttctctcct ctgtcttttt ctctctcttg      60
ctatcctttt ggctannggc actgctgcaa gtgcanctcc aagaagcgca gtgccaagcc    120
accatgtttc aacattcaac agaagccttt tccttccac ttttctcttt gganttggtt    180
cttctgctta ccaggcagaa ggagcagcaa gtgtagatgg gagaggacca agcatatggg    240
acacctacac ttagacagca tactgaaagg                                      270
```

<210> SEQ ID NO 655
<211> LENGTH: 253
<212> TYPE: DNA
<213> ORGANISM: Glycine max
<220> FEATURE:
<221> NAME/KEY: unsure
<222> LOCATION: (1)...(253)
<223> OTHER INFORMATION: unsure at all n locations

<400> SEQUENCE: 655

```
gatcgaagca aaaatgaaa acccaaagtg cttctctcct actgtctttt tctctctctt      60
gctatccttt tggctagtng cactgctgca agtgcaactc caagaagcgc agtgccaagc    120
caccatgttt caacattcaa cagaagccct tttccttcca cttttctctt tgganttggt    180
tcttctgctt accaggcaga aggagcagca agtgtagatg ggagaggacc aagcatatgg    240
gacacctaca cta                                                        253
```

<210> SEQ ID NO 656
<211> LENGTH: 270
<212> TYPE: DNA
<213> ORGANISM: Glycine max
<220> FEATURE:
<221> NAME/KEY: unsure
<222> LOCATION: (1)...(270)
<223> OTHER INFORMATION: unsure at all n locations

<400> SEQUENCE: 656

```
gggacatcga agcaaaaaat gaaaacccaa agtgctttct nctcctctgt cttttctctc      60
cctcttgcta tccttttggg ctagtgngca ctgctgcaag tgcaactccc aagaagcgca    120
gtgccaagcc accatgtttc aacattcaac agaagccttt tccttccac ttttctcttt    180 ggaattggtt cttctgctta ccaggcagaa ggagcagnaa gtgtagatgg gagaggncca    240
agcatatggg acacctacnc taganagcnt                                      270
```

<210> SEQ ID NO 657
<211> LENGTH: 247

```
<212> TYPE: DNA
<213> ORGANISM: Glycine max
<220> FEATURE:
<221> NAME/KEY: unsure
<222> LOCATION: (1)...(247)
<223> OTHER INFORMATION: unsure at all n locations

<400> SEQUENCE: 657
gaaaacccaa agtgcttctc tcacctgtcc tttttctcta nccttgctat ccttttggct    60
agtngcactg ctgcaagtgc aactccaaga agcgcagtgc caagccacca tgtttcaaca   120
ttcaacagaa gccttttttcc ttccactttt ctctttggan ttggttcttc tgctttccag   180
gcagaaggag cagcaagtgt agatgggaga ggaccaagca tatgggacac ctncactaga   240
cagcata                                                              247

<210> SEQ ID NO 658
<211> LENGTH: 254
<212> TYPE: DNA
<213> ORGANISM: Glycine max
<220> FEATURE:
<221> NAME/KEY: unsure
<222> LOCATION: (1)...(254)
<223> OTHER INFORMATION: unsure at all n locations

<400> SEQUENCE: 658
gatcgaagca aaaatgaaa acccaaagtg cttctctcct ctgtcttttt ctnctctctt     60
ngctatcctt ttggctagtn gcactgctgc aagtgcaact ccaagaagcg cagtgccaag   120
ccaccatgtt tcaacattca acagaagcct tttccttcc actttctctt ttggaattgg    180
ttcttctgct taccaggcag aaggagcagc aagtgtagat gggagaggac caagcatatg   240
ggacacctac atag                                                      254

<210> SEQ ID NO 659
<211> LENGTH: 169
<212> TYPE: DNA
<213> ORGANISM: Glycine max
<220> FEATURE:
<221> NAME/KEY: unsure
<222> LOCATION: (1)...(169)
<223> OTHER INFORMATION: unsure at all n locations

<400> SEQUENCE: 659
cagtgccaag ccacatgttt caacattcaa cagaagcctt tttccttcca cttttctctt    60
tggaattggt tcttctgctt accaggcaga aggagcagca agtgtagatn nngagaggac   120
caagcatatg ggacacctac actagacagc atactgaaaa gattgggat                169

<210> SEQ ID NO 660
<211> LENGTH: 267
<212> TYPE: DNA
<213> ORGANISM: Glycine max
<220> FEATURE:
<221> NAME/KEY: unsure
<222> LOCATION: (1)...(267)
<223> OTHER INFORMATION: unsure at all n locations

<400> SEQUENCE: 660
gaaaacccaa agtgcttctc tcctctgtct tttctctct cttgctatcc ttttggctag     60
tngcactgct gcaagtgcaa cttccaagaa gcgcagtgcc aagccaccat gtttcaacat   120
tcaacagaag ccttttttcct tccactttttc tctttggant tggttcttct gcttaccagg   180
cagaaggagc agcaagtgta gatgggagag gaccaagcat atggncacct ncantagaca   240
```

```
gcatactgaa aagatttggg gatcatc                                          267
```

<210> SEQ ID NO 661
<211> LENGTH: 169
<212> TYPE: DNA
<213> ORGANISM: Glycine max
<220> FEATURE:
<221> NAME/KEY: unsure
<222> LOCATION: (1)...(169)
<223> OTHER INFORMATION: unsure at all n locations

<400> SEQUENCE: 661

```
cctgaatctg ctgccacatt atacaagaca aaatatcagg ctcgtcnaaa aggacaaatt       60
gggatcacta atccaacaca ctactttttg ccaaaatctc aaagcgctgc agattacaag      120
gcagcaagta gagctctggn cttcttcttt ggtggtattc tganccggt                  169
```

<210> SEQ ID NO 662
<211> LENGTH: 247
<212> TYPE: DNA
<213> ORGANISM: Glycine max
<220> FEATURE:
<221> NAME/KEY: unsure
<222> LOCATION: (1)...(247)
<223> OTHER INFORMATION: unsure at all n locations

<400> SEQUENCE: 662

```
gatcgaagca aaaatgaaa acccaaagtg cttctactcc tctgtctntt tctctctctt        60
gctatccttt tgggctagtn ggcactgctg caagtggcaa ctcccaagaa gcgcagtgcc      120
aagccaccat gnttcaacat tcaacagaag ccttttttcct tcnactttc tctttggaat     180 tggttcttct gcttaccagg cagaaggagc agcaagtgta gatgggagag gaccaagcat      240
atgggac                                                                247
```

<210> SEQ ID NO 663
<211> LENGTH: 247
<212> TYPE: DNA
<213> ORGANISM: Glycine max
<220> FEATURE:
<221> NAME/KEY: unsure
<222> LOCATION: (1)...(247)
<223> OTHER INFORMATION: unsure at all n locations

<400> SEQUENCE: 663

```
gatcgaagca aaaatgaaa acccaaagtg cttctctcct ctgtcttttt ctctctcttg        60
ctatcctttt ggctagtngc actgctgcaa gtgcaactcc aagaagcgca gtgccaagcc      120
accatgtttc aacattcaac agaagccttt ttccttccac ttttctcttt ggaattggtt      180
cttctgctta ccaggcagaa ggagcagcaa gtgtagatgg gagaggacca agcatatggg      240
acaccta                                                                247
```

<210> SEQ ID NO 664
<211> LENGTH: 248
<212> TYPE: DNA
<213> ORGANISM: Glycine max
<220> FEATURE:
<221> NAME/KEY: unsure
<222> LOCATION: (1)...(248)
<223> OTHER INFORMATION: unsure at all n locations

<400> SEQUENCE: 664

```
gggacatcga agcaaaaaat gaaacccaa agtgcttctc tcctctgtct ttttctctct        60
cttgctatcc ttttggctag tggcactgct gcaagtgcaa ctccaagaag cgcagtgcca      120
```

```
agccaccatg tttcaacatt cancagaagc cttttccctt ccactttct ctttggaatt        180 ggttcttctg cttaccaggc agaaggagca gcaagtgtag atgggagagg accaagcata       240
tgggacac                                                                248

<210> SEQ ID NO 665
<211> LENGTH: 248
<212> TYPE: DNA
<213> ORGANISM: Glycine max
<220> FEATURE:
<221> NAME/KEY: unsure
<222> LOCATION: (1)...(248)
<223> OTHER INFORMATION: unsure at all n locations

<400> SEQUENCE: 665
gatcgaagca aaaatgaaa acccaaagtg cttctctcct ctgtcttttt ctctctcttg         60
ctatccnttt ggctagtngc actgctgcaa gtgcaactcc aagaagcgca gtgccaagcc      120
ancatgttcc aacattcaac agaagccttt tccttccac ttttctcttt ggaattggtt       180
cttctgctta ccaggcagaa ggagcagcaa gtgtagatgg gagaggacca agcatatggg      240
gcacctac                                                                248

<210> SEQ ID NO 666
<211> LENGTH: 242
<212> TYPE: DNA
<213> ORGANISM: Glycine max

<400> SEQUENCE: 666
gatcgaagca aaaatgaaa acccaaagtg cttctctcct ctgtcttttt ctctctcttg         60 ctatccttt ggctagtggc actgctgcaa gtgcaactcc aagaagcgca gtgccaagcc       120 accatgttc aacattcaac agaagccttt tccttccac ttttctcttt ggaattggtt        180
cttctgctta ccaggcagaa ggagcagcaa gtgtagatgg gagaggacca agcatatggg      240
ac                                                                      242

<210> SEQ ID NO 667
<211> LENGTH: 247
<212> TYPE: DNA
<213> ORGANISM: Glycine max
<220> FEATURE:
<221> NAME/KEY: unsure
<222> LOCATION: (1)...(247)
<223> OTHER INFORMATION: unsure at all n locations

<400> SEQUENCE: 667
gatcgaagca aaaatgaaa acccaaagtg cttctctcct ctgtcttttt ctctctcttg         60 ctatccttt ggctagtggc actgctgcaa gtgcaactcc aagaagcgca gtgccaagcc       120 accatgttc aacattcaac agaagccttt tccttccac ttttctcttt ggaattggtt        180
cttctgctta ccaggcagaa ggagcagcaa gtgtagatgg nngaggaccn nnnatatggg      240
acaccta                                                                 247

<210> SEQ ID NO 668
<211> LENGTH: 274
<212> TYPE: DNA
<213> ORGANISM: Glycine max
<220> FEATURE:
<221> NAME/KEY: unsure
<222> LOCATION: (1)...(274)
<223> OTHER INFORMATION: unsure at all n locations
```

```
<400> SEQUENCE: 668
caaaaaatga aaacccaaag tgcttctctc ctgntgtctt tttctctctc ttgctatcct      60
tttggctagt ngcactgctg caagtncaac tccaagaagc gcagtgccaa gncagcatgt     120
ttcaacattc aacagaagcc tttttccttc cactttttctc tttgganatg gttcttctgc    180
ttaccaggca gaaggagcag caagtgtaga tgggagnagn ccaagcatat gggacaccta    240
catagacagc atactgaaaa gattgggatn atac                                274

<210> SEQ ID NO 669
<211> LENGTH: 244
<212> TYPE: DNA
<213> ORGANISM: Glycine max
<220> FEATURE:
<221> NAME/KEY: unsure
<222> LOCATION: (1)...(244)
<223> OTHER INFORMATION: unsure at all n locations

<400> SEQUENCE: 669
gatcgaagca aaaatgaaa acccaaagtg cttctctcct ctgtcttttt ctctctcttg      60
ctatcctttt ggctagtngc actgctgcaa gtgcaactcc aagaagcgca gtgccaagcc    120
accatgtttc aacattcaac agaagccttt ttccttccac tttttctctt ggaattggtt    180
cttctgctta ccaggcagaa ggagcagcaa gtgtagatgg gagaggacca agcatatggg    240
acac                                                                 244

<210> SEQ ID NO 670
<211> LENGTH: 243
<212> TYPE: DNA
<213> ORGANISM: Glycine max
<220> FEATURE:
<221> NAME/KEY: unsure
<222> LOCATION: (1)...(243)
<223> OTHER INFORMATION: unsure at all n locations

<400> SEQUENCE: 670
gatcgaagca aaaatgaaa acccaaagtg cttctctcct ctgtcttttt ctctctcttg      60
ctatcctttt ggctagtngc actgctgcaa gtgcaactcc aagaagcgca gtgccaagcc    120
accatgtttc aacattcaac agaagccttt ttccttccac tttttctctt ggaattggtt    180
cttctgctta ccaggcagaa ggagcagcaa gtgtagatgg gagaggacca agcatatggg    240
acc                                                                  243

<210> SEQ ID NO 671
<211> LENGTH: 251
<212> TYPE: DNA
<213> ORGANISM: Glycine max
<220> FEATURE:
<221> NAME/KEY: unsure
<222> LOCATION: (1)...(251)
<223> OTHER INFORMATION: unsure at all n locations

<400> SEQUENCE: 671
gatcgaagca aaaatgaaa acccaaagtg cttctctcct ctgtcttttt ctctctcttg      60
ctatcctttt ggctagtngc actgctgcaa gtgcaactcc aagaagcgca gtgccaagcc    120
accatgtttc aacattcaac agaagccttt ttccttccac tttttctctt gganttggtt    180
cttctgctta ccaggcagaa ggagcagcaa gtgtagatgg gagaggacca gcatatggga    240
cacctacact a                                                         251
```

```
<210> SEQ ID NO 672
<211> LENGTH: 275
<212> TYPE: DNA
<213> ORGANISM: Glycine max
<220> FEATURE:
<221> NAME/KEY: unsure
<222> LOCATION: (1)...(275)
<223> OTHER INFORMATION: unsure at all n locations

<400> SEQUENCE: 672
gggaatcctn cgtaaggtaa acggcnaagg tngtaaggaa tcattgccat ctttctactt      60
tactttgtgg anagctncca gggacaccta cactagacag catactgaaa agatttggga    120
tcatagcacc ggtgacatgg gagctgattt ttatcatcga tacaagggtg acatacanca    180
agcganagan attgggctgg actctttcag attctctatc tcatggtcaa gaatattccc    240
aanggcnagg gagcagttaa cccccttggg gttaa                               275

<210> SEQ ID NO 673
<211> LENGTH: 241
<212> TYPE: DNA
<213> ORGANISM: Glycine max

<400> SEQUENCE: 673
gatcgaagca aaaaatgaaa acccaaagtg cttctctcct ctgtcttttt ctctctcttg      60
ctatcctttt ggctagtggc actgctgcaa gtgcaactcc aagaagcgca gtgccaagcc    120
accatgtttc aacattcaac agaagccttt tccttccac ttttctcttt ggaattggtt     180
cttctgctta ccaggcagaa ggagcagcaa gtgtagatgg gagagggcca agcatatggg    240
a                                                                    241

<210> SEQ ID NO 674
<211> LENGTH: 223
<212> TYPE: DNA
<213> ORGANISM: Glycine max
<220> FEATURE:
<221> NAME/KEY: unsure
<222> LOCATION: (1)...(223)
<223> OTHER INFORMATION: unsure at all n locations

<400> SEQUENCE: 674
gaaaacccaa agtgcttctc tcctctgtct ttttctctct cttgctatcc ttttggctag      60
tggcactgct gcaagtgcaa ctccaagaag cgcagtgcca agccaccatg tttcaacatt    120
caacagaagc cttttttcctt ccactttct ctttggannt ggttcttctg cttaccaggc    180
agaaggagca gcaagtgtag atgggagagg accaagcata tgg                      223

<210> SEQ ID NO 675
<211> LENGTH: 286
<212> TYPE: DNA
<213> ORGANISM: Glycine max
<220> FEATURE:
<221> NAME/KEY: unsure
<222> LOCATION: (1)...(286)
<223> OTHER INFORMATION: unsure at all n locations

<400> SEQUENCE: 675
gtaacagcaa tggagctgtc ttccagtgca tttgtggtaa tattgttggc agtcgcagct      60
acagcagtac tctgcaaatg ggttggatct atctttcntg cccagcgatt tcctcnttgg    120
cattgcttct tcctcttacc agtatgaagg agcttacaag agtgacggca aaggactgag    180
caactgggat aactacactc acggaccagg tagaagtgta ataatggatg gaagcaatgg    240
```

```
ggatatcgcg attgatcatt atcatcgcta cctggaggat atagat            286
```

<210> SEQ ID NO 676
<211> LENGTH: 261
<212> TYPE: DNA
<213> ORGANISM: Glycine max

<400> SEQUENCE: 676

```
gttggcagtc gcagctacag cagtactctc aaatggttg gatctatctt tcttgcccag    60
cgatttcctc tttggcattg cttcttcctc ttaccagtat gaaggagctt acaagagtga   120
cggcaaagga ctgagcaact gggataacta cactcacgga ccaggtagaa gtgtaataat   180
ggatggaagc aatggggata tcgcgattga tcattatcat cgctacctgg aggatataga   240
tttaatggaa actttgggag t                                             261
```

<210> SEQ ID NO 677
<211> LENGTH: 260
<212> TYPE: DNA
<213> ORGANISM: Glycine max
<220> FEATURE:
<221> NAME/KEY: unsure
<222> LOCATION: (1)...(260)
<223> OTHER INFORMATION: unsure at all n locations

<400> SEQUENCE: 677

```
cagatagaag gagcagcagc tatagatggc agaggaccaa gtatatggga cacctatact    60
aaacagcaac cagggaagat tgggatcat agtgatggaa gtctagcaat tgattttat    120 caccggtaca agacgacata aagatggtga nagaagtngg gttggattca tacagatttt   180
ccatctcatg gtccagaata ttccccaagg gcaagggagc agttaacacc ttggggtca    240 agttctacaa cgatctcatt                                               260
```

<210> SEQ ID NO 678
<211> LENGTH: 263
<212> TYPE: DNA
<213> ORGANISM: Glycine max
<220> FEATURE:
<221> NAME/KEY: unsure
<222> LOCATION: (1)...(263)
<223> OTHER INFORMATION: unsure at all n locations

<400> SEQUENCE: 678

```
agatagaagg agcagcagct atagatggca gaggaccaag tatatccgga cacctatact    60
aaacagcaac canggaagat tgggatcan agtgatggaa gtctagcaat tgattttat    120 caccggtaca agagcacata aagatggtga aagaagttgg gttggattca tacagatttt   180
ccatctcatg gtccagnata tttccccnng gggcnaggga gcagtaacac cntngggggc   240
ccantctncc aagancncct ttt                                           263
```

<210> SEQ ID NO 679
<211> LENGTH: 301
<212> TYPE: DNA
<213> ORGANISM: Glycine max
<220> FEATURE:
<221> NAME/KEY: unsure
<222> LOCATION: (1)...(301)
<223> OTHER INFORMATION: unsure at all n locations

<400> SEQUENCE: 679

```
anatgaacca tatggctaca gcgtgaatgg ctacagtggt ggaaattttg caccaggtag    60
atgttctaac tangttggaa aatgccctgc nggtgattct tccaccgagc cctacattgt   120
```

```
taaccaccac ttaatacttg ctcatggagc agcagtcaat tgctacaaga acaaatacca    180
ggctcatcag anaggacaaa ttggngtcac catagtgact ttcttctttg aaccaaaatc    240
taatagtgat gctgatcgca aggcagcaag gcgagctctg gacttatgtt tggctggttt    300
g                                                                    301

<210> SEQ ID NO 680
<211> LENGTH: 271
<212> TYPE: DNA
<213> ORGANISM: Glycine max
<220> FEATURE:
<221> NAME/KEY: unsure
<222> LOCATION: (1)...(271)
<223> OTHER INFORMATION: unsure at all n locations

<400> SEQUENCE: 680
angtttgaga attganttcg ttcagatttg aaaatgtggg ttaaggttgt tccttcttct     60
ccttgcagca ctttctcttt ttcacttagc cgcagcttac tcttaatcgt agcagttttt    120
cagcagattt cttctttgga acagcttctt cagcttacca gtatgaaggt gcagcacgtg    180
aaggtggcaa gggacctagt atatgggaca ccttcactgc atagccaccc agatagaata    240
gcagaccaca gtaatgggga gttgccatga t                                   271

<210> SEQ ID NO 681
<211> LENGTH: 452
<212> TYPE: DNA
<213> ORGANISM: Glycine max

<400> SEQUENCE: 681
aacaaagtaa gagttcactc aatctcactg tgttgtgagt tgtgtgtgag caccaaccaa     60
caatggtgtc tctgactccg ttatgtttct ttattacctt gttgatcgct ggtgcagacg    120
cagcggcgga gccccaaacg gtgcgttttg acaccggggg gttgagcaga gacacctttc    180
ccaaaggatt cttattcgga acggccacgt ctgcgtacca agtggagggt atggcccaca    240
aagacggtcg cggcccaagc atttgggacg tcttcatcaa aaaacccggg attgtcgcaa    300
ataatggcac gggagaagtt tctgttgatc aagtaccatc gctacaaaga agatatagat    360
ctcatggcca gcctgaattt tgatgcctac cggttctcaa tctcgtggtc cagaattttt    420
ccaaatggaa ctggccaagt aaattggaaa ag                                  452

<210> SEQ ID NO 682
<211> LENGTH: 357
<212> TYPE: DNA
<213> ORGANISM: Glycine max
<220> FEATURE:
<221> NAME/KEY: unsure
<222> LOCATION: (1)...(357)
<223> OTHER INFORMATION: unsure at all n locations

<400> SEQUENCE: 682
cttcatcaaa aaacccggga ttgtcgcaaa taatggcacg ggagaagttt ctgttgatca     60
gtaccatcgc tacaaagaag atatagatct catggccagc ctgaattttg atgcctaccg    120
gttctcaatc tcgtggtcca gaattttccc aaatggaact ggccaagtaa attggaaggg    180
tgtagcatac tacaataggt tgatcaatta cttgctagag aaaggtatta ctccatatgc    240
aaatctctac cattatgatc ttcctttagc acttgaggag aggtacaacg gattattgag    300
tcgccaagtt gtgaaagatt ttgcagatta tgcagaattt tgtttcaaga cttttgg       357
```

```
<210> SEQ ID NO 683
<211> LENGTH: 444
<212> TYPE: DNA
<213> ORGANISM: Glycine max
<220> FEATURE:
<221> NAME/KEY: unsure
<222> LOCATION: (1)...(444)
<223> OTHER INFORMATION: unsure at all n locations

<400> SEQUENCE: 683
aaacanagta agagttcact caatctcact gtgttgtgag ttgtgtgtga gcaccaacca      60
acaatggtgt ctctgactcc gttatgtttc tttattacct tgttgatcgc tggtgcagac     120
gcagcggcgg agccccaaac ggtgcgtttt gacaccgngg ggttgagcag agacaccttt     180
cccaaaggat tcttattcgg aacgccacg tctgcgtacc aagtggaggg tatgccccac     240
aaagacggtc gcggcccaag catttgggac gtcttcatca aaaacccgg gattgtcgca     300
aataatggca cggagaagt ttctgttgat cagtnccatc nctacaaagg aagatataga     360
tctcatggnc agcctgaatt ttgatgccta ccggttttna atctcgtggt ccagaaattt     420
ttcnaatggn acttggccaa gtaa                                            444

<210> SEQ ID NO 684
<211> LENGTH: 430
<212> TYPE: DNA
<213> ORGANISM: Glycine max
<220> FEATURE:
<221> NAME/KEY: unsure
<222> LOCATION: (1)...(430)
<223> OTHER INFORMATION: unsure at all n locations

<400> SEQUENCE: 684
caaaaacaaa aacaaagtaa gagttcactc aatctcactg tgttgtgagt tgtgtgtgag      60
caccaaccaa caatggtgtc tctgactccg ttatgtttct ttattacctt gttgatcgct     120
ggtgcagacn cagcggcgga gccccaaacg gtgcgttttg acaccggggg gttgagcaga     180
gacacctttc ccaaaggatt cttattcgga acgccacgt ctgcgtacca agtggaggt     240
atgcccaca aagacggtcg cggnccaagc atttgggacg tcttcatcaa aaacccggg     300
attgtcgcaa ataatggcac gggagaagtt tctgttgatc aagtaccatc gctacaaaga     360
agatattagg gatctcatgg ccagcctgaa ttttgatgcc taccggttct caatctcgtg     420
gtccagaatt                                                            430

<210> SEQ ID NO 685
<211> LENGTH: 382
<212> TYPE: DNA
<213> ORGANISM: Glycine max

<400> SEQUENCE: 685
caaaaacaaa aacaaagtaa gagttcactc aatctcactg tgttgtgagt tgtgtgtgag      60
caccaaccaa caatggtgtc tctgactccg ttatgtttct ttattacctt gttgatcgct     120
ggtgcagacg cagcggcgga gccccaaacg gtgcgttttg acaccggggg gttgagcaga     180
gacacctttc ccaaaggatt cttattcgga acgccacgt ctgcgtacca agtggaggt     240
atgcccaca aagacggtcg cggcccaagc atttgggacg tcttcatcaa aaacccggg     300
attgtcgcaa ataatggcac gggagaagtt tctgttgatc agtaccatcg ctacaaagaa     360
gatatagatc tcatggccag cc                                              382
```

<210> SEQ ID NO 686
<211> LENGTH: 277
<212> TYPE: DNA
<213> ORGANISM: Glycine max

<400> SEQUENCE: 686

```
gtaaattgga aaggtgtagc atactacaat aggttgatca attacttgct agagaaaggt      60
attactccat atgcaaatct ctaccattat gatcttcctt tagcacttga ggagaggtac     120
aacggattat tgagtcgcca agttgtgaaa gattttgcag attatgcaga attttgttta     180
tacgactttt ggagatagag ttaagaattg gatgacgttt aacgaacctc gtgtggtggc     240
tgctcttggc tatgataatg gtttctttgc cccggaa                              277
```

<210> SEQ ID NO 687
<211> LENGTH: 262
<212> TYPE: DNA
<213> ORGANISM: Glycine max

<400> SEQUENCE: 687

```
gcgacgtctg cgtaccaagt ggagggtatg gcccacaaag acggtcgcgg cccaagcatt      60
tgggacctct tcatcaaaaa acccgggatt gttgcaaata atggcacggg agaagtttct     120
gttgatcagt accatcgcta caaagaagat atagatctca tggccagctt gaattttgat     180
gcctaccggt tctcaatctc gtggtccaga atttttccaa atggaactgg ccaagtaaat     240
tggaaaggtg tagcatacta ca                                             262
```

<210> SEQ ID NO 688
<211> LENGTH: 272
<212> TYPE: DNA
<213> ORGANISM: Glycine max
<220> FEATURE:
<221> NAME/KEY: unsure
<222> LOCATION: (1)...(272)
<223> OTHER INFORMATION: unsure at all n locations

<400> SEQUENCE: 688

```
ctaaattgga aaggtgtagc atactacaat aggttgatca attacttgct agagaaaggt      60
attactccat atgcaaatct ctaccattat gatcttcctt tagcacttga ggagaggtac     120
aacggattat tgagtcgcca agttgtgaaa gattttgcag attatggcag aattttgttt     180
caagactttt ggagatagag ttaagaatgg gatgangttn aacgaacctc gtgtggtggc     240
tgctcttggc tatgataang gttctttgcc cc                                  272
```

<210> SEQ ID NO 689
<211> LENGTH: 271
<212> TYPE: DNA
<213> ORGANISM: Glycine max

<400> SEQUENCE: 689

```
tggaataaaa ctatgtgagc taaagtatgt ttaatttgac aggaagatat agatctcatg      60
gccagcttga attttgatgc ctaccggttc tcaatctcgt ggtccagaat ttttccaaat     120
ggaactggcc aagtaaattg gaaaggtgta gcatactaca ataggctgat caattacttg     180
ctagaaaaag gtattactcc atatgcaaat ctctaccatt atgatcttcc tttagcactt     240
gaggagaggt acaacggatt attgagccgg c                                    271
```

<210> SEQ ID NO 690
<211> LENGTH: 368
<212> TYPE: DNA

```
<213> ORGANISM: Glycine max

<400> SEQUENCE: 690
aagacgacag aagggggaca ttatctttc tcttcacaaa aacaaaaaca aagtaagagt      60
tcactcaatc tcactgtgtt gtgagttgtg tgtgagcacc aaccaacaat ggtgtctctg    120
actccgttat gtttctttat taccttgttg atcgctggtg cagacgcagc ggcggagccc    180
caaacggtgc gttttgacac cggggggttg agcaagagac cctttcccca aaggattctt    240
attcggaacg ccacgtctg cgtaccaagt ggagggtatg cccacaaag acggtcgcgg      300
cccaagcatt tgggacgtct tcatcaaaaa acccgggatt gtcgcaaata atggcacggg    360
agaagttt                                                             368

<210> SEQ ID NO 691
<211> LENGTH: 246
<212> TYPE: DNA
<213> ORGANISM: Glycine max

<400> SEQUENCE: 691
gccaagtaaa ttggaaaggt gtagcatact acaataggct gatcaattac ttgctagaaa     60
aaggtattac tccatatgca aatctctacc attatgatct tcctttagca cttgaggaga    120
ggtacaacgg attattgagc cggcaagttg tgaatgattt tgcagattat gcagaatttt    180
gtttcaagac ttttggagat agagttaaga attggatgac gtttaatgaa cctcgtgtgg    240
tggctg                                                               246

<210> SEQ ID NO 692
<211> LENGTH: 277
<212> TYPE: DNA
<213> ORGANISM: Glycine max
<220> FEATURE:
<221> NAME/KEY: unsure
<222> LOCATION: (1)...(277)
<223> OTHER INFORMATION: unsure at all n locations

<400> SEQUENCE: 692
agtaagagtt cactcaatct cactgtgttg tgagttgtgt gtgagcacca accaacaatg     60
gtgtctctga ctccgttatg tttctttatt accttgttga tcgctggtgc anacgcagcg    120
gcggagcccc aaacggtgcg ttttgacacc gggggttga ncagagacac ctttcccaaa     180
ggattcttat tcggaacggc cacgtctgcg taccaagtgg agggtatggc ccacaaagac    240
ggtcgcggcc caagcatttg gacgtcttc atcaaaa                              277

<210> SEQ ID NO 693
<211> LENGTH: 294
<212> TYPE: DNA
<213> ORGANISM: Glycine max
<220> FEATURE:
<221> NAME/KEY: unsure
<222> LOCATION: (1)...(294)
<223> OTHER INFORMATION: unsure at all n locations

<400> SEQUENCE: 693
caaaaacaaa acaaagtaa gagttcactc aatctcactg tgttgtgagt tgtgtgtnag      60
caccaaccaa caatggtgtc tctgactccg ttatgtttct ttattacctt gttgatcgct    120
ggtgcagacg cagcggcgga ncccaaacg gtgcgttttg acaccggggg gttgagcaga     180
gacacctttc ccaaaggatt cttattcgga acgccacgt ctgcgtacca agtgagggt      240
atggcccaca agacggtcg cggcccaagc atttgggacg tcttcatcaa aaaa           294
```

```
<210> SEQ ID NO 694
<211> LENGTH: 291
<212> TYPE: DNA
<213> ORGANISM: Glycine max
<220> FEATURE:
<221> NAME/KEY: unsure
<222> LOCATION: (1)...(291)
<223> OTHER INFORMATION: unsure at all n locations

<400> SEQUENCE: 694
caaanacaaa gtaaganttc antcaatctc actgtgttgt gagttgtgtg tgagcnccaa    60
ccaacaattg gtgtctctga ntccgttatg tttctttatt accttgttga tcgctggtgc   120
agacgcagcn gcggatcccc aaacggtgcg ttttgacacc gggggtgga gcagagacac    180 ctttcccaaa ggnttcttat tcggaacggc cacgtctgcg taccaagtgg agggtatggc    240
ccacaaagac ggtcgcggcc caagcatttg gacgtcttc atcaaaaaac c             291

<210> SEQ ID NO 695
<211> LENGTH: 280
<212> TYPE: DNA
<213> ORGANISM: Glycine max
<220> FEATURE:
<221> NAME/KEY: unsure
<222> LOCATION: (1)...(280)
<223> OTHER INFORMATION: unsure at all n locations

<400> SEQUENCE: 695
caaaaacaaa gtaagagttc actcaatctc actgtgttgt gagttgtgtg tgagcaccaa    60
ccaacaatgg tgtctctgac tccgttatgt ttctttatta ccttgttgat cgctggtgca   120
gacgngngcg gagccccaaa cggtgcgttt tgacaccggg gggttgagca gagacacctt   180
tcccaaagga ttcttattcg gaacggccac gtctgcgtac caagtggagg gtatggccca   240
caaagacggt cgcggcccaa gcatttggga cgncttcatc                         280

<210> SEQ ID NO 696
<211> LENGTH: 263
<212> TYPE: DNA
<213> ORGANISM: Glycine max
<220> FEATURE:
<221> NAME/KEY: unsure
<222> LOCATION: (1)...(263)
<223> OTHER INFORMATION: unsure at all n locations

<400> SEQUENCE: 696
ctcaatctca ctgtgttgtg agtngtgtgt gagcaccaac caacaatngt gtctctgact    60
ccgttatgtt tctttattac cttgttgacc gctggtgcag acgcagcggc ggancccaa    120 acggtgcgtt ttgacaccgg ggggttgagc agagacacct ttcccaaagg attcttattc   180
ggaacggcca cgtctgcgta ccaagtggag ggtatggccc acaaagacgg tcgcggccca   240
agcatttggg acgtcttcat caa                                           263

<210> SEQ ID NO 697
<211> LENGTH: 285
<212> TYPE: DNA
<213> ORGANISM: Glycine max

<400> SEQUENCE: 697
aaaacaaaaa caaagtaaga gttcactcaa tctcactgtg ttgtgagttg tgtgtgagca    60
ccaaccaaca atggtgtctc tgactccgtt atgtttcttt attaccttgt tgatcgctgg   120
```

```
tgcagacgca ccggcggagc cccaaacgtg cgttttgaca ccgggggggtt gagcagagac    180 acctttccca aaggattctt attcggaacg gccacgtctg cgtaccaagt ggagggtatg    240
gcccacaaag acggtcgcgg cccaagcatt tgggacgtct tcatc                    285
```

```
<210> SEQ ID NO 698
<211> LENGTH: 287
<212> TYPE: DNA
<213> ORGANISM: Glycine max
<220> FEATURE:
<221> NAME/KEY: unsure
<222> LOCATION: (1)...(287)
<223> OTHER INFORMATION: unsure at all n locations

<400> SEQUENCE: 698
caaaaacaaa aacaaagtaa ganttcactc aatctcactg tgttgtgagt tgtgtgtgag     60
caccaaccaa caatngtgtc tctgactccg ttatgtttct ttattaccttt gttgatcgct   120 ggtgcagacg cagcggcgga ccccaaacgg tgcgttttga caccgggggg ttgagcagag   180
acacctttcc caaggattc ttattcggaa cggccacgtc tgcgtaccaa gtggagggta    240
tggcccacaa agacggtcgc ggcccaagca tttgggacgt cttcatc                  287
```

```
<210> SEQ ID NO 699
<211> LENGTH: 274
<212> TYPE: DNA
<213> ORGANISM: Glycine max
<220> FEATURE:
<221> NAME/KEY: unsure
<222> LOCATION: (1)...(274)
<223> OTHER INFORMATION: unsure at all n locations

<400> SEQUENCE: 699
ctcaatctca ctgtgttgtg agttgtgtgt gagcaccaac caacaatggt gtctctgact     60
ccgttatgtt tctttattac cttgttgatc gctggtgcag acgcagcggc ggannnccaa   120
acggtgcgtt ttgacaccgg ggggttgagc agagacacct ttcccaaagg attcttattc   180
ggaacggcca cgtctgcgta ccaagtggag ggtatggccc acaaagacgg tcgcggccca   240
agcatttggg acgtcttcat caaaaaaccc ggga                                274
```

```
<210> SEQ ID NO 700
<211> LENGTH: 262
<212> TYPE: DNA
<213> ORGANISM: Glycine max
<220> FEATURE:
<221> NAME/KEY: unsure
<222> LOCATION: (1)...(262)
<223> OTHER INFORMATION: unsure at all n locations

<400> SEQUENCE: 700
ctcaatctca ctgngttatg agttatgtgt gagcnccaac caacaanggn gtctctgact     60
accgtnatgg ttctntatta ccttgtngat cgctggtgca gacgcagcgg cggagcccaa   120
acggngcgtn ttgacaccgg ggggntgagc agagacacct ttcccaaagg nttcttattc   180
ggaacggcca cgtctgcgta ccaagtggag ggtatggccc acaaagacgg tcgcggccca   240
agcatttggg acgtctncat ca                                             262
```

```
<210> SEQ ID NO 701
<211> LENGTH: 254
<212> TYPE: DNA
<213> ORGANISM: Glycine max
<220> FEATURE:
<221> NAME/KEY: unsure
```

```
<222> LOCATION: (1)...(254)
<223> OTHER INFORMATION: unsure at all n locations

<400> SEQUENCE: 701
gttcactcaa tctcactgtg ttgtgagtng tgtgtgagca ccaaccaaca atggtgtctc    60
tgactccgtt atgtttcttt attaccttgt tgatcgctgg tgcagancca gcggcggagc   120
cccaaacggt gcgttttgac accgggggggt tgagcagaga cacctttccc aaaggattct  180
tattcggaac ggccacgtct gcgtaccaag tggagggtat ggcccacaaa gacggtcgcg   240
gcccaagcat ttgg                                                     254

<210> SEQ ID NO 702
<211> LENGTH: 264
<212> TYPE: DNA
<213> ORGANISM: Glycine max
<220> FEATURE:
<221> NAME/KEY: unsure
<222> LOCATION: (1)...(264)
<223> OTHER INFORMATION: unsure at all n locations

<400> SEQUENCE: 702
caaaaacaaa aacaaagtaa gagttcactc aatctcactg tgttgtgagt tgtgtgtgag    60
caccaaccaa caatggtgtc tctgactccg ttatgtttct ttattacctt gttgatcgct   120
ggtgcagacg cagcggcgga nccccaaacg gtgcgttttg acaccggggg gttgagcaga   180
gacacctttc ccaaaggatt cttattcgga acggccacgt ctgcgtacca agtggagggt   240
atggcccaca agacggtcg cggc                                           264

<210> SEQ ID NO 703
<211> LENGTH: 261
<212> TYPE: DNA
<213> ORGANISM: Glycine max
<220> FEATURE:
<221> NAME/KEY: unsure
<222> LOCATION: (1)...(261)
<223> OTHER INFORMATION: unsure at all n locations

<400> SEQUENCE: 703
acaaaaacaa agtaagagtt cactcaatct cactgtgttg tgagttgtgt gtgagcacca    60
accaacaatg gtgtctctga ctccgttatg tttctttatt accttgttga tcgctggtgc   120
agacgcagcg gcggannccc aaacggtgcg ttttgacacc gggggttga gcagagacac    180 ctttcccaaa ggattcttat tcggaacggc cacgtctgcg taccaagtgg agggtatggc   240
ccacaaagac ggtcgcggcc c                                             261

<210> SEQ ID NO 704
<211> LENGTH: 251
<212> TYPE: DNA
<213> ORGANISM: Glycine max
<220> FEATURE:
<221> NAME/KEY: unsure
<222> LOCATION: (1)...(251)
<223> OTHER INFORMATION: unsure at all n locations

<400> SEQUENCE: 704
caaaaacaaa gtaagagttc actcaatctc actgtgttgt gagttgtgtg tgagcaccaa    60
ccaacaatgg tgtctctgac tccgttatgt ttctttatta ccttgttgat cgctggtgca   120
gacgcagcgg cggnccccaa acggtgcgttt tgacaccggg gggttgagca gagacacctt  180
```

```
tcccaaagga ttcttattcg aacggccac gtctgcgtac caagtggagg gtatggccca      240
caaagacggt c                                                          251

<210> SEQ ID NO 705
<211> LENGTH: 247
<212> TYPE: DNA
<213> ORGANISM: Glycine max
<220> FEATURE:
<221> NAME/KEY: unsure
<222> LOCATION: (1)...(247)
<223> OTHER INFORMATION: unsure at all n locations

<400> SEQUENCE: 705
caaaaacaaa aacaaagtaa gngttcactc aatctcactg tgttgtgagt tgtgtgtgag      60
caccaaccaa caatggtgtc tctgactccg ttatgtttct ttattacctt gttgatcgct     120
ggtgcagacg cagcggcgga nccccaaacg gtgcgttttg acaccggggg gttgagcaga     180
gacacctttc ccaaaggatt cttattcgga acggccacgt ctgcgtacca agtggagggt     240
atggccc                                                              247

<210> SEQ ID NO 706
<211> LENGTH: 246
<212> TYPE: DNA
<213> ORGANISM: Glycine max

<400> SEQUENCE: 706
caaaaacaaa aacaaagtaa gagttcactc aatctcactg tgttgtgagt tgtgtgtgag      60
caccaaccaa caatggtgtc tctgactccg ttatgtttct ttattacctt gttgatcgct     120
ggtgcagacg cagcggcgga gccccaaacg gtgcgttttg acaccggggg gttgagcaga     180
gacacctttc ccaaaggatt cttattcgga acggccacgt ctgcgtacca agtggagggt     240
atggcc                                                               246

<210> SEQ ID NO 707
<211> LENGTH: 256
<212> TYPE: DNA
<213> ORGANISM: Glycine max
<220> FEATURE:
<221> NAME/KEY: unsure
<222> LOCATION: (1)...(256)
<223> OTHER INFORMATION: unsure at all n locations

<400> SEQUENCE: 707
caaaaacaaa aacaaagtaa gagttcactc aatctcactg tgttgtgagt tgtgtgtgag      60
caccaaccaa caatggtgtc tctgactccg ttatgtttct ttattacctt gttgatcgct     120
ggtgcagacg cagcggcgga nccccaaacg gtgcgttttg acaccggggg gttgagcaga     180
gacacctttc ccaaaggatt cttattcgga acggccacgt ctgcgtacca agtggagggt     240
atggcccaca aagacg                                                    256

<210> SEQ ID NO 708
<211> LENGTH: 246
<212> TYPE: DNA
<213> ORGANISM: Glycine max
<220> FEATURE:
<221> NAME/KEY: unsure
<222> LOCATION: (1)...(246)
<223> OTHER INFORMATION: unsure at all n locations

<400> SEQUENCE: 708
```

```
caaaaacaaa gtaagagttc actacntctc actgtgttnn nagttgtgtg tgagcaccca     60
ccaacaatgg tgtctctgac tccgttatgt ttctttatta ccttgttgat cgctggtgca    120
gacgcagcgg cggagcccca aacggtgcgt tttgacaccg gggggttgag cagagacacc    180
tttcccaaag gattcttatt cggaacggcc acgtctgcgt accaagtgga gggtatggcc    240
cacaaa                                                              246

<210> SEQ ID NO 709
<211> LENGTH: 233
<212> TYPE: DNA
<213> ORGANISM: Glycine max
<220> FEATURE:
<221> NAME/KEY: unsure
<222> LOCATION: (1)...(233)
<223> OTHER INFORMATION: unsure at all n locations

<400> SEQUENCE: 709
gtngagcacc aaccaacatt ggtgtctctg actncgttat gtttctttat taccttgttg     60
atcgtggtgc agacgcagcg gcggancccc nnacggtgcg ttttgacacc ggngggttga    120
gctgagacac ctttcccaaa ggattcttat tcgnaacggc cacgtntgcg taccatgtgg    180
agggtatngc ccacaaagat ggtcgcggcc naagcatttg gnacgtcttc acc           233

<210> SEQ ID NO 710
<211> LENGTH: 239
<212> TYPE: DNA
<213> ORGANISM: Glycine max

<400> SEQUENCE: 710
caaaaacaaa gtaagagttc actcaatctc actgtgttgt gagttgtgtg tgagcaccaa     60
ccaacaatgg tgtctctgac tccgttatgt ttctttatta ccttgttgat cgctggtgca    120
gacgcagcgg cggagcccca aacggtgcgt tttgacaccg gggggttgag cagagacacc    180
tttcccaaag gattcttatt cggaacggcc acgtctgcgt accaagtgga gggtatggc     239

<210> SEQ ID NO 711
<211> LENGTH: 424
<212> TYPE: DNA
<213> ORGANISM: Glycine max
<220> FEATURE:
<221> NAME/KEY: unsure
<222> LOCATION: (1)...(424)
<223> OTHER INFORMATION: unsure at all n locations

<400> SEQUENCE: 711
cagagaacga ncaagcncaa agccaaagct actagtcata acggggcccc accgcttccg     60
ggaagtcgaa gctagccgtg gatttggcct cccacttccc cggcgaactc atcaacgccg    120
attccatgca ggtctaccgc ggcctngatg ttctcaccaa caaactccct ntctctcacc    180
agaacggagt tccgcatcat ctcttgggta ccgtaagccc caacgtggaa ttcactgcca    240
aagcgtttcg ggattccgnt attcccatta ttgatgatat attggctcgt aatcacttgc    300
ctgttatagt tgggggcact aattactata tccaggctct tgtgagtccg tttcttttag    360
atgattctgc agaagatatg gatgaaagct ggttgggtga tccaactggg tctggaacaa    420
tttc                                                                424
```

NUCLEIC ACID MOLECULES AND OTHER MOLECULES ASSOCIATED WITH THE CYTOKININ PATHWAY

CROSS REFERENCE TO RELATED APPLICATIONS

This application claims priority under 35 U.S.C. §120 as a continuation-in-part of application Ser. No. 09/199,129 filed Nov. 24, 1998 now abandoned; as a continuation-in-part of application Ser. No. 09/210,297 filed Dec. 8, 1998 (now abandoned); and as a continuation of application Ser. No. 09/227,586 filed Jan. 8, 1999 (now abandoned); and claims priority under 35 U.S.C. §119(e) to U.S. Provisional Applications No. 60/067,000 filed Nov. 24, 1997; No. 60/069,472 filed Dec. 9, 1997; No. 60/071,064 filed Jan. 9, 1998; No. 60/074,201 filed Feb. 10, 1998; No. 60/074,281 filed Feb. 10, 1998; No. 60/074,567 filed Feb. 12, 1998; No. 60/074,565 filed Feb. 12, 1998; No. 60/075,462 filed Feb. 19, 1998; No. 60/075,461 filed Feb. 19, 1998; No. 60/075,464 filed Feb. 19, 1998; No. 60/075,460 filed Feb. 19, 1998; No. 60/075,463 filed Feb. 19, 1998; No. 60/077,231 filed Mar. 9, 1998; No. 60/077,229 filed Mar. 9, 1998; No. 60/077,230 filed Mar. 9, 1998; No. 60/078,368 filed Mar. 18, 1998; No. 60/080,844 filed Apr. 7, 1998; No. 60/083,067 filed Apr. 27, 1998; No. 60/083,387 filed Apr. 29, 1998; No. 60/083,388 filed Apr. 29, 1998; No. 60/085,224 filed May 13, 1998; No. 60/085,223 filed May 13, 1998; No. 60/085,222 filed May 13, 1998; No. 60/086,186 filed May 21, 1998; No. 60/086,187 filed May 21, 1998; No. 60/086,185 filed May 21, 1998; No. 60/086,184 filed May 21, 1998; No. 60/086,188 filed May 21, 1998; No. 60/089,524 filed Jun. 16, 1998; No. 60/089,810 filed Jun. 18, 1998; No. 60/089,814 filed Jun. 18, 1998; No. 60/090,170 filed Jun. 22, 1998; No. 60/092,036 filed Jul. 8, 1998; No. 60/099,670 filed Sep. 9, 1998; No. 60/099,697 filed Sep. 9, 1998; No. 60/100,674 filed Sep. 16, 1998; No. 60/101,132 filed Sep. 21, 1998; No. 60/101,130 filed Sep. 21, 1998; No. 60/101,508 filed Sep. 22, 1998; No. 60/101,344 filed Sep. 22, 1998; No. 60/101,347 filed Sep. 22, 1998; No. 60/101,343 filed Sep. 22, 1998; No. 60/104,126 filed Oct. 13, 1998; No. 60/104,127 filed Oct. 13, 1998; No. 60/104,124 filed Oct. 13, 1998; No. 60/104,121 filed Oct. 13, 1998; and No. 60/111,981 filed Dec. 11, 1998 the disclosures of which applications are herein incorporated by reference in their entirety.

INCORPORATION OF SEQUENCE LISTING

A paper copy of the Sequence Listing and a computer readable form of the Sequence Listing on diskette, containing the file cytoseq2.txt, which is 393,815 bytes in size (measured in MS-DOS) and created on Sep. 27, 2001, are herein incorporated by reference.

FIELD OF THE INVENTION

The present invention is in the field of plant biochemistry. More specifically the invention relates to nucleic acid sequences from plant cells, in particular, nucleic acid sequences from maize and soybean plants associated with the cytokinin pathway. The invention encompasses nucleic acid molecules that encode proteins and fragments of proteins. In addition, the invention also encompasses proteins and fragments of proteins so encoded and antibodies capable of binding these proteins or fragments. The invention also relates to methods of using the nucleic acid molecules, proteins and fragments of proteins and antibodies, for example for genome mapping, gene identification and analysis, plant breeding, preparation of constructs for use in plant gene expression and transgenic plants.

BACKGROUND OF THE INVENTION

Plant hormones, produced in response to genetic, environmental or chemical stimuli (Goldberg, Science 240: 1460-1467 (1988); Letham, In: *Phytohormones and Related Compounds—A Comprehensive Treatise, eds.* Letham et al., Amsterdam, Elsevier North Holland. 1: 205-263 (1978); von Sachs, *Arb. Bot. Inst. Wurzburg* 2:452-488 (1880), all of which are herein incorporated by reference in their entirety), play a role in controlling the growth, development and environmental responses of plants.

Cytokinins are a class of plant hormones with a structure resembling adenine. Cytokinins, in combination with auxin, promote cell division. Cytokinins are associated with many aspects of plant growth and development (Horgan, *Advanced Plant Physiology*, ed. Wilkins, Pitman, London: 90-116 (1984); Skoog et al., *Biochemical Actions of Hormones*, ed. Litwack, Academic Press, London, vol. VI: 335-413 (1979), all of which are herein incorporated by reference in their entirety). Cytokinins have been found in almost all higher plants as well as mosses, fungi, and bacteria. In addition to occurring in higher plants as free compounds, cytokinins may also occur as component nucleosides in tRNA of plants, animals, and microorganisms.

Kinetin, the first cytokinin to be discovered, was so named because of its ability to promote cytokinesis (cell division). Although kinetin is a natural compound, it is not made in plants, and is therefore usually considered a "synthetic" cytokinin. Two common forms of cytokinin in plants are zeatin and zeatin riboside (maize)(Letham, *Life Sci.* 2: 569-573 (1963), the entirety of which is herein incorporated by reference). More than 200 known natural and synthetic cytokinins have been reported.

Several cytokinin related mutations have also been reported. For example, the ckrl mutant of *Arabidopsis* is resistant to the cytokinin bezyladenine (Su and Howell, *Plant Physiol.* 99:1569-1574 (1992), the entirety of which is herein incorporated by reference). The *Arabidopsis* mutant amp1 has been reported to be a negative regulator of cytokinin biosynthesis (Chadbury et al., *Plant J.* 4:907-916 (1993), the entirety of which is herein incorporated by reference).

Cytokinin concentrations are highest in meristematic regions and areas of continuous growth potential such as roots, young leaves, developing fruits, and seeds (Arteca, *Plant Growth Substances: Principles and Applications*, eds. Chapman & Hall, New York (1996); Mauseth, Botany: *An Introduction to Plant Biology*, ed. Saunders, Philadelphia: 348-415 (1991); Raven et al., *Biology of Plants*, ed. Worth, N.Y.: 545-572 (1992); Salisbury and Ross, *Plant Physiology*, ed. Wadsworth, Belmont, Calif.: 357-407, 531-548 (1992), all of which are herein incorporated by reference in their entirety).

It has been reported that the induced cytokinin response varies depending on the type of cytokinin and plant species (Davies, Plant Hormones: *Physiology, Biochemistry and Molecular Biology*, Kluwer, Dordrecht (1995); Mauseth, Botany: *An Introduction to Plant Biology*, Saunders, Philadelphia: 348-415 (1991); Raven et al., *Biology of Plants*, ed. Worth, N.Y.: 545-572 (1992); Salisbury and Ross, *Plant Physiology*, ed. Wadsworth, Belmont, Calif.: 357-407, 531-548 (1992), all of which are herein incorporated by reference in their entirety). Elevated cytokinin levels are associated with the development of seeds in higher plants, and have been demonstrated to coincide with maximal mitotic activity in the endosperm of developing maize kernels, cereal grains, and fruits. Exogenous cytokinin application (via stem injection) has been shown to directly correlate with increased kernel yield in maize. In addition, plant cells transformed with the ipt gene from *Agrobacterium tumefaciens* showed increased growth corresponding to an increase in endogenous cytokinin levels upon induction of the enzyme. Cytokinins have been reported to confer thermotolerance in certain physiological processes such as plastid biogenesis and endosperm cell division (Cheikh and Jones, *Plant Physiol*. 106: 45-51 (1994); Parthier, *Biochem. Physiol Pflanz* 174:173-214 (1979); Jones et al., *Crop Science* 25: 830-834 (1985), all of which are herein incorporated by reference in their entirety).

Reviews of cytokinin metabolism, compartmentalization, conjugation and cytokinin metabolic enzymes have been presented by Jameson, Cytokinins, eds. Mok and Mok, Boca Raton, Fla., 113-128 (1994); Letham and Palni, *Ann. Rev. Plant Physiol*. 34: 163-197 (1983); McGaw et al. *In: Biosynthesis and metabolism of plant hormones*, Soc. Exp. Biol. Seminar Series, eds. Crozier and Hillman, Cambridge University Press, Cambridge, Vol. 23, chapter 5 (1984); McGaw and Horgan, *Biol. Plant* 27: 180 (1985); McGaw et al., *In: Plant Hormones: Physiology, Biochemistry and Molecular Biology*, ed. Davies, Kluwer, Dordrecht, 98-117 (1995); Mok and Martin, *Cytokinins, eds*. Mok and Mok, Boca Raton, Fla., 129-137 (1994); Salisbury and Ross, *Plant Physiology*, Belmont, Calif.: ed. Wadsworth, 357-407, 531-548 (1992), all of which are hereby incorporated by reference in their entirety.

I. Biosynthesis of Cytokinins

Cytokinins are generally found in higher concentrations in meristematic regions and growing tissues. It has been reported that cytokinins are synthesized in the roots and translocated via the xylem to the meristematic regions and growing shoots of the plant. Although cytokinin biosynthesis in developed plants takes place mainly in roots (Engelbrecht, *Biochem. Physiol. Pflanzen* 163: 335-343 (1972); Henson et al., *J. Exp. Bot* 27: 1268-1278 (1976); Sossountzov et al., *Planta* 175: 291-304 (1988); Van Staden et al., *Ann. Bot*. 42: 751-753 (1978), all of which are herein incorporated by reference in their entirety), smaller amounts can be synthesized by the shoot apex and some other plant tissues.

The level of active cytokinin at a particular site of action has been reported to be influenced by a large number of factors: de novo synthesis; oxidative degradation; reduction; formation and hydrolysis of inactive conjugates; transport into and out of particular cells; subcellular compartmentalization to or away from sites of action. It has also been reported that physiological responses may be modulated by variations in the ability of cells to respond to a particular concentration of free cytokinin.

Cytokinin biosynthesis happens through the biochemical modification of adenine (McGaw et al., *In: Plant Hormones: Physiology, Biochemistry and Molecular Biology*, ed. Davies, Kluwer, Dordrecht: 98-117 (1995), the entirety of which is herein incorporated by reference; Salisbury and Ross, *Plant Physiology*, Belmont, Calif.: ed. Wadsworth, 357-407, 531-548 (1992), the entirety of which is herein incorporated by reference). Plants appear to synthesize cytokinins either directly by addition of isopentenylpyrophosphate to AMP by an adenylate:isopentenyltransferase (cytokinin synthase) producing isopentenyladenosine 5' phosphate ("[9R-5'P]iP"), which in turn serves as an intermediate for further modifications, or indirectly via isopentenylation of adenosine residues of tRNA by tRNA:isopentenyltransferase (McGaw et al., *In: Plant Hormones: Physiology, Biochemistry and Molecular Biology*, ed. Davies, Kluwer, Dordrecht: 98-117 (1995)). [9R-5'P]iP may be modified by dephosphorylation, deribosylation, hydroxylation and reduction to produce a variety of derivatives with potential activity (Binns, *Annu. Rev. Plant Physiol. Plant Mol. Biol*. 45: 173-196 (1994), the entirety of which is herein incorporated by reference). Further, conjugation may modulate levels of active cytokinins (Letham and Palni, *Ann. Rev. Plant Physiol*. 34: 163-197 (1983), the entirety of which is herein incorporated by reference).

In the biosynthesis of tRNA cytokinins, mevalonic acid pyrophosphate undergoes decarboxylation, dehydration and isomerization to yield 2-isopentyl pyrophosphate ("iPP"). iPP then condenses with the relevant adenosine residue in the tRNA to give the N6(Δ2-isopentenyl)adenosine ("[9R]iP") moiety. With the exception of [9R]iP and to a lessor extent cis- and trans-[9R]Z, the free and tRNA cytokinins are structurally distinct (e.g., free Zeatin ("Z") is mainly the trans isomer (trans-Zeatin while Z present in tRNA is mainly the cis isomer (McGaw et al., *In: Plant Hormones: Physiology, Biochemistry and Molecular Biology*, ed. Davies, Kluwer, Dordrecht, 98-117 (1995).

The de novo biosynthesis pathway of cytokinins in plants includes the following enzymes: isopentyltransferase, 5'-nucleosidase, adenine nucleotidase, adenine phosphorylase, adenine kinase, adenine phosphoribosyl transferase, microsomal mixed function oxidases, Zeatin reductase, O-glucosyltransferase, O-xylosyltransferase, β-(9-cytokinin-alanino)synthase, cytokinin oxidase, β-glucosidase, and Zeatin cis-trans isomerase.

Isopentyltransferase catalyzes the first reaction of the pathway in which N6(Δ2-isopentenyl) adenosine-5'-monophosphate ("[9R-5'P]iP") is generated from iPP and AMP.

5'-nucleotidase catalyzes the conversion of [9R-5'P]iP to [9R]iP. The reaction catalyzed by the enzyme 5'-nucleotidase has been found in wheat germ extract (Chen et al., Plant Physiol. 67:494-498 (1981); Chen et al., Plant Physiol. 68:1020-1023 (1981), both of which are herein incorporated by reference in their entirety) and in tomato leaf and root extracts (Burch and Stuchbury, *Phytochemistry* 25:2445-2449 (1986); Burch and Stuchbury, *J. Plant Physiol*. 125: 267-273 (1986), both of which are herein incorporated by reference in their entirety). Adenine kinase catalyzes the reversion of [9R]iP to [9R-5'P]iP. Alternatively, [9R-5'P]iP can be converted to t-Zeatin riboside-5'-monophosphate ("[9R-5'P]Z") by a microsomal mixed function oxidase.

Adenosine nucleotidase catalyzes the conversion of [9R]iP to iP. This reaction can be reversed by the enzyme adenine phosphorylase. Alternatively, [9R]iP can be converted to t-Zeatin riboside ("[9R]Z") by a microsomal mixed function oxidase. Under another reaction mechanism, adenosine can be cleaved from [9R]iP by cytokinin oxidase. The enzyme adenine phosphoribosyl transferase can catalyze the conversion of iP to [9R-5'P]iP. Adenine phosphoribosyl transferase which is one of the salvage routes in plants for converting adenosine to AMP has also been shown to catalyze the phosphoribolyzation of cytokinin bases from a number of plant sources, including wheat germ (Chen et al., *Arch. Biochem. Biophys*. 214:634-641 (1982), the entirety of which is herein incorporated by reference), tomato (Burch et al., *Physiol. Plant* 69:283-288 (1987), the entirety of which is herein incorporated by reference), *A. thaliana* (Moffatt et al., *Plant Physiol* 95:900-908 (1991), the entirety of which is herein incorporated by reference) and *Acer psudoplatanus* (Doree and Guern, *Biochem. Biophys. Acta* 304:611-622 (1973); Sadorge et al., *Physiol. Veg*. 8:499-514 (1970), both of which are herein incorporated by reference in their entirety).

The cytokinins N6(Δ2-isopentenyl) adenosine-7-glucoside ("[7G]iP") and N6(Δ2-isopentenyl) adenosine-9-glucoside ("[9G]iP") are generated from iP from the enzymes Zeatin reductase and O-glucosyltransferase (such as cytokinin-9-glucosyl transferase), respectively. Under another reaction mechanism, adenine can be cleaved from iP by cytokinin oxidase.

In addition to converting [9R-5'P]iP to [9R]iP, 5'-nucleotidase can also catalyze the conversion of [9R-5'P]Z to [9R]Z. Adenine kinase can catalyze the conversion of [9R]Z to [9R-5'P]Z.

O-glucosyltransferase catalyzes the conversion of [9R]Z to t-Zeatin riboside-O-glucoside ("(OG)[9R]Z"). O-glucosyltransferase can also remove the glucoside group from (OG)[9R]Z to regenerate [9R]Z. Adenosine can be cleaved from [9R]Z by cytokinin oxidase. Alternatively, adenine nucleotidase can convert [9R]Z to Z. Adenine phosphorylase can catalyze the conversion of Z back into [9R]Z.

The cytokinins dihidroZeatin ("(diH)Z"), Zeatin-7-glucoside ([7G]Z), Zeatin-9-glucoside ("[9G]Z"), and lupinic acid ("[9Ala]Z") are generated from Z by the enzymes Zeatin reductase, O-glucosyltansferase, Zeatin reductase and β-(9-cytokinin alanino) synthase, respectively. Zeatin cis-trans isomerase catalyzes the isomerization of Zeatin between its cis and trans isomers. O-glucosyltransferase catalyzes the addition of a glucoside residue to Z to form t-Zeatin-O-glucoside ("(OG)Z") or removal of a glucoside residue from (OG)Z to form Z.

The cytokinins dihydroZeatin-9-glucoside ("(diH)[9G]Z"), dihydroZeatin-7-glucoside ("(diH)[7G]Z"), and dihydrolupinic acid ("(diH)[9Ala]Z") are generated from (diH)Z by the enzymes β-(9-cytokinin alanino)synthase, Zeatin reductase, and O-glucosyltansferase, respectively. O-glucosyltransferase catalyzes the addition of a glucoside residue to (diH)Z to form t-Zeatin-O-glucoside ("(diHOG)Z") or removal of a glucoside residue from (diHOG)Z to form (diH)Z. Alternatively, (diH)Z can be converted into dihydroZeatin riboside ((diH)[9R]Z) by adenine phosphorylase. The enzyme adenine nucleotidase can catalyze the conversion of (diH)[9R]Z to (diH)Z.

O-glucosyltransferase catalyzes the addition of a glucoside residue to (diH)[9R]Z to form t-dihydroZeatin riboside-O-glucoside ("(diHOG)[9R]Z") or the removal of a glucoside residue from (diHOG)[9R]Z to form (diH)[9R]Z. The cytokinin dihydroZeatin riboside-5'-monophosphate ("(diH)[9R-5'P]Z") is generated from (diH)[9R]Z by the enzyme adenine kinase. This reaction can be reversed by the enzyme 5'-nucleotidase.

It is understood that the above description of the de novo biosynthesis of cytokinins only describes the core of the biosynthesis pathway. Other enzymes have been reported to be involved in this pathway.

Active cytokinins can be inactivated by degradation or conjugation to different low-molecular-weight metabolites, such as sugars and amino acids. The enzyme cytokinin oxidase plays a role in the degradation of cytokinins. This enzyme removes the side chain and releases adenine, the backbone of all cytokinins. Cytokinin oxidases are reported to remove cytokinins from plant cells after cell division. Cytokinin derivatives are also made.

β-glucosidase (EC 3.2.1.21) has been reported to cleave the biologically inactive hormone conjugates of cytokinin-O-glucoside to release the active cytokinin (Brzobohaty et al., Science 262:1051-1054 (1993); Campos et al., Plant J. 2:675-684 (1992), both of which are herein incorporated by reference in their entirety). β-glucosidase catalyzes the hydrolysis of aryl and alkyl β-D-glucosides and/or cellobiose with the release of β-D-glucose (Reese, Recent Adv. Phytochem. 11:311 (1977), the entirety of which is herein incorporated by reference). The enzyme has been purified from maize and has a molecular weight of 60 kD (Esen, Plant Physiol. 98:174-182 (1992); Esen et al., Biochem. Genet. 28:319-336 (1990), both of which are herein incorporated by reference). Esen et al. have identified the rolC gene of Agrobacterium rhizogenes which encodes for a cytokinin β-glucosidase and which effects the growth and development of transgenic plants (Esen et al., EMBO J. 10:2889-2895 (1991), the entirety of which is herein incorporated by reference).

Conjugation is often reported as a way of removing free and active hormones from a tissue. The conjugation process is often reversible, and, as conjugates can frequently accumulate in excess of free forms of phytohormone. The conjugate pools are also considered as sources of free hormone and may represent storage or inactive transportable forms of the hormone.

II. Expressed Sequence Tag Nucleic Acid Molecules

Expressed sequence tags, or ESTs are randomly sequenced members of a cDNA library (or complementary DNA)(McCombie et al., Nature Genetics 1:124-130 (1992); Kurata et al., Nature Genetics 8:365-372 (1994); Okubo et al., Nature Genetics 2:173-179 (1992), all of which references are incorporated herein in their entirety). The randomly selected clones comprise insets that can represent a copy of up to the full length of a mRNA transcript.

Using conventional methodologies, cDNA libraries can be constructed from the mRNA (messenger RNA) of a given tissue or organism using poly dT primers and reverse transcriptase (Efstratiadis et al., Cell 7:279-3680 (1976), the entirety of which is herein incorporated by reference; Higuchi et al., Proc. Natl. Acad. Sci. (U.S.A.) 73:3146-3150 (1976), the entirety of which is herein incorporated by reference; Maniatis et al., Cell 8:163-182 (1976) the entirety of which is herein incorporated by reference; Land et al., Nucleic Acids Res. 9:2251-2266 (1981), the entirety of which is herein incorporated by reference; Okayama et al., Mol. Cell. Biol. 2:161-170 (1982), the entirety of which is herein incorporated by reference; Gubler et al., Gene 25:263-269 (1983), the entirety of which is herein incorporated by reference).

Several methods may be employed to obtain full-length cDNA constructs. For example, terminal transferase can be used to add homopolymeric tails of dC residues to the free 3' hydroxyl groups (Land et al., Nucleic Acids Res. 9:2251-2266 (1981), the entirety of which is herein incorporated by reference). This tail can then be hybridized by a poly dG oligo which can act as a primer for the synthesis of full length second strand cDNA. Okayama and Berg, Mol. Cell. Biol. 2:161-170 (1982), the entirety of which is herein incorporated by reference, report a method for obtaining full length cDNA constructs. This method has been simplified by using synthetic primer-adapters that have both homopolymeric tails for priming the synthesis of the first and second strands and restriction sites for cloning into plasmids (Coleclough et al., Gene 34:305-314 (1985), the entirety of which is herein incorporated by reference) and bacteriophage vectors (Krawinkel et al., Nucleic Acids Res. 14:1913 (1986), the entirety of which is herein incorporated by reference; Han et al., Nucleic Acids Res. 15:6304 (1987), the entirety of which is herein incorporated by reference).

These strategies have been coupled with additional strategies for isolating rare mRNA populations. For example, a typical mammalian cell contains between 10,000 and 30,000 different mRNA sequences (Davidson, Gene Activity in Early Development, 2nd ed., Academic Press, New York (1976), the entirety of which is herein incorporated by reference). The number of clones required to achieve a given probability that a low-abundance mRNA will be present in a cDNA library is $N=(\ln(1-P))/(\ln(1-1/n))$ where N is the number of clones required, P is the probability desired and 1/n is the fractional proportion of the total mRNA that is represented by a single rare mRNA (Sambrook et al., *Molecular Cloning: A Laboratory Manual,* 2nd ed., Cold Spring Harbor Laboratory Press (1989), the entirety of which is herein incorporated by reference).

A method to enrich preparations of mRNA for sequences of interest is to fractionate by size. One such method is to fractionate by electrophoresis through an agarose gel (Pennica et al., *Nature* 301:214-221 (1983), the entirety of which is herein incorporated by reference). Another such method employs sucrose gradient centrifugation in the presence of an agent, such as methylmercuric hydroxide, that denatures secondary structure in RNA (Schweinfest et al., *Proc. Natl. Acad. Sci. (U.S.A.)* 79:4997-5000 (1982), the entirety of which is herein incorporated by reference).

A frequently adopted method is to construct equalized or normalized cDNA libraries (Ko, *Nucleic Acids Res.* 18:5705-5711 (1990), the entirety of which is herein incorporated by reference; Patanjali et al., *Proc. Natl. Acad. Sci. (U.S.A.)* 88:1943-1947 (1991), the entirety of which is herein incorporated by reference). Typically, the cDNA population is normalized by subtractive hybridization (Schmid et al., *J. Neurochem.* 48:307-312 (1987), the entirety of which is herein incorporated by reference; Fargnoli et al., *Anal. Biochem.* 187:364-373 (1990), the entirety of which is herein incorporated by reference; Travis et al., *Proc. Natl. Acad. Sci. (U.S.A.)* 85:1696-1700 (1988), the entirety of which is herein incorporated by reference; Kato, *Eur. J. Neurosci.* 2:704-711 (1990); and Schweinfest et al., *Genet. Anal. Tech. Appl.* 7:64-70 (1990), the entirety of which is herein incorporated by reference). Subtraction represents another method for reducing the population of certain sequences in the cDNA library (Swaroop et al., *Nucleic Acids Res.* 19:1954 (1991), the entirety of which is herein incorporated by reference).

ESTs can be sequenced by a number of methods. Two basic methods may be used for DNA sequencing, the chain termination method of Sanger et al., *Proc. Natl. Acad. Sci. (U.S.A.)* 74:5463-5467 (1977), the entirety of which is herein incorporated by reference and the chemical degradation method of Maxam and Gilbert, *Proc. Nat. Acad. Sci. (U.S.A.)* 74:560-564 (1977), the entirety of which is herein incorporated by reference. Automation and advances in technology such as the replacement of radioisotopes with fluorescence-based sequencing have reduced the effort required to sequence DNA (Craxton, *Methods* 2:20-26 (1991), the entirety of which is herein incorporated by reference; Ju et al., *Proc. Natl. Acad. Sci. (U.S.A.)* 92:4347-4351 (1995), the entirety of which is herein incorporated by reference; Tabor and Richardson, *Proc. Natl. Acad. Sci. (U.S.A.)* 92:6339-6343 (1995), the entirety of which is herein incorporated by reference). Automated sequencers are available from, for example, Pharmacia Biotech, Inc., Piscataway, N.J. (Pharmacia ALF), LI-COR, Inc., Lincoln, Nebr. (LI-COR 4,000) and Millipore, Bedford, Mass. (Millipore BaseStation).

In addition, advances in capillary gel electrophoresis have also reduced the effort required to sequence DNA and such advances provide a rapid high resolution approach for sequencing DNA samples (Swerdlow and Gesteland, *Nucleic Acids Res.* 18:1415-1419 (1990); Smith, *Nature* 349:812-813 (1991); Luckey et al., *Methods Enzymol.* 218:154-172 (1993); Lu et al., *J. Chromatog. A.* 680:497-501 (1994); Carson et al., *Anal. Chem.* 65:3219-3226 (1993); Huang et al., *Anal. Chem.* 64:2149-2154 (1992); Kheterpal et al., *Electrophoresis* 17:1852-1859 (1996); Quesada and Zhang, *Electrophoresis* 17:1841-1851 (1996); Baba, *Yakugaku Zasshi* 117:265-281 (1997), all of which are herein incorporated by reference in their entirety).

ESTs longer than 150 nucleotides have been found to be useful for similarity searches and mapping (Adams et al., *Science* 252:1651-1656 (1991), herein incorporated by reference). ESTs, which can represent copies of up to the full length transcript, may be partially or completely sequenced. Between 150-450 nucleotides of sequence information is usually generated as this is the length of sequence information that is routinely and reliably produced using single run sequence data. Typically, only single run sequence data is obtained from the cDNA library (Adams et al., *Science* 252: 1651-1656 (1991). Automated single run sequencing typically results in an approximately 2-3% error or base ambiguity rate (Boguski et al., *Nature Genetics* 4:332-333 (1993), the entirety of which is herein incorporated by reference).

EST databases have been constructed or partially constructed from, for example, *C. elegans* (McCombrie et al., *Nature Genetics* 1:124-131 (1992)), human liver cell line HepG2 (Okubo et al., *Nature Genetics* 2:173-179 (1992)), human brain RNA (Adams et al., *Science* 252:1651-1656 (1991); Adams et al., *Nature* 355:632-635 (1992)), *Arabidopsis,* (Newman et al., *Plant Physiol.* 106:1241-1255 (1994)); and rice (Kurata et al., *Nature Genetics* 8:365-372 (1994)).

III. Sequence Comparisons

A characteristic feature of a DNA sequence is that it can be compared with other DNA sequences. Sequence comparisons can be undertaken by determining the similarity of the test or query sequence with sequences in publicly available or proprietary databases ("similarity analysis") or by searching for certain motifs ("intrinsic sequence analysis")(e.g. cis elements)(Coulson, *Trends in Biotechnology* 12:76-80 (1994), the entirety of which is herein incorporated by reference); Birren et al., *Genome Analysis* 1: Cold Spring Harbor Laboratory Press, Cold Spring Harbor, N.Y. 543-559 (1997), the entirety of which is herein incorporated by reference).

Similarity analysis includes database search and alignment. Examples of public databases include the DNA Database of Japan (DDBJ) (www-ddbj.nig.ac.jp/); Genebank (www-ncbi.nlm.nih.gov/Web/Search/Index.html); and the European Molecular Biology Laboratory Nucleic Acid Sequence Database (EMBL) (www-ebi.ac.uk/ebi_docs/embl_db/embl_db.html). Other appropriate databases include dbEST (www-ncbi.nlm.nih.gov/ dbEST/index.html), Swiss Prot (www-ebi.ac.uk/ebi_docs/swisprot$_{13}$db/swisshome.html), PIR (www-nbrt.georgetown.edu/pir/) and The Institute for Genome Research (www-tigr. org/tdb/tdb.html).

A number of different search algorithms have been developed, one example of which are the suite of programs referred to as BLAST programs. There are five implementations of BLAST, three designed for nucleotide sequences queries (BLASTN, BLASTX and TBLASTX) and two designed for protein sequence queries (BLASTP and TBLASTN) (Coulson, *Trends in Biotechnology* 12:76-80 (1994); Birren et al., *Genome Analysis* 1, Cold Spring Harbor Laboratory Press, Cold Spring Harbor, N.Y. 543-559 (1997)).

BLASTN takes a nucleotide sequence (the query sequence) and its reverse complement and searches them against a nucleotide sequence database. BLASTN was designed for speed, not maximum sensitivity and may not find distantly related coding sequences. BLASTX takes a nucleotide sequence, translates it in three forward reading frames and three reverse complement reading frames and then compares the six translations against a protein sequence database. BLASTX is useful for sensitive analysis of preliminary (single-pass) sequence data and is tolerant of sequencing errors (Gish and States, *Nature Genetics* 3:266-272 (1993), the entirety of which is herein incorporated by reference). BLASTN and BLASTX may be used in concert for analyzing EST data (Coulson, *Trends in Biotechnology* 12:76-80 (1994); Birren et al., *Genome Analysis* 1:543-559 (1997)).

Given a coding nucleotide sequence and the protein it encodes, it is often preferable to use the protein as the query sequence to search a database because of the greatly increased sensitivity to detect more subtle relationships. This is due to the larger alphabet of proteins (20 amino acids) compared with the alphabet of nucleic acid sequences (4 bases), where it is far easier to obtain a match by chance. In addition, with nucleotide alignments, only a match (positive score) or a mismatch (negative score) is obtained, but with proteins, the presence of conservative amino acid substitutions can be taken into account. Here, a mismatch may yield a positive score if the non-identical residue has physical/chemical properties similar to the one it replaced. Various scoring matrices are used to supply the substitution scores of all possible amino acid pairs. A general purpose scoring system is the BLOSUM62 matrix (Henikoff and Henikoff, *Proteins* 17:49-61 (1993), the entirety of which is herein incorporated by reference), which is currently the default choice for BLAST programs. BLOSUM62 is tailored for alignments of moderately diverged sequences and thus may not yield the best results under all conditions. Altschul, *J. Mol. Biol.* 36:290-300 (1993), the entirety of which is herein incorporated by reference, describes a combination of three matrices to cover all contingencies. This may improve sensitivity, but at the expense of slower searches. In practice, a single BLOSUM62 matrix is often used but others (PAM40 and PAM250) may be attempted when additional analysis is necessary. Low PAM matrices are directed at detecting very strong but localized sequence similarities, whereas high PAM matrices are directed at detecting long but weak alignments between very distantly related sequences.

Homologues in other organisms are available that can be used for comparative sequence analysis. Multiple alignments are performed to study similarities and differences in a group of related sequences. CLUSTAL W is a multiple sequence alignment package available that performs progressive multiple sequence alignments based on the method of Feng and Doolittle, *J. Mol. Evol.* 25: 351-360 (1987), the entirety of which is herein incorporated by reference. Each pair of sequences is aligned and the distance between each pair is calculated; from this distance matrix, a guide tree is calculated, and all of the sequences are progressively aligned based on this tree. A feature of the program is its sensitivity to the effect of gaps on the alignment; gap penalties are varied to encourage the insertion of gaps in probable loop regions instead of in the middle of structured regions. Users can specify gap penalties, choose between a number of scoring matricies, or supply their own scoring matrix for both the pairwise alignments and the multiple alignments. CLUSTAL W for UNIX and VMS systems is available by ftp at: ebi.ac.uk. Another program is MACAW (Schuler et al., *Proteins, Stuct. Func. Genet,* 9:180-190 (1991), the entirety of which is herein incorporated by reference), for which both Macintosh and Microsoft Windows versions are available. MACAW uses a graphical interface, provides a choice of several alignment algorithms, and is available by anonymous ftp at: ncbi.nlm.nih.gov (directory/pub/macaw).

Sequence motifs are derived from multiple alignments and can be used to examine individual sequences or an entire database for subtle patterns. With motifs, it is sometimes possible to detect distant relationships that may not be demonstrable based on comparisons of primary sequences alone. Currently, the largest collection of sequence motifs in the world is PROSITE (Bairoch and Bucher, *Nucleic Acid Research* 22:3583-3589 (1994), the entirety of which is herein incorporated by reference). PROSITE may be accessed via either the ExPASy server on the World Wide Web or anonymous ftp site. Many commercial sequence analysis packages also provide search programs that use PROSITE data.

A resource for searching protein motifs is the BLOCKS E-mail server developed by Henikoff, *Trends Biochem Sci.* 18:267-268 (1993), the entirety of which is herein incorporated by reference; Henikoff and Henikoff, *Nucleic Acid Research* 19:6565-6572 (1991), the entirety of which is herein incorporated by reference; Henikoff and Henikoff, *Proteins* 17:49-61 (1993). BLOCKS searches a protein or nucleotide sequence against a database of protein motifs or "blocks." Blocks are defined as short, ungapped multiple alignments that represent highly conserved protein patterns. The blocks themselves are derived from entries in PROSITE as well as other sources. Either a protein query or a nucleotide query can be submitted to the BLOCKS server; if a nucleotide sequence is submitted, the sequence is translated in all six reading frames and motifs are sought for these conceptual translations. Once the search is completed, the server will return a ranked list of significant matches, along with an alignment of the query sequence to the matched BLOCKS entries.

Conserved protein domains can be represented by two-dimensional matrices, which measure either the frequency or probability of the occurrences of each amino acid residue and deletions or insertions in each position of the domain. This type of model, when used to search against protein databases, is sensitive and usually yields more accurate results than simple motif searches. Two popular implementations of this approach are profile searches such as GCG program ProfileSearch and Hidden Markov Models (HMMs)(Krough et al., *J. Mol. Biol.* 235:1501-1531, (1994); Eddy, *Current Opinion in Structural Biology* 6:361-365, (1996), both of which are herein incorporated by reference in their entirety). In both cases, a large number of common protein domains have been converted into profiles, as present in the PROSITE library, or HHM models, as in the Pfam protein domain library (Sonnhammer et al., *Proteins* 28:405-420 (1997), the entirety of which is herein incorporated by reference). Pfam contains more than 500 HMM models for enzymes, transcription factors, signal transduction molecules and structural proteins. Protein databases can be queried with these profiles or HMM models, which will identify proteins containing the domain of interest. For example, HMMSW or HMMFS, two programs in a public domain package called HMMER (Sonnhammer et al., *Proteins* 28:405-420 (1997)) can be used.

PROSITE and BLOCKS represent collected families of protein motifs. Thus, searching these databases entails submitting a single sequence to determine whether or not that sequence is similar to the members of an established family. Programs working in the opposite direction compare a collection of sequences with individual entries in the protein databases. An example of such a program is the Motif Search Tool, or MoST (Tatusov et al., *Proc. Natl. Acad. Sci.* (*U.S.A.*) 91:12091-12095 (1994), the entirety of which is herein incorporated by reference). On the basis of an aligned set of input sequences, a weight matrix is calculated by using one of four methods (selected by the user). A weight matrix is simply a representation, position by position of how likely a particular amino acid will appear. The calculated weight matrix is then used to search the databases. To increase sensitivity, newly found sequences are added to the original data set, the weight matrix is recalculated and the search is performed again. This procedure continues until no new sequences are found.

SUMMARY OF THE INVENTION

The present invention provides a substantially purified nucleic acid molecule that encodes a maize or a soybean enzyme or fragment thereof, wherein the maize or the soybean enzyme is selected from the group consisting of: (a) adenine phosphoribosyl transferase (b) β glucosidase and (c) isopentyltransferase.

The present invention also provides a substantially purified nucleic acid molecule that encodes a plant cytokinin pathway enzyme or fragment thereof, wherein the nucleic acid molecule is selected from the group consisting of a nucleic acid molecule that encodes a maize or a soybean adenine phosphoribosyl transferase enzyme or fragment thereof, a nucleic acid molecule that encodes a maize or a soybean β glucosidase enzyme or fragment thereof and a nucleic acid molecule that encodes a soybean isopentyltransferase enzyme or fragment thereof.

The present invention also provides a substantially purified maize or soybean enzyme or fragment thereof, wherein the maize or soybean enzyme is selected from the group consisting of (a) adenine phosphoribosyl transferase or fragment thereof, (b) β glucosidase or fragment thereof; and (c) isopentyltransferase or fragment thereof.

The present invention also provides a substantially purified maize or soybean cytokinin pathway protein or fragment thereof encoded by a first nucleic acid molecule which specifically hybridizes to a second nucleic acid molecule, the second nucleic acid molecule having a nucleic acid sequence selected from the group consisting of a complement of SEQ ID NO: 1 through SEQ ID NO: 711.

The present invention also provides a substantially purified maize or soybean adenine phosphoribosyl transferase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 1 through SEQ ID NO: 40 and SEQ ID NO: 480 through SEQ ID NO: 515.

The present invention also provides a substantially purified maize or soybean adenine phosphoribosyl transferase enzyme or fragment thereof encoded by a nucleic acid sequence selected from the group consisting of SEQ ID NO: 1 through SEQ ID NO: 40 and SEQ ID NO: 480 through SEQ ID NO: 515.

The present invention also provides a substantially purified maize or soybean β glucosidase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 41 through SEQ ID NO: 479 and SEQ ID NO: 516 through SEQ ID NO: 710.

The present invention also provides a substantially purified maize or soybean β glucosidase enzyme or fragment thereof encoded by a nucleic acid sequence selected from the group consisting of SEQ ID NO: 41 through SEQ ID NO: 479 and SEQ ID NO: 516 through SEQ ID NO: 710.

The present invention also provides a substantially purified soybean isopentyltransferase enzyme or fragment thereof encoded by a first nucleic acid molecule which specifically hybridizes to a second nucleic acid molecule, the second nucleic acid molecule having a nucleic acid sequence consisting of a complement of SEQ ID NO: 711.

The present invention also provides a substantially purified soybean isopentyltransferase enzyme or fragment thereof encoded by a nucleic acid sequence comprising SEQ ID NO: 711.

The present invention also provides a purified antibody or fragment thereof which is capable of specifically binding to a maize or soybean enzyme or fragment thereof, wherein the maize or soybean enzyme or fragment thereof is encoded by a nucleic acid molecule comprising a nucleic acid sequence selected from the group consisting of consisting of SEQ ID NO: 1 through SEQ ID NO: 711.

The present invention also provides a substantially purified antibody or fragment thereof, the antibody or fragment thereof capable of specifically binding to a maize or a soybean adenine phosphoribosyl transferase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 1 through SEQ ID NO: 40 and SEQ ID NO: 480 through SEQ ID NO: 515 and a maize or soybean adenine phosphoribosyl transferase enzyme or fragment thereof encoded by a nucleic acid sequence selected from the group consisting of SEQ ID NO: 1 through SEQ ID NO: 40 and SEQ ID NO: 480 through SEQ ID NO: 515.

The present invention also provides a substantially purified antibody or fragment thereof, the antibody or fragment thereof capable of specifically binding to a maize or a soybean β glucosidase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 41 through SEQ ID NO: 479 and SEQ ID NO: 516 through SEQ ID NO: 710 and a maize or soybean β glucosidase enzyme or fragment thereof encoded by a nucleic acid sequence selected from the group consisting of SEQ ID NO: 41 through SEQ ID NO: 479 and SEQ ID NO: 516 through SEQ ID NO: 710.

The present invention also provides a substantially purified antibody or fragment thereof, the antibody or fragment thereof capable of specifically binding to a soybean isopentyltransferase enzyme or fragment thereof encoded by a first nucleic acid molecule which specifically hybridizes to a second nucleic acid molecule, the second nucleic acid molecule consisting of a compliment of a nucleic acid sequence having SEQ ID NO: 711 or a soybean isopentyltransferase enzyme or fragment thereof encoded by a nucleic acid sequence comprising SEQ ID NO: 711.

The present invention also provides a transformed plant having a nucleic acid molecule which comprises: (A) an exogenous promoter region which functions in a plant cell to cause the production of a mRNA molecule; (B) a structural nucleic acid molecule comprising a nucleic acid sequence selected from the group consisting of (a) a nucleic acid sequence which encodes for adenine phosphoribosyl transferase or fragment thereof; (b) a nucleic acid sequence which encodes for β glucosidase or fragment thereof; and (c) a nucleic acid sequence which encodes for isopentyltransferase or fragment thereof; and (d) a nucleic acid sequence which is complementary to any of the nucleic acid sequences of (a) through (c); and (C) a 3' non-translated sequence that functions in the plant cell to cause termination of transcription and addition of polyadenylated ribonucleotides to a 3' end of the mRNA molecule.

The present invention also provides a transformed plant having a nucleic acid molecule which comprises: (A) an exogenous promoter region which functions in a plant cell to cause the production of a mRNA molecule; which is linked to (B) a structural nucleic acid molecule, wherein the structural nucleic acid molecule encodes a plant cytokinin pathway enzyme or fragment thereof, the structural nucleic acid molecule comprising a nucleic acid sequence selected from the group consisting of SEQ ID NO: 1 through SEQ ID NO: 711 or fragment thereof; which is linked to (C) a 3' non-translated sequence that functions in the plant cell to cause termination of transcription and addition of polyadenylated ribonucleotides to a 3' end of the mRNA molecule.

The present invention also provides a transformed plant having a nucleic acid molecule which comprises: (A) an exogenous promoter region which functions in a plant cell to cause the production of a mRNA molecule; which is linked to (B) a structural nucleic acid molecule, wherein the structural nucleic acid molecule is selected from the group consisting of a nucleic acid molecule that encodes a maize or a soybean adenine phosphoribosyl transferase enzyme or fragment thereof, a nucleic acid molecule that encodes a maize or a soybean β glucosidase enzyme or fragment thereof and a nucleic acid molecule that encodes a soybean isopentyltransferase enzyme or fragment thereof; which is linked to (C) a 3' non-translated sequence that functions in the plant cell to cause termination of transcription and addition of polyadenylated ribonucleotides to a 3' end of the mRNA molecule.

The present invention also provides a transformed plant having a nucleic acid molecule which comprises: (A) an exogenous promoter region which functions in a plant cell to cause the production of a mRNA molecule; which is linked to (B) a transcribed nucleic acid molecule with a transcribed strand and a non-transcribed strand, wherein the transcribed strand is complementary to a nucleic acid molecule comprising a nucleic acid sequence selected from the group consisting of SEQ ID NO: 1 through SEQ ID NO: 711 or fragment thereof; which is linked to (C) a 3' non-translated sequence that functions in plant cells to cause termination of transcription and addition of polyadenylated ribonucleotides to a 3' end of the mRNA molecule.

The present invention also provides a transformed plant having a nucleic acid molecule which comprises: (A) an exogenous promoter region which functions in a plant cell to cause the production of a mRNA molecule; which is linked to: (B) a transcribed nucleic acid molecule with a transcribed strand and a non-transcribed strand, wherein a transcribed mRNA of the transcribed strand is complementary to an endogenous mRNA molecule having a nucleic acid sequence selected from the group consisting of an endogenous mRNA molecule that encodes a maize or a soybean adenine phosphoribosyl transferase enzyme or fragment thereof, an endogenous mRNA molecule that encodes a maize or a soybean β glucosidase enzyme or fragment thereof and an endogenous mRNA molecule that encodes a soybean isopentyltransferase enzyme or fragment thereof; which is linked to (C) a 3' non-translated sequence that functions in the plant cell to cause termination of transcription and addition of polyadenylated ribonucleotides to a 3' end of the mRNA molecule.

The present invention also provides a method for determining a level or pattern in a plant cell of an enzyme in a plant metabolic pathway comprising: (A) incubating, under conditions permitting nucleic acid hybridization, a marker nucleic acid molecule, the marker nucleic acid molecule selected from the group of marker nucleic acid molecules which specifically hybridize to a nucleic acid molecule having the nucleic acid sequence of SEQ ID NO: 1 through SEQ ID NO: 711 or compliments thereof, with a complementary nucleic acid molecule obtained from the plant cell or plant tissue, wherein nucleic acid hybridization between the marker nucleic acid molecule and the complementary nucleic acid molecule obtained from the plant cell or plant tissue permits the detection of an mRNA for the enzyme; (B) permitting hybridization between the marker nucleic acid molecule and the complementary nucleic acid molecule obtained from the plant cell or plant tissue; and (C) detecting the level or pattern of the complementary nucleic acid, wherein the detection of the complementary nucleic acid is predictive of the level or pattern of the enzyme in the plant metabolic pathway.

The present invention also provides a method for determining a level or pattern of a plant cytokinin pathway enzyme in a plant cell or plant tissue comprising: (A) incubating, under conditions permitting nucleic acid hybridization, a marker nucleic acid molecule, the marker nucleic acid molecule having a nucleic acid sequence selected from the group consisting of SEQ ID NO: 1 through SEQ ID NO: 711 or complements thereof or fragment of either, with a complementary nucleic acid molecule obtained from the plant cell or plant tissue, wherein nucleic acid hybridization between the marker nucleic acid molecule and the complementary nucleic acid molecule obtained from the plant cell or plant tissue permits the detection of the plant cytokinin pathway enzyme; (B) permitting hybridization between the marker nucleic acid molecule and the complementary nucleic acid molecule obtained from the plant cell or plant tissue; and (C) detecting the level or pattern of the complementary nucleic acid, wherein the detection of the complementary nucleic acid is predictive of the level or pattern of the plant cytokinin pathway enzyme.

The present invention also provides a method for determining a level or pattern of a plant cytokinin pathway enzyme in a plant cell or plant tissue comprising: (A) incubating, under conditions permitting nucleic acid hybridization, a marker nucleic acid molecule, the marker nucleic acid molecule comprising a nucleic acid molecule that encodes a maize or a soybean adenine phosphoribosyl transferase enzyme or complement thereof or fragment of either, a nucleic acid molecule that encodes a maize or a soybean β glucosidase enzyme or complement thereof or fragment of either and a nucleic acid molecule that encodes a soybean isopentyltransferase enzyme or complement thereof or fragment of either, with a complementary nucleic acid molecule obtained from the plant cell or plant tissue, wherein nucleic acid hybridization between the marker nucleic acid molecule and the complementary nucleic acid molecule obtained from the plant cell or plant tissue permits the detection of the plant cytokinin pathway enzyme; (B) permitting hybridization between the marker nucleic acid molecule and the complementary nucleic acid molecule obtained from the plant cell or plant tissue; and (C) detecting the level or pattern of the complementary nucleic acid, wherein the detection of the complementary nucleic acid is predictive of the level or pattern of the plant cytokinin pathway enzyme.

The present invention also provides a method for determining a level or pattern of a plant cytokinin pathway enzyme in a plant cell or plant tissue under evaluation which comprises assaying the concentration of a molecule, whose concentration is dependent upon the expression of a gene, the gene specifically hybridizes to a nucleic acid molecule having a nucleic acid sequence selected from the group consisting of SEQ ID NO: 1 through SEQ ID NO: 711 or complements thereof, in comparison to the concentration of that molecule present in a reference plant cell or a reference plant tissue with a known level or pattern of the plant cytokinin pathway enzyme, wherein the assayed concentration of the molecule is compared to the assayed concentration of the molecule in the reference plant cell or reference plant tissue with the known level or pattern of the plant cytokinin pathway enzyme.

The present invention also provides a method for determining a level or pattern of a plant cytokinin pathway enzyme in a plant cell or plant tissue under evaluation which comprises assaying the concentration of a molecule, whose concentration is dependent upon the expression of a gene, the gene specifically hybridizes to a nucleic acid molecule selected from the group consisting of a nucleic acid molecule that encodes a maize or a soybean adenine phosphoribosyl transferase enzyme or complement thereof, a nucleic acid molecule that encodes a maize or a soybean β glucosidase enzyme or complement thereof and a nucleic acid molecule that encodes a soybean isopentyltransferase enzyme or complement thereof, in comparison to the concentration of that molecule present in a reference plant cell or a reference plant tissue with a known level or pattern of the plant cytokinin pathway enzyme, wherein the assayed concentration of the molecule is compared to the assayed concentration of the molecule in the reference plant cell or the reference plant tissue with the known level or pattern of the plant cytokinin pathway enzyme.

The present invention provides a method of determining a mutation in a plant whose presence is predictive of a mutation affecting a level or pattern of a protein comprising the steps: (A) incubating, under conditions permitting nucleic acid hybridization, a marker nucleic acid, the marker nucleic acid selected from the group of marker nucleic acid molecules which specifically hybridize to a nucleic acid molecule having a nucleic acid sequence selected from the group of SEQ ID NO: 1 through SEQ ID NO: 711 or complements thereof and a complementary nucleic acid molecule obtained from the plant, wherein nucleic acid hybridization between the marker nucleic acid molecule and the complementary nucleic acid molecule obtained from the plant permits the detection of a polymorphism whose presence is predictive of a mutation affecting the level or pattern of the plant cytokinin pathway enzyme in the plant; (B) permitting hybridization between the marker nucleic acid molecule and the complementary nucleic acid molecule obtained from the plant; and (C) detecting the presence of the polymorphism, wherein the detection of the polymorphism is predictive of the mutation.

The present invention also provides a method for determining a mutation in a plant whose presence is predictive of a mutation affecting the level or pattern of a plant cytokinin pathway enzyme comprising the steps: (A) incubating, under conditions permitting nucleic acid hybridization, a marker nucleic acid molecule, the marker nucleic acid molecule comprising a nucleic acid molecule that is linked to a gene, the gene specifically hybridizes to a nucleic acid molecule having a nucleic acid sequence selected from the group consisting of SEQ ID NO: 1 through SEQ ID NO: 711 or complements thereof and a complementary nucleic acid molecule obtained from the plant, wherein nucleic acid hybridization between the marker nucleic acid molecule and the complementary nucleic acid molecule obtained from the plant permits the detection of a polymorphism whose presence is predictive of a mutation affecting the level or pattern of the plant cytokinin pathway enzyme in the plant; (B) permitting hybridization between the marker nucleic acid molecule and the complementary nucleic acid molecule obtained from the plant; and (C) detecting the presence of the polymorphism, wherein the detection of the polymorphism is predictive of the mutation.

The present invention also provides a method for determining a mutation in a plant whose presence is predictive of a mutation affecting the level or pattern of a plant cytokinin pathway enzyme comprising the steps: (A) incubating, under conditions permitting nucleic acid hybridization, a marker nucleic acid molecule, the marker nucleic acid molecule comprising a nucleic acid molecule that is linked to a gene, the gene specifically hybridizes to a nucleic acid molecule selected from the group consisting of a nucleic acid molecule that encodes a maize or a soybean adenine phosphoribosyl transferase enzyme or complement thereof, a nucleic acid molecule that encodes a soybean β glucosidase enzyme or complement thereof and a nucleic acid molecule that encodes a soybean isopentyltransferase enzyme or complement thereof and a complementary nucleic acid molecule obtained from the plant, wherein nucleic acid hybridization between the marker nucleic acid molecule and the complementary nucleic acid molecule obtained from the plant permits the detection of a polymorphism whose presence is predictive of a mutation affecting the level or pattern of the plant cytokinin pathway enzyme in the plant; (B) permitting hybridization between the marker nucleic acid molecule and the complementary nucleic acid molecule obtained from the plant; and (C) detecting the presence of the polymorphism, wherein the detection of the polymorphism is predictive of the mutation.

The present invention also provides a method of producing a plant containing an overexpressed protein comprising: (A) transforming the plant with a functional nucleic acid molecule, wherein the functional nucleic acid molecule comprises a promoter region, wherein the promoter region is linked to a structural region, wherein the structural region has a nucleic acid sequence selected from group consisting of SEQ ID NO: 1 through SEQ ID NO: 711 wherein the structural region is linked to a 3' non-translated sequence that functions in the plant to cause termination of transcription and addition of polyadenylated ribonucleotides to a 3' end of a mRNA molecule; and wherein the functional nucleic acid molecule results in overexpression of the protein; and (B) growing the transformed plant.

The present invention also provides a method of producing a plant containing an overexpressed plant cytokinin enzyme comprising: (A) transforming the plant with a functional nucleic acid molecule, wherein the functional nucleic acid molecule comprises a promoter region, wherein the promoter region is linked to a structural region, wherein the structural region comprises a nucleic acid molecule having a nucleic acid sequence selected from the group consisting of SEQ ID NO: 1 through SEQ ID NO: 711 or fragment thereof; wherein the structural region is linked to a 3' non-translated sequence that functions in the plant to cause termination of transcription and addition of polyadenylated ribonucleotides to a 3' end of a mRNA molecule; and wherein the functional nucleic acid molecule results in overexpression of the plant cytokinin pathway enzyme; and (B) growing the transformed plant.

The present invention also provides a method of producing a plant containing an overexpressed plant cytokinin pathway enzyme comprising: (A) transforming the plant with a functional nucleic acid molecule, wherein the functional nucleic acid molecule comprises a promoter region, wherein the promoter region is linked to a structural region, wherein the structural region comprises a nucleic acid molecule selected from the group consisting of a nucleic acid molecule that encodes a maize or a soybean adenine phosphoribosyl transferase enzyme or fragment thereof, a nucleic acid molecule that encodes a soybean glucosidase enzyme or fragment thereof and a nucleic acid molecule that encodes a soybean isopentyltransferase enzyme or fragment thereof, wherein the structural region is linked to a 3' non-translated sequence that functions in the plant to cause termination of transcription and addition of polyadenylated ribonucleotides to a 3' end of a mRNA molecule; and wherein the functional nucleic acid molecule results in overexpression of the plant cytokinin pathway enzyme protein; and (B) growing the transformed plant.

The present invention also provides a method of producing a plant containing reduced levels of a plant cytokinin pathway enzyme comprising: (A) transforming the plant with a functional nucleic acid molecule, wherein the functional nucleic acid molecule comprises a promoter region, wherein the promoter region is linked to a structural region, wherein the structural region comprises a nucleic acid molecule having a nucleic acid sequence selected from the group consisting of SEQ ID NO: 1 through SEQ ID NO: 711; wherein the structural region is linked to a 3' non-translated sequence that functions in the plant to cause termination of transcription and addition of polyadenylated ribonucleotides to a 3' end of a mRNA molecule; and wherein the functional nucleic acid molecule results in co-suppression of the plant cytokinin pathway enzyme protein; and (B) growing the transformed plant.

The present invention also provides a method of producing a plant containing reduced levels of a plant cytokinin pathway enzyme comprising: (A) transforming the plant with a functional nucleic acid molecule, wherein the functional nucleic acid molecule comprises a promoter region, wherein the promoter region is linked to a structural region, wherein the structural region comprises a nucleic acid molecule having a nucleic acid sequence selected from the group consisting of a nucleic acid molecule that encodes a maize or a soybean adenine phosphoribosyl transferase enzyme or fragment thereof, a nucleic acid molecule that encodes a maize or a soybean β glucosidase enzyme or fragment thereof and a nucleic acid molecule that encodes a soybean isopentyltransferase enzyme or fragment thereof, wherein the structural region is linked to a 3' non-translated sequence that functions in the plant to cause termination of transcription and addition of polyadenylated ribonucleotides to a 3' end of a mRNA molecule; and wherein the functional nucleic acid molecule results in co-suppression of the plant cytokinin pathway enzyme; and (B) growing the transformed plant.

The present invention also provides a method for reducing expression of a plant cytokinin pathway enzyme in a plant comprising: (A) transforming the plant with a nucleic acid molecule, the nucleic acid molecule having an exogenous promoter region which functions in a plant cell to cause the production of a mRNA molecule, wherein the exogenous promoter region is linked to a transcribed nucleic acid molecule having a transcribed strand and a non-transcribed strand, wherein the transcribed strand is complementary to a nucleic acid molecule having a nucleic acid sequence selected from the group consisting of SEQ ID NO: 1 through SEQ ID NO: 711 or complements thereof or fragments of either and the transcribed strand is complementary to an endogenous mRNA molecule; and wherein the transcribed nucleic acid molecule is linked to a 3' non-translated sequence that functions in the plant cell to cause termination of transcription and addition of polyadenylated ribonucleotides to a 3' end of a mRNA molecule; and (B) growing the transformed plant.

The present invention also provides a method for reducing expression of a plant cytokinin pathway enzyme in a plant comprising: (A) transforming the plant with a nucleic acid molecule, the nucleic acid molecule having an exogenous promoter region which functions in a plant cell to cause the production of a mRNA molecule, wherein the exogenous promoter region is linked to a transcribed nucleic acid molecule having a transcribed strand and a non-transcribed strand, wherein a transcribed mRNA of the transcribed strand is complementary to a nucleic acid molecule selected from the group consisting of an endogenous mRNA molecule that encodes a maize or a soybean adenine phosphoribosyl transferase enzyme or fragment thereof, an endogenous mRNA molecule that encodes a maize or a soybean β glucosidase enzyme or fragment thereof and an endogenous mRNA molecule that encodes a soybean isopentyltransferase enzyme or fragment thereof, and wherein the transcribed nucleic acid molecule is linked to a 3' non-translated sequence that functions in the plant cell to cause termination of transcription and addition of polyadenylated ribonucleotides to a 3' end of a mRNA molecule; and (B) growing the transformed plant.

The present invention also provides a method of determining an association between a polymorphism and a plant trait comprising: (A) hybridizing a nucleic acid molecule specific for the polymorphism to genetic material of a plant, wherein the nucleic acid molecule has a nucleic acid sequence selected from the group consisting of SEQ ID NO: 1 through SEQ ID NO: 711 or complements thereof or fragment of either; and (B) calculating the degree of association between the polymorphism and the plant trait.

The present invention also provides a method of determining an association between a polymorphism and a plant trait comprising: (A) hybridizing a nucleic acid molecule specific for the polymorphism to genetic material of a plant, wherein the nucleic acid molecule is selected from the group consisting of a nucleic acid molecule that encodes a maize or a soybean adenine phosphoribosyl transferase enzyme or complement thereof or fragment of either, a nucleic acid molecule that encodes a maize or a soybean β glucosidase enzyme complement thereof or fragment of either and a nucleic acid molecule that encodes a soybean isopentyltransferase enzyme complement thereof or fragment of either and (B) calculating the degree of association between the polymorphism and the plant trait.

The present invention also provides a method of isolating a nucleic acid that encodes a plant cytokinin pathway enzyme or fragment thereof comprising: (A) incubating under conditions permitting nucleic acid hybridization, a first nucleic acid molecule comprising a nucleic acid sequence selected from the group consisting of SEQ ID NO: 1 through SEQ ID NO: 711 or complements thereof or fragment of either with a complementary second nucleic acid molecule obtained from a plant cell or plant tissue; (B) permitting hybridization between the first nucleic acid molecule and the second nucleic acid molecule obtained from the plant cell or plant tissue; and (C) isolating the second nucleic acid molecule.

The present invention also provides a method of isolating a nucleic acid molecule that encodes a plant cytokinin pathway enzyme or fragment thereof comprising: (A) incubating under conditions permitting nucleic acid hybridization, a first nucleic acid molecule selected from the group consisting of a nucleic acid molecule that encodes a maize or a soybean adenine phosphoribosyl transferase enzyme complement thereof or fragment of either, a nucleic acid molecule that encodes a maize or a soybean β glucosidase enzyme or complement thereof or fragment of either and a nucleic acid molecule that encodes a soybean isopentyltransferase enzyme complement thereof or fragment of either, with a complementary second nucleic acid molecule obtained from a plant cell or plant tissue; (B) permitting hybridization between the plant cytokinin pathway nucleic acid molecule and the complementary nucleic acid molecule obtained from the plant cell or plant tissue; and (C) isolating the second nucleic acid molecule.

DETAILED DESCRIPTION OF THE INVENTION

Definitions and Agents of the Present Invention

Definitions:

As used herein, a cytokinin pathway enzyme is any enzyme that is associated with the synthesis or degradation of cytokinin.

As used herein, a cytokinin synthesis enzyme is any enzyme that is associated with the synthesis of cytokinin.

As used herein, a cytokinin degradation enzyme is any enzyme that is associated with the degradation of cytokinin.

As used herein, adenine phosphoribosyl transferase is any enzyme that catalyzes the conversion of iP to [9R-5'P]iP.

As used herein, β glucosidase is any enzyme that catalyzes the hydrolysis of aryl and alkyl β-D-glucosides and/or cellobiose with release of β-D-glucose.

As used herein, isopentyltransferase is any enzyme that catalyzes the first reaction of the pathway in which N6(Δ2-isopentenyl) adenosine-5'-monophosphate ("[9R-5'P]iP") is generated from iPP and AMP.

Agents (a) Nucleic Acid Molecules

Agents of the present invention include plant nucleic acid molecules and more preferably include maize and soybean nucleic acid molecules and more preferably include nucleic acid molecules of the maize genotypes B73 (Illinois Foundation Seeds, Champaign, Ill. U.S.A.), B73 x Mol7 (Illinois Foundation Seeds, Champaign, Ill. U.S.A.), DK604 (Dekalb Genetics, Dekalb, Ill. U.S.A.), H99 (Illinois Foundation Seeds, Champaign, Ill. U.S.A.), RX601 (Asgrow Seed Company, Des Moines, Iowa), Mo17 (Illinois Foundation Seeds, Champaign, Ill. U.S.A.), and soybean types Asgrow 3244 (Asgrow Seed Company, Des Moines, Iowa), C1944 (United States Department of Agriculture (USDA) Soybean Germplasm Collection, Urbana, Ill. U.S.A.), Cristalina (USDA Soybean Germplasm Collection, Urbana, Ill. U.S.A.), FT108 (Monsoy, Brazil), Hartwig (USDA Soybean Germplasm Collection, Urbana, Ill. U.S.A.), BW211S Null (Tohoku University, Morioka, Japan), PI507354 (USDA Soybean Germplasm Collection, Urbana, Ill. U.S.A.), Asgrow A4922 (Asgrow Seed Company, Des Moines, Iowa U.S.A.), PI227687 (USDA Soybean Germplasm Collection, Urbana, Ill. U.S.A.), PI229358 (USDA Soybean Germplasm Collection, Urbana, Ill. U.S.A.) and Asgrow A3237 (Asgrow Seed Company, Des Moines, Iowa U.S.A.).

A subset of the nucleic acid molecules of the present invention includes nucleic acid molecules that are marker molecules. Another subset of the nucleic acid molecules of the present invention include nucleic acid molecules that encode a protein or fragment thereof. Another subset of the nucleic acid molecules of the present invention are EST molecules.

Fragment nucleic acid molecules may encode significant portion(s) of, or indeed most of, these nucleic acid molecules. Alternatively, the fragments may comprise smaller oligonucleotides (having from about 15 to about 250 nucleotide residues and more preferably, about 15 to about 30 nucleotide residues).

As used herein, an agent, be it a naturally occurring molecule or otherwise may be "substantially purified," if desired, such that one or more molecules that is or may be present in a naturally occurring preparation containing that molecule will have been removed or will be present at a lower concentration than that at which it would normally be found.

The agents of the present invention will preferably be "biologically active" with respect to either a structural attribute, such as the capacity of a nucleic acid to hybridize to another nucleic acid molecule, or the ability of a protein to be bound by an antibody (or to compete with another molecule for such binding). Alternatively, such an attribute may be catalytic and thus involve the capacity of the agent to mediate a chemical reaction or response.

The agents of the present invention may also be recombinant. As used herein, the term recombinant means any agent (e.g. DNA, peptide etc.), that is, or results, however indirect, from human manipulation of a nucleic acid molecule.

It is understood that the agents of the present invention may be labeled with reagents that facilitate detection of the agent (e.g. fluorescent labels, Prober et al., *Science* 238:336-340 (1987); Albarella et al., EP 144914; chemical labels, Sheldon et al., U.S. Pat. No. 4,582,789; Albarella et al., U.S. Pat. No. 4,563,417; modified bases, Miyoshi et al., EP 119448, all of which are hereby incorporated by reference in their entirety).

It is further understood, that the present invention provides recombinant bacterial, mammalian, microbial, insect, fungal and plant cells and viral constructs comprising the agents of the present invention. (See, for example, Uses of the Agents of the Invention, Section (a) Plant Constructs and Plant Transformants; Section (b) Fungal Constructs and Fungal Transformants; Section (c) Mammalian Constructs and Transformed Mammalian Cells; Section (d) Insect Constructs and Transformed Insect Cells; and Section (e) Bacterial Constructs and Transformed Bacterial Cells)

Nucleic acid molecules or fragments thereof of the present invention are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., *Molecular Cloning*, A Laboratory Manual, 2nd Ed., Cold Spring Harbor Press, Cold Spring Harbor, N.Y. (1989) and by Haymes et al., *Nucleic Acid Hybridization, A Practical Approach*, IRL Press, Washington, D.C. (1985), the entirety of which is herein incorporated by reference. Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed.

Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in

*Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2× SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

In a preferred embodiment, a nucleic acid of the present invention will specifically hybridize to one or more of the nucleic acid molecules set forth in SEQ ID NO: 1 through SEQ ID NO: 711 or complements thereof under moderately stringent conditions, for example at about 2.0×SSC and about 65° C.

In a particularly preferred embodiment, a nucleic acid of the present invention will include those nucleic acid molecules that specifically hybridize to one or more of the nucleic acid molecules set forth in SEQ ID NO: 1 through SEQ ID NO: 711 or complements thereof under high stringency conditions such as 0.2×SSC and about 65° C.

In one aspect of the present invention, the nucleic acid molecules of the present invention have one or more of the nucleic acid sequences set forth in SEQ ID NO: 1 through SEQ ID NO: 711 or complements thereof. In another aspect of the present invention, one or more of the nucleic acid molecules of the present invention share between 100% and 90% sequence identity with one or more of the nucleic acid sequences set forth in SEQ ID NO: 1 through SEQ ID NO: 711 or complements thereof. In a further aspect of the present invention, one or more of the nucleic acid molecules of the present invention share between 100% and 95% sequence identity with one or more of the nucleic acid sequences set forth in SEQ ID NO: 1 through SEQ ID NO: 711 or complements thereof. In a more preferred aspect of the present invention, one or more of the nucleic acid molecules of the present invention share between 100% and 98% sequence identity with one or more of the nucleic acid sequences set forth in SEQ ID NO: 1 through SEQ ID NO: 711 or complements thereof. In an even more preferred aspect of the present invention, one or more of the nucleic acid molecules of the present invention share between 100% and 99% sequence identity with one or more of the sequences set forth in SEQ ID NO: 1 through SEQ ID NO: 711 or complements thereof.

In a further more preferred aspect of the present invention, one or more of the nucleic acid molecules of the present invention exhibit 100% sequence identity with a nucleic acid molecule present within MONN01, SATMON001 through SATMON031, SATMON033, SATMON034, SATMON~001, SATMONN01, SATMONN04 through SATMONN006, CMz029 through CMz031, CMz033, CMz035 through CMz037, CMz039 through CMz042, CMz044 through CMz045, CMz047 through CMz050, SOYMON001 through SOYMON038, Soy51 through Soy56, Soy58 through Soy62, Soy65 through Soy66, Soy 68 through Soy73 and Soy76 through Soy77, Lib9, Lib22 through Lib25, Lib35, Lib80 through Lib81, Lib 144, Lib146, Lib147, Lib190, Lib3032 through Lib3036 and Lib3099 (Monsanto Company, St. Louis, Mo. U.S.A.).

(i) Nucleic Acid Molecules Encoding Proteins or Fragments Thereof

Nucleic acid molecules of the present invention can comprise sequences that encode a cytokinin pathway protein or fragment thereof. Such proteins or fragments thereof include homologues of known proteins in other organisms.

In a preferred embodiment of the present invention, a maize or a soybean protein or fragment thereof of the present invention is a homologue of another plant protein. In another preferred embodiment of the present invention, a maize or a soybean protein or fragment thereof of the present invention is a homologue of a fungal protein. In another preferred embodiment of the present invention, a maize or a soybean protein of the present invention is a homologue of mammalian protein. In another preferred embodiment of the present invention, a maize or a soybean protein or fragment thereof of the present invention is a homologue of a bacterial protein. In another preferred embodiment of the present invention, a soybean protein or fragment thereof of the present invention is a homologue of a maize protein. In another preferred embodiment of the present invention, a maize protein homologue or fragment thereof of the present invention is a homologue of a soybean protein.

In a preferred embodiment of the present invention, the nucleic molecule of the present invention encodes a maize or a soybean protein or fragment thereof where a maize or a soybean protein exhibits a BLAST probability score of greater than 1E-12, preferably a BLAST probability score of between about 1E-30 and about 1E-12, even more preferably a BLAST probability score of greater than 1E-30 with its homologue.

In another preferred embodiment of the present invention, the nucleic acid molecule encoding a maize or a soybean protein or fragment thereof exhibits a % identity with its homologue of between about 25% and about 40%, more preferably of between about 40 and about 70%, even more preferably of between about 70% and about 90% and even more preferably between about 90% and 99%. In another preferred embodiment, of the present invention, a maize or a soybean protein or fragments thereof exhibits a % identity with its homologue of 100%.

In a preferred embodiment of the present invention, the nucleic molecule of the present invention encodes a maize or a soybean protein or fragment thereof where a maize or a soybean protein exhibits a BLAST score of greater than 120, preferably a BLAST score of between about 1450 and about 120, even more preferably a BLAST score of greater than 1450 with its homologue.

Nucleic acid molecules of the present invention also include non-maize, non-soybean homologues. Preferred non-homologues are selected from the group consisting of alfalfa, *Arabidopsis*, barley, *Brassica*, broccoli, cabbage, citrus, cotton, garlic, oat, oilseed rape, onion, canola, flax, an ornamental plant, pea, peanut, pepper, potato, rice, rye, sorghum, strawberry, sugarcane, sugarbeet, tomato, wheat, poplar, pine, fir, eucalyptus, apple, lettuce, lentils, grape, banana, tea, turf grasses, sunflower, oil palm and *Phaseolus*.

In a preferred embodiment, nucleic acid molecules having SEQ ID NO: 1 through SEQ ID NO: 711 or complements and fragments of either can be utilized to obtain such homologues.

The degeneracy of the genetic code, which allows different nucleic acid sequences to code for the same protein or peptide, is known in the literature. (U.S. Pat. No. 4,757,006, the entirety of which is herein incorporated by reference).

In an aspect of the present invention, one or more of the nucleic acid molecules of the present invention differ in nucleic acid sequence from those encoding a maize or a soybean protein or fragment thereof in SEQ ID NO: 1 through SEQ ID NO: 711 due to the degeneracy in the genetic code in that they encode the same protein but differ in nucleic acid sequence.

In another further aspect of the present invention, one or more of the nucleic acid molecules of the present invention differ in nucleic acid sequence from those encoding a maize or a soybean protein or fragment thereof in SEQ ID NO: 1 through SEQ ID NO: 711 due to fact that the different nucleic acid sequence encodes a protein having one or more conservative amino acid residue. Examples of conservative substitutions are set forth in Table 1. It is understood that codons capable of coding for such conservative substitutions are known in the art.

TABLE 1

| Original Residue | Conservative Substitutions |
| --- | --- |
| Ala | Ser |
| Arg | Lys |
| Asn | Gln; His |
| Asp | Glu |
| Cys | Ser; Ala |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

In a further aspect of the present invention, one or more of the nucleic acid molecules of the present invention differ in nucleic acid sequence from those encoding a maize or a soybean protein or fragment thereof set forth in SEQ ID NO: 1 through SEQ ID NO: 711 or fragment thereof due to the fact that one or more codons encoding an amino acid has been substituted for a codon that encodes a nonessential substitution of the amino acid originally encoded.

Agents of the present invention include nucleic acid molecules that encode a maize or a soybean cytokinin pathway protein or fragment thereof and particularly substantially purified nucleic acid molecules selected from the group consisting of a nucleic acid molecule that encodes a maize or a soybean adenine phosphoribosyl transferase protein or fragment thereof, a nucleic acid molecule that encodes a maize or a soybean β glucosidase protein or fragment thereof and a nucleic acid molecule that encodes a soybean isopentyltransferase protein or fragment thereof.

Non-limiting examples of such nucleic acid molecules of the present invention are nucleic acid molecules comprising: SEQ ID NO: 1 through SEQ ID NO: 711 or fragment thereof that encode for a cytokinin pathway protein or fragment thereof, SEQ ID NO: 1 through SEQ ID NO: 40 and SEQ ID NO: 480 through SEQ ID NO: 515 or fragment thereof that encode for an adenine phosphoribosyl transferase protein or fragment thereof, SEQ ID NO: 41 through SEQ ID NO: 479 and SEQ ID NO: 516 through SEQ ID NO: 710 or fragment thereof that encode for a glucosidase protein or fragment thereof and SEQ ID NO: 711 or fragment thereof that encodes for an isopentyltransferase protein or fragment thereof.

A nucleic acid molecule of the present invention can also encode an homologue of a maize or a soybean adenine phosphoribosyl transferase or fragment thereof, a maize or a soybean β glucosidase or fragment thereof or a soybean isopentyltransferase or fragment thereof. As used herein a homologue protein molecule or fragment thereof is a counterpart protein molecule or fragment thereof in a second species (e.g., maize adenine phosphoribosyl transferase protein is a homologue of *Arabidopsis*' adenine phosphoribosyl transferase protein).

(ii) Nucleic Acid Molecule Markers and Probes

One aspect of the present invention concerns markers that include nucleic acid molecules SEQ ID NO: 1 through SEQ ID NO: 711 or complements thereof or fragments of either that can act as markers or other nucleic acid molecules of the present invention that can act as markers. Genetic markers of the present invention include "dominant" or "codominant" markers "Codominant markers" reveal the presence of two or more alleles (two per diploid individual) at a locus. "Dominant markers" reveal the presence of only a single allele per locus. The presence of the dominant marker phenotype (e.g., a band of DNA) is an indication that one allele is present in either the homozygous or heterozygous condition. The absence of the dominant marker phenotype (e.g. absence of a DNA band) is merely evidence that "some other" undefined allele is present. In the case of populations where individuals are predominantly homozygous and loci are predominately dimorphic, dominant and codominant markers can be equally valuable. As populations become more heterozygous and multi-allelic, codominant markers often become more informative of the genotype than dominant markers. Marker molecules can be, for example, capable of detecting polymorphisms such as single nucleotide polymorphisms (SNPs).

SNPs are single base changes in genomic DNA sequence. They occur at greater frequency and are spaced with a greater uniformly throughout a genome than other reported forms of polymorphism. The greater frequency and uniformity of SNPs means that there is greater probability that such a polymorphism will be found near or in a genetic locus of interest than would be the case for other polymorphisms. SNPs are located in protein-coding regions and noncoding regions of a genome. Some of these SNPs may result in defective or variant protein expression (e.g., as a results of mutations or defective splicing). Analysis (genotyping) of characterized SNPs can require only a plus/minus assay rather than a lengthy measurement, permitting easier automation.

SNPs can be characterized using any of a variety of methods. Such methods include the direct or indirect sequencing of the site, the use of restriction enzymes (Botstein et al., *Am. J. Hum. Genet.* 32:314-331 (1980), the entirety of which is herein incorporated reference; Konieczny and Ausubel, *Plant J.* 4:403-410 (1993), the entirety of which is herein incorporated by reference), enzymatic and chemical mismatch assays (Myers et al., *Nature* 313:495-498 (1985), the entirety of which is herein incorporated by reference), allele-specific PCR (Newton et al., *Nucl. Acids Res.* 17:2503-2516 (1989), the entirety of which is herein incorporated by reference; Wu et al., *Proc. Natl. Acad. Sci. (U.S.A.)* 86:2757-2760 (1989), the entirety of which is herein incorporated by reference), ligase chain reaction (Barany, *Proc. Natl. Acad. Sci. (U.S.A.)* 88:189-193 (1991), the entirety of which is herein incorporated by reference), single-strand conformation polymorphism analysis (Labrune et al., *Am. J. Hum. Genet.* 48: 1115-1120 (1991), the entirety of which is herein incorporated by reference), primer-directed nucleotide incorporation assays (Kuppuswami et al., *Proc. Natl. Acad. Sci. USA* 88:1143-1147 (1991), the entirety of which is herein incorporated by reference), dideoxy fingerprinting (Sarkar et al., *Genomics* 13:441-443 (1992), the entirety of which is herein incorporated by reference), solid-phase ELISA-based oligonucleotide ligation assays (Nikiforov et al., *Nucl. Acids Res.* 22:4167-4175 (1994), the entirety of which is herein incorporated by reference), oligonucleotide fluorescence-quenching assays (Livak et al., *PCR Methods Appl.* 4:357-362 (1995), the entirety of which is herein incorporated by reference), 5'-nuclease allele-specific hybridization TaqMan assay (Livak et al., *Nature Genet.* 9:341-342 (1995), the entirety of which is herein incorporated by reference), template-directed dye-terminator incorporation (TDI) assay (Chen and Kwok, *Nucl. Acids Res.* 25:347-353 (1997), the entirety of which is herein incorporated by reference), allele-specific molecular beacon assay (Tyagi et al., *Nature Biotech.* 16: 49-53 (1998), the entirety of which is herein incorporated by reference), PinPoint assay (Haff and Smirnov, *Genome Res.* 7: 378-388 (1997), the entirety of which is herein incorporated by reference) and dCAPS analysis (Neff et al., *Plant J.* 14:387-392 (1998), the entirety of which is herein incorporated by reference).

Additional markers, such as AFLP markers, RFLP markers and RAPD markers, can be utilized (Walton, *Seed World* 22-29 (July, 1993), the entirety of which is herein incorporated by reference; Burow and Blake, *Molecular Dissection of Complex Traits,* 13-29, Paterson (ed.), CRC Press, New York (1988), the entirety of which is herein incorporated by reference). DNA markers can be developed from nucleic acid molecules using restriction endonucleases, the PCR and/or DNA sequence information. RFLP markers result from single base changes or insertions/deletions. These codominant markers are highly abundant in plant genomes, have a medium level of polymorphism and are developed by a combination of restriction endonuclease digestion and Southern blotting hybridization. CAPS are similarly developed from restriction nuclease digestion but only of specific PCR products. These markers are also codominant, have a medium level of polymorphism and are highly abundant in the genome. The CAPS result from single base changes and insertions/deletions.

Another marker type, RAPDs, are developed from DNA amplification with random primers and result from single base changes and insertions/deletions in plant genomes. They are dominant markers with a medium level of polymorphisms and are highly abundant. AFLP markers require using the PCR on a subset of restriction fragments from extended adapter primers. These markers are both dominant and codominant are highly abundant in genomes and exhibit a medium level of polymorphism.

SSRs require DNA sequence information. These codominant markers result from repeat length changes, are highly polymorphic and do not exhibit as high a degree of abundance in the genome as CAPS, AFLPs and RAPDs SNPs also require DNA sequence information. These codominant markers result from single base substitutions. They are highly abundant and exhibit a medium of polymorphism (Rafalski et al., In: *Nonmammalian Genomic Analysis*, Birren and Lai (ed.), Academic Press, San Diego, Calif., pp. 75-134 (1996), the entirety of which is herein incorporated by reference). It is understood that a nucleic acid molecule of the present invention may be used as a marker.

A PCR probe is a nucleic acid molecule capable of initiating a polymerase activity while in a double-stranded structure with another nucleic acid. Various methods for determining the structure of PCR probes and PCR techniques exist in the art. Computer generated searches using programs such as Primer3 (available on the World Wide Web at genome.wi.mit.edu/cgi-bin/primer/primer3.cgi), STSPipeline (available on the World Wide Web at genome.wi.mit.edu/cgi-bin/www-STS_Pipleine) or GeneUp (Pesole et al., *BioTechniques* 25:112-123 (1998) the entirety of which is herein incorporated by reference), for example, can be used to identify potential PCR primers.

It is understood that a fragment of one or more of the nucleic acid molecules of the present invention may be a probe and specifically a PCR probe.

(b) Protein and Peptide Molecules

A class of agents comprises one or more of the protein or fragments thereof or peptide molecules encoded by SEQ ID NO: 1 through SEQ ID NO: 711 or one or more of the protein or fragment thereof and peptide molecules encoded by other nucleic acid agents of the present invention. As used herein, the term "protein molecule" or "peptide molecule" includes any molecule that comprises five or more amino acids. It is well known in the art that proteins may undergo modification, including post-translational modifications, such as, but not limited to, disulfide bond formation, glycosylation, phosphorylation, or oligomerization. Thus, as used herein, the term "protein molecule" or "peptide molecule" includes any protein molecule that is modified by any biological or non-biological process. The terms "amino acid" and "amino acids" refer to all naturally occurring L-amino acids. This definition is meant to include norleucine, ornithine, homocysteine and homoserine.

Non-limiting examples of the protein or fragment thereof of the present invention include a maize or a soybean cytokinin pathway protein or fragment thereof, a maize or a soybean adenine phosphoribosyl transferase or fragment thereof, a maize or β glucosidase or fragment thereof or a soybean isopentyltransferase or fragment thereof.

Non-limiting examples of the protein or fragment molecules of the present invention are an cytokinin pathway protein or fragment thereof encoded by: SEQ ID NO: 1 through SEQ ID NO: 711 or fragment thereof that encode for a cytokinin pathway protein or fragment thereof, SEQ ID NO: 1 through SEQ ID NO: 40 and SEQ ID NO: 480 through SEQ ID NO: 515 or fragment thereof that encode for an adenine phosphoribosyl transferase protein or fragment thereof, SEQ ID NO: 41 through SEQ ID NO: 479 and SEQ ID NO: 516 through SEQ ID NO: 710 or fragment thereof that encode for a β glucosidase protein or fragment thereof and SEQ ID NO: 711 or fragment thereof that encodes for an isopentyltransferase protein or fragment thereof.

One or more of the protein or fragment of peptide molecules may be produced via chemical synthesis, or more preferably, by expressing in a suitable bacterial or eucaryotic host. Suitable methods for expression are described by Sambrook et al., (In: *Molecular Cloning, A Laboratory Manual, 2nd Edition, Cold Spring Harbor Press*, Cold Spring Harbor, N.Y. (1989)), or similar texts. For example, the protein may be expressed in, for example, Uses of the Agents of the Invention, Section (a) Plant Constructs and Plant Transformants; Section (b) Fungal Constructs and Fungal Transformants; Section (c) Mammalian Constructs and Transformed Mammalian Cells; Section (d) Insect Constructs and Transformed Insect Cells; and Section (e) Bacterial Constructs and Transformed Bacterial Cells.

A "protein fragment" is a peptide or polypeptide molecule whose amino acid sequence comprises a subset of the amino acid sequence of that protein. A protein or fragment thereof that comprises one or more additional peptide regions not derived from that protein is a "fusion" protein. Such molecules may be derivatized to contain carbohydrate or other moieties (such as keyhole limpet hemocyanin, etc.). Fusion protein or peptide molecules of the present invention are preferably produced via recombinant means.

Another class of agents comprise protein or peptide molecules or fragments or fusions thereof encoded by SEQ ID NO: 1 through SEQ ID NO: 711 or complements thereof in which conservative, non-essential or non-relevant amino acid residues have been added, replaced or deleted. Computerized means for designing modifications in protein structure are known in the art (Dahiyat and Mayo, *Science* 278:82-87 (1997), the entirety of which is herein incorporated by reference).

The protein molecules of the present invention include plant homologue proteins. An example of such a homologue is a homologue protein of a non-maize or non soybean plant species, that include but not limited to alfalfa, *Arabidopsis*, barley, *Brassica*, broccoli, cabbage, citrus, cotton, garlic, oat, oilseed rape, onion, canola, flax, an ornamental plant, pea, peanut, pepper, potato, rice, rye, sorghum, strawberry, sugarcane, sugarbeet, tomato, wheat, poplar, pine, fir, eucalyptus, apple, lettuce, lentils, grape, banana, tea, turf grasses, sunflower, oil palm, *Phaseolus* etc. Particularly preferred non-maize or non-soybean for use for the isolation of homologs would include, *Arabidopsis*, barley, cotton, oat, oilseed rape, rice, canola, ornamentals, sugarcane, sugarbeet, tomato, potato, wheat and turf grasses. Such a homologue can be obtained by any of a variety of methods. Most preferably, as indicated above, one or more of the disclosed sequences (SEQ ID NO: 1 through SEQ ID NO: 711 or complements thereof) will be used to define a pair of primers that may be used to isolate the homologue-encoding nucleic acid molecules from any desired species. Such molecules can be expressed to yield homologues by recombinant means.

(c) Antibodies

One aspect of the present invention concerns antibodies, single-chain antigen binding molecules, or other proteins that specifically bind to one or more of the protein or peptide molecules of the present invention and their homologues, fusions or fragments. Such antibodies may be used to quantitatively or qualitatively detect the protein or peptide molecules of the present invention. As used herein, an antibody or peptide is said to "specifically bind" to a protein or peptide molecule of the present invention if such binding is not competitively inhibited by the presence of non-related molecules.

Nucleic acid molecules that encode all or part of the protein of the present invention can be expressed, via recombinant means, to yield protein or peptides that can in turn be used to elicit antibodies that are capable of binding the expressed protein or peptide. Such antibodies may be used in immunoassays for that protein. Such protein-encoding molecules, or their fragments may be a "fusion" molecule (i.e., a part of a larger nucleic acid molecule) such that, upon expression, a fusion protein is produced. It is understood that any of the nucleic acid molecules of the present invention may be expressed, via recombinant means, to yield proteins or peptides encoded by these nucleic acid molecules.

The antibodies that specifically bind proteins and protein fragments of the present invention may be polyclonal or monoclonal and may comprise intact immunoglobulins, or antigen binding portions of immunoglobulins fragments (such as (F(ab'), F(ab')$_2$), or single-chain immunoglobulins producible, for example, via recombinant means. It is understood that practitioners are familiar with the standard resource materials which describe specific conditions and procedures for the construction, manipulation and isolation of antibodies (see, for example, Harlow and Lane, In: *Antibodies: A Laboratory Manual*, Cold Spring Harbor Press, Cold Spring Harbor, N.Y. (1988), the entirety of which is herein incorporated by reference).

Murine monoclonal antibodies are particularly preferred. BALB/c mice are preferred for this purpose, however, equivalent strains may also be used. The animals are preferably immunized with approximately 25 µg of purified protein (or fragment thereof) that has been emulsified in a suitable adjuvant (such as TiterMax adjuvant (Vaxcel, Norcross, Ga.)). Immunization is preferably conducted at two intramuscular sites, one intraperitoneal site and one subcutaneous site at the base of the tail. An additional i.v. injection of approximately 25 µg of antigen is preferably given in normal saline three weeks later. After approximately 11 days following the second injection, the mice may be bled and the blood screened for the presence of anti-protein or peptide antibodies. Preferably, a direct binding Enzyme-Linked Immunoassay (ELISA) is employed for this purpose.

More preferably, the mouse having the highest antibody titer is given a third i.v. injection of approximately 25 µg of the same protein or fragment. The splenic leukocytes from this animal may be recovered 3 days later and then permitted to fuse, most preferably, using polyethylene glycol, with cells of a suitable myeloma cell line (such as, for example, the P3X63Ag8.653 myeloma cell line). Hybridoma cells are selected by culturing the cells under "HAT" (hypoxanthine-aminopterin-thymine) selection for about one week. The resulting clones may then be screened for their capacity to produce monoclonal antibodies ("mAbs"), preferably by direct ELISA.

In one embodiment, anti-protein or peptide monoclonal antibodies are isolated using a fusion of a protein or peptide of the present invention, or conjugate of a protein or peptide of the present invention, as immunogens. Thus, for example, a group of mice can be immunized using a fusion protein emulsified in Freund's complete adjuvant (e.g. approximately 50 µg of antigen per immunization). At three week intervals, an identical amount of antigen is emulsified in Freund's incomplete adjuvant and used to immunize the animals. Ten days following the third immunization, serum samples are taken and evaluated for the presence of antibody. If antibody titers are too low, a fourth booster can be employed. Polysera capable of binding the protein or peptide can also be obtained using this method.

In a preferred procedure for obtaining monoclonal antibodies, the spleens of the above-described immunized mice are removed, disrupted and immune splenocytes are isolated over a ficoll gradient. The isolated splenocytes are fused, using polyethylene glycol with BALB/c-derived HGPRT (hypoxanthine guanine phosphoribosyl transferase) deficient P3x63xAg8.653 plasmacytoma cells. The fused cells are plated into 96 well microtiter plates and screened for hybridoma fusion cells by their capacity to grow in culture medium supplemented with hypothanthine, aminopterin and thymidine for approximately 2-3 weeks.

Hybridoma cells that arise from such incubation are preferably screened for their capacity to produce an immunoglobulin that binds to a protein of interest. An indirect ELISA may be used for this purpose. In brief, the supernatants of hybridomas are incubated in microtiter wells that contain immobilized protein. After washing, the titer of bound immunoglobulin can be determined using, for example, a goat anti-mouse antibody conjugated to horseradish peroxidase. After additional washing, the amount of immobilized enzyme is determined (for example through the use of a chromogenic substrate). Such screening is performed as quickly as possible after the identification of the hybridoma in order to ensure that a desired clone is not overgrown by non-secreting neighbor cells. Desirably, the fusion plates are screened several times since the rates of hybridoma growth vary. In a preferred sub-embodiment, a different antigenic form may be used to screen the hybridoma. Thus, for example, the splenocytes may be immunized with one immunogen, but the resulting hybridomas can be screened using a different immunogen. It is understood that any of the protein or peptide molecules of the present invention may be used to raise antibodies.

As discussed below, such antibody molecules or their fragments may be used for diagnostic purposes. Where the antibodies are intended for diagnostic purposes, it may be desirable to derivatize them, for example with a ligand group (such as biotin) or a detectable marker group (such as a fluorescent group, a radioisotope or an enzyme).

The ability to produce antibodies that bind the protein or peptide molecules of the present invention permits the identification of mimetic compounds of those molecules. A "mimetic compound" is a compound that is not that compound, or a fragment of that compound, but which nonetheless exhibits an ability to specifically bind to antibodies directed against that compound.

It is understood that any of the agents of the present invention can be substantially purified and/or be biologically active and/or recombinant.

Uses of the Agents of the Invention

Nucleic acid molecules and fragments thereof of the present invention may be employed to obtain other nucleic acid molecules from the same species (e.g., ESTs or fragment thereof from maize may be utilized to obtain other nucleic acid molecules from maize). Such nucleic acid molecules include the nucleic acid molecules that encode the complete coding sequence of a protein and promoters and flanking sequences of such molecules. In addition, such nucleic acid molecules include nucleic acid molecules that encode for other isozymes or gene family members. Such molecules can be readily obtained by using the above-described nucleic acid molecules or fragments thereof to screen cDNA or genomic libraries obtained from maize or soybean. Methods for forming such libraries are well known in the art.

Nucleic acid molecules and fragments thereof of the present invention may also be employed to obtain nucleic acid homologues. Such homologues include the nucleic acid molecule of other plants or other organisms (e.g., alfalfa, *Arabidopsis*, barley, *Brassica*, broccoli, cabbage, citrus, cotton, garlic, oat, oilseed rape, onion, canola, flax, an ornamental plant, pea, peanut, pepper, potato, rice, rye, sorghum, strawberry, sugarcane, sugarbeet, tomato, wheat, poplar, pine, fir, eucalyptus, apple, lettuce, lentils, grape, banana, tea, turf grasses, sunflower, oil palm, *Phaseolus*, etc.) including the nucleic acid molecules that encode, in whole or in part, protein homologues of other plant species or other organisms, sequences of genetic elements such as promoters and transcriptional regulatory elements. Such molecules can be readily obtained by using the above-described nucleic acid molecules or fragments thereof to screen cDNA or genomic libraries obtained from such plant species. Methods for forming such libraries are well known in the art. Such homologue molecules may differ in their nucleotide sequences from those found in one or more of SEQ ID NO: 1 through SEQ ID NO: 711 or complements thereof because complete complementarity is not needed for stable hybridization. The nucleic acid molecules of the present invention therefore also include molecules that, although capable of specifically hybridizing with the nucleic acid molecules may lack "complete complementarity."

Any of a variety of methods may be used to obtain one or more of the above-described nucleic acid molecules (Zamechik et al., *Proc. Natl. Acad. Sci.* (*U.S.A.*) 83:4143-4146 (1986), the entirety of which is herein incorporated by reference; Goodchild et al., *Proc. Natl. Acad. Sci.* (*U.S.A.*) 85:5507-5511 (1988), the entirety of which is herein incorporated by reference; Wickstrom et al., *Proc. Natl. Acad. Sci.*(*U.S.A.*) 85:1028-1032 (1988), the entirety of which is herein incorporated by reference; Holt et al., *Molec. Cell. Biol.* 8:963-973 (1988), the entirety of which is herein incorporated by reference; Gerwirtz et al., *Science* 242:1303-1306 (1988), the entirety of which is herein incorporated by reference; Anfossi et al., *Proc. Natl. Acad. Sci.* (*U.S.A.*) 86:3379-3383 (1989), the entirety of which is herein incorporated by reference; Becker et al., *EMBO J.* 8:3685-3691 (1989); the entirety of which is herein incorporated by reference). Automated nucleic acid synthesizers may be employed for this purpose. In lieu of such synthesis, the disclosed nucleic acid molecules may be used to define a pair of primers that can be used with the polymerase chain reaction (Mullis et al., *Cold Spring Harbor Symp. Quant. Biol.* 51:263-273 (1986); Erlich et al., European Patent 50,424; European Patent 84,796; European Patent 258,017; European Patent 237,362; Mullis, European Patent 201,184; Mullis et al., U.S. Pat. No. 4,683,202; Erlich, U.S. Pat. No. 4,582,788; and Saiki et al., U.S. Pat. No. 4,683,194, all of which are herein incorporated by reference in their entirety) to amplify and obtain any desired nucleic acid molecule or fragment.

Promoter sequence(s) and other genetic elements, including but not limited to transcriptional regulatory flanking sequences, associated with one or more of the disclosed nucleic acid sequences can also be obtained using the disclosed nucleic acid sequence provided herein. In one embodiment, such sequences are obtained by incubating EST nucleic acid molecules or preferably fragments thereof with members of genomic libraries (e.g. maize and soybean) and recovering clones that hybridize to the EST nucleic acid molecule or fragment thereof. In a second embodiment, methods of "chromosome walking," or inverse PCR may be used to obtain such sequences (Frohman et al., *Proc. Natl. Acad. Sci.* (*U.S.A.*) 85:8998-9002 (1988); Ohara et al., *Proc. Natl. Acad. Sci.* (*U.S.A.*) 86:5673-5677 (1989); Pang et al., *Biotechniques* 22:1046-1048 (1977); Huang et al., *Methods Mol. Biol.* 69:89-96 (1997); Huang et al., *Method Mol. Biol.* 67:287-294 (1997); Benkel et al., *Genet. Anal.* 13:123-127 (1996); Hartl et al., *Methods Mol. Biol.* 58:293-301 (1996), all of which are herein incorporated by reference in their entirety).

The nucleic acid molecules of the present invention may be used to isolate promoters of cell enhanced, cell specific, tissue enhanced, tissue specific, developmentally or environmentally regulated expression profiles. Isolation and functional analysis of the 5' flanking promoter sequences of these genes from genomic libraries, for example, using genomic screening methods and PCR techniques would result in the isolation of useful promoters and transcriptional regulatory elements. These methods are known to those of skill in the art and have been described (See, for example, Birren et al., *Genome Analysis: Analyzing DNA*, 1, (1997), Cold Spring Harbor Laboratory Press, Cold Spring Harbor, N.Y., the entirety of which is herein incorporated by reference). Promoters obtained utilizing the nucleic acid molecules of the present invention could also be modified to affect their control characteristics. Examples of such modifications would include but are not limited to enhanced sequences as reported in Uses of the Agents of the Invention, Section (a) Plant Constructs and Plant Transformants. Such genetic elements could be used to enhance gene expression of new and existing traits for crop improvements.

In one sub-aspect, such an analysis is conducted by determining the presence and/or identity of polymorphism(s) by one or more of the nucleic acid molecules of the present invention and more preferably one or more of the EST nucleic acid molecule or fragment thereof which are associated with a phenotype, or a predisposition to that phenotype.

Any of a variety of molecules can be used to identify such polymorphism(s). In one embodiment, one or more of the EST nucleic acid molecules (or a sub-fragment thereof) may be employed as a marker nucleic acid molecule to identify such polymorphism(s). Alternatively, such polymorphisms can be detected through the use of a marker nucleic acid molecule or a marker protein that is genetically linked to (i.e., a polynucleotide that co-segregates with) such polymorphism(s).

In an alternative embodiment, such polymorphisms can be detected through the use of a marker nucleic acid molecule that is physically linked to such polymorphism(s). For this purpose, marker nucleic acid molecules comprising a nucleotide sequence of a polynucleotide located within 1 mb of the polymorphism(s) and more preferably within 100 kb of the polymorphism(s) and most preferably within 10 kb of the polymorphism(s) can be employed.

The genomes of animals and plants naturally undergo spontaneous mutation in the course of their continuing evolution (Gusella, *Ann. Rev. Biochem.* 55:831-854 (1986)). A "polymorphism" is a variation or difference in the sequence of the gene or its flanking regions that arises in some of the members of a species. The variant sequence and the "original" sequence co-exist in the species' population. In some instances, such co-existence is in stable or quasi-stable equilibrium.

A polymorphism is thus said to be "allelic," in that, due to the existence of the polymorphism, some members of a species may have the original sequence (i.e., the original "allele") whereas other members may have the variant sequence (i.e., the variant "allele"). In the simplest case, only one variant sequence may exist and the polymorphism is thus said to be di-allelic. In other cases, the species' population may contain multiple alleles and the polymorphism is termed tri-allelic, etc. A single gene may have multiple different unrelated polymorphisms. For example, it may have a di-allelic polymorphism at one site and a multi-allelic polymorphism at another site.

The variation that defines the polymorphism may range from a single nucleotide variation to the insertion or deletion of extended regions within a gene. In some cases, the DNA sequence variations are in regions of the genome that are characterized by short tandem repeats (STRs) that include tandem di- or tri-nucleotide repeated motifs of nucleotides. Polymorphisms characterized by such tandem repeats are referred to as "variable number tandem repeat" ("VNTR") polymorphisms. VNTRs have been used in identity analysis (Weber, U.S. Pat. No. 5,075,217; Armour et al., *FEBS Lett.* 307:113-115 (1992); Jones et al., *Eur. J. Haematol.* 39:144-147 (1987); Horn et al., PCT Patent Application WO91/14003; Jeffreys, European Patent Application 370,719; Jeffreys, U.S. Pat. No. 5,175,082; Jeffreys et al., *Amer. J. Hum. Genet.* 39:11-24 (1986); Jeffreys et al., *Nature* 316:76-79 (1985); Gray et al., *Proc. R. Acad. Soc. Lond.* 243:241-253 (1991); Moore et al., *Genomics* 10:654-660 (1991); Jeffreys et al., *Anim. Genet.* 18:1-15 (1987); Hillel et al., *Anim. Genet.* 20:145-155 (1989); Hillel et al., *Genet.* 124:783-789 (1990), all of which are herein incorporated by reference in their entirety).

The detection of polymorphic sites in a sample of DNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis or other means.

The most preferred method of achieving such amplification employs the polymerase chain reaction ("PCR") (Mullis et al., Cold Spring Harbor Symp. Quant. Biol. 51:263-273 (1986); Erlich et al., European Patent Appln. 50,424; European Patent Appln. 84,796; European Patent Application 258,017; European Patent Appln. 237,362; Mullis, European Patent Appln. 201,184; Mullis et al., U.S. Pat. No. 4,683,202; Erlich, U.S. Pat. No. 4,582,788; and Saiki et al., U.S. Pat. No. 4,683,194), using primer pairs that are capable of hybridizing to the proximal sequences that define a polymorphism in its double-stranded form.

In lieu of PCR, alternative methods, such as the "Ligase Chain Reaction" ("LCR") may be used (Barany, *Proc. Natl. Acad. Sci. (U.S.A.)* 88:189-193 (1991), the entirety of which is herein incorporated by reference). LCR uses two pairs of oligonucleotide probes to exponentially amplify a specific target. The sequences of each pair of oligonucleotides is selected to permit the pair to hybridize to abutting sequences of the same strand of the target. Such hybridization forms a substrate for a template-dependent ligase. As with PCR, the resulting products thus serve as a template in subsequent cycles and an exponential amplification of the desired sequence is obtained.

LCR can be performed with oligonucleotides having the proximal and distal sequences of the same strand of a polymorphic site. In one embodiment, either oligonucleotide will be designed to include the actual polymorphic site of the polymorphism. In such an embodiment, the reaction conditions are selected such that the oligonucleotides can be ligated together only if the target molecule either contains or lacks the specific nucleotide that is complementary to the polymorphic site present on the oligonucleotide. Alternatively, the oligonucleotides may be selected such that they do not include the polymorphic site (see, Segev, PCT Application WO 90/01069, the entirety of which is herein incorporated by reference).

The "Oligonucleotide Ligation Assay" ("OLA") may alternatively be employed (Landegren et al., *Science* 241:1077-1080 (1988), the entirety of which is herein incorporated by reference). The OLA protocol uses two oligonucleotides which are designed to be capable of hybridizing to abutting sequences of a single strand of a target. OLA, like LCR, is particularly suited for the detection of point mutations. Unlike LCR, however, OLA results in "linear" rather than exponential amplification of the target sequence.

Nickerson et al., have described a nucleic acid detection assay that combines attributes of PCR and OLA (Nickerson et al., *Proc. Natl. Acad. Sci. (U.S.A.)* 87:8923-8927 (1990), the entirety of which is herein incorporated by reference). In this method, PCR is used to achieve the exponential amplification of target DNA, which is then detected using OLA. In addition to requiring multiple and separate, processing steps, one problem associated with such combinations is that they inherit all of the problems associated with PCR and OLA.

Schemes based on ligation of two (or more) oligonucleotides in the presence of nucleic acid having the sequence of the resulting "di-oligonucleotide", thereby amplifying the di-oligonucleotide, are also known (Wu et al., *Genomics* 4:560-569 (1989), the entirety of which is herein incorporated by reference) and may be readily adapted to the purposes of the present invention.

Other known nucleic acid amplification procedures, such as allele-specific oligomers, branched DNA technology, transcription-based amplification systems, or isothermal amplification methods may also be used to amplify and analyze such polymorphisms (Malek et al., U.S. Pat. No. 5,130,238; Davey et al., European Patent Application 329,822; Schuster et al., U.S. Pat. No. 5,169,766; Miller et al., PCT Patent Application WO 89/06700; Kwoh et al., *Proc. Natl. Acad. Sci. (U.S.A.)* 86:1173-1177 (1989); Gingeras et al., PCT Patent Application WO 88/10315; Walker et al., *Proc. Natl. Acad. Sci. (U.S.A.)* 89:392-396 (1992), all of which are herein incorporated by reference in their entirety).

The identification of a polymorphism can be determined in a variety of ways. By correlating the presence or absence of it in a plant with the presence or absence of a phenotype, it is possible to predict the phenotype of that plant. If a polymorphism creates or destroys a restriction endonuclease cleavage site, or if it results in the loss or insertion of DNA (e.g., a VNTR polymorphism), it will alter the size or profile of the DNA fragments that are generated by digestion with that restriction endonuclease. As such, individuals that possess a variant sequence can be distinguished from those having the original sequence by restriction fragment analysis. Polymorphisms that can be identified in this manner are termed "restriction fragment length polymorphisms" ("RFLPs"). RFLPs have been widely used in human and plant genetic analyses (Glassberg, UK Patent Application 2135774; Skolnick et al., *Cytogen. Cell Genet.* 32:58-67 (1982); Botstein et al., *Ann. J. Hum. Genet.* 32:314-331 (1980); Fischer et al., (PCT Application WO90/13668); Uhlen, PCT Application WO90/11369).

Polymorphisms can also be identified by Single Strand Conformation Polymorphism (SSCP) analysis. SSCP is a method capable of identifying most sequence variations in a single strand of DNA, typically between 150 and 250 nucleotides in length (Elles, *Methods in Molecular Medicine Molecular Diagnosis of Genetic Diseases*, Humana Press (1996), the entirety of which is herein incorporated by reference); Orita et al., *Genomics* 5:874-879 (1989), the entirety of which is herein incorporated by reference). Under denaturing conditions a single strand of DNA will adopt a conformation that is uniquely dependent on its sequence conformation. This conformation usually will be different, even if only a single base is changed. Most conformations have been reported to alter the physical configuration or size sufficiently to be detectable by electrophoresis. A number of protocols have been described for SSCP including, but not limited to, Lee et al., *Anal. Biochem.* 205:289-293 (1992), the entirety of which is herein incorporated by reference; Suzuki et al., *Anal. Biochem.* 192:82-84 (1991), the entirety of which is herein incorporated by reference; Lo et al., *Nucleic Acids Research* 20:1005-1009 (1992), the entirety of which is herein incorporated by reference; Sarkar et al., *Genomics* 13:441-443 (1992), the entirety of which is herein incorporated by reference. It is understood that one or more of the nucleic acids of the present invention, may be utilized as markers or probes to detect polymorphisms by SSCP analysis.

Polymorphisms may also be found using a DNA fingerprinting technique called amplified fragment length polymorphism (AFLP), which is based on the selective PCR amplification of restriction fragments from a total digest of genomic DNA to profile that DNA (Vos et al., *Nucleic Acids Res.* 23:4407-4414 (1995), the entirety of which is herein incorporated by reference). This method allows for the specific co-amplification of high numbers of restriction fragments, which can be visualized by PCR without knowledge of the nucleic acid sequence.

AFLP employs basically three steps. Initially, a sample of genomic DNA is cut with restriction enzymes and oligonucleotide adapters are ligated to the restriction fragments of the DNA. The restriction fragments are then amplified using PCR by using the adapter and restriction sequence as target sites for primer annealing. The selective amplification is achieved by the use of primers that extend into the restriction fragments, amplifying only those fragments in which the primer extensions match the nucleotide flanking the restriction sites. These amplified fragments are then visualized on a denaturing polyacrylamide gel.

AFLP analysis has been performed on *Salix* (Beismann et al., *Mol. Ecol.* 6:989-993 (1997), the entirety of which is herein incorporated by reference), *Acinetobacter* (Janssen et al., *Int. J. Syst. Bacteriol.* 47:1179-1187 (1997), the entirety of which is herein incorporated by reference), *Aeromonas popoffi* (Huys et al., *Int. J. Syst. Bacteriol.* 47:1165-1171 (1997), the entirety of which is herein incorporated by reference), rice (McCouch et al., *Plant Mol. Biol.* 35:89-99 (1997), the entirety of which is herein incorporated by reference; Nandi et al., *Mol. Gen. Genet.* 255:1-8 (1997), the entirety of which is herein incorporated by reference; Cho et al., *Genome* 39:373-378 (1996), the entirety of which is herein incorporated by reference), barley (*Hordeum vulgare*)(Simons et al., *Genomics* 44:61-70 (1997), the entirety of which is herein incorporated by reference; Waugh et al., *Mol. Gen. Genet.* 255:311-321 (1997), the entirety of which is herein incorporated by reference; Qi et al., *Mol. Gen. Genet.* 254:330-336 (1997), the entirety of which is herein incorporated by reference; Becker et al., *Mol. Gen. Genet.* 249:65-73 (1995), the entirety of which is herein incorporated by reference), potato (Van der Voort et al., *Mol. Gen. Genet.* 255:438-447 (1997), the entirety of which is herein incorporated by reference; Meksem et al., *Mol. Gen. Genet.* 249:74-81 (1995), the entirety of which is herein incorporated by reference), *Phytophthora infestans* (Van der Lee et al., *Fungal Genet. Biol.* 21:278-291 (1997), the entirety of which is herein incorporated by reference), *Bacillus anthracis* (Keim et al., *J. Bacteriol.* 179:818-824 (1997), the entirety of which is herein incorporated by reference), *Astragalus cremnophylax* (Travis et al., *Mol. Ecol.* 5:735-745 (1996), the entirety of which is herein incorporated by reference), *Arabidopsis* (Cnops et al., *Mol. Gen. Genet.* 253:32-41 (1996), the entirety of which is herein incorporated by reference), *Escherichia coli* (Lin et al., *Nucleic Acids Res.* 24:3649-3650 (1996), the entirety of which is herein incorporated by reference), *Aeromonas* (Huys et al., *Int. J. Syst. Bacteriol.* 46:572-580 (1996), the entirety of which is herein incorporated by reference), nematode (Folkertsma et al., *Mol. Plant Microbe Interact.* 9:47-54 (1996), the entirety of which is herein incorporated by reference), tomato (Thomas et al., *Plant J.* 8:785-794 (1995), the entirety of which is herein incorporated by reference) and human (Latorra et al., *PCR Methods Appl.* 3:351-358 (1994), the entirety of which is herein incorporated by reference). AFLP analysis has also been used for fingerprinting mRNA (Money et al., *Nucleic Acids Res.* 24:2616-2617 (1996), the entirety of which is herein incorporated by reference; Bachem et al., *Plant J.* 9:745-753 (1996), the entirety of which is herein incorporated by reference). It is understood that one or more of the nucleic acids of the present invention, may be utilized as markers or probes to detect polymorphisms by AFLP analysis or for fingerprinting RNA.

Polymorphisms may also be found using random amplified polymorphic DNA (RAPD) (Williams et al., *Nucl. Acids Res.* 18:6531-6535 (1990), the entirety of which is herein incorporated by reference) and cleaveable amplified polymorphic sequences (CAPS) (Lyamichev et al., *Science* 260:778-783 (1993), the entirety of which is herein incorporated by reference). It is understood that one or more of the nucleic acid molecules of the present invention, may be utilized as markers or probes to detect polymorphisms by RAPD or CAPS analysis.

Through genetic mapping, a fine scale linkage map can be developed using DNA markers and, then, a genomic DNA library of large-sized fragments can be screened with molecular markers linked to the desired trait. Molecular markers are advantageous for agronomic traits that are otherwise difficult to tag, such as resistance to pathogens, insects and nematodes, tolerance to abiotic stress, quality parameters and quantitative traits such as high yield potential.

The essential requirements for marker-assisted selection in a plant breeding program are: (1) the marker(s) should co-segregate or be closely linked with the desired trait; (2) an efficient means of screening large populations for the molecular marker(s) should be available; and (3) the screening technique should have high reproducibility across laboratories and preferably be economical to use and be user-friendly.

The genetic linkage of marker molecules can be established by a gene mapping model such as, without limitation, the flanking marker model reported by Lander and Botstein, *Genetics* 121:185-199 (1989) and the interval mapping, based on maximum likelihood methods described by Lander and Botstein, *Genetics* 121:185-199 (1989) and implemented in the software package MAPMAKER/QTL (Lincoln and Lander, *Mapping Genes Controlling Quantitative Traits Using MAPMAKER/QTL*, Whitehead Institute for Biomedical Research, Massachusetts, (1990). Additional software includes Qgene, Version 2.23 (1996), Department of Plant Breeding and Biometry, 266 Emerson Hall, Cornell University, Ithaca, N.Y., the manual of which is herein incorporated by reference in its entirety). Use of Qgene software is a particularly preferred approach.

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$(MLE for the presence of a QTL/MLE given no linked QTL).

The LOD score essentially indicates how much more likely the data are to have arisen assuming the presence of a QTL than in its absence. The LOD threshold value for avoiding a false positive with a given confidence, say 95%, depends on the number of markers and the length of the genome. Graphs indicating LOD thresholds are set forth in Lander and Botstein, *Genetics* 121:185-199 (1989) the entirety of which is herein incorporated by reference and further described by Arś and Moreno-González, *Plant Breeding*, Hayward et al., (eds.) Chapman & Hall, London, pp. 314-331 (1993), the entirety of which is herein incorporated by reference.

Additional models can be used. Many modifications and alternative approaches to interval mapping have been reported, including the use non-parametric methods (Kruglyak and Lander, *Genetics* 139:1421-1428 (1995), the entirety of which is herein incorporated by reference). Multiple regression methods or models can be also be used, in which the trait is regressed on a large number of markers (Jansen, *Biometrics in Plant Breeding*, van Oijen and Jansen (eds.), Proceedings of the Ninth Meeting of the Eucarpia Section Biometrics in Plant Breeding, The Netherlands, pp. 116-124 (1994); Weber and Wricke, *Advances in Plant Breeding*, Blackwell, Berlin, 16 (1994), both of which is herein incorporated by reference in their entirety). Procedures combining interval mapping with regression analysis, whereby the phenotype is regressed onto a single putative QTL at a given marker interval and at the same time onto a number of markers that serve as 'cofactors,' have been reported by Jansen and Stam, *Genetics* 136:1447-1455 (1994), the entirety of which is herein incorporated by reference and Zeng, *Genetics* 136:1457-1468 (1994) the entirety of which is herein incorporated by reference. Generally, the use of cofactors reduces the bias and sampling error of the estimated QTL positions (Utz and Melchinger, *Biometrics in Plant Breeding*, van Oijen and Jansen (eds.) Proceedings of the Ninth Meeting of the Eucarpia Section Biometrics in Plant Breeding, The Netherlands, pp. 195-204 (1994), the entirety of which is herein incorporated by reference, thereby improving the precision and efficiency of QTL mapping (Zeng, *Genetics* 136:1457-1468 (1994)). These models can be extended to multi-environment experiments to analyze genotype-environment interactions (Jansen et al., *Theo. Appl. Genet.* 91:33-37 (1995), the entirety of which is herein incorporated by reference).

Selection of an appropriate mapping populations is important to map construction. The choice of appropriate mapping population depends on the type of marker systems employed (Tanksley et al., *Molecular mapping plant chromosomes. Chromosome structure and function: Impact of new concepts*, Gustafson and Appels (eds.), Plenum Press, New York, pp 157-173 (1988), the entirety of which is herein incorporated by reference). Consideration must be given to the source of parents (adapted vs. exotic) used in the mapping population. Chromosome pairing and recombination rates can be severely disturbed (suppressed) in wide crosses (adapted×exotic) and generally yield greatly reduced linkage distances. Wide crosses will usually provide segregating populations with a relatively large array of polymorphisms when compared to progeny in a narrow cross (adapted×adapted).

An $F_2$ population is the first generation of selfing after the hybrid seed is produced. Usually a single $F_1$ plant is selfed to generate a population segregating for all the genes in Mendelian (1:2:1) fashion. Maximum genetic information is obtained from a completely classified $F_2$ population using a codominant marker system (Mather, *Measurement of Linkage in Heredity*, Methuen and Co., (1938), the entirety of which is herein incorporated by reference). In the case of dominant markers, progeny tests (e.g. $F_3$, $BCF_2$) are required to identify the heterozygotes, thus making it equivalent to a completely classified $F_2$ population. However, this procedure is often prohibitive because of the cost and time involved in progeny testing. Progeny testing of $F_2$ individuals is often used in map construction where phenotypes do not consistently reflect genotype (e.g. disease resistance) or where trait expression is controlled by a QTL. Segregation data from progeny test populations (e.g. $F_3$ or $BCF_2$) can be used in map construction. Marker-assisted selection can then be applied to cross progeny based on marker-trait map associations ($F_2$, $F_3$), where linkage groups have not been completely disassociated by recombination events (i.e., maximum disequillibrium).

Recombinant inbred lines (RIL) (genetically related lines; usually $>F_5$, developed from continuously selfing $F_2$ lines towards homozygosity) can be used as a mapping population. Information obtained from dominant markers can be maximized by using RIL because all loci are homozygous or nearly so. Under conditions of tight linkage (i.e., about <10% recombination), dominant and co-dominant markers evaluated in RIL populations provide more information per individual than either marker type in backcross populations (Reiter et al., *Proc. Natl. Acad. Sci.* (*U.S.A.*) 89:1477-1481 (1992), the entirety of which is herein incorporated by reference). However, as the distance between markers becomes larger (i.e., loci become more independent), the information in RIL populations decreases dramatically when compared to codominant markers.

Backcross populations (e.g., generated from a cross between a successful variety (recurrent parent) and another variety (donor parent) carrying a trait not present in the former) can be utilized as a mapping population. A series of backcrosses to the recurrent parent can be made to recover most of its desirable traits. Thus a population is created consisting of individuals nearly like the recurrent parent but each individual carries varying amounts or mosaic of genomic regions from the donor parent. Backcross populations can be useful for mapping dominant markers if all loci in the recurrent parent are homozygous and the donor and recurrent parent have contrasting polymorphic marker alleles (Reiter et al., *Proc. Natl. Acad. Sci. (U.S.A.)* 89:1477-1481 (1992)). Information obtained from backcross populations using either codominant or dominant markers is less than that obtained from $F_2$ populations because one, rather than two, recombinant gametes are sampled per plant. Backcross populations, however, are more informative (at low marker saturation) when compared to RILs as the distance between linked loci increases in RIL populations (i.e. about 15% recombination). Increased recombination can be beneficial for resolution of tight linkages, but may be undesirable in the construction of maps with low marker saturation.

Near-isogenic lines (NIL) created by many backcrosses to produce an array of individuals that are nearly identical in genetic composition except for the trait or genomic region under interrogation can be used as a mapping population. In mapping with NILs, only a portion of the polymorphic loci are expected to map to a selected region.

Bulk segregant analysis (BSA) is a method developed for the rapid identification of linkage between markers and traits of interest (Michelmore et al., *Proc. Natl. Acad. Sci. (U.S.A.)* 88:9828-9832 (1991), the entirety of which is herein incorporated by reference). In BSA, two bulked DNA samples are drawn from a segregating population originating from a single cross. These bulks contain individuals that are identical for a particular trait (resistant or susceptible to particular disease) or genomic region but arbitrary at unlinked regions (i.e. heterozygous). Regions unlinked to the target region will not differ between the bulked samples of many individuals in BSA.

It is understood that one or more of the nucleic acid molecules of the present invention may be used as molecular markers. It is also understood that one or more of the protein molecules of the present invention may be used as molecular markers.

In accordance with this aspect of the present invention, a sample nucleic acid is obtained from plants cells or tissues. Any source of nucleic acid may be used. Preferably, the nucleic acid is genomic DNA. The nucleic acid is subjected to restriction endonuclease digestion. For example, one or more nucleic acid molecule or fragment thereof of the present invention can be used as a probe in accordance with the above-described polymorphic methods. The polymorphism obtained in this approach can then be cloned to identify the mutation at the coding region which alters the protein's structure or regulatory region of the gene which affects its expression level.

In an aspect of the present invention, one or more of the nucleic molecules of the present invention are used to determine the level (i.e., the concentration of mRNA in a sample, etc.) in a plant (preferably maize or soybean) or pattern (i.e., the kinetics of expression, rate of decomposition, stability profile, etc.) of the expression of a protein encoded in part or whole by one or more of the nucleic acid molecule of the present invention (collectively, the "Expression Response" of a cell or tissue). As used herein, the Expression Response manifested by a cell or tissue is said to be "altered" if it differs from the Expression Response of cells or tissues of plants not exhibiting the phenotype. To determine whether a Expression Response is altered, the Expression Response manifested by the cell or tissue of the plant exhibiting the phenotype is compared with that of a similar cell or tissue sample of a plant not exhibiting the phenotype. As will be appreciated, it is not necessary to re-determine the Expression Response of the cell or tissue sample of plants not exhibiting the phenotype each time such a comparison is made; rather, the Expression Response of a particular plant may be compared with previously obtained values of normal plants. As used herein, the phenotype of the organism is any of one or more characteristics of an organism (e.g. disease resistance, pest tolerance, environmental tolerance such as tolerance to abiotic stress, male sterility, quality improvement or yield etc.). A change in genotype or phenotype may be transient or permanent. Also as used herein, a tissue sample is any sample that comprises more than one cell. In a preferred aspect, a tissue sample comprises cells that share a common characteristic (e.g. derived from root, seed, flower, leaf, stem or pollen etc.).

In one aspect of the present invention, an evaluation can be conducted to determine whether a particular mRNA molecule is present. One or more of the nucleic acid molecules of the present invention, preferably one or more of the EST nucleic acid molecules or fragments thereof of the present invention are utilized to detect the presence or quantity of the mRNA species. Such molecules are then incubated with cell or tissue extracts of a plant under conditions sufficient to permit nucleic acid hybridization. The detection of double-stranded probe-mRNA hybrid molecules is indicative of the presence of the mRNA; the amount of such hybrid formed is proportional to the amount of mRNA. Thus, such probes may be used to ascertain the level and extent of the mRNA production in a plant's cells or tissues. Such nucleic acid hybridization may be conducted under quantitative conditions (thereby providing a numerical value of the amount of the mRNA present). Alternatively, the assay may be conducted as a qualitative assay that indicates either that the mRNA is present, or that its level exceeds a user set, predefined value.

A principle of in situ hybridization is that a labeled, single-stranded nucleic acid probe will hybridize to a complementary strand of cellular DNA or RNA and, under the appropriate conditions, these molecules will form a stable hybrid. When nucleic acid hybridization is combined with histological techniques, specific DNA or RNA sequences can be identified within a single cell. An advantage of in situ hybridization over more conventional techniques for the detection of nucleic acids is that it allows an investigator to determine the precise spatial population (Angerer et al., *Dev. Biol.* 101:477-484 (1984), the entirety of which is herein incorporated by reference; Angerer et al., *Dev. Biol.* 112:157-166 (1985), the entirety of which is herein incorporated by reference; Dixon et al., *EMBO J.* 10:1317-1324 (1991), the entirety of which is herein incorporated by reference). In situ hybridization may be used to measure the steady-state level of RNA accumulation. It is a sensitive technique and RNA sequences present in as few as 5-10 copies per cell can be detected (Hardin et al., *J. Mol. Biol.* 202:417-431 (1989), the entirety of which is herein incorporated by reference). A number of protocols have been devised for in situ hybridization, each with tissue preparation, hybridization and washing conditions (Meyerowitz, *Plant Mol. Biol. Rep.* 5:242-250 (1987), the entirety of which is herein incorporated by reference; Cox and Goldberg, In: *Plant Molecular Biology: A Practical Approach*, Shaw (ed.), pp 1-35, IRL Press, Oxford (1988), the entirety of which is herein incorporated by reference; Raikhel et al., *In situ RNA*

*hybridization in plant tissues*, In: *Plant Molecular Biology Manual*, vol. B9: 1-32, Kluwer Academic Publisher, Dordrecht, Belgium (1989), the entirety of which is herein incorporated by reference).

In situ hybridization also allows for the localization of proteins within a tissue or cell (Wilkinson, *In Situ Hybridization*, Oxford University Press, Oxford (1992), the entirety of which is herein incorporated by reference; Langdale, *In Situ Hybridization In: The Maize Handbook*, Freeling and Walbot (eds.), pp 165-179, Springer-Verlag, New York (1994), the entirety of which is herein incorporated by reference). It is understood that one or more of the molecules of the present invention, preferably one or more of the EST nucleic acid molecules or fragments thereof of the present invention or one or more of the antibodies of the present invention may be utilized to detect the level or pattern of a cytokinin pathway protein or mRNA thereof by in situ hybridization.

Fluorescent in situ hybridization allows the localization of a particular DNA sequence along a chromosome which is useful, among other uses, for gene mapping, following chromosomes in hybrid lines or detecting chromosomes with translocations, transversions or deletions. In situ hybridization has been used to identify chromosomes in several plant species (Griffor et al., *Plant Mol. Biol.* 17:101-109 (1991), the entirety of which is herein incorporated by reference; Gustafson et al., *Proc. Natl. Acad. Sci.* (*U.S.A.*) 87:1899-1902 (1990), herein incorporated by reference; Mukai and Gill, *Genome* 34:448-452 (1991), the entirety of which is herein incorporated by reference; Schwarzacher and Heslop-Harrison, *Genome* 34:317-323 (1991); Wang et al., *Jpn. J. Genet.* 66:313-316 (1991), the entirety of which is herein incorporated by reference; Parra and Windle, *Nature Genetics* 5:17-21 (1993), the entirety of which is herein incorporated by reference). It is understood that the nucleic acid molecules of the present invention may be used as probes or markers to localize sequences along a chromosome.

Another method to localize the expression of a molecule is tissue printing. Tissue printing provides a way to screen, at the same time on the same membrane many tissue sections from different plants or different developmental stages. Tissue-printing procedures utilize films designed to immobilize proteins and nucleic acids. In essence, a freshly cut section of a tissue is pressed gently onto nitrocellulose paper, nylon membrane or polyvinylidene difluoride membrane. Such membranes are commercially available (e.g. Millipore, Bedford, Mass. U.S.A.). The contents of the cut cell transfer onto the membrane and the contents and are immobilized to the membrane. The immobilized contents form a latent print that can be visualized with appropriate probes. When a plant tissue print is made on nitrocellulose paper, the cell walls leave a physical print that makes the anatomy visible without further treatment (Varner and Taylor, *Plant Physiol.* 91:31-33 (1989), the entirety of which is herein incorporated by reference).

Tissue printing on substrate films is described by Daoust, *Exp. Cell Res.* 12:203-211 (1957), the entirety of which is herein incorporated by reference, who detected amylase, protease, ribonuclease and deoxyribonuclease in animal tissues using starch, gelatin and agar films. These techniques can be applied to plant tissues (Yomo and Taylor, *Planta* 112:35-43 (1973); the entirety of which is herein incorporated by reference; Harris and Chrispeels, *Plant Physiol.* 56:292-299 (1975), the entirety of which is herein incorporated by reference). Advances in membrane technology have increased the range of applications of Daoust's tissue-printing techniques allowing (Cassab and Varner, *J. Cell. Biol.* 105:2581-2588 (1987), the entirety of which is herein incorporated by reference) the histochemical localization of various plant enzymes and deoxyribonuclease on nitrocellulose paper and nylon (Spruce et al., *Phytochemistry* 26:2901-2903 (1987), the entirety of which is herein incorporated by reference; Barres et al., *Neuron* 5:527-544 (1990), the entirety of which is herein incorporated by reference; Reid and Pont-Lezica, *Tissue Printing: Tools for the Study of Anatomy, Histochemistry and Gene Expression*, Academic Press, New York, N.Y. (1992), the entirety of which is herein incorporated by reference; Reid et al., *Plant Physiol.* 93:160-165 (1990), the entirety of which is herein incorporated by reference; Ye et al., *Plant J.* 1:175-183 (1991), the entirety of which is herein incorporated by reference).

It is understood that one or more of the molecules of the present invention, preferably one or more of the EST nucleic acid molecules or fragments thereof of the present invention or one or more of the antibodies of the present invention may be utilized to detect the presence or quantity of a cytokinin pathway protein by tissue printing.

Further it is also understood that any of the nucleic acid molecules of the present invention may be used as marker nucleic acids and or probes in connection with methods that require probes or marker nucleic acids. As used herein, a probe is an agent that is utilized to determine an attribute or feature (e.g. presence or absence, location, correlation, etc.) of a molecule, cell, tissue or plant. As used herein, a marker nucleic acid is a nucleic acid molecule that is utilized to determine an attribute or feature (e.g., presence or absence, location, correlation, etc.) or a molecule, cell, tissue or plant.

A microarray-based method for high-throughput monitoring of plant gene expression may be utilized to measure gene-specific hybridization targets. This 'chip'-based approach involves using microarrays of nucleic acid molecules as gene-specific hybridization targets to quantitatively measure expression of the corresponding plant genes (Schena et al., *Science* 270:467-470 (1995), the entirety of which is herein incorporated by reference; Shalon, Ph.D. Thesis, Stanford University (1996), the entirety of which is herein incorporated by reference). Every nucleotide in a large sequence can be queried at the same time. Hybridization can be used to efficiently analyze nucleotide sequences.

Several microarray methods have been described. One method compares the sequences to be analyzed by hybridization to a set of oligonucleotides representing all possible subsequences (Bains and Smith, *J. Theor. Biol.* 135:303-307 (1989), the entirety of which is herein incorporated by reference). A second method hybridizes the sample to an array of oligonucleotide or cDNA molecules. An array consisting of oligonucleotides complementary to subsequences of a target sequence can be used to determine the identity of a target sequence, measure its amount and detect differences between the target and a reference sequence. Nucleic acid molecules microarrays may also be screened with protein molecules or fragments thereof to determine nucleic acid molecules that specifically bind protein molecules or fragments thereof.

The microarray approach may be used with polypeptide targets (U.S. Pat. Nos. 5,445,934; 5,143,854; 5,079,600; 4,923,901, all of which are herein incorporated by reference in their entirety). Essentially, polypeptides are synthesized on a substrate (microarray) and these polypeptides can be screened with either protein molecules or fragments thereof or nucleic acid molecules in order to screen for either protein molecules or fragments thereof or nucleic acid molecules that specifically bind the target polypeptides. (Fodor et al., *Science* 251:767-773 (1991), the entirety of which is herein incorporated by reference). It is understood that one or more of the nucleic acid molecules or protein or fragments thereof of the present invention may be utilized in a microarray based method.

In a preferred embodiment of the present invention microarrays may be prepared that comprise nucleic acid molecules where such nucleic acid molecules encode at least one, preferably at least two, more preferably at least three cytokinin pathway enzymes. In a preferred embodiment the nucleic acid molecules are selected from the group consisting of a nucleic acid molecule that encodes a maize or a soybean adenine phosphoribosyl transferase enzyme or fragment thereof, a nucleic acid molecule that encodes a maize or a soybean β glucosidase enzyme or fragment thereof and a nucleic acid molecule that encodes a soybean isopentyltransferase enzyme or fragment thereof.

Site directed mutagenesis may be utilized to modify nucleic acid sequences, particularly as it is a technique that allows one or more of the amino acids encoded by a nucleic acid molecule to be altered (e.g. a threonine to be replaced by a methionine). Three basic methods for site directed mutagenesis are often employed. These are cassette mutagenesis (Wells et al., *Gene* 34:315-323 (1985), the entirety of which is herein incorporated by reference), primer extension (Gilliam et al., *Gene* 12:129-137 (1980), the entirety of which is herein incorporated by reference; Zoller and Smith, *Methods Enzymol.* 100:468-500 (1983), the entirety of which is herein incorporated by reference; Dalbadie-McFarland et al., *Proc. Natl. Acad. Sci. (U.S.A.)* 79:6409-6413 (1982), the entirety of which is herein incorporated by reference) and methods based upon PCR (Scharf et al., *Science* 233:1076-1078 (1986), the entirety of which is herein incorporated by reference; Higuchi et al., *Nucleic Acids Res.* 16:7351-7367 (1988), the entirety of which is herein incorporated by reference). Site directed mutagenesis approaches are also described in European Patent 0 385 962, the entirety of which is herein incorporated by reference; European Patent 0 359 472, the entirety of which is herein incorporated by reference; and PCT Patent Application WO 93/07278, the entirety of which is herein incorporated by reference.

Site directed mutagenesis strategies have been applied to plants for both in vitro as well as in vivo site directed mutagenesis (Lanz et al., *J. Biol. Chem.* 266:9971-9976 (1991), the entirety of which is herein incorporated by reference; Kovgan and Zhdanov, *Biotekhnologiya* 5:148-154, No. 207160n, Chemical Abstracts 110:225 (1989), the entirety of which is herein incorporated by reference; Ge et al., *Proc. Natl. Acad. Sci. (U.S.A.)* 86:4037-4041 (1989), the entirety of which is herein incorporated by reference; Zhu et al., *J. Biol. Chem.* 271:18494-18498 (1996), the entirety of which is herein incorporated by reference; Chu et al., *Biochemistry* 33:6150-6157 (1994), the entirety of which is herein incorporated by reference; Small et al., *EMBO J.* 11:1291-1296 (1992), the entirety of which is herein incorporated by reference; Cho et al., *Mol. Biotechnol.* 8:13-16 (1997), the entirety of which is herein incorporated by reference; Kita et al., *J. Biol. Chem.* 271:26529-26535 (1996), the entirety of which is herein incorporated by reference, Jin et al., *Mol. Microbiol.* 7:555-562 (1993), the entirety of which is herein incorporated by reference; Hatfield and Vierstra, *J. Biol. Chem.* 267:14799-14803 (1992), the entirety of which is herein incorporated by reference; Zhao et al., *Biochemistry* 31:5093-5099 (1992), the entirety of which is herein incorporated by reference).

Any of the nucleic acid molecules of the present invention may either be modified by site directed mutagenesis or used as, for example, nucleic acid molecules that are used to target other nucleic acid molecules for modification. It is understood that mutants with more than one altered nucleotide can be constructed using techniques that practitioners are familiar with such as isolating restriction fragments and ligating such fragments into an expression vector (see, for example, Sambrook et al., *Molecular Cloning: A Laboratory Manual*, Cold Spring Harbor Press (1989)).

Sequence-specific DNA-binding proteins play a role in the regulation of transcription. The isolation of recombinant cDNAs encoding these proteins facilitates the biochemical analysis of their structural and functional properties. Genes encoding such DNA-binding proteins have been isolated using classical genetics (Vollbrecht et al., *Nature* 350: 241-243 (1991), the entirety of which is herein incorporated by reference) and molecular biochemical approaches, including the screening of recombinant cDNA libraries with antibodies (Landschulz et al., *Genes Dev.* 2:786-800 (1988), the entirety of which is herein incorporated by reference) or DNA probes (Bodner et al., *Cell* 55:505-518 (1988), the entirety of which is herein incorporated by reference). In addition, an in situ screening procedure has been used and has facilitated the isolation of sequence-specific DNA-binding proteins from various plant species (Gilmartin et al., *Plant Cell* 4:839-849 (1992), the entirety of which is herein incorporated by reference; Schindler et al., *EMBO J.* 11:1261-1273 (1992), the entirety of which is herein incorporated by reference). An in situ screening protocol does not require the purification of the protein of interest (Vinson et al., *Genes Dev.* 2:801-806 (1988), the entirety of which is herein incorporated by reference; Singh et al., *Cell* 52:415-423 (1988), the entirety of which is herein incorporated by reference).

Two steps may be employed to characterize DNA-protein interactions. The first is to identify promoter fragments that interact with DNA-binding proteins, to titrate binding activity, to determine the specificity of binding and to determine whether a given DNA-binding activity can interact with related DNA sequences (Sambrook et al., *Molecular Cloning: A Laboratory Manual*, $2^{nd}$ edition, Cold Spring Harbor Laboratory Press, Cold Spring Harbor, N.Y. (1989)). Electrophoretic mobility-shift assay is a widely used assay. The assay provides a rapid and sensitive method for detecting DNA-binding proteins based on the observation that the mobility of a DNA fragment through a nondenaturing, low-ionic strength polyacrylamide gel is retarded upon association with a DNA-binding protein (Fried and Crother, *Nucleic Acids Res.* 9:6505-6525 (1981), the entirety of which is herein incorporated by reference). When one or more specific binding activities have been identified, the exact sequence of the DNA bound by the protein may be determined. Several procedures for characterizing protein/DNA-binding sites are used, including methylation and ethylation interference assays (Maxam and Gilbert, *Methods Enzymol.* 65:499-560 (1980), the entirety of which is herein incorporated by reference; Wissman and Hillen, *Methods Enzymol.* 208:365-379 (1991), the entirety of which is herein incorporated by reference), footprinting techniques employing DNase I (Galas and Schmitz, *Nucleic Acids Res.* 5:3157-3170 (1978), the entirety of which is herein incorporated by reference), 1,10-phenanthroline-copper ion methods (Sigman et al., *Methods Enzymol.* 208:414-433 (1991), the entirety of which is herein incorporated by reference) and hydroxyl radicals methods (Dixon et al., *Methods Enzymol.* 208:414-433 (1991), the entirety of which is herein incorporated by reference). It is understood that one or more of the nucleic acid molecules of the present invention may be utilized to identify a protein or fragment thereof that specifically binds to a nucleic acid molecule of the present invention. It is also understood that one or more of the protein molecules or fragments thereof of the present invention may be utilized to identify a nucleic acid molecule that specifically binds to it.

A two-hybrid system is based on the fact that many cellular functions are carried out by proteins, such as transcription factors, that interact (physically) with one another. Two-hybrid systems have been used to probe the function of new proteins (Chien et al., *Proc. Natl. Acad. Sci.* (*U.S.A.*) 88:9578-9582 (1991) the entirety of which is herein incorporated by reference; Durfee et al., *Genes Dev.* 7:555-569 (1993) the entirety of which is herein incorporated by reference; Choi et al., *Cell* 78:499-512 (1994), the entirety of which is herein incorporated by reference; Kranz et al., *Genes Dev.* 8:313-327 (1994), the entirety of which is herein incorporated by reference).

Interaction mating techniques have facilitated a number of two-hybrid studies of protein-protein interaction. Interaction mating has been used to examine interactions between small sets of tens of proteins (Finley and Brent, *Proc. Natl. Acad. Sci.* (*U.S.A.*) 91:12098-12984 (1994), the entirety of which is herein incorporated by reference), larger sets of hundreds of proteins (Bendixen et al., *Nucl. Acids Res.* 22:1778-1779 (1994), the entirety of which is herein incorporated by reference) and to comprehensively map proteins encoded by a small genome (Bartel et al., *Nature Genetics* 12:72-77 (1996), the entirety of which is herein incorporated by reference). This technique utilizes proteins fused to the DNA-binding domain and proteins fused to the activation domain. They are expressed in two different haploid yeast strains of opposite mating type and the strains are mated to determine if the two proteins interact. Mating occurs when haploid yeast strains come into contact and result in the fusion of the two haploids into a diploid yeast strain. An interaction can be determined by the activation of a two-hybrid reporter gene in the diploid strain. An advantage of this technique is that it reduces the number of yeast transformations needed to test individual interactions. It is understood that the protein-protein interactions of protein or fragments thereof of the present invention may be investigated using the two-hybrid system and that any of the nucleic acid molecules of the present invention that encode such proteins or fragments thereof may be used to transform yeast in the two-hybrid system.

(a) Plant Constructs and Plant Transformants

One or more of the nucleic acid molecules of the present invention may be used in plant transformation or transfection. Exogenous genetic material may be transferred into a plant cell and the plant cell regenerated into a whole, fertile or sterile plant. Exogenous genetic material is any genetic material, whether naturally occurring or otherwise, from any source that is capable of being inserted into any organism. Such genetic material may be transferred into either monocotyledons and dicotyledons including, but not limited to maize (pp 63-69), soybean (pp 50-60), *Arabidopsis* (p 45), *phaseolus* (pp 47-49), peanut (pp 49-50), alfalfa (p 60), wheat (pp 69-71), rice (pp 72-79), oat (pp 80-81), sorghum (p 83), rye (p 84), tritordeum (p 84), millet (p85), fescue (p 85), perennial ryegrass (p 86), sugarcane (p87), cranberry (p101), papaya (pp 101-102), banana (p 103), banana (p 103), muskmelon (p 104), apple (p 104), cucumber (p 105), dendrobium (p 109), gladiolus (p 110), chrysanthemum (p 110), liliacea (p 111), cotton (pp113-114), eucalyptus (p 115), sunflower (p 118), canola (p 118), turfgrass (p121), sugarbeet (p 122), coffee (p 122) and dioscorea (p 122), (Christou, In: *Particle Bombardment for Genetic Engineering of Plants*, Biotechnology Intelligence Unit. Academic Press, San Diego, Calif. (1996), the entirety of which is herein incorporated by reference).

Transfer of a nucleic acid that encodes for a protein can result in overexpression of that protein in a transformed cell or transgenic plant. One or more of the proteins or fragments thereof encoded by nucleic acid molecules of the present invention may be overexpressed in a transformed cell or transformed plant. Particularly, any of the cytokinin pathway proteins or fragments thereof may be overexpressed in a transformed cell or transgenic plant. Such overexpression may be the result of transient or stable transfer of the exogenous genetic material.

Exogenous genetic material may be transferred into a plant cell and the plant cell by the use of a DNA vector or construct designed for such a purpose. Design of such a vector is generally within the skill of the art (See, *Plant Molecular Biology: A Laboratory Manual*, Clark (ed.), Springier, N.Y. (1997), the entirety of which is herein incorporated by reference).

A construct or vector may include a plant promoter to express the protein or protein fragment of choice. A number of promoters which are active in plant cells have been described in the literature. These include the nopaline synthase (NOS) promoter (Ebert et al., *Proc. Natl. Acad. Sci.* (*U.S.A.*) 84:5745-5749 (1987), the entirety of which is herein incorporated by reference), the octopine synthase (OCS) promoter (which are carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315-324 (1987), the entirety of which is herein incorporated by reference) and the CAMV 35S promoter (Odell et al., *Nature* 313:810-812 (1985), the entirety of which is herein incorporated by reference), the figwort mosaic virus 35S-promoter, the light-inducible promoter from the small subunit of ribulose-1,5-bis-phosphate carboxylase (ssRUBISCO), the Adh promoter (Walker et al., *Proc. Natl. Acad. Sci.* (*U.S.A.*) 84:6624-6628 (1987), the entirety of which is herein incorporated by reference), the sucrose synthase promoter (Yang et al., *Proc. Natl. Acad. Sci.* (*U.S.A.*) 87:4144-4148 (1990), the entirety of which is herein incorporated by reference), the R gene complex promoter (Chandler et al., *The Plant Cell* 1: 1175-1183 (1989), the entirety of which is herein incorporated by reference) and the chlorophyll a/b binding protein gene promoter, etc. These promoters have been used to create DNA constructs which have been expressed in plants; see, e.g., PCT publication WO 84/02913, herein incorporated by reference in its entirety.

Promoters which are known or are found to cause transcription of DNA in plant cells can be used in the present invention. Such promoters may be obtained from a variety of sources such as plants and plant viruses. It is preferred that the particular promoter selected should be capable of causing sufficient expression to result in the production of an effective amount of the cytokinin pathway protein to cause the desired phenotype. In addition to promoters that are known to cause transcription of DNA in plant cells, other promoters may be identified for use in the current invention by screening a plant cDNA library for genes which are selectively or preferably expressed in the target tissues or cells.

For the purpose of expression in source tissues of the plant, such as the leaf, seed, root or stem, it is preferred that the promoters utilized in the present invention have relatively high expression in these specific tissues. For this purpose, one may choose from a number of promoters for genes with tissue- or cell-specific or -enhanced expression. Examples of such promoters reported in the literature include the chloroplast glutamine synthetase GS2 promoter from pea (Edwards et al., *Proc. Natl. Acad. Sci.* (*U.S.A.*) 87:3459-3463 (1990), herein incorporated by reference in its entirety), the chloroplast fructose-1,6-biphosphatase (FBPase) promoter from wheat (Lloyd et al., *Mol. Gen. Genet.* 225:209-216 (1991), herein incorporated by reference in its entirety), the nuclear photosynthetic ST-LS1 promoter from potato (Stockhaus et al., *EMBO J.* 8:2445-2451 (1989), herein incorporated by reference in its entirety), the serine/threonine kinase (PAL) promoter and the glucoamylase (CHS) promoter from *Arabidopsis thaliana*. Also reported to be active in photosynthetically active tissues are the ribulose-1,5-bisphosphate carboxylase (RbcS) promoter from eastern larch (*Larix laricina*), the promoter for the cab gene, cab6, from pine (Yamamoto et al., *Plant Cell Physiol.* 35:773-778 (1994), herein incorporated by reference in its entirety), the promoter for the Cab-1 gene from wheat (Fejes et al., *Plant Mol. Biol.* 15:921-932 (1990), herein incorporated by reference in its entirety), the promoter for the CAB-1 gene from spinach (Lubberstedt et al., *Plant Physiol.* 104:997-1006 (1994), herein incorporated by reference in its entirety), the promoter for the cab1R gene from rice (Luan et al., *Plant Cell.* 4:971-981 (1992), the entirety of which is herein incorporated by reference), the pyruvate, orthophosphate dikinase (PPDK) promoter from maize (Matsuoka et al., *Proc. Natl. Acad. Sci. (U.S.A.)* 90: 9586-9590 (1993), herein incorporated by reference in its entirety), the promoter for the tobacco Lhcb1*2 gene (Cerdan et al., *Plant Mol. Biol.* 33:245-255 (1997), herein incorporated by reference in its entirety), the *Arabidopsis thaliana* SUC2 sucrose-H+ symporter promoter (Truernit et al., *Planta.* 196:564-570 (1995), herein incorporated by reference in its entirety) and the promoter for the thylakoid membrane proteins from spinach (psaD, psaF, psaE, PC, FNR, atpC, atpD, cab, rbcS). Other promoters for the chlorophyll a/b-binding proteins may also be utilized in the present invention, such as the promoters for LhcB gene and PsbP gene from white mustard (*Sinapis alba*; Kretsch et al., *Plant Mol. Biol.* 28:219-229 (1995), the entirety of which is herein incorporated by reference).

For the purpose of expression in sink tissues of the plant, such as the tuber of the potato plant, the fruit of tomato, or the seed of maize, wheat, rice and barley, it is preferred that the promoters utilized in the present invention have relatively high expression in these specific tissues. A number of promoters for genes with tuber-specific or -enhanced expression are known, including the class I patatin promoter (Bevan et al., *EMBO J.* 8:1899-1906 (1986); Jefferson et al., *Plant Mol. Biol.* 14:995-1006 (1990), both of which are herein incorporated by reference in its entirety), the promoter for the potato tuber ADPGPP genes, both the large and small subunits, the sucrose synthase promoter (Salanoubat and Belliard, *Gene.* 60:47-56 (1987), Salanoubat and Belliard, *Gene.* 84:181-185 (1989), both of which are incorporated by reference in their entirety), the promoter for the major tuber proteins including the 22 kd protein complexes and proteinase inhibitors (Hannapel, *Plant Physiol.* 101:703-704 (1993), herein incorporated by reference in its entirety), the promoter for the granule bound starch synthase gene (GBSS) (Visser et al., *Plant Mol. Biol.* 17:691-699 (1991), herein incorporated by reference in its entirety) and other class I and II patatins promoters (Koster-Topfer et al., *Mol Gen Genet.* 219:390-396 (1989); Mignery et al., *Gene.* 62:27-44 (1988), both of which are herein incorporated by reference in their entirety).

Other promoters can also be used to express a cytokinin pathway protein or fragment thereof in specific tissues, such as seeds or fruits. The promoter for β-conglycinin (Chen et al., *Dev. Genet.* 10: 112-122 (1989), herein incorporated by reference in its entirety) or other seed-specific promoters such as the napin and phaseolin promoters, can be used. The zeins are a group of storage proteins found in maize endosperm. Genomic clones for zein genes have been isolated (Pedersen et al., *Cell* 29:1015-1026 (1982), herein incorporated by reference in its entirety) and the promoters from these clones, including the 15 kD, 16 kD, 19 kD, 22 kD, 27 kD and genes, could also be used. Other promoters known to function, for example, in maize include the promoters for the following genes: waxy, Brittle, Shrunken 2, Branching enzymes I and II, starch synthases, debranching enzymes, oleosins, glutelins and sucrose synthases. A particularly preferred promoter for maize endosperm expression is the promoter for the glutelin gene from rice, more particularly the Osgt-1 promoter (Zheng et al., *Mol Cell Biol.* 13:5829-5842 (1993), herein incorporated by reference in its entirety). Examples of promoters suitable for expression in wheat include those promoters for the ADPglucose pyrosynthase (ADPGPP) subunits, the granule bound and other starch synthase, the branching and debranching enzymes, the embryogenesis-abundant proteins, the gliadins and the glutenins. Examples of such promoters in rice include those promoters for the ADPGPP subunits, the granule bound and other starch synthase, the branching enzymes, the debranching enzymes, sucrose synthases and the glutelins. A particularly preferred promoter is the promoter for rice glutelin, Osgt-1. Examples of such promoters for barley include those for the ADPGPP subunits, the granule bound and other starch synthase, the branching enzymes, the debranching enzymes, sucrose synthases, the hordeins, the embryo globulins and the aleurone specific proteins.

Root specific promoters may also be used. An example of such a promoter is the promoter for the acid chitinase gene (Samac et al., *Plant Mol. Biol.* 25:587-596 (1994), the entirety of which is herein incorporated by reference). Expression in root tissue could also be accomplished by utilizing the root specific subdomains of the CaMV35S promoter that have been identified (Lam et al., *Proc. Natl. Acad. Sci. (U.S.A.)* 86:7890-7894 (1989), herein incorporated by reference in its entirety). Other root cell specific promoters include those reported by Conkling et al. (Conkling et al., *Plant Physiol.* 93:1203-1211 (1990), the entirety of which is herein incorporated by reference).

Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435; and 4,633,436, all of which are herein incorporated in their entirety. In addition, a tissue specific enhancer may be used (Fromm et al., *The Plant Cell* 1:977-984 (1989), the entirety of which is herein incorporated by reference).

Constructs or vectors may also include with the coding region of interest a nucleic acid sequence that acts, in whole or in part, to terminate transcription of that region. For example, such sequences have been isolated including the Tr7 3' sequence and the NOS 3' sequence (Ingelbrecht et al., *The Plant Cell* 1:671-680 (1989), the entirety of which is herein incorporated by reference; Bevan et al., *Nucleic Acids Res.* 11:369-385 (1983), the entirety of which is herein incorporated by reference), or the like.

A vector or construct may also include regulatory elements. Examples of such include the Adh intron 1 (Callis et al., *Genes and Develop.* 1:1183-1200 (1987), the entirety of which is herein incorporated by reference), the sucrose synthase intron (Vasil et al., *Plant Physiol.* 91:1575-1579 (1989), the entirety of which is herein incorporated by reference) and the TMV omega element (Gallie et al., *The Plant Cell* 1:301-311 (1989), the entirety of which is herein incorporated by reference). These and other regulatory elements may be included when appropriate.

A vector or construct may also include a selectable marker. Selectable markers may also be used to select for plants or plant cells that contain the exogenous genetic material. Examples of such include, but are not limited to, a neo gene (Potrykus et al., *Mol. Gen. Genet.* 199:183-188 (1985), the entirety of which is herein incorporated by reference) which codes for kanamycin resistance and can be selected for using kanamycin, G418, etc.; a bar gene which codes for bialaphos resistance; a mutant EPSP synthase gene (Hinchee et al., *Bio/Technology* 6:915-922 (1988), the entirety of which is herein incorporated by reference) which encodes glyphosate resistance; a nitrilase gene which confers resistance to bromoxynil (Stalker et al., *J. Biol. Chem.* 263:6310-6314 (1988), the entirety of which is herein incorporated by reference); a mutant acetolactate synthase gene (ALS) which confers imidazolinone or sulphonylurea resistance (European Patent Application 154,204 (Sep. 11, 1985), the entirety of which is herein incorporated by reference); and a methotrexate resistant DHFR gene (Thillet et al., *J. Biol. Chem.* 263:12500-12508 (1988), the entirety of which is herein incorporated by reference).

A vector or construct may also include a transit peptide. Incorporation of a suitable chloroplast transit peptide may also be employed (European Patent Application Publication Number 0218571, the entirety of which is herein incorporated by reference). Translational enhancers may also be incorporated as part of the vector DNA. DNA constructs could contain one or more 5' non-translated leader sequences which may serve to enhance expression of the gene products from the resulting mRNA transcripts. Such sequences may be derived from the promoter selected to express the gene or can be specifically modified to increase translation of the mRNA. Such regions may also be obtained from viral RNAs, from suitable eukaryotic genes, or from a synthetic gene sequence. For a review of optimizing expression of transgenes, see Koziel et al., *Plant Mol. Biol.* 32:393-405 (1996), the entirety of which is herein incorporated by reference.

A vector or construct may also include a screenable marker. Screenable markers may be used to monitor expression. Exemplary screenable markers include a β-glucuronidase or uidA gene (GUS) which encodes an enzyme for which various chromogenic substrates are known (Jefferson, *Plant Mol. Biol, Rep.* 5:387-405 (1987), the entirety of which is herein incorporated by reference; Jefferson et al., *EMBO J.* 6:3901-3907 (1987), the entirety of which is herein incorporated by reference); an R-locus gene, which encodes a product that regulates the production of anthocyanin pigments (red color) in plant tissues (Dellaporta et al., Stadler Symposium 11:263-282 (1988), the entirety of which is herein incorporated by reference); a β-lactamase gene (Sutcliffe et al., *Proc. Natl. Acad. Sci.* (*U.S.A.*) 75:3737-3741 (1978), the entirety of which is herein incorporated by reference), a gene which encodes an enzyme for which various chromogenic substrates are known (e.g., PADAC, a chromogenic cephalosporin); a luciferase gene (Ow et al., *Science* 234:856-859 (1986), the entirety of which is herein incorporated by reference); a xylE gene (Zukowsky et al., *Proc. Natl. Acad. Sci.* (*U.S.A.*) 80:1101-1105 (1983), the entirety of which is herein incorporated by reference) which encodes a catechol diozygenase that can convert chromogenic catechols; an α-amylase gene (Ikatu et al., *Bio/Technol.* 8:241-242 (1990), the entirety of which is herein incorporated by reference); a tyrosinase gene (Katz et al., *J. Gen. Microbiol.* 129:2703-2714 (1983), the entirety of which is herein incorporated by reference) which encodes an enzyme capable of oxidizing tyrosine to DOPA and dopaquinone which in turn condenses to melanin; an α-galactosidase, which will turn a chromogenic α-galactose substrate.

Included within the terms "selectable or screenable marker genes" are also genes which encode a secretable marker whose secretion can be detected as a means of identifying or selecting for transformed cells. Examples include markers which encode a secretable antigen that can be identified by antibody interaction, or even secretable enzymes which can be detected catalytically. Secretable proteins fall into a number of classes, including small, diffusible proteins which are detectable, (e.g., by ELISA), small active enzymes which are detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco PR-S). Other possible selectable and/or screenable marker genes will be apparent to those of skill in the art.

There are many methods for introducing transforming nucleic acid molecules into plant cells. Suitable methods are believed to include virtually any method by which nucleic acid molecules may be introduced into a cell, such as by *Agrobacterium* infection or direct delivery of nucleic acid molecules such as, for example, by PEG-mediated transformation, by electroporation or by acceleration of DNA coated particles, etc (Potrykus, *Ann. Rev. Plant Physiol. Plant Mol. Biol.* 42:205-225 (1991), the entirety of which is herein incorporated by reference; Vasil, *Plant Mol. Biol.* 25:925-937 (1994), the entirety of which is herein incorporated by reference). For example, electroporation has been used to transform maize protoplasts (Fromm et al., *Nature* 312:791-793 (1986), the entirety of which is herein incorporated by reference).

Other vector systems suitable for introducing transforming DNA into a host plant cell include but are not limited to binary artificial chromosome (BIBAC) vectors (Hamilton et al., *Gene* 200:107-116 (1997), the entirety of which is herein incorporated by reference); and transfection with RNA viral vectors (Della-Cioppa et al., *Ann. N.Y. Acad. Sci.* (1996), 792 (Engineering Plants for Commercial Products and Applications), 57-61, the entirety of which is herein incorporated by reference). Additional vector systems also include plant selectable YAC vectors such as those described in Mullen et al., *Molecular Breeding* 4:449-457 (1988), the entirety of which is herein incorporated by reference).

Technology for introduction of DNA into cells is well known to those of skill in the art. Four general methods for delivering a gene into cells have been described: (1) chemical methods (Graham and van der Eb, *Virology* 54:536-539 (1973), the entirety of which is herein incorporated by reference); (2) physical methods such as microinjection (Capecchi, *Cell* 22:479-488 (1980), the entirety of which is herein incorporated by reference), electroporation (Wong and Neumann, *Biochem. Biophys. Res. Commun.* 107:584-587 (1982); Fromm et al., *Proc. Natl. Acad. Sci.* (*U.S.A.*) 82:5824-5828 (1985); U.S. Pat. No. 5,384,253, all of which are herein incorporated in their entirety); and the gene gun (Johnston and Tang, *Methods Cell Biol.* 43:353-365 (1994), the entirety of which is herein incorporated by reference); (3) viral vectors (Clapp, *Clin. Perinatol.* 20:155-168 (1993); Lu et al., *J. Exp. Med.* 178:2089-2096 (1993); Eglitis and Anderson, *Biotechniques* 6:608-614 (1988), all of which are herein incorporated in their entirety); and (4) receptor-mediated mechanisms (Curiel et al., *Hum. Gen. Ther.* 3:147-154 (1992), Wagner et al., *Proc. Natl. Acad. Sci.* (*U.S.A.*) 89:6099-6103 (1992), both of which are incorporated by reference in their entirety).

Acceleration methods that may be used include, for example, microprojectile bombardment and the like. One example of a method for delivering transforming nucleic acid molecules to plant cells is microprojectile bombardment. This method has been reviewed by Yang and Christou (eds.), *Particle Bombardment Technology for Gene Transfer*, Oxford Press, Oxford, England (1994), the entirety of which is herein incorporated by reference). Non-biological particles (microprojectiles) that may be coated with nucleic acids and delivered into cells by a propelling force. Exemplary particles include those comprised of tungsten, gold, platinum and the like.

A particular advantage of microprojectile bombardment, in addition to it being an effective means of reproducibly transforming monocots, is that neither the isolation of protoplasts (Cristou et al., *Plant Physiol.* 87:671-674 (1988), the entirety of which is herein incorporated by reference) nor the susceptibility of *Agrobacterium* infection are required. An illustrative embodiment of a method for delivering DNA into maize cells by acceleration is a biolistics α-particle delivery system, which can be used to propel particles coated with DNA through a screen, such as a stainless steel or Nytex screen, onto a filter surface covered with corn cells cultured in suspension. Gordon-Kamm et al., describes the basic procedure for coating tungsten particles with DNA (Gordon-Kamm et al., *Plant Cell* 2:603-618 (1990), the entirety of which is herein incorporated by reference). The screen disperses the tungsten nucleic acid particles so that they are not delivered to the recipient cells in large aggregates. A particle delivery system suitable for use with the present invention is the helium acceleration PDS-1000/He gun is available from Bio-Rad Laboratories (Bio-Rad, Hercules, Calif.)(Sanford et al., *Technique* 3:3-16 (1991), the entirety of which is herein incorporated by reference).

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from one to ten and average one to three.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment and also the nature of the transforming DNA, such as linearized DNA or intact supercoiled plasmids. It is believed that pre-bombardment manipulations are especially important for successful transformation of immature embryos.

In another alternative embodiment, plastids can be stably transformed. Methods disclosed for plastid transformation in higher plants include the particle gun delivery of DNA containing a selectable marker and targeting of the DNA to the plastid genome through homologous recombination (Svab et al., *Proc. Natl. Acad. Sci.* (*U.S.A.*) 87:8526-8530 (1990); Svab and Maliga, *Proc. Natl. Acad. Sci.* (*U.S.A.*) 90:913-917 (1993); Staub and Maliga, *EMBO J.* 12:601-606 (1993); U.S. Pat. Nos. 5,451,513 and 5,545,818, all of which are herein incorporated by reference in their entirety).

Accordingly, it is contemplated that one may wish to adjust various aspects of the bombardment parameters in small scale studies to fully optimize the conditions. One may particularly wish to adjust physical parameters such as gap distance, flight distance, tissue distance and helium pressure. One may also minimize the trauma reduction factors by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example the methods described by Fraley et al., *Bio/Technology* 3:629-635 (1985) and Rogers et al., *Methods Enzymol.* 153:253-277 (1987), both of which are herein incorporated by reference in their entirety. Further, the integration of the Ti-DNA is a relatively precise process resulting in few rearrangements. The region of DNA to be transferred is defined by the border sequences and intervening DNA is usually inserted into the plant genome as described (Spielmann et al., *Mol. Gen. Genet.* 205:34 (1986), the entirety of which is herein incorporated by reference).

Modern *Agrobacterium* transformation vectors are capable of replication in *E. coli* as well as *Agrobacterium*, allowing for convenient manipulations as described (Klee et al., In: *Plant DNA Infectious Agents*, Hohn and Schell (eds.), Springer-Verlag, New York, pp. 179-203 (1985), the entirety of which is herein incorporated by reference. Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes (Rogers et al., *Methods Enzymol.* 153:253-277 (1987)). In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

A transgenic plant formed using *Agrobacterium* transformation methods typically contains a single gene on one chromosome. Such transgenic plants can be referred to as being heterozygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for the gene of interest.

It is also to be understood that two different transgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated, as is vegetative propagation.

Transformation of plant protoplasts can be achieved using methods based on calcium phosphate precipitation, polyethylene glycol treatment, electroporation and combinations of these treatments (See, for example, Potrykus et al., *Mol. Gen. Genet.* 205:193-200 (1986); Lorz et al., *Mol. Gen. Genet.* 199:178 (1985); Fromm et al., *Nature* 319:791 (1986); Uchimiya et al., *Mol. Gen. Genet.* 204:204 (1986); Marcotte et al., *Nature* 335:454-457 (1988), all of which are herein incorporated by reference in their entirety).

Application of these systems to different plant strains depends upon the ability to regenerate that particular plant strain from protoplasts. Illustrative methods for the regeneration of cereals from protoplasts are described (Fujimura et al., *Plant Tissue Culture Letters* 2:74 (1985); Toriyama et al., *Theor Appl. Genet.* 205:34 (1986); Yamada et al., *Plant Cell Rep.* 4:85 (1986); Abdullah et al., *Biotechnolog* 4:1087 (1986), all of which are herein incorporated by reference in their entirety).

To transform plant strains that cannot be successfully regenerated from protoplasts, other ways to introduce DNA into intact cells or tissues can be utilized. For example, regeneration of cereals from immature embryos or explants can be effected as described (Vasil, *Biotechnology* 6:397 (1988), the entirety of which is herein incorporated by reference). In addition, "particle gun" or high-velocity microprojectile technology can be utilized (Vasil et al., *Bio/Technology* 10:667 (1992), the entirety of which is herein incorporated by reference).

Using the latter technology, DNA is carried through the cell wall and into the cytoplasm on the surface of small metal particles as described (Klein et al., *Nature* 328:70 (1987); Klein et al., *Proc. Natl. Acad. Sci.* (*U.S.A.*) 85:8502-8505 (1988); McCabe et al., *Bio/Technology* 6:923 (1988), all of which are herein incorporated by reference in their entirety). The metal particles penetrate through several layers of cells and thus allow the transformation of cells within tissue explants.

Other methods of cell transformation can also be used and include but are not limited to introduction of DNA into plants by direct DNA transfer into pollen (Zhou et al., *Methods Enzymol.* 101:433 (1983); Hess et al., *Intern Rev. Cytol.* 107: 367 (1987); Luo et al., *Plant Mol Biol. Reporter* 6:165 (1988), all of which are herein incorporated by reference in their entirety), by direct injection of DNA into reproductive organs of a plant (Pena et al., *Nature* 325:274 (1987), the entirety of which is herein incorporated by reference), or by direct injection of DNA into the cells of immature embryos followed by the rehydration of desiccated embryos (Neuhaus et al., *Theor. Appl. Genet.* 75:30 (1987), the entirety of which is herein incorporated by reference).

The regeneration, development and cultivation of plants from single plant protoplast transformants or from various transformed explants is well known in the art (Weissbach and Weissbach, In: *Methods for Plant Molecular Biology*, Academic Press, San Diego, Calif., (1988), the entirety of which is herein incorporated by reference). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

There are a variety of methods for the regeneration of plants from plant tissue. The particular method of regeneration will depend on the starting plant tissue and the particular plant species to be regenerated.

Methods for transforming dicots, primarily by use of *Agrobacterium tumefaciens* and obtaining transgenic plants have been published for cotton (U.S. Pat. No. 5,004,863; U.S. Pat. No. 5,159,135; U.S. Pat. No. 5,518,908, all of which are herein incorporated by reference in their entirety); soybean (U.S. Pat. No. 5,569,834; U.S. Pat. No. 5,416,011; McCabe et. al., *Biotechnology* 6:923 (1988); Christou et al., *Plant Physiol.* 87:671-674 (1988); all of which are herein incorporated by reference in their entirety); *Brassica* (U.S. Pat. No. 5,463,174, the entirety of which is herein incorporated by reference); peanut (Cheng et al., *Plant Cell Rep.* 15:653-657 (1996), McKently et al., *Plant Cell Rep.* 14:699-703 (1995), all of which are herein incorporated by reference in their entirety); papaya; and pea (Grant et al., *Plant Cell Rep.* 15:254-258 (1995), the entirety of which is herein incorporated by reference).

Transformation of monocotyledons using electroporation, particle bombardment and *Agrobacterium* have also been reported. Transformation and plant regeneration have been achieved in asparagus (Bytebier et al., *Proc. Natl. Acad. Sci.* (*U.S.A.*) 84:5354 (1987), the entirety of which is herein incorporated by reference); barley (Wan and Lemaux, *Plant Physiol* 104:37 (1994), the entirety of which is herein incorporated by reference); maize (Rhodes et al., *Science* 240:204 (1988); Gordon-Kamm et al., *Plant Cell* 2:603-618 (1990); Fromm et al., *Bio/Technology* 8:833 (1990); Koziel et al., *Bio/Technology* 11:194 (1993); Armstrong et al., *Crop Science* 35:550-557 (1995); all of which are herein incorporated by reference in their entirety); oat (Somers et al., *Bio/Technology* 10:1589 (1992), the entirety of which is herein incorporated by reference); orchard grass (Horn et al., *Plant Cell Rep.* 7:469 (1988), the entirety of which is herein incorporated by reference); rice (Toriyama et al., *Theor Appl. Genet.* 205:34 (1986); Part et al., *Plant Mol. Biol.* 32:1135-1148 (1996); Abedinia et al., *Aust. J. Plant Physiol* 24:133-141 (1997); Zhang and Wu, *Theor. Appl. Genet.* 76:835 (1988); Zhang et al., *Plant Cell Rep.* 7:379 (1988); Battraw and Hall, *Plant Sci* 86:191-202 (1992); Christou et al., *Bio/Technology* 9:957 (1991), all of which are herein incorporated by reference in their entirety); rye (De la Pena et al., *Nature* 325:274 (1987), the entirety of which is herein incorporated by reference); sugarcane (Bower and Birch, *Plant J.* 2:409 (1992), the entirety of which is herein incorporated by reference); tall fescue (Wang et al., *Bio/Technology* 10:691 (1992), the entirety of which is herein incorporated by reference) and wheat (Vasil et al., *Bio/Technology* 10:667 (1992), the entirety of which is herein incorporated by reference; U.S. Pat. No. 5,631,152, the entirety of which is herein incorporated by reference.)

Assays for gene expression based on the transient expression of cloned nucleic acid constructs have been developed by introducing the nucleic acid molecules into plant cells by polyethylene glycol treatment, electroporation, or particle bombardment (Marcotte et al., *Nature* 335:454-457 (1988), the entirety of which is herein incorporated by reference; Marcotte et al., *Plant Cell* 1:523-532 (1989), the entirety of which is herein incorporated by reference; McCarty et al., *Cell* 66:895-905 (1991), the entirety of which is herein incorporated by reference; Hattori et al., *Genes Dev.* 6:609-618 (1992), the entirety of which is herein incorporated by reference; Goff et al., *EMBO J.* 9:2517-2522 (1990), the entirety of which is herein incorporated by reference). Transient expression systems may be used to functionally dissect gene constructs (see generally, Mailga et al., *Methods in Plant Molecular Biology*, Cold Spring Harbor Press (1995)).

Any of the nucleic acid molecules of the present invention may be introduced into a plant cell in a permanent or transient manner in combination with other genetic elements such as vectors, promoters, enhancers etc. Further, any of the nucleic acid molecules of the present invention may be introduced into a plant cell in a manner that allows for overexpression of the protein or fragment thereof encoded by the nucleic acid molecule.

Cosuppression is the reduction in expression levels, usually at the level of RNA, of a particular endogenous gene or gene family by the expression of a homologous sense construct that is capable of transcribing mRNA of the same strandedness as the transcript of the endogenous gene (Napoli et al., *Plant Cell* 2:279-289 (1990), the entirety of which is herein incorporated by reference; van der Krol et al., *Plant Cell* 2:291-299 (1990), the entirety of which is herein incorporated by reference). Cosuppression may result from stable transformation with a single copy nucleic acid molecule that is homologous to a nucleic acid sequence found with the cell (Prolls and Meyer, *Plant J.* 2:465-475 (1992), the entirety of which is herein incorporated by reference) or with multiple copies of a nucleic acid molecule that is homologous to a nucleic acid sequence found with the cell (Mittlesten et al., *Mol. Gen. Genet.* 244:325-330 (1994), the entirety of which is herein incorporated by reference). Genes, even though different, linked to homologous promoters may result in the cosuppression of the linked genes (Vaucheret, *C.R. Acad. Sci. III* 316:1471-1483 (1993), the entirety of which is herein incorporated by reference).

This technique has, for example, been applied to generate white flowers from red petunia and tomatoes that do not ripen on the vine. Up to 50% of petunia transformants that contained a sense copy of the glucoamylase (CHS) gene produced white flowers or floral sectors; this was as a result of the post-transcriptional loss of mRNA encoding CHS (Flavell, *Proc. Natl. Acad. Sci. (U.S.A.)* 91:3490-3496 (1994), the entirety of which is herein incorporated by reference); van Blokland et al., *Plant J.* 6:861-877 (1994), the entirety of which is herein incorporated by reference). Cosuppression may require the coordinate transcription of the transgene and the endogenous gene and can be reset by a developmental control mechanism (Jorgensen, *Trends Biotechnol.* 8:340-344 (1990), the entirety of which is herein incorporated by reference; Meins and Kunz, In: *Gene Inactivation and Homologous Recombination in Plants*, Paszkowski (ed.), pp. 335-348, Kluwer Academic, Netherlands (1994), the entirety of which is herein incorporated by reference).

It is understood that one or more of the nucleic acids of the present invention may be introduced into a plant cell and transcribed using an appropriate promoter with such transcription resulting in the cosuppression of an endogenous cytokinin pathway protein.

Antisense approaches are a way of preventing or reducing gene function by targeting the genetic material (Mol et al., *FEBS Lett.* 268:427-430 (1990), the entirety of which is herein incorporated by reference). The objective of the antisense approach is to use a sequence complementary to the target gene to block its expression and create a mutant cell line or organism in which the level of a single chosen protein is selectively reduced or abolished. Antisense techniques have several advantages over other 'reverse genetic' approaches. The site of inactivation and its developmental effect can be manipulated by the choice of promoter for antisense genes or by the timing of external application or microinjection. Antisense can manipulate its specificity by selecting either unique regions of the target gene or regions where it shares homology to other related genes (Hiatt et al., In: *Genetic Engineering*, Setlow (ed.), Vol. 11, New York: Plenum 49-63 (1989), the entirety of which is herein incorporated by reference).

The principle of regulation by antisense RNA is that RNA that is complementary to the target mRNA is introduced into cells, resulting in specific RNA:RNA duplexes being formed by base pairing between the antisense substrate and the target mRNA (Green et al., *Annu. Rev. Biochem.* 55:569-597 (1986), the entirety of which is herein incorporated by reference). Under one embodiment, the process involves the introduction and expression of an antisense gene sequence. Such a sequence is one in which part or all of the normal gene sequences are placed under a promoter in inverted orientation so that the 'wrong' or complementary strand is transcribed into a noncoding antisense RNA that hybridizes with the target mRNA and interferes with its expression (Takayama and Inouye, *Crit. Rev. Biochem. Mol. Biol.* 25:155-184 (1990), the entirety of which is herein incorporated by reference). An antisense vector is constructed by standard procedures and introduced into cells by transformation, transfection, electroporation, microinjection, infection, etc. The type of transformation and choice of vector will determine whether expression is transient or stable. The promoter used for the antisense gene may influence the level, timing, tissue, specificity, or inducibility of the antisense inhibition.

It is understood that the activity of a cytokinin pathway protein in a plant cell may be reduced or depressed by growing a transformed plant cell containing a nucleic acid molecule whose non-transcribed strand encodes a cytokinin pathway protein or fragment thereof.

Antibodies have been expressed in plants (Hiatt et al., *Nature* 342:76-78 (1989), the entirety of which is herein incorporated by reference; Conrad and Fielder, *Plant Mol. Biol.* 26:1023-1030 (1994), the entirety of which is herein incorporated by reference). Cytoplamsic expression of a scFv (single-chain Fv antibodies) has been reported to delay infection by artichoke mottled crinkle virus. Transgenic plants that express antibodies directed against endogenous proteins may exhibit a physiological effect (Philips et al., *EMBO J.* 16:4489-4496 (1997), the entirety of which is herein incorporated by reference; Marion-Poll, *Trends in Plant Science* 2:447-448 (1997), the entirety of which is herein incorporated by reference). For example, expressed anti-abscisic antibodies have been reported to result in a general perturbation of seed development (Philips et al., *EMBO J.* 16: 4489-4496 (1997)).

Antibodies that are catalytic may also be expressed in plants (abzymes). The principle behind abzymes is that since antibodies may be raised against many molecules, this recognition ability can be directed toward generating antibodies that bind transition states to force a chemical reaction forward (Persidas, *Nature Biotechnology* 15:1313-1315 (1997), the entirety of which is herein incorporated by reference; Baca et al., *Ann. Rev. Biophys. Biomol. Struct.* 26:461-493 (1997), the entirety of which is herein incorporated by reference). The catalytic abilities of abzymes may be enhanced by site directed mutagenesis. Examples of abzymes are, for example, set forth in U.S. Pat. Nos. 5,658,753; 5,632,990; 5,631,137; 5,602,015; 5,559,538; 5,576,174; 5,500,358; 5,318,897; 5,298,409; 5,258,289 and 5,194,585, all of which are herein incorporated in their entirety.

It is understood that any of the antibodies of the present invention may be expressed in plants and that such expression can result in a physiological effect. It is also understood that any of the expressed antibodies may be catalytic.

(b) Fungal Constructs and Fungal Transformants

The present invention also relates to a fungal recombinant vector comprising exogenous genetic material. The present invention also relates to a fungal cell comprising a fungal recombinant vector. The present invention also relates to methods for obtaining a recombinant fungal host cell comprising introducing into a fungal host cell exogenous genetic material.

Exogenous genetic material may be transferred into a fungal cell. In a preferred embodiment the exogenous genetic material includes a nucleic acid molecule of the present invention having a sequence selected from the group consisting of SEQ ID NO: 1 through SEQ ID NO: 711 or complements thereof or fragments of either or other nucleic acid molecule of the present invention. The fungal recombinant vector may be any vector which can be conveniently subjected to recombinant DNA procedures. The choice of a vector will typically depend on the compatibility of the vector with the fungal host cell into which the vector is to be introduced. The vector may be a linear or a closed circular plasmid. The vector system may be a single vector or plasmid or two or more vectors or plasmids which together contain the total DNA to be introduced into the genome of the fungal host.

The fungal vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the fungal cell, is integrated into the genome and replicated together with the chromosome(s) into which it has been integrated. For integration, the vector may rely on the nucleic acid sequence of the vector for stable integration of the vector into the genome by homologous or nonhomologous recombination. Alternatively, the vector may contain additional nucleic acid sequences for directing integration by homologous recombination into the genome of the fungal host. The additional nucleic acid sequences enable the vector to be integrated into the host cell genome at a precise location(s) in the chromosome(s). To increase the likelihood of integration at a precise location, there should be preferably two nucleic acid sequences which individually contain a sufficient number of nucleic acids, preferably 400 bp to 1500 bp, more preferably 800 bp to 1000 bp, which are highly homologous with the corresponding target sequence to enhance the probability of homologous recombination. These nucleic acid sequences may be any sequence that is homologous with a target sequence in the genome of the fungal host cell and, furthermore, may be non-encoding or encoding sequences.

For autonomous replication, the vector may further comprise an origin of replication enabling the vector to replicate autonomously in the host cell in question. Examples of origin of replications for use in a yeast host cell are the 2 micron origin of replication and the combination of CEN3 and ARS 1. Any origin of replication may be used which is compatible with the fungal host cell of choice.

The fungal vectors of the present invention preferably contain one or more selectable markers which permit easy selection of transformed cells. A selectable marker is a gene the product of which provides, for example biocide or viral resistance, resistance to heavy metals, prototrophy to auxotrophs and the like. The selectable marker may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase) and sC (sulfate adenyltransferase) and trpC (anthranilate synthase). Preferred for use in an *Aspergillus* cell are the amdS and pyrG markers of *Aspergillus nidulans* or *Aspergillus oryzae* and the bar marker of *Streptomyces hygroscopicus*. Furthermore, selection may be accomplished by co-transformation, e.g., as described in WO 91/17243, the entirety of which is herein incorporated by reference. A nucleic acid sequence of the present invention may be operably linked to a suitable promoter sequence. The promoter sequence is a nucleic acid sequence which is recognized by the fungal host cell for expression of the nucleic acid sequence. The promoter sequence contains transcription and translation control sequences which mediate the expression of the protein or fragment thereof.

A promoter may be any nucleic acid sequence which shows transcriptional activity in the fungal host cell of choice and may be obtained from genes encoding polypeptides either homologous or heterologous to the host cell. Examples of suitable promoters for directing the transcription of a nucleic acid construct of the invention in a filamentous fungal host are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase and hybrids thereof. In a yeast host, a useful promoter is the *Saccharomyces cerevisiae* enolase (eno-1) promoter. Particularly preferred promoters are the TAKA amylase, NA2-tpi (a hybrid of the promoters from the genes encoding *Aspergillus niger* neutral alpha-amylase and *Aspergillus oryzae* triose phosphate isomerase) and glaA promoters.

A protein or fragment thereof encoding nucleic acid molecule of the present invention may also be operably linked to a terminator sequence at its 3' terminus. The terminator sequence may be native to the nucleic acid sequence encoding the protein or fragment thereof or may be obtained from foreign sources. Any terminator which is functional in the fungal host cell of choice may be used in the present invention, but particularly preferred terminators are obtained from the genes encoding *Aspergillus oryzae* TAKA amylase, *Aspergillus niger* glucoamylase, *Aspergillus nidulans* anthranilate synthase, *Aspergillus niger* alpha-glucosidase and *Saccharomyces cerevisiae* enolase.

A protein or fragment thereof encoding nucleic acid molecule of the present invention may also be operably linked to a suitable leader sequence. A leader sequence is a nontranslated region of a mRNA which is important for translation by the fungal host. The leader sequence is operably linked to the 5' terminus of the nucleic acid sequence encoding the protein or fragment thereof. The leader sequence may be native to the nucleic acid sequence encoding the protein or fragment thereof or may be obtained from foreign sources. Any leader sequence which is functional in the fungal host cell of choice may be used in the present invention, but particularly preferred leaders are obtained from the genes encoding *Aspergillus oryzae* TAKA amylase and *Aspergillus oryzae* triose phosphate isomerase.

A polyadenylation sequence may also be operably linked to the 3' terminus of the nucleic acid sequence of the present invention. The polyadenylation sequence is a sequence which when transcribed is recognized by the fungal host to add polyadenosine residues to transcribed mRNA. The polyadenylation sequence may be native to the nucleic acid sequence encoding the protein or fragment thereof or may be obtained from foreign sources. Any polyadenylation sequence which is functional in the fungal host of choice may be used in the present invention, but particularly preferred polyadenylation sequences are obtained from the genes encoding *Aspergillus oryzae* TAKA amylase, *Aspergillus niger* glucoamylase, *Aspergillus nidulans* anthranilate synthase and *Aspergillus niger* alpha-glucosidase.

To avoid the necessity of disrupting the cell to obtain the protein or fragment thereof and to minimize the amount of possible degradation of the expressed protein or fragment thereof within the cell, it is preferred that expression of the protein or fragment thereof gives rise to a product secreted outside the cell. To this end, a protein or fragment thereof of the present invention may be linked to a signal peptide linked to the amino terminus of the protein or fragment thereof. A signal peptide is an amino acid sequence which permits the secretion of the protein or fragment thereof from the fungal host into the culture medium. The signal peptide may be native to the protein or fragment thereof of the invention or may be obtained from foreign sources. The 5' end of the coding sequence of the nucleic acid sequence of the present invention may inherently contain a signal peptide coding region naturally linked in translation reading frame with the segment of the coding region which encodes the secreted protein or fragment thereof. Alternatively, the 5' end of the coding sequence may contain a signal peptide coding region which is foreign to that portion of the coding sequence which encodes the secreted protein or fragment thereof. The foreign signal peptide may be required where the coding sequence does not normally contain a signal peptide coding region. Alternatively, the foreign signal peptide may simply replace the natural signal peptide to obtain enhanced secretion of the desired protein or fragment thereof. The foreign signal peptide coding region may be obtained from a glucoamylase or an amylase gene from an *Aspergillus* species, a lipase or proteinase gene from *Rhizomucor miehei*, the gene for the alpha-factor from *Saccharomyces cerevisiae*, or the calf preprochymosin gene. An effective signal peptide for fungal host cells is the *Aspergillus oryzae* TAKA amylase signal, *Aspergillus niger* neutral amylase signal, the *Rhizomucor miehei* aspartic proteinase signal, the *Humicola lanuginosus* cellulase signal, or the *Rhizomucor miehei* lipase signal. However, any signal peptide capable of permitting secretion of the protein or fragment thereof in a fungal host of choice may be used in the present invention.

A protein or fragment thereof encoding nucleic acid molecule of the present invention may also be linked to a propeptide coding region. A propeptide is an amino acid sequence found at the amino terminus of aproprotein or proenzyme. Cleavage of the propeptide from the proprotein yields a mature biochemically active protein. The resulting polypeptide is known as a propolypeptide or proenzyme (or a zymogen in some cases). Propolypeptides are generally inactive and can be converted to mature active polypeptides by catalytic or autocatalytic cleavage of the propeptide from the propolypeptide or proenzyme. The propeptide coding region may be native to the protein or fragment thereof or may be obtained from foreign sources. The foreign propeptide coding region may be obtained from the *Saccharomyces cerevisiae* alpha-factor gene or *Myceliophthora thermophila* laccase gene (WO 95/33836, the entirety of which is herein incorporated by reference).

The procedures used to ligate the elements described above to construct the recombinant expression vector of the present invention are well known to one skilled in the art (see, for example, Sambrook et al., *Molecular Cloning, A Laboratory Manual,* 2nd ed., Cold Spring Harbor, N.Y., (1989)).

The present invention also relates to recombinant fungal host cells produced by the methods of the present invention which are advantageously used with the recombinant vector of the present invention. The cell is preferably transformed with a vector comprising a nucleic acid sequence of the invention followed by integration of the vector into the host chromosome. The choice of fungal host cells will to a large extent depend upon the gene encoding the protein or fragment thereof and its source. The fungal host cell may, for example, be a yeast cell or a filamentous fungal cell.

"Yeast" as used herein includes Ascosporogenous yeast (Endomycetales), Basidiosporogenous yeast and yeast belonging to the Fungi Imperfecti (Blastomycetes). The Ascosporogenous yeasts are divided into the families Spermophthoraceae and Saccharomycetaceae. The latter is comprised of four subfamilies, Schizosaccharomycoideae (for example, genus *Schizosaccharomyces*), Nadsonioideae, Lipomycoideae and Saccharomycoideae (for example, genera *Pichia, Kluyveromyces* and *Saccharomyces*). The Basidiosporogenous yeasts include the genera *Leucosporidim, Rhodosporidium, Sporidiobolus, Filobasidium* and *Filobasidiella*. Yeast belonging to the Fungi Imperfecti are divided into two families, Sporobolomycetaceae (for example, genera *Sorobolomyces* and *Bullera*) and Cryptococcaceae (for example, genus *Candida*). Since the classification of yeast may change in the future, for the purposes of this invention, yeast shall be defined as described in Biology and Activities of Yeast (Skinner et al., *Soc. App. Bacteriol. Symposium Series* No. 9, (1980), the entirety of which is herein incorporated by reference). The biology of yeast and manipulation of yeast genetics are well known in the art (see, for example, *Biochemistry and Genetics of Yeast*, Bacil et al. (ed.), 2nd edition, 1987; *The Yeasts*, Rose and Harrison (eds.), 2nd ed., (1987); and *The Molecular Biology of the Yeast Saccharomyces,* Strathern et al. (eds.), (1981), all of which are herein incorporated by reference in their entirety).

"Fungi" as used herein includes the phyla Ascomycota, Basidiomycota, Chytridiomycota and Zygomycota (as defined by Hawksworth et al., In: Ainsworth and Bisby's *Dictionary of The Fungi,* 8th edition, 1995, CAB International, University Press, Cambridge, UK; the entirety of which is herein incorporated by reference) as well as the Oomycota (as cited in Hawksworth et al., In: Ainsworth and Bisby's *Dictionary of The Fungi,* 8th edition, 1995, CAB International, University Press, Cambridge, UK) and all mitosporic fungi (Hawksworth et al., In: Ainsworth and Bisby's *Dictionary of The Fungi,* 8th edition, 1995, CAB International, University Press, Cambridge, UK). Representative groups of Ascomycota include, for example, *Neurospora, Eupenicillium* (=*Penicillium*), *Emericella* (=*Aspergillus*),

*Eurotiun* (=*Aspergillus*) and the true yeasts listed above. Examples of Basidiomycota include mushrooms, rusts and smuts. Representative groups of Chytridiomycota include, for example, *Allomyces, Blastocladiella, Coelomomyces* and aquatic fungi. Representative groups of Oomycota include, for example, Saprolegniomycetous aquatic fungi (water molds) such as *Achlya*. Examples of mitosporic fungi include *Aspergillus, Penicilliun, Candida* and *Alternaria*. Representative groups of Zygomycota include, for example, *Rhizopus* and *Mucor*.

"Filamentous fungi" include all filamentous forms of the subdivision Eumycota and Oomycota (as defined by Hawksworth et al., In: Ainsworth and Bisby's *Dictionary of The Fungi*, 8th edition, 1995, CAB International, University Press, Cambridge, UK). The filamentous fungi are characterized by a vegetative mycelium composed of chitin, cellulose, glucan, chitosan, mannan and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In one embodiment, the fungal host cell is a yeast cell. In a preferred embodiment, the yeast host cell is a cell of the species of *Candida, Kluyveromyces, Saccharomyces, Schizosaccharomyces, Pichia* and *Yarrowia*. In a preferred embodiment, the yeast host cell is a *Saccharomyces cerevisiae* cell, a *Saccharomyces carlsbergensis, Saccharomyces diastaticus* cell, a *Saccharomyces douglasii* cell, a *Saccharomyces kluyveri* cell, a *Saccharomyces norbensis* cell, or a *Saccharomyces oviformis* cell. In another preferred embodiment, the yeast host cell is a *Kluyveromyces lactis* cell. In another preferred embodiment, the yeast host cell is a *Yarrowia lipolytica* cell.

In another embodiment, the fungal host cell is a filamentous fungal cell. In a preferred embodiment, the filamentous fungal host cell is a cell of the species of, but not limited to, *Acremonium, Aspergillus, Fusarium, Humicola, Myceliophthora, Mucor, Neurospora, Penicillium, Thielavia, Tolypocladium* and *Trichoderma*. In a preferred embodiment, the filamentous fungal host cell is an *Aspergillus* cell. In another preferred embodiment, the filamentous fungal host cell is an *Acremonium* cell. In another preferred embodiment, the filamentous fungal host cell is a *Fusarium* cell. In another preferred embodiment, the filamentous fungal host cell is a *Humicola* cell. In another preferred embodiment, the filamentous fungal host cell is a *Myceliophthora* cell. In another even preferred embodiment, the filamentous fungal host cell is a *Mucor* cell. In another preferred embodiment, the filamentous fungal host cell is a *Neurospora* cell. In another preferred embodiment, the filamentous fungal host cell is a *Penicillium* cell. In another preferred embodiment, the filamentous fungal host cell is a *Thielavia* cell. In another preferred embodiment, the filamentous fungal host cell is a *Tolypocladiun* cell. In another preferred embodiment, the filamentous fungal host cell is a *Trichoderma* cell. In a preferred embodiment, the filamentous fungal host cell is an *Aspergillus oryzae* cell, an *Aspergillus niger* cell, an *Aspergillus foetidus* cell, or an *Aspergillus japonicus* cell. In another preferred embodiment, the filamentous fungal host cell is a *Fusarium oxysporum* cell or a *Fusarium graminearum* cell. In another preferred embodiment, the filamentous fungal host cell is a *Humicola insolens* cell or a *Humicola lanuginosus* cell. In another preferred embodiment, the filamentous fungal host cell is a *Myceliophthora thermophila* cell. In a most preferred embodiment, the filamentous fungal host cell is a *Mucor miehei* cell. In a most preferred embodiment, the filamentous fungal host cell is a *Neurospora crassa* cell. In a most preferred embodiment, the filamentous fungal host cell is a *Penicillium purpurogenum* cell. In another most preferred embodiment, the filamentous fungal host cell is a *Thielavia terrestris* cell. In another most preferred embodiment, the *Trichoderma* cell is a *Trichoderma reesei* cell, a *Trichoderma viride* cell, a *Trichoderma longibrachiatum* cell, a *Trichoderma harzianum* cell, or a *Trichoderma koningii* cell. In a preferred embodiment, the fungal host cell is selected from an *A. nidulans* cell, an *A. niger* cell, an *A. oryzae* cell and an *A. sojae* cell. In a further preferred embodiment, the fungal host cell is an *A. nidulans* cell.

The recombinant fungal host cells of the present invention may further comprise one or more sequences which encode one or more factors that are advantageous in the expression of the protein or fragment thereof, for example, an activator (e.g., a trans-acting factor), a chaperone and a processing protease. The nucleic acids encoding one or more of these factors are preferably not operably linked to the nucleic acid encoding the protein or fragment thereof. An activator is a protein which activates transcription of a nucleic acid sequence encoding a polypeptide (Kudla et al., *EMBO* 9:1355-1364(1990); Jarai and Buxton, *Current Genetics* 26:2238-244(1994); Verdier, *Yeast* 6:271-297(1990), all of which are herein incorporated by reference in their entirety). The nucleic acid sequence encoding an activator may be obtained from the genes encoding *Saccharomyces cerevisiae* heme activator protein 1 (hap 1), *Saccharomyces cerevisiae* galactose metabolizing protein 4 (gal4) and *Aspergillus nidulans* ammonia regulation protein (areA). For further examples, see Verdier, *Yeast* 6:271-297 (1990); MacKenzie et al., *Journal of Gen. Microbiol.* 139:2295-2307 (1993), both of which are herein incorporated by reference in their entirety). A chaperone is a protein which assists another protein in folding properly (Hartl et al., *TIBS*19:20-25 (1994); Bergeron et al., *TIBS* 19:124-128 (1994); Demolder et al., *J. Biotechnology* 32:179-189 (1994); Craig, *Science* 260:1902-1903(1993); Gething and Sambrook, *Nature* 355:33-45 (1992); Puig and Gilbert, *J Biol. Chem.* 269:7764-7771 (1994); Wang and Tsou, *FASEB Journal* 7:1515-11157 (1993); Robinson et al., *Bio/Technology* 1:381-384 (1994), all of which are herein incorporated by reference in their entirety). The nucleic acid sequence encoding a chaperone may be obtained from the genes encoding *Aspergillus oryzae* protein disulphide isomerase, *Saccharomyces cerevisiae* calnexin, *Saccharomyces cerevisiae* BiP/GRP78 and *Saccharomyces cerevisiae* Hsp70. For further examples, see Gething and Sambrook, *Nature* 355:33-45 (1992); Hartl et al., *TIBS* 19:20-25 (1994). A processing protease is a protease that cleaves a propeptide to generate a mature biochemically active polypeptide (Enderlin and Ogrydziak, *Yeast* 10:67-79 (1994); Fuller et al., *Proc. Natl. Acad. Sci.* (*U.S.A.*) 86:1434-1438 (1989); Julius et al., *Cell* 37:1075-1089 (1984); Julius et al., *Cell* 32:839-852 (1983), all of which are incorporated by reference in their entirety). The nucleic acid sequence encoding a processing protease may be obtained from the genes encoding *Aspergillus niger* Kex2, *Saccharomyces cerevisiae* dipeptidylaminopeptidase, *Saccharomyces cerevisiae* Kex2 and *Yarrowia lipolytica* dibasic processing endoprotease (xpr6). Any factor that is functional in the fungal host cell of choice may be used in the present invention.

Fungal cells may be transformed by a process involving protoplast formation, transformation of the protoplasts and regeneration of the cell wall in a manner known per se. Suitable procedures for transformation of *Aspergillus* host cells are described in EP 238 023 and Yelton et al., *Proc. Natl. Acad. Sci.* (*U.S.A.*) 81:1470-1474 (1984), both of which are herein incorporated by reference in their entirety. A suitable method of transforming *Fusarium* species is described by Malardier et al., *Gene* 78:147-156 (1989), the entirety of which is herein incorporated by reference. Yeast may be transformed using the procedures described by Becker and Guarente, In: Abelson and Simon, (eds.), *Guide to Yeast Genetics and Molecular Biology, Methods Enzymol.* Volume 194, pp 182-187, Academic Press, Inc., New York; Ito et al., *J. Bacteriology* 153:163 (1983); Hinnen et al., *Proc. Natl. Acad. Sci.* (*U.S.A.*) 75:1920 (1978), all of which are herein incorporated by reference in their entirety.

The present invention also relates to methods of producing the protein or fragment thereof comprising culturing the recombinant fungal host cells under conditions conducive for expression of the protein or fragment thereof. The fungal cells of the present invention are cultivated in a nutrient medium suitable for production of the protein or fragment thereof using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the protein or fragment thereof to be expressed and/or isolated. The cultivation takes place in a suitable nutrient medium comprising carbon and nitrogen sources and inorganic salts, using procedures known in the art (see, e.g., Bennett and LaSure (eds.), *More Gene Manipulations in Fungi*, Academic Press, CA, (1991), the entirety of which is herein incorporated by reference). Suitable media are available from commercial suppliers or may be prepared according to published compositions (e.g., in catalogues of the American Type Culture Collection, Manassas, Va.). If the protein or fragment thereof is secreted into the nutrient medium, a protein or fragment thereof can be recovered directly from the medium. If the protein or fragment thereof is not secreted, it is recovered from cell lysates.

The expressed protein or fragment thereof may be detected using methods known in the art that are specific for the particular protein or fragment. These detection methods may include the use of specific antibodies, formation of an enzyme product, or disappearance of an enzyme substrate. For example, if the protein or fragment thereof has enzymatic activity, an enzyme assay may be used. Alternatively, if polyclonal or monoclonal antibodies specific to the protein or fragment thereof are available, immunoassays may be employed using the antibodies to the protein or fragment thereof. The techniques of enzyme assay and immunoassay are well known to those skilled in the art.

The resulting protein or fragment thereof may be recovered by methods known in the arts. For example, the protein or fragment thereof may be recovered from the nutrient medium by conventional procedures including, but not limited to, centrifugation, filtration, extraction, spray-drying, evaporation, or precipitation. The recovered protein or fragment thereof may then be further purified by a variety of chromatographic procedures, e.g., ion exchange chromatography, gel filtration chromatography, affinity chromatography, or the like.

(c) Mammalian Constructs and Transformed Mammalian Cells

The present invention also relates to methods for obtaining a recombinant mammalian host cell, comprising introducing into a mammalian host cell exogenous genetic material. The present invention also relates to a mammalian cell comprising a mammalian recombinant vector. The present invention also relates to methods for obtaining a recombinant mammalian host cell, comprising introducing into a mammalian cell exogenous genetic material. In a preferred embodiment the exogenous genetic material includes a nucleic acid molecule of the present invention having a sequence selected from the group consisting of SEQ ID NO: 1 through SEQ ID NO: 711 or complements thereof or fragments of either or other nucleic acid molecule of the present invention.

Mammalian cell lines available as hosts for expression are known in the art and include many immortalized cell lines available from the American Type Culture Collection (ATCC, Manassas, Va.), such as HeLa cells, Chinese hamster ovary (CHO) cells, baby hamster kidney (BHK) cells and a number of other cell lines. Suitable promoters for mammalian cells are also known in the art and include viral promoters such as that from Simian Virus 40 (SV40) (Fiers et al., *Nature* 273: 113 (1978), the entirety of which is herein incorporated by reference), Rous sarcoma virus (RSV), adenovirus (ADV) and bovine papilloma virus (BPV). Mammalian cells may also require terminator sequences and poly-A addition sequences. Enhancer sequences which increase expression may also be included and sequences which promote amplification of the gene may also be desirable (for example methotrexate resistance genes).

Vectors suitable for replication in mammalian cells may include viral replicons, or sequences which insure integration of the appropriate sequences encoding HCV epitopes into the host genome. For example, another vector used to express foreign DNA is vaccinia virus. In this case, for example, a nucleic acid molecule encoding a protein or fragment thereof is inserted into the vaccinia genome. Techniques for the insertion of foreign DNA into the vaccinia virus genome are known in the art and may utilize, for example, homologous recombination. Such heterologous DNA is generally inserted into a gene which is non-essential to the virus, for example, the thymidine kinase gene (tk), which also provides a selectable marker. Plasmid vectors that greatly facilitate the construction of recombinant viruses have been described (see, for example, Mackett et al, *J Virol.* 49:857 (1984); Chakrabarti et al., *Mol. Cell. Biol.* 5:3403 (1985); Moss, In: *Gene Transfer Vectors For Mammalian Cells* (Miller and Calos, eds., Cold Spring Harbor Laboratory, N.Y., p. 10, (1987); all of which are herein incorporated by reference in their entirety). Expression of the HCV polypeptide then occurs in cells or animals which are infected with the live recombinant vaccinia virus.

The sequence to be integrated into the mammalian sequence may be introduced into the primary host by any convenient means, which includes calcium precipitated DNA, spheroplast fusion, transformation, electroporation, biolistics, lipofection, microinjection, or other convenient means. Where an amplifiable gene is being employed, the amplifiable gene may serve as the selection marker for selecting hosts into which the amplifiable gene has been introduced. Alternatively, one may include with the amplifiable gene another marker, such as a drug resistance marker, e.g. neomycin resistance (G418 in mammalian cells), hygromycin in resistance etc., or an auxotrophy marker (HIS3, TRP1, LEU2, URA3, ADE2, LYS2, etc.) for use in yeast cells.

Depending upon the nature of the modification and associated targeting construct, various techniques may be employed for identifying targeted integration. Conveniently, the DNA may be digested with one or more restriction enzymes and the fragments probed with an appropriate DNA fragment which will identify the properly sized restriction fragment associated with integration.

One may use different promoter sequences, enhancer sequences, or other sequence which will allow for enhanced levels of expression in the expression host. Thus, one may combine an enhancer from one source, a promoter region from another source, a 5'-noncoding region upstream from the initiation cytokinin from the same or different source as the other sequences and the like. One may provide for an intron in the non-coding region with appropriate splice sites or for an alternative 3'-untranslated sequence or polyadenylation site. Depending upon the particular purpose of the modification, any of these sequences may be introduced, as desired.

Where selection is intended, the sequence to be integrated will have with it a marker gene, which allows for selection. The marker gene may conveniently be downstream from the target gene and may include resistance to a cytotoxic agent, e.g. antibiotics, heavy metals, or the like, resistance or susceptibility to HAT, gancyclovir, etc., complementation to an auxotrophic host, particularly by using an auxotrophic yeast as the host for the subject manipulations, or the like. The marker gene may also be on a separate DNA molecule, particularly with primary mammalian cells. Alternatively, one may screen the various transformants, due to the high efficiency of recombination in yeast, by using hybridization analysis, PCR, sequencing, or the like.

For homologous recombination, constructs can be prepared where the amplifiable gene will be flanked, normally on both sides with DNA homologous with the DNA of the target region. Depending upon the nature of the integrating DNA and the purpose of the integration, the homologous DNA will generally be within 100 kb, usually 50 kb, preferably about 25 kb, of the transcribed region of the target gene, more preferably within 2 kb of the target gene. Where modeling of the gene is intended, homology will usually be present proximal to the site of the mutation. The homologous DNA may include the 5'-upstream region outside of the transcriptional regulatory region or comprising any enhancer sequences, transcriptional initiation sequences, adjacent sequences, or the like. The homologous region may include a portion of the coding region, where the coding region may be comprised only of an open reading frame or combination of exons and introns. The homologous region may comprise all or a portion of an intron, where all or a portion of one or more exons may also be present. Alternatively, the homologous region may comprise the 3'-region, so as to comprise all or a portion of the transcriptional termination region, or the region 3' of this region. The homologous regions may extend over all or a portion of the target gene or be outside the target gene comprising all or a portion of the transcriptional regulatory regions and/or the structural gene.

The integrating constructs may be prepared in accordance with conventional ways, where sequences may be synthesized, isolated from natural sources, manipulated, cloned, ligated, subjected to in vitro mutagenesis, primer repair, or the like. At various stages, the joined sequences may be cloned and analyzed by restriction analysis, sequencing, or the like. Usually during the preparation of a construct where various fragments are joined, the fragments, intermediate constructs and constructs will be carried on a cloning vector comprising a replication system functional in a prokaryotic host, e.g., *E. coli* and a marker for selection, e.g., biocide resistance, complementation to an auxotrophic host, etc. Other functional sequences may also be present, such as polylinkers, for ease of introduction and excision of the construct or portions thereof, or the like. A large number of cloning vectors are available such as pBR322, the pUC series, etc. These constructs may then be used for integration into the primary mammalian host.

In the case of the primary mammalian host, a replicating vector may be used. Usually, such vector will have a viral replication system, such as SV40, bovine papilloma virus, adenovirus, or the like. The linear DNA sequence vector may also have a selectable marker for identifying transfected cells. Selectable markers include the neo gene, allowing for selection with G418, the herpes tk gene for selection with HAT medium, the gpt gene with mycophenolic acid, complementation of an auxotrophic host, etc.

The vector may or may not be capable of stable maintenance in the host. Where the vector is capable of stable maintenance, the cells will be screened for homologous integration of the vector into the genome of the host, where various techniques for curing the cells may be employed. Where the vector is not capable of stable maintenance, for example, where a temperature sensitive replication system is employed, one may change the temperature from the permissive temperature to the non-permissive temperature, so that the cells may be cured of the vector. In this case, only those cells having integration of the construct comprising the amplifiable gene and, when present, the selectable marker, will be able to survive selection.

Where a selectable marker is present, one may select for the presence of the targeting construct by means of the selectable marker. Where the selectable marker is not present, one may select for the presence of the construct by the amplifiable gene. For the neo gene or the herpes tk gene, one could employ a medium for growth of the transformants of about 0.1-1 mg/ml of G418 or may use HAT medium, respectively. Where DHFR is the amplifiable gene, the selective medium may include from about 0.01-0.5 M of methotrexate or be deficient in glycine-hypoxanthine-thymidine and have dialysed serum (GHT media).

The DNA can be introduced into the expression host by a variety of techniques that include calcium phosphate/DNA co-precipitates, microinjection of DNA into the nucleus, electroporation, yeast protoplast fusion with intact cells, transfection, polycations, e.g., polybrene, polyornithine, etc., or the like. The DNA may be single or double stranded DNA, linear or circular. The various techniques for transforming mammalian cells are well known (see Keown et al., *Methods Enzymol.* (1989); Keown et al., *Methods Enzymol.* 185:527-537 (1990); Mansour et al., *Nature* 336:348-352, (1988); all of which are herein incorporated by reference in their entirety).

(d) Insect Constructs and Transformed Insect Cells

The present invention also relates to an insect recombinant vectors comprising exogenous genetic material. The present invention also relates to an insect cell comprising an insect recombinant vector. The present invention also relates to methods for obtaining a recombinant insect host cell, comprising introducing into an insect cell exogenous genetic material. In a preferred embodiment the exogenous genetic material includes a nucleic acid molecule of the present invention having a sequence selected from the group consisting of SEQ ID NO: 1 through SEQ ID NO: 711 or complements thereof or fragments of either or other nucleic acid molecule of the present invention.

The insect recombinant vector may be any vector which can be conveniently subjected to recombinant DNA procedures and can bring about the expression of the nucleic acid sequence. The choice of a vector will typically depend on the compatibility of the vector with the insect host cell into which the vector is to be introduced. The vector may be a linear or a closed circular plasmid. The vector system may be a single vector or plasmid or two or more vectors or plasmids which together contain the total DNA to be introduced into the genome of the insect host. In addition, the insect vector may be an expression vector. Nucleic acid molecules can be suitably inserted into a replication vector for expression in the insect cell under a suitable promoter for insect cells. Many vectors are available for this purpose and selection of the appropriate vector will depend mainly on the size of the nucleic acid molecule to be inserted into the vector and the particular host cell to be transformed with the vector. Each vector contains various components depending on its function (amplification of DNA or expression of DNA) and the particular host cell with which it is compatible. The vector components for insect cell transformation generally include, but are not limited to, one or more of the following: a signal sequence, origin of replication, one or more marker genes and an inducible promoter.

The insect vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the insect cell, is integrated into the genome and replicated together with the chromosome(s) into which it has been integrated. For integration, the vector may rely on the nucleic acid sequence of the vector for stable integration of the vector into the genome by homologous or nonhomologous recombination. Alternatively, the vector may contain additional nucleic acid sequences for directing integration by homologous recombination into the genome of the insect host. The additional nucleic acid sequences enable the vector to be integrated into the host cell genome at a precise location(s) in the chromosome(s). To increase the likelihood of integration at a precise location, there should be preferably two nucleic acid sequences which individually contain a sufficient number of nucleic acids, preferably 400 bp to 1500 bp, more preferably 800 bp to 1000 bp, which are highly homologous with the corresponding target sequence to enhance the probability of homologous recombination. These nucleic acid sequences may be any sequence that is homologous with a target sequence in the genome of the insect host cell and, furthermore, may be non-encoding or encoding sequences.

Baculovirus expression vectors (BEVs) have become important tools for the expression of foreign genes, both for basic research and for the production of proteins with direct clinical applications in human and veterinary medicine (Doerfler, *Curr. Top. Microbiol. Immunol.* 131:51-68 (1968); Luckow and Summers, *Bio/Technology* 6:47-55 (1988a); Miller, *Annual Review of Microbiol.* 42:177-199 (1988); Summers, *Curr. Comm. Molecular Biology*, Cold Spring Harbor Press, Cold Spring Harbor, N.Y. (1988); all of which are herein incorporated by reference in their entirety). BEVs are recombinant insect viruses in which the coding sequence for a chosen foreign gene has been inserted behind a baculovirus promoter in place of the viral gene, e.g., polyhedrin (Smith and Summers, U.S. Pat. No., 4,745,051, the entirety of which is incorporated herein by reference).

The use of baculovirus vectors relies upon the host cells being derived from Lepidopteran insects such as *Spodoptera frugiperda* or *Trichoplusia ni*. The preferred *Spodoptera frugiperda* cell line is the cell line Sf9. The *Spodoptera frugiperda* Sf9 cell line was obtained from American Type Culture Collection (Manassas, Va.) and is assigned accession number ATCC CRL 1711 (Summers and Smith, *A Manual of Methods for Baculovirus Vectors and Insect Cell Culture Procedures*, Texas Ag. Exper. Station Bulletin No. 1555 (1988), the entirety of which is herein incorporated by reference). Other insect cell systems, such as the silkworm *B. mori* may also be used.

The proteins expressed by the BEVs are, therefore, synthesized, modified and transported in host cells derived from Lepidopteran insects. Most of the genes that have been inserted and produced in the baculovirus expression vector system have been derived from vertebrate species. Other baculovirus genes in addition to the polyhedrin promoter may be employed to advantage in a baculovirus expression system. These include immediate-early (alpha), delayed-early ( ), late ( ), or very late (delta), according to the phase of the viral infection during which they are expressed. The expression of these genes occurs sequentially, probably as the result of a "cascade" mechanism of transcriptional regulation. (Guarino and Summers, *J. Virol.* 57:563-571 (1986); Guarino and Summers, *J. Virol.* 61:2091-2099 (1987); Guarino and Summers, *Virol.* 162:444-451 (1988); all of which are herein incorporated by reference in their entirety).

Insect recombinant vectors are useful as intermediates for the infection or transformation of insect cell systems. For example, an insect recombinant vector containing a nucleic acid molecule encoding a baculovirus transcriptional promoter followed downstream by an insect signal DNA sequence is capable of directing the secretion of the desired biologically active protein from the insect cell. The vector may utilize a baculovirus transcriptional promoter region derived from any of the over 500 baculoviruses generally infecting insects, such as for example the Orders Lepidoptera, Diptera, Orthoptera, Coleoptera and Hymenoptera, including for example but not limited to the viral DNAs of *Autographa californica* MNPV, *Bombyx mori* NPV, *Trichoplusia ni* MNPV, *Rachiplusia ou* MNPV or *Galleria mellonella* MNPV, wherein said baculovirus transcriptional promoter is a baculovirus immediate-early gene IEl or IEN promoter; an immediate-early gene in combination with a baculovirus delayed-early gene promoter region selected from the group consisting of 39K and a HindIII-k fragment delayed-early gene; or a baculovirus late gene promoter. The immediate-early or delayed-early promoters can be enhanced with transcriptional enhancer elements. The insect signal DNA sequence may code for a signal peptide of a Lepidopteran adipokinetic hormone precursor or a signal peptide of the *Manduca sexta* adipokinetic hormone precursor (Summers, U.S. Pat. No. 5,155,037; the entirety of which is herein incorporated by reference). Other insect signal DNA sequences include a signal peptide of the *Orthoptera Schistocerca gregaria* locust adipokinetic hormone precurser and the *Drosophila melanogaster* cuticle genes CP1, CP2, CP3 or CP4 or for an insect signal peptide having substantially a similar chemical composition and function (Summers, U.S. Pat. No. 5,155,037).

Insect cells are distinctly different from animal cells. Insects have a unique life cycle and have distinct cellular properties such as the lack of intracellular plasminogen activators in which are present in vertebrate cells. Another difference is the high expression levels of protein products ranging from 1 to greater than 500 mg/liter and the ease at which cDNA can be cloned into cells (Frasier, *In Vitro Cell. Dev. Biol.* 25:225 (1989); Summers and Smith, In: *A Manual of Methods for Baculovirus Vectors and Insect Cell Culture Procedures*, Texas Ag. Exper. Station Bulletin No. 1555 (1988), both of which are incorporated by reference in their entirety).

Recombinant protein expression in insect cells is achieved by viral infection or stable transformation. For viral infection, the desired gene is cloned into baculovirus at the site of the wild-type polyhedron gene (Webb and Summers, *Technique* 2:173 (1990); Bishop and Posse, *Adv. Gene Technol.* 1:55 (1990); both of which are incorporated by reference in their entirety). The polyhedron gene is a component of a protein coat in occlusions which encapsulate virus particles. Deletion or insertion in the polyhedron gene results the failure to form occlusion bodies. Occlusion negative viruses are morphologically different from occlusion positive viruses and enable one skilled in the art to identify and purify recombinant viruses.

The vectors of present invention preferably contain one or more selectable markers which permit easy selection of transformed cells. A selectable marker is a gene the product of which provides, for example biocide or viral resistance, resistance to heavy metals, prototrophy to auxotrophs and the like. Selection may be accomplished by co-transformation, e.g., as described in WO 91/17243, a nucleic acid sequence of the present invention may be operably linked to a suitable promoter sequence. The promoter sequence is a nucleic acid sequence which is recognized by the insect host cell for expression of the nucleic acid sequence. The promoter sequence contains transcription and translation control sequences which mediate the expression of the protein or fragment thereof. The promoter may be any nucleic acid sequence which shows transcriptional activity in the insect host cell of choice and may be obtained from genes encoding polypeptides either homologous or heterologous to the host cell.

For example, a nucleic acid molecule encoding a protein or fragment thereof may also be operably linked to a suitable leader sequence. A leader sequence is a nontranslated region of a mRNA which is important for translation by the fungal host. The leader sequence is operably linked to the 5' terminus of the nucleic acid sequence encoding the protein or fragment thereof. The leader sequence may be native to the nucleic acid sequence encoding the protein or fragment thereof or may be obtained from foreign sources. Any leader sequence which is functional in the insect host cell of choice may be used in the present invention.

A polyadenylation sequence may also be operably linked to the 3' terminus of the nucleic acid sequence of the present invention. The polyadenylation sequence is a sequence which when transcribed is recognized by the insect host to add polyadenosine residues to transcribed mRNA. The polyadenylation sequence may be native to the nucleic acid sequence encoding the protein or fragment thereof or may be obtained from foreign sources. Any polyadenylation sequence which is functional in the fungal host of choice may be used in the present invention.

To avoid the necessity of disrupting the cell to obtain the protein or fragment thereof and to minimize the amount of possible degradation of the expressed polypeptide within the cell, it is preferred that expression of the polypeptide gene gives rise to a product secreted outside the cell. To this end, the protein or fragment thereof of the present invention may be linked to a signal peptide linked to the amino terminus of the protein or fragment thereof. A signal peptide is an amino acid sequence which permits the secretion of the protein or fragment thereof from the insect host into the culture medium. The signal peptide may be native to the protein or fragment thereof of the invention or may be obtained from foreign sources. The 5' end of the coding sequence of the nucleic acid sequence of the present invention may inherently contain a signal peptide coding region naturally linked in translation reading frame with the segment of the coding region which encodes the secreted protein or fragment thereof.

At present, a mode of achieving secretion of a foreign gene product in insect cells is by way of the foreign gene's native signal peptide. Because the foreign genes are usually from non-insect organisms, their signal sequences may be poorly recognized by insect cells and hence, levels of expression may be suboptimal. However, the efficiency of expression of foreign gene products seems to depend primarily on the characteristics of the foreign protein. On average, nuclear localized or non-structural proteins are most highly expressed, secreted proteins are intermediate and integral membrane proteins are the least expressed. One factor generally affecting the efficiency of the production of foreign gene products in a heterologous host system is the presence of native signal sequences (also termed presequences, targeting signals, or leader sequences) associated with the foreign gene. The signal sequence is generally coded by a DNA sequence immediately following (5' to 3') the translation start site of the desired foreign gene.

The expression dependence on the type of signal sequence associated with a gene product can be represented by the following example: If a foreign gene is inserted at a site downstream from the translational start site of the baculovirus polyhedrin gene so as to produce a fusion protein (containing the N-terminus of the polyhedrin structural gene), the fused gene is highly expressed. But less expression is achieved when a foreign gene is inserted in a baculovirus expression vector immediately following the transcriptional start site and totally replacing the polyhedrin structural gene.

Insertions into the region −50 to −1 significantly alter (reduce) steady state transcription which, in turn, reduces translation of the foreign gene product. Use of the pVL941 vector optimizes transcription of foreign genes to the level of the polyhedrin gene transcription. Even though the transcription of a foreign gene may be optimal, optimal translation may vary because of several factors involving processing: signal peptide recognition, mRNA and ribosome binding, glycosylation, disulfide bond formation, sugar processing, oligomerization, for example.

The properties of the insect signal peptide are expected to be more optimal for the efficiency of the translation process in insect cells than those from vertebrate proteins. This phenomenon can generally be explained by the fact that proteins secreted from cells are synthesized as precursor molecules containing hydrophobic N-terminal signal peptides. The signal peptides direct transport of the select protein to its target membrane and are then cleaved by a peptidase on the membrane, such as the endoplasmic reticulum, when the protein passes through it.

Another exemplary insect signal sequence is the sequence encoding for *Drosophila* cuticle proteins such as CP1, CP2, CP3 or CP4 (Summers, U.S. Pat. No. 5,278,050; the entirety of which is herein incorporated by reference). Most of a 9 kb region of the *Drosophila* genome containing genes for the cuticle proteins has been sequenced. Four of the five cuticle genes contains a signal peptide coding sequence interrupted by a short intervening sequence (about 60 base pairs) at a conserved site. Conserved sequences occur in the 5' mRNA untranslated region, in the adjacent 35 base pairs of upstream flanking sequence and at −200 base pairs from the mRNA start position in each of the cuticle genes.

Standard methods of insect cell culture, cotransfection and preparation of plasmids are set forth in Summers and Smith (Summers and Smith, *A Manual of Methods for Baculovirus Vectors and Insect Cell Culture Procedures*, Texas Agricultural Experiment Station Bulletin No. 1555, Texas A&M University (1987)). Procedures for the cultivation of viruses and cells are described in Volkman and Summers, *J. Virol* 19:820-832 (1975) and Volkman et al., *J. Virol* 19:820-832 (1976); both of which are herein incorporated by reference in their entirety.

(e) Bacterial Constructs and Transformed Bacterial Cells

The present invention also relates to a bacterial recombinant vector comprising exogenous genetic material. The present invention also relates to a bacteria cell comprising a bacterial recombinant vector. The present invention also relates to methods for obtaining a recombinant bacteria host cell, comprising introducing into a bacterial host cell exogenous genetic material. In a preferred embodiment the exogenous genetic material includes a nucleic acid molecule of the present invention having a sequence selected from the group consisting of SEQ ID NO: 1 through SEQ ID NO: 711 or complements thereof or fragments of either or other nucleic acid molecule of the present invention.

The bacterial recombinant vector may be any vector which can be conveniently subjected to recombinant DNA procedures. The choice of a vector will typically depend on the compatibility of the vector with the bacterial host cell into which the vector is to be introduced. The vector may be a linear or a closed circular plasmid. The vector system may be a single vector or plasmid or two or more vectors or plasmids which together contain the total DNA to be introduced into the genome of the bacterial host. In addition, the bacterial vector may be an expression vector. Nucleic acid molecules encoding protein homologues or fragments thereof can, for example, be suitably inserted into a replicable vector for expression in the bacterium under the control of a suitable promoter for bacteria. Many vectors are available for this purpose and selection of the appropriate vector will depend mainly on the size of the nucleic acid to be inserted into the vector and the particular host cell to be transformed with the vector. Each vector contains various components depending on its function (amplification of DNA or expression of DNA) and the particular host cell with which it is compatible. The vector components for bacterial transformation generally include, but are not limited to, one or more of the following: a signal sequence, an origin of replication, one or more marker genes and an inducible promoter.

In general, plasmid vectors containing replicon and control sequences that are derived from species compatible with the host cell are used in connection with bacterial hosts. The vector ordinarily carries a replication site, as well as marking sequences that are capable of providing phenotypic selection in transformed cells. For example, E. coli is typically transformed using pBR322, a plasmid derived from an E. coli species (see, e.g., Bolivar et al., Gene 2:95 (1977); the entirety of which is herein incorporated by reference). pBR322 contains genes for ampicillin and tetracycline resistance and thus provides easy means for identifying transformed cells. The pBR322 plasmid, or other microbial plasmid or phage, also generally contains, or is modified to contain, promoters that can be used by the microbial organism for expression of the selectable marker genes.

Nucleic acid molecules encoding protein or fragments thereof may be expressed not only directly, but also as a fusion with another polypeptide, preferably a signal sequence or other polypeptide having a specific cleavage site at the N-terminus of the mature polypeptide. In general, the signal sequence may be a component of the vector, or it may be a part of the polypeptide DNA that is inserted into the vector. The heterologous signal sequence selected should be one that is recognized and processed (i.e., cleaved by a signal peptidase) by the host cell. For bacterial host cells that do not recognize and process the native polypeptide signal sequence, the signal sequence is substituted by a bacterial signal sequence selected, for example, from the group consisting of the alkaline phosphatase, penicillinase, lpp, or heat-stable enterotoxin II leaders.

Both expression and cloning vectors contain a nucleic acid sequence that enables the vector to replicate in one or more selected host cells. Generally, in cloning vectors this sequence is one that enables the vector to replicate independently of the host chromosomal DNA and includes origins of replication or autonomously replicating sequences. Such sequences are well known for a variety of bacteria. The origin of replication from the plasmid pBR322 is suitable for most Gram-negative bacteria.

Expression and cloning vectors also generally contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. One example of a selection scheme utilizes a drug to arrest growth of a host cell. Those cells that are successfully transformed with a heterologous protein homologue or fragment thereof produce a protein conferring drug resistance and thus survive the selection regimen.

The expression vector for producing a protein or fragment thereof can also contains an inducible promoter that is recognized by the host bacterial organism and is operably linked to the nucleic acid encoding, for example, the nucleic acid molecule encoding the protein homologue or fragment thereof of interest. Inducible promoters suitable for use with bacterial hosts include the -lactamase and lactose promoter systems (Chang et al., Nature 275:615 (1978); Goeddel et al., Nature 281:544 (1979); both of which are herein incorporated by reference in their entirety), the arabinose promoter system (Guzman et al., J. Bacteriol. 174:7716-7728 (1992); the entirety of which is herein incorporated by reference), alkaline phosphatase, a tryptophan (trp) promoter system (Goeddel, Nucleic Acids Res. 8:4057 (1980); EP 36,776; both of which are herein incorporated by reference in their entirety) and hybrid promoters such as the tac promoter (deBoer et al., Proc. Natl. Acad. Sci. (U.S.A.) 80:21-25 (1983); the entirety of which is herein incorporated by reference). However, other known bacterial inducible promoters are suitable (Siebenlist et al., Cell 20:269 (1980); the entirety of which is herein incorporated by reference).

Promoters for use in bacterial systems also generally contain a Shine-Dalgarno (S.D.) sequence operably linked to the DNA encoding the polypeptide of interest. The promoter can be removed from the bacterial source DNA by restriction enzyme digestion and inserted into the vector containing the desired DNA.

Construction of suitable vectors containing one or more of the above-listed components employs standard ligation techniques. Isolated plasmids or DNA fragments are cleaved, tailored and re-ligated in the form desired to generate the plasmids required. Examples of available bacterial expression vectors include, but are not limited to, the multifunctional E. coli cloning and expression vectors such as Bluescript™ (Stratagene, La Jolla, Calif.), in which, for example, encoding an A. nidulans protein homologue or fragment thereof homologue, may be ligated into the vector in frame with sequences for the amino-terminal Met and the subsequent 7 residues of galactosidase so that a hybrid protein is produced; pIN vectors (Van Heeke and Schuster, J. Biol. Chem. 264:5503-5509 (1989), the entirety of which is herein incorporated by reference); and the like. pGEX vectors (Promega, Madison Wis. U.S.A.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

Suitable host bacteria for a bacterial vector include archaebacteria and eubacteria, especially eubacteria and most preferably Enterobacteriaceae. Examples of useful bacteria include *Escherichia, Enterobacter, Azotobacter, Erwinia, Bacillus, Pseudomonas, Klebsiella, Proteus, Salmonella, Serratia, Shigella, Rhizobia, Vitreoscilla* and *Paracoccus*. Suitable *E. coli* hosts include *E. coli* W3110 (American Type Culture Collection (ATCC) 27,325, Manassas, Va. U.S.A.), *E. coli* 294 (ATCC 31,446), *E. coli* B and *E. coli* X1776 (ATCC 31,537). These examples are illustrative rather than limiting. Mutant cells of any of the above-mentioned bacteria may also be employed. It is, of course, necessary to select the appropriate bacteria taking into consideration replicability of the replicon in the cells of a bacterium. For example, *E. coli, Serratia*, or *Salmonella* species can be suitably used as the host when well known plasmids such as pBR322, pBR325, pACYC177, or pKN410 are used to supply the replicon. *E. coli* strain W3110 is a preferred host or parent host because it is a common host strain for recombinant DNA product fermentations. Preferably, the host cell should secrete minimal amounts of proteolytic enzymes.

Host cells are transfected and preferably transformed with the above-described vectors and cultured in conventional nutrient media modified as appropriate for inducing promoters, selecting transformants, or amplifying the genes encoding the desired sequences.

Numerous methods of transfection are known to the ordinarily skilled artisan, for example, calcium phosphate and electroporation. Depending on the host cell used, transformation is done using standard techniques appropriate to such cells. The calcium treatment employing calcium chloride, as described in section 1.82 of Sambrook et al., *Molecular Cloning: A Laboratory Manual*, New York: Cold Spring Harbor Laboratory Press, (1989), is generally used for bacterial cells that contain substantial cell-wall barriers. Another method for transformation employs polyethylene glycol/DMSO, as described in Chung and Miller (Chung and Miller, *Nucleic Acids Res.* 16:3580 (1988); the entirety of which is herein incorporated by reference). Yet another method is the use of the technique termed electroporation.

Bacterial cells used to produce the polypeptide of interest for purposes of this invention are cultured in suitable media in which the promoters for the nucleic acid encoding the heterologous polypeptide can be artificially induced as described generally, e.g., in Sambrook et al., *Molecular Cloning: A Laboratory Manual*, New York: Cold Spring Harbor Laboratory Press, (1989). Examples of suitable media are given in U.S. Pat. Nos. 5,304,472 and 5,342,763; both of which are incorporated by reference in their entirety.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., *Molecular Cloning: A Laboratory Manual*, Cold Spring Harbor Press (1989); Mailga et al., *Methods in Plant Molecular Biology*, Cold Spring Harbor Press (1995), the entirety of which is herein incorporated by reference: Birren et al., *Genome Analysis: Analyzing DNA*, 1, Cold Spring Harbor, N.Y., the entirety of which is herein incorporated by reference).

(f) Computer Readable Media

The nucleotide sequence provided in SEQ ID NO: 1 through SEQ ID NO: 711 or fragment thereof, or complement thereof, or a nucleotide sequence at least 90% identical, preferably 95%, identical even more preferably 99% or 100% identical to the sequence provided in SEQ ID NO: 1 through SEQ ID NO: 711 or fragment thereof, or complement thereof, can be "provided" in a variety of mediums to facilitate use. Such a medium can also provide a subset thereof in a form that allows a skilled artisan to examine the sequences.

A preferred subset of nucleotide sequences are those nucleic acid sequences that encode a maize or a soybean adenine phosphoribosyl transferase enzyme or complement thereof or fragment of either, a nucleic acid molecule that encodes a maize or a soybean β glucosidase enzyme or complement thereof or fragment of either and a nucleic acid molecule that encodes a soybean isopentyltransferase enzyme or complement thereof or fragment of either.

A further preferred subset of nucleic acid sequences is where the subset of sequences is two proteins or fragments thereof, more preferably three proteins or fragments thereof and even more preferable four proteins or fragments thereof, these nucleic acid sequences are selected from the group that comprises a maize or a soybean adenine phosphoribosyl transferase enzyme or complement thereof or fragment of either, a nucleic acid molecule that encodes a maize or a soybean β glucosidase enzyme or complement thereof or fragment of either and a nucleic acid molecule that encodes a soybean isopentyltransferase enzyme or complement thereof or fragment of either.

In one application of this embodiment, a nucleotide sequence of the present invention can be recorded on computer readable media. As used herein, "computer readable media" refers to any medium that can be read and accessed directly by a computer. Such media include, but are not limited to: magnetic storage media, such as floppy discs, hard disc, storage medium and magnetic tape: optical storage media such as CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon a nucleotide sequence of the present invention.

As used herein, "recorded" refers to a process for storing information on computer readable medium. A skilled artisan can readily adopt any of the presently known methods for recording information on computer readable medium to generate media comprising the nucleotide sequence information of the present invention. A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. A skilled artisan can readily adapt any number of data processor structuring formats (e.g. text file or database) in order to obtain computer readable medium having recorded thereon the nucleotide sequence information of the present invention.

By providing one or more of nucleotide sequences of the present invention, a skilled artisan can routinely access the sequence information for a variety of purposes. Computer software is publicly available which allows a skilled artisan to access sequence information provided in a computer readable medium. The examples which follow demonstrate how software which implements the BLAST (Altschul et al., *J. Mol. Biol.* 215:403-410 (1990), the entirety of which is herein incorporated by reference) and BLAZE (Brutlag et al., *Comp. Chem.* 17:203-207 (1993), the entirety of which is herein incorporated by reference) search algorithms on a Sybase system can be used to identify open reading frames (ORFs) within the genome that contain homology to ORFs or proteins from other organisms. Such ORFs are protein-encoding fragments within the sequences of the present invention and are useful in producing commercially important proteins such as enzymes used in amino acid biosynthesis, metabolism, transcription, translation, RNA processing, nucleic acid and a protein degradation, protein modification and DNA replication, restriction, modification, recombination and repair.

The present invention further provides systems, particularly computer-based systems, which contain the sequence information described herein. Such systems are designed to identify commercially important fragments of the nucleic acid molecule of the present invention. As used herein, "a computer-based system" refers to the hardware means, software means and data storage means used to analyze the nucleotide sequence information of the present invention. The minimum hardware means of the computer-based systems of the present invention comprises a central processing unit (CPU), input means, output means and data storage means. A skilled artisan can readily appreciate that any one of the currently available computer-based system are suitable for use in the present invention.

As indicated above, the computer-based systems of the present invention comprise a data storage means having stored therein a nucleotide sequence of the present invention and the necessary hardware means and software means for supporting and implementing a search means. As used herein, "data storage means" refers to memory that can store nucleotide sequence information of the present invention, or a memory access means which can access manufactures having recorded thereon the nucleotide sequence information of the present invention. As used herein, "search means" refers to one or more programs which are implemented on the computer-based system to compare a target sequence or target structural motif with the sequence information stored within the data storage means. Search means are used to identify fragments or regions of the sequence of the present invention that match a particular target sequence or target motif. A variety of known algorithms are disclosed publicly and a variety of commercially available software for conducting search means are available can be used in the computer-based systems of the present invention. Examples of such software include, but are not limited to, MacPattern (EMBL), BLASTIN and BLASTIX (NCBIA). One of the available algorithms or implementing software packages for conducting homology searches can be adapted for use in the present computer-based systems.

The most preferred sequence length of a target sequence is from about 10 to 100 amino acids or from about 30 to 300 nucleotide residues. However, it is well recognized that during searches for commercially important fragments of the nucleic acid molecules of the present invention, such as sequence fragments involved in gene expression and protein processing, may be of shorter length.

As used herein, "a target structural motif," or "target motif," refers to any rationally selected sequence or combination of sequences in which the sequences the sequence(s) are chosen based on a three-dimensional configuration which is formed upon the folding of the target motif. There are a variety of target motifs known in the art. Protein target motifs include, but are not limited to, enzymatic active sites and signal sequences. Nucleic acid target motifs include, but are not limited to, promoter sequences, cis elements, hairpin structures and inducible expression elements (protein binding sequences).

Thus, the present invention further provides an input means for receiving a target sequence, a data storage means for storing the target sequences of the present invention sequence identified using a search means as described above and an output means for outputting the identified homologous sequences. A variety of structural formats for the input and output means can be used to input and output information in the computer-based systems of the present invention. A preferred format for an output means ranks fragments of the sequence of the present invention by varying degrees of homology to the target sequence or target motif. Such presentation provides a skilled artisan with a ranking of sequences which contain various amounts of the target sequence or target motif and identifies the degree of homology contained in the identified fragment.

A variety of comparing means can be used to compare a target sequence or target motif with the data storage means to identify sequence fragments sequence of the present invention. For example, implementing software which implement the BLAST and BLAZE algorithms (Altschul et al., *J. Mol. Biol.* 215:403-410 (1990)) can be used to identify open frames within the nucleic acid molecules of the present invention. A skilled artisan can readily recognize that any one of the publicly available homology search programs can be used as the search means for the computer-based systems of the present invention.

Having now generally described the invention, the same will be more readily understood through reference to the following examples which are provided by way of illustration and are not intended to be limiting of the present invention, unless specified.

EXAMPLE 1

The MONN01 cDNA library is a normalized library generated from maize (DK604, Dekalb Genetics, Dekalb, Ill. U.S.A.) total leaf tissue at the V6 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6-leaf development stage. The older, more juvenile leaves, which are in a basal position, as well as the younger, more adult leaves, which are more apical are cut at the base of the leaves. The leaves are then pooled and immediately transferred to liquid nitrogen containers in which the pooled leaves are crushed. The harvested tissue is then stored at −80° C. until RNA preparation.

The SATMON001 cDNA library is generated from maize (B73, Illinois Foundation Seeds, Champaign, Ill. U.S.A.) immature tassels at the V6 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Tissue from the maize plant is collected at the V6 stage. At that stage the tassel is an immature tassel of about 2-3 cm in length. The tassels are removed and frozen in liquid nitrogen. The harvested tissue is then stored at −80° C. until RNA preparation.

The SATMON003 library is generated from maize (B73 x Mo17, Illinois Foundation Seeds, Champaign, Ill. U.S.A.) roots at the V6 developmental stage. Seeds are planted at a depth of approximately 3 cm in coil into 2-3 inch peat pots containing Metro 200 growing medium. After 2-3 weeks growth, the seedlings are transplanted into 10 inch pots containing the Metro 200 growing medium. Plants are watered daily before transplantation and approximately 3 times a week after transplantation. Peters 15-16-17 fertilizer is applied approximately three times per week after transplanting at a concentration of 150 ppm N. Two to three times during the life time of the plant from transplanting to flowering a total of approximately 900 mg Fe is added to each pot. Maize plants are grown in the green house in approximately 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6 leaf development stage. The root system is cut from maize plant and washed with water to free it from the soil. The tissue is then immediately frozen in liquid nitrogen. The harvested tissue is then stored at −80° C. until RNA preparation.

The SATMON004 cDNA library is generated from maize (B73 x Mo1 7, Illinois Foundation Seeds, Champaign, Ill. U.S.A.) total leaf tissue at the V6 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6-leaf development stage. The older, more juvenile leaves, which are in a basal position, as well as the younger, more adult leaves, which are more apical are cut at the base of the leaves. The leaves are then pooled and immediately transferred to liquid nitrogen containers in which the pooled leaves are crushed. The harvested tissue is then stored at −80° C. until RNA preparation.

The SATMON005 cDNA library is generated from maize (B73 x Mo 17, Illinois Foundation Seeds, Champaign Ill., U.S.A.) root tissue at the V6 development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6-leaf development stage. The root system is cut from the mature maize plant and washed with water to free it from the soil. The tissue is immediately frozen in liquid nitrogen and the harvested tissue is then stored at −80° C. until RNA preparation.

The SATMON006 cDNA library is generated from maize (B73 x Mo17, Illinois Foundation Seeds, Champaign Ill., U.S.A.) total leaf tissue at the V6 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6-leaf development stage. The older more juvenile leaves, which are in a basal position, as well as the younger more adult leaves, which are more apical are cut at the base of the leaves. The leaves are then pooled and immediately transferred to liquid nitrogen containers in which the pooled leaves are crushed. The harvested tissue is then stored at −80° C. until RNA preparation.

The SATMON007 cDNA library is generated from the primary root tissue of 5 day old maize (DK604, Dekalb Genetics, Dekalb, Ill. U.S.A.) seedlings. Seeds are planted on a moist filter paper on a covered tray that is kept in the dark until germination (one day). After germination, the trays, along with the moist paper, are moved to a greenhouse where the maize plants are grown in the greenhouse in 15 hr day/9 hr night cycles for approximately 5 days. The daytime temperature is approximately 80° F. and the nighttime temperature is approximately 70° F. Supplemental lighting is provided by 1000 W sodium vapor lamps. The primary root tissue is collected when the seedlings are 5 days old. At this stage, the primary root (radicle) is pushed through the coleorhiza which itself is pushed through the seed coat. The primary root, which is about 2-3 cm long, is cut and immediately frozen in liquid nitrogen and then stored at −80° C. until RNA preparation.

The SATMON008 cDNA library is generated from the primary shoot (coleoptile 2-3 cm) of maize (DK604, Dekalb Genetics, Dekalb, Ill. U.S.A.) seedlings which are approximately 5 days old. Seeds are planted on a moist filter paper on a covered tray that is kept in the dark until germination (one day). Then the trays containing the seeds are moved to a greenhouse at 15 hr daytime/9 hr nighttime cycles and grown until they are 5 days post germination. The daytime temperature is approximately 80° F. and the nighttime temperature is approximately 70° F. Tissue is collected when the seedlings are 5 days old. At this stage, the primary shoot (coleoptile) is pushed through the seed coat and is about 2-3 cm long. The coleoptile is dissected away from the rest of the seedling, immediately frozen in liquid nitrogen and then stored at −80° C. until RNA preparation.

The SATMON009 cDNA library is generated from maize (DK604, Dekalb Genetics, Dekalb, Ill. U.S.A.) leaves at the 8 leaf stage (V8 plant development stage). Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is 80° F. and the nighttime temperature is 70° F. Supplemental lighting is provided by 1000 W sodium vapor lamps. Tissue is collected when the maize plant is at the 8-leaf development stage. The older more juvenile leaves, which are in a basal position, as well as the younger more adult leaves, which are more apical, are cut at the base of the leaves. The leaves are then pooled and then immediately transferred to liquid nitrogen containers in which the pooled leaves are crushed. The harvested tissue is then stored at −80° C. until RNA preparation.

The SATMON010 cDNA library is generated from maize (DK604, Dekalb Genetics, Dekalb, Ill. U.S.A.) root tissue at the V8 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is 80° F. and the nighttime temperature is 70° F. Supplemental lighting is provided by 1000 W sodium vapor lamps. Tissue is collected when the maize plant is at the V8 development stage. The root system is cut from this mature maize plant and washed with water to free it from the soil. The tissue is immediately frozen in liquid nitrogen. The harvested tissue is then stored at −80° C. until RNA preparation.

The SATMON011 cDNA library is generated from undeveloped maize (DK604, Dekalb Genetics, Dekalb, Ill. U.S.A.) leaf at the V6 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6-leaf development stage. The second youngest leaf which is at the base of the apical leaf of V6 stage maize plant is cut at the base and immediately transferred to liquid nitrogen containers in which the leaf is crushed. The harvested tissue is then stored at −80° C. until RNA preparation.

The SATMON012 cDNA library is generated from 2 day post germination maize (DK604, Dekalb Genetics, Dekalb, Ill. U.S.A.) seedlings. Seeds are planted on a moist filter paper on a covered tray that is kept in the dark until germination (one day). Then the trays containing the seeds are moved to the greenhouse and grown at 15 hr daytime/9 hr nighttime cycles until 2 days post germination. The daytime temperature is approximately 80° F. and the nighttime temperature is approximately 70° F. Tissue is collected when the seedlings are 2 days old. At the two day stage, the coleorhiza is pushed through the seed coat and the primary root (the radicle) is pierced through the coleorhiza but is barely visible. Also, at this two day stage, the coleoptile is just emerging from the seed coat. The 2 days post germination seedlings are then immersed in liquid nitrogen and crushed. The harvested tissue is stored at −80° C. until preparation of total RNA.

The SATMON013 cDNA library is generated from apical maize (DK604, Dekalb Genetics, Dekalb, Ill. U.S.A.) meristem founder at the V4 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Prior to tissue collection, the plant is at the 4 leaf stage. The lead at the apex of the V4 stage maize plant is referred to as the meristem founder. This apical meristem founder is cut, immediately frozen in liquid nitrogen and crushed. The harvested tissue is then stored at −80° C. until RNA preparation.

The SATMON014 cDNA library is generated from maize (DK604, Dekalb Genetics, Dekalb, Ill. U.S.A.) endosperm fourteen days after pollination. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. After the V10 stage, the maize plant ear shoots are ready for fertilization. At this stage, the ear shoots are enclosed in a paper bag before silk emergence to withhold the pollen. The ear shoots are pollinated and 14 days after pollination, the ears are pulled out and then the kernels are plucked out of the ears. Each kernel is then dissected into the embryo and the endosperm and the aleurone layer is removed. After dissection, the endosperms are immediately frozen in liquid nitrogen and then stored at −80° C. until RNA preparation.

The SATMON016 library is a maize (DK604, Dekalb Genetics, Dekalb, Ill. U.S.A.) sheath library collected at the V8 developmental stage. Seeds are planted in a depth of approximately 3 cm in solid into 2-3 inch pots containing Metro growing medium. After 2-3 weeks growth, they are transplanted into 10" pots containing the same. Plants are watered daily before transplantation and approximately the times a week after transplantation. Peters 15-16-17 fertilizer is applied approximately three times per week after transplanting, at a strength of 150 ppm N. Two to three times during the life time of the plant from transplanting to flowering, a total of approximately 900 mg Fe is added to each pot. Maize plants are grown in the green house in 15 hr day/9 hr night cycles. The daytime temperature is approximately 80° F. and the nighttime temperature is approximately 70° F. Supplemental lighting is provided by 1000 W sodium vapor lamps. When the maize plants are at the V8 stage the $5^{th}$ and $6^{th}$ leaves from the bottom exhibit fully developed leaf blades. At the base of these leaves, the ligule is differentiated and the leaf blade is joined to the sheath. The sheath is dissected away from the base of the leaf then the sheath is frozen in liquid nitrogen and crushed. The tissue is then stored at −80° C. until RNA preparation.

The SATMON017 cDNA library is generated from maize (DK604, Dekalb Genetics, Dekalb, Ill. U.S.A.) embryo seventeen days after pollination. Seeds are planted at a depth of approximately 3 cm into 2-3 inch peat pots containing Metro 200 growing medium. After 2-3 weeks growth the seeds are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is approximately 80° F. and the nighttime temperature is approximately 70° F. Supplemental lighting is provided by 1000 W sodium vapor lamps. After the V10 stage, the ear shoots of maize plant, which are ready for fertilization, are enclosed in a paper bag before silk emergence to withhold the pollen. The ear shoots are fertilized and 21 days after pollination, the ears are pulled out and the kernels are plucked out of the ears. Each kernel is then dissected into the embryo and the endosperm and the aleurone layer is removed. After dissection, the embryos are immediately frozen in liquid nitrogen and then stored at −80° C. until RNA preparation.

The SATMON019 (Lib3054) cDNA library is generated from maize (DK604, Dekalb Genetics, Dekalb, Ill. U.S.A.) culm (stem) at the V8 developmental stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is approximately 80° F. and the nighttime temperature is approximately 70° F. Supplemental lighting is provided by 1000 W sodium vapor lamps. When the maize plant is at the V8 stage, the 5th and 6th leaves from the bottom have fully developed leaf blades. The region between the nodes of the 5th and the sixth leaves from the bottom is the region of the stem that is collected. The leaves are pulled out and the sheath is also torn away from the stem. This stem tissue is completely free of any leaf and sheath tissue. The stem tissue is then frozen in liquid nitrogen and stored at −80° C. until RNA preparation.

The SATMON020 cDNA library is from a maize (DK604, Dekalb Genetics, Dekalb, Ill. U.S.A.) Hill Type II-Initiated Callus. Petri plates containing approximately 25 ml of Type II initiation media are prepared. This medium contains N6 salts and vitamins, 3% sucrose, 2.3 g/liter proline 0.1 g/liter enzymatic casein hydrolysate, 2 mg/liter 2,4-dichloro phenoxyacetic acid (2,4, D), 15.3 mg/liter $AgNO_3$ and 0.8% bacto agar and is adjusted to pH 6.0 before autoclaving. At 9-11 days after pollination, an ear with immature embryos measuring approximately 1-2 mm in length is chosen. The husks and silks are removed and then the ear is broken into halves and placed in an autoclaved solution of Clorox/TWEEN 20 sterilizing solution. Then the ear is rinsed with deionized water. Then each embryo is extracted from the kernel. Intact embryos are placed in contact with the medium, scutellar side up). Multiple embryos are plated on each plate and the plates are incubated in the dark at 25° C. Type II calluses are friable, can be subcultured with a spatula, frequently regenerate via somatic embryogenesis and are relatively undifferentiated. As seen in the microscope, the Tape II calluses show color ranging from translucent to light yellow and heterogeneity on with respect to embryoid structure as well as stage of embryoid development. Once Type II callus are formed, the calluses is transferred to type II callus maintenance medium without $AgNO_3$. Every 7-10 days, the callus is subcultured. About 4 weeks after embryo isolation the callus is removed from the plates and then frozen in liquid nitrogen. The harvested tissue is stored at −80° C. until RNA preparation.

The SATMON021 cDNA library is generated from the immature maize (DK604, Dekalb Genetics, Dekalb Ill., U.S.A.) tassel at the V8 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is approximately 80° F. and the nighttime temperature is approximately 70° F. Supplemental lighting is provided by 1000 W sodium vapor lamps. As the maize plant enters the V8 stage, tassels which are 15-20 cm in length are collected and frozen in liquid nitrogen. The harvested tissue is stored at −80° C. until RNA preparation.

The SATMON022 cDNA library is generated from maize (DK604, Dekalb Genetics, Dekalb, Ill. U.S.A.) ear (growing silks) at the V8 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. *Zea mays* plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the plant is in the V8 stage. At this stage, some immature ear shoots are visible. The immature ear shoots (approximately 1 cm in length) are pulled out, frozen in liquid nitrogen and then stored at −80° C. until RNA preparation.

The SATMON23 cDNA library is generated from maize (DK604, Dekalb Genetics, Dekalb, Ill. U.S.A.) ear (growing silk) at the V8 development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. When the tissue is harvested at the V8 stage, the length of the ear that is harvested is about 10-15 cm and the silks are just exposed (approximately 1 inch). The ear along with the silks is frozen in liquid nitrogen and then the tissue is stored at −80° C. until RNA preparation.

The SATMON024 cDNA library is generated from the immature maize (DK604, Dekalb Genetics, Dekalb, Ill. U.S.A.) tassel at the V9 development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is approximately 80° F. and the nighttime temperature is approximately 70° F. As a maize plant enters the V9 stage, the tassel is rapidly developing and a 37 cm tassel along with the glume, anthers and pollen is collected and frozen in liquid nitrogen. The harvested tissue is stored at −80° C. until RNA preparation.

The SATMON025 cDNA library is from maize (DK604, Dekalb Genetics, Dekalb, Ill. U.S.A.) Hill Type II-Regenerated Callus. Type II callus is grown in initiation media as described for SATMON020 and then the embryoids on the surface of the Type II callus are allowed to mature and germinate. The 1-2 gm fresh weight of the soft friable type callus containing numerous embryoids are transferred to 100×15 mm petri plates containing 25 ml of regeneration media. Regeneration media consists of Murashige and Skoog (MS) basal salts, modified White's vitamins (0.2 g/liter glycine and 0.5 g/liter myo-inositol and 0.8% bacto agar (6SMS0D)). The plates are then placed in the dark after covering with parafilm. After 1 week, the plates are moved to a lighted growth chamber with 16 hr light and 8 hr dark photoperiod. Three weeks after plating the Type II callus to 6SMS0D, the callus exhibit shoot formation. The callus and the shoots are transferred to fresh 6SMS0D plates for another 2 weeks. The callus and the shoots are then transferred to petri plates with reduced sucrose (3SMSOD). Upon distinct formation of a root and shoot, the newly developed green plants are then removed out with a spatula and frozen in liquid nitrogen containers. The harvested tissue is then stored at −80° C. until RNA preparation.

The SATMON026 cDNA library is generated from maize (DK604, Dekalb Genetics, Dekalb, Ill. U.S.A.) juvenile/adult shift leaves at the V8 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plants are at the 8-leaf development stage. Leaves are founded sequentially around the meristem over weeks of time and the older, more juvenile leaves arise earlier and in a more basal position than the younger, more adult leaves, which are in a more apical position. In a V8 plant, some leaves which are in the middle portion of the plant exhibit characteristics of both juvenile as well as adult leaves. They exhibit a yellowing color but also exhibit, in part, a green color. These leaves are termed juvenile/adult shift leaves. The juvenile/adult shift leaves (the 4th, 5th leaves from the bottom) are cut at the base, pooled and transferred to liquid nitrogen in which they are then crushed. The harvested tissue is then stored at −80° C. until RNA preparation.

The SATMON027 cDNA library is generated from 6 day maize (DK604, Dekalb Genetics, Dekalb, Ill. U.S.A.) leaves. Seeds are planted at a depth of approximately 3 cm into 2-3 inch peat pots containing Metro 200 growing medium. After 2-3 weeks growth they are transplanted into 10 inch pots containing the Metro 200 growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. *Zea mays* plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Prior to tissue collection, when the plant is at the 8-leaf stage, water is held back for six days. The older, more juvenile leaves, which are in a basal position, as well as the younger, more adult leaves, which are more apical, are all cut at the base of the leaves. All the leaves exhibit significant wilting. The leaves are then pooled and immediately transferred to liquid nitrogen containers in which the pooled leaves are then crushed. The harvested tissue is then stored at −80° C. until RNA preparation.

The SATMON028 cDNA library is generated from maize (DK604, Dekalb Genetics, Dekalb, Ill. U.S.A.) roots at the V8 developmental stage that are subject to six days water stress. Seeds are planted at a depth of approximately 3 cm into 2-3 inch peat pots containing Metro 200 growing medium. After 2-3 weeks growth they are transplanted into 10 inch pots containing the Metro 200 growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Prior to tissue collection, when the plant is at the 8-leaf stage, water is held back for six days. The root system is cut, shaken and washed to remove soil. Root tissue is then pooled and immediately transferred to liquid nitrogen containers in which the pooled leaves are then crushed. The harvested tissue is then stored at −80° C. until RNA preparation.

The SATMON029 cDNA library is generated from maize (DK604, Dekalb Genetics, Dekalb, Ill. U.S.A.) seedlings at the etiolated stage. Seeds are planted on a moist filter paper on a covered tray that is kept in the dark for 4 days at approximately 70° F. Tissue is collected when the seedlings are 4 days old. By 4 days, the primary root has penetrated the coleorhiza and is about 4-5 cm and the secondary lateral roots have also made their appearance. The coleoptile has also pushed through the seed coat and is about 4-5 cm long. The seedlings are frozen in liquid nitrogen and crushed. The harvested tissue is then stored at −80° C. until RNA preparation.

The SATMON030 cDNA library is generated from maize (DK604, Dekalb Genetics, Dekalb, Ill. U.S.A.) root tissue at the V4 plant development stage. Seeds are planted at a depth of approximately 3 cm into 2-3 inch peat pots containing Metro 200 growing medium. After 2-3 weeks growth, they are transplanted into 10 inch pots containing the same. Plants are watered daily before transplantation and approximately 3 times a week after transplantation. Peters 15-16-17 fertilizer is applied approximately three times per week after transplanting, at a strength of 150 ppm N. Two to three times during the life time of the plant, from transplanting to flowering, a total of approximately 900 mg Fe is added to each pot. Maize plants are grown in the green house in 15 hr day/9 hr night cycles. The daytime temperature is approximately 80° F. and the nighttime temperature is approximately 70° F. Supplemental lighting is provided by 1000 sodium vapor lamps. Tissue is collected when the maize plant is at the 4 leaf development stage. The root system is cut from the mature maize plant and washed with water to free it from the soil. The tissue is then immediately frozen in liquid nitrogen. The harvested tissue is then stored at −80° C. until RNA preparation.

The SATMON031 cDNA library is generated from the maize (DK604, Dekalb Genetics, Dekalb, Ill. U.S.A.) leaf tissue at the V4 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is 80° F. and the nighttime temperature is 70° F. Supplemental lighting is provided by 1000 W sodium vapor lamps. Tissue is collected when the maize plant is at the 4-leaf development stage. The third leaf from the bottom is cut at the base and immediately frozen in liquid nitrogen and crushed. The tissue is immediately frozen in liquid nitrogen. The harvested tissue is then stored at −80° C. until RNA preparation.

The SATMON033 cDNA library is generated from maize (DK604, Dekalb Genetics, Dekalb, Ill. U.S.A.) embryo tissue 13 days after pollination. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. After the V10 stage, the ear shoots of the maize plant, which are ready for fertilization, are enclosed in a paper bag before silk emergent to withhold the pollen. The ear shoots are pollinated and 13 days after pollination, the ears are pulled out and then the kernels are plucked out of the ears. Each kernel is then dissected into the embryo and the endosperm and the aleurone layer is removed. After dissection, the embryos are immediately frozen in liquid nitrogen and then stored at −80° C. until RNA preparation.

The SATMON034 cDNA library is generated from cold stressed maize (DK604, Dekalb Genetics, Dekalb, Ill. U.S.A.) seedlings. Seeds are planted on a moist filter paper on a covered tray that is kept on at 10° C. for 7 days. After 7 days, the temperature is shifted to 15° C. for one day until germination of the seed. Tissue is collected once the seedlings are 1 day old. At this point, the coleorhiza has just pushed out of the seed coat and the primary root is just making its appearance. The coleoptile has not yet pushed completely through the seed coat and is also just making its appearance. These 1 day old cold stressed seedlings are frozen in liquid nitrogen and crushed. The harvested tissue is then stored at −80° C. until RNA preparation.

The SATMON~001 (Lib36, Lib83, Lib84) cDNA library is generated from maize leaves at the V8 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Tissue from the maize plant is collected at the V8 stage. The older more juvenile leaves in a basal position was well as the younger more adult leaves which are more apical are all cut at the base, pooled and frozen in liquid nitrogen. The harvested tissue is then stored at −80° C. until RNA preparation.

The SATMONN01 cDNA library is generated from maize (B73, Illinois Foundation Seeds, Champaign, Ill. U.S.A.) normalized immature tassels at the V6 plant development stage normalized tissue. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Tissue from the maize plant is collected at the V6 stage. At that stage the tassel is an immature tassel of about 2-3 cm in length. The tassels are removed and frozen in liquid nitrogen. The harvested tissue is then stored at −80° C. until RNA preparation. Single stranded and double stranded DNA representing approximately $1 \times 10^6$ colony forming units are isolated using standard protocols. RNA, complementary to the single stranded DNA, is synthesized using the double stranded DNA as a template. Biotinylated dATP is incorporated into the RNA during the synthesis reaction. The single stranded DNA is mixed with the biotinylated RNA in a 1:10 molar ratio) and allowed to hybridize. DNA-RNA hybrids are captured on Dynabeads M280 streptavidin (Dynabeads, Dynal Corporation, Lake Success, N.Y. U.S.A.). The dynabeads with captured hybrids are collected with a magnet. The non-hybridized single stranded molecules remaining after hybrid capture are converted to double stranded form and represent the primary normalized library.

The SATMONN04 cDNA library is generated from maize (B73 x Mo17, Illinois Foundation Seeds, Champaign, Ill. U.S.A.) normalized total leaf tissue at the V6 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6-leaf development stage. The older, more juvenile leaves, which are in a basal position, as well as the younger, more adult leaves, which are more apical are cut at the base of the leaves. The leaves are then pooled and immediately transferred to liquid nitrogen containers in which the pooled leaves are crushed. The harvested tissue is then stored at −80° C. until RNA preparation. Single stranded and double stranded DNA representing approximately $1 \times 10^6$ colony forming units are isolated using standard protocols. RNA, complementary to the single stranded DNA, is synthesized using the double stranded DNA as a template. Biotinylated dATP is incorporated into the RNA during the synthesis reaction. The single stranded DNA is mixed with the biotinylated RNA in a 1:10 molar ratio) and allowed to hybridize. DNA-RNA hybrids are captured on Dynabeads M280 streptavidin (Dynabeads, Dynal Corporation, Lake Success, N.Y. U.S.A.). The dynabeads with captured hybrids are collected with a magnet. The non-hybridized single stranded molecules remaining after hybrid capture are converted to double stranded form and represent the primary normalized library.

The SATMONN05 cDNA library is generated from maize (B73 x Mo 17, Illinois Foundation Seeds, Champaign Ill., U.S.A.) normalized root tissue at the V6 development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6-leaf development stage. The root system is cut from the mature maize plant and washed with water to free it from the soil. The tissue is immediately frozen in liquid nitrogen and the harvested tissue is then stored at −80° C. until RNA preparation. The single stranded and double stranded DNA representing approximately $1 \times 10^6$ colony forming units are isolated using standard protocols. RNA, complementary to the single stranded DNA, is synthesized using the double stranded DNA as a template. Biotinylated dATP is incorporated into the RNA during the synthesis reaction. The single stranded DNA is mixed with the biotinylated RNA in a 1:10 molar ratio) and allowed to hybridize. DNA-RNA hybrids are captured on Dynabeads M280 streptavidin (Dynabeads, Dynal Corporation, Lake Success, N.Y. U.S.A.). The dynabeads with captured hybrids are collected with a magnet. The non-hybridized single stranded molecules remaining after hybrid capture are converted to double stranded form and represent the primary normalized library.

The SATMONN06 cDNA library is generated from maize (B73 x Mo 17, Illinois Foundation Seeds, Champaign Ill., U.S.A.) normalized total leaf tissue at the V6 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6-leaf development stage. The older more juvenile leaves, which are in a basal position, as well as the younger more adult leaves, which are more apical are cut at the base of the leaves. The leaves are then pooled and immediately transferred to liquid nitrogen containers in which the pooled leaves are crushed. The harvested tissue is then stored at −80° C. until RNA preparation. Single stranded and double stranded DNA representing approximately $1 \times 10^6$ colony forming units are isolated using standard protocols. RNA, complementary to the single stranded DNA, is synthesized using the double stranded DNA as a template. Biotinylated dATP is incorporated into the RNA during the synthesis reaction. The single stranded DNA is mixed with the biotinylated RNA in a 1:10 molar ratio) and allowed to hybridize. DNA-RNA hybrids are captured on Dynabeads M280 streptavidin (Dynabeads, Dynal Corporation, Lake Success, N.Y. U.S.A.). The dynabeads with captured hybrids are collected with a magnet. The non-hybridized single stranded molecules remaining after hybrid capture are converted to double stranded form and represent the primary normalized library.

The CMZ029 (SATMON036) cDNA library is generated from maize (DK604, Dekalb Genetics, Dekalb, Ill. U.S.A.) endosperm 22 days after pollination. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is approximately 80° F. and the nighttime temperature is approximately 70° F. Supplemental lighting is provided by 1000 W sodium vapor lamps. After the V10 stage, the ear shoots of the maize plant, which are ready for fertilization, are enclosed in a paper bag before silk emergent to withhold the pollen. The ear shoots are pollinated and 22 days after pollination, the ears are pulled out and then the kernels are plucked out of the ears. Each kernel is then dissected into the embryo and the endosperm and the alurone layer is removed. After dissection, the endosperms are immediately frozen in liquid nitrogen and then stored at −80° C. until RNA preparation.

The CMz030 (Lib143) cDNA library is generated from maize seedling tissue two days post germination. Seeds are planted on a moist filter paper on a covered try that is keep in the dark until germination. The trays are then moved to the bench top at 15 hr daytime/9 hr nighttime cycles for 2 days post-germination. The day time temperature is 80° F. and the nighttime temperature is 70° F. Tissue is collected when the seedlings are 2 days old. At this stage, the colehrhiza has pushed through the seed coat and the primary root (the radicle) is just piercing the colehrhiza and is barely visible. The seedlings are placed at 42° C. for 1 hour. Following the heat shock treatment, the seedlings are immersed in liquid nitrogen and crushed. The harvested tissue is stored at −80° until RNA preparation.

The CMz031 (Lib148) cDNA library is generated from maize pollen tissue at the V10+ plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from V10+ stage plants. The ear shoots, which are ready for fertilization, are enclosed in a paper bag to withhold pollen. Twenty-one days after pollination, prior to removing the ears, the paper bag is shaken to collect the mature pollen. The mature pollen is immediately frozen in liquid nitrogen containers and the pollen is crushed. The harvested tissue is then stored at −80° C. until RNA preparation.

The CMz033 (Lib189) cDNA library is generated from maize pooled leaf tissue. Samples are harvested from open pollinated plants. Tissue is collected from maize leaves at the anthesis stage. The leaves are collect from 10-12 plants and frozen in liquid nitrogen. The harvested tissue is then stored at −80° C. until RNA preparation.

The CMz034 (Lib3060) cDNA library is generated from maize mature tissue at 40 days post pollination plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from leaves located two leaves below the ear leaf. This sample represents those genes expressed during onset and early stages of leaf senescence. The leaves are pooled and immediately transferred to liquid nitrogen. The harvested tissue is then stored at −80° C. until RNA preparation.

The CMz035 (Lib3061) cDNA library is generated from maize endosperm tissue at the V10+ plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from V10+ stage plants. The ear shoots, which are ready for fertilization, are enclosed in a paper bag prior to silk emergence to withhold pollen. Thirty-two days after pollination, the ears are pulled out and the kernels are removed from the cob. Each kernel is dissected into the embryo and the endosperm and the aleurone layer is removed. After dissection, the endosperms are immediately transferred to liquid nitrogen. The harvested tissue is then stored at −80° C. until RNA preparation.

The CMz036 (Lib3062) cDNA library is generated from maize husk tissue at the 8 week old plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from 8 week old plants. The husk is separated from the ear and immediately transferred to liquid nitrogen containers. The harvested tissue is then stored at −80° C. until RNA preparation.

The CMz037 (Lib3059) cDNA library is generated from maize pooled kernal at 12-15 days after pollienation plant development stage. Sample were collected from field grown material. Whole kernals from hand pollinated (control pollination) are harvested as whole ears and immediately frozen on dry ice. Kernels from 10-12 ears were pooled and ground together in liquid nitrogen. The harvested tissue is then stored at −80° C. until RNA preparation.

The CMz039 (Lib3066) cDNA library is generated from maize immature anther tissue at the 7 week old immature tassel stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 7 week old immature tassel stage. At this stage, prior to anthesis, the immature anthers are green and enclosed in the staminate spikelet. The developing anthers are dissected away from the 7 week old immature tassel and immediately frozen in liquid nitrogen. The harvested tissue is then stored at −80° C. until RNA preparation.

The CMz040 (Lib3067) cDNA library is generated from maize kernel tissue at the V10+ plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from V10+ stage plants. The ear shoots, which are ready for fertilization, are enclosed in a paper bag before silk emergence to withhold pollen. Five to eight days after controlled pollination. The ears are pulled and the kernels removed. The kernels are immediately frozen in liquid nitrogen. The harvested kernels tissue is then stored at −80° C. until RNA preparation. This sample represents gene expressed in early kernel development, during periods of cell division, amyloplast biogenesis and early carbon flow across the material to filial tissue.

The CMz041 (Lib3068) cDNA library is generated from maize pollen germinating silk tissue at the V10+ plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from V10+ stage plants when the ear shoots are ready for fertilization at the silk emergence stage. The emerging silks are pollinated with an excess of pollen under controlled pollination conditions in the green house. Eighteen hours after pollination the silks are removed from the ears and immediately frozen in liquid nitrogen containers. This sample represents genes expressed in both pollen and silk tissue early in pollination. The harvested tissue is then stored at −80° C. until RNA preparation.

The CMz042 (Lib3069) cDNA library is generated from maize ear tissue excessively pollinated at the V10+ plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from V10+ stage plants and the ear shoots which are ready for fertilization are at the silk emergence stage. The immature ears are pollinated with an excess of pollen under controlled pollination conditions. Eighteen hours post-pollination, the ears are removed and immediately transferred to liquid nitrogen containers. The harvested tissue is then stored at −80° C. until RNA preparation.

The CMz044 (Lib3075) cDNA library is generated from maize microspore tissue at the V10+ plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from immature anthers from 7 week old tassels. The immature anthers are first dissected from the 7 week old tassel with a scalpel on a glass slide covered with water. The microspores (immature pollen) are released into the water and are recovered by centrifugation. The microspore suspension is immediately frozen in liquid nitrogen. The harvested tissue is then stored at −80° C. until RNA preparation.

The CMz045 (Lib3076) cDNA library is generated from maize immature ear megaspore tissue. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from immature ear (megaspore) obtained from 7 week old plants. The immature ears are harvested from the 7 week old plants and are approximately 2.5 to 3 cm in length. The kernels are removed from the cob immediately frozen in liquid nitrogen. The harvested tissue is then stored at −80° C. until RNA preparation.

The CMz047 (Lib3078) cDNA library is generated from maize $CO_2$ treated high-exposure shoot tissue at the V10+ plant development stage. RX601 maize seeds are sterilized for 1 minute with a 10% clorox solution. The seeds are rolled in germination paper, and germinated in 0.5 mM calcium sulfate solution for two days at 30° C. The seedlings are planted at a depth of approximately 3 cm into 2-3 inch peat pots containing Metro 200 growing medium at a rate of 2-3 seedlings per pot. Twenty pots are placed into a high $CO_2$ environment (approximately 1000 ppm $CO_2$). Twenty plants were grown under ambient greenhouse $CO_2$ (approximately 450 ppm $CO_2$). Plants are watered daily before transplantation and three times a week after transplantation. Peters 20-20-20 fertilizer is also lightly applied. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. At ten days post planting, the shoots from both atmosphere are frozen in liquid nitrogen and lightly ground. The roots are washed in deionized water to remove the support media and the tissue is immediately transferred to liquid nitrogen containers. The harvested tissue is then stored at −80° C. until RNA preparation.

The CMz048 (Lib3079) cDNA library is generated from maize basal endosperm transfer layer tissue at the V 10+ plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from V10+ maize plants. The ear shoots, which are ready for fertilization, are enclosed in a paper bag prior to silk emergence, to withhold the pollen. Kernels are harvested at 12 days post-pollination and placed on wet ice for dissection. The kernels are cross sectioned laterally, dissecting just above the pedicel region, including 1-2 mm of the lower endosperm and the basal endosperm transfer region. The pedicel and lower endosperm region containing the basal endosperm transfer layer is pooled and immediately frozen in liquid nitrogen. The harvested tissue is then stored at −80° C. until RNA preparation.

The CMz049 (Lib3088) cDNA library is generated from maize immature anther tissue at the 7 week old immature tassel stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 7 week old immature tassel stage. At this stage, prior to anthesis, the immature anthers are green and enclosed in the staminate spikelet. The developing anthers are dissected away from the 7 week old immature tassel and immediately transferred to liquid nitrogen container. The harvested tissue is then stored at −80° C. until RNA preparation.

The CMz050 (Lib3114) cDNA library is generated from maize silk tissue at the V10+ plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is beyond the 10-leaf development stage and the ear shoots are approximately 15-20 cm in length. The ears are pulled and silks are separated from the ears and immediately transferred to liquid nitrogen containers. The harvested tissue is then stored at −80° C. until RNA preparation.

The SOYMON001 cDNA library is generated from soybean cultivar Asgrow 3244 (Asgrow Seed Company, Des Moines, Iowa U.S.A.) total leaf tissue at the V4 plant development stage. Leaf tissue from 38, field grown V4 stage plants is harvested from the $4^{th}$ node. Leaf tissue is removed from the plants and immediately frozen in dry-ice. The harvested tissue is then stored at −80° C. until RNA preparation.

The SOYMON002 cDNA library is generated from soybean cultivar Asgrow 3244 (Asgrow Seed Company, Des Moines, Iowa U.S.A.) root tissue at the V4 plant development stage. Root tissue from 76, field grown V4 stage plants is harvested. The root systems is cut from the soybean plant and washed with water to free it from the soil and immediately frozen in dry-ice. The harvested tissue is then stored at −80° C. until RNA preparation.

The SOYMON003 cDNA library is generated from soybean cultivar Asgrow 3244 (Asgrow Seed Company, Des Moines, Iowa U.S.A.) seedling hypocotyl axis tissue harvested 2 day post-imbibition. Seeds are planted at a depth of approximately 2 cm into 2-3 inch peat pots containing Metromix 350 medium. Trays are placed in an environmental chamber and grown at 12 hr daytime/12 hr nighttime cycles. The daytime temperature is approximately 29° C. and the nighttime temperature approximately 24° C. Soil is checked and watered daily to maintain even moisture conditions. Tissue is collected 2 days after the start of imbibition. The 2 days after imbibition samples are separated into 3 collections after removal of any adhering seed coat. At the 2 day stage, the hypocotyl axis is emerging from the soil. A few seedlings have cracked the soil surface and exhibited slight greening of the exposed cotyledons. The seedlings are washed in water to remove soil, hypocotyl axis harvested and immediately frozen in liquid nitrogen. The harvested tissue is then stored at −80° C. until RNA preparation.

The SOYMON004 cDNA library is generated from soybean cultivar Asgrow 3244 (Asgrow Seed Company, Des Moines, Iowa U.S.A.) seedling cotyledon tissue harvested 2 day post-imbibition. Seeds are planted at a depth of approximately 2 cm into 2-3 inch peat pots containing Metromix 350 medium. Trays are placed in an environmental chamber and grown at 12 hr daytime/12 hr nighttime cycles. The daytime temperature is approximately 29° C. and the nighttime temperature approximately 24° C. Soil is checked and watered daily to maintain even moisture conditions. Tissue is collected 2 days after the start of imbibition. The 2 days after imbibition samples are separated into 3 collections after removal of any adhering seed coat. At the 2 day stage, the hypocotyl axis is emerging from the soil. A few seedlings have cracked the soil surface and exhibited slight greening of the exposed cotyledons. The seedlings are washed in water to remove soil, hypocotyl axis harvested and immediately frozen in liquid nitrogen. The harvested tissue is then stored at −80° C. until RNA preparation.

The SOYMON005 cDNA library is generated from soybean cultivar Asgrow 3244 (Asgrow Seed Company, Des Moines, Iowa U.S.A.) seedling hypocotyl axis tissue harvested 6 hour post-imbibition. Seeds are planted at a depth of approximately 2 cm into 2-3 inch peat pots containing Metromix 350 medium. Trays are placed in an environmental chamber and grown at 12 hr daytime/12 hr nighttime cycles. The daytime temperature is approximately 29° C. and the nighttime temperature approximately 24° C. Soil is checked and watered daily to maintain even moisture conditions. Tissue is collected 6 hours after the start of imbibition. The 6 hours after imbibition samples are separated into 3 collections after removal of any adhering seed coat. The 6 hours after imbibition sample is collected over the course of approximately 2 hours starting at 6 hours post imbibition. At the 6 hours after imbibition stage, not all cotyledons have become fully hydrated and germination, or radicle protrusion, has not occurred. The seedlings are washed in water to remove soil, hypocotyl axis harvested and immediately frozen in liquid nitrogen. The harvested tissue is then stored at −80° C. until RNA preparation.

The SOYMON006 cDNA library is generated from soybean cultivar Asgrow 3244 (Asgrow Seed Company, Des Moines, Iowa U.S.A.) seedling cotyledons tissue harvest 6 hour post-imbibition. Seeds are planted at a depth of approximately 2 cm into 2-3 inch peat pots containing Metromix 350 medium. Trays are placed in an environmental chamber and grown at 12 hr daytime/12 hr nighttime cycles. The daytime temperature is approximately 29° C. and the nighttime temperature approximately 24° C. Soil is checked and watered daily to maintain even moisture conditions. Tissue is collected 6 hours after imbibition. The 6 hours after imbibition samples are separated into 3 collections after removal of any adhering seed coat. The 6 hours after imbibition sample is collected over the course of approximately 2 hours starting at 6 hours post-imbibition. At the 6 hours after imbibition, not all cotyledons have become fully hydrated and germination or radicle protrusion, have not occurred. The seedlings are washed in water to remove soil, cotyledon harvested and immediately frozen in liquid nitrogen. The harvested tissue is then stored at −80° C. until RNA preparation.

The SOYMON007 cDNA library is generated from soybean cultivar Asgrow 3244 (Asgrow Seed Company, Des Moines, Iowa U.S.A.) seed tissue harvested 25 and 35 days post-flowering. Seed pods from field grown plants are harvested 25 and 35 days after flowering and the seeds extracted from the pods. Approximately 4.4 g and 19.3 g of seeds are harvested from the respective seed pods and immediately frozen in dry ice. The harvested tissue is then stored at −80° C. until RNA preparation.

The SOYMON008 cDNA library is generated from soybean cultivar Asgrow 3244 (Asgrow Seed Company, Des Moines, Iowa U.S.A.) leaf tissue harvested from 25 and 35 days post-flowering plants. Total leaf tissue is harvested from field grown plants. Approximately 19 g and 29 g of leaves are harvested from the fourth node of the plant 25 and 35 days post-flowering and immediately frozen in dry ice. The harvested tissue is then stored at −80° C. until RNA preparation.

The SOYMON009 cDNA library is generated from soybean cultivar C1944 (USDA Soybean Germplasm Collection, Urbana, Ill. U.S.A.) pod and seed tissue harvested 15 days post-flowering. Pods from field grown plants are harvested 15 days post-flowering. Approximately 3 g of pod tissue is harvested and immediately frozen in dry-ice. The harvested tissue is then stored at −80° C. until RNA preparation.

The SOYMON010 cDNA library is generated from soybean cultivar C1944 (USDA Soybean Germplasm Collection, Urbana, Ill. U.S.A.) seed tissue harvested 40 days post-flowering. Pods from field grown plants are harvested 40 days post-flowering. Pods and seeds are separated, approximately 19 g of seed tissue is harvested and immediately frozen in dry-ice. The harvested tissue is then stored at −80° C. until RNA preparation.

The SOYMON011 cDNA library is generated from soybean cultivars Cristalina (USDA Soybean Germplasm Collection, Urbana, Ill. U.S.A.) and FT108 (Monsoy, Brazil) (tropical germ plasma) leaf tissue. Leaves are harvested from plants grown in an environmental chamber under 12 hr daytime/12 hr nighttime cycles. The daytime temperature is approximately 29° C. and the nighttime temperature approximately 24° C. Soil is checked and watered daily to maintain even moisture conditions. Approximately 30 g of leaves are harvested from the $4^{th}$ node of each of the Cristalina and FT108 cultivars and immediately frozen in dry ice. The harvested tissue is then stored at −80° C. until RNA preparation.

The SOYMON012 cDNA library is generated from soybean cultivar Asgrow 3244 (Asgrow Seed Company, Des Moines, Iowa U.S.A.) leaf tissue. Leaves from field grown plants are harvested from the fourth node 15 days post-flowering. Approximately 12 g of leaves are harvested and immediately frozen in dry ice. The harvested tissue is then stored at −80° C. until RNA preparation.

The SOYMON013 cDNA library is generated from soybean cultivar Asgrow 3244 (Asgrow Seed Company, Des Moines, Iowa U.S.A.) root and nodule tissue. Approximately, 28 g of root tissue from field grown plants is harvested 15 days post-flowering. The root system is cut from the soybean plant, washed with water to free it from the soil and immediately frozen in dry-ice. The harvested tissue is then stored at −80° C. until RNA preparation.

The SOYMON014 cDNA library is generated from soybean cultivar Asgrow 3244 (Asgrow Seed Company, Des Moines, Iowa U.S.A.) seed tissue harvested 25 and 35 days after flowering. Seed pods from field grown plants are harvested 15 days after flowering and the seeds extracted from the pods. Approximately 5 g of seeds are harvested from the respective seed pods and immediately frozen in dry ice. The harvested tissue is then stored at −80° C. until RNA preparation.

The SOYMON015 cDNA is generated from soybean cultivar Asgrow 3244 (Asgrow Seed Company, Des Moines, Iowa U.S.A.) seed tissue harvested 45 and 55 days post-flowering. Seed pods from field grown plants are harvested 45 and 55 days after flowering and the seeds extracted from the pods. Approximately 19 g and 31 g of seeds are harvested from the respective seed pods and immediately frozen in dry ice. The harvested tissue is then stored at −80° C. until RNA preparation.

The SOYMON016 cDNA library is generated from soybean cultivar Asgrow 3244 (Asgrow Seed Company, Des Moines, Iowa U.S.A.) root tissue. Approximately, 61 g and 38 g of root tissue from field grown plants is harvested 25 and 35 days post-flowering is harvested. The root system is cut from the soybean plant and washed with water to free it from the soil. The tissue is placed in 14 ml polystyrene tubes and immediately frozen in dry-ice. The harvested tissue is then stored at −80° C. until RNA preparation.

The SOYMON017 cDNA library is generated from soybean cultivar Asgrow 3244 (Asgrow Seed Company, Des Moines, Iowa U.S.A.) root tissue. Approximately 28 g of root tissue from field grown plants is harvested 45 and 55 days post-flowering. The root system is cut from the soybean plant, washed with water to free it from the soil and immediately frozen in dry-ice. The harvested tissue is then stored at −80° C. until RNA preparation.

The SOYMON018 cDNA is generated from soybean cultivar Asgrow 3244 (Asgrow Seed Company, Des Moines, Iowa U.S.A.) leaf tissue harvested 45 and 55 days post-flowering. Leaves from field grown plants are harvested 45 and 55 days after flowering from the fourth node. Approximately 27 g and 33 g of seeds are harvested from the respective seed pods and immediately frozen in dry ice. The harvested tissue is then stored at −80° C. until RNA preparation.

The SOYMON019 cDNA library is generated from soybean cultivars Cristalina (USDA Soybean Germplasm Collection, Urbana, Ill. U.S.A.) and FT108 (Monsoy, Brazil) (tropical germ plasma) root tissue. Roots are harvested from plants grown in an environmental chamber under 12 hr daytime/12 hr nighttime cycles. The daytime temperature is approximately 29° C. and the nighttime temperature approximately 24° C. Soil is checked and watered daily to maintain even moisture conditions. Approximately 50 g and 56 g of roots are harvested from each of the Cristalina and FT108 cultivars and immediately frozen in dry ice. The harvested tissue is then stored at −80° C. until RNA preparation.

The SOYMON020 cDNA is generated from soybean cultivar Asgrow 3244 (Asgrow Seed Company, Des Moines, Iowa U.S.A.) seed tissue harvested 65 and 75 days post-flowering. Seed pods from field grown plants are harvested 45 and 55 days after flowering and the seeds extracted from the pods. Approximately 14 g and 31 g of seeds are harvested from the respective seed pods and immediately frozen in dry ice. The harvested tissue is then stored at −80° C. until RNA preparation.

The SOYMON021 cDNA library is generated from Soybean Cyst Nematode-resistant soybean cultivar Hartwig (USDA Soybean Germplasm Collection, Urbana, Ill. U.S.A.) root tissue. Plants are grown in tissue culture at room temperature. At approximately 6 weeks post-germination, the plants are exposed to sterilized Soybean Cyst Nematode eggs. Infection is then allowed to progress for 10 days. After the 10 day infection process, the tissue is harvested. Agar from the culture medium and nematodes are removed and the root tissue is immediately frozen in dry ice. The harvested tissue is then stored at −80° C. until RNA preparation.

The SOYMON022 (Lib3030) cDNA library is generated from soybean cultivar Asgrow 3244 (Asgrow Seed Company, Des Moines, Iowa U.S.A.) partially opened flower tissue. Partially to fully opened flower tissue is harvested from plants grown in an environmental chamber under 12 hr daytime/12 hr nighttime cycles. The daytime temperature is approximately 29° C. and the nighttime temperature approximately 24° C. Soil is checked and watered daily to maintain even moisture conditions. A total of 3 g of flower tissue is harvested and immediately frozen in dry ice. The harvested tissue is then stored at −80° C. until RNA preparation.

The SOYMON023 cDNA library is generated from soybean genotype BW211S Null (Tohoku University, Morioka, Japan) seed tissue harvested 15 and 40 days post-flowering. Seed pods from field grown plants are harvested 15 and 40 days post-flowering and the seeds extracted from the pods. Approximately 0.7 g and 14.2 g of seeds are harvested from the respective seed pods and immediately frozen in dry ice. The harvested tissue is then stored at −80° C. until RNA preparation.

The SOYMON024 cDNA library is generated from soybean cultivar Asgrow 3244 (Asgrow Seed Company, Des Moines, Iowa U.S.A.) internode-2 tissue harvested 18 days post-imbibition. Seeds are planted at a depth of approximately 2 cm into 2-3 inch peat pots containing Metromix 350 medium. The plants are grown in a greenhouse for 18 days after the start of imbibition at ambient temperature. Soil is checked and watered daily to maintain even moisture conditions. Stem tissue is harvested 18 days after the start of imbibition. The samples are divided into hypocotyl and internodes 1 through 5. The fifth internode contains some leaf bud material. Approximately 3 g of each sample is harvested and immediately frozen in dry ice. The harvested tissue is then stored at −80° C. until RNA preparation.

The SOYMON025 cDNA library is generated from soybean cultivar Asgrow 3244 (Asgrow Seed Company, Des Moines, Iowa U.S.A.) leaf tissue harvested 65 days post-flowering. Leaves are harvested from the fourth node of field grown plants 65 days post-flowering. Approximately 18.4 g of leaf tissue is harvested and immediately frozen in dry ice. The harvested tissue is then stored at −80° C. until RNA preparation.

SOYMON026 cDNA library is generated from soybean cultivar Asgrow 3244 (Asgrow Seed Company, Des Moines, Iowa U.S.A.) root tissue harvested 65 and 75 days post-flowering. Approximately 27 g and 40 g of root tissue from field grown plants is harvested 65 and 75 days post-flowering. The root system is cut from the soybean plant, washed with water to free it from the soil and immediately frozen in dry-ice. The harvested tissue is then stored at −80° C. until RNA preparation.

The SOYMON027 cDNA library is generated from soybean cultivar Asgrow 3244 (Asgrow Seed Company, Des Moines, Iowa U.S.A.) seed tissue harvested 25 days post-flowering. Seed pods from field grown plants are harvested 25 days post-flowering and the seeds extracted from the pods. Approximately 17 g of seeds are harvested from the seed pods and immediately frozen in dry ice. The harvested tissue is then stored at −80° C. until RNA preparation.

The SOYMON028 cDNA library is generated from soybean cultivar Asgrow 3244 (Asgrow Seed Company, Des Moines, Iowa U.S.A.) drought-stressed root tissue. The plants are grown in an environmental chamber under 12 hr daytime/12 hr nighttime cycles. The daytime temperature is approximately 29° C. and the nighttime temperature 24° C. Soil is checked and watered daily to maintain even moisture conditions. At the R3 stage of development, water is withheld from half of the plant collection (drought stressed population). After 3 days, half of the plants from the drought stressed condition and half of the plants from the control population are harvested. After another 3 days (6 days post drought induction) the remaining plants are harvested. A total of 27 g and 40 g of root tissue is harvested and immediately frozen in dry ice. The harvested tissue is then stored at −80° C. until RNA preparation.

The SOYMON029 cDNA library is generated from Soybean Cyst Nematode-resistant soybean cultivar PI07354 (USDA Soybean Germplasm Collection, Urbana, Ill. U.S.A.) root tissue. Late fall to early winter greenhouse grown plants are exposed to Soybean Cyst Nematode eggs. At 10 days post-infection, the plants are uprooted, rinsed briefly and the roots frozen in liquid nitrogen. Approximately 20 grams of root tissue is harvested from the infected plants. The harvested tissue is then stored at −80° C. until RNA preparation.

The SOYMON030 cDNA library is generated from soybean cultivar Asgrow 3244 (Asgrow Seed Company, Des Moines, Iowa U.S.A.) flower bud tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature approximately 24° C. Soil is checked and watered daily to maintain even moisture conditions. Flower buds are removed from the plant at the pedicel. A total of 100 mg of flower buds are harvested and immediately frozen in liquid nitrogen. The harvested tissue is then stored at −80° C. until RNA preparation.

The SOYMON031 cDNA library is generated from soybean cultivar Asgrow 3244 (Asgrow Seed Company, Des Moines, Iowa U.S.A.) carpel and stamen tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature approximately 24° C. Soil is checked and watered daily to maintain even moisture conditions. Flower buds are removed from the plant at the pedicel. Flowers are dissected to separate petals, sepals and reproductive structures (carpels and stamens). A total of 300 mg of carpel and stamen tissue are harvested and immediately frozen in liquid nitrogen. The harvested tissue is then stored at −80° C. until RNA preparation.

The SOYMON032 cDNA library is prepared from the Asgrow cultivar A4922 (Asgrow Seed Company, Des Moines, Iowa U.S.A.) rehydrated dry soybean seed meristem tissue. Surface sterilized seeds are germinated in liquid media for 24 hours. The seed axis is then excised from the barely germinating seed, placed on tissue culture media and incubated overnight at 20° C. in the dark. The supportive tissue is removed from the explant prior to harvest. Approximately 570 mg of tissue is harvested and frozen in liquid nitrogen. The harvested tissue is then stored at −80° C. until RNA preparation.

The SOYMON033 cDNA library is generated from soybean cultivar Asgrow 3244 (Asgrow Seed Company, Des Moines, Iowa U.S.A.) heat-shocked seedling tissue without cotyledons. Seeds are imbibed and germinated in vermiculite for 2 days under constant illumination. After 48 hours, the seedlings are transferred to an incubator set at 40° C. under constant illumination. After 30, 60 and 180 minutes seedlings are harvested and dissected. A portion of the seedling consisting of the root, hypocotyl and apical hook is frozen in liquid nitrogen and stored at −80° C. The seedlings after 2 days of imbibition are beginning to emerge from the vermiculite surface. The apical hooks are dark green in appearance. Total RNA and poly A$^+$ RNA is prepared from equal amounts of pooled tissue.

The SOYMON034 cDNA library is generated from soybean cultivar Asgrow 3244 (Asgrow Seed Company, Des Moines, Iowa U.S.A.) cold-shocked seedling tissue without cotyledons. Seeds are imbibed and germinated in vermiculite for 2 days under constant illumination. After 48 hours, the seedlings are transferred to a cold room set at 5° C. under constant illumination. After 30, 60 and 180 minutes seedlings are harvested and dissected. A portion of the seedling consisting of the root, hypocotyl and apical hook is frozen in liquid nitrogen and stored at −80° C. The seedlings after 2 days of imbibition are beginning to emerge from the vermiculite surface. The apical hooks are dark green in appearance.

The SOYMON035 cDNA library is generated from soybean cultivar Asgrow 3244 (Asgrow Seed Company, Des Moines, Iowa U.S.A.) seed coat tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature 24° C. Soil is checked and watered daily to maintain even moisture conditions. Seeds are harvested from mid to nearly full maturation (seed coats are not yellowing). The entire embryo proper is removed from the seed coat sample and the seed coat tissue are harvested and immediately frozen in liquid nitrogen. The harvested tissue is then stored at −80° C. until RNA preparation.

The SOYMON036 cDNA library is generated from soybean cultivars PI171451, PI227687 and PI229358 (USDA Soybean Germplasm Collection, Urbana, Ill. U.S.A.) insect challenged leaves. Plants from each of the three cultivars are grown in screenhouse conditions. The screenhouse is divided in half and one half of the screenhouse is infested with soybean looper and the other half infested with velvetbean caterpillar. A single leaf is taken from each of the representative plants at 3 different time points, 11 days after infestation, 2 weeks after infestation and 5 weeks after infestation and immediately frozen in liquid nitrogen. The harvested tissue is then stored at −80° C. until RNA preparation. Total RNA and poly A+ RNA is isolated from pooled tissue consisting of equal quantities of all 18 samples (3 genotypes×3 sample times×2 insect genotypes).

The SOYMON037 cDNA library is generated from soybean cultivar A3244 (Asgrow Seed Company, Des Moines, Iowa U.S.A.) etiolated axis and radical tissue. Seeds are planted in moist vermiculite, wrapped and kept at room temperature in complete darkness until harvest. Etiolated axis and hypocotyl tissue is harvested at 2, 3 and 4 days post-planting. A total of 1 gram of each tissue type is harvested at 2, 3 and 4 days after planting and immediately frozen in liquid nitrogen. The harvested tissue is then stored at −80° C. until RNA preparation.

The SOYMON038 cDNA library is generated from soybean variety Asgrow A3237 (Asgrow Seed Company, Des Moines, Iowa U.S.A.) rehydrated dry seeds. Explants are prepared for transformation after germination of surface-sterilized seeds on solid tissue media. After 6 days, at 28° C. and 18 hours of light per day, the germinated seeds are cold shocked at 4° C. for 24 hours. Meristemic tissue and part of the hypocotyl is remove and cotyledon excised. The prepared explant is then wounded for *Agrobacterium* infection. The 2 grams of harvested tissue is frozen in liquid nitrogen and stored at −80° C. until RNA preparation.

The Soy51 (LIB3027) cDNA library is prepared from equal amounts tissue harvested from SOYMON007, SOYMON015 and SOYMON020 prepared tissue. Single stranded and double stranded DNA representing approximately $1\times10^6$ colony forming units are isolated using standard protocols. RNA, complementary to the single stranded DNA, is synthesized using the double stranded DNA as a template. Biotinylated dATP is incorporated into the RNA during the synthesis reaction. The single stranded DNA is mixed with the biotinylated RNA in a 1:10 molar ratio) and allowed to hybridize. DNA-RNA hybrids are captured on Dynabeads M280 streptavidin (Dynabeads, Dynal Corporation, Lake Success, N.Y. U.S.A.). The dynabeads with captured hybrids are collected with a magnet. The non-hybridized single stranded molecules remaining after hybrid capture are converted to double stranded form and represent the primary normalized library.

The Soy52 (LIB3028) cDNA library is generated from normalized flower DNA. Single stranded DNA representing approximately $1\times10^6$ colony forming units of SOYMON022 harvested tissue is used as the starting material for normalization. RNA, complementary to the single stranded DNA, is synthesized using the double stranded DNA as a template. Biotinylated dATP is incorporated into the RNA during the synthesis reaction. The single stranded DNA is mixed with the biotinylated RNA in a 1:10 molar ratio) and allowed to hybridize. DNA-RNA hybrids are captured on Dynabeads M280 streptavidin (Dynabeads, Dynal Corporation, Lake Success, N.Y. U.S.A.). The dynabeads with captured hybrids are collected with a magnet. The non-hybridized single stranded molecules remaining after hybrid capture are converted to double stranded form and represent the primary normalized library.

The Soy53 (LIB3039) cDNA library is generated from soybean cultivar Asgrow 3244 (Asgrow Seed Company, Des Moines, Iowa U.S.A.) seedling shoot apical meristem tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature 24° C. Soil is checked and watered daily to maintain even moisture conditions. Apical tissue is harvested from seedling shoot meristem tissue, 7-8 days after the start of imbibition. The apex of each seedling is dissected to include the fifth node to the apical meristem. The fifth node corresponds to the third trifoliate leaf in the very early stages of development. Stipules completely envelop the leaf primordia at this time. A total of 200 mg of apical tissue is harvested and immediately frozen in liquid nitrogen. The harvested tissue is then stored at −80° C. until RNA preparation.

The Soy54 (LIB3040) cDNA library is generated from soybean cultivar Asgrow 3244 (Asgrow Seed Company, Des Moines, Iowa U.S.A.) heart to torpedo stage embryo tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature 24° C. Soil is checked and watered daily to maintain even moisture conditions. Seeds are collected and embryos removed from surrounding endosperm and maternal tissues. Embryos from globular to young torpedo stages (by corresponding analogy to *Arabidopsis*) are collected with a bias towards the middle of this spectrum. Embryos which are beginning to show asymmetric development of cotyledons are considered the upper developmental boundary for the collection and are excluded. A total of 12 mg embryo tissue is frozen in liquid nitrogen. The harvested tissue is stored at −80° C. until RNA preparation.

Soy55 (LIB3049) cDNA library is generated from soybean cultivar Asgrow 3244 (Asgrow Seed Company, Des Moines, Iowa U.S.A.) young seed tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature 24° C. Soil is checked and watered daily to maintain even moisture conditions. Seeds are collected from very young pods (5 to 15 days after flowering). A total of 100 mg of seeds are harvested and frozen in liquid nitrogen. The harvested tissue is stored at −80° C. until RNA preparation.

Soy56 (LIB3029) cDNA library is prepared from equal amounts tissue harvested from SOYMON007, SOYMON015 and SOYMON020 prepared tissue. Single stranded and double stranded DNA representing approximately $1\times10^6$ colony forming units are isolated using standard protocols. RNA, complementary to the single stranded DNA, is synthesized using the double stranded DNA as a template. Biotinylated dATP is incorporated into the RNA during the synthesis reaction. The single stranded DNA is mixed with the biotinylated RNA in a 1:10 molar ratio and allowed to hybridize. DNA-RNA hybrids are captured on Dynabeads M280 streptavidin (Dynabeads, Dynal Corporation, Lake Success, N.Y. U.S.A.). The dynabeads with captured hybrids are collected with a magnet. The non-hybridized single stranded molecules remaining after hybrid capture are not converted to double stranded form and represent a non-normalized seed pool for comparison to Soy51 cDNA libraries.

The Soy58 (LIB3050) cDNA library is generated from soybean cultivar Asgrow 3244 (Asgrow Seed Company, Des Moines, Iowa U.S.A.) drought stressed root tissue subtracted from control root tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature 24° C. Soil is checked and watered daily to maintain even moisture conditions. At the R3 stage of the plant drought is induced by withholding water. After 3 and 6 days root tissue from both drought stressed and control (watered regularly) plants are collected and frozen in dry-ice. The harvested tissue is stored at −80° C. until RNA preparation. For subtraction, target cDNA is made from the drought stressed tissue total RNA using the SMART cDNA synthesis system from Clonetech (Clonetech Laboratories, Palo Alto, Calif. U.S.A.). Driver first strand cDNA is covalently linked to Dynabeads following a protocol similar to that described in the Dynal literature (Dynabeads, Dynal Corporation, Lake Success, N.Y. U.S.A.). The target cDNA is then heat denatured and the second strand trapped using Dynabeads oligo-dT. The target second strand cDNA is then hybridized to the driver cDNA in 400 1 2× SSPE for two rounds of hybridization at 65° C. and 20 hours. After each hybridization, the hybridization solution is removed from the system and the hybridized target cDNA removed from the driver by heat denaturation in water. After hybridization, the remaining cDNA is trapped with Dynabeads oligo-dT. The trapped cDNA is then amplified as in previous PCR based libraries and the resulting cDNA ligated into the pSPORT vector (Invitrogen, Carlsbad Calif. U.S.A.).

The Soy59 (LIB3051) cDNA library is generated from soybean cultivar Asgrow 3244 (Asgrow Seed Company, Des Moines, Iowa U.S.A.) endosperm tissue. Seeds are germinated on paper towels under laboratory ambient light conditions. At 8, 10 and 14 hours after imbibition, the seed coats are harvested. The endosperm consists of a very thin layer of tissue affixed to the inside of the seed coat. The seed coat and endosperm are frozen immediately after harvest in liquid nitrogen. The harvested tissue is stored at −80° C. until RNA preparation.

The Soy60 (LIB3072) cDNA library is generated from soybean cultivar Asgrow 3244 (Asgrow Seed Company, Des Moines, Iowa U.S.A.) drought stressed seed plus pod subtracted from control seed plus pod tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 26° C. and the nighttime temperature 21° C. and 70% relative humidity. Soil is checked and watered daily to maintain even moisture conditions. At the R3 stage of the plant drought is induced by withholding water. After 3 and 6 days seeds and pods from both drought stressed and control (watered regularly) plants are collected from the fifth and sixth node and frozen in dry-ice. The harvested tissue is stored at −80° C. until RNA preparation. For subtraction, target cDNA is made from the drought stressed tissue total RNA using the SMART cDNA synthesis system from Clonetech (Clonetech Laboratories, Palo Alto, Calif. U.S.A.). Driver first strand cDNA is covalently linked to Dynabeads following a protocol similar to that described in the Dynal literature (Dynabeads, Dynal Corporation, Lake Success, N.Y. U.S.A.). The target cDNA is then heat denatured and the second strand trapped using Dynabeads oligo-dT. The target second strand cDNA is then hybridized to the driver cDNA in 400 1 2× SSPE for two rounds of hybridization at 65° C. and 20 hours. After each hybridization, the hybridization solution is removed from the system and the hybridized target cDNA removed from the driver by heat denaturation in water. After hybridization, the remaining cDNA is trapped with Dynabeads oligo-dT. The trapped cDNA is then amplified as in previous PCR based libraries and the resulting cDNA ligated into the pSPORT vector (Invitrogen, Carlsbad Calif. U.S.A.).

The Soy61 (LIB3073) cDNA library is generated from soybean cultivar Asgrow 3244 (Asgrow Seed Company, Des Moines, Iowa U.S.A.) jasmonic acid treated seedling subtracted from control tissue. Seeds are planted at a depth of approximately 2 cm into 2-3 inch peat pots containing Metromix 350 medium and the plants are grown in a greenhouse. The daytime temperature is approximately 29.4° C. and the nighttime temperature 20° C. Soil is checked and watered daily to maintain even moisture conditions. At 9 days post planting, the plantlets are sprayed with either control buffer of 0.1% Tween-20 or jasmonic acid (Sigma J-2500, Sigma, St. Louis, Mo. U.S.A.) at 1 mg/ml in 0.1% Tween-20. Plants are sprayed until runoff and the soil and the stem is socked with the spraying solution. At 18 hours post application of jasmonic acid, the soybean plantlets appear growth retarded. After 18 hours, 24 hours and 48 hours post treatment, the cotyledons are removed and the remaining leaf and stem tissue above the soil is harvested and frozen in liquid nitrogen. The harvested tissue is stored at −80° C. until RNA preparation. To make RNA, the three sample timepoints were combined and ground. For subtraction, target cDNA is made from the jasmonic acid treated tissue total RNA using the SMART cDNA synthesis system from Clonetech (Clonetech Laboratories, Palo Alto, Calif. U.S.A.). Driver first strand cDNA is covalently linked to Dynabeads following a protocol similar to that described in the Dynal literature (Dynabeads, Dynal Corporation, Lake Success, N.Y. U.S.A.). The target cDNA is then heat denatured and the second strand trapped using Dynabeads oligo-dT. The target second strand cDNA is then hybridized to the driver cDNA in 400 1 2× SSPE for two rounds of hybridization at 65° C. and 20 hours. After each hybridization, the hybridization solution is removed from the system and the hybridized target cDNA removed from the driver by heat denaturation in water. After hybridization, the remaining cDNA is trapped with Dynabeads oligo-dT. The trapped cDNA is then amplified as in previous PCR based libraries and the resulting cDNA ligated into the pSPORT vector (Invitrogen, Carlsbad Calif. U.S.A.). For this library's construction, the eighth fraction of the cDNA size fractionation step was used for ligation.

The Soy62 (LIB3074) cDNA library is generated from soybean cultivar Asgrow 3244 (Asgrow Seed Company, Des Moines, Iowa U.S.A.) jasmonic acid treated seedling subtracted from control tissue. Seeds are planted at a depth of approximately 2 cm into 2-3 inch peat pots containing Metromix 350 medium and the plants are grown in a greenhouse. The daytime temperature is approximately 29.4° C. and the nighttime temperature 20° C. Soil is checked and watered daily to maintain even moisture conditions. At 9 days post planting, the plantlets are sprayed with either control buffer of 0.1% Tween-20 or jasmonic acid (Sigma J-2500, Sigma, St. Louis, Mo. U.S.A.) at 1 mg/ml in 0.1% Tween-20. Plants are sprayed until runoff and the soil and the stem is socked with the spraying solution. At 18 hours post application of jasmonic acid, the soybean plantlets appear growth retarded. After 18 hours, 24 hours and 48 hours post treatment, the cotyledons are removed and the remaining leaf and stem tissue above the soil is harvested and frozen in liquid nitrogen. The harvested tissue is stored at −80° C. until RNA preparation. To make RNA, the three sample timepoints were combined and ground. For subtraction, target cDNA is made from the jasmonic acid treated tissue total RNA using the SMART cDNA synthesis system from Clonetech (Clonetech Laboratories, Palo Alto, Calif. U.S.A.). Driver first strand cDNA is covalently linked to Dynabeads following a protocol similar to that described in the Dynal literature (Dynabeads, Dynal Corporation, Lake Success, N.Y. U.S.A.). The target cDNA is then heat denatured and the second strand trapped using Dynabeads oligo-dT. The target second strand cDNA is then hybridized to the driver cDNA in 400 1 2× SSPE for two rounds of hybridization at 65° C. and 20 hours. After each hybridization, the hybridization solution is removed from the system and the hybridized target cDNA removed from the driver by heat denaturation in water. After hybridization, the remaining cDNA is trapped with Dynabeads oligo-dT. The trapped cDNA is then amplified as in previous PCR based libraries and the resulting cDNA ligated into the pSPORT vector (Invitrogen, Carlsbad Calif. U.S.A.). For this library's construction, the ninth fraction of the cDNA size fractionation step was used for ligation.

The Soy65 (LIB3107) 07cDNA library is generated from soybean cultivar Asgrow 3244 (Asgrow Seed Company, Des Moines, Iowa U.S.A.) drought-stressed abscission zone tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature 24° C. Soil is checked and watered daily to maintain even moisture conditions. Plants are irrigated with 15-16-17 Peter's Mix. At the R3 stage of development, drought is imposed by withholding water. At 3, 4, 5 and 6 days, tissue is harvested and wilting is not obvious until the fourth day. Abscission layers from reproductive organs are harvested by cutting less than one millimeter proximal and distal to the layer and immediately frozen in liquid nitrogen. The harvested tissue is stored at −80° C. until RNA preparation.

The Soy66 (LIB3109) cDNA library is generated from soybean cultivar Asgrow 3244 (Asgrow Seed Company, Des Moines, Iowa U.S.A.) non-drought stressed abscission zone tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature approximately 24° C. Soil is checked and watered daily to maintain even moisture conditions. Plants are irrigated with 15-16-17 Peter's Mix. At 3, 4, 5 and 6 days, control abscission layer tissue is harvested. Abscission layers from reproductive organs are harvested by cutting less than one millimeter proximal and distal to the layer and immediately frozen in liquid nitrogen. The harvested tissue is stored at −80° C. until RNA preparation.

Soy67 (LIB3065) cDNA library is prepared from equal amounts tissue harvested from SOYMON007, SOYMON015 and SOYMON020 prepared tissue. Single stranded and double stranded DNA representing approximately $1 \times 10^6$ colony forming units are isolated using standard protocols. RNA, complementary to the single stranded DNA, is synthesized using the double stranded DNA as a template. Biotinylated dATP is incorporated into the RNA during the synthesis reaction. The single stranded DNA is mixed with the biotinylated RNA in a 1:10 molar ratio) and allowed to hybridize. DNA-RNA hybrids are captured on Dynabeads M280 streptavidin (Dynabeads, Dynal Corporation, Lake Success, N.Y. U.S.A.). The dynabeads with captured hybrids are collected with a magnet. Captured hybrids are eluted with water.

Soy68 (LIB3052) cDNA library is prepared from equal amounts tissue harvested from SOYMON007, SOYMON015 and SOYMON020 prepared tissue. Single stranded and double stranded DNA representing approximately $1 \times 10^6$ colony forming units are isolated using standard protocols. RNA, complementary to the single stranded DNA, is synthesized using the double stranded DNA as a template. Biotinylated dATP is incorporated into the RNA during the synthesis reaction. The single stranded DNA is mixed with the biotinylated RNA in a 1:10 molar ratio) and allowed to hybridize. DNA-RNA hybrids are captured on Dynabeads M280 streptavidin (Dynabeads, Dynal Corporation, Lake Success, N.Y. U.S.A.). The dynabeads with captured hybrids are collected with a magnet. Captured hybrids are eluted with water.

Soy69 (LIB3053) cDNA library is generated from soybean cultivars Cristalina (USDA Soybean Germplasm Collection, Urbana, Ill. U.S.A.) and FT108 (Monsoy, Brazil) (tropical germ plasma) normalized leaf tissue. Leaves are harvested from plants grown in an environmental chamber under 12 hr daytime/12 hr nighttime cycles. The daytime temperature is approximately 29° C. and the nighttime temperature approximately 24° C. Soil is checked and watered daily to maintain even moisture conditions. Approximately 30 g of leaves are harvested from the $4^{th}$ node of each of the Cristalina and FT108 cultivars and immediately frozen in dry ice. The harvested tissue is then stored at −80° C. until RNA preparation. Single stranded and double stranded DNA representing approximately $1 \times 10^6$ colony forming units are isolated using standard protocols. RNA, complementary to the single stranded DNA, is synthesized using the double stranded DNA as a template. Biotinylated dATP is incorporated into the RNA during the synthesis reaction. The single stranded DNA is mixed with the biotinylated RNA in a 1:10 molar ratio) and allowed to hybridize. DNA-RNA hybrids are captured on Dynabeads M280 streptavidin (Dynabeads, Dynal Corporation, Lake Success, N.Y. U.S.A.). The dynabeads with captured hybrids are collected with a magnet. The non-hybridized single stranded molecules remaining after hybrid capture are converted to double stranded form and represent the primary normalized library.

Soy70 (LIB3055) cDNA library is generated from soybean cultivars Cristalina (USDA Soybean Germplasm Collection, Urbana, Ill. U.S.A.) and FT108 (Monsoy, Brazil) (tropical germ plasma) leaf tissue. Leaves are harvested from plants grown in an environmental chamber under 12 hr daytime/12 hr nighttime cycles. The daytime temperature is approximately 29° C. and the nighttime temperature approximately 24° C. Soil is checked and watered daily to maintain even moisture conditions. Approximately 30 g of leaves are harvested from the $4^{th}$ node of each of the Cristalina and FT108 cultivars and immediately frozen in dry ice. The harvested tissue is then stored at −80° C. until RNA preparation.

Soy71 (LIB3056) cDNA library is generated from soybean cultivars Cristalina and FT108 (tropical germ plasma) root tissue. Roots are harvested from plants grown in an environmental chamber under 12 hr daytime/12 hr nighttime cycles. The daytime temperature is approximately 29° C. and the nighttime temperature approximately 24° C. Soil is checked and watered daily to maintain even moisture conditions. Approximately 50 g and 56 g of roots are harvested from each of the Cristalina and FT108 cultivars and immediately frozen in dry ice. The harvested tissue is then stored at −80° C. until RNA preparation.

Soy72 (LIB3093) cDNA library is generated from soybean cultivar Asgrow 3244 (Asgrow Seed Company, Des Moines, Iowa U.S.A.) drought stressed leaf control tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 26° C. and the nighttime temperature 21° C. and 70% relative humidity. Soil is checked and watered daily to maintain even moisture conditions. At the R3 stage of the plant drought is induced by withholding water. After 3 and 6 days seeds and pods from both drought stressed and control (watered regularly) plants are collected from the fifth and sixth node and frozen in dry-ice. The harvested tissue is stored at −80° C. until RNA preparation. For subtraction, target cDNA is made from the drought stressed tissue total RNA using the SMART cDNA synthesis system from Clonetech (Clonetech Laboratories, Palo Alto, Calif. U.S.A.). Driver first strand cDNA is covalently linked to Dynabeads following a protocol similar to that described in the Dynal literature (Dynabeads, Dynal Corporation, Lake Success, N.Y. U.S.A.). The target cDNA is then heat denatured and the second strand trapped using Dynabeads oligo-dT. The target second strand cDNA is then hybridized to the driver cDNA in 400 1 2× SSPE for two rounds of hybridization at 65° C. and 20 hours. After each hybridization, the hybridization solution is removed from the system and the hybridized target cDNA removed from the driver by heat denaturation in water. After hybridization, the remaining cDNA is trapped with Dynabeads oligo-dT. The trapped cDNA is then amplified as in previous PCR based libraries and the resulting cDNA ligated into the pSPORT vector (Invitrogen, Carlsbad Calif. U.S.A.).

Soy73 (LIB3093) cDNA library is generated from soybean cultivar Asgrow 3244 (Asgrow Seed Company, Des Moines, Iowa U.S.A.) drought stressed leaf subtracted from control tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 26° C. and the nighttime temperature 21° C. and 70% relative humidity. Soil is checked and watered daily to maintain even moisture conditions. At the R3 stage of the plant drought is induced by withholding water. After 3 and 6 days seeds and pods from both drought stressed and control (watered regularly) plants are collected from the fifth and sixth node and frozen in dry-ice. The harvested tissue is stored at −80° C. until RNA preparation. For subtraction, target cDNA is made from the drought stressed tissue total RNA using the SMART cDNA synthesis system from Clonetech (Clonetech Laboratories, Palo Alto, Calif. U.S.A.). Driver first strand cDNA is covalently linked to Dynabeads following a protocol similar to that described in the Dynal literature (Dynabeads, Dynal Corporation, Lake Success, N.Y. U.S.A.). The target cDNA is then heat denatured and the second strand trapped using Dynabeads oligo-dT. The target second strand cDNA is then hybridized to the driver cDNA in 400 1 2×SSPE for two rounds of hybridization at 65° C. and 20 hours. After each hybridization, the hybridization solution is removed from the system and the hybridized target cDNA removed from the driver by heat denaturation in water. After hybridization, the remaining cDNA is trapped with Dynabeads oligo-dT. The trapped cDNA is then amplified as in previous PCR based libraries and the resulting cDNA ligated into the pSPORT vector (Invitrogen, Carlsbad Calif. U.S.A.).

The Soy76 (Lib3106) cDNA library is generated from soybean cultivar Asgrow 3244 (Asgrow Seed Company, Des Moines, Iowa U.S.A.) jasmonic acid and arachidonic treated seedling subtracted from control tissue. Seeds are planted at a depth of approximately 2 cm into 2-3 inch peat pots containing Metromix 350 medium and the plants are grown in a greenhouse. The daytime temperature is approximately 29.4° C. and the nighttime temperature 20° C. Soil is checked and watered daily to maintain even moisture conditions. At 9 days post planting, the plantlets are sprayed with either control buffer of 0.1% Tween-20 or jasmonic acid (Sigma J-2500, Sigma, St. Louis, Mo. U.S.A.) at 1 mg/ml in 0.1% Tween-20. Plants are sprayed until runoff and the soil and the stem is socked with the spraying solution. At 18 hours post application of jasmonic acid, the soybean plantlets appear growth retarded. Arachidonic treated seedlings are sprayed with 1 m/ml arachidonic acid in 0.1% Tween-20. After 18 hours, 24 hours and 48 hours post treatment, the cotyledons are removed and the remaining leaf and stem tissue above the soil is harvested and frozen in liquid nitrogen. The harvested tissue is stored at −80° C. until RNA preparation. To make RNA, the three sample timepoints were combined and ground. The RNA from the arachidonic treated seedlings is isolated separately. For subtraction, target cDNA is made from the jasmonic acid treated tissue total RNA using the SMART cDNA synthesis system from Clonetech (Clonetech Laboratories, Palo Alto, Calif. U.S.A.). Driver first strand cDNA is covalently linked to Dynabeads following a protocol similar to that described in the Dynal literature (Dynabeads, Dynal Corporation, Lake Success, N.Y. U.S.A.). The target cDNA is then heat denatured and the second strand trapped using Dynabeads oligo-dT. The target second strand cDNA is then hybridized to the driver cDNA in 400 1 2× SSPE for two rounds of hybridization at 65° C. and 20 hours. After each hybridization, the hybridization solution is removed from the system and the hybridized target cDNA removed from the driver by heat denaturation in water. After hybridization, the remaining cDNA is trapped with Dynabeads oligo-dT. The trapped cDNA is then amplified as in previous PCR based libraries and the resulting cDNA ligated into the pSPORT vector (Invitrogen, Carlsbad Calif. U.S.A.). Fraction 10 of the size fractionated cDNA is ligated into the pSPORT vector (Invitrogen, Carlsbad Calif. U.S.A.) in order to capture some of the smaller transcripts characteristic of antifungal proteins.

Soy77 (LIB3108) cDNA library is generated from soybean cultivar Asgrow 3244 (Asgrow Seed Company, Des Moines, Iowa U.S.A.) jasmonic acid control tissue. Seeds are planted at a depth of approximately 2 cm into 2-3 inch peat pots containing Metromix 350 medium and the plants are grown in a greenhouse. The daytime temperature is approximately 29.4° C. and the nighttime temperature 20° C. Soil is checked and watered daily to maintain even moisture conditions. At 9 days post planting, the plantlets are sprayed with either control buffer of 0.1% Tween-20 or jasmonic acid (Sigma J-2500, Sigma, St. Louis, Mo. U.S.A.) at 1 mg/ml in 0.1% Tween-20. Plants are sprayed until runoff and the soil and the stem is socked with the spraying solution. At 18 hours post application of jasmonic acid, the soybean plantlets appear growth retarded. Arachidonic treated seedlings are sprayed with 1 m/ml arachidonic acid in 0.1% Tween-20. After 18 hours, 24 hours and 48 hours post treatment, the cotyledons are removed and the remaining leaf and stem tissue above the soil is harvested and frozen in liquid nitrogen. The harvested tissue is stored at −80° C. until RNA preparation. To make RNA, the three sample timepoints were combined and ground. The RNA from the arachidonic treated seedlings is isolated separately. For subtraction, target cDNA is made from the jasmonic acid treated tissue total RNA using the SMART cDNA synthesis system from Clonetech (Clonetech Laboratories, Palo Alto, Calif. U.S.A.). Driver first strand cDNA is covalently linked to Dynabeads following a protocol similar to that described in the Dynal literature (Dynabeads, Dynal Corporation, Lake Success, N.Y. U.S.A.). The target cDNA is then heat denatured and the second strand trapped using Dynabeads oligo-dT. The target second strand cDNA is then hybridized to the driver cDNA in 400 1 2× SSPE for two rounds of hybridization at 65° C. and 20 hours. After each hybridization, the hybridization solution is removed from the system and the hybridized target cDNA removed from the driver by heat denaturation in water. After hybridization, the remaining cDNA is trapped with Dynabeads oligo-dT. The trapped cDNA is then amplified as in previous PCR based libraries and the resulting cDNA ligated into the pSPORT vector (Invitrogen, Carlsbad Calif. U.S.A.). Fraction 10 of the size fractionated cDNA is ligated into the pSPORT vector in order to capture some of the smaller transcripts characteristic of antifungal proteins.

The stored RNA is purified using Trizol reagent from Life Technologies (Gibco BRL, Life Technologies, Gaithersburg, Md. U.S.A.), essentially as recommended by the manufacturer. Poly A+ RNA (mRNA) is purified using magnetic oligo dT beads essentially as recommended by the manufacturer (Dynabeads, Dynal Corporation, Lake Success, N.Y. U.S.A.).

Construction of plant cDNA libraries is well-known in the art and a number of cloning strategies exist. A number of cDNA library construction kits are commercially available. The Superscript™ Plasmid System for cDNA synthesis and Plasmid Cloning (Gibco BRL, Life Technologies, Gaithersburg, Md. U.S.A.) is used, following the conditions suggested by the manufacturer.

Normalized libraries are made using essentially the Soares procedure (Soares et al., *Proc. Natl. Acad. Sci. (U.S.A.)* 91:9228-9232 (1994), the entirety of which is herein incorporated by reference). This approach is designed to reduce the initial 10,000-fold variation in individual cDNA frequencies to achieve abundances within one order of magnitude while maintaining the overall sequence complexity of the library. In the normalization process, the prevalence of high-abundance cDNA clones decreases dramatically, clones with mid-level abundance are relatively unaffected and clones for rare transcripts are effectively increased in abundance.

EXAMPLE 2

The cDNA libraries are plated on LB agar containing the appropriate antibiotics for selection and incubated at 37° for a sufficient time to allow the growth of individual colonies. Single colonies are individually placed in each well of a 96-well microtiter plates containing LB liquid including the selective antibiotics. The plates are incubated overnight at approximately 37° C. with gentle shaking to promote growth of the cultures. The plasmid DNA is isolated from each clone using Qiaprep plasmid isolation kits, using the conditions recommended by the manufacturer (Qiagen Inc., Santa Clara, Calif. U.S.A.).

Template plasmid DNA clones are used for subsequent sequencing. For sequencing, the ABI PRISM dRhodamine Terminator Cycle Sequencing Ready Reaction Kit with AmpliTaq® DNA Polymerase, FS, is used (PE Applied Biosystems, Foster City, Calif. U.S.A.).

EXAMPLE 3

Nucleic acid sequences that encode for the following proteins: adenine phosphoribosyl transferase, β glucosidase and isopentyltransferase are identified from the Monsanto EST PhytoSeq database using TBLASTN (default values) (TBLASTN compares a protein query against the six reading frames of a nucleic acid sequence). Matches found with BLAST P values equal or less than 0.001 (probability) or BLAST Score of equal or greater than 90 are classified as hits. If the program used to determine the hit is HMMSW then the score refers to HMMSW score.

In addition, the GenBank database is searched with BLASTN and BLASTX (default values) using ESTs as queries. EST that pass the hit probability threshold of $10e^{-8}$ for the following enzymes are combined with the hits generated by using TBLASTN (described above) and classified by enzyme (see Table A below).

A cluster refers to a set of overlapping clones in the PhytoSeq database. Such an overlapping relationship among clones is designated as a "cluster" when BLAST scores from pairwise sequence comparisons of the member clones meets a predetermined minimum value or product score of 50 or more (Product Score=(BLAST SCORE×Percentage Identity)/(5×minimum [length (Seq1), length (Seq2)]))

Since clusters are formed on the basis of single-linkage relationships, it is possible for two non-overlapping clones to be members of the same cluster if, for instance, they both overlap a third clone with at least the predetermined minimum BLAST score (stringency). A cluster ID is arbitrarily assigned to all of those clones which belong to the same cluster at a given stringency and a particular clone will belong to only one cluster at a given stringency. If a cluster contains only a single clone (a "singleton"), then the cluster ID number will be negative, with an absolute value equal to the clone ID number of its single member. Clones grouped in a cluster in most cases represent a contiguous sequence.

TABLE A*

| Seq No. | Cluster ID | CloneID | Library | NCBI gi | Method | Score | P-value | % Ident |
|---|---|---|---|---|---|---|---|---|
| MAIZE ADENINE PHOSPHORIBOSYL TRANSFERASE (EC 2.4.2.7) | | | | | | | | |
| 1 | -700193568 | 700193568H1 | SATMON014 | g726304 | BLASTN | 490 | 1e-32 | 73 |
| 2 | -700432807 | 700432807H1 | SATMONN01 | gl6164 | BLASTX | 212 | 1e-26 | 68 |
| 3 | -700475820 | 700475820H1 | SATMON025 | g726305 | BLASTX | 87 | 1e-11 | 84 |
| 4 | -700552966 | 700552966H1 | SATMON022 | g726304 | BLASTN | 927 | 1e-68 | 81 |
| 5 | -L30612612 | LIB3061-015-Q1-K1-H2 | LIB3061 | g726304 | BLASTN | 447 | 1e-26 | 73 |
| 6 | -L30682155 | LIB3068-004-Q1-K1-B3 | LIB3068 | g726304 | BLASTN | 320 | 1e-27 | 77 |
| 7 | -L30691613 | LIB3069-005-Q1-K1-D1 | LIB3069 | g726304 | BLASTN | 478 | 1e-28 | 76 |
| 8 | -L30784520 | LIB3078-039-Q1-K1-D9 | LIB3078 | g726304 | BLASTN | 374 | 1e-32 | 74 |
| 9 | -L831334 | LIB83-003-Q1-E1-F6 | LIB83 | gl402893 | BLASTN | 461 | 1e-27 | 66 |
| 10 | 10045 | LIB3067-006-Q1-K1-H12 | LIB3067 | gl321681 | BLASTX | 241 | 1e-44 | 71 |
| 11 | 10045 | 700338620H1 | SATMON020 | gl321681 | BLASTX | 173 | 1e-29 | 62 |
| 12 | 10045 | 700335677H1 | SATMON019 | gl321681 | BLASTX | 86 | 1e-19 | 52 |
| 13 | 5380 | LIB3061-047-Q1-K1-B4 | LIB3061 | g726304 | BLASTN | 1205 | 1e-92 | 82 |
| 14 | 5380 | 700082054H1 | SATMON011 | g726304 | BLASTN | 1032 | 1e-77 | 82 |
| 15 | 5380 | 700242515H1 | SATMON010 | g726304 | BLASTN | 1008 | 1e-75 | 83 |
| 16 | 5380 | 700339222H1 | SATMON020 | g726304 | BLASTN | 842 | 1e-74 | 82 |
| 17 | 5380 | 700027757H1 | SATMON003 | g726304 | BLASTN | 939 | 1e-69 | 83 |
| 18 | 5380 | 700029386H1 | SATMON003 | g726304 | BLASTN | 900 | 1e-66 | 82 |
| 19 | 5380 | 700241615H1 | SATMON010 | g726304 | BLASTN | 894 | 1e-65 | 81 |
| 20 | 5380 | 700172169H1 | SATMON013 | g726304 | BLASTN | 724 | 1e-51 | 80 |
| 21 | 5380 | 700045315H1 | SATMON004 | g726304 | BLASTN | 655 | 1e-45 | 83 |
| 22 | 5380 | 700018155H1 | SATMON001 | g726304 | BLASTN | 614 | 1e-42 | 85 |
| 23 | 5380 | 700157175H1 | SATMON012 | g726304 | BLASTN | 618 | 1e-42 | 83 |
| 24 | 5380 | 700335263H1 | SATMON019 | g726304 | BLASTN | 296 | 1e-36 | 82 |
| 25 | 5380 | 700022056H1 | SATMON001 | g726305 | BLASTX | 147 | 1e-13 | 93 |
| 26 | 5380 | 700196739H1 | SATMON014 | g726305 | BLASTX | 89 | 1e-10 | 93 |

TABLE A*-continued

| Seq No. | Cluster ID | CloneID | Library | NCBI gi | Method | Score | P-value | % Ident |
|---|---|---|---|---|---|---|---|---|
| 27 | 6937 | LIB189-003-Q1-E1-F5 | LIB189 | g726304 | BLASTN | 947 | 1e-70 | 80 |
| 28 | 6937 | LIB3059-015-Q1-K1-A2 | LIB3059 | g726304 | BLASTN | 905 | 1e-66 | 82 |
| 29 | 6937 | LIB143-061-Q1-E1-B3 | LIB143 | g726304 | BLASTN | 779 | 1e-55 | 80 |
| 30 | 6937 | LIB3067-052-Q1-K1-A1 | LIB3067 | g726304 | BLASTN | 532 | 1e-54 | 79 |
| 31 | 6937 | 700334619H1 | SATMON019 | g726304 | BLASTN | 711 | 1e-50 | 81 |
| 32 | 6937 | 700219612H1 | SATMON011 | g726304 | BLASTN | 588 | 1e-40 | 79 |
| 33 | 6937 | 700405177H1 | SATMON028 | g726304 | BLASTN | 589 | 1e-40 | 81 |
| 34 | 6937 | 700236956H1 | SATMON010 | g726304 | BLASTN | 573 | 1e-39 | 81 |
| 35 | 6937 | 700238553H1 | SATMON010 | g726304 | BLASTN | 387 | 1e-37 | 81 |
| 36 | 6937 | 700104336H1 | SATMON010 | g726304 | BLASTN | 537 | 1e-36 | 76 |
| 37 | 6937 | LIB3068-059-Q1-K1-H7 | LIB3068 | g726304 | BLASTN | 385 | 1e-33 | 73 |
| 38 | 6937 | 700238576H1 | SATMON010 | g726304 | BLASTN | 407 | 1e-23 | 69 |
| 39 | 6937 | 700142447H1 | SATMON012 | g16164 | BLASTX | 135 | 1e-14 | 79 |
| 40 | 6937 | 700204679H1 | SATMON003 | g726304 | BLASTN | 185 | 1e-13 | 76 |
| MAIZE β GLUCOSIDASE (EC 3.2.1.21) | | | | | | | | |
| 41 | -700019404 | 700019404H1 | SATMON001 | g1206012 | BLASTN | 587 | 1e-40 | 85 |
| 42 | -700051621 | 700051621H1 | SATMON003 | g1206012 | BLASTN | 417 | 1e-55 | 76 |
| 43 | -700072125 | 700072125H1 | SATMON007 | g1518673 | BLASTN | 320 | 1e-16 | 93 |
| 44 | -700073309 | 700073309H1 | SATMON007 | g21953 | BLASTX | 97 | 1e-21 | 50 |
| 45 | -700077116 | 700077116H1 | SATMON007 | g1518673 | BLASTN | 297 | 1e-14 | 90 |
| 46 | -700084705 | 700084705H1 | SATMON011 | g1206012 | BLASTN | 235 | 1e-9 | 100 |
| 47 | -700085269 | 700085269H1 | SATMON011 | g1143864 | BLASTX | 151 | 1e-16 | 53 |
| 48 | -700088245 | 700088245H1 | SATMON011 | g435312 | BLASTN | 537 | 1e-59 | 75 |
| 49 | -700094593 | 700094593H1 | SATMON008 | g1399389 | BLASTN | 197 | 1e-14 | 85 |
| 50 | -700104334 | 700104334H1 | SATMON010 | g1399389 | BLASTN | 760 | 1e-79 | 96 |
| 51 | -700160044 | 700160044H1 | SATMON012 | g804656 | BLASTX | 252 | 1e-37 | 79 |
| 52 | -700168880 | 700168880H1 | SATMON013 | g435312 | BLASTN | 703 | 1e-49 | 81 |
| 53 | -700207934 | 700207934H1 | SATMON016 | g1155255 | BLASTX | 172 | 1e-16 | 54 |
| 54 | -700208416 | 700208416H1 | SATMON016 | g1518674 | BLASTN | 459 | 1e-36 | 96 |
| 55 | -700220501 | 700220501H1 | SATMON011 | g1399389 | BLASTN | 598 | 1e-40 | 81 |
| 56 | -700221075 | 700221075H1 | SATMON011 | g1143863 | BLASTN | 640 | 1e-44 | 75 |
| 57 | -700235295 | 700235295H1 | SATMON010 | g1399389 | BLASTN | 1166 | 1e-91 | 93 |
| 58 | -700258664 | 700258664H1 | SATMON017 | g804656 | BLASTX | 195 | 1e-28 | 66 |
| 59 | -700265357 | 700265357H1 | SATMON017 | g1143863 | BLASTN | 367 | 1e-39 | 80 |
| 60 | -700338753 | 700338753H1 | SATMON020 | g804655 | BLASTN | 955 | 1e-70 | 82 |
| 61 | -700343160 | 700343160H1 | SATMON021 | g1143863 | BLASTN | 714 | 1e-50 | 82 |
| 62 | -700352084 | 700352084H1 | SATMON023 | g1518673 | BLASTN | 796 | 1e-59 | 90 |
| 63 | -700353902 | 700353902H1 | SATMON024 | g804656 | BLASTX | 238 | 1e-25 | 60 |
| 64 | -700356246 | 700356246H1 | SATMON024 | g1143864 | BLASTX | 237 | 1e-26 | 66 |
| 65 | -700356858 | 700356858H1 | SATMON024 | g804656 | BLASTX | 101 | 1e-23 | 54 |
| 66 | -700444014 | 700444014H1 | SATMON027 | g1399389 | BLASTN | 426 | 1e-24 | 82 |
| 67 | -700468671 | 700468671H1 | SATMON025 | g1155255 | BLASTX | 63 | 1e-10 | 47 |
| 68 | -700468683 | 700468683H1 | SATMON025 | g804655 | BLASTN | 360 | 1e-44 | 81 |
| 69 | -700468738 | 700468738H1 | SATMON025 | g804655 | BLASTN | 301 | 1e-47 | 87 |
| 70 | -700469144 | 700469144H1 | SATMON025 | g1399389 | BLASTN | 292 | 1e-45 | 88 |
| 71 | -700471979 | 700471979H1 | SATMON025 | g804656 | BLASTX | 172 | 1e-16 | 76 |
| 72 | -700472168 | 700472168H1 | SATMON025 | g804656 | BLASTX | 117 | 1e-23 | 66 |
| 73 | -700477783 | 700477783H1 | SATMON025 | g804655 | BLASTN | 341 | 1e-59 | 88 |
| 74 | -700548872 | 700548872H1 | SATMON022 | g804656 | BLASTX | 234 | 1e-25 | 70 |
| 75 | -700573216 | 700573216H1 | SATMON030 | g1399389 | BLASTN | 472 | 1e-46 | 90 |
| 76 | -700619394 | 700619394H1 | SATMON034 | g435312 | BLASTN | 354 | 1e-33 | 84 |
| 77 | -700621680 | 700621680H1 | SATMON034 | g21953 | BLASTX | 90 | 1e-22 | 61 |
| 78 | -700623741 | 700623741H1 | SATMON034 | g1399390 | BLASTX | 152 | 1e-13 | 100 |
| 79 | -700624575 | 700624575H1 | SATMON034 | g804655 | BLASTN | 345 | 1e-30 | 77 |
| 80 | -701164553 | 701164553H1 | SATMONN04 | g1518673 | BLASTN | 329 | 1e-19 | 88 |
| 81 | -701165120 | 701165120H1 | SATMONN04 | g1206012 | BLASTN | 597 | 1e-42 | 84 |
| 82 | -L1431868 | LIB143-029-Q1-E1-H4 | LIB143 | g804656 | BLASTX | 308 | 1e-51 | 76 |
| 83 | -L1435738 | LIB143-047-Q1-E1-C2 | LIB143 | g804656 | BLASTX | 123 | 1e-25 | 63 |
| 84 | -L1486423 | LIB148-051-Q1-E1-A8 | LIB148 | g1518673 | BLASTN | 466 | 1e-44 | 81 |
| 85 | -L1892203 | LIB189-005-Q1-E1-G3 | LIB189 | g757740 | BLASTX | 152 | 1e-28 | 50 |
| 86 | -L1893440 | LIB189-023-Q1-E1-E2 | LIB189 | g21953 | BLASTX | 129 | 1e-35 | 44 |
| 87 | -L30624187 | LIB3062-035-Q1-K1-G11 | LIB3062 | g435312 | BLASTN | 397 | 1e-22 | 67 |
| 88 | -L30625219 | LIB3062-020-Q1-K1-A12 | LIB3062 | g1143863 | BLASTN | 221 | 1e-12 | 74 |

TABLE A*-continued

| Seq No. | Cluster ID | CloneID | Library | NCBI gi | Method | Score | P-value | % Ident |
|---|---|---|---|---|---|---|---|---|
| 89 | -L30626353 | LIB3062-024-Q1-K1-E2 | LIB3062 | g1206012 | BLASTN | 317 | 1e-30 | 74 |
| 90 | -L30626596 | LIB3062-038-Q1-K1-A12 | LIB3062 | g142586 | BLASTX | 220 | 1e-39 | 56 |
| 91 | -L30665817 | LIB3066-006-Q1-K1-B12 | LIB3066 | g1143864 | BLASTX | 182 | 1e-34 | 84 |
| 92 | -L30676013 | LIB3067-057-Q1-K1-A5 | LIB3067 | g1143863 | BLASTN | 663 | 1e-58 | 77 |
| 93 | -L30692578 | LIB3069-019-Q1-K1-E5 | LIB3069 | g1206013 | BLASTX | 138 | 1e-26 | 36 |
| 94 | -L30692596 | LIB3069-019-Q1-K1-A8 | LIB3069 | g799376 | BLASTN | 246 | 1e-9 | 51 |
| 95 | -L30694297 | LIB3069-051-Q1-K1-C1 | LIB3069 | g1143864 | BLASTX | 133 | 1e-36 | 54 |
| 96 | -L30784416 | LIB3078-039-Q1-K1-H3 | LIB3078 | g1206012 | BLASTN | 630 | 1e-102 | 81 |
| 97 | 10283 | 700356224H1 | SATMON024 | g804655 | BLASTN | 436 | 1e-25 | 68 |
| 98 | 10283 | 700354663H1 | SATMON024 | g804656 | BLASTX | 186 | 1e-18 | 64 |
| 99 | 10343 | LIB3062-041-Q1-K1-B1 | LIB3062 | g1143863 | BLASTN | 860 | 1e-81 | 74 |
| 100 | 10343 | 700212710H1 | SATMON016 | g1143863 | BLASTN | 805 | 1e-63 | 79 |
| 101 | 10343 | 700023123H1 | SATMON003 | g1143863 | BLASTN | 834 | 1e-60 | 80 |
| 102 | 10343 | 700168364H1 | SATMON013 | g1143863 | BLASTN | 816 | 1e-59 | 80 |
| 103 | 10343 | 700281856H2 | SATMON021 | g1143863 | BLASTN | 615 | 1e-42 | 73 |
| 104 | 10343 | 700170973H1 | SATMON013 | g1143863 | BLASTN | 587 | 1e-40 | 75 |
| 105 | 10343 | 700222918H1 | SATMON011 | g1143863 | BLASTN | 529 | 1e-35 | 65 |
| 106 | 10343 | 700623415H1 | SATMON034 | g1143864 | BLASTX | 215 | 1e-22 | 52 |
| 107 | 10343 | 700262090H1 | SATMON017 | g1143863 | BLASTN | 165 | 1e-9 | 76 |
| 108 | 10564 | 700572950H1 | SATMON030 | g1206012 | BLASTN | 491 | 1e-85 | 85 |
| 109 | 10564 | 700573795H1 | SATMON030 | g1206012 | BLASTN | 881 | 1e-74 | 85 |
| 110 | 10564 | 700157129H1 | SATMON012 | g1206012 | BLASTN | 523 | 1e-63 | 86 |
| 111 | 10712 | 700073072H1 | SATMON007 | g1206012 | BLASTN | 469 | 1e-59 | 86 |
| 112 | 10712 | 700072996H1 | SATMON007 | g1206012 | BLASTN | 454 | 1e-58 | 85 |
| 113 | 10712 | 700076579H1 | SATMON007 | g435312 | BLASTN | 315 | 1e-41 | 80 |
| 114 | 10712 | 700075075H1 | SATMON007 | g435312 | BLASTN | 315 | 1e-34 | 80 |
| 115 | 10712 | 700155128H1 | SATMON007 | g1399390 | BLASTX | 136 | 1e-14 | 78 |
| 116 | 11895 | 700169369H1 | SATMON013 | g1143863 | BLASTN | 744 | 1e-53 | 79 |
| 117 | 11895 | 700622210H1 | SATMON034 | g1143863 | BLASTN | 516 | 1e-50 | 79 |
| 118 | 11895 | 700020586H1 | SATMON001 | g1143863 | BLASTN | 646 | 1e-45 | 79 |
| 119 | 12484 | 700473715H1 | SATMON025 | g804655 | BLASTN | 474 | 1e-67 | 84 |
| 120 | 12484 | 700474014H1 | SATMON025 | g804655 | BLASTN | 338 | 1e-54 | 86 |
| 121 | 13406 | 700202816H1 | SATMON003 | g804656 | BLASTX | 223 | 1e-23 | 50 |
| 122 | 13553 | 700345013H1 | SATMON021 | g1143864 | BLASTX | 150 | 1e-13 | 96 |
| 123 | 13553 | 700346887H1 | SATMON021 | g1143864 | BLASTX | 114 | 1e-8 | 95 |
| 124 | 14210 | 700106119H1 | SATMON010 | g1206012 | BLASTN | 936 | 1e-78 | 83 |
| 125 | 14210 | 700236969H1 | SATMON010 | g435312 | BLASTN | 945 | 1e-69 | 84 |
| 126 | 14210 | 700569967H1 | SATMON030 | g1399389 | BLASTN | 609 | 1e-41 | 80 |
| 127 | 14713 | LIB3066-054-Q1-K1-H11 | LIB3066 | g1769814 | BLASTX | 183 | 1e-36 | 63 |
| 128 | 14713 | LIB3066-053-Q1-K1-H12 | LIB3066 | g21955 | BLASTX | 162 | 1e-34 | 71 |
| 129 | 14713 | 700103716H1 | SATMON010 | g1769814 | BLASTX | 111 | 1e-12 | 63 |
| 130 | 14713 | 700096365H1 | SATMON008 | g21955 | BLASTX | 135 | 1e-11 | 65 |
| 131 | 15366 | LIB143-060-Q1-E1-B6 | LIB143 | g804655 | BLASTN | 605 | 1e-85 | 82 |
| 132 | 15366 | 700469301H1 | SATMON025 | g804655 | BLASTN | 524 | 1e-55 | 87 |
| 133 | 15366 | 700573405H2 | SATMON030 | g804655 | BLASTN | 388 | 1e-45 | 84 |
| 134 | 15366 | 700473205H1 | SATMON025 | g804655 | BLASTN | 374 | 1e-27 | 79 |
| 135 | 15366 | 700263901H1 | SATMON017 | g804656 | BLASTX | 69 | 1e-24 | 86 |
| 136 | 15944 | LIB3062-042-Q1-K1-D8 | LIB3062 | g1206012 | BLASTN | 928 | 1e-124 | 83 |
| 137 | 15944 | LIB3062-038-Q1-K1-F5 | LIB3062 | g1206012 | BLASTN | 1103 | 1e-121 | 81 |
| 138 | 15944 | LIB3062-010-Q1-K1-F8 | LIB3062 | g1206012 | BLASTN | 826 | 1e-116 | 83 |
| 139 | 15944 | LIB3062-039-Q1-K1-H1 | LIB3062 | g1206012 | BLASTN | 842 | 1e-97 | 84 |
| 140 | 15944 | LIB3062-002-Q1-K2-D6 | LIB3062 | g1206012 | BLASTN | 940 | 1e-97 | 81 |
| 141 | 15944 | 700104654H1 | SATMON010 | g435312 | BLASTN | 815 | 1e-89 | 85 |
| 142 | 15944 | LIB3062-015-Q1-K1-H3 | LIB3062 | g1206012 | BLASTN | 1060 | 1e-79 | 76 |
| 143 | 15944 | LIB3062-029-Q1-K1-D9 | LIB3062 | g1206012 | BLASTN | 1008 | 1e-75 | 81 |
| 144 | 15944 | LIB3062-027-Q1-K1-D11 | LIB3062 | g1206012 | BLASTN | 848 | 1e-72 | 82 |
| 145 | 15944 | 700221092H1 | SATMON011 | g1206012 | BLASTN | 643 | 1e-71 | 88 |

TABLE A*-continued

| Seq No. | Cluster ID | CloneID | Library | NCBI gi | Method | Score | P-value | % Ident |
|---|---|---|---|---|---|---|---|---|
| 146 | 15944 | 700020487H1 | SATMON001 | g1399389 | BLASTN | 655 | 1e−45 | 83 |
| 147 | 16295 | LIB3062-011-Q1-K1-A5 | LIB3062 | g1206012 | BLASTN | 1263 | 1e−101 | 80 |
| 148 | 16295 | LIB3062-005-Q1-K1-B1 | LIB3062 | g1206012 | BLASTN | 966 | 1e−87 | 79 |
| 149 | 16295 | LIB3062-053-Q1-K1-C7 | LIB3062 | g435312 | BLASTN | 1142 | 1e−86 | 79 |
| 150 | 16295 | LIB3062-009-Q1-K1-F11 | LIB3062 | g1206012 | BLASTN | 558 | 1e−71 | 84 |
| 151 | 16295 | 700020626H1 | SATMON001 | g435312 | BLASTN | 819 | 1e−59 | 83 |
| 152 | 16295 | 700218004H1 | SATMON016 | g1206012 | BLASTN | 800 | 1e−57 | 81 |
| 153 | 16464 | 700282508H2 | SATMON024 | g21955 | BLASTX | 87 | 1e−22 | 58 |
| 154 | 16478 | 700333375H1 | SATMON019 | g1399390 | BLASTX | 76 | 1e−8 | 58 |
| 155 | 19731 | 700282461H2 | SATMON024 | g1769814 | BLASTX | 156 | 1e−14 | 56 |
| 156 | 22706 | 700172681H1 | SATMON013 | g1805413 | BLASTX | 148 | 1e−13 | 62 |
| 157 | 22706 | 700172682H1 | SATMON013 | g1805413 | BLASTX | 133 | 1e−11 | 59 |
| 158 | 295 | LIB3067-037-Q1-K1-C6 | LIB3067 | g435312 | BLASTN | 2303 | 1e−183 | 99 |
| 159 | 295 | LIB3062-013-Q1-K1-G1 | LIB3062 | g435312 | BLASTN | 2294 | 1e−182 | 99 |
| 160 | 295 | LIB3078-053-Q1-K1-B7 | LIB3078 | g1206012 | BLASTN | 2216 | 1e−179 | 98 |
| 161 | 295 | LIB3062-036-Q1-K1-G11 | LIB3062 | g435312 | BLASTN | 2182 | 1e−173 | 99 |
| 162 | 295 | LIB3062-004-Q1-K1-B11 | LIB3062 | g435312 | BLASTN | 2183 | 1e−173 | 98 |
| 163 | 295 | LIB3069-038-Q1-K1-D1 | LIB3069 | g435312 | BLASTN | 2187 | 1e−173 | 95 |
| 164 | 295 | LIB3067-046-Q1-K1-C11 | LIB3067 | g435312 | BLASTN | 2163 | 1e−171 | 99 |
| 165 | 295 | LIB3069-051-Q1-K1-G1 | LIB3069 | g435312 | BLASTN | 1998 | 1e−166 | 97 |
| 166 | 295 | LIB3062-038-Q1-K1-G10 | LIB3062 | g435312 | BLASTN | 2066 | 1e−163 | 98 |
| 167 | 295 | LIB3062-050-Q1-K1-E4 | LIB3062 | g435312 | BLASTN | 1382 | 1e−162 | 92 |
| 168 | 295 | LIB3078-039-Q1-K1-H6 | LIB3078 | g1206012 | BLASTN | 1603 | 1e−158 | 95 |
| 169 | 295 | LIB3069-004-Q1-K1-A9 | LIB3069 | g435312 | BLASTN | 1724 | 1e−158 | 96 |
| 170 | 295 | LIB3062-039-Q1-K1-H6 | LIB3062 | g435312 | BLASTN | 1712 | 1e−157 | 99 |
| 171 | 295 | LIB3062-056-Q1-K1-D3 | LIB3062 | g435312 | BLASTN | 1990 | 1e−157 | 94 |
| 172 | 295 | LIB3069-048-Q1-K1-A10 | LIB3069 | g435312 | BLASTN | 1851 | 1e−156 | 95 |
| 173 | 295 | LIB83-004-Q1-E2-F6 | LIB83 | g1206012 | BLASTN | 1928 | 1e−154 | 98 |
| 174 | 295 | LIB3069-033-Q1-K1-G7 | LIB3069 | g435312 | BLASTN | 1939 | 1e−152 | 98 |
| 175 | 295 | LIB3067-058-Q1-K1-B7 | LIB3067 | g435312 | BLASTN | 1753 | 1e−151 | 99 |
| 176 | 295 | LIB3069-017-Q1-K1-F10 | LIB3069 | g435312 | BLASTN | 1812 | 1e−148 | 94 |
| 177 | 295 | LIB143-011-Q1-E1-A1 | LIB143 | g435312 | BLASTN | 1822 | 1e−143 | 95 |
| 178 | 295 | 700571031H1 | SATMON030 | g435312 | BLASTN | 1348 | 1e−136 | 99 |
| 179 | 295 | 700094755H1 | SATMON008 | g435312 | BLASTN | 1703 | 1e−133 | 99 |
| 180 | 295 | LIB3069-002-Q1-K1-G7 | LIB3069 | g1399389 | BLASTN | 1275 | 1e−132 | 95 |
| 181 | 295 | LIB143-031-Q1-E1-B3 | LIB143 | g799376 | BLASTN | 895 | 1e−131 | 94 |
| 182 | 295 | 700623229H1 | SATMON034 | g435312 | BLASTN | 1671 | 1e−130 | 99 |
| 183 | 295 | 700572265H1 | SATMON030 | g435312 | BLASTN | 1529 | 1e−129 | 98 |
| 184 | 295 | LIB143-030-Q1-E1-H1 | LIB143 | g435312 | BLASTN | 1605 | 1e−129 | 100 |
| 185 | 295 | LIB3078-018-Q1-K1-C11 | LIB3078 | g1206012 | BLASTN | 1643 | 1e−128 | 99 |
| 186 | 295 | 700047584H1 | SATMON003 | g799376 | BLASTN | 1645 | 1e−128 | 100 |
| 187 | 295 | 700095023H1 | SATMON008 | g435312 | BLASTN | 1653 | 1e−128 | 99 |
| 188 | 295 | LIB3062-032-Q1-K1-C1 | LIB3062 | g435312 | BLASTN | 991 | 1e−127 | 81 |
| 189 | 295 | 700619910H1 | SATMON034 | g435312 | BLASTN | 1258 | 1e−127 | 95 |
| 190 | 295 | 700048340H1 | SATMON003 | g435312 | BLASTN | 1620 | 1e−126 | 100 |
| 191 | 295 | 700095521H1 | SATMON008 | g435312 | BLASTN | 1620 | 1e−126 | 100 |
| 192 | 295 | 700071964H1 | SATMON007 | g435312 | BLASTN | 1610 | 1e−125 | 100 |

TABLE A*-continued

| Seq No. | Cluster ID | CloneID | Library | NCBI gi | Method | Score | P-value | % Ident |
|---|---|---|---|---|---|---|---|---|
| 193 | 295 | LIB143-012-Q1-E1-A8 | LIB143 | g435312 | BLASTN | 1615 | 1e-125 | 100 |
| 194 | 295 | 700620843H1 | SATMON034 | g435312 | BLASTN | 870 | 1e-124 | 100 |
| 195 | 295 | 700623282H1 | SATMON034 | g435312 | BLASTN | 1600 | 1e-124 | 100 |
| 196 | 295 | 700405326H1 | SATMON029 | g435312 | BLASTN | 1603 | 1e-124 | 99 |
| 197 | 295 | 700201262H1 | SATMON003 | g435312 | BLASTN | 1394 | 1e-123 | 99 |
| 198 | 295 | 700096113H1 | SATMON008 | g435312 | BLASTN | 1590 | 1e-123 | 100 |
| 199 | 295 | 700092753H1 | SATMON008 | g435312 | BLASTN | 1590 | 1e-123 | 100 |
| 200 | 295 | 700091708H1 | SATMON011 | g1206012 | BLASTN | 941 | 1e-122 | 98 |
| 201 | 295 | 700207847H1 | SATMON016 | g435312 | BLASTN | 1161 | 1e-121 | 99 |
| 202 | 295 | 700106675H1 | SATMON010 | g435312 | BLASTN | 1523 | 1e-121 | 99 |
| 203 | 295 | 700405420H1 | SATMON029 | g435312 | BLASTN | 1560 | 1e-121 | 100 |
| 204 | 295 | 700094707H1 | SATMON008 | g435312 | BLASTN | 1552 | 1e-120 | 99 |
| 205 | 295 | 700099904H1 | SATMON009 | g1206012 | BLASTN | 1556 | 1e-120 | 99 |
| 206 | 295 | 700047601H1 | SATMON003 | g799376 | BLASTN | 541 | 1e-119 | 99 |
| 207 | 295 | 700573387H1 | SATMON030 | g435312 | BLASTN | 1353 | 1e-119 | 96 |
| 208 | 295 | 700571123H1 | SATMON030 | g435312 | BLASTN | 1446 | 1e-119 | 98 |
| 209 | 295 | 700092870H1 | SATMON008 | g435312 | BLASTN | 1535 | 1e-119 | 100 |
| 210 | 295 | 700099718H1 | SATMON009 | g1206012 | BLASTN | 1535 | 1e-119 | 97 |
| 211 | 295 | 700092358H1 | SATMON008 | g435312 | BLASTN | 1540 | 1e-119 | 100 |
| 212 | 295 | 700047779H1 | SATMON003 | g435312 | BLASTN | 1526 | 1e-118 | 99 |
| 213 | 295 | 700100960H1 | SATMON009 | g1206012 | BLASTN | 1510 | 1e-117 | 95 |
| 214 | 295 | 700072841H1 | SATMON007 | g435312 | BLASTN | 1520 | 1e-117 | 100 |
| 215 | 295 | 700094663H1 | SATMON008 | g1206012 | BLASTN | 1521 | 1e-117 | 99 |
| 216 | 295 | 700093094H1 | SATMON008 | g435312 | BLASTN | 760 | 1e-116 | 98 |
| 217 | 295 | 700103422H1 | SATMON010 | g435312 | BLASTN | 1508 | 1e-116 | 99 |
| 218 | 295 | 700093551H1 | SATMON008 | g435312 | BLASTN | 1508 | 1e-116 | 99 |
| 219 | 295 | 700075211H1 | SATMON007 | g435312 | BLASTN | 1429 | 1e-115 | 99 |
| 220 | 295 | 700095166H1 | SATMON008 | g435312 | BLASTN | 1486 | 1e-115 | 99 |
| 221 | 295 | 700075959H1 | SATMON007 | g435312 | BLASTN | 1487 | 1e-115 | 98 |
| 222 | 295 | 700334933H1 | SATMON019 | g435312 | BLASTN | 1490 | 1e-115 | 100 |
| 223 | 295 | 700093526H1 | SATMON008 | g435312 | BLASTN | 1286 | 1e-114 | 99 |
| 224 | 295 | 700623754H1 | SATMON034 | g435312 | BLASTN | 1392 | 1e-114 | 98 |
| 225 | 295 | 700205454H1 | SATMON003 | g435312 | BLASTN | 1485 | 1e-114 | 100 |
| 226 | 295 | 700623202H1 | SATMON034 | g435312 | BLASTN | 789 | 1e-113 | 97 |
| 227 | 295 | 700095616H1 | SATMON008 | g435312 | BLASTN | 1229 | 1e-113 | 95 |
| 228 | 295 | LIB3067-032-Q1-K1-A2 | LIB3067 | g435312 | BLASTN | 1376 | 1e-113 | 96 |
| 229 | 295 | 700202823H1 | SATMON003 | g1399389 | BLASTN | 1438 | 1e-113 | 97 |
| 230 | 295 | 700096024H1 | SATMON008 | g435312 | BLASTN | 1465 | 1e-113 | 100 |
| 231 | 295 | 700096336H1 | SATMON008 | g435312 | BLASTN | 1465 | 1e-113 | 100 |
| 232 | 295 | LIB143-063-Q1-E1-B2 | LIB143 | g1206012 | BLASTN | 1000 | 1e-112 | 96 |
| 233 | 295 | 700238549H1 | SATMON010 | g435312 | BLASTN | 1450 | 1e-112 | 100 |
| 234 | 295 | 700244114H1 | SATMON010 | g435312 | BLASTN | 1450 | 1e-112 | 100 |
| 235 | 295 | 700028461H1 | SATMON003 | g799376 | BLASTN | 1455 | 1e-112 | 100 |
| 236 | 295 | 700093584H1 | SATMON008 | g435312 | BLASTN | 1440 | 1e-111 | 100 |
| 237 | 295 | 700075942H1 | SATMON007 | g435312 | BLASTN | 1440 | 1e-111 | 100 |
| 238 | 295 | 700096338H1 | SATMON008 | g435312 | BLASTN | 1443 | 1e-111 | 99 |
| 239 | 295 | 700101061H1 | SATMON009 | g1206012 | BLASTN | 1446 | 1e-111 | 99 |
| 240 | 295 | 700072221H1 | SATMON007 | g435312 | BLASTN | 1448 | 1e-111 | 99 |
| 241 | 295 | 700202889H1 | SATMON003 | g435312 | BLASTN | 1294 | 1e-110 | 95 |
| 242 | 295 | 700096691H1 | SATMON008 | g435312 | BLASTN | 1430 | 1e-110 | 100 |
| 243 | 295 | 700092770H1 | SATMON008 | g435312 | BLASTN | 1431 | 1e-110 | 99 |
| 244 | 295 | 700048119H1 | SATMON003 | g435312 | BLASTN | 1434 | 1e-110 | 92 |
| 245 | 295 | 700220654H1 | SATMON011 | g1206012 | BLASTN | 1420 | 1e-109 | 100 |
| 246 | 295 | 700048558H1 | SATMON003 | g435312 | BLASTN | 1423 | 1e-109 | 98 |
| 247 | 295 | 700096602H1 | SATMON008 | g435312 | BLASTN | 1271 | 1e-108 | 99 |
| 248 | 295 | 700094103H1 | SATMON008 | g435312 | BLASTN | 1406 | 1e-108 | 99 |
| 249 | 295 | 700333041H1 | SATMON019 | g435312 | BLASTN | 1413 | 1e-108 | 99 |
| 250 | 295 | 700239210H1 | SATMON010 | g435312 | BLASTN | 1213 | 1e-107 | 97 |
| 251 | 295 | 700030527H1 | SATMON003 | g435312 | BLASTN | 1339 | 1e-107 | 95 |
| 252 | 295 | 700101347H1 | SATMON009 | g1206012 | BLASTN | 1401 | 1e-107 | 97 |
| 253 | 295 | 700457234H1 | SATMON029 | g435312 | BLASTN | 1379 | 1e-106 | 97 |
| 254 | 295 | 700030281H1 | SATMON003 | g799376 | BLASTN | 1381 | 1e-106 | 99 |
| 255 | 295 | 700095440H1 | SATMON008 | g435312 | BLASTN | 1387 | 1e-106 | 98 |
| 256 | 295 | 700220367H1 | SATMON011 | g1206012 | BLASTN | 1302 | 1e-105 | 99 |
| 257 | 295 | 700573418H2 | SATMON030 | g435312 | BLASTN | 1369 | 1e-105 | 99 |
| 258 | 295 | 700469112H1 | SATMON025 | g1399389 | BLASTN | 1370 | 1e-105 | 100 |
| 259 | 295 | 700221610H1 | SATMON011 | g1206012 | BLASTN | 1370 | 1e-105 | 100 |
| 260 | 295 | 700096680H1 | SATMON008 | g435312 | BLASTN | 1374 | 1e-105 | 99 |
| 261 | 295 | 700029615H1 | SATMON003 | g435312 | BLASTN | 1377 | 1e-105 | 99 |
| 262 | 295 | 700456615H1 | SATMON029 | g435312 | BLASTN | 1356 | 1e-104 | 99 |
| 263 | 295 | 700221707H1 | SATMON011 | g1206012 | BLASTN | 1357 | 1e-104 | 98 |
| 264 | 295 | 700105740H1 | SATMON010 | g435312 | BLASTN | 1359 | 1e-104 | 98 |
| 265 | 295 | 700235691H1 | SATMON010 | g435312 | BLASTN | 1363 | 1e-104 | 99 |
| 266 | 295 | 700348545H1 | SATMON023 | g435312 | BLASTN | 1050 | 1e-103 | 100 |

TABLE A*-continued

| Seq No. | Cluster ID | CloneID | Library | NCBI gi | Method | Score | P-value | % Ident |
|---|---|---|---|---|---|---|---|---|
| 267 | 295 | 700028370H1 | SATMON003 | g435312 | BLASTN | 1065 | 1e-103 | 100 |
| 268 | 295 | 700027182H1 | SATMON003 | g435312 | BLASTN | 1348 | 1e-103 | 99 |
| 269 | 295 | 700106536H1 | SATMON010 | g435312 | BLASTN | 1350 | 1e-103 | 100 |
| 270 | 295 | 700105843H1 | SATMON010 | g435312 | BLASTN | 1353 | 1e-103 | 99 |
| 271 | 295 | 700106129H1 | SATMON010 | g435312 | BLASTN | 1079 | 1e-102 | 97 |
| 272 | 295 | 700242556H1 | SATMON010 | g435312 | BLASTN | 1225 | 1e-102 | 100 |
| 273 | 295 | 700027085H1 | SATMON003 | g435312 | BLASTN | 1335 | 1e-102 | 100 |
| 274 | 295 | 700085893H1 | SATMON011 | g1206012 | BLASTN | 1335 | 1e-102 | 98 |
| 275 | 295 | 700029004H1 | SATMON003 | g799376 | BLASTN | 1335 | 1e-102 | 100 |
| 276 | 295 | 700457191H1 | SATMON029 | g435312 | BLASTN | 1336 | 1e-102 | 99 |
| 277 | 295 | 700096560H1 | SATMON008 | g435312 | BLASTN | 1339 | 1e-102 | 99 |
| 278 | 295 | 700237805H1 | SATMON010 | g435312 | BLASTN | 1340 | 1e-102 | 100 |
| 279 | 295 | 700096210H1 | SATMON008 | g435312 | BLASTN | 916 | 1e-101 | 99 |
| 280 | 295 | 700222320H1 | SATMON011 | g1206012 | BLASTN | 1320 | 1e-101 | 100 |
| 281 | 295 | 700240040H1 | SATMON010 | g435312 | BLASTN | 1320 | 1e-101 | 100 |
| 282 | 295 | 700052948H1 | SATMON007 | g435312 | BLASTN | 1325 | 1e-101 | 100 |
| 283 | 295 | 700048831H1 | SATMON003 | g435312 | BLASTN | 835 | 1e-100 | 98 |
| 284 | 295 | 700041531H1 | SATMON004 | g1206012 | BLASTN | 1188 | 1e-100 | 98 |
| 285 | 295 | 700029745H1 | SATMON003 | g435312 | BLASTN | 1310 | 1e-100 | 100 |
| 286 | 295 | 700243513H1 | SATMON010 | g435312 | BLASTN | 1311 | 1e-100 | 99 |
| 287 | 295 | 700029026H1 | SATMON003 | g435312 | BLASTN | 1315 | 1e-100 | 100 |
| 288 | 295 | 700241584H1 | SATMON010 | g435312 | BLASTN | 1316 | 1e-100 | 99 |
| 289 | 295 | 700073024H1 | SATMON007 | g1399389 | BLASTN | 853 | 1e-99 | 96 |
| 290 | 295 | 700223548H1 | SATMON011 | g1206012 | BLASTN | 1301 | 1e-99 | 99 |
| 291 | 295 | 700236626H1 | SATMON010 | g1399389 | BLASTN | 1305 | 1e-99 | 100 |
| 292 | 295 | LIB143-008-Q1-E1-E8 | LIB143 | g1399389 | BLASTN | 738 | 1e-98 | 92 |
| 293 | 295 | 700095640H1 | SATMON008 | g1399389 | BLASTN | 1285 | 1e-98 | 95 |
| 294 | 295 | 700084078H1 | SATMON011 | g1206012 | BLASTN | 1287 | 1e-98 | 97 |
| 295 | 295 | 700422134H1 | SATMONN01 | g1206012 | BLASTN | 1290 | 1e-98 | 100 |
| 296 | 295 | 700162241H1 | SATMON012 | g435312 | BLASTN | 1290 | 1e-98 | 100 |
| 297 | 295 | 700102975H1 | SATMON010 | g435312 | BLASTN | 613 | 1e-97 | 98 |
| 298 | 295 | 700050492H1 | SATMON003 | g1399389 | BLASTN | 1010 | 1e-97 | 99 |
| 299 | 295 | 700204531H1 | SATMON003 | g1399389 | BLASTN | 1216 | 1e-96 | 98 |
| 300 | 295 | 700103594H1 | SATMON010 | g435312 | BLASTN | 1260 | 1e-96 | 100 |
| 301 | 295 | 701163840H1 | SATMONN04 | g435312 | BLASTN | 1262 | 1e-96 | 99 |
| 302 | 295 | 700332403H1 | SATMON019 | g435312 | BLASTN | 1268 | 1e-96 | 99 |
| 303 | 295 | 700236618H1 | SATMON010 | g435312 | BLASTN | 1248 | 1e-95 | 99 |
| 304 | 295 | 700149854H1 | SATMON007 | g435312 | BLASTN | 1255 | 1e-95 | 100 |
| 305 | 295 | 700104119H1 | SATMON010 | g435312 | BLASTN | 1255 | 1e-95 | 92 |
| 306 | 295 | 700167667H1 | SATMON013 | g435312 | BLASTN | 1255 | 1e-95 | 100 |
| 307 | 295 | 700096406H1 | SATMON008 | g435312 | BLASTN | 1235 | 1e-94 | 100 |
| 308 | 295 | 700573958H1 | SATMON030 | g435312 | BLASTN | 1239 | 1e-94 | 98 |
| 309 | 295 | 700154663H1 | SATMON007 | g435312 | BLASTN | 1240 | 1e-94 | 100 |
| 310 | 295 | 700243347H1 | SATMON010 | g435312 | BLASTN | 1243 | 1e-94 | 99 |
| 311 | 295 | 700350103H1 | SATMON023 | g435312 | BLASTN | 580 | 1e-93 | 96 |
| 312 | 295 | 700106454H1 | SATMON010 | g435312 | BLASTN | 803 | 1e-92 | 87 |
| 313 | 295 | 700105284H1 | SATMON010 | g1399389 | BLASTN | 1098 | 1e-92 | 97 |
| 314 | 295 | 700053186H1 | SATMON008 | g435312 | BLASTN | 1220 | 1e-92 | 100 |
| 315 | 295 | 700050806H1 | SATMON003 | g1399389 | BLASTN | 895 | 1e-90 | 100 |
| 316 | 295 | 700153593H1 | SATMON007 | g435312 | BLASTN | 1195 | 1e-90 | 100 |
| 317 | 295 | 700156871H1 | SATMON012 | g435312 | BLASTN | 1195 | 1e-90 | 96 |
| 318 | 295 | 700152345H1 | SATMON007 | g435312 | BLASTN | 1063 | 1e-89 | 98 |
| 319 | 295 | 700237990H1 | SATMON010 | g435312 | BLASTN | 1175 | 1e-89 | 100 |
| 320 | 295 | 700152994H1 | SATMON007 | g435312 | BLASTN | 1180 | 1e-89 | 100 |
| 321 | 295 | 701158395H1 | SATMONN04 | g799376 | BLASTN | 1180 | 1e-89 | 98 |
| 322 | 295 | 700622836H1 | SATMON034 | g435312 | BLASTN | 845 | 1e-88 | 96 |
| 323 | 295 | 700454336H1 | SATMON029 | g1399389 | BLASTN | 1018 | 1e-88 | 91 |
| 324 | 295 | 700574985H1 | SATMON030 | g435312 | BLASTN | 1030 | 1e-88 | 91 |
| 325 | 295 | 700094208H1 | SATMON008 | g1399389 | BLASTN | 690 | 1e-87 | 93 |
| 326 | 295 | 700094580H1 | SATMON008 | g435312 | BLASTN | 916 | 1e-87 | 99 |
| 327 | 295 | 700088251H1 | SATMON011 | g1206012 | BLASTN | 1154 | 1e-87 | 94 |
| 328 | 295 | 700203573H1 | SATMON003 | g799376 | BLASTN | 1155 | 1e-87 | 100 |
| 329 | 295 | 700152986H1 | SATMON007 | g435312 | BLASTN | 1157 | 1e-87 | 98 |
| 330 | 295 | 700457987H1 | SATMON029 | g435312 | BLASTN | 490 | 1e-86 | 95 |
| 331 | 295 | 700156186H1 | SATMON007 | g435312 | BLASTN | 1140 | 1e-86 | 100 |
| 332 | 295 | 700162244H1 | SATMON012 | g435312 | BLASTN | 1142 | 1e-86 | 98 |
| 333 | 295 | 700161070H1 | SATMON012 | g435312 | BLASTN | 1147 | 1e-86 | 98 |
| 334 | 295 | 700241478H1 | SATMON010 | g435312 | BLASTN | 790 | 1e-85 | 96 |
| 335 | 295 | 700238324H1 | SATMON010 | g435312 | BLASTN | 1126 | 1e-85 | 97 |
| 336 | 295 | 700156421H1 | SATMON012 | g435312 | BLASTN | 1127 | 1e-85 | 96 |
| 337 | 295 | 700162187H1 | SATMON012 | g435312 | BLASTN | 1130 | 1e-85 | 100 |
| 338 | 295 | 700161129H1 | SATMON012 | g435312 | BLASTN | 1135 | 1e-85 | 100 |
| 339 | 295 | 700156075H1 | SATMON007 | g435312 | BLASTN | 681 | 1e-84 | 98 |
| 340 | 295 | 700351086H1 | SATMON023 | g1399389 | BLASTN | 1045 | 1e-84 | 95 |
| 341 | 295 | 700155517H1 | SATMON007 | g435312 | BLASTN | 1115 | 1e-84 | 100 |
| 342 | 295 | 700157475H1 | SATMON012 | g435312 | BLASTN | 1115 | 1e-84 | 98 |

TABLE A*-continued

| Seq No. | Cluster ID | CloneID | Library | NCBI gi | Method | Score | P-value | % Ident |
|---|---|---|---|---|---|---|---|---|
| 343 | 295 | 700169796H1 | SATMON013 | g435312 | BLASTN | 1120 | 1e−84 | 100 |
| 344 | 295 | 700201343H1 | SATMON003 | g435312 | BLASTN | 1104 | 1e−83 | 99 |
| 345 | 295 | 700102333H1 | SATMON010 | g435312 | BLASTN | 1106 | 1e−83 | 87 |
| 346 | 295 | 700235624H1 | SATMON010 | g1206012 | BLASTN | 1108 | 1e−83 | 86 |
| 347 | 295 | 700622378H1 | SATMON034 | g435312 | BLASTN | 412 | 1e−82 | 90 |
| 348 | 295 | 700072123H1 | SATMON007 | g435312 | BLASTN | 935 | 1e−82 | 89 |
| 349 | 295 | 700017263H1 | SATMON001 | g799376 | BLASTN | 1100 | 1e−82 | 100 |
| 350 | 295 | LIB3062-051-Q1-K1-G10 | LIB3062 | g435312 | BLASTN | 487 | 1e−81 | 88 |
| 351 | 295 | 700457620H1 | SATMON029 | g1206012 | BLASTN | 511 | 1e−81 | 91 |
| 352 | 295 | 700164773H1 | SATMON013 | g1399389 | BLASTN | 1087 | 1e−81 | 96 |
| 353 | 295 | 700020206H1 | SATMON001 | g799376 | BLASTN | 1089 | 1e−81 | 98 |
| 354 | 295 | 700456365H1 | SATMON029 | g435312 | BLASTN | 1041 | 1e−80 | 99 |
| 355 | 295 | 700238182H1 | SATMON010 | g435312 | BLASTN | 1055 | 1e−79 | 100 |
| 356 | 295 | 700201830H1 | SATMON003 | g435312 | BLASTN | 1058 | 1e−79 | 99 |
| 357 | 295 | 700155920H1 | SATMON007 | g435312 | BLASTN | 873 | 1e−77 | 97 |
| 358 | 295 | 701158695H1 | SATMONN04 | g435312 | BLASTN | 913 | 1e−77 | 94 |
| 359 | 295 | 700029134H1 | SATMON003 | g435312 | BLASTN | 1031 | 1e−77 | 99 |
| 360 | 295 | 701185615H1 | SATMONN06 | g1399389 | BLASTN | 465 | 1e−75 | 100 |
| 361 | 295 | 700621515H1 | SATMON034 | g1399389 | BLASTN | 616 | 1e−75 | 88 |
| 362 | 295 | 700094517H1 | SATMON008 | g435312 | BLASTN | 581 | 1e−74 | 92 |
| 363 | 295 | 700162382H1 | SATMON012 | g435312 | BLASTN | 846 | 1e−74 | 96 |
| 364 | 295 | LIB143-028-Q1-E1-C5 | LIB143 | g1206012 | BLASTN | 995 | 1e−74 | 100 |
| 365 | 295 | 700158308H1 | SATMON012 | g435312 | BLASTN | 1000 | 1e−74 | 100 |
| 366 | 295 | 700242248H1 | SATMON010 | g1206012 | BLASTN | 1001 | 1e−74 | 86 |
| 367 | 295 | 700153633H1 | SATMON007 | g435312 | BLASTN | 1001 | 1e−74 | 99 |
| 368 | 295 | 701158495H1 | SATMONN04 | g799376 | BLASTN | 970 | 1e−72 | 87 |
| 369 | 295 | LIB143-028-Q1-E1-G8 | LIB143 | g435312 | BLASTN | 975 | 1e−72 | 100 |
| 370 | 295 | 700093581H1 | SATMON008 | g435312 | BLASTN | 965 | 1e−71 | 100 |
| 371 | 295 | 700051874H1 | SATMON003 | g435312 | BLASTN | 738 | 1e−70 | 94 |
| 372 | 295 | 700570142H1 | SATMON030 | g1206012 | BLASTN | 559 | 1e−69 | 86 |
| 373 | 295 | 700238661H1 | SATMON010 | g435312 | BLASTN | 831 | 1e−69 | 98 |
| 374 | 295 | 700153172H1 | SATMON007 | g435312 | BLASTN | 941 | 1e−69 | 95 |
| 375 | 295 | 700153988H1 | SATMON007 | g435312 | BLASTN | 921 | 1e−67 | 98 |
| 376 | 295 | 700352641H1 | SATMON024 | g1206012 | BLASTN | 842 | 1e−66 | 97 |
| 377 | 295 | 700030142H1 | SATMON003 | g435312 | BLASTN | 900 | 1e−66 | 100 |
| 378 | 295 | 701164693H1 | SATMONN04 | g435312 | BLASTN | 317 | 1e−64 | 94 |
| 379 | 295 | 700159524H1 | SATMON012 | g1399389 | BLASTN | 535 | 1e−64 | 86 |
| 380 | 295 | 700164779H1 | SATMON013 | g1399389 | BLASTN | 647 | 1e−63 | 93 |
| 381 | 295 | 700467312H1 | SATMON025 | g435312 | BLASTN | 836 | 1e−63 | 99 |
| 382 | 295 | 700161392H1 | SATMON012 | g1206012 | BLASTN | 676 | 1e−62 | 87 |
| 383 | 295 | 700334631H1 | SATMON019 | g435312 | BLASTN | 823 | 1e−59 | 99 |
| 384 | 295 | 700242893H1 | SATMON010 | g435312 | BLASTN | 793 | 1e−57 | 94 |
| 385 | 295 | 700621992H1 | SATMON034 | g1399389 | BLASTN | 235 | 1e−55 | 93 |
| 386 | 295 | 700349745H1 | SATMON023 | g435312 | BLASTN | 750 | 1e−53 | 100 |
| 387 | 295 | 700050250H1 | SATMON003 | g435312 | BLASTN | 483 | 1e−52 | 98 |
| 388 | 295 | 700456624H1 | SATMON029 | g435312 | BLASTN | 726 | 1e−51 | 98 |
| 389 | 295 | 700149879H1 | SATMON007 | g1206012 | BLASTN | 602 | 1e−50 | 83 |
| 390 | 295 | 700458589H1 | SATMON029 | g435312 | BLASTN | 436 | 1e−48 | 93 |
| 391 | 295 | 700168245H1 | SATMON013 | g435312 | BLASTN | 690 | 1e−48 | 100 |
| 392 | 295 | 700151362H1 | SATMON007 | g435312 | BLASTN | 430 | 1e−47 | 100 |
| 393 | 295 | 700075679H1 | SATMON007 | g435312 | BLASTN | 505 | 1e−44 | 90 |
| 394 | 295 | 700456649H1 | SATMON029 | g1206012 | BLASTN | 644 | 1e−44 | 97 |
| 395 | 295 | 700236165H1 | SATMON010 | g435312 | BLASTN | 645 | 1e−44 | 100 |
| 396 | 295 | 700236174H1 | SATMON010 | g435312 | BLASTN | 623 | 1e−43 | 99 |
| 397 | 295 | 700095081H1 | SATMON008 | g435312 | BLASTN | 630 | 1e−43 | 100 |
| 398 | 295 | 700150082H1 | SATMON007 | g1399389 | BLASTN | 612 | 1e−42 | 91 |
| 399 | 295 | 700456926H1 | SATMON029 | g435312 | BLASTN | 331 | 1e−41 | 99 |
| 400 | 295 | 700281403H2 | SATMON019 | g435312 | BLASTN | 303 | 1e−33 | 92 |
| 401 | 295 | 700095048H1 | SATMON008 | g435312 | BLASTN | 503 | 1e−33 | 99 |
| 402 | 295 | 700053540H1 | SATMON010 | g1206012 | BLASTN | 478 | 1e−31 | 89 |
| 403 | 295 | 700241965H1 | SATMON010 | g435312 | BLASTN | 313 | 1e−30 | 90 |
| 404 | 295 | 700623494H1 | SATMON034 | g435312 | BLASTN | 448 | 1e−28 | 91 |
| 405 | 295 | 700076766H1 | SATMON007 | g435312 | BLASTN | 433 | 1e−27 | 98 |
| 406 | 3015 | LIB3069-005-Q1-K1-F9 | LIB3069 | g804655 | BLASTN | 648 | 1e−74 | 80 |
| 407 | 3015 | 700475354H1 | SATMON025 | g804655 | BLASTN | 299 | 1e−46 | 81 |
| 408 | 3015 | 700456167H1 | SATMON025 | g804655 | BLASTN | 253 | 1e−38 | 78 |
| 409 | 3015 | 700473368H1 | SATMON025 | g804656 | BLASTX | 270 | 1e−37 | 66 |
| 410 | 3015 | 700350439H1 | SATMON023 | g1143863 | BLASTN | 533 | 1e−35 | 65 |
| 411 | 3015 | 700469778H1 | SATMON025 | g804656 | BLASTX | 148 | 1e−23 | 74 |
| 412 | 31009 | LIB3066-030-Q1-K1-A2 | LIB3066 | g804656 | BLASTX | 304 | 1e−51 | 56 |
| 413 | 31009 | 700355331H1 | SATMON024 | g804656 | BLASTX | 235 | 1e−25 | 51 |

TABLE A*-continued

| Seq No. | Cluster ID | CloneID | Library | NCBI gi | Method | Score | P-value | % Ident |
|---|---|---|---|---|---|---|---|---|
| 414 | 31970 | LIB3067-027-Q1-K1-B9 | LIB3067 | g804656 | BLASTX | 202 | 1e-36 | 58 |
| 415 | 32475 | LIB3066-035-Q1-K1-F1 | LIB3066 | g40644 | BLASTX | 138 | 1e-32 | 56 |
| 416 | 32588 | LIB143-030-Q1-E1-G7 | LIB143 | g804655 | BLASTN | 463 | 1e-27 | 85 |
| 417 | 32588 | 700096317H1 | SATMON008 | g804656 | BLASTX | 119 | 1e-10 | 71 |
| 418 | 32784 | 700027379H1 | SATMON003 | g21955 | BLASTX | 118 | 1e-9 | 56 |
| 419 | 3311 | LIB3062-026-Q1-K1-H8 | LIB3062 | g1143863 | BLASTN | 1526 | 1e-118 | 81 |
| 420 | 3311 | LIB3078-022-Q1-K1-A8 | LIB3078 | g1143863 | BLASTN | 1394 | 1e-107 | 82 |
| 421 | 3311 | LIB3062-021-Q1-K1-C6 | LIB3062 | g1143863 | BLASTN | 1396 | 1e-107 | 82 |
| 422 | 3311 | LIB143-021-Q1-E1-C8 | LIB143 | g1143863 | BLASTN | 811 | 1e-88 | 78 |
| 423 | 3311 | LIB3062-020-Q1-K1-A11 | LIB3062 | g1143863 | BLASTN | 404 | 1e-87 | 81 |
| 424 | 3311 | LIB3062-052-Q1-K1-H2 | LIB3062 | g1143863 | BLASTN | 712 | 1e-86 | 83 |
| 425 | 3311 | 700207937H1 | SATMON016 | g1143863 | BLASTN | 1127 | 1e-85 | 84 |
| 426 | 3311 | LIB3078-022-Q1-K1-C8 | LIB3078 | g1143863 | BLASTN | 1127 | 1e-85 | 79 |
| 427 | 3311 | 700613304H1 | SATMON033 | g1143863 | BLASTN | 709 | 1e-84 | 84 |
| 428 | 3311 | 700083153H1 | SATMON011 | g1143863 | BLASTN | 1087 | 1e-81 | 84 |
| 429 | 3311 | LIB3059-044-Q1-K1-D4 | LIB3059 | g1143863 | BLASTN | 1087 | 1e-81 | 86 |
| 430 | 3311 | 700083988H1 | SATMON011 | g1143863 | BLASTN | 1074 | 1e-80 | 82 |
| 431 | 3311 | 700091689H1 | SATMON011 | g1143863 | BLASTN | 1061 | 1e-79 | 83 |
| 432 | 3311 | 700211382H1 | SATMON016 | g1143863 | BLASTN | 1065 | 1e-79 | 83 |
| 433 | 3311 | 700093849H1 | SATMON008 | g1143863 | BLASTN | 1065 | 1e-79 | 81 |
| 434 | 3311 | 700265072H1 | SATMON017 | g1143863 | BLASTN | 1052 | 1e-78 | 84 |
| 435 | 3311 | 700224821H1 | SATMON011 | g1143863 | BLASTN | 1039 | 1e-77 | 84 |
| 436 | 3311 | LIB3068-010-Q1-K1-E12 | LIB3068 | g1143863 | BLASTN | 455 | 1e-76 | 74 |
| 437 | 3311 | 700073004H1 | SATMON007 | g1143863 | BLASTN | 540 | 1e-76 | 83 |
| 438 | 3311 | 700351608H1 | SATMON023 | g1143863 | BLASTN | 1026 | 1e-76 | 82 |
| 439 | 3311 | 700077236H1 | SATMON007 | g1143863 | BLASTN | 1029 | 1e-76 | 85 |
| 440 | 3311 | 700614027H1 | SATMON033 | g1143863 | BLASTN | 1017 | 1e-75 | 86 |
| 441 | 3311 | 700333838H1 | SATMON019 | g1143863 | BLASTN | 1004 | 1e-74 | 82 |
| 442 | 3311 | LIB3061-009-Q1-K1-G12 | LIB3061 | g804656 | BLASTX | 433 | 1e-73 | 62 |
| 443 | 3311 | LIB3067-044-Q1-K1-H4 | LIB3067 | g1143863 | BLASTN | 587 | 1e-71 | 76 |
| 444 | 3311 | 700469775H1 | SATMON025 | g1143863 | BLASTN | 960 | 1e-71 | 84 |
| 445 | 3311 | 700214450H1 | SATMON016 | g1143863 | BLASTN | 968 | 1e-71 | 85 |
| 446 | 3311 | 700571763H1 | SATMON030 | g1143863 | BLASTN | 702 | 1e-70 | 82 |
| 447 | 3311 | 700256818H1 | SATMON017 | g1143863 | BLASTN | 949 | 1e-70 | 79 |
| 448 | 3311 | 700087102H1 | SATMON011 | g1143863 | BLASTN | 951 | 1e-70 | 79 |
| 449 | 3311 | 700614486H1 | SATMON033 | g1143863 | BLASTN | 774 | 1e-68 | 79 |
| 450 | 3311 | LIB3069-003-Q1-K1-D3 | LIB3069 | g1143863 | BLASTN | 918 | 1e-67 | 70 |
| 451 | 3311 | 700351075H1 | SATMON023 | g1143863 | BLASTN | 920 | 1e-67 | 84 |
| 452 | 3311 | LIB143-034-Q1-E1-F3 | LIB143 | g804656 | BLASTX | 406 | 1e-64 | 70 |
| 453 | 3311 | 700469282H1 | SATMON025 | g1143863 | BLASTN | 469 | 1e-61 | 85 |
| 454 | 3311 | 700224535H1 | SATMON011 | g1143863 | BLASTN | 840 | 1e-61 | 80 |
| 455 | 3311 | 700457618H1 | SATMON029 | g1143863 | BLASTN | 845 | 1e-61 | 80 |
| 456 | 3311 | 700469464H1 | SATMON025 | g1143863 | BLASTN | 481 | 1e-60 | 83 |
| 457 | 3311 | 700161193H1 | SATMON012 | g1143863 | BLASTN | 820 | 1e-59 | 84 |
| 458 | 3311 | 700196802H1 | SATMON014 | g1143863 | BLASTN | 777 | 1e-55 | 79 |
| 459 | 3311 | LIB3068-029-Q1-K1-H10 | LIB3068 | g1143863 | BLASTN | 703 | 1e-50 | 79 |
| 460 | 3311 | 700205028H1 | SATMON003 | g1143863 | BLASTN | 354 | 1e-45 | 79 |
| 461 | 3311 | 700334602H1 | SATMON019 | g804656 | BLASTX | 382 | 1e-45 | 77 |
| 462 | 3311 | 700018146H1 | SATMON001 | g1143863 | BLASTN | 629 | 1e-43 | 80 |
| 463 | 3311 | 700351771H1 | SATMON023 | g1143863 | BLASTN | 611 | 1e-42 | 81 |
| 464 | 3311 | 700206661H1 | SATMON003 | g1143863 | BLASTN | 604 | 1e-41 | 79 |
| 465 | 3311 | 700616407H1 | SATMON033 | g1143863 | BLASTN | 522 | 1e-38 | 83 |
| 466 | 3311 | 700053754H1 | SATMON011 | g804655 | BLASTN | 401 | 1e-37 | 70 |
| 467 | 3311 | 700469563H1 | SATMON025 | g1143863 | BLASTN | 510 | 1e-33 | 88 |
| 468 | 3311 | 700616186H1 | SATMON033 | g1143864 | BLASTX | 128 | 1e-31 | 72 |
| 469 | 3311 | 700261867H1 | SATMON017 | g804656 | BLASTX | 175 | 1e-27 | 79 |
| 470 | 3311 | 700223387H1 | SATMON011 | g1143863 | BLASTN | 427 | 1e-25 | 82 |
| 471 | 3311 | 700334681H1 | SATMON019 | g804656 | BLASTX | 226 | 1e-24 | 77 |
| 472 | 3311 | 700086604H1 | SATMON011 | g1143863 | BLASTN | 349 | 1e-20 | 85 |

TABLE A*-continued

| Seq No. | Cluster ID | CloneID | Library | NCBI gi | Method | Score | P-value | % Ident |
|---|---|---|---|---|---|---|---|---|
| 473 | 3311 | LIB3069-018-Q1-K1-B8 | LIB3069 | g1143863 | BLASTN | 234 | 1e-16 | 86 |
| 474 | 7962 | 700088807H1 | SATMON011 | g1143863 | BLASTN | 977 | 1e-72 | 83 |
| 475 | 7962 | 700582628H1 | SATMON031 | g1143863 | BLASTN | 838 | 1e-61 | 77 |
| 476 | 8824 | 700266114H1 | SATMON017 | g804655 | BLASTN | 514 | 1e-40 | 78 |
| 477 | 8824 | 700258493H1 | SATMON017 | g804655 | BLASTN | 361 | 1e-21 | 84 |
| 478 | 8824 | LIB143-050-Q1-E1-D9 | LIB143 | g804655 | BLASTN | 241 | 1e-9 | 83 |
| 479 | 9273 | 700153802H1 | SATMON007 | g1143864 | BLASTX | 151 | 1e-14 | 59 |
| SOYBEAN ADENINE PHOSPHORIBOSYL TRANSFERASE (EC 2.4.2.7) | | | | | | | | |
| 480 | -700661182 | 700661182H1 | SOYMON005 | g16164 | BLASTX | 151 | 1e-14 | 70 |
| 481 | -700832379 | 700832379H1 | SOYMON019 | g16164 | BLASTX | 134 | 1e-33 | 76 |
| 482 | -700942837 | 700942837H1 | SOYMON024 | g16163 | BLASTX | 472 | 1e-30 | 71 |
| 483 | -701038319 | 701038319H1 | SOYMON029 | g16164 | BLASTX | 196 | 1e-20 | 84 |
| 484 | -701052195 | 701052195H1 | SOYMON032 | g1321681 | BLASTX | 223 | 1e-33 | 74 |
| 485 | -701054342 | 701054342H1 | SOYMON032 | g16163 | BLASTN | 383 | 1e-21 | 68 |
| 486 | -701099058 | 701099058H1 | SOYMON028 | g16163 | BLASTX | 782 | 1e-56 | 76 |
| 487 | -701103094 | 701103094H1 | SOYMON028 | g1321681 | BLASTX | 150 | 1e-13 | 71 |
| 488 | -701205435 | 701205435H1 | SOYMON035 | g16164 | BLASTX | 298 | 1e-39 | 65 |
| 489 | -GM1685 | LIB3028-009-Q1-B1-H2 | LIB3028 | g16163 | BLASTN | 408 | 1e-38 | 73 |
| 490 | 11402 | 700898558H1 | SOYMON027 | g1402893 | BLASTN | 690 | 1e-48 | 73 |
| 491 | 11402 | 700734213H1 | SOYMON010 | g1321681 | BLASTX | 194 | 1e-40 | 76 |
| 492 | 24349 | 701055830H1 | SOYMON032 | g1321681 | BLASTX | 221 | 1e-24 | 81 |
| 493 | 24349 | 701211541H1 | SOYMON035 | g1321681 | BLASTX | 191 | 1e-19 | 86 |
| 494 | 26036 | 701044219H1 | SOYMON032 | g1402893 | BLASTN | 474 | 1e-29 | 73 |
| 495 | 26036 | 701053252H1 | SOYMON032 | g1321681 | BLASTX | 194 | 1e-20 | 81 |
| 496 | 26036 | 701051166H1 | SOYMON032 | g1321681 | BLASTX | 176 | 1e-17 | 81 |
| 497 | 26036 | 700977973H1 | SOYMON009 | g1321681 | BLASTX | 177 | 1e-17 | 83 |
| 498 | 4852 | 701121868H1 | SOYMON037 | g16163 | BLASTN | 786 | 1e-56 | 77 |
| 499 | 4852 | 701206156H1 | SOYMON035 | g16163 | BLASTN | 568 | 1e-38 | 77 |
| 500 | 4852 | 700651407H1 | SOYMON003 | g16163 | BLASTN | 492 | 1e-30 | 75 |
| 501 | 4852 | 701127525H1 | SOYMON037 | g16163 | BLASTN | 473 | 1e-29 | 75 |
| 502 | 4852 | 700895694H1 | SOYMON027 | g16163 | BLASTN | 434 | 1e-27 | 77 |
| 503 | 4852 | 700560253H1 | SOYMON001 | g16164 | BLASTX | 199 | 1e-21 | 82 |
| 504 | 4852 | 701138208H1 | SOYMON038 | g16164 | BLASTX | 175 | 1e-17 | 80 |
| 505 | 4852 | 701137650H1 | SOYMON038 | g16163 | BLASTN | 317 | 1e-15 | 75 |
| 506 | 4852 | LIB3040-031-Q1-E2-D4 | LIB3040 | g16163 | BLASTN | 308 | 1e-14 | 80 |
| 507 | 4852 | 701066549H1 | SOYMON034 | g16164 | BLASTX | 142 | 1e-12 | 84 |
| 508 | 4852 | 700893483H1 | SOYMON024 | g16164 | BLASTX | 134 | 1e-11 | 83 |
| 509 | 8624 | 700653006H1 | SOYMON003 | g16163 | BLASTN | 605 | 1e-40 | 70 |
| 510 | 8624 | LIB3039-040-Q1-E1-C8 | LIB039 | g16163 | BLASTN | 511 | 1e-31 | 67 |
| 511 | 8624 | 701135156H1 | SOYMON038 | g16164 | BLASTX | 207 | 1e-22 | 72 |
| 512 | 8624 | 701054685H1 | SOYMON032 | g726305 | BLASTX | 199 | 1e-21 | 80 |
| 513 | 8624 | 700834123H1 | SOYMON019 | g16164 | BLASTX | 182 | 1e-18 | 67 |
| 514 | 8624 | 700830624H1 | SOYMON019 | g1321681 | BLASTX | 128 | 1e-10 | 73 |
| 515 | 8624 | 700833413H1 | SOYMON019 | g1321681 | BLASTX | 129 | 1e-10 | 65 |
| SOYBEAN β GLUCOSIDASE (EC 3.2.1.21) | | | | | | | | |
| 516 | -700747805 | 700747805H1 | SOYMON013 | g1155090 | BLASTX | 152 | 1e-13 | 65 |
| 517 | -700749102 | 700749102H1 | SOYMON013 | g1155255 | BLASTX | 141 | 1e-12 | 69 |
| 518 | -700749944 | 700749944H1 | SOYMON013 | g1155255 | BLASTX | 169 | 1e-18 | 54 |
| 519 | -700837183 | 700837183H1 | SOYMON020 | g804656 | BLASTX | 161 | 1e-15 | 81 |
| 520 | -700894885 | 700894885H1 | SOYMON024 | g142580 | BLASTX | 114 | 1e-8 | 61 |
| 521 | -700907258 | 700907258H1 | SOYMON022 | g804656 | BLASTX | 187 | 1e-18 | 46 |
| 522 | -700965238 | 700965238H1 | SOYMON022 | g1155255 | BLASTX | 145 | 1e-23 | 51 |
| 523 | -700967625 | 700967625H1 | SOYMON032 | g21953 | BLASTX | 165 | 1e-15 | 64 |
| 524 | -700978836 | 700978836H1 | SOYMON009 | g804656 | BLASTX | 187 | 1e-18 | 43 |
| 525 | -700982375 | 700982375H1 | SOYMON009 | g1155090 | BLASTX | 109 | 1e-9 | 44 |
| 526 | -701043315 | 701043315H1 | SOYMON029 | g1155255 | BLASTX | 170 | 1e-19 | 57 |
| 527 | -701054964 | 701054964H1 | SOYMON032 | g757740 | BLASTX | 173 | 1e-16 | 61 |
| 528 | -701055914 | 701055914H1 | SOYMON032 | g21953 | BLASTX | 176 | 1e-25 | 69 |
| 529 | -701127573 | 701127573H1 | SOYMON037 | g21953 | BLASTX | 121 | 1e-20 | 74 |
| 530 | -701131494 | 701131494H1 | SOYMON038 | g1143864 | BLASTX | 133 | 1e-21 | 68 |
| 531 | -701138450 | 701138450H1 | SOYMON038 | g21955 | BLASTX | 235 | 1e-25 | 55 |
| 532 | -701146550 | 701146550H1 | SOYMON031 | g21955 | BLASTX | 65 | 1e-9 | 66 |
| 533 | -701203719 | 701203719H2 | SOYMON035 | g1143864 | BLASTX | 160 | 1e-14 | 46 |
| 534 | -701213534 | 701213534H1 | SOYMON035 | g1483154 | BLASTX | 78 | 1e-9 | 48 |
| 535 | -GM10346 | LIB3049-006-Q1-E1-H5 | LIB3049 | g3201553 | BLASTN | 742 | 1e-51 | 63 |
| 536 | -GM12457 | LIB3049-044-Q1-E1-A10 | LIB3049 | g3201553 | BLASTN | 683 | 1e-48 | 65 |
| 537 | -GM34028 | LIB3051-038-Q1-K1-D2 | LIB3051 | g249262 | BLASTX | 78 | 1e-27 | 53 |

TABLE A*-continued

| Seq No. | Cluster ID | CloneID | Library | NCBI gi | Method | Score | P-value | % Ident |
|---|---|---|---|---|---|---|---|---|
| 538 | -GM37305 | LIB3051-073-Q1-K1-G10 | LIB3051 | g804656 | BLASTX | 258 | 1e-44 | 68 |
| 539 | -GM40790 | LIB3051-105-Q1-K1-F4 | LIB3051 | g804656 | BLASTX | 362 | 1e-72 | 69 |
| 540 | 11009 | 700660118H1 | SOYMON004 | g804656 | BLASTX | 244 | 1e-26 | 79 |
| 541 | 11009 | 700746718H1 | SOYMON013 | g804656 | BLASTX | 121 | 1e-11 | 61 |
| 542 | 11009 | 701061014H1 | SOYMON033 | g804656 | BLASTX | 117 | 1e-9 | 72 |
| 543 | 12181 | 701146853H1 | SOYMON031 | g21955 | BLASTX | 162 | 1e-22 | 62 |
| 544 | 12181 | 701040693H1 | SOYMON029 | g21955 | BLASTX | 162 | 1e-21 | 63 |
| 545 | 12181 | 701212713H1 | SOYMON035 | g21955 | BLASTX | 162 | 1e-19 | 67 |
| 546 | 12623 | 701141106H1 | SOYMON038 | g142580 | BLASTX | 163 | 1e-15 | 65 |
| 547 | 12623 | 700975287H1 | SOYMON009 | g142580 | BLASTX | 126 | 1e-10 | 65 |
| 548 | 12814 | LIB3051-053-Q1-K2-H12 | LIB3051 | g804656 | BLASTX | 243 | 1e-42 | 61 |
| 549 | 12814 | LIB3052-007-Q1-B1-G11 | LIB3052 | g1143863 | BLASTN | 613 | 1e-40 | 66 |
| 550 | 12814 | LIB3051-111-Q1-K1-C12 | LIB3051 | g1143863 | BLASTN | 608 | 1e-39 | 67 |
| 551 | 12814 | 700656613H1 | SOYMON004 | g1143863 | BLASTN | 572 | 1e-38 | 67 |
| 552 | 12814 | 701068027H2 | SOYMON034 | g804656 | BLASTX | 205 | 1e-35 | 86 |
| 553 | 12814 | 701211582H1 | SOYMON035 | g804656 | BLASTX | 247 | 1e-35 | 82 |
| 554 | 12814 | 700986671H1 | SOYMON009 | g804656 | BLASTX | 201 | 1e-31 | 58 |
| 555 | 12814 | 701153690H1 | SOYMON031 | g804656 | BLASTX | 270 | 1e-30 | 63 |
| 556 | 12814 | 701066513H1 | SOYMON034 | g804656 | BLASTX | 120 | 1e-28 | 88 |
| 557 | 12814 | 700838612H1 | SOYMON020 | g1143863 | BLASTN | 348 | 1e-18 | 70 |
| 558 | 13173 | LIB3049-018-Q1-E1-B7 | LIB3049 | g1143863 | BLASTN | 745 | 1e-51 | 66 |
| 559 | 13173 | LIB3049-001-Q1-E1-G7 | LIB3049 | g1143863 | BLASTN | 623 | 1e-41 | 65 |
| 560 | 13173 | LIB3051-111-Q1-K1-B12 | LIB3051 | g804656 | BLASTX | 215 | 1e-40 | 64 |
| 561 | 13173 | 700837342H1 | SOYMON020 | g804656 | BLASTX | 337 | 1e-39 | 70 |
| 562 | 13173 | 700838567H1 | SOYMON020 | g804656 | BLASTX | 339 | 1e-39 | 69 |
| 563 | 13173 | LIB3051-111-Q1-K1-B10 | LIB3051 | g1143863 | BLASTN | 574 | 1e-36 | 67 |
| 564 | 13173 | LIB3051-114-Q1-K1-B10 | LIB3051 | g804656 | BLASTX | 89 | 1e-31 | 53 |
| 565 | 13173 | 700761996H1 | SOYMON015 | g804656 | BLASTX | 279 | 1e-31 | 64 |
| 566 | 13173 | 700971311H1 | SOYMON005 | g804656 | BLASTX | 270 | 1e-30 | 58 |
| 567 | 13173 | 700854217H1 | SOYMON023 | g804656 | BLASTX | 158 | 1e-27 | 58 |
| 568 | 13173 | 701063334H1 | SOYMON033 | g1143863 | BLASTN | 460 | 1e-27 | 62 |
| 569 | 13173 | 700900778H1 | SOYMON027 | g804656 | BLASTX | 199 | 1e-20 | 76 |
| 570 | 1499 | LIB3039-014-Q1-E1-D8 | LIB3039 | g1155090 | BLASTX | 144 | 1e-44 | 53 |
| 571 | 1499 | 701069538H1 | SOYMON034 | g1155255 | BLASTX | 221 | 1e-23 | 52 |
| 572 | 1499 | 701064351H1 | SOYMON034 | g21953 | BLASTX | 153 | 1e-17 | 50 |
| 573 | 1499 | 700651844H1 | SOYMON003 | g1155090 | BLASTX | 91 | 1e-10 | 55 |
| 574 | 1499 | 701068724H1 | SOYMON034 | g1155090 | BLASTX | 125 | 1e-9 | 48 |
| 575 | 150 | 700653669H1 | SOYMON003 | g21953 | BLASTX | 219 | 1e-23 | 58 |
| 576 | 150 | 700651748H1 | SOYMON003 | g21953 | BLASTX | 193 | 1e-19 | 60 |
| 577 | 150 | 701127306H1 | SOYMON037 | g21953 | BLASTX | 188 | 1e-18 | 58 |
| 578 | 150 | 700561901H1 | SOYMON002 | g21955 | BLASTX | 156 | 1e-14 | 64 |
| 579 | 150 | 701129795H1 | SOYMON037 | g21955 | BLASTX | 143 | 1e-12 | 68 |
| 580 | 150 | 701126390H1 | SOYMON037 | g21955 | BLASTX | 143 | 1e-12 | 68 |
| 581 | 150 | 701125867H1 | SOYMON037 | g21955 | BLASTX | 134 | 1e-11 | 63 |
| 582 | 150 | 701142724H1 | SOYMON038 | g21955 | BLASTX | 135 | 1e-11 | 69 |
| 583 | 150 | 701060152H1 | SOYMON033 | g1155255 | BLASTX | 135 | 1e-11 | 62 |
| 584 | 150 | 701141927H1 | SOYMON038 | g581738 | BLASTX | 127 | 1e-10 | 64 |
| 585 | 150 | 701125996H1 | SOYMON037 | g21955 | BLASTX | 127 | 1e-10 | 66 |
| 586 | 150 | 701061767H1 | SOYMON033 | g21955 | BLASTX | 89 | 1e-9 | 65 |
| 587 | 21571 | 701098566H1 | SOYMON028 | g21955 | BLASTX | 152 | 1e-34 | 59 |
| 588 | 21571 | 700846795H1 | SOYMON021 | g21955 | BLASTX | 158 | 1e-31 | 59 |
| 589 | 21571 | 701037773H1 | SOYMON029 | g21953 | BLASTX | 94 | 1e-22 | 59 |
| 590 | 22050 | 701039143H1 | SOYMON029 | g21955 | BLASTX | 86 | 1e-14 | 63 |
| 591 | 24776 | 701149235H1 | SOYMON031 | g21955 | BLASTX | 181 | 1e-17 | 55 |
| 592 | 30906 | LIB3028-006-Q1-B1-F2 | LIB3028 | g2077896 | BLASTX | 113 | 1e-24 | 47 |
| 593 | 3094 | 700564240H1 | SOYMON002 | g21955 | BLASTX | 197 | 1e-20 | 80 |
| 594 | 3094 | 700564288H1 | SOYMON002 | g21955 | BLASTX | 199 | 1e-20 | 79 |
| 595 | 3094 | 701042714H1 | SOYMON029 | g21955 | BLASTX | 179 | 1e-17 | 77 |
| 596 | 3094 | 700565738H1 | SOYMON002 | g21955 | BLASTX | 160 | 1e-16 | 85 |
| 597 | 32420 | LIB3030-008-Q1-B1-H11 | LIB3030 | g1143863 | BLASTN | 551 | 1e-35 | 61 |
| 598 | 32420 | 700963106H1 | SOYMON022 | g804656 | BLASTX | 219 | 1e-23 | 50 |
| 599 | 33821 | 700847344H1 | SOYMON021 | g21955 | BLASTX | 163 | 1e-26 | 58 |
| 600 | 4085 | LIB3053-005-Q1-N1-F10 | LIB3053 | g40665 | BLASTX | 195 | 1e-42 | 59 |

TABLE A*-continued

| Seq No. | Cluster ID | CloneID | Library | NCBI gi | Method | Score | P-value | % Ident |
|---|---|---|---|---|---|---|---|---|
| 601 | 4085 | 700548207H1 | SOYMON002 | g1155255 | BLASTX | 144 | 1e-24 | 60 |
| 602 | 587 | LIB3039-005-Q1-E1-F2 | LIB3039 | g1155090 | BLASTX | 199 | 1e-38 | 56 |
| 603 | 587 | LIB3039-048-Q1-E1-A6 | LIB3039 | g21955 | BLASTX | 142 | 1e-27 | 65 |
| 604 | 587 | 701145333H1 | SOYMON031 | g21953 | BLASTX | 149 | 1e-27 | 66 |
| 605 | 587 | 700653427H1 | SOYMON003 | g1155090 | BLASTX | 230 | 1e-26 | 56 |
| 606 | 587 | 700652854H1 | SOYMON003 | g1155090 | BLASTX | 188 | 1e-25 | 60 |
| 607 | 587 | 700751375H1 | SOYMON014 | g21955 | BLASTX | 161 | 1e-23 | 64 |
| 608 | 587 | 701063494H1 | SOYMON033 | g1155090 | BLASTX | 223 | 1e-23 | 60 |
| 609 | 587 | 700955066H1 | SOYMON022 | g1155090 | BLASTX | 216 | 1e-22 | 59 |
| 610 | 587 | 700982238H1 | SOYMON009 | g1155090 | BLASTX | 185 | 1e-20 | 61 |
| 611 | 587 | 701109014H1 | SOYMON036 | g1155090 | BLASTX | 189 | 1e-20 | 58 |
| 612 | 587 | 701145904H1 | SOYMON031 | g21953 | BLASTX | 204 | 1e-20 | 59 |
| 613 | 587 | 700982608H1 | SOYMON009 | g1155090 | BLASTX | 180 | 1e-19 | 59 |
| 614 | 587 | 700986368H1 | SOYMON009 | g1155090 | BLASTX | 184 | 1e-19 | 62 |
| 615 | 587 | 701139123H1 | SOYMON038 | g21953 | BLASTX | 155 | 1e-18 | 63 |
| 616 | 587 | 701138844H1 | SOYMON038 | g1155090 | BLASTX | 178 | 1e-17 | 61 |
| 617 | 587 | 700791212H1 | SOYMON011 | g1155090 | BLASTX | 142 | 1e-15 | 59 |
| 618 | 587 | 700646575H1 | SOYMON014 | g1155090 | BLASTX | 150 | 1e-15 | 63 |
| 619 | 587 | 700991712H1 | SOYMON011 | g1155090 | BLASTX | 153 | 1e-15 | 57 |
| 620 | 587 | 700904947H1 | SOYMON022 | g21955 | BLASTX | 159 | 1e-15 | 59 |
| 621 | 587 | 700730081H1 | SOYMON009 | g21955 | BLASTX | 159 | 1e-15 | 59 |
| 622 | 587 | 701060675H1 | SOYMON033 | g21955 | BLASTX | 160 | 1e-15 | 59 |
| 623 | 587 | 700983905H1 | SOYMON009 | g21953 | BLASTX | 114 | 1e-14 | 47 |
| 624 | 587 | 701135826H1 | SOYMON038 | g21955 | BLASTX | 155 | 1e-14 | 58 |
| 625 | 587 | 701142683H1 | SOYMON038 | g21953 | BLASTX | 155 | 1e-14 | 60 |
| 626 | 587 | 700656303H1 | SOYMON004 | g1155255 | BLASTX | 96 | 1e-13 | 41 |
| 627 | 587 | 701064503H1 | SOYMON034 | g21953 | BLASTX | 118 | 1e-13 | 62 |
| 628 | 587 | 700959789H1 | SOYMON022 | g1155090 | BLASTX | 145 | 1e-13 | 57 |
| 629 | 587 | 701104579H1 | SOYMON036 | g21955 | BLASTX | 146 | 1e-13 | 55 |
| 630 | 587 | 700975311H1 | SOYMON009 | g21955 | BLASTX | 148 | 1e-13 | 55 |
| 631 | 587 | 700987858H1 | SOYMON009 | g1155090 | BLASTX | 151 | 1e-13 | 58 |
| 632 | 587 | 700787696H2 | SOYMON011 | g21953 | BLASTX | 151 | 1e-13 | 60 |
| 633 | 587 | 700755020H1 | SOYMON014 | g21955 | BLASTX | 124 | 1e-12 | 58 |
| 634 | 587 | 700961408H1 | SOYMON022 | g1155090 | BLASTX | 126 | 1e-12 | 47 |
| 635 | 587 | 700975523H1 | SOYMON009 | g1155090 | BLASTX | 128 | 1e-12 | 50 |
| 636 | 587 | 700956261H1 | SOYMON022 | g1155090 | BLASTX | 139 | 1e-12 | 60 |
| 637 | 587 | 700986691H1 | SOYMON009 | g1155090 | BLASTX | 140 | 1e-12 | 60 |
| 638 | 587 | 700751271H1 | SOYMON014 | g1155090 | BLASTX | 141 | 1e-12 | 59 |
| 639 | 587 | 700730156H1 | SOYMON009 | g1155090 | BLASTX | 141 | 1e-12 | 59 |
| 640 | 587 | 701141713H1 | SOYMON038 | g21955 | BLASTX | 141 | 1e-12 | 60 |
| 641 | 587 | 701157330H1 | SOYMON031 | g1155090 | BLASTX | 141 | 1e-12 | 59 |
| 642 | 587 | 700967834H1 | SOYMON033 | g21955 | BLASTX | 142 | 1e-12 | 55 |
| 643 | 587 | 701155566H1 | SOYMON031 | g21955 | BLASTX | 142 | 1e-12 | 61 |
| 644 | 587 | 700751706H1 | SOYMON014 | g21955 | BLASTX | 144 | 1e-12 | 61 |
| 645 | 587 | 701145403H1 | SOYMON031 | g21953 | BLASTX | 131 | 1e-11 | 63 |
| 646 | 587 | 700959567H1 | SOYMON022 | g757740 | BLASTX | 134 | 1e-11 | 60 |
| 647 | 587 | 701064274H1 | SOYMON034 | g505279 | BLASTX | 135 | 1e-11 | 41 |
| 648 | 587 | 701151995H1 | SOYMON031 | g21953 | BLASTX | 135 | 1e-11 | 63 |
| 649 | 587 | 701050236H1 | SOYMON032 | g21955 | BLASTX | 135 | 1e-11 | 62 |
| 650 | 587 | 701152375H1 | SOYMON031 | g21955 | BLASTX | 135 | 1e-11 | 67 |
| 651 | 587 | 701155583H1 | SOYMON031 | g21953 | BLASTX | 135 | 1e-11 | 63 |
| 652 | 587 | 701156782H1 | SOYMON031 | g21953 | BLASTX | 135 | 1e-11 | 63 |
| 653 | 587 | 701149881H1 | SOYMON031 | g21955 | BLASTX | 136 | 1e-11 | 65 |
| 654 | 587 | 701151802H1 | SOYMON031 | g21953 | BLASTX | 136 | 1e-11 | 63 |
| 655 | 587 | 701147107H1 | SOYMON031 | g21953 | BLASTX | 136 | 1e-11 | 63 |
| 656 | 587 | 701157340H1 | SOYMON031 | g21955 | BLASTX | 137 | 1e-11 | 60 |
| 657 | 587 | 701142839H1 | SOYMON038 | g21953 | BLASTX | 138 | 1e-11 | 61 |
| 658 | 587 | 701148320H1 | SOYMON038 | g21955 | BLASTX | 138 | 1e-11 | 60 |
| 659 | 587 | 701156604H1 | SOYMON031 | g1155090 | BLASTX | 86 | 1e-10 | 60 |
| 660 | 587 | 701139062H1 | SOYMON038 | g21955 | BLASTX | 125 | 1e-10 | 60 |
| 661 | 587 | 701068825H1 | SOYMON034 | g21953 | BLASTX | 125 | 1e-10 | 55 |
| 662 | 587 | 701147382H1 | SOYMON031 | g21955 | BLASTX | 127 | 1e-10 | 68 |
| 663 | 587 | 701154153H1 | SOYMON031 | g21953 | BLASTX | 127 | 1e-10 | 64 |
| 664 | 587 | 701155501H1 | SOYMON031 | g21955 | BLASTX | 129 | 1e-10 | 61 |
| 665 | 587 | 701155731H1 | SOYMON031 | g21953 | BLASTX | 129 | 1e-10 | 58 |
| 666 | 587 | 701157725H1 | SOYMON031 | g21955 | BLASTX | 130 | 1e-10 | 61 |
| 667 | 587 | 700967321H1 | SOYMON031 | g21953 | BLASTX | 120 | 1e-9 | 61 |
| 668 | 587 | 701108022H1 | SOYMON036 | g21953 | BLASTX | 121 | 1e-9 | 60 |
| 669 | 587 | 701150196H1 | SOYMON031 | g21953 | BLASTX | 122 | 1e-9 | 63 |
| 670 | 587 | 701150439H1 | SOYMON031 | g21953 | BLASTX | 122 | 1e-9 | 63 |
| 671 | 587 | 701145973H1 | SOYMON031 | g1155090 | BLASTX | 99 | 1e-8 | 63 |
| 672 | 587 | 701130507H1 | SOYMON038 | g1155090 | BLASTX | 116 | 1e-8 | 50 |
| 673 | 587 | 701155886H1 | SOYMON031 | g21953 | BLASTX | 116 | 1e-8 | 62 |
| 674 | 587 | 700753795H1 | SOYMON014 | g21953 | BLASTX | 117 | 1e-8 | 62 |
| 675 | 7163 | 700560905H1 | SOYMON001 | g1206013 | BLASTX | 125 | 1e-16 | 59 |

TABLE A*-continued

| Seq No. | Cluster ID | CloneID | Library | NCBI gi | Method | Score | P-value | % Ident |
|---|---|---|---|---|---|---|---|---|
| 676 | 7163 | 700964094H1 | SOYMON022 | g1155255 | BLASTX | 106 | 1e-15 | 61 |
| 677 | 7535 | 701065656H1 | SOYMON034 | g1155255 | BLASTX | 161 | 1e-28 | 59 |
| 678 | 7535 | 701065608H1 | SOYMON034 | g1155255 | BLASTX | 92 | 1e-20 | 61 |
| 679 | 7535 | 701063444H1 | SOYMON033 | g1155090 | BLASTX | 195 | 1e-19 | 62 |
| 680 | 9186 | 700995628H1 | SOYMON011 | g21953 | BLASTX | 161 | 1e-18 | 68 |
| 681 | 921 | LIB3051-108-Q1-K1-H11 | LIB3051 | g804656 | BLASTX | 217 | 1e-58 | 67 |
| 682 | 921 | 700651438H1 | SOYMON003 | g804656 | BLASTX | 454 | 1e-55 | 67 |
| 683 | 921 | LIB3051-101-Q1-K1-A6 | LIB3051 | g804656 | BLASTX | 228 | 1e-51 | 62 |
| 684 | 921 | LIB3051-091-Q1-K1-G8 | LIB3051 | g804656 | BLASTX | 217 | 1e-50 | 67 |
| 685 | 921 | LIB3051-096-Q1-K1-A7 | LIB3051 | g804656 | BLASTX | 269 | 1e-46 | 65 |
| 686 | 921 | 701068457H1 | SOYMON034 | g804656 | BLASTX | 230 | 1e-43 | 73 |
| 687 | 921 | 701134773H2 | SOYMON038 | g804656 | BLASTX | 332 | 1e-38 | 66 |
| 688 | 921 | 700978751H1 | SOYMON009 | g804656 | BLASTX | 211 | 1e-37 | 68 |
| 689 | 921 | 700727744H1 | SOYMON009 | g804656 | BLASTX | 305 | 1e-35 | 71 |
| 690 | 921 | LIB3049-024-Q1-E1-G5 | LIB3049 | g804656 | BLASTX | 187 | 1e-34 | 61 |
| 691 | 921 | 700757238H1 | SOYMON015 | g1143863 | BLASTN | 465 | 1e-29 | 68 |
| 692 | 921 | 700972951H1 | SOYMON005 | g804656 | BLASTX | 168 | 1e-16 | 69 |
| 693 | 921 | 700986340H1 | SOYMON009 | g804656 | BLASTX | 172 | 1e-16 | 72 |
| 694 | 921 | 700564114H1 | SOYMON002 | g804656 | BLASTX | 172 | 1e-16 | 72 |
| 695 | 921 | 700851301H1 | SOYMON023 | g804656 | BLASTX | 172 | 1e-16 | 72 |
| 696 | 921 | 701104026H1 | SOYMON036 | g804656 | BLASTX | 172 | 1e-16 | 72 |
| 697 | 921 | 701060132H1 | SOYMON033 | g804656 | BLASTX | 172 | 1e-16 | 72 |
| 698 | 921 | 701211625H1 | SOYMON035 | g804656 | BLASTX | 172 | 1e-16 | 72 |
| 699 | 921 | 701136164H1 | SOYMON038 | g804656 | BLASTX | 173 | 1e-16 | 68 |
| 700 | 921 | 701137640H1 | SOYMON038 | g804656 | BLASTX | 160 | 1e-15 | 67 |
| 701 | 921 | 701142240H1 | SOYMON038 | g804656 | BLASTX | 157 | 1e-14 | 74 |
| 702 | 921 | 700842016H1 | SOYMON020 | g804656 | BLASTX | 136 | 1e-11 | 74 |
| 703 | 921 | 701210015H1 | SOYMON035 | g804656 | BLASTX | 136 | 1e-11 | 74 |
| 704 | 921 | 701204245H2 | SOYMON035 | g804656 | BLASTX | 125 | 1e-10 | 72 |
| 705 | 921 | 700841069H1 | SOYMON020 | g804656 | BLASTX | 119 | 1e-9 | 79 |
| 706 | 921 | 700852034H1 | SOYMON023 | g804656 | BLASTX | 119 | 1e-9 | 79 |
| 707 | 921 | 700837045H1 | SOYMON020 | g804656 | BLASTX | 120 | 1e-9 | 74 |
| 708 | 921 | 701210726H1 | SOYMON035 | g804656 | BLASTX | 120 | 1e-9 | 74 |
| 709 | 921 | 700840844H1 | SOYMON020 | g804656 | BLASTX | 122 | 1e-9 | 57 |
| 710 | 921 | 700839037H1 | SOYMON020 | g804656 | BLASTX | 115 | 1e-8 | 79 |
| | | SOYBEAN ISOPENTYLTRANSFERASE | | | | | | |
| 711 | -GM17896 | LIB3055-003-Q1-N1-B10 | LIB3055 | g1419759 | BLASTX | 241 | 1e-42 | 40 |

*Table Headings

Cluster ID

A cluster ID is arbitrarily assigned to all of those clones which belong to the same cluster at a given stringency and a particular clone will belong to only one cluster at a given stringency. If a cluster contains only a single clone (a "singleton"), then the cluster ID number will be negative, with an absolute value equal to the clone ID number of its single member. The cluster ID entries in the table refer to the cluster with which the particular clone in each row is associated.

Clone ID

The clone ID number refers to the particular clone in the PhytoSeq database. Each clone ID entry in the table refers to the clone whose sequence is used for (1) the sequence comparison whose scores are presented and/or (2) assignment to the particular cluster which is presented. Note that a clone may be included in this table even if its sequence comparison scores fail to meet the minimum standards for similarity. In such a case, the clone is included due solely to its association with a particular cluster for which sequences of one or more other member clones possess the required level of similarity.

Library

The library ID refers to the particular cDNA library from which a given clone is obtained. Each cDNA library is associated with the particular tissue(s), line(s) and developmental stage(s) from which it is isolated.

NCBI gi

Each sequence in the GenBank public database is arbitrarily assigned a unique NCBI gi (National Center for Biotechnology Information GenBank Identifier) number. In this table, the NCBI gi number which is associated (in the same row) with a given clone refers to the particular GenBank sequence which is used in the sequence comparison. This entry is omitted when a clone is included solely due to its association with a particular cluster.

Method

The entry in the "Method" column of the table refers to the type of BLAST search that is used for the sequence comparison. "CLUSTER" is entered when the sequence comparison scores for a given clone fail to meet the minimum values required for significant similarity. In such cases, the clone is listed in the table solely as a result of its association with a given cluster for which sequences of one or more other member clones possess the required level of similarity.

Score

Each entry in the "Score" column of the table refers to the BLAST score that is generated by sequence comparison of the designated clone with the designated GenBank sequence using the designated BLAST method. This entry is omitted when a clone is included solely due to its association with a particular cluster. If the program used to determine the hit is HMMSW then the score refers to HMMSW score.

P-Value

The entries in the P-Value column refer to the probability that such matches occur by chance.

% Ident

The entries in the "% Ident" column of the table refer to the percentage of identically matched nucleotides (or residues) that exist along the length of that portion of the sequences which is aligned by the BLAST comparison to generate the statistical scores presented. This entry is omitted when a clone is included solely due to its association with a particular cluster.

We claim:

1. A substantially purified nucleic acid molecule comprising a nucleic acid sequence having the full-length sequence of SEQ ID NO: 5 or complement thereof.

2. The substantially purified nucleic acid molecule according to claim 1, wherein said nucleic acid molecule consists of a nucleic acid sequence having the frill-length sequence of SEQ ID NO: 5 or complement thereof.

3. A transformed plant comprising a recombinant nucleic acid molecule having the nucleic acid sequence of claim 1.

4. A transformed host cell comprising a recombinant nucleic acid molecule having the nucleic acid molecule of claim 1.

5. The host cell of claim 4, wherein said host cell is a plant cell.

6. A transformed plant comprising the host cell of claim 4.

7. A transformed plant consisting of host cells of claim 4.

8. A substantially purified nucleic acid molecule having between 90% and 100% sequence identity with a nucleic acid molecule having the full-length sequence of SEQ ID NO: 5 or complement thereof.

9. The substantially purified nucleic acid molecule of claim 8, wherein said substantially purified nucleic acid molecule has between 95% and 100% sequence identity with SEQ ID NO: 5 or complement thereof.

10. The substantially purified nucleic acid molecule of claim 9, wherein said substantially purified nucleic acid molecule has between 98% and 100% sequence identity with SEQ ID NO: 5 or complement thereof.

11. The substantially purified nucleic acid molecule of claim 10, wherein said substantially purified nucleic acid molecule has between 99% and 100% sequence identity with SEQ ID NO: 5 or complement thereof.

* * * * *

UNITED STATES PATENT AND TRADEMARK OFFICE
CERTIFICATE OF CORRECTION

PATENT NO. : 7,655,469 B2  Page 1 of 1
APPLICATION NO. : 09/976054
DATED : February 2, 2010
INVENTOR(S) : Cheikh et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 914 days.

Signed and Sealed this

Twenty-third Day of November, 2010

David J. Kappos
*Director of the United States Patent and Trademark Office*